US012139553B2

(12) United States Patent
Bacac et al.

(10) Patent No.: US 12,139,553 B2
(45) Date of Patent: Nov. 12, 2024

(54) T CELL ACTIVATING BISPECIFIC ANTIGEN BINDING MOLECULES

(71) Applicant: Hoffmann-La Roche Inc., Little Falls, NJ (US)

(72) Inventors: Marina Bacac, Zurich (CH); Peter Bruenker, Hittnau (CH); Anne Freimoser-Grundschober, Zurich (CH); Ralf Hosse, Cham (CH); Christian Klein, Bonstetten (CH); Ekkehard Moessner, Kreuzlingen (CH); Pablo Umana, Wollerau (CH); Tina Weinzierl, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 471 days.

(21) Appl. No.: 17/580,248

(22) Filed: Jan. 20, 2022

(65) Prior Publication Data

US 2022/0220224 A1 Jul. 14, 2022

Related U.S. Application Data

(60) Division of application No. 16/016,209, filed on Jun. 22, 2018, now abandoned, which is a continuation of application No. 14/947,657, filed on Nov. 20, 2015, now abandoned.

(30) Foreign Application Priority Data

Nov. 20, 2014 (EP) .................................. 14194147

(51) Int. Cl.
*C07K 16/46* (2006.01)
*C07K 16/28* (2006.01)
*A61K 39/00* (2006.01)

(52) U.S. Cl.
CPC ............ *C07K 16/468* (2013.01); *C07K 16/28* (2013.01); *C07K 16/2803* (2013.01); *C07K 16/2809* (2013.01); *A61K 2039/505* (2013.01); *C07K 16/46* (2013.01); *C07K 2317/14* (2013.01); *C07K 2317/24* (2013.01); *C07K 2317/31* (2013.01); *C07K 2317/33* (2013.01); *C07K 2317/34* (2013.01); *C07K 2317/35* (2013.01); *C07K 2317/41* (2013.01); *C07K 2317/515* (2013.01); *C07K 2317/52* (2013.01); *C07K 2317/526* (2013.01); *C07K 2317/55* (2013.01); *C07K 2317/56* (2013.01); *C07K 2317/64* (2013.01); *C07K 2317/66* (2013.01); *C07K 2317/71* (2013.01); *C07K 2317/73* (2013.01); *C07K 2317/732* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 5,547,668 A | 8/1996 | Kranz et al. |
| 5,571,894 A | 11/1996 | Wels et al. |
| 5,587,458 A | 12/1996 | King et al. |
| 5,591,828 A | 1/1997 | Bosslet et al. |
| 5,731,168 A | 3/1998 | Carter et al. |
| 5,821,337 A | 10/1998 | Carter et al. |
| 5,869,046 A | 2/1999 | Presta et al. |
| 6,248,516 B1 | 6/2001 | Winter et al. |
| 6,737,056 B1 | 5/2004 | Presta |
| 6,809,185 B1 | 10/2004 | Schoonjans et al. |
| 7,332,581 B2 | 2/2008 | Presta |
| 7,608,413 B1 | 10/2009 | Joseloff et al. |
| 7,695,936 B2 | 4/2010 | Carter et al. |
| 8,227,577 B2 | 7/2012 | Klein et al. |
| 8,242,247 B2 | 8/2012 | Klein et al. |
| 8,703,132 B2 | 4/2014 | Imhof-Jung et al. |
| 8,709,421 B2 | 4/2014 | Heiss et al. |
| 8,796,424 B2 | 8/2014 | Croasdale et al. |
| 8,834,877 B2 | 9/2014 | O'Shannessy |
| 8,969,526 B2 | 3/2015 | Baehner et al. |
| 9,068,008 B2 | 6/2015 | Mossner et al. |
| 9,266,938 B2 | 2/2016 | Ast et al. |
| 9,266,967 B2 | 2/2016 | Klein et al. |

(Continued)

FOREIGN PATENT DOCUMENTS

| CN | 103748114 A | 4/2014 |
| EA | 201791121 A1 | 4/2018 |

(Continued)

OTHER PUBLICATIONS

Atwell et al., "Stable heterodimers from remodeling the domain interface of a homodimer using a phage display library," J Mol Biol. 270(1):26-35 (1997).
Booy et al., "Monoclonal and bispecific antibodies as novel therapeutics," Arch Immunol Ther Exp (Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. April 17-21, Washington, DC. 70(8 Suppl) Abstract 5621 (2010).
Carreno et al., "Cross-species reactivity of the anti-idiotype anti-OKT3 cascade between mice and humans," Hum Immunol. 33(4):249-58 (1992).
Carreno et al., "First step toward the murine idiotypic network generated by OKT3," Human Immunology. 32:12:8.4 (1991) (Abstract only) (1 page).

(Continued)

*Primary Examiner* — Meera Natarajan
(74) *Attorney, Agent, or Firm* — Clark & Elbing LLP; Karen L. Elbing

(57) ABSTRACT

The present invention generally relates to novel bispecific antigen binding molecules for T cell activation and redirection to specific target 511cells. In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

20 Claims, 64 Drawing Sheets

Specification includes a Sequence Listing.

(56) References Cited

U.S. PATENT DOCUMENTS

| | | | |
|---|---|---|---|
| 9,382,323 | B2 | 7/2016 | Brinkmann et al. |
| 9,447,159 | B2 | 9/2016 | Ast et al. |
| 9,526,797 | B2 | 12/2016 | Gerdes et al. |
| 10,017,578 | B2 * | 7/2018 | Ab .................. G01N 33/57492 |
| 2007/0111281 | A1 | 5/2007 | Sondermann et al. |
| 2008/0241152 | A1 | 10/2008 | Alitalo et al. |
| 2009/0252683 | A1 | 10/2009 | Kischel et al. |
| 2010/0015133 | A1 | 1/2010 | Igawa et al. |
| 2010/0150918 | A1 | 6/2010 | Kufer et al. |
| 2010/0310571 | A1 | 12/2010 | Cheung |
| 2010/0316645 | A1 | 12/2010 | Imhof-Jung et al. |
| 2011/0293613 | A1 | 12/2011 | Brinkmann et al. |
| 2012/0164137 | A1 | 6/2012 | Sass et al. |
| 2012/0189620 | A1 | 7/2012 | Oyesiku |
| 2012/0225071 | A1 | 9/2012 | Klein et al. |
| 2012/0276125 | A1 | 11/2012 | Ast et al. |
| 2013/0022601 | A1 | 1/2013 | Brinkmann et al. |
| 2013/0058936 | A1 | 3/2013 | Bruenker et al. |
| 2013/0058937 | A1 | 3/2013 | Auer et al. |
| 2013/0060011 | A1 | 3/2013 | Bruenker et al. |
| 2013/0078249 | A1 | 3/2013 | Ast et al. |
| 2013/0171095 | A1 | 7/2013 | Bernett et al. |
| 2013/0266579 | A1 | 10/2013 | Wei et al. |
| 2014/0088295 | A1 | 3/2014 | Smith et al. |
| 2014/0099254 | A1 | 4/2014 | Chang et al. |
| 2014/0112914 | A1 | 4/2014 | Nezu et al. |
| 2014/0120096 | A1 | 5/2014 | Bakker et al. |
| 2014/0154254 | A1 | 6/2014 | Kannan et al. |
| 2014/0205610 | A1 | 7/2014 | Ando et al. |
| 2014/0242079 | A1 | 8/2014 | Bacac et al. |
| 2014/0242080 | A1 | 8/2014 | Jaeger et al. |
| 2014/0288275 | A1 | 9/2014 | Moore et al. |
| 2014/0294823 | A1 | 10/2014 | Moore et al. |
| 2014/0294833 | A1 | 10/2014 | Desjarlais et al. |
| 2014/0302064 | A1 | 10/2014 | Moore |
| 2014/0308285 | A1 | 10/2014 | Yan et al. |
| 2014/0322217 | A1 | 10/2014 | Moore et al. |
| 2014/0363426 | A1 | 12/2014 | Moore et al. |
| 2014/0370013 | A1 | 12/2014 | Desjarlais et al. |
| 2014/0377270 | A1 | 12/2014 | Moore et al. |
| 2015/0079088 | A1 | 3/2015 | Lowman et al. |
| 2015/0094451 | A1 | 4/2015 | Fischer et al. |
| 2015/0166661 | A1 | 6/2015 | Chen et al. |
| 2015/0218274 | A1 | 8/2015 | Sabatos-Peyton et al. |
| 2015/0274845 | A1 | 10/2015 | Bruenker et al. |
| 2015/0315296 | A1 | 11/2015 | Schaefer et al. |
| 2015/0343088 | A1 | 12/2015 | Matsuyama et al. |
| 2015/0368351 | A1 | 12/2015 | Vu et al. |
| 2015/0376287 | A1 | 12/2015 | Vu et al. |
| 2016/0075785 | A1 | 3/2016 | Ast et al. |
| 2016/0130347 | A1 | 5/2016 | Bruenker et al. |
| 2016/0145354 | A1 | 5/2016 | Bacac et al. |
| 2016/0175397 | A1 | 6/2016 | Umana et al. |
| 2016/0208017 | A1 | 7/2016 | Ast et al. |
| 2016/0208019 | A1 | 7/2016 | Bacac et al. |
| 2016/0263240 | A1 | 9/2016 | Ast et al. |
| 2016/0297881 | A1 | 10/2016 | Vu et al. |
| 2016/0368985 | A1 | 12/2016 | Hotzel et al. |
| 2017/0008971 | A1 | 1/2017 | Dennis et al. |
| 2017/0096485 | A1 | 4/2017 | Bacac et al. |
| 2017/0096495 | A1 | 4/2017 | Bacac et al. |
| 2017/0114146 | A1 | 4/2017 | Klein et al. |
| 2017/0174786 | A1 | 6/2017 | Bacac et al. |
| 2017/0190783 | A1 | 7/2017 | Bacac et al. |
| 2017/0209573 | A1 | 7/2017 | Bacac et al. |
| 2017/0253670 | A1 | 9/2017 | Klein et al. |
| 2017/0267783 | A1 | 9/2017 | Nezu et al. |
| 2017/0306018 | A1 | 10/2017 | Vu et al. |
| 2017/0306036 | A1 | 10/2017 | Vu et al. |
| 2017/0306044 | A1 | 10/2017 | Vu et al. |
| 2017/0327579 | A1 | 11/2017 | Vu et al. |
| 2017/0327580 | A1 | 11/2017 | Vu et al. |

FOREIGN PATENT DOCUMENTS

| | | |
|---|---|---|
| EP | 0404097 B1 | 9/1996 |
| EP | 1870459 A1 | 12/2007 |
| EP | 1870459 A4 | 9/2010 |
| EP | 2578230 A1 | 4/2013 |
| EP | 2647707 A1 | 10/2013 |
| EP | 2647707 A4 | 4/2014 |
| EP | 2982694 A1 | 2/2016 |
| EP | 1870459 B1 | 6/2016 |
| JP | 2012-522523 A | 9/2012 |
| TW | 201439117 A | 10/2014 |
| WO | WO-91/03493 A1 | 3/1991 |
| WO | WO-93/16185 A2 | 8/1993 |
| WO | WO-96/01126 A1 | 1/1996 |
| WO | WO-96/27011 A1 | 9/1996 |
| WO | WO-96/40210 A1 | 12/1996 |
| WO | WO-98/50431 A2 | 11/1998 |
| WO | WO-98/50431 A3 | 1/1999 |
| WO | WO-02/09573 A2 | 2/2002 |
| WO | WO-2004/113388 A2 | 12/2004 |
| WO | WO-2005/044859 A2 | 5/2005 |
| WO | WO-2005/080431 A2 | 9/2005 |
| WO | WO-2006/082515 A2 | 8/2006 |
| WO | WO-2006/099141 A2 | 9/2006 |
| WO | WO-2006/116592 A2 | 11/2006 |
| WO | WO-2006/116592 A3 | 11/2006 |
| WO | WO-2007/024715 A2 | 3/2007 |
| WO | WO-2007/042261 A2 | 4/2007 |
| WO | WO-2007/075270 A2 | 7/2007 |
| WO | WO-2007/110205 A2 | 10/2007 |
| WO | WO-2007/146968 A2 | 12/2007 |
| WO | WO-2007/147901 A1 | 12/2007 |
| WO | WO-2008/031577 A1 | 3/2008 |
| WO | WO-2007/024715 A3 | 10/2008 |
| WO | WO-2008/119566 A2 | 10/2008 |
| WO | WO-2008/119567 A2 | 10/2008 |
| WO | WO-2007/024715 A9 | 4/2009 |
| WO | WO-2009/070642 A1 | 6/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2010/115553 A1 | 10/2010 |
| WO | WO-2010/115589 A1 | 10/2010 |
| WO | WO-2010/129304 A2 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2010/129304 A3 | 2/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/106528 A1 | 9/2011 |
| WO | WO-2011/143545 A1 | 11/2011 |
| WO | WO-2012/054654 A2 | 4/2012 |
| WO | WO-2012/058768 A1 | 5/2012 |
| WO | WO-2012/061759 A2 | 5/2012 |
| WO | WO-2012/058768 A8 | 6/2012 |
| WO | WO-2012/073985 A1 | 6/2012 |
| WO | WO-2012/130831 A1 | 10/2012 |
| WO | WO-2012/135675 A2 | 10/2012 |
| WO | WO-2012/158818 A2 | 11/2012 |
| WO | WO-2012/162067 A2 | 11/2012 |
| WO | WO-2013/012722 A1 | 1/2013 |
| WO | WO-2013/026831 A1 | 2/2013 |
| WO | WO-2013/026833 A1 | 2/2013 |
| WO | WO-2013/026837 A1 | 2/2013 |
| WO | WO-2013/072406 A1 | 5/2013 |
| WO | WO-2013/096291 A2 | 6/2013 |
| WO | WO-2013/157953 A1 | 10/2013 |
| WO | WO-2013/157954 A1 | 10/2013 |
| WO | WO-2013/172951 A1 | 11/2013 |
| WO | WO-2014/004549 A2 | 1/2014 |
| WO | WO-2014/022540 A1 | 2/2014 |
| WO | WO-2014/028560 A2 | 2/2014 |
| WO | WO-2014/047231 A1 | 3/2014 |
| WO | WO-2014/051433 A1 | 4/2014 |

(56) References Cited

FOREIGN PATENT DOCUMENTS

| | | |
|---|---|---|
| WO | WO-2014/028560 A3 | 5/2014 |
| WO | WO-2014/081955 A1 | 5/2014 |
| WO | WO-2014/087863 A1 | 6/2014 |
| WO | WO-2014/104270 A1 | 7/2014 |
| WO | WO-2014/122143 A1 | 8/2014 |
| WO | WO-2014/122144 A1 | 8/2014 |
| WO | WO-2014/122251 A2 | 8/2014 |
| WO | WO-2014/131694 A1 | 9/2014 |
| WO | WO-2014/131712 A1 | 9/2014 |
| WO | WO-2014/141152 A2 | 9/2014 |
| WO | WO-2014/144357 A1 | 9/2014 |
| WO | WO-2014/144722 A2 | 9/2014 |
| WO | WO-2014/151910 A1 | 9/2014 |
| WO | WO-2014/153002 A1 | 9/2014 |
| WO | WO-2014/122251 A3 | 10/2014 |
| WO | WO-2014/161845 A1 | 10/2014 |
| WO | WO-2014/167022 A1 | 10/2014 |
| WO | WO-2014/141152 A3 | 12/2014 |
| WO | WO-2014/191113 A1 | 12/2014 |
| WO | WO-2015/001085 A1 | 1/2015 |
| WO | WO-2015/013671 A1 | 1/2015 |
| WO | WO-2014/191113 A8 | 2/2015 |
| WO | WO-2015/018085 A1 | 2/2015 |
| WO | WO-2015/048272 A1 | 4/2015 |
| WO | WO-2015/150447 A1 | 10/2015 |
| WO | WO-2016/014974 A2 | 1/2016 |
| WO | WO-2016/020065 A1 | 2/2016 |
| WO | WO-2016/020332 A1 | 2/2016 |
| WO | WO-2016/036678 A1 | 3/2016 |
| WO | WO-2016/055592 A1 | 4/2016 |
| WO | WO-2016/055593 A1 | 4/2016 |
| WO | WO-2016/077505 A2 | 5/2016 |
| WO | WO-2016/079076 A1 | 5/2016 |
| WO | WO-2016/079081 A1 | 5/2016 |
| WO | WO-2016/079177 A1 | 5/2016 |
| WO | WO-2016/087531 A1 | 6/2016 |
| WO | WO-2016/146894 A1 | 9/2016 |
| WO | WO-2016/179003 A1 | 11/2016 |
| WO | WO-2017/021450 A1 | 2/2017 |

OTHER PUBLICATIONS

Carter, "Bispecific human IgG by design," J Immunol Methods. 248(1-2):7-15 (2001).
Casset et al., "A peptide mimetic of an anti-CD4 monoclonal antibody by rational design," Biochem Biophys Res Commun. 307(1):198-205 (2003).
Chan et al., "Variable region domain exchange in human IgGs promotes antibody complex formation with accompanying structural changes and altered effector functions," Mol Immunol. 41(5):527-38 (2004).
Chen et al., "Selection and analysis of an optimized anti-VEGF antibody: crystal structure of an affinity-matured Fab in complex with antigen," J Mol Biol. 293(4):865-81 (1999).
Cui et al., "Chemically programmed bispecific antibodies that recruit and activate T cells," J Biol Chem. 287(34):28206-14 (10 Pages) (2012).
De Pascalis et al., "Grafting of 'abbreviated' complementarity-determining regions containing specificity-determining residues essential for ligand contact to engineer a less immunogenic humanized monoclonal antibody," J Immunol. 169(6):3076-84 (2002).
Diamond et al., "Somatic mutation of the T15 heavy chain gives rise to an antibody with autoantibody specificity," Proc Natl Acad Sci U S A. 81(18):5841-5844 (1984).
Ebel et al., "Preclinical evaluation of MORAb-003, a humanized monoclonal antibody antagonizing folate receptor-alpha," Cancer Immun. 7:6 (2007).
Edelman et al., "The covalent structure of an entire gammaG immunoglobulin molecule," Proc Natl Acad Sci U S A. 63(1):78-85 (1969).
Hasemann et al., "Mutational analysis of arsonate binding by a CRIA+ antibody. VH and VL junctional diversity are essential for binding activity," J Biol Chem. 266(12):7626-32 (1991) (7 pages).

Holliger et al., "Diabodies': small bivalent and bispecific antibody fragments," Proc Natl Acad Sci USA. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hudson et al., "Engineered antibodies," Nat Med. 9(1):129-34 (2003).
Kang et al., "Antibody redesign by chain shuffling from random combinatorial immunoglobulin libraries," Proc Natl Acad Sci U.S. A. 88(24):11120-3 (1991).
Katayose et al., "MUC1-specific targeting immunotherapy with bispecific antibodies: inhibition of xenografted human bile duct carcinoma growth," Cancer Res. 56(18):4205-12 (1996) (9 pages).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Lamminmäki et al., "Crystal Structure of a Recombinant Anti-Estradiol Fab Fragment in Complex With 17beta -Estradiol," J Biol Chem. 276(39):36687-94 (2001).
Luiten et al., "Chimeric bispecific OC/TR monoclonal antibody mediates lysis of tumor cells expressing the folate-binding protein (MOv18) and displays decreased immunogenicity in patients," J Immunother. 20(6):496-504 (1997).
MacCallum et al., "Antibody-antigen interactions: contact analysis and binding site topography," J Mol Biol. 262(5):732-45 (1996) (14 pages).
Merchant et al., "An efficient route to human bispecific IgG," Nat Biotechnol. 16(7):677-81 (1998).
Mezzanzanica et al., "Human ovarian carcinoma lysis by cytotoxic T cells targeted by bispecific monoclonal antibodies: analysis of the antibody components," Int J Cancer. 41(4):609-15 (1988).
Miller et al., "Design, construction, and in vitro analyses of multivalent antibodies," J Immunol. 170(9):4854-61 (2003).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
Ohno et al., "Antigen-binding specificities of antibodies are primarily determined by seven residues of VH," Proc Natl Acad Sci USA. 82(9):2945-9 (1985).
Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).
Padlan et al., "Structure of an antibody-antigen complex: crystal structure of the HyHEL-10 Fab-lysozyme complex," Proc Natl Acad Sci USA. 86(15):5938-5942 (1989).
Pessano et al., "The T3/T cell receptor complex: antigenic distinction between the two 20-kd T3 (T3-delta and T3-epsilon) subunits," EMBO J. 4(2):337-44 (1985).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Riemer et al., "Matching of trastuzumab (Herceptin®) epitope mimics onto the surface of Her-2_neu—a new method of epitope definition—ScienceDirect," Mol Immunol. 42(9):1121-1124 (2005).

(56) References Cited

OTHER PUBLICATIONS

Rudikoff et al., "Single amino acid substitution altering antigen-binding specificity," Proc Natl Acad Sci U S A. 79(6):1979-83 (1982).
Schaefer et al., "Immunoglobulin domain crossover as a generic approach for the production of bispecific IgG antibodies," Proc Natl Acad Sci U S A. 108(27):11187-92 (2011).
Seimetz et al., "Development and approval of the trifunctional antibody catumaxomab (anti- EpCAM x anti-CD3) as a targeted cancer immunotherapy," Cancer Treat Rev. 36(6):458-67 (2010).
Stancovski et al., "Mechanistic aspects of the opposing effects of monoclonal antibodies to the ERBB2 receptor on tumor growth," Proc Natl Acad Sci U S A. 88(19):8691-8695 (1991).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Torisu-Itakura et al., "Redirected lysis of human melanoma cells by a MCSP/CD3-bispecific BITE antibody that engages patient-derived T cells," J Immunother. 34(8):597-605 (2011).
Tutt et al., "Trispecific F(ab')$_3$ derivatives that use cooperative signaling via the TCR/CD3 complex and CD2 to activate and redirect resting cytotoxic T cells," J Immunol. 147(1):60-9 (1991).
Vajdos et al., "Comprehensive functional maps of the antigen-binding site of an anti-ErbB2 antibody obtained with shotgun scanning mutagenesis," J Mol Biol. 320(2):415-28 (2002).
Weidle et al., "The intriguing options of multispecific antibody formats for treatment of cancer," Cancer Genomics Proteomics. 10(1):1-18 (2013).
Wolf et al., "BiTEs: bispecific antibody constructs with unique anti-tumor activity," Drug Discov Today. 10(18):1237-44 (2005).
Wu et al., "Humanization of a murine monoclonal antibody by simultaneous optimization of framework and CDR residues," J Mol Biol. 294(1):151-62 (1999).

Zhu et al., "Identification of heavy chain residues in a humanized anti-CD3 antibody important for efficient antigen binding and T cell activation," J Immunol. 155(4):1903-10 (1995).
English Translation of Notice of Reasons for Rejection for Japanese Patent Application No. 2017-527224, issued Oct. 15, 2019 (5 pages).
English Translation of Office Action for Colombian Patent Application No. NC2018/0012438, dated Jun. 26, 2019 (8 pages).
First Office Action for Chinese Patent Application No. 201580073062.8, dated Jul. 3, 2020 (21 pages).
Invitation to Pay Additional Fees for International Patent Application No. PCT/EP2015/076739, mailed Feb. 23, 2016 (7 pages).
Invitation to Respond to Written Opinion for Singaporean Patent Application No. 11201702976T, dated Jun. 22, 2018 (13 pages).
Office Action for Chinese Patent Application No. 201580059475.0, dated Jun. 22, 2020 (15 pages).
Office Action for Chinese Patent Application No. 201580073564.0, dated Jul. 21, 2020 (5 pages).
Office Action for U.S. Appl. No. 16/138,417, dated May 18, 2020 (20 pages).
Search Report and Written Opinion for Brazilian Patent Application No. BR112017007086-3, dated Oct. 4, 2020 (4 pages).
Search Report and Written Opinion for Singaporean Patent Application No. 11201704056X, dated Jul. 6, 2018 (11 pages).
Search Report and Written Opinion for Singaporean Patent Application No. 11201808085, dated Mar. 3, 2020 (10 pages).
Search Report for Chinese Patent Application No. 201580073062.8, dated Jun. 28, 2020 (3 pages).
Search Report from Office Action for Chinese Patent Application No. 201580073564.0, dated Jul. 21, 2020 (1 page).
Second Written Opinion for Singaporean Patent Application No. 11201702976T, dated Apr. 15, 2020 (10 pages).
Almagro et al., "Humanization of antibodies," Front Biosci. 13:1619-33 (2008).
De Genst et al., "Antibody repertoire development in camelids," Dev Comp Immunol. 30(1-2):187-98 (2006).
Yoshinaga et al., "Ig L-chain shuffling for affinity maturation of phage library-derived human anti-human MCP-1 antibody blocking its chemotactic activity," J Biochem. 143(5):593-601 (2008).

\* cited by examiner

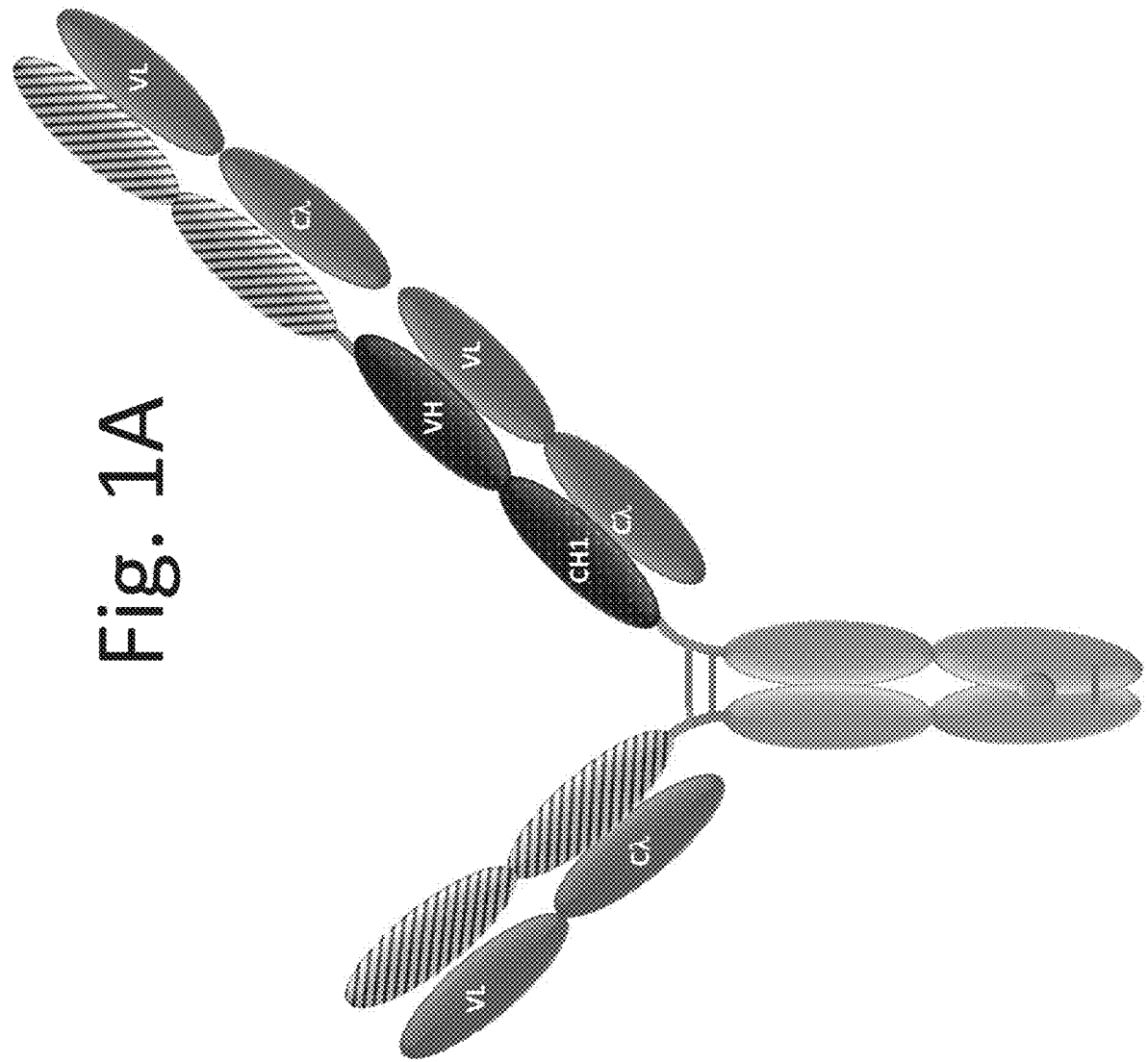

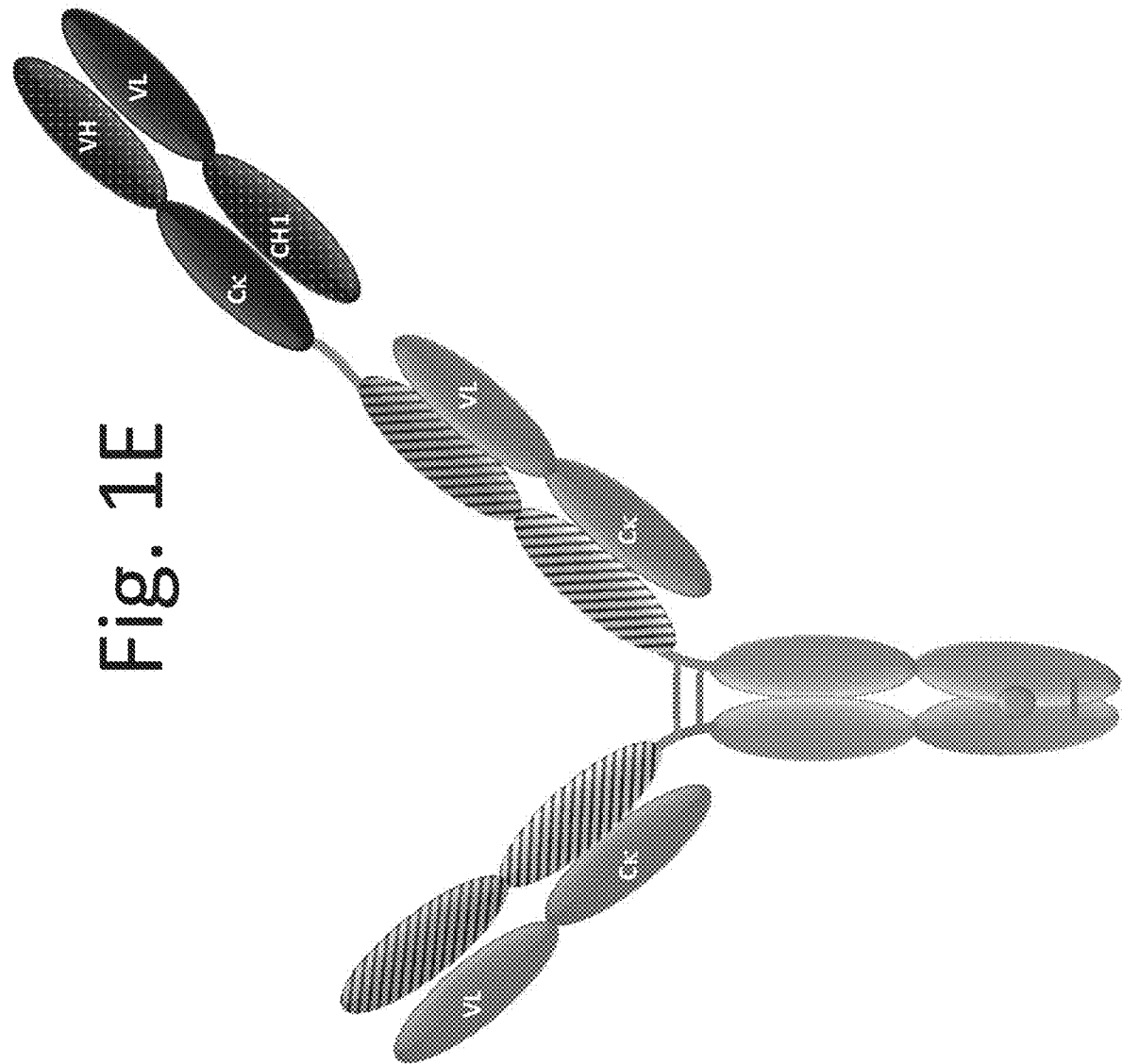

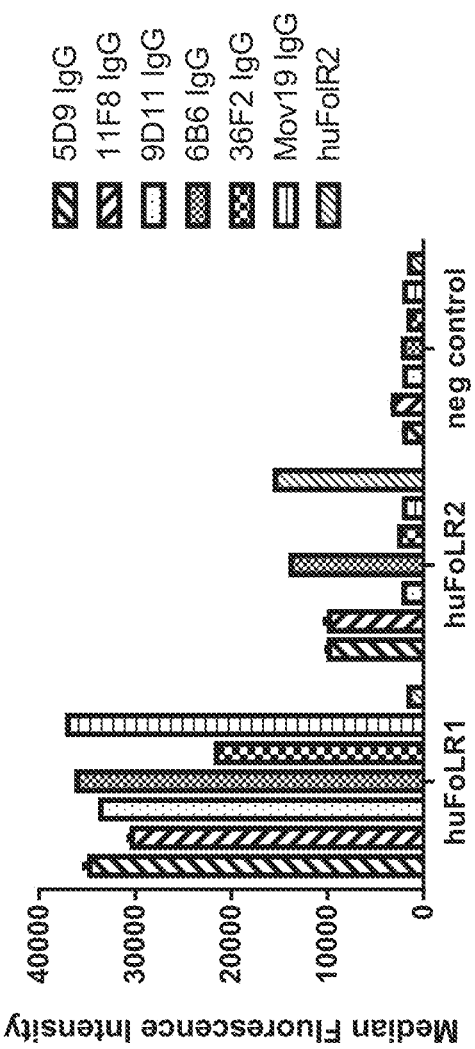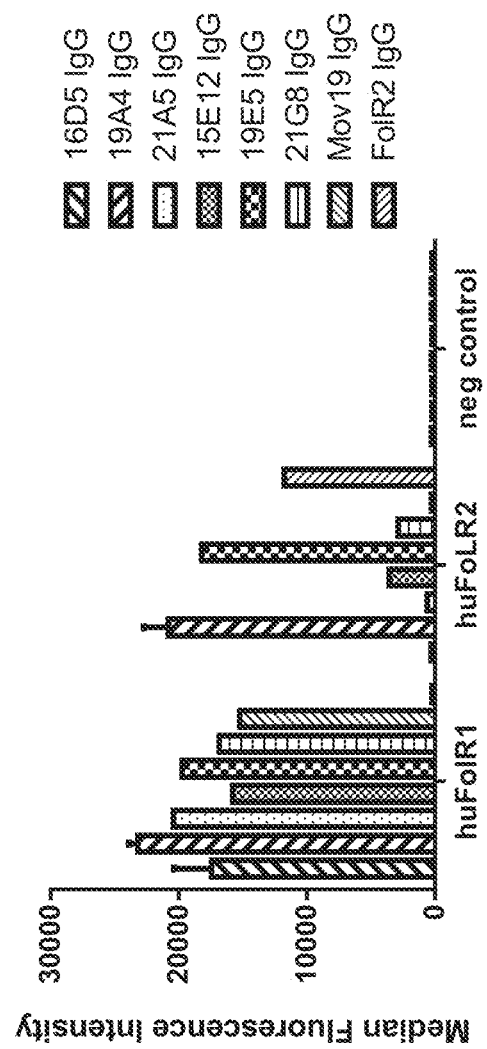
Fig. 3A
Fig. 3B

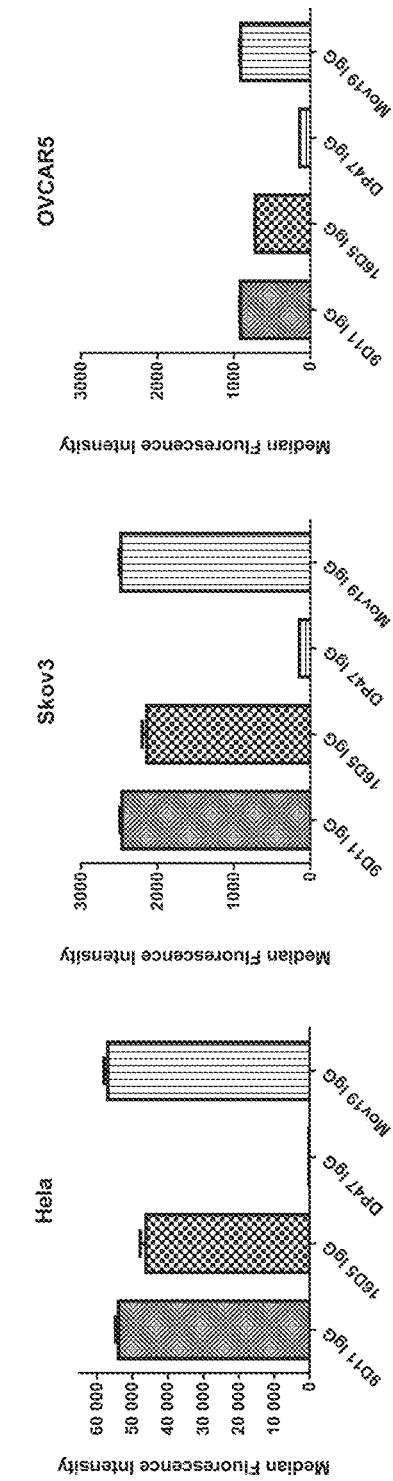

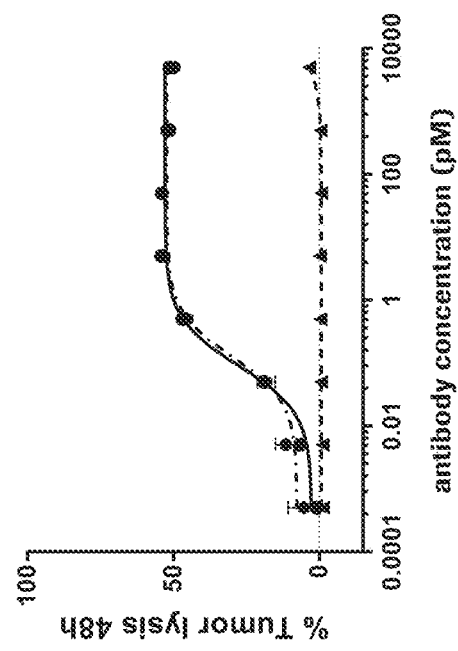
Fig. 7A (HT29)
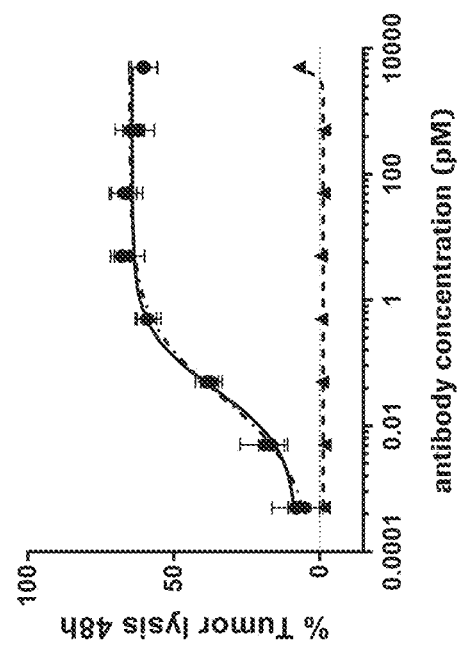
Fig. 7B
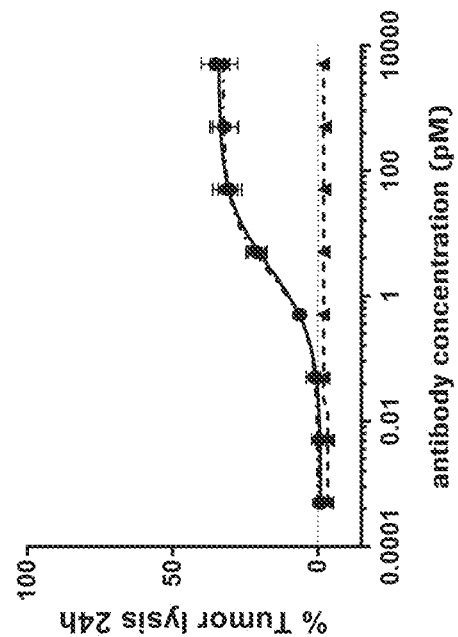
Fig. 7C (SKOV3)
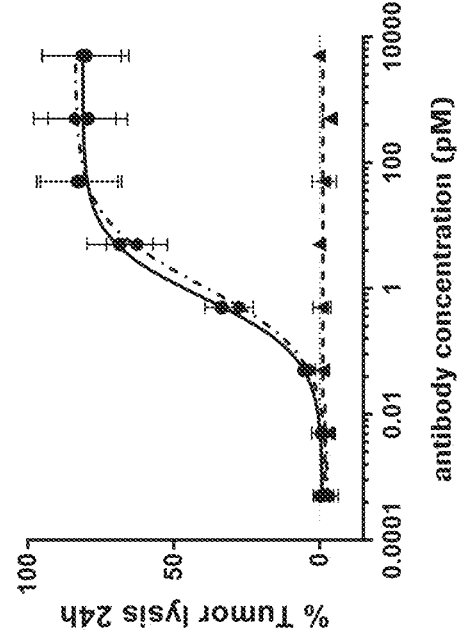
Fig. 7D
─●─ 16D5 FolR1 TCB   ─■─ 9D11 FolR1 TCB   ─▲─ DP47 TCB — 16D5 FolR1 TCB   -●- 9D11 FolR1 TCB   -▲- DP47 TCB

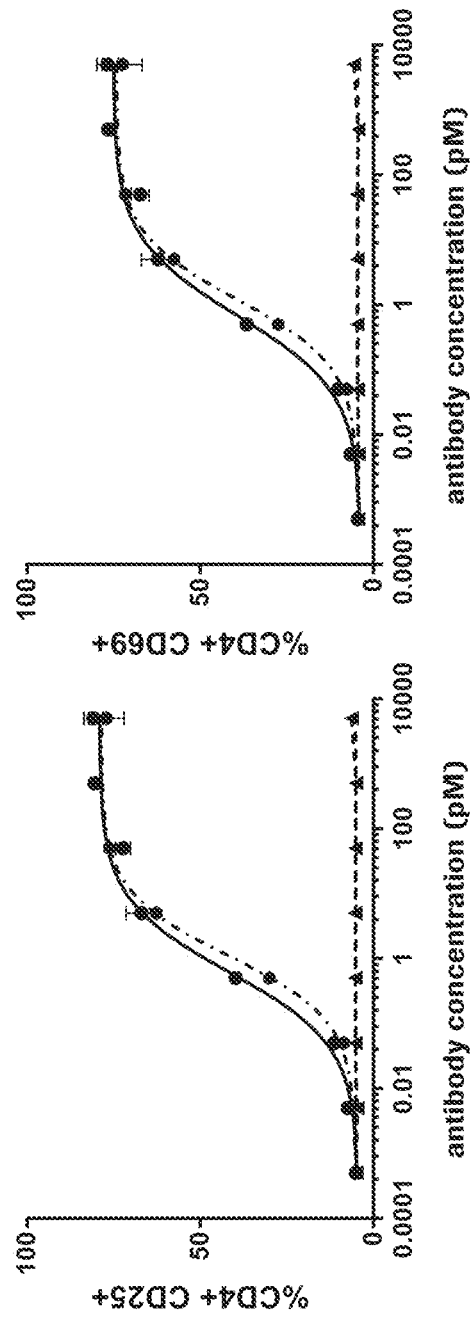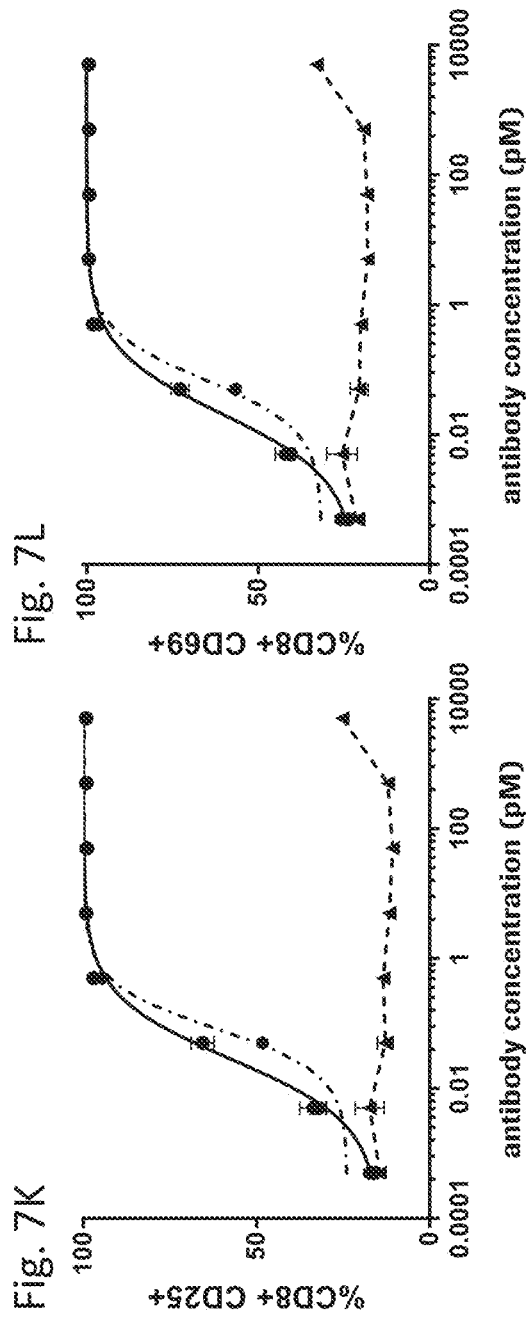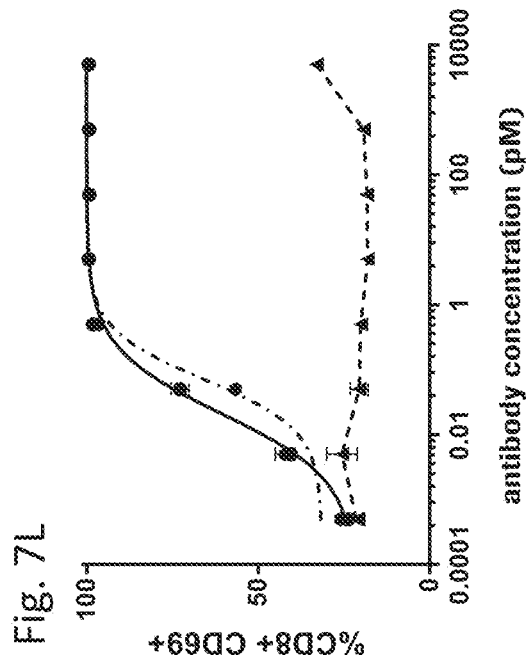

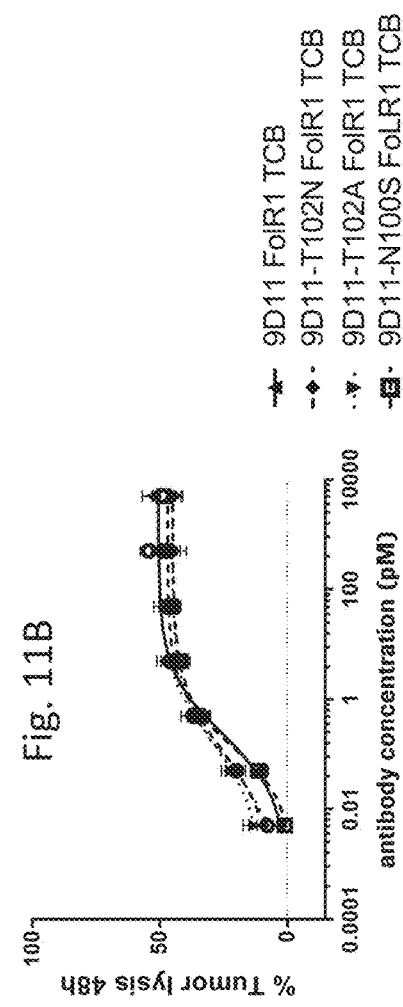
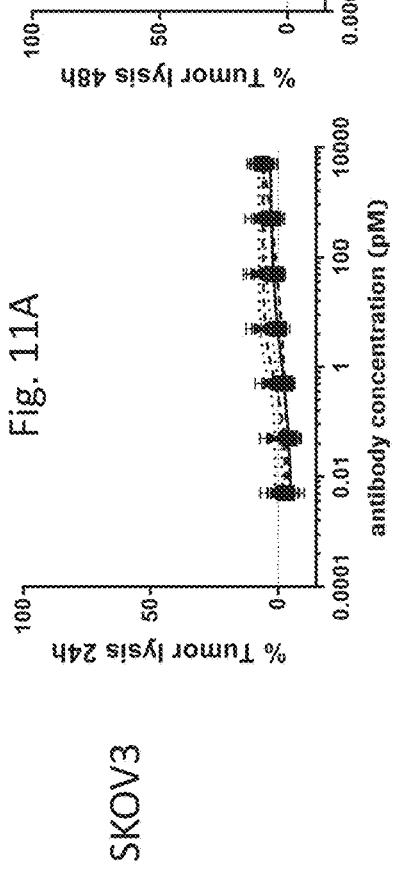
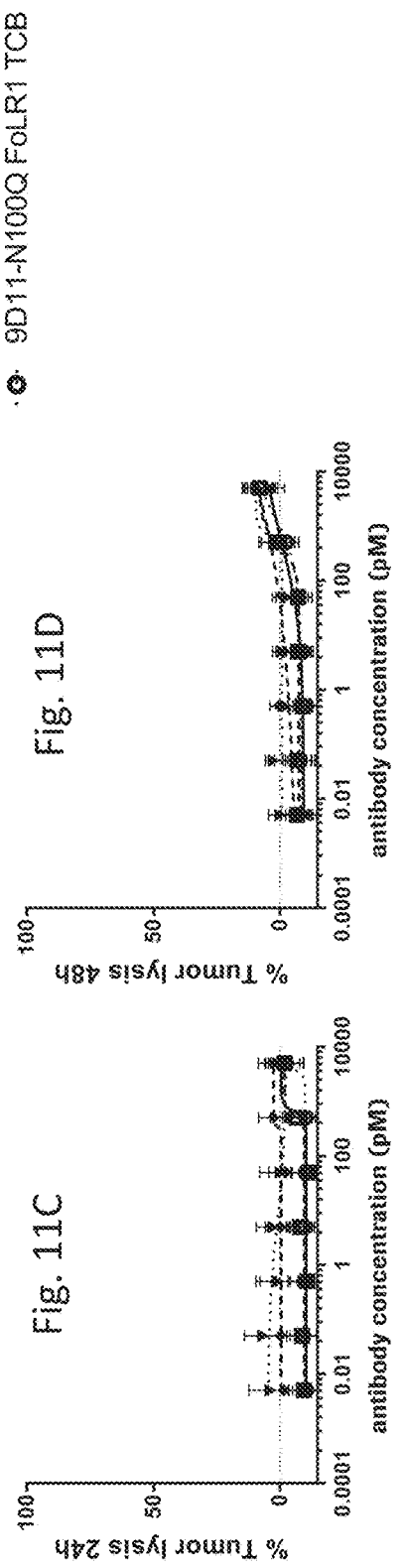

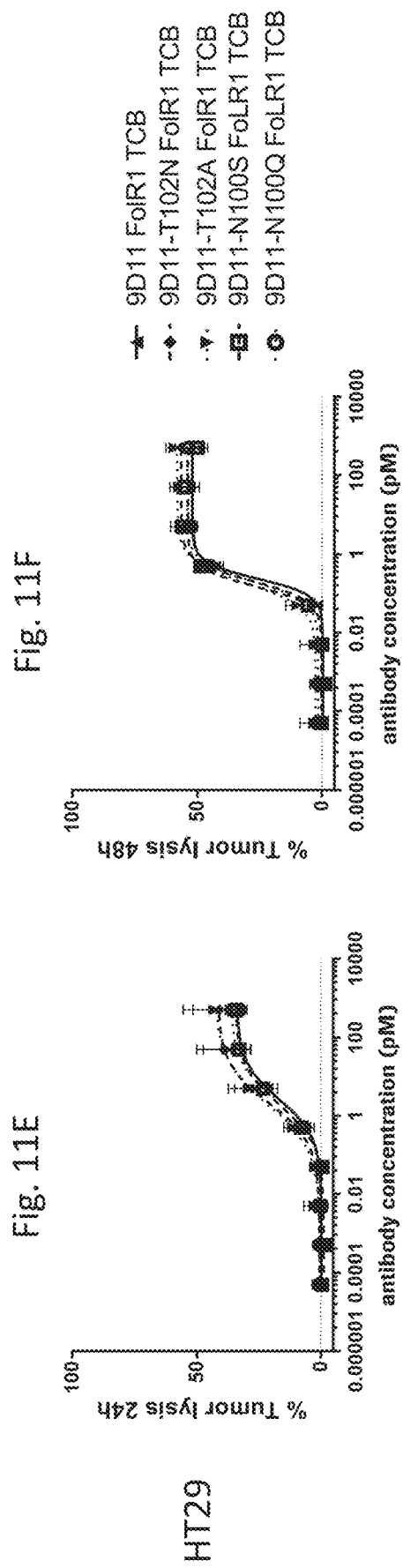

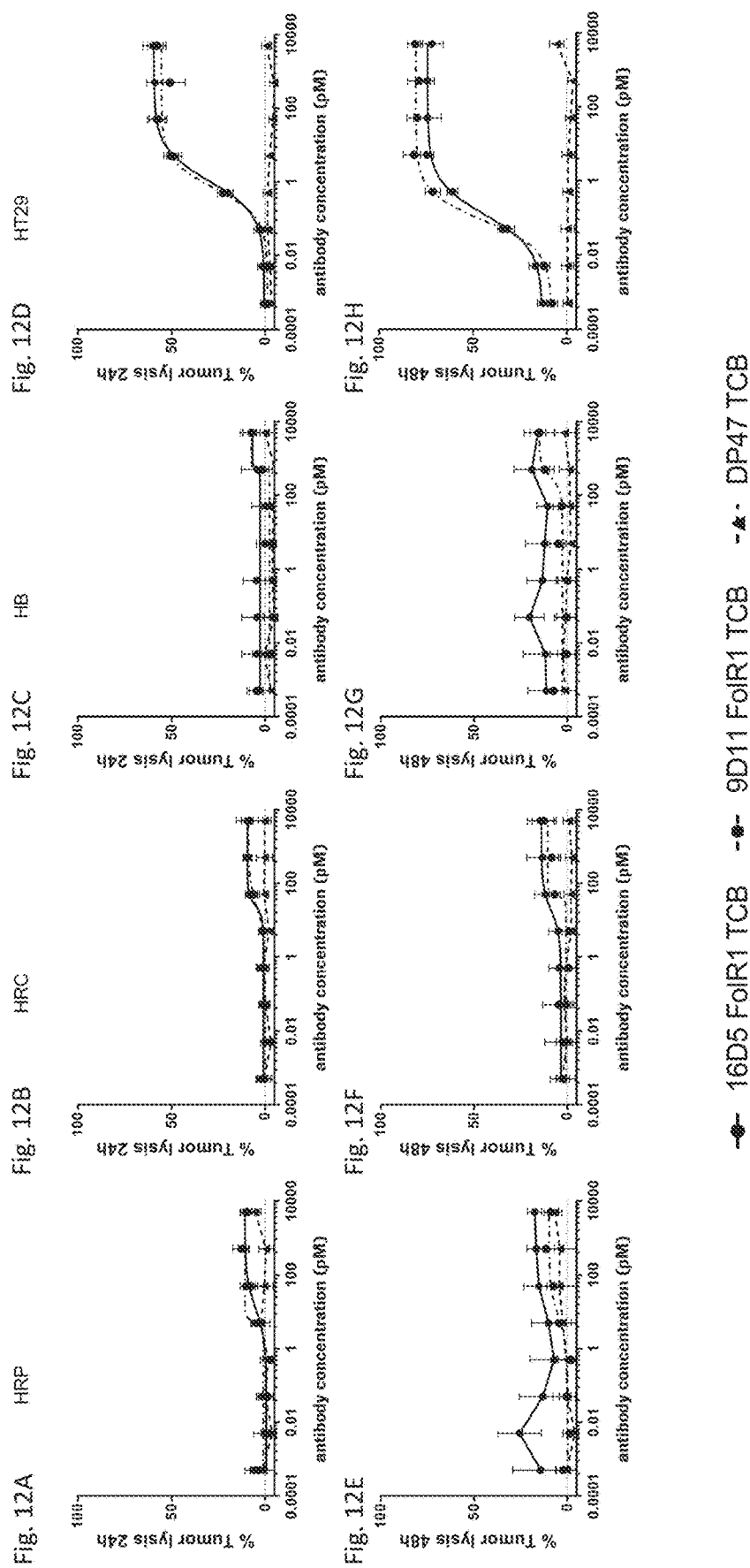

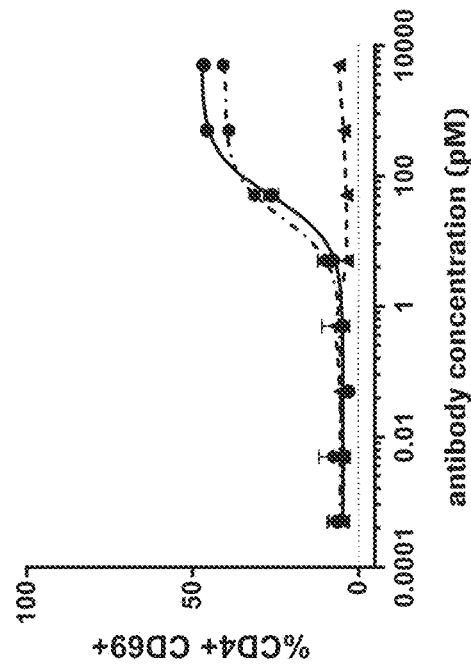
Fig. 12Q
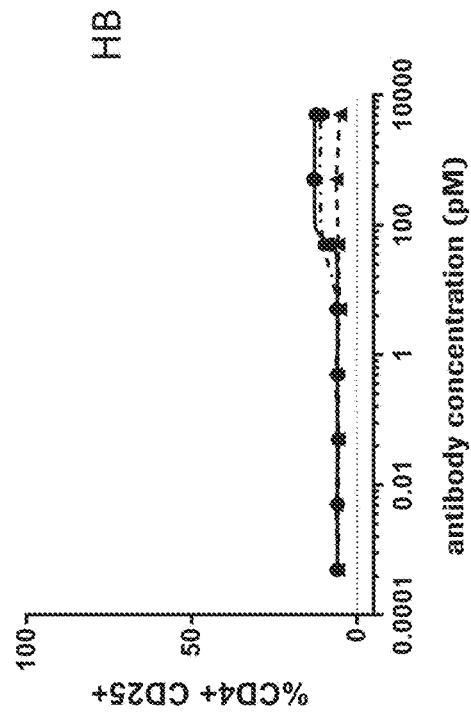
Fig. 12S
HB
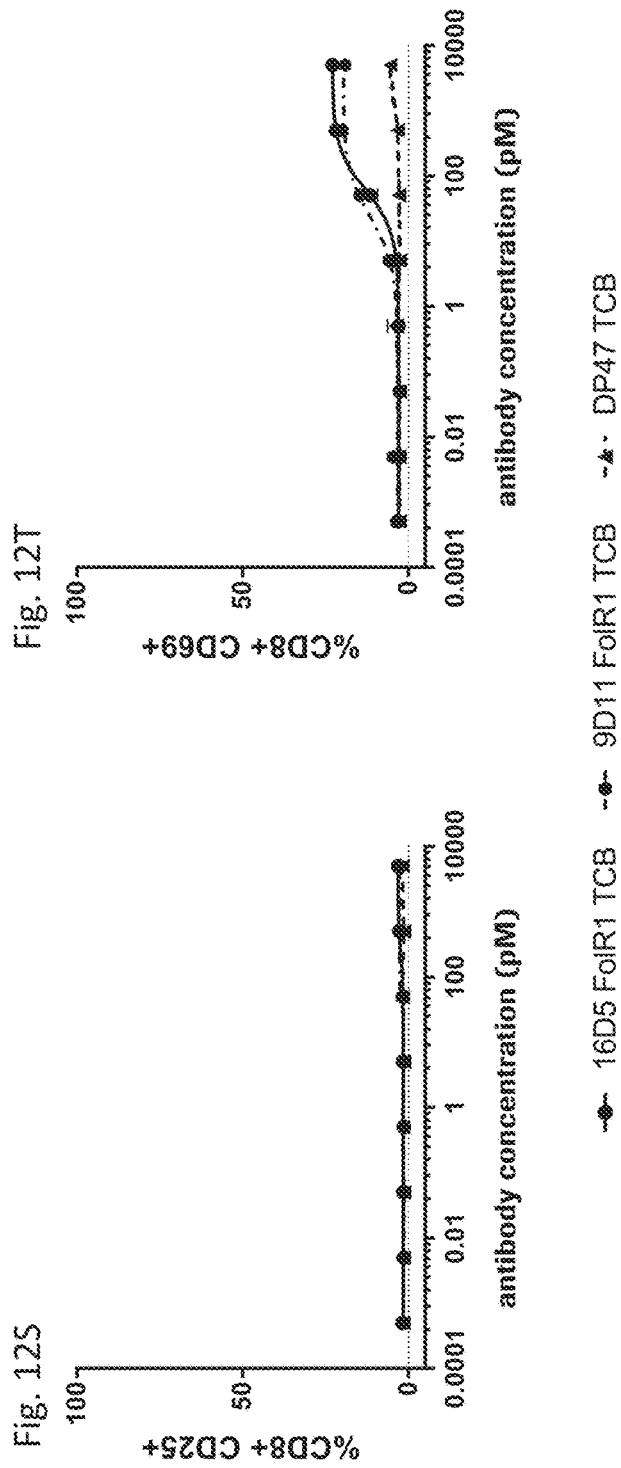
Fig. 12R
Fig. 12T

HT29

— 16D5 FolR1 TCB   — 9D11 FolR1 TCB   — DP47 TCB

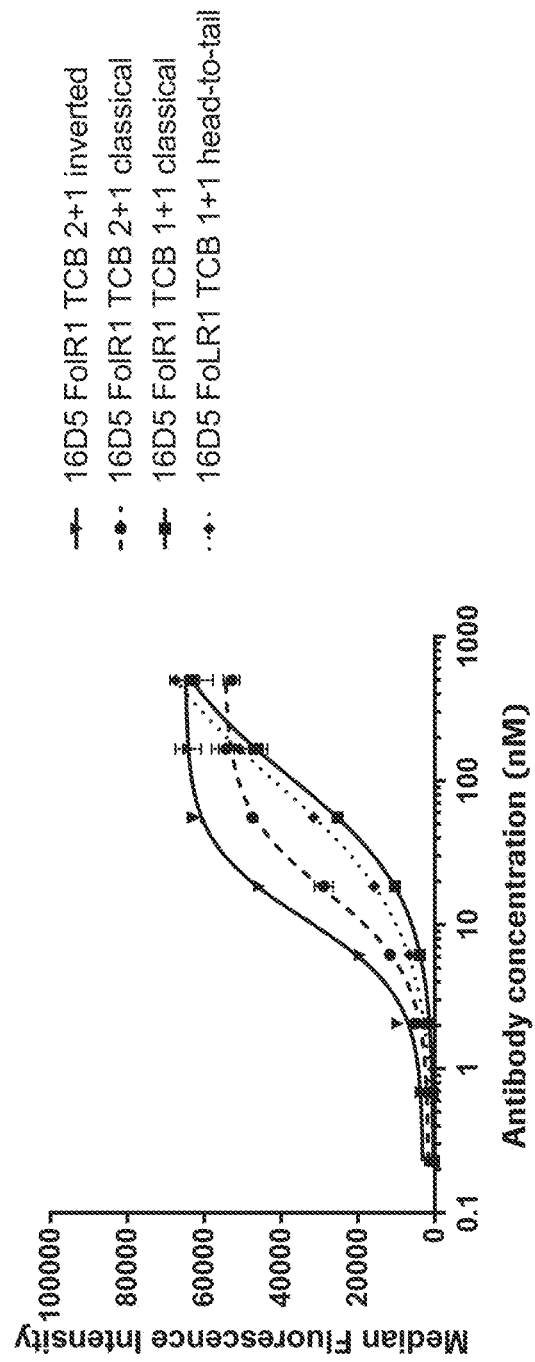

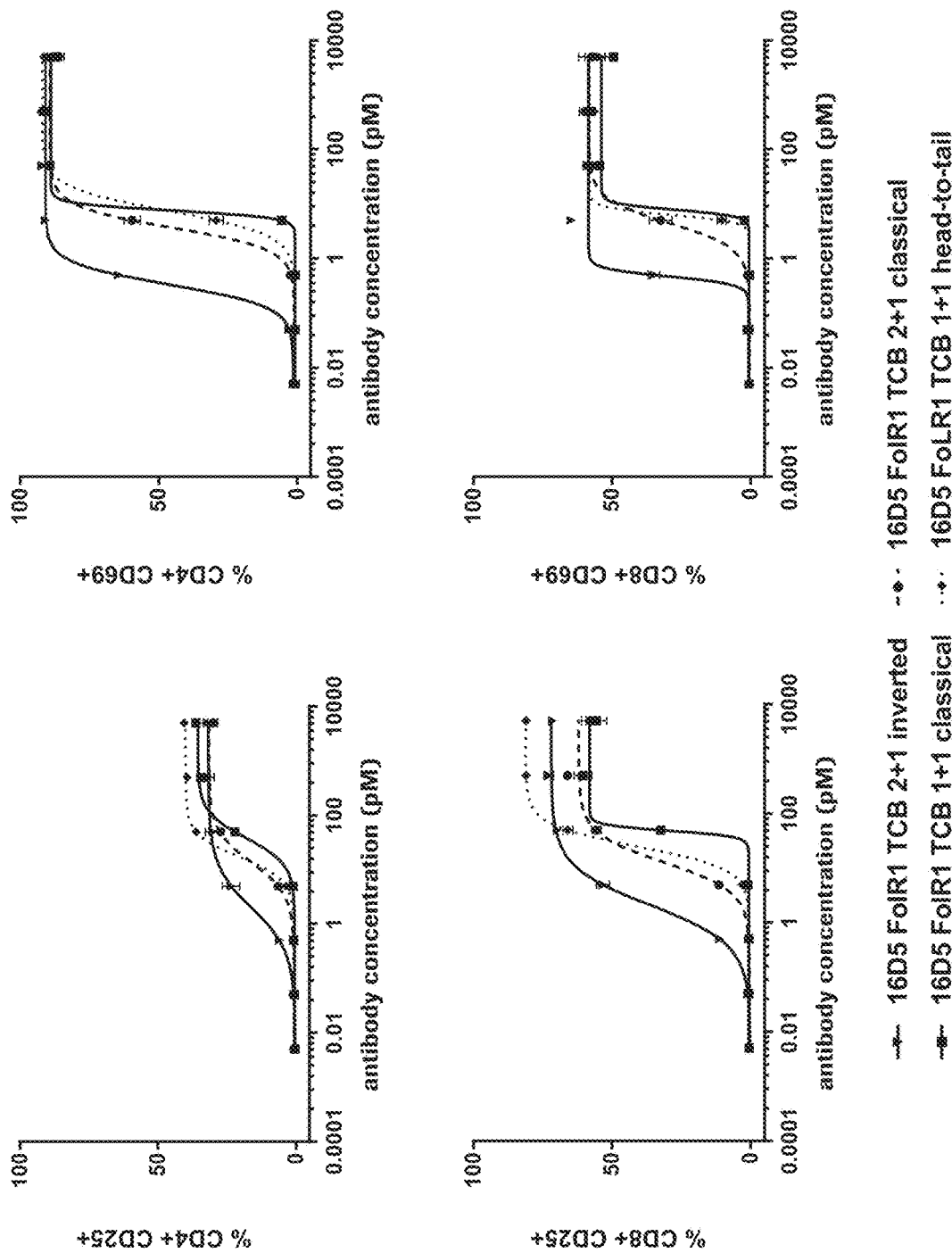

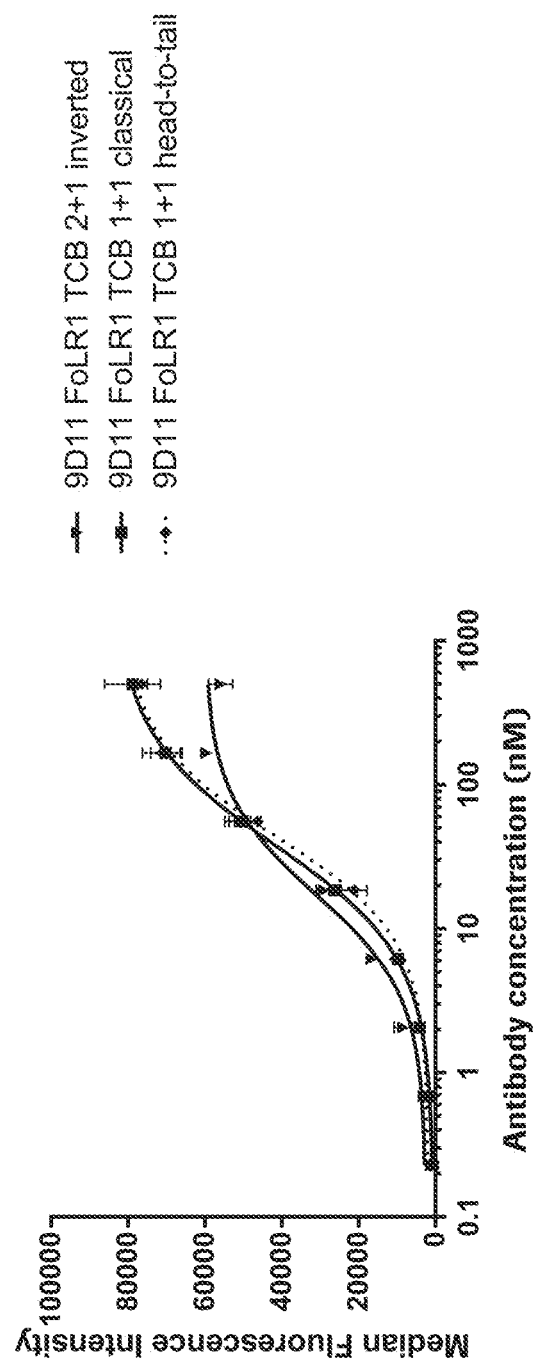

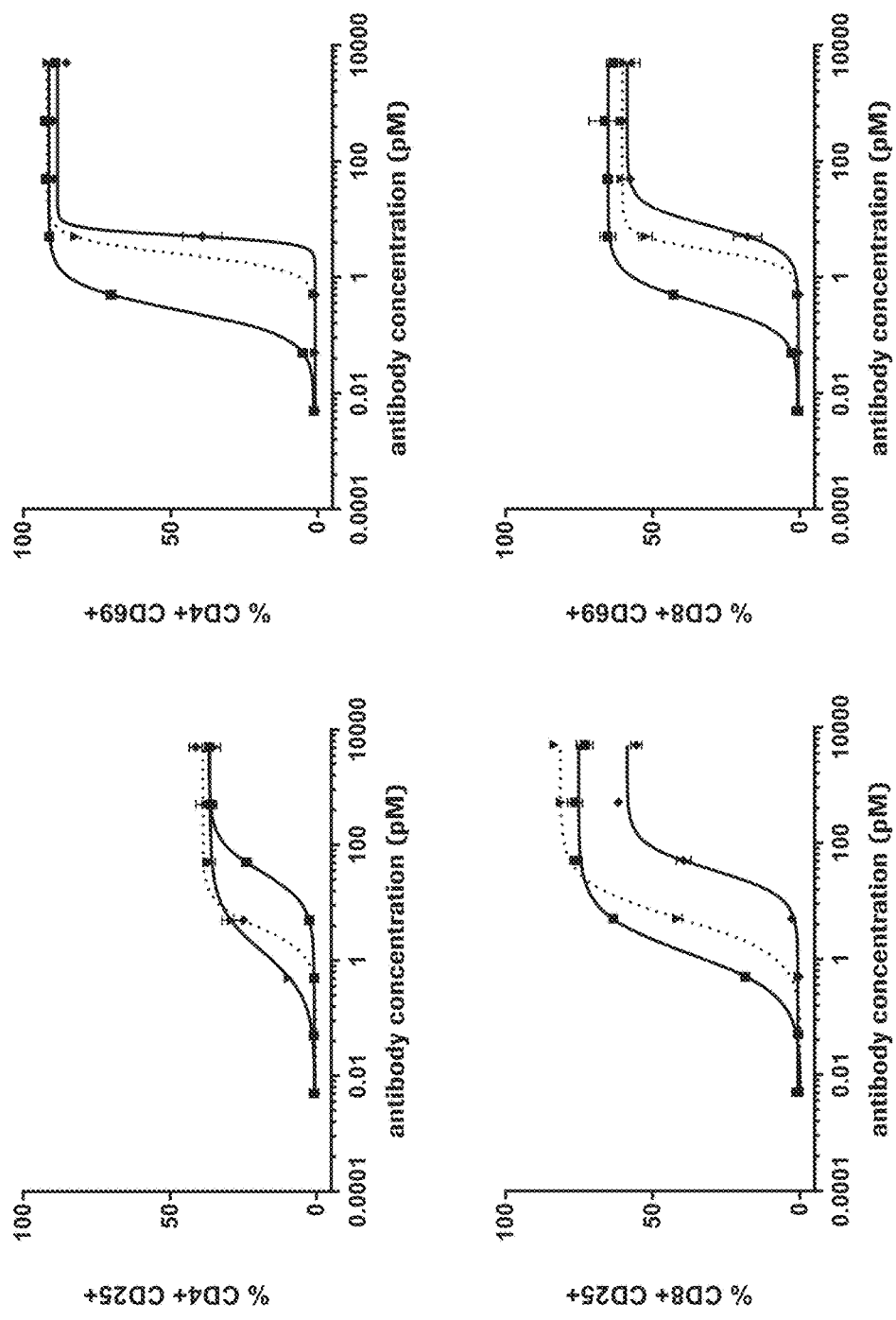

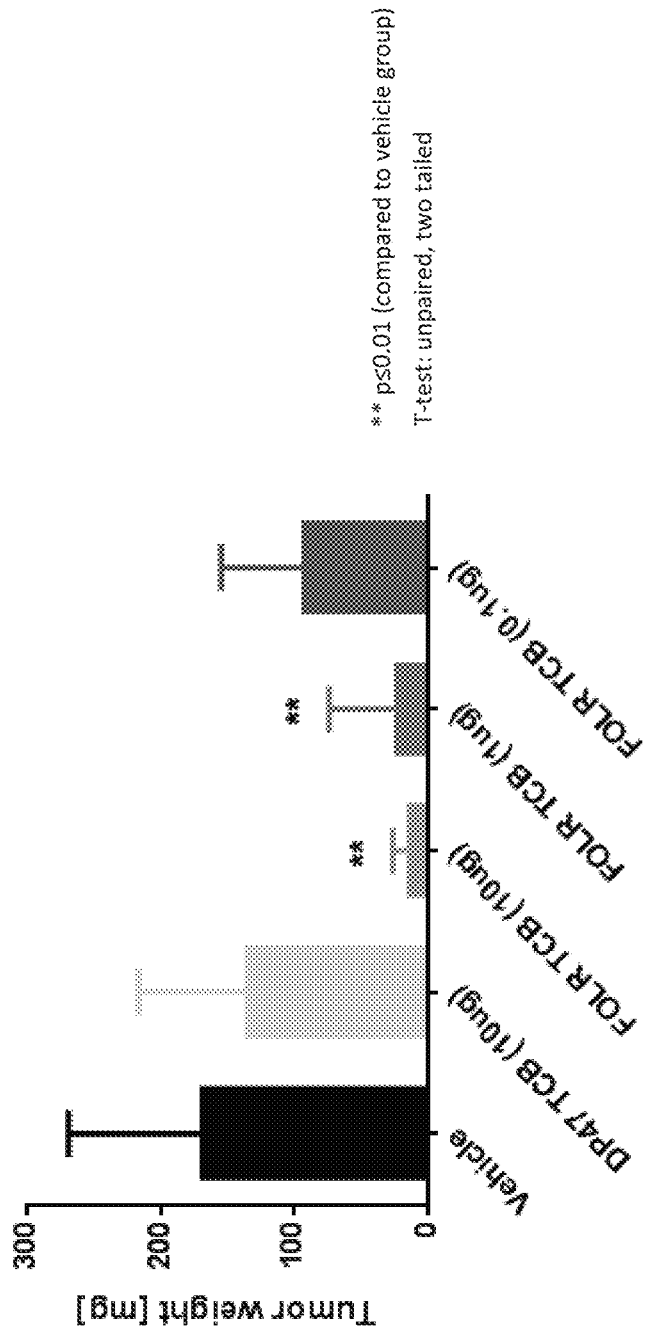

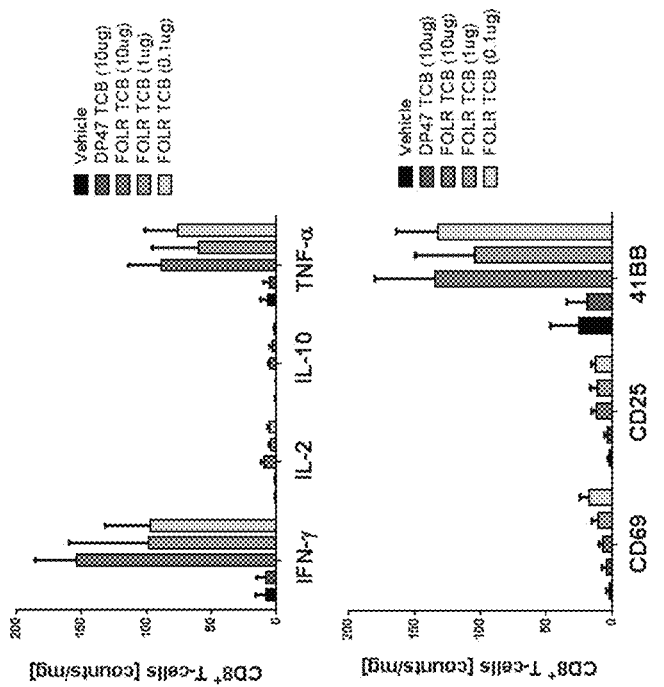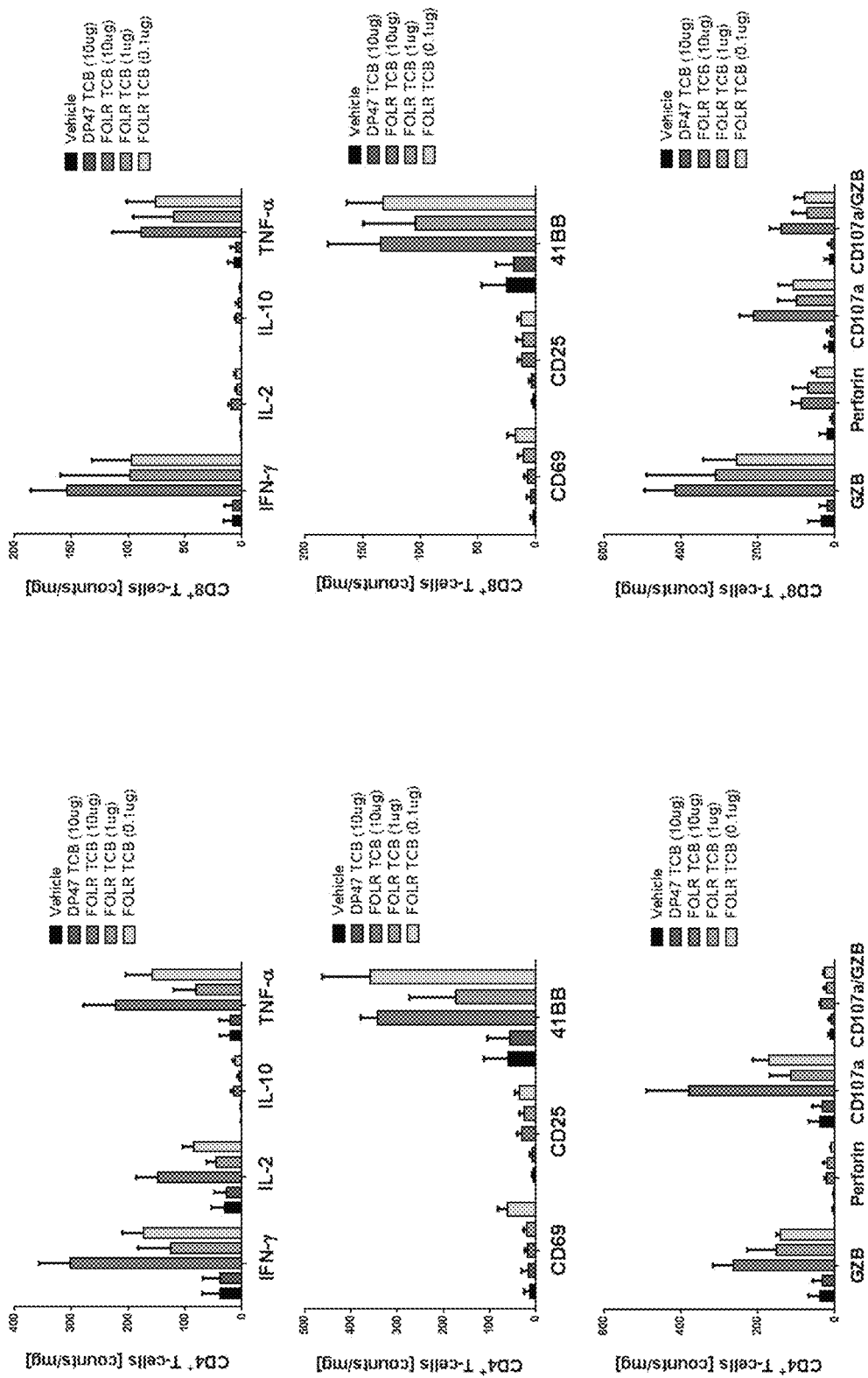

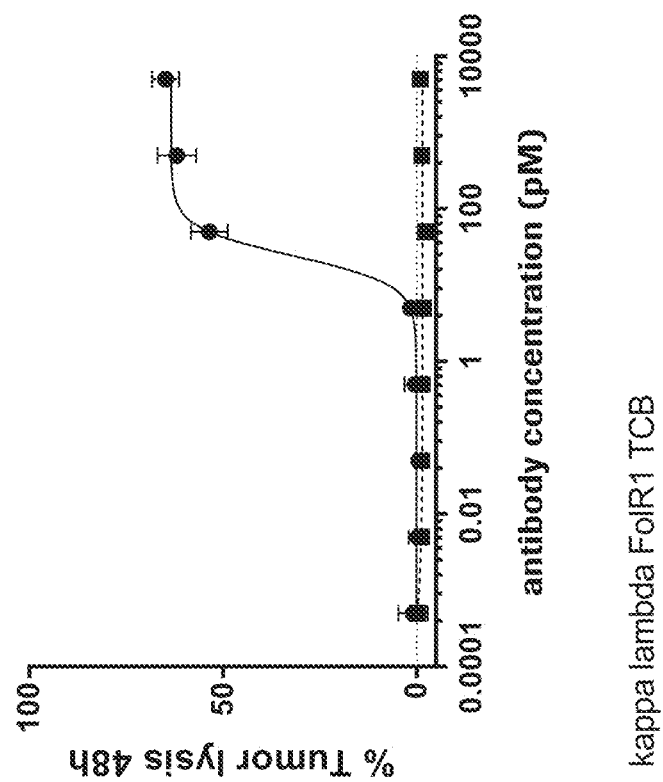
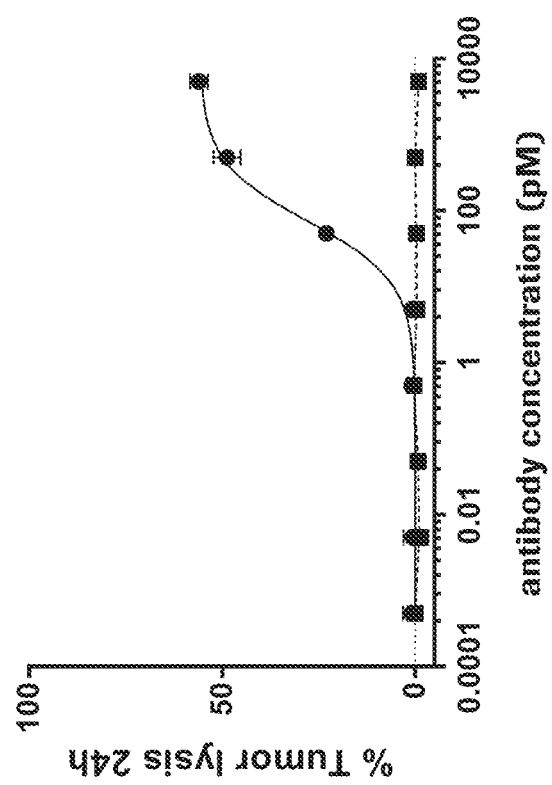
Fig. 21A
Fig. 21B

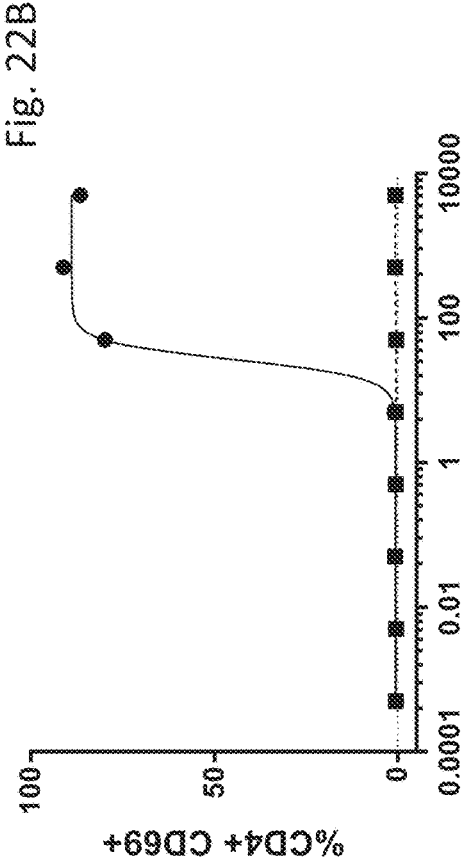

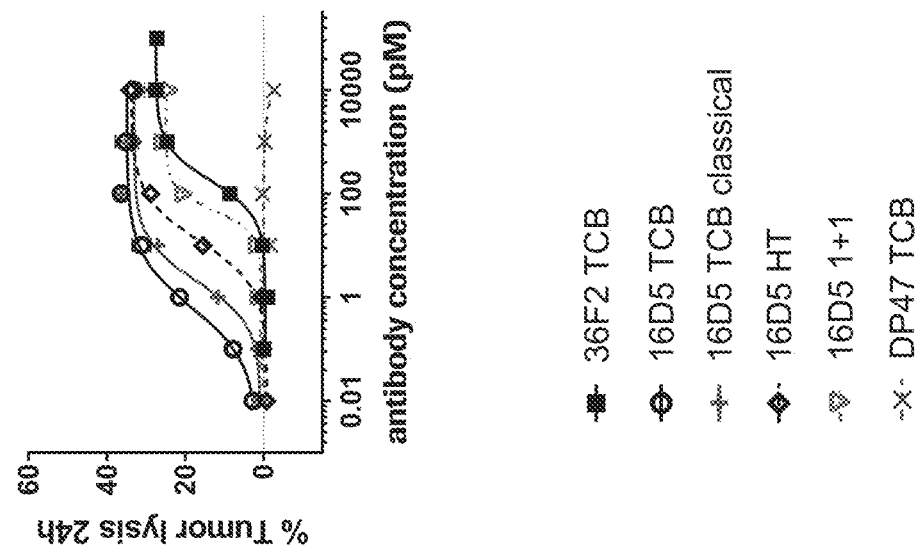
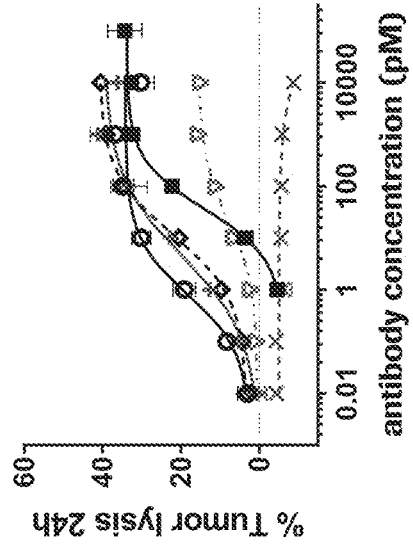
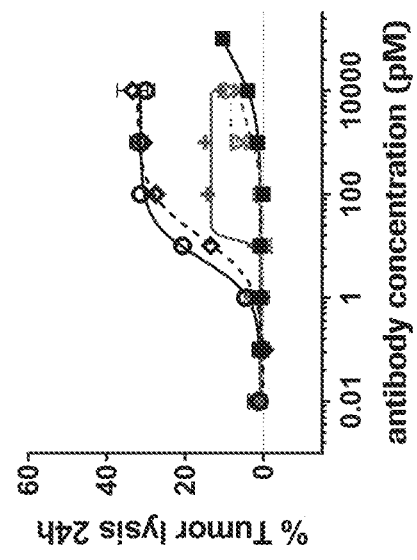

Fig. 27

| Cell line | Binding sites | Cell line | Binding sites |
|---|---|---|---|
| Hela | 2'240'716 | Bronchial epithelium | 492 |
| Skov3 | 91'510 | Choroid plexus epithelium | 104 |
| OVCAR5 | 22'077 | Renal cortical epithelium | 312 |
| HT29 | 10'135 | Retinal pigment epithelium | 822 |
| MKN45 | 54 | Skov3 | 69'890 |

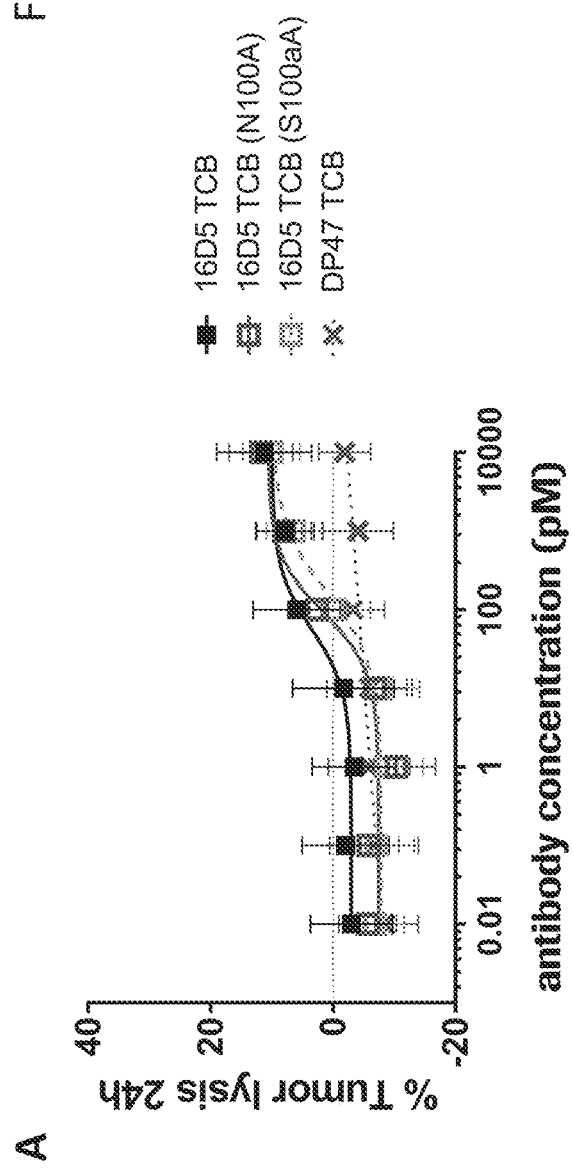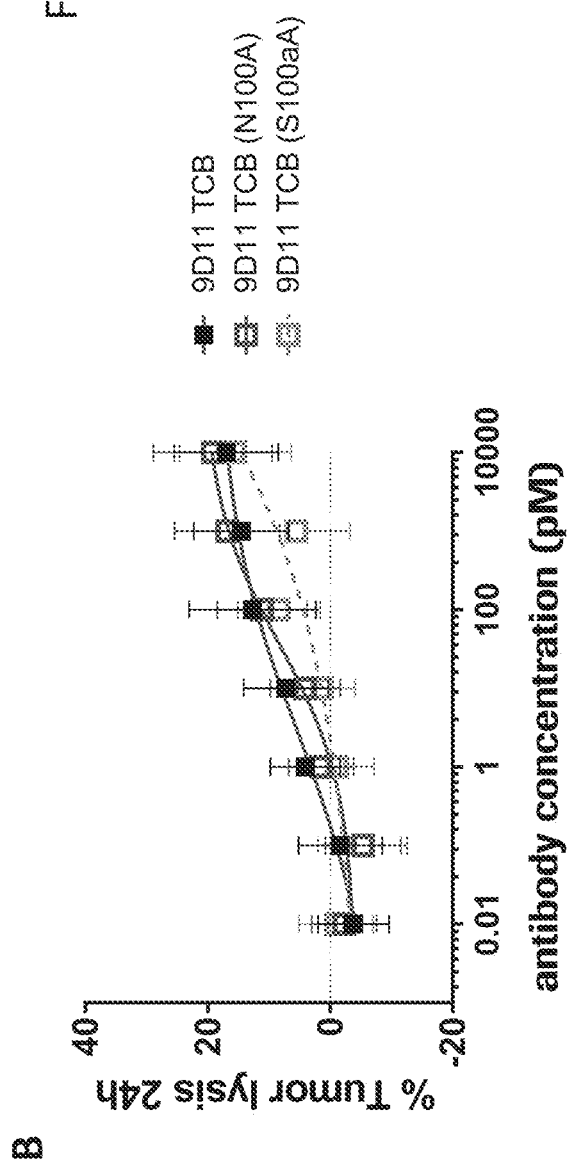

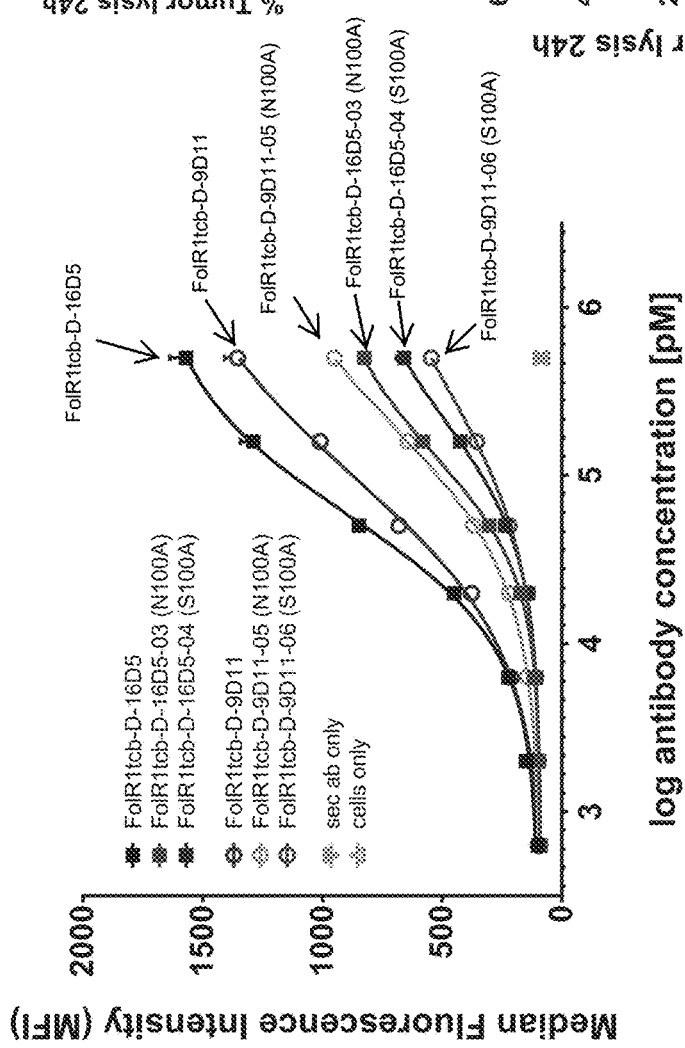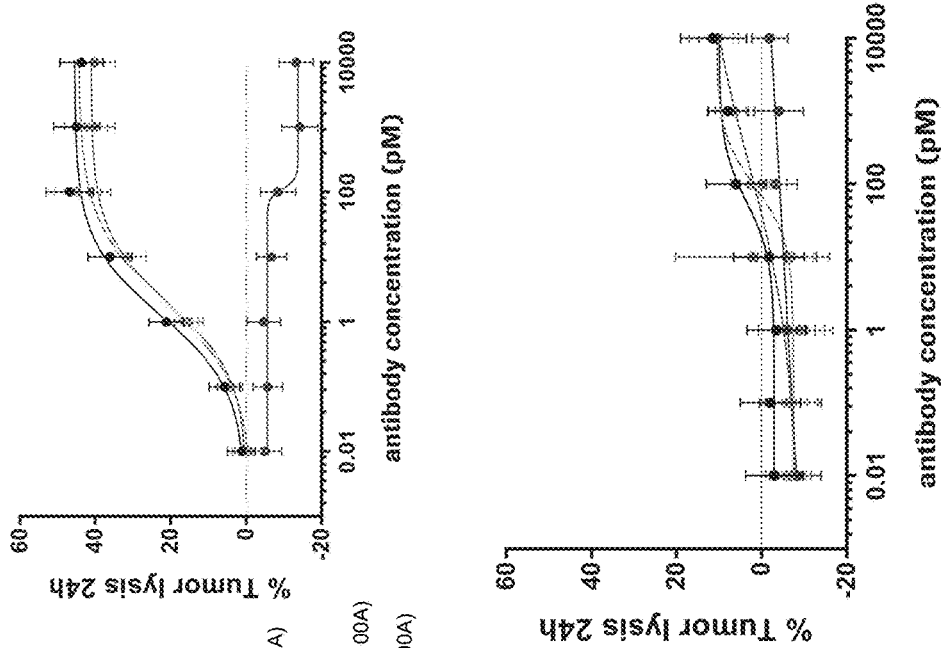
Fig. 31A
Fig. 31B
Fig. 31C

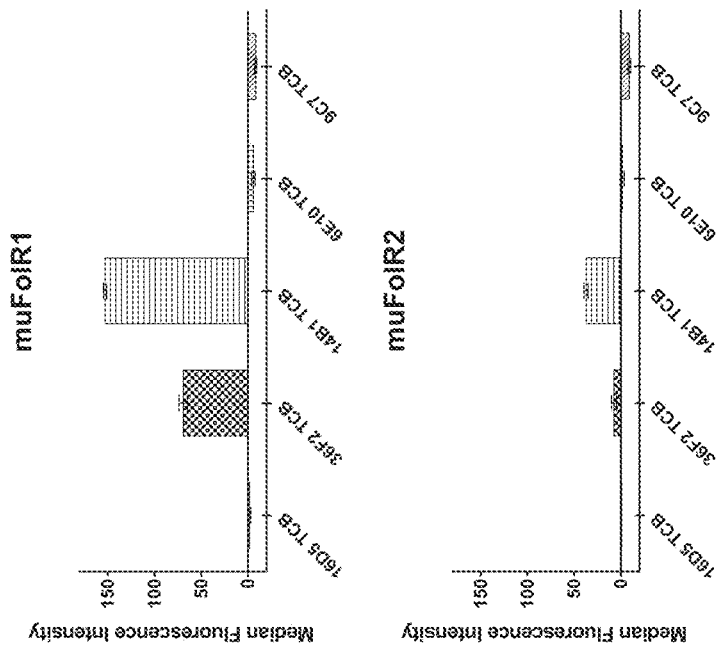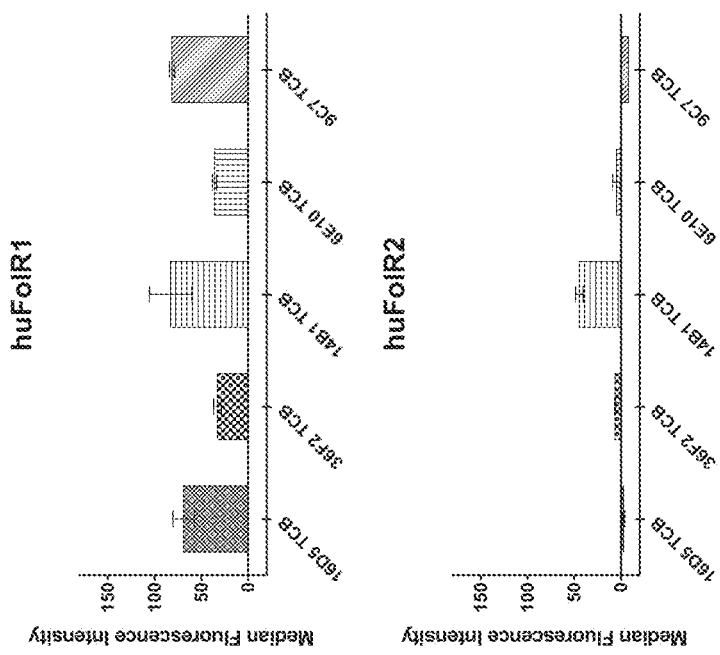

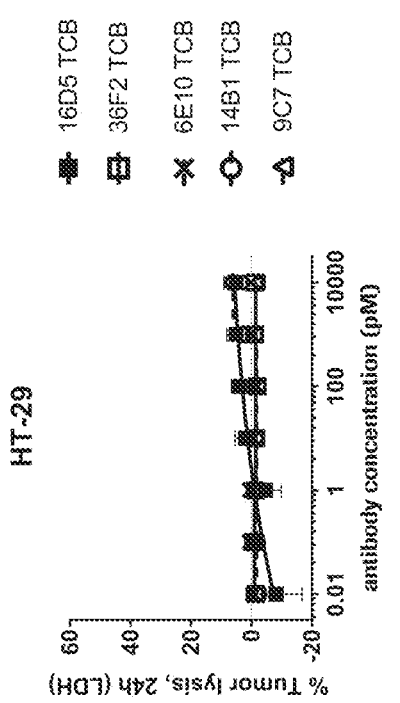
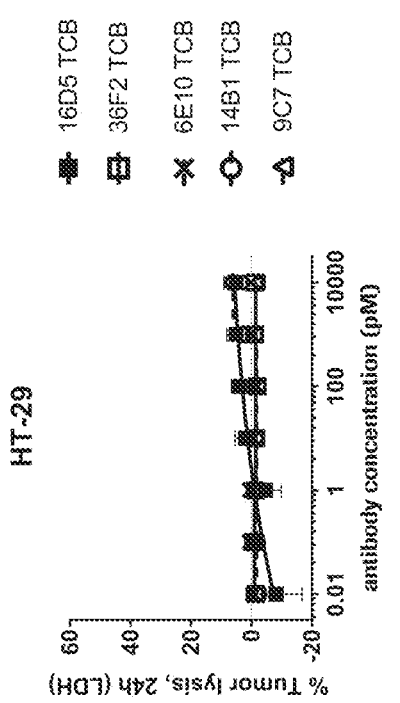
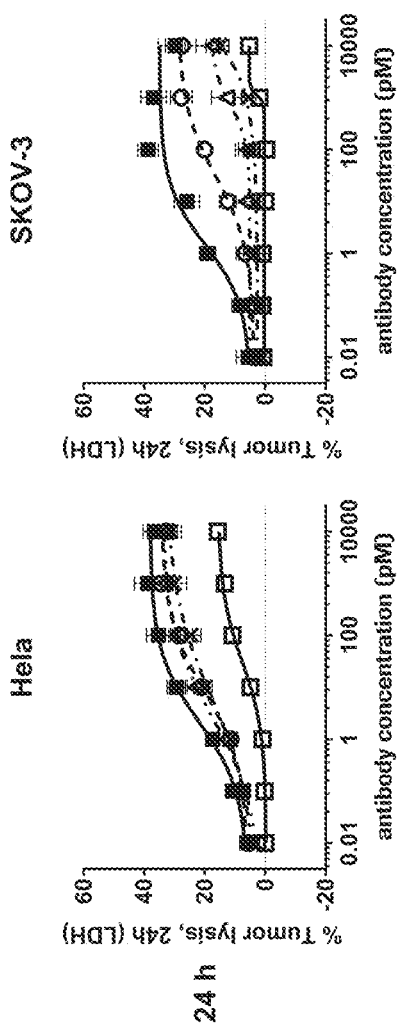
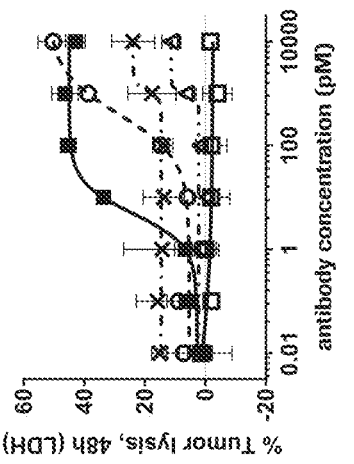
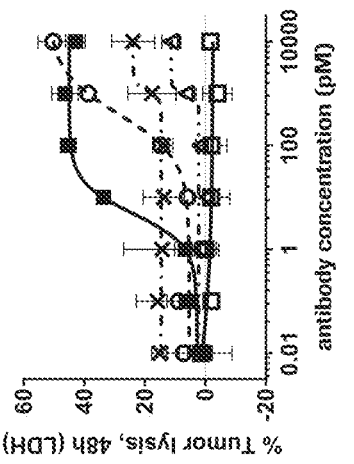
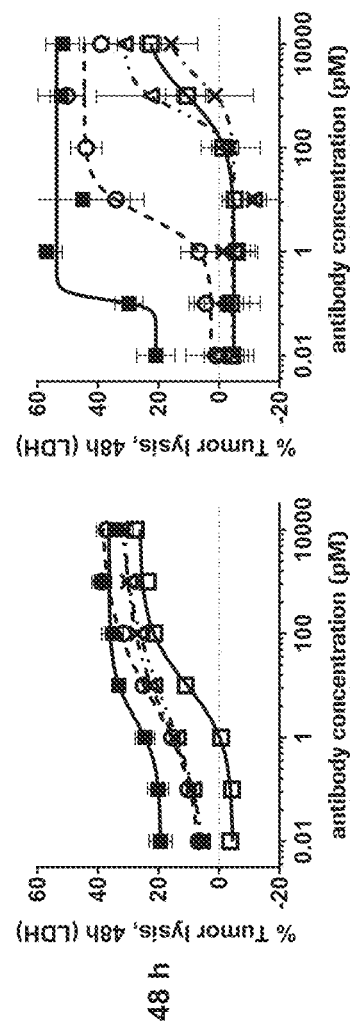

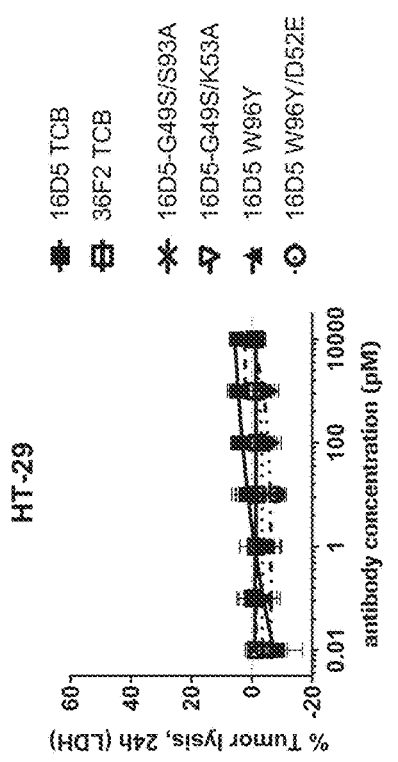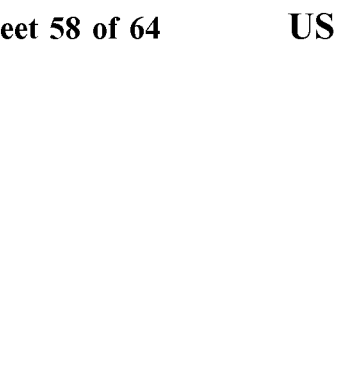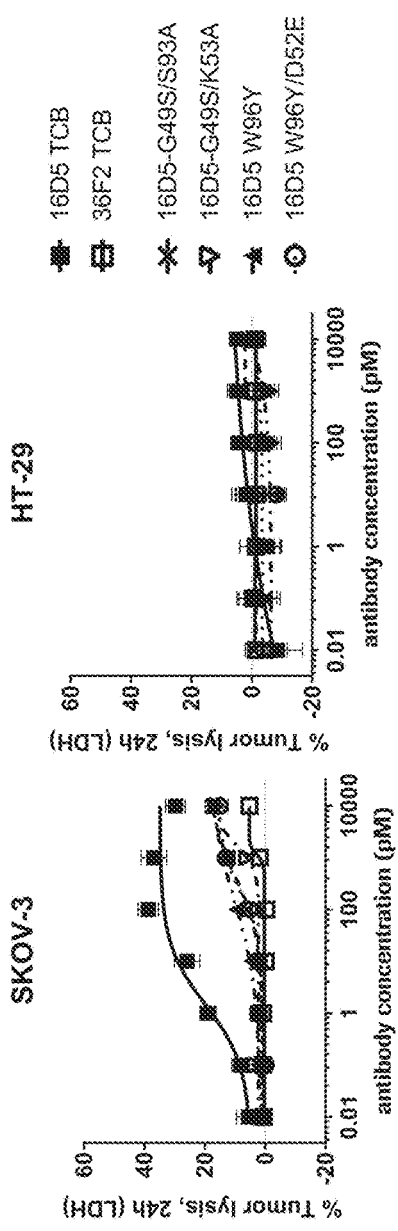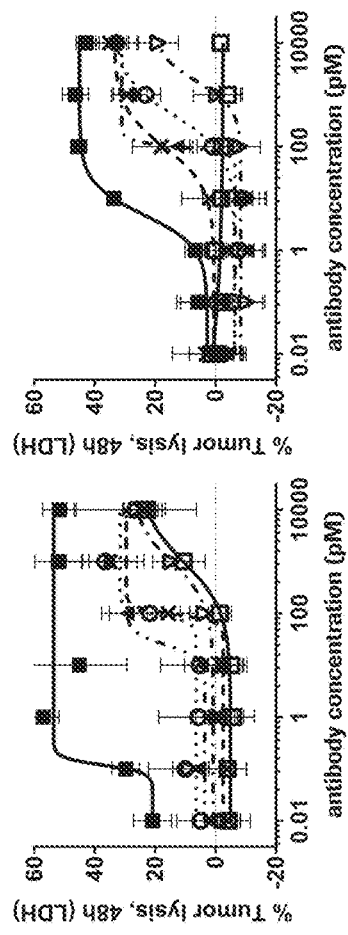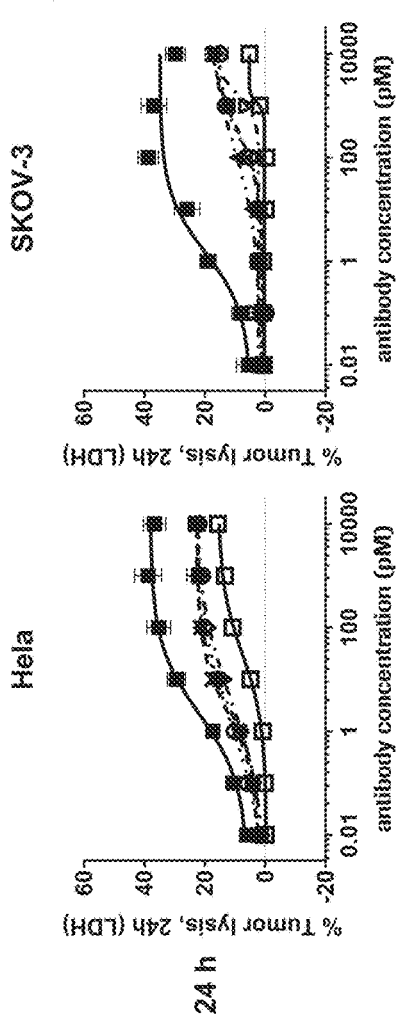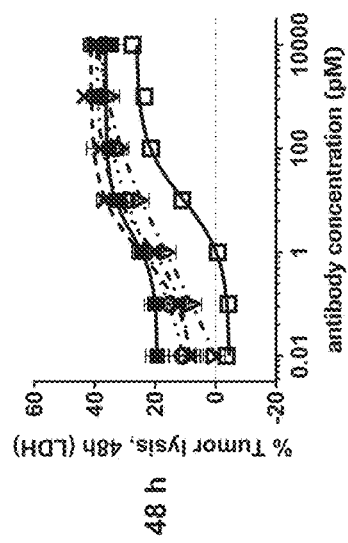
Fig. 37A Hela
Fig. 37B SKOV-3
Fig. 37C HT-29
Fig. 37D
Fig. 37E
Fig. 37F

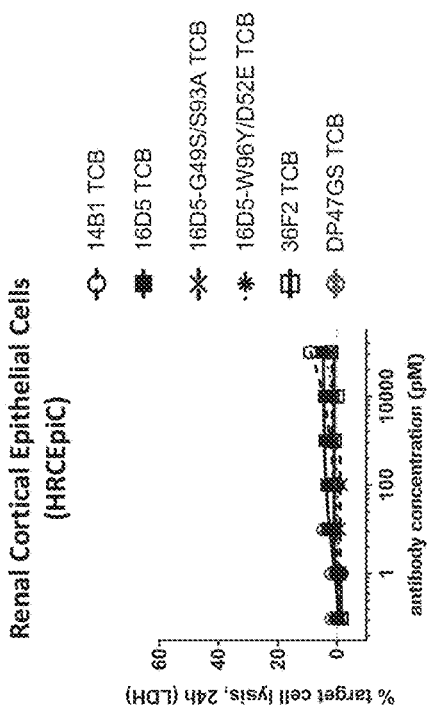
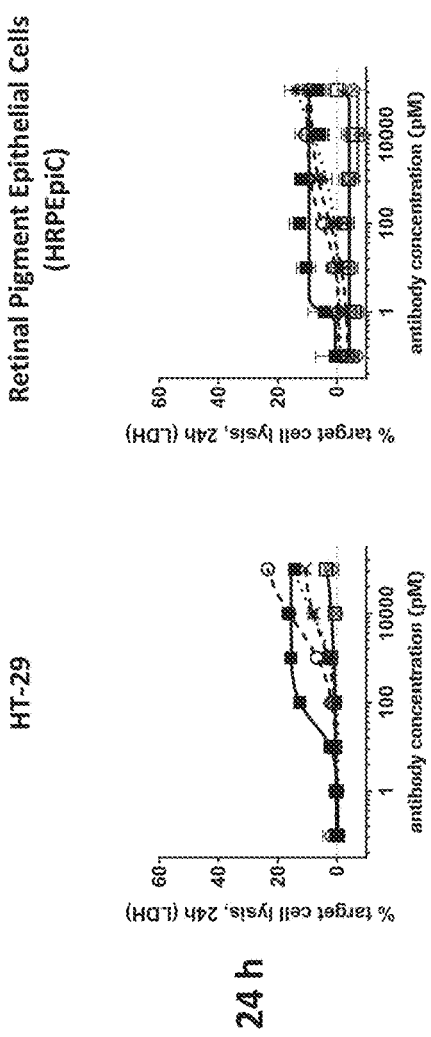
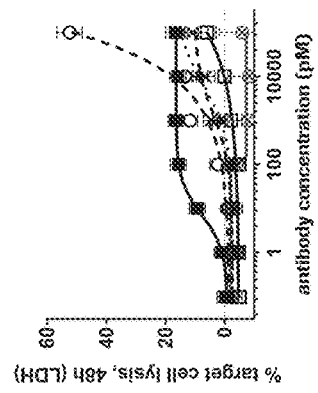
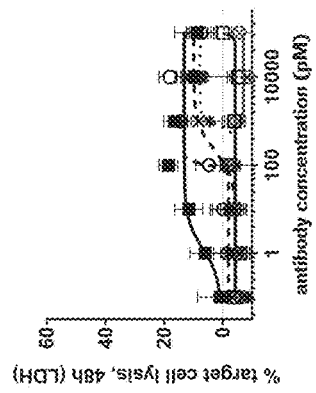
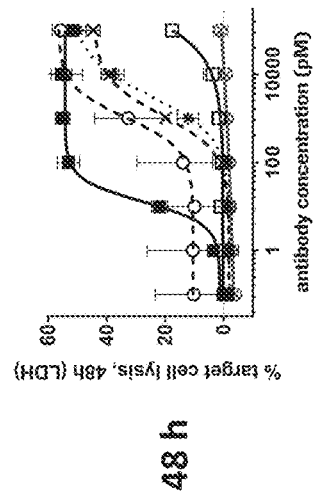
Fig. 38A, Fig. 38B, Fig. 38C, Fig. 38D, Fig. 38E, Fig. 38F

Fig. 40A

| Group | Construct | PBMC injection (day 30) | Tumor (s.c.) | Start of treatment | Dose(mg/kg) | Scheduling |
|---|---|---|---|---|---|---|
| A | Vehicle | 10x10⁶ | HELA | Day 32 | -- | once per week |
| B | FOLR1 TCB (clone: 16D5) | 10x10⁶ | HELA | Day 32 | 0.5 | once per week |
| C | FOLR1 TCB (clone: 16D5 W96Y/D52E) | 10x10⁶ | HELA | Day 32 | 2.5 | once per week |
| D | FOLR1 TCB (clone: 16D5 W96Y/D52E) | 10x10⁶ | HELA | Day 32 | 0.5 | once per week |
| E | FOLR1 TCB (clone: 16D5 G49S/S93A) | 10x10⁶ | HELA | Day 32 | 2.5 | once per week |
| F | FOLR1 TCB (clone: 16D5 G49S/S93A) | 10x10⁶ | HELA | Day 32 | 0.5 | once per week |

Study protocol:

Fig. 40B

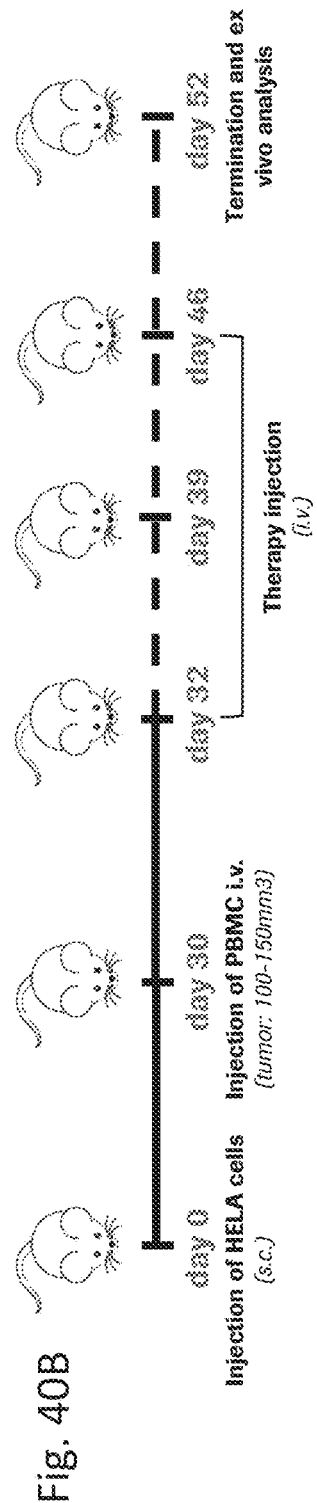

T CELL ACTIVATING BISPECIFIC ANTIGEN BINDING MOLECULES

SEQUENCE LISTING

The instant application contains a Sequence Listing which has been submitted electronically in ASCII format and is hereby incorporated by reference in its entirety. Said ASCII copy, created on Jan. 20, 2022, is named 51177-011003_Sequence_Listing_1_20_22_ST25 and is 445,642 bytes in size.

FIELD OF THE INVENTION

The present invention generally relates to bispecific antigen binding molecules for activating T cells, in particular to bispecific antibodies targeting CD3 and Folate Receptor 1 (FolR1). In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

BACKGROUND

The selective destruction of an individual cell or a specific cell type is often desirable in a variety of clinical settings. For example, it is a primary goal of cancer therapy to specifically destroy tumor cells, while leaving healthy cells and tissues intact and undamaged.

An attractive way of achieving this is by inducing an immune response against the tumor, to make immune effector cells such as natural killer (NK) cells or cytotoxic T lymphocytes (CTLs) attack and destroy tumor cells. CTLs constitute the most potent effector cells of the immune system, however they cannot be activated by the effector mechanism mediated by the Fc domain of conventional therapeutic antibodies.

In this regard, bispecific antibodies designed to bind with one "arm" to a surface antigen on target cells, and with the second "arm" to an activating, invariant component of the T cell receptor (TCR) complex, have become of interest in recent years. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e. the immunological synapse is mimicked. Particularly desirable are bispecific antibodies that do not require lymphocyte preconditioning or co-stimulation in order to elicit efficient lysis of target cells.

FOLR1 is expressed on epithelial tumor cells of various origins, e.g., ovarian cancer, lung cancer, breast cancer, renal cancer, colorectal cancer, endometrial cancer. Several approaches to target FOLR1 with therapeutic antibodies, such as farletuzumab, antibody drug conjugates, or adoptive T cell therapy for imaging of tumors have been described (Kandalaft et al., J Transl Med. 2012 Aug. 3; 10:157. doi: 10.1186/1479-5876-10-157; van Dam et al., Nat Med. 2011 Sep. 18; 17(10):1315-9. doi: 10.1038/nm.2472; Cliftonet al., Hum Vaccin. 2011 February; 7(2):183-90. Epub 2011 Feb. 1; Kelemen et al., Int J Cancer. 2006 Jul. 15; 119(2):243-50; Vaitilingam et al., J Nucl Med. 2012 July; 53(7); Teng et al., 2012 August; 9(8):901-8. doi: 10.1517/17425247.2012.694863. Epub 2012 Jun. 5. Some attempts have been made to target folate receptor-positive tumors with constructs that target the folate receptor and CD3 (Kranz et al., Proc Natl Acad Sci USA. Sep. 26, 1995; 92(20): 9057-9061; Roy et al., Adv Drug Deliv Rev. 2004 Apr. 29; 56(8):1219-31; Huiting Cui et al Biol Chem. Aug. 17, 2012; 287(34): 28206-28214; Lamers et al., Int. J. Cancer. 60(4):450 (1995); Thompson et al., MAbs. 2009 July-August; 1(4):348-56. Epub 2009 Jul. 19; Mezzanzanca et al., Int. J. Cancer, 41, 609-615 (1988). However, the approaches taken so far have many disadvantages. The molecules used thus far could not be readily and reliably produced as they require chemical cross linking. Similarly, hybrid molecules cannot be produced at large scale as human proteins and require the use of rat, murine or other proteins that are highly immunogenic when administered to humans and, thus, of limited therapeutic value. Further, many of the existing molecules retained FcgR binding.

Thus, there remains a need for novel, improved bispecific antibodies for targeted T cell mediated immunotherapy. The present invention provides bispecific antigen binding molecules designed for targeted T cell activation, particularly, bispecific antigen binding molecules suitable as effective and safe therapeutics that can be readily produced and dosed.

SUMMARY OF THE INVENTION

In one aspect, the invention provides a T cell activating bispecific antigen binding molecule comprising
 (i) a first antigen binding moiety which is a Fab molecule capable of specific binding to CD3, and which comprises at least one heavy chain complementarity determining region (CDR) amino acid sequence selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34; and
 (ii) a second antigen binding moiety capable of specific binding to Folate Receptor 1 (FolR1).

In one embodiment, the T cell activating bispecific antigen binding molecule comprises a first antigen binding moiety that comprises a variable heavy chain comprising an amino acid sequence of SEQ ID NO: 36 and a variable light chain comprising an amino acid sequence of SEQ ID NO: 31. In one embodiment, the T cell activating bispecific antigen binding molecule additionally comprises (iii) a third antigen binding moiety capable of specific binding to FolR1. In one embodiment, the second and third antigen binding moiety capable of specific binding to FolR1 comprise identical heavy chain complementarity determining region (CDR) and light chain CDR sequences. In one embodiment, the third antigen binding moiety is identical to the second antigen binding moiety.

In one embodiment of the T cell activating bispecific antigen binding molecule of the above embodiments, at least one of the second and third antigen binding moiety is a Fab molecule. In one embodiment, the T cell activating bispecific antigen binding molecule of the above embodiments, additionally comprises an Fc domain composed of a first and a second subunit capable of stable association. In some embodiments, the first antigen binding moiety and the second antigen binding moiety are each connected at the C-terminus of the Fab heavy chain to the N-terminus of the first or second subunit of the Fc domain. In some embodiments, a third antigen binding moiety is fused at the C-terminus of the Fab heavy chain to the N-terminus of the Fab heavy chain of the first antigen binding moiety, optionally via a peptide linker.

In one embodiment of the T cell activating bispecific antigen binding molecule of the above embodiments, the antigen binding moiety capable of specific binding to Folate Receptor 1 (FolR1) comprises at least one heavy chain complementarity determining region (CDR) amino acid sequence selected from the group consisting of SEQ ID NO: 16, SEQ ID NO: 17 and SEQ ID NO: 18 and at least one light chain CDR selected from the group of SEQ ID NO: 32, SEQ ID NO: 33, SEQ ID NO: 34. In one embodiment, the antigen binding moiety capable of specific binding to Folate Receptor 1 (FolR1) comprises a variable heavy chain comprising an amino acid sequence of SEQ ID NO: 15 and a variable light chain comprising an amino acid sequence of SEQ ID NO: 31. In one embodiment, the antigen binding moiety capable of specific binding to Folate Receptor 1 (FolR1) comprises at least one heavy chain complementarity determining region (CDR) amino acid sequence selected from the group consisting of SEQ ID NO: 8, SEQ ID NO: 56 and SEQ ID NO: 57 and at least one light chain CDR selected from the group of SEQ ID NO: 59, SEQ ID NO: 60, SEQ ID NO: 65. In one embodiment, the antigen binding moiety capable of specific binding to Folate Receptor 1 (FolR1) comprises a variable heavy chain comprising an amino acid sequence of SEQ ID NO: 55 and a variable light chain comprising an amino acid sequence of SEQ ID NO: 64.

In another embodiment, the antigen binding moiety capable of specific binding to Folate Receptor 1 (FolR1) comprises at least one heavy chain complementarity determining region (CDR) amino acid sequence selected from the group consisting of SEQ ID NO: 8, SEQ ID NO: 9 and SEQ ID NO: 50 and at least one light chain CDR selected from the group of SEQ ID NO: 52, SEQ ID NO: 53, SEQ ID NO: 54. In one embodiment, the antigen binding moiety capable of specific binding to FolR1 comprises (a) a complementarity determining region heavy chain 1 (CDR-H1) amino acid sequences of SEQ ID NO: 8; (b) a CDR-H2 amino acid sequence of SEQ ID NO: 9; (c) a CDR-H3 amino acid sequence of SEQ ID NO: 50; (d) a complementarity determining region light chain 1 (CDR-L1) amino acid sequence of SEQ ID NO: 52; (e) a CDR-L2 amino acid sequence of SEQ ID NO: 53, and (f) a CDR-L3 amino acid sequence of SEQ ID NO: 54. In one embodiment, the antigen binding moiety capable of specific binding to FolR1 comprises a variable heavy chain comprising an amino acid sequence of SEQ ID NO: 49 and a variable light chain comprising an amino acid sequence of SEQ ID NO: 51.

In another embodiment, the antigen binding moiety capable of specific binding to Folate Receptor 1 (FolR1) comprises at least one heavy chain complementarity determining region (CDR) amino acid sequence selected from the group consisting of SEQ ID NO: 16, SEQ ID NO: 275 and SEQ ID NO: 315 and at least one light chain CDR selected from the group of SEQ ID NO: 32, SEQ ID NO: 33, SEQ ID NO: 34. In one embodiment, the antigen binding moiety capable of specific binding to FolR1 comprises (a) a complementarity determining region heavy chain 1 (CDR-H1) amino acid sequences of SEQ ID NO: 16; (b) a CDR-H2 amino acid sequence of SEQ ID NO: 275; (c) a CDR-H3 amino acid sequence of SEQ ID NO: 315; (d) a complementarity determining region light chain 1 (CDR-L1) amino acid sequence of SEQ ID NO: 32; (e) a CDR-L2 amino acid sequence of SEQ ID NO: 33, and (f) a CDR-L3 amino acid sequence of SEQ ID NO: 34. In one embodiment, the antigen binding moiety capable of specific binding to FolR1 comprises a variable heavy chain domain (VH) comprising an amino acid sequence of SEQ ID NO: 274 and a variable light chain domain (VL) comprising an amino acid sequence of SEQ ID NO: 31.

In one embodiment, the T cell activating bispecific antigen binding molecule of the above embodiments binds to a human FolR1. In one embodiment, the T cell activating bispecific antigen binding molecule of the above embodiments binds to a human FolR1 and a cynomolgus monkey FolR1. In one embodiment, the T cell activating bispecific antigen binding molecule of the above embodiments binds to a human FolR1, a cynomolgus monkey FolR1 and a murine FolR1. In one embodiment, the T cell activating bispecific antigen binding molecule of the above embodiments binds to a human FolR1, a cynomolgus monkey FolR1 and not a murine FolR1.

In one embodiment of the T cell activating bispecific antigen binding molecule of any of the above embodiments, the first antigen binding moiety is a crossover Fab molecule wherein either the variable or the constant regions of the Fab light chain and the Fab heavy chain are exchanged. In one embodiment, the T cell activating bispecific antigen binding molecule of any of the above embodiments comprises not more than one antigen binding moiety capable of specific binding to CD3. In one embodiment of the T cell activating bispecific antigen binding molecule, the first and the second antigen binding moiety and the Fc domain are part of an immunoglobulin molecule. In one embodiment, the Fc domain is an IgG class immunoglobulin, specifically an IgG$_1$ or IgG$_4$, Fc domain. In one embodiment, the Fc domain is a human Fc domain.

In one embodiment of the T cell activating bispecific antigen binding molecule of any of the above embodiments, the Fc domain comprises a modification promoting the association of the first and the second subunit of the Fc domain. In one embodiment, in the CH3 domain of the first subunit of the Fc domain an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. In one embodiment, the Fc domain comprises at least one amino acid substitution that reduces binding to an Fc receptor and/or effector function, as compared to a native IgG$_1$ Fc domain. In one embodiment, each subunit of the Fc domain comprises three amino acid substitutions that reduce binding to an activating Fc receptor and/or effector function wherein said amino acid substitutions are L234A, L235A and P329G (Kabat numbering). In one embodiment, the Fc receptor is an Fcγ receptor. In one embodiment, the effector function is antibody-dependent cell-mediated cytotoxicity (ADCC).

In one embodiment of the T cell activating bispecific antigen binding molecule of any of the above embodiments, the T cell activating bispecific antigen binding molecule induces proliferation of a human CD3 positive T cell in vitro. In one embodiment, the T cell activating bispecific antigen binding molecule induces human peripheral blood mononuclear cell mediated killing of a FolR1-expressing human tumor cell in vitro. In one embodiment, the T cell activating bispecific antigen binding molecule induces T cell mediated killing of a FolR1-expressing human tumor cell in vitro. In one embodiment, the T cell is a CD8 positive T cell. In one embodiment, the FolR1-expressing human tumor cell is a Hela, Skov-3, HT-29, or HRCEpiC cell. In one embodiment, the T cell activating bispecific antigen binding molecule induces T cell mediated killing of the FolR1-expressing human tumor cell in vitro with an EC50 of between about 36 pM and about 39573 pM after 24 hours. In one embodiment, the T cell activating bispecific antigen binding molecule induces T cell mediated killing of the FolR1-expressing tumor cell in vitro with an EC50 of about 36 pM after 24 hours. In one embodiment, the T cell activating bispecific antigen binding molecule induces T cell mediated killing of the FolR1-expressing tumor cell in vitro with an EC50 of about 178.4 pM after 24 hours. In one embodiment, the T cell activating bispecific antigen binding molecule induces T cell mediated killing of the FolR1-expressing tumor cell in vitro with an EC50 of about 134.5 pM or greater after 48 hours.

In one embodiment, the T cell activating bispecific antigen binding molecule of any of the above embodiments induces upregulation of cell surface expression of at least one of CD25 and CD69 on the T cell as measured by flow cytometry. In one embodiment, the T cell is a CD4 positive T cell or a CD8 positive T cell. In one embodiment, the T cell activating bispecific antigen binding molecule of any of the above embodiments binds human FolR1 with an apparent $K_D$ of about 5.36 pM to about 4 nM. In one embodiment, the T cell activating bispecific antigen binding molecule binds human and cynomolgus FolR1 with an apparent $K_D$ of about 4 nM. In one embodiment, the T cell activating bispecific antigen binding molecule binds murine FolR1 with an apparent $K_D$ of about 1.5 nM. In one embodiment, the T cell activating bispecific antigen binding molecule binds human FolR1 with a monovalent binding $K_D$ of at least about 1000 nM.

In one embodiment, the T cell activating bispecific antigen binding molecule of any of the above embodiments is specific for FolR1 and does not bind to FolR2 or FolR3. In one embodiment, the T cell activating bispecific antigen binding molecule of any of the above embodiments has an affinity (monovalent binding) of 1 μM or greater. In one embodiment, the affinity is around 1.4 μM for human FolR1. In one embodiment, the T cell activating bispecific antigen binding molecule of any of the above embodiments has an avidity (bivalent binding) of about 1-100 nM or lower. In one embodiment, the avidity is about 10 nM or less. In one embodiment, the avidity is 10 nM.

In one embodiment, the T cell activating bispecific antigen binding molecule of any of the above embodiments binds to FolR1 expressed on a human tumor cell. In one embodiment, the T cell activating bispecific antigen binding molecule of any of the above embodiments binds to a conformational epitope on human FolR1. In one embodiment, the T cell activating bispecific antigen binding molecule of any of the above embodiments does not bind to human Folate Receptor 2 (FolR2) or to human Folate Receptor 3 (FolR3). In one embodiment of the T cell activating bispecific antigen binding molecule of any of the above embodiments, the antigen binding moiety binds to a FolR1 polypeptide comprising the amino acids 25 to 234 of human FolR1 (SEQ ID NO:227). In one embodiment of the T cell activating bispecific antigen binding molecule of any of the above embodiments, the FolR1 antigen binding moiety binds to a FolR1 polypeptide comprising the amino acid sequence of SEQ ID NOs:227, 230 and 231, and wherein the FolR1 antigen binding moiety does not bind to a FolR polypeptide comprising the amino acid sequence of SEQ ID NOs:228 and 229.

In another aspect, the invention provides for a bispecific antibody comprising a) a first antigen-binding site that competes for binding to human FolR1 with a reference antibody comprising a variable heavy chain domain (VH) of SEQ ID NO: 49 and a variable light chain domain of SEQ ID NO: 51; and b) a second antigen-binding site that competes for binding to human CD3 with a reference antibody comprising a variable heavy chain domain (VH) of SEQ ID NO: 36 and a variable light chain domain of SEQ ID NO: 31, wherein binding competition is measured using a surface plasmon resonance assay.

In another aspect, the invention provides for a bispecific antibody comprising a) a first antigen-binding site that competes for binding to human FolR1 with a reference antibody comprising a variable heavy chain domain (VH) of SEQ ID NO: 274 and a variable light chain domain of SEQ ID NO: 31; and b) a second antigen-binding site that competes for binding to human CD3 with a reference antibody comprising a variable heavy chain domain (VH) of SEQ ID NO: 36 and a variable light chain domain of SEQ ID NO: 31, wherein binding competition is measured using a surface plasmon resonance assay.

In another aspect, the invention provides for a T cell activating bispecific antigen binding molecule comprising a first antigen binding moiety capable of specific binding to CD3, and a second antigen binding moiety capable of specific binding to Folate Receptor 1 (FolR1), wherein the T cell activating bispecific antigen binding molecule binds to the same epitope on human FolR1 as a first reference antibody comprising a variable heavy chain domain (VH) of SEQ ID NO: 49 and a variable light chain domain of SEQ ID NO: 51; and wherein the T cell activating bispecific antigen binding molecule binds to the same epitope on human CD3 as a second reference antibody comprising a variable heavy chain domain (VH) of SEQ ID NO: 36 and a variable light chain domain of SEQ ID NO: 31.

In another aspect, the invention provides for a T cell activating bispecific antigen binding molecule comprising a first antigen binding moiety capable of specific binding to CD3, and a second antigen binding moiety capable of specific binding to Folate Receptor 1 (FolR1), wherein the T cell activating bispecific antigen binding molecule binds to the same epitope on human FolR1 as a first reference antibody comprising a variable heavy chain domain (VH) of SEQ ID NO: 274 and a variable light chain domain (VL) of SEQ ID NO: 31; and wherein the T cell activating bispecific antigen binding molecule binds to the same epitope on human CD3 as a second reference antibody comprising a variable heavy chain domain (VH) of SEQ ID NO: 36 and a variable light chain domain (VL) of SEQ ID NO: 31.

In another aspect, the invention relates to an antibody or an antigen-binding fragment thereof that competes for binding to human FolR1 with an antibody that comprises a variable heavy chain domain (VH) of SEQ ID NO: 274 and a variable light chain domain of SEQ ID NO: 31, wherein binding competition is measured using a surface plasmon resonance assay.

In one aspect, the invention provides for a T cell activating bispecific antigen binding molecule, wherein the antigen binding molecule comprises a first, second, third, fourth and fifth polypeptide chain that form a first, a second and a third antigen binding moiety, wherein the first antigen binding moiety is capable of binding CD3 and the second and the third antigen binding moiety each are capable of binding Folate Receptor 1 (FolR1), wherein a) the first and the second polypeptide chain comprise, in amino (N)-terminal to carboxyl (C)-terminal direction, VLD1 and CLD1; b) the third polypeptide chain comprises, in N-terminal to C-terminal direction, VLD2 and CH1D2; c) the fourth polypeptide chain comprises, in N-terminal to C-terminal direction, VHD1, CH1D1, CH2D1 and CH3D1; d) the fifth polypeptide chain comprises VHD1, CH1D1, VHD2, CLD2, CH2D2 and CH3D2; wherein VLD1 is a first light chain variable domain, VLD2 is a second light chain variable domain, CLD1 is a first light chain constant domain, CLD2 is a second light chain constant domain, VHD1 is a first heavy chain variable domain, VHD2 is a second heavy chain variable domain, CH1D1 is a first heavy chain constant domain 1, CH1D2 is a second heavy chain constant domain 1, CH2D1 is a first heavy chain constant domain 2, CH2D2 is a second heavy chain constant domain 2, CH3D1 is a first heavy chain constant domain 3, and CH3D2 is a second heavy chain constant domain 3.

In one embodiment of the T cell activating bispecific antigen binding molecule, (i) the third polypeptide chain and VHD2 and CLD2 of the fifth polypeptide chain form the first antigen binding moiety capable of binding CD3; (ii) the first polypeptide chain and VHD1 and CH1D1 of the fourth polypeptide chain form the second binding moiety capable of binding to FolR1; and (iii) the second polypeptide chain and VHD1 and CH of the fifth polypeptide chain form the third binding moiety capable of binding to FolR1. In one embodiment, CH2D1, CH3D1, CH2D2 and CH3D2 form an Fc domain of an IgG class immunoglobulin. In one embodiment, the Fc domain is a human Fc domain. In one embodiment, the Fc domain comprises a modification promoting the association of the first and the second subunit of the Fc domain. In one embodiment, CH3D2 comprises an amino acid residue having a larger side chain volume, which is positionable in a cavity within CH3D1. In one embodiment, the Fc domain comprises at least one amino acid substitution that reduces binding to an Fc receptor and/or effector function, as compared to a native IgG$_1$ Fc domain. In one embodiment, each subunit of the Fc domain comprises three amino acid substitutions that reduce at least one of binding to an activating Fc receptor and effector function wherein said amino acid substitutions are L234A, L235A and P329G according to Kabat numbering. In one embodiment, the Fc receptor is an Fcγ receptor. In one of the above embodiments, the T cell activating bispecific antigen binding molecule induces proliferation of a human CD3 positive T cell in vitro. In one of the above embodiments, the T cell activating bispecific antigen binding molecule induces human peripheral blood mononuclear cell mediated killing of a FolR1-expressing human tumor cell in vitro. In one of the above embodiments, the T cell activating bispecific antigen binding molecule induces T cell mediated killing of a FolR1-expressing human tumor cell in vitro. In one such embodiment, the FolR1-expressing human tumor cell is a Hela, Skov-3, HT-29, or HRCEpiC cell. In one of the above embodiments, the T cell activating bispecific antigen binding molecule induces T cell mediated killing of the FolR1-expressing tumor cell in vitro with an EC50 of between about 36 pM and about 39573 pM after 24 hours. In one of the above embodiments, the T cell activating bispecific antigen binding molecule induces T cell mediated killing of the FolR1-expressing tumor cell in vitro with an EC50 of about 36 pM after 24 hours. In one of the above embodiments, the T cell activating bispecific antigen binding molecule induces T cell mediated killing of the FolR1-expressing tumor cell in vitro with an EC50 of about 178.4 pM after 24 hours. In one of the above embodiments, the T cell activating bispecific antigen binding molecule induces T cell mediated killing of the FolR1-expressing tumor cell in vitro with an EC50 of about 134.5 pM or greater after 48 hours. In one of the above embodiments, the T cell activating bispecific antigen binding molecule induces upregulation of cell surface expression of at least one of CD25 and CD69 on the T cell as measured by flow cytometry. In one such embodiments, the T cell is a CD4 positive T cell or a CD8 positive T cell. In one of the above embodiments, wherein the T cell activating bispecific antigen binding molecule binds human FolR1 with an apparent $K_D$ of about 5.36 pM to about 4 nM. In one of the above embodiments, the T cell activating bispecific antigen binding molecule binds human and cynomolgus FolR1 with an apparent $K_D$ of about 4 nM. In one of the above embodiments, the T cell activating bispecific antigen binding molecule binds murine FolR1 with an apparent $K_D$ of about 1.5 nM. In one of the above embodiments, the T cell activating bispecific antigen binding molecule binds human FolR1 with a monovalent binding $K_D$ of at least about 1000 nM. In one of the above embodiments, the T cell activating bispecific antigen binding molecule binds to FolR1 expressed on a human tumor cell. In one of the above embodiments, the T cell activating bispecific antigen binding molecule binds to a conformational epitope on human FolR1. In one of the above embodiments, the T cell activating bispecific antigen binding molecule does not bind to human Folate Receptor 2 (FolR2) or to human Folate Receptor 3 (FolR3). In one of the above embodiments, the antigen binding moiety binds to a FolR1 polypeptide comprising the amino acids 25 to 234 of human FolR1 (SEQ ID NO:227). In one of the above embodiments, the FolR1 antigen binding moiety binds to a FolR1 polypeptide comprising the amino acid sequence of SEQ ID NOs:227, 230 and 231, and wherein the FolR1 antigen binding moiety does not bind to a FolR polypeptide comprising the amino acid sequence of SEQ ID NOs:228 and 229. In one of the above embodiments, the T cell activating bispecific antigen binding molecule is a humanized or a chimeric molecule. In one of the above embodiments, VHD2 and CH1D1 are linked through a peptide linker.

In one of the above embodiments of the T cell activating bispecific antigen binding molecule, the first and second polypeptide chain comprise the amino acid sequence of SEQ ID NO:230. In one of the above embodiments of the T cell activating bispecific antigen binding molecule, the third polypeptide chain comprises the amino acid sequence of SEQ ID NO:86. In one of the above embodiments of the T cell activating bispecific antigen binding molecule, the fourth polypeptide chain comprises the amino acid sequence of SEQ ID NO:309. In one of the above embodiments of the T cell activating bispecific antigen binding molecule, the fifth polypeptide chain comprises the amino acid sequence of SEQ ID NO:308. In one of the above embodiments of the T cell activating bispecific antigen binding molecule, the first and second polypeptide chain comprise the amino acid sequence of SEQ ID NO:230; the third polypeptide chain comprises the amino acid sequence of SEQ ID NO:86; the fourth polypeptide chain comprises the amino acid sequence of SEQ ID NO:309; and the fifth polypeptide chain comprise the amino acid sequence of SEQ ID NO:308.

In one aspect, the invention provides for a T cell activating bispecific antigen binding molecule comprising the amino acid sequence of SEQ ID NO:308. In one embodiment, the T cell activating bispecific antigen binding molecule of the above embodiment further comprises the amino acid sequence of SEQ ID NO:230 and of SEQ ID NO:86.

In one aspect, the invention provides for an isolated polypeptide comprising the amino acid sequence of SEQ ID NO:308. In one aspect, the invention provides for an isolated polypeptide comprising the amino acid sequence of SEQ ID NO:309.

In one aspect, the invention provides for a T cell activating bispecific antigen binding molecule comprising the amino acid sequence of SEQ ID NO:276. In one embodiment, the T cell activating bispecific antigen binding molecule of the above embodiment further comprises the amino acid sequence of SEQ ID NO:277 and of SEQ ID NO:35.

In one aspect, the invention provides for an isolated polypeptide comprising the amino acid sequence of SEQ ID NO:277. In one aspect, the invention provides for an isolated polypeptide comprising the amino acid sequence of SEQ ID NO:276.

In one aspect, the invention provides for an isolated polynucleotide encoding the T cell activating bispecific antigen binding molecule of any one of the embodiments disclosed herein. In one embodiment, the invention provides for an isolated polynucleotide encoding a T cell activating bispecific antigen binding molecule comprising the nucleotide sequence of SEQ ID NO:169. In one embodiment, the invention provides for an isolated polynucleotide encoding a T cell activating bispecific antigen binding molecule comprising the nucleotide sequence of SEQ ID NO:246. In one embodiment, the invention provides for an isolated polynucleotide encoding a T cell activating bispecific antigen binding molecule comprising the nucleotide sequence of SEQ ID NO:247. In one embodiment, the invention provides for an isolated polynucleotide encoding a T cell activating bispecific antigen binding molecule comprising the nucleotide sequence of SEQ ID NO:97. In one embodiment, the invention provides for an isolated polynucleotide encoding a T cell activating bispecific antigen binding molecule comprising the nucleotide sequence of SEQ ID NO:198.

In one embodiment, the invention provides for an isolated polynucleotide encoding a T cell activating bispecific antigen binding molecule comprising the nucleotide sequence of SEQ ID NO:287. In one embodiment, the invention provides for an isolated polynucleotide encoding a T cell activating bispecific antigen binding molecule comprising the nucleotide sequence of SEQ ID NO:288. In one embodiment, the invention provides for an isolated polynucleotide encoding a T cell activating bispecific antigen binding molecule comprising the nucleotide sequence of SEQ ID NO:289.

In one aspect, the invention provides for an isolated polypeptide encoded by the polynucleotide of the above embodiment. In another aspect, the invention provides for a vector, particularly an expression vector, comprising the polynucleotide encoding the T cell activating bispecific antigen binding molecule of any one of the embodiments disclosed herein. In another aspect, the invention provides for a host cell comprising a polynucleotide or a vector of any of the embodiments disclosed herein.

In one aspect, the invention provides for a method of producing the T cell activating bispecific antigen binding molecule capable of specific binding to CD3 and a target cell antigen, comprising the steps of a) culturing the host cell of the above embodiments under conditions suitable for the expression of the T cell activating bispecific antigen binding molecule and b) recovering the T cell activating bispecific antigen binding molecule.

In one aspect, the invention provides for T cell activating bispecific antigen binding molecule produced by the method of the above embodiment.

In one aspect, the invention provides for a pharmaceutical composition comprising the T cell activating bispecific antigen binding molecule of any one of the above embodiments and a pharmaceutically acceptable carrier. In one aspect, the invention provides for the T cell activating bispecific antigen binding molecule of any one of the above embodiments or the pharmaceutical composition of any of the above embodiments for use as a medicament.

In one aspect, the invention provides for the T cell activating bispecific antigen binding molecule of any one of the above embodiments or the pharmaceutical composition of any one of the above embodiments for use in the treatment of a disease in an individual in need thereof. In some embodiments, the disease is cancer. In one aspect, the invention provides for a use of the T cell activating bispecific antigen binding molecule of any one of the above embodiments for the manufacture of a medicament for the treatment of a disease in an individual in need thereof.

In one aspect, the invention provides for a method of treating a disease in an individual, comprising administering to said individual a therapeutically effective amount of a composition comprising the T cell activating bispecific antigen binding molecule of any one of the above embodiments in a pharmaceutically acceptable form. In some embodiments, said disease is a cancer.

In one aspect, the invention provides for a method for inducing lysis of a target cell, comprising contacting a target cell with the T cell activating bispecific antigen binding molecule of any one of the above embodiments in the presence of a T cell.

In one aspect, the invention provides for a the invention as described hereinbefore.

BRIEF DESCRIPTION OF THE DRAWINGS

FIGS. 1A-I illustrate exemplary configurations of the T cell activating bispecific antigen binding molecules (TCBs) of the invention. All constructs except the kappa-lambda format in (FIG. 1I) have P329G LALA mutations and comprise knob-into-hole Fc fragments with knob-into-hole modifications. (FIG. 1A) Illustration of the "FolR1 TCB 2+1 inverted (common light chain)". The FolR1 binder is fused at the C-terminus of the Fab heavy chain to the N-terminus of the first subunit of the Fc domain comprising the knob modification. These constructs are not crossed and have three times the same VLCL light chain. (FIG. 1B) Illustration of the "FolR1 TCB 1+1 head-to-tail (common light chain)". These constructs are not crossed and have two times the same VLCL light chain. (FIG. 1C) Illustration of the "FolR1 TCB 1+1 classical (common light chain)". These constructs are not crossed and have two times the same VLCL light chain. (FIG. 1D) Illustration of the "FolR1 TCB 2+1 classical (common light chain)". The CD3 binder is fused at the C-terminus of the Fab heavy chain to the N-terminus of the first subunit of the Fc domain comprising the knob modification. These constructs are not crossed and have three times the same VLCL light chain. (FIG. 1E) Illustration of the "FolR1 TCB 2+1 crossfab classical". These constructs comprise a Ck-VH chain for the CD3 binder instead of the conventional CH1-VH chain. The CD3 binder is fused at the C-terminus of the Fab heavy chain to the N-terminus of the first subunit of the Fc domain comprising the knob modification. (FIG. 1F) Illustration of the "FolR1 TCB 2+1 crossfab inverted". These constructs comprise a Ck-VH chain for the CD3 binder instead of the conventional CH1-VH chain. The FolR1 binder is fused at the C-terminus of the Fab heavy chain to the N-terminus of the first subunit of the Fc domain comprising the knob modification. (FIG. 1G) Illustration of the "FolR1 TCB 1+1 crossfab head-to-tail". These constructs comprise a Ck-VH chain for the CD3 binder instead of the conventional CH1-VH chain. (FIG. 1H) Illustration of the "FolR1 TCB 1+1 crossfab classical". These constructs comprise a Ck-VH chain for the CD3 binder instead of the conventional CH1-VH chain. FIG. 1I illustrates the CD3/FolR1 kappa-lambda antibody format. These constructs comprise a crossed common light chain VLCH1 and one crossed VHCL chain specific for CD3 and one crossed VHCL chain specific for FolR1.

FIGS. 3A-B depict graphs summarizing specificity of FolR1 binders for FolR1. Binding of FolR1 IgGs to HEK cells transiently transfected with either FolR1 or FolR2 was analyzed by flow cytometry to identify clones which bind specifically to FolR1 and not to FolR2. The antibodies were detected with a fluorescently labeled anti-human secondary antibody.

FIGS. 6A-E depict graphs summarizing binding of FolR1 IgGs to cells with different FolR1 expression levels. Binding of 9D11, 16D5 and Mov19 IgG to tumor cells with different FolR1 expression levels was analyzed by flow cytometry. DP47 IgG was included as isotype control and MKN-45 were included as FolR1 negative cell line. The antibodies were detected with a fluorescently labeled anti-human secondary antibody.

FIGS. 7A-L depict graphs summarizing T cell mediated killing of HT-29 and SKOV3 cells. FolR1 TCBs were used to test T cell mediated killing of HT-29 and SKOV3 tumor cells and upregulation of activation marker on T cells upon killing. (FIGS. 7A-D) T cell mediated killing of HT-29 and SKOV3 cells in the presence of 9D11 FolR1 TCB and 16D5 FolR1 TCB was measured by LDH release after 24 h and 48 h. DP47 TCB was included as negative control. After 48 h incubation upregulation of the activation marker CD25 and CD69 on CD8 T cells and CD4 T cells upon killing of SKOV3 (FIGS. 7E-H) or HT-29 (FIG. 7I-L) tumor cells was assessed by flow cytometry.

FIGS. 11A-F depict graphs summarizing T cell mediated killing with 9D11 FolR1 TCB a-glyco variants of tumor cells. 9D11 FolR1 TCB a-glyco variants were used to test T cell mediated killing of (FIG. 11A-D) SKOV3, MKN-45 (as FolR1 negative control) and (FIG. 11E-F) HT-29 tumor cells in comparison to killing with the original 9D11 FolR1 TCB. As read-out LDH release after 24 h and 48 h was used.

FIGS. 12A-X depict graphs summarizing T cell mediated killing of primary epithelial cells. Primary epithelial cells with very low levels of FolR1 were used to test T cell mediated killing with 16D5 FolR1 TCB and 9D11 FolR1 TCB, DP47 TCB was included as a negative control and HT29 cells were included as positive control. (FIGS. 12A-H) LDH release of human retinal pigment (HRP), human renal cortical (HRC), human bronchial (HB) and of HT29 cells was determined after 24 h and 48 h. CD25 and CD69 activation marker upregulation on CD4 T cells and CD8 T cells upon killing of (FIGS. 12I-L) HRP, (FIGS. 12M-P) HRC, (FIGS. 12Q-T) HB and (FIG. 12 U-X) HT29 was determined after 48 h by flow cytometry.

FIGS. 13A-C show a comparison of different TCB formats with 16D5. Four different TCB formats containing the FolR1 binder 16D5 were compared in FIG. 13A binding to HeLa cells, in FIG. 14 B T cell mediated killing of SKOV3 cells after 24 h and 48 h and in FIG. 14C CD25 and CD69 activation marker upregulation on CD4 T cells and CD8 T cells 48 h after killing.

FIGS. 14A-C depict a comparison of different TCB formats with 9D11. Three different TCB formats containing the FolR1 binder 9D11 were compared in A) binding to HeLa cells, in B) T cell mediated killing of SKOV3 cells after 24 h and 48 h and in C) CD25 and CD69 activation marker upregulation on CD4 T cells and CD8 T cells 48 h after killing.

(FIG. 17A) Mean values and SEM of tumor volumes in the different treatment groups. (FIG. 17B) Tumor growth of single mice in all treatment groups. TGI (tumor growth inhibition) give the percentage of the Mean tumor volume compared to vehicle group.

FIG. 18 shows tumor weights at study termination.

(FIG. 19A) Tumor single cells suspensions were stained with anti-human CD3/CD4/CD8 and analyzed by flow cytometry. (FIG. 19B) Mean values and SEM of T-cell counts per mg tumor tissue in different treatment groups.

FIGS. 20A-B show FACS analysis for T-cell activation/degranulation and cytokine secretion at study day 32. CD4+ (FIG. 20A) and CD8+(FIG. 20B) tumor infiltrating T-cells were stained for cytokines, activation and degranulation markers. Displayed are the mean values and SEM of T-cell counts per mg tumor tissue in different treatment groups.

FIGS. 21A-B show percent tumor lysis. SKOV3 cells were incubated with PBMCs in the presence of either kappa lambda FoLR1 TCB or DP47 TCB. After 24 h (FIG. 21A) and 48 h (FIG. 21B) killing of tumor cells was determined by measuring LDH release.

FIGS. 22A-D show CD25 and CD69 upregulation on CD4 T cells. SKOV3 cells were incubated with PBMCs in the presence of either kappa lambda FoLR1 TCB or DP47 TCB. After 48 h CD25 and CD69 upregulation on CD4 T cells (FIG. 22A-B) and CD8 T cells (FIG. 22C-D) was measured by flow cytometry.

FIGS. 24A-C show T-cell killing induced by 36F2 TCB, 16D5 TCB, 16D5 TCB classical, 16D5 TCB 1+1 and 16D5 TCB HT of Hela (high FolR1) (FIG. 24A), Skov-3 (medium FolR1) (FIG. 24B) and HT-29 (low FolR1) (FIG. 24C) human tumor cells (E:T=10:1, effectors human PBMCs, incubation time 24 h). DP47 TCB was included as non-binding control.

FIG. 27 depicts a table summarizing quantification of FolR1 binding sites on various normal and cancer cells lines.

FIG. 30A-B show T-cell killing of HT-29 (low FolR1) human tumor cells induced by 16D5 TCB and its corresponding CD3 deamidation variants 16D5 TCB N100A and 16D5 TCB S100aA (FIG. 30A) and 9D11 TCB and its demidation variants 9D11 TCB N100A and 9D11 TCB S100aA (FIG. 30B) (E:T=10:1, effectors human PBMCs, incubation time 24 h). DP47 TCB was included as non-binding control.

FIGS. 31A-C show mean fluorescence intensity and tumor cell lysis.

FIGS. 35A-D show binding of intermediate FolR1 binders (6E10 TCB, 14B1 TCB and 9C7 TCB), 16D5 TCB and 36F2 TCB to HEK293T cells expressing either human or mouse FolR1 or FolR2.

FIG. 36A-F show T-cell killing of Hela (high FolR1 expression), SKov-3 (medium FolR1 expression) and HT-29 (low FolR1 expression) human tumor cells induced by intermediate FolR1 binders (6E10 TCB, 14B1 TCB and 9C7 TCB), 16D5 TCB and 36F2 TCB after 24 h (A-C) and 48 h (D-F) of incubation. Human PBMCs were used as effector cells (E:T=10:1).

FIG. 37A-F shows T-cell killing of Hela (high FolR1 expression), SKov-3 (medium FolR1 expression) and HT-29 (low FolR1 expression) human tumor cells induced by affinity reduced 16D5 variants (16D5-G49S/S93A TCB, 16D5-G49S/K53A TCB, 16D5 W96Y TCB, 16D5 W96Y/D52E TCB), 16D5 TCB and 36F2 TCB after 24 h (FIG. 38A-C) and 48 h (FIG. 38D-F) of incubation. Human PBMCs were used as effector cells (E:T=10:1).

FIG. 38A-F show T-cell killing of primary human cells from retinal pigment epithelium and renal cortical epithelium induced by affinity reduced 16D5 variants (16D5-G49S/S93A TCB, 16D5 W96Y/D52E TCB), 16D5 TCB, 36F2 TCB and the intermediate FolR1 binder 14B1 TCB was assessed after 24 h (FIG. 39A-C) and 48 h (FIG. 39D-F) of incubation (E:T=10:1, effectors human PBMCs). HT-29 cells (low FolR1expression) were included as control cell line and DP47 TCB served as non-binding control.

FIGS. 40A-G show in vivo efficacy of FOLR1 TCB constructs (16D5, 16D5 G49S/S93A and 16D5 W96Y/D52E) after human PBMC transfer in Hela-bearing NOG mice.

DETAILED DESCRIPTION OF THE INVENTION

Definitions

Figure 1B:
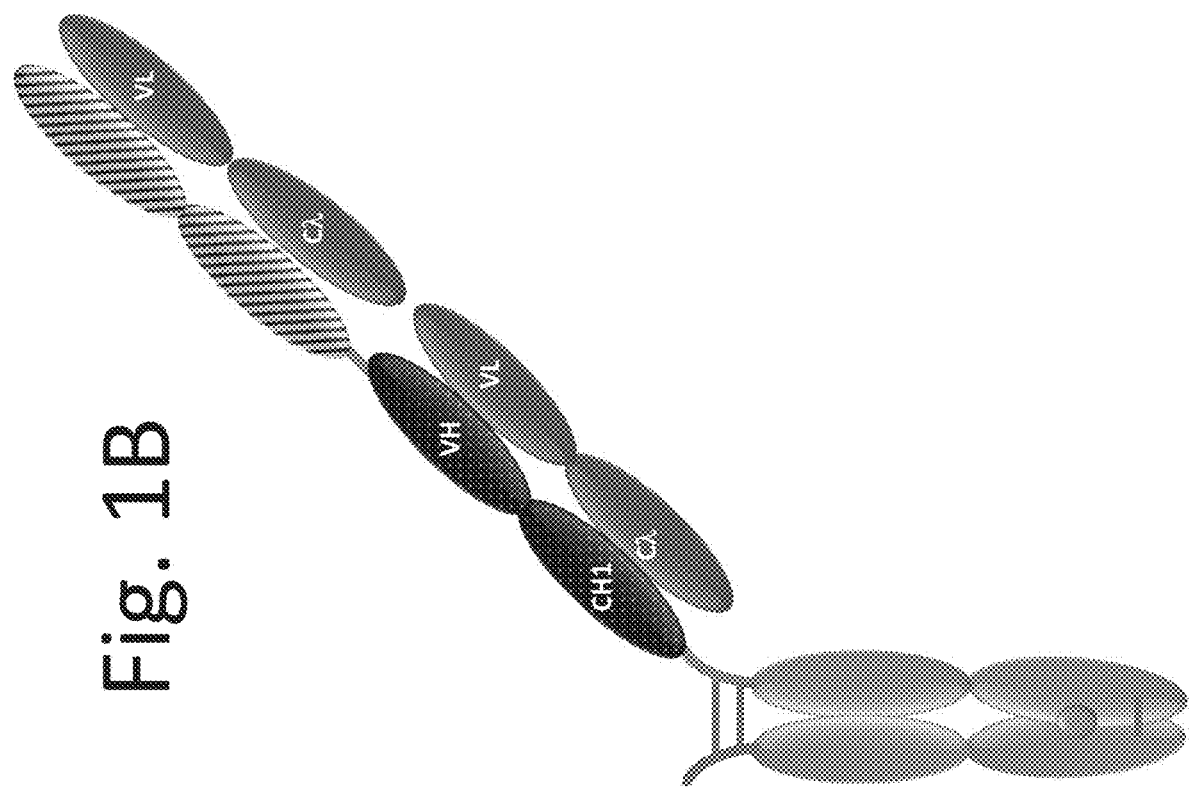
Figure 1C:
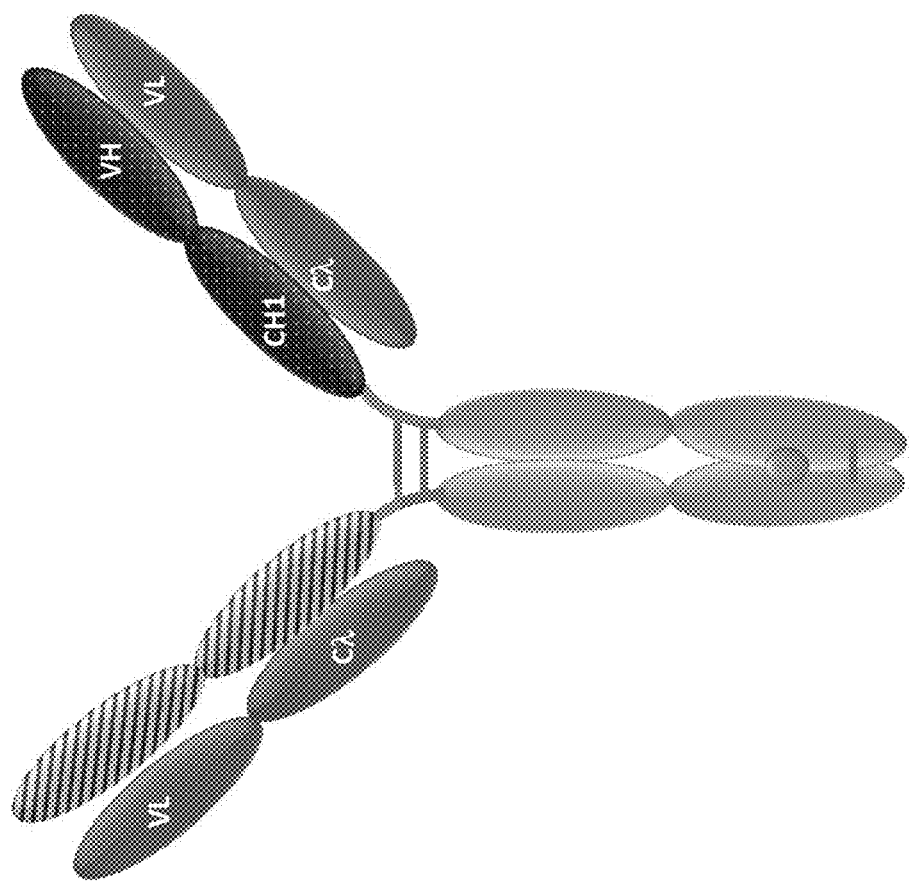
Figure 1D:
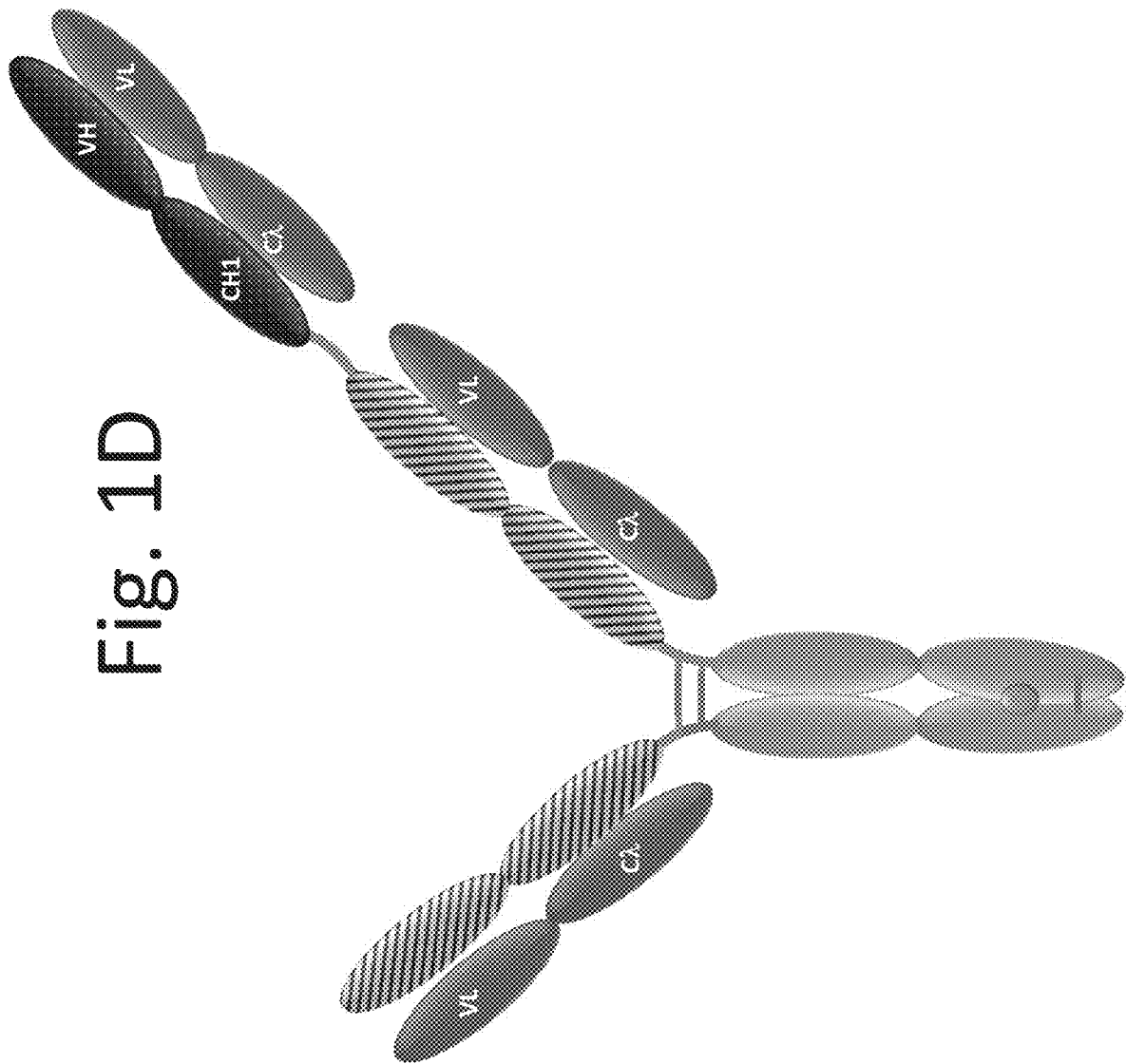

Terms are used herein as generally used in the art, unless otherwise defined in the following.

As used herein, the term "antigen binding molecule" refers in its broadest sense to a molecule that specifically binds an antigenic determinant. Examples of antigen binding molecules are immunoglobulins and derivatives, e.g. fragments, thereof.

The term "bispecific" means that the antigen binding molecule is able to specifically bind to at least two distinct antigenic determinants. Typically, a bispecific antigen binding molecule comprises at least two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigen binding moiety" refers to a polypeptide molecule that specifically binds to an antigenic determinant. In one embodiment, an antigen binding moiety is able to direct the entity to which it is attached (e.g. a second antigen binding moiety) to a target site, for example to a specific type of tumor cell or tumor stroma bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein, e.g., FolR1 and CD3, can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants. Exemplary human proteins useful as antigens include, but are not limited to: FolR1 (Folate receptor alpha (FRA); Folate binding protein (FBP); human FolR1 UniProt no.: P15328; murine FolR1 UniProt no.: P35846; cynomolgus FolR1 UniProt no.: G7PR14) and CD3, particularly the epsilon subunit of CD3 (see UniProt no. P07766 (version 130), NCBI RefSeq no. NP_000724.1, SEQ ID NO:150 for the human sequence; or UniProt no. Q95LI5 (version 49), NCBI GenBank no. BAB71849.1, for the cynomolgus [Macaca fascicularis] sequence). The T cell activating bispecific antigen binding molecule of the invention binds to an epitope of CD3 or a target cell antigen that is conserved among the CD3 or target antigen from different species. In certain embodiments the T cell activating bispecific antigen binding molecule of the invention binds to CD3 and FolR1, but does not bind to FolR2 (Folate receptor beta; FRB; human FolR2 UniProt no.: P14207) or FolR3 (Folate receptor gamma; human FolR3 UniProt no.: P41439).

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma. In particular "target cell antigen" refers to Folate Receptor 1.

As used herein, the terms "first" and "second" with respect to antigen binding moieties etc., are used for convenience of distinguishing when there is more than one of each type of moiety. Use of these terms is not intended to confer a specific order or orientation of the T cell activating bispecific antigen binding molecule unless explicitly so stated.

A "Fab molecule" refers to a protein consisting of the VH and CH1 domain of the heavy chain (the "Fab heavy chain") and the VL and CL domain of the light chain (the "Fab light chain") of an immunoglobulin.

The term "Fab molecules having identical VLCL light chains" as used therein refers to binders that share one light chain but still have separate specificities, e.g., can bind CD3 or FolR1. In some embodiments the T- cell activating bispecific molecules comprise at least two Fab molecules having identical VLCL light chains. The corresponding heavy chains are remodeled and confer specific binding to the T cell activating bispecific antigen CD3 and the target cell antigen FolR1, respectively.

By "fused" is meant that the components (e.g. a Fab molecule and an Fc domain subunit) are linked by peptide bonds, either directly or via one or more peptide linkers.

As used herein, the term "single-chain" refers to a molecule comprising amino acid monomers linearly linked by peptide bonds. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule.

By a "crossover" Fab molecule (also termed "Crossfab") is meant a Fab molecule wherein either the variable regions or the constant regions of the Fab heavy and light chain are exchanged, i.e. the crossover Fab molecule comprises a peptide chain composed of the light chain variable region and the heavy chain constant region, and a peptide chain composed of the heavy chain variable region and the light chain constant region. For clarity, in a crossover Fab molecule wherein the variable regions of the Fab light chain and the Fab heavy chain are exchanged, the peptide chain comprising the heavy chain constant region is referred to herein as the "heavy chain" of the crossover Fab molecule. Conversely, in a crossover Fab molecule wherein the constant regions of the Fab light chain and the Fab heavy chain are exchanged, the peptide chain comprising the heavy chain variable region is referred to herein as the "heavy chain" of the crossover Fab molecule. An antibody that comprises one or more CrossFabs is referred to herein as "CrossMab."

In contrast thereto, by a "conventional" Fab molecule is meant a Fab molecule in its natural format, i.e. comprising a heavy chain composed of the heavy chain variable and constant regions (VH-CH1), and a light chain composed of the light chain variable and constant regions (VL-CL).

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

The polypeptide sequences of the sequence listing are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, G329, P329G, or Pro329Gly.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator. By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, T cell activating bispecific antigen binding molecules of the invention are used to delay development of a disease or to slow the progression of a disease.

The term "antagonist" is used in the broadest sense, and includes any molecule that partially or fully blocks, inhibits, or neutralizes a biological activity of a native polypeptide disclosed herein. In a similar manner, the term "agonist" is used in the broadest sense and includes any molecule that induces a biological activity of a native polypeptide disclosed herein. Suitable agonist or antagonist molecules specifically include agonist or antagonist antibodies or antibody fragments, including engineered antibody fragments, fragments or amino acid sequence variants of native polypeptides, peptides, antisense oligonucleotides, small organic molecules, etc. Methods for identifying agonists or antagonists of a polypeptide may comprise contacting a polypeptide with a candidate agonist or antagonist molecule and measuring a detectable change in one or more biological activities normally associated with the polypeptide.

The term "package insert" is used to refer to instructions customarily included in commercial packages of therapeutic products, that contain information about the indications, usage, dosage, administration, combination therapy, contraindications and/or warnings concerning the use of such therapeutic products.

All references, publication, patents and patent applications disclosed herein are hereby incorporated by reference in their entirety.

DETAILED DESCRIPTION OF THE EMBODIMENTS

The T cell activating bispecific antigen binding molecule of the invention is bispecific, i.e. it comprises at least two antigen binding moieties capable of specific binding to two distinct antigenic determinants, i.e. to CD3 and to FolR1. According to the invention, the antigen binding moieties are Fab molecules (i.e. antigen binding domains composed of a heavy and a light chain, each comprising a variable and a constant region). In one embodiment said Fab molecules are human. In another embodiment said Fab molecules are humanized. In yet another embodiment said Fab molecules comprise human heavy and light chain constant regions.

The T cell activating bispecific antigen binding molecule of the invention is capable of simultaneous binding to the target cell antigen FolR1 and CD3. In one embodiment, the T cell activating bispecific antigen binding molecule is capable of crosslinking a T cell and a FolR1 expressing target cell by simultaneous binding to the target cell antigen FolR1 and CD3. In an even more particular embodiment, such simultaneous binding results in lysis of the FolR1 expressing target cell, particularly a FolR1 expressing tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the T cell activating bispecific antigen binding molecule to CD3 without simultaneous binding to the target cell antigen FolR1 does not result in T cell activation.

In one embodiment, the T cell activating bispecific antigen binding molecule is capable of re-directing cytotoxic activity of a T cell to a FolR1 expressing target cell. In a particular embodiment, said re-direction is independent of MHC-mediated peptide antigen presentation by the target cell and and/or specificity of the T cell.

Particularly, a T cell according to some of the embodiments of the invention is a cytotoxic T cell. In some embodiments the T cell is a CD4$^+$ or a CD8$^+$ T cell, particularly a CD8$^+$ T cell. The T cell activating bispecific antigen binding molecule of the invention comprises at least one antigen binding moiety capable of binding to CD3 (also referred to herein as an "CD3 antigen binding moiety" or "first antigen binding moiety"). In a particular embodiment, the T cell activating bispecific antigen binding molecule comprises not more than one antigen binding moiety capable of specific binding to CD3. In one embodiment the T cell activating bispecific antigen binding molecule provides monovalent binding to CD3. In a particular embodiment CD3 is human CD3 or cynomolgus CD3, most particularly human CD3. In a particular embodiment the CD3 antigen binding moiety is cross-reactive for (i.e. specifically binds to) human and cynomolgus CD3. In some embodiments, the first antigen binding moiety is capable of specific binding to the epsilon subunit of CD3 (see UniProt no. P07766 (version 130), NCBI RefSeq no. NP_000724.1, SEQ ID NO:150 for the human sequence; UniProt no. Q95LI5 (version 49), NCBI GenBank no. BAB71849.1, for the cynomolgus [*Macaca fascicularis*] sequence).

In some embodiments, the CD3 antigen binding moiety comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34.

In one embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34.

In one embodiment the CD3 antigen binding moiety comprises a variable heavy chain comprising an amino acid sequence of: SEQ ID NO: 36 and a variable light chain comprising an amino acid sequence of: SEQ ID NO: 31.

In one embodiment the CD3 antigen binding moiety comprises a heavy chain variable region sequence that is at least about 95%, 96%, 97%, 98%, 99% or 100% identical to SEQ ID NO: 36 and a light chain variable region sequence that is at least about 95%, 96%, 97%, 98%, 99% or 100% identical to SEQ ID NO: 31.

The T cell activating bispecific antigen binding molecule of the invention comprises at least one antigen binding moiety capable of binding to the target cell antigen FolR1 (also referred to herein as an "FolR1 binding moiety" or "second" or "third" antigen binding moiety). In one embodiment, the antigen binding moiety capable of binding to the target cell antigen FolR1 does not bind to FolR2 or FolR3. In a particular embodiment the FolR1 antigen binding moiety is cross-reactive for (i.e. specifically binds to) human and cynomolgus FolR1. In certain embodiments, the T cell activating bispecific antigen binding molecule comprises two antigen binding moieties capable of binding to the target cell antigen FolR1. In a particular such embodiment, each of these antigen binding moieties specifically binds to the same antigenic determinant. In an even more particular embodiment, all of these antigen binding moieties are identical. In one embodiment the T cell activating bispecific antigen binding molecule comprises not more than two antigen binding moieties capable of binding to FolR1.

The FolR1 binding moiety is generally a Fab molecule that specifically binds to FolR1 and is able to direct the T cell activating bispecific antigen binding molecule to which it is connected to a target site, for example to a specific type of tumor cell that expresses FolR1.

In one aspect the present invention provides a T cell activating bispecific antigen binding molecule comprising
  (i) a first antigen binding moiety which is a Fab molecule capable of specific binding to CD3, and which comprises at least one heavy chain complementarity determining region (CDR) selected from the group consisting SEQ ID NO: 37, SEQ ID NO: 38 and SEQ ID NO: 39 and at least one light chain CDR selected from the group of SEQ ID NO: 32, SEQ ID NO: 33, SEQ ID NO: 34; and
  (ii) a second antigen binding moiety which is a Fab molecule capable of specific binding to Folate Receptor 1 (FolR1).

In one embodiment the first antigen binding moiety which is a Fab molecule capable of specific binding to CD3 comprises a variable heavy chain comprising an amino acid sequence of SEQ ID NO: 36 and a variable light chain comprising an amino acid sequence of SEQ ID NO: 31.

In one embodiment the T cell activating bispecific antigen binding molecule additionally comprises
  (iii) a third antigen binding moiety which is a Fab molecule capable of specific binding to FolR1.

In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

In one embodiment the T cell activating bispecific antigen binding molecule of any of the above embodiments additionally comprises an Fc domain composed of a first and a second subunit capable of stable association.

In one embodiment the first antigen binding moiety and the second antigen binding moiety are each fused at the C-terminus of the Fab heavy chain to the N-terminus of the first or second subunit of the Fc domain.

In one embodiment the third antigen binding moiety is fused at the C-terminus of the Fab heavy chain to the N-terminus of the Fab heavy chain of the first antigen binding moiety, optionally via a peptide linker.

In a further particular embodiment, not more than one antigen binding moiety capable of specific binding to CD3 is present in the T cell activating bispecific antigen binding molecule (i.e. the T cell activating bispecific antigen binding molecule provides monovalent binding to CD3).

T Cell Activating Bispecific Antigen Binding Molecule with a Common Light Chain

The inventors of the present invention generated a bispecific antibody wherein the binding moieties share a common light chain that retains the specificity and efficacy of the parent monospecific antibody for CD3 and can bind a second antigen (e.g., FolR1) using the same light chain. The generation of a bispecific molecule with a common light chain that retains the binding properties of the parent antibody is not straight-forward as the common CDRs of the hybrid light chain have to effectuate the binding specificity for both targets. In one aspect the present invention provides a T cell activating bispecific antigen binding molecule comprising a first and a second antigen binding moiety, one of which is a Fab molecule capable of specific binding to CD3 and the other one of which is a Fab molecule capable of specific binding to FolR1, wherein the first and the second Fab molecule have identical VLCL light chains. In one embodiment said identical light chain (VLCL) comprises the light chain CDRs of SEQ ID NO: 32, SEQ ID NO: 33 and SEQ ID NO: 34. In one embodiment said identical light chain (VLCL) comprises SEQ ID NO. 35.

In one embodiment the present invention provides a T cell activating bispecific antigen binding molecule comprising
  (i) a first antigen binding moiety which is a Fab molecule capable of specific binding to CD3, and which comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
  (ii) a second antigen binding moiety which is a Fab molecule capable of specific binding to Folate Receptor 1 (FolR1) and which comprises at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 33, SEQ ID NO: 34.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 16, the heavy chain CDR2 of SEQ ID NO: 17, the heavy chain CDR3 of SEQ ID NO:18, the light chain CDR1 of SEQ ID NO: 32, the light chain CDR2 of SEQ ID NO: 33, and the light chain CDR3 of SEQ ID NO:34.

In one embodiment the present invention provides a T cell activating bispecific antigen binding molecule comprising
(i) a first antigen binding moiety which is a Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO: 15 and a variable light chain comprising an amino acid sequence of SEQ ID NO: 31.

In one embodiment the present invention provides a T cell activating bispecific antigen binding molecule comprising
(i) a first antigen binding moiety which is a Fab molecule capable of specific binding to CD3, and which comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety which is a Fab molecule capable of specific binding to Folate Receptor 1 (FolR1) and which comprises at least one heavy chain complementarity determining region (CDR) selected from the group consisting of SEQ ID NO: 16, SEQ ID NO: 275 and SEQ ID NO: 315 and at least one light chain CDR selected from the group of SEQ ID NO: 32, SEQ ID NO: 33, SEQ ID NO: 34.

In one embodiment the present invention provides a T cell activating bispecific antigen binding molecule comprising
(i) a first antigen binding moiety which is a Fab molecule capable of specific binding to CD3, and which comprises the heavy chain complementarity determining region (CDR) amino acid sequences of SEQ ID NO: 37, SEQ ID NO: 38 and SEQ ID NO: 39, and the light chain CDR amino acid sequences of SEQ ID NO: 32, SEQ ID NO: 33 and SEQ ID NO: 34;
(ii) a second antigen binding moiety which is a Fab molecule capable of specific binding to Folate Receptor 1 (FolR1) and which comprises the heavy chain complementarity determining region (CDR) amino acid sequences of SEQ ID NO: 16, SEQ ID NO: 275 and SEQ ID NO: 315, and the light chain CDR amino acid sequences of SEQ ID NO: 32, SEQ ID NO: 33, and SEQ ID NO: 34.

In one embodiment the present invention provides a T cell activating bispecific antigen binding molecule comprising
(i) a first antigen binding moiety which is a Fab molecule capable of specific binding to CD3 comprising a variable heavy chain comprising an amino acid sequence of SEQ ID NO: 36 and a variable light chain comprising an amino acid sequence of SEQ ID NO: 31;
(ii) a second antigen binding moiety which is a Fab molecule capable of specific binding to Folate Receptor 1 (FolR1) comprising a variable heavy chain comprising an amino acid sequence of SEQ ID NO: 274 and a variable light chain comprising an amino acid sequence of SEQ ID NO: 31.

In one embodiment the present invention provides a T cell activating bispecific antigen binding molecule comprising
(i) a first antigen binding moiety which is a Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO: 15 and a variable light chain comprising an amino acid sequence of SEQ ID NO: 31.

In a further embodiment, the antigen binding moiety that is specific for FolR1 comprises a heavy chain variable region sequence that is at least about 95%, 96%, 97%, 98%, 99% or 100% identical to SEQ ID NO:15 and a light chain variable region sequence that is at least about 95%, 96%, 97%, 98%, 99% or 100% identical to SEQ ID NO: 31 or variants thereof that retain functionality. In one embodiment the T cell activating bispecific antigen binding molecule comprises a polypeptide sequence that is at least about 95%, 96%, 97%, 98%, 99% or 100% identical to SEQ ID NO: 36, a polypeptide sequence that is at least about 95%, 96%, 97%, 98%, 99% or 100% identical to SEQ ID NO:15, and a polypeptide sequence that is at least about 95%, 96%, 97%, 98%, 99% or 100% identical to SEQ ID NO: 31.

In one embodiment the T cell activating bispecific antigen binding molecule additionally comprises
(iii) a third antigen binding moiety (which is a Fab molecule) capable of specific binding to FolR1.

In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

Hence in one embodiment the present invention provides a T cell activating bispecific antigen binding molecule comprising
(i) a first antigen binding moiety which is a Fab molecule capable of specific binding to CD3, and which comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety which is a Fab molecule capable of specific binding to Folate Receptor 1 (FolR1) and which comprises at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 33, SEQ ID NO: 34.
(iii) a third antigen binding moiety which is a Fab molecule capable of specific binding to Folate Receptor 1 (FolR1) and which comprises at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 33, SEQ ID NO: 34.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 16, the heavy chain CDR2 of SEQ ID NO: 17, the heavy chain CDR3 of SEQ ID NO:18, the light chain CDR1 of SEQ ID NO: 32, the light chain CDR2 of SEQ ID NO: 33, and the light chain CDR3 of SEQ ID NO:34.

In one embodiment the present invention provides a T cell activating bispecific antigen binding molecule comprising
(i) a first antigen binding moiety which is a Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO: 15 and a variable light chain comprising an amino acid sequence of SEQ ID NO: 31.
(iii) a third antigen binding moiety which is a Fab molecule capable of specific binding to Folate Receptor 1 (FolR1) comprising a variable heavy chain comprising an amino acid sequence of SEQ ID NO: 15 and a variable light chain comprising an amino acid sequence of SEQ ID NO: 31.

Thus, in one embodiment, the invention relates to bispecific molecules wherein at least two binding moieties have identical light chains and corresponding remodeled heavy chains that confer the specific binding to the T cell activating antigen CD3 and the target cell antigen FolR1, respectively. The use of this so-called 'common light chain' principle, i.e. combining two binders that share one light chain but still have separate specificities, prevents light chain mispairing. Thus, there are less side products during production, facilitating the homogenous preparation of T cell activating bispecific antigen binding molecules.

The components of the T cell activating bispecific antigen binding molecule can be fused to each other in a variety of configurations. Exemplary configurations are depicted in FIGS. 1A-I and are further described below.

In some embodiments, said T cell activating bispecific antigen binding molecule further comprises an Fc domain composed of a first and a second subunit capable of stable association. Below exemplary embodiments of T cell activating bispecific antigen binding molecule comprising an Fc domain are described.

T Cell Activating Bispecific Antigen Binding Molecule with a Crossover Fab Fragment The inventors of the present invention generated a second bispecific antibody format wherein one of the binding moieties is a crossover Fab fragment. In one aspect of the invention a monovalent bispecific antibody is provided, wherein one of the Fab fragments of an IgG molecule is replaced by a crossover Fab fragment. Crossover Fab fragments are Fab fragments wherein either the variable regions or the constant regions of the heavy and light chain are exchanged. Bispecific antibody formats comprising crossover Fab fragments have been described, for example, in WO2009080252, WO2009080253, WO2009080251, WO2009080254, WO2010/136172, WO2010/145792 and WO2013/026831. In a particular embodiment, the first antigen binding moiety is a crossover Fab molecule wherein either the variable or the constant regions of the Fab light chain and the Fab heavy chain are exchanged. Such modification prevent mispairing of heavy and light chains from different Fab molecules, thereby improving the yield and purity of the T cell activating bispecific antigen binding molecule of the invention in recombinant production. In a particular crossover Fab molecule useful for the T cell activating bispecific antigen binding molecule of the invention, the variable regions of the Fab light chain and the Fab heavy chain are exchanged. In another crossover Fab molecule useful for the T cell activating bispecific antigen binding molecule of the invention, the constant regions of the Fab light chain and the Fab heavy chain are exchanged.

In one embodiment the T cell activating bispecific antigen binding molecule comprises
(i) a first antigen binding moiety which is a crossover Fab molecule capable of specific binding to CD3, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
(ii) a second antigen binding moiety capable of specific binding to Folate Receptor 1 (FolR1) comprising at least one heavy chain complementarity determining region (CDR) selected from the group consisting of SEQ ID NO: 8, SEQ ID NO: 56 and SEQ ID NO: 57 and at least one light chain CDR selected from the group of SEQ ID NO: 59, SEQ ID NO: 60, SEQ ID NO: 65.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 8, the heavy chain CDR2 of SEQ ID NO: 56, the heavy chain CDR3 of SEQ ID NO:57, the light chain CDR1 of SEQ ID NO: 59, the light chain CDR2 of SEQ ID NO: 60, and the light chain CDR3 of SEQ ID NO:65.

In one embodiment, the second antigen binding moiety is a conventional Fab molecule.

In one embodiment the T cell activating bispecific antigen binding molecule comprises
(i) a first antigen binding moiety which is a crossover Fab molecule capable of specific binding to CD3 comprising a variable heavy chain comprising an amino acid sequence of SEQ ID NO: 36 and a variable light chain comprising an amino acid sequence of SEQ ID NO: 31.
(ii) a second antigen binding moiety which is a Fab molecule capable of specific binding to Folate Receptor 1 (FolR1) comprising a variable heavy chain comprising an amino acid sequence of SEQ ID NO: 55 and a variable light chain comprising an amino acid sequence of SEQ ID NO: 64.

In one embodiment, the second antigen binding moiety is a conventional Fab molecule.

In a further embodiment, the antigen binding moiety that is specific for FolR1 comprises a heavy chain variable region sequence that is at least about 95%, 96%, 97%, 98%, 99% or 100% identical to SEQ ID NO:55 and a light chain variable region sequence that is at least about 95%, 96%, 97%, 98%, 99% or 100% identical to SEQ ID NO: 64 or variants thereof that retain functionality.

In one embodiment the T cell activating bispecific antigen binding molecule comprises a polypeptide sequence that is at least about 95%, 96%, 97%, 98%, 99% or 100% identical to SEQ ID NO: 36, a polypeptide sequence that is at least about 95%, 96%, 97%, 98%, 99% or 100% identical to SEQ ID NO: 31, a polypeptide sequence that is at least about 95%, 96%, 97%, 98%, 99% or 100% identical to SEQ ID NO:55, and a polypeptide sequence that is at least about 95%, 96%, 97%, 98%, 99% or 100% identical to SEQ ID NO: 64.

In one embodiment the T cell activating bispecific antigen binding molecule additionally comprises
  (iii) a third antigen binding moiety capable of specific binding to FolR1.

In one embodiment, the third antigen binding moiety is a conventional Fab molecule. In one embodiment, the third antigen binding moiety is a crossover Fab molecule.

In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

In one embodiment the T cell activating bispecific antigen binding molecule comprises
  (i) a first antigen binding moiety which is a crossover Fab molecule capable of specific binding to CD3, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
  (ii) a second antigen binding moiety capable of specific binding to Folate Receptor 1 (FolR1) comprising at least one heavy chain complementarity determining region (CDR) selected from the group consisting of SEQ ID NO: 8, SEQ ID NO: 56 and SEQ ID NO: 57 and at least one light chain CDR selected from the group of SEQ ID NO: 59, SEQ ID NO: 60, SEQ ID NO: 65.
  (iii) a third antigen binding moiety capable of specific binding to Folate Receptor 1 (FolR1) comprising at least one heavy chain complementarity determining region (CDR) selected from the group consisting of SEQ ID NO: 8, SEQ ID NO: 56 and SEQ ID NO: 57 and at least one light chain CDR selected from the group of SEQ ID NO: 59, SEQ ID NO: 60, SEQ ID NO: 65.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 8, the heavy chain CDR2 of SEQ ID NO: 56, the heavy chain CDR3 of SEQ ID NO:57, the light chain CDR1 of SEQ ID NO: 59, the light chain CDR2 of SEQ ID NO: 60, and the light chain CDR3 of SEQ ID NO:65.

In one embodiment, the second antigen binding moiety and the third antigen binding moiety are both a conventional Fab molecule.

In one embodiment the T cell activating bispecific antigen binding molecule comprises
  (i) a first antigen binding moiety which is a crossover Fab molecule capable of specific binding to CD3 comprising a variable heavy chain comprising an amino acid sequence of SEQ ID NO: 36 and a variable light chain comprising an amino acid sequence of SEQ ID NO: 31.
  (ii) a second antigen binding moiety which is a Fab molecule capable of specific binding to Folate Receptor 1 (FolR1) comprising a variable heavy chain comprising an amino acid sequence of SEQ ID NO: 55 and a variable light chain comprising an amino acid sequence of SEQ ID NO: 64.
  (iii) a third antigen binding moiety which is a Fab molecule capable of specific binding to Folate Receptor 1 (FolR1) comprising a variable heavy chain comprising an amino acid sequence of SEQ ID NO: 55 and a variable light chain comprising an amino acid sequence of SEQ ID NO: 64.

In one embodiment, the second antigen binding moiety and the third antigen binding moiety are both a conventional Fab molecule.

In one embodiment the T cell activating bispecific antigen binding molecule comprises
  (i) a first antigen binding moiety which is a crossover Fab molecule capable of specific binding to CD3, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;
  (ii) a second antigen binding moiety capable of specific binding to Folate Receptor 1 (FolR1) comprising at least one heavy chain complementarity determining region (CDR) selected from the group consisting of SEQ ID NO: 8, SEQ ID NO: 9 and SEQ ID NO: 50 and at least one light chain CDR selected from the group of SEQ ID NO: 52, SEQ ID NO: 53, SEQ ID NO: 54.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

In one embodiment, the second antigen binding moiety is a conventional Fab molecule. In one embodiment, the second antigen binding moiety is a crossover Fab molecule.

In one embodiment the T cell activating bispecific antigen binding molecule comprises
  (i) a first antigen binding moiety which is a crossover Fab molecule capable of specific binding to CD3 comprising a variable heavy chain comprising an amino acid sequence of SEQ ID NO: 36 and a variable light chain comprising an amino acid sequence of SEQ ID NO: 31.
  (ii) a second antigen binding moiety which is a Fab molecule capable of specific binding to Folate Receptor 1 (FolR1) comprising a variable heavy chain comprising an amino acid sequence of SEQ ID NO: 49 and a variable light chain comprising an amino acid sequence of SEQ ID NO: 51.

In one embodiment, the second antigen binding moiety is a conventional Fab molecule. In one embodiment, the second antigen binding moiety is a crossover Fab molecule.

In a further embodiment, the antigen binding moiety that is specific for FolR1 comprises a heavy chain variable region sequence that is at least about 95%, 96%, 97%, 98%, 99% or 100% identical to SEQ ID NO:49 and a light chain variable region sequence that is at least about 95%, 96%, 97%, 98%, 99% or 100% identical to SEQ ID NO: 51 or variants thereof that retain functionality. In one embodiment the T cell activating bispecific antigen binding molecule comprises a polypeptide sequence that is at least about 95%, 96%, 97%, 98%, 99% or 100% identical to SEQ ID NO: 36, a polypeptide sequence that is at least about 95%, 96%, 97%, 98%, 99% or 100% identical to SEQ ID NO: 31, a polypeptide sequence that is at least about 95%, 96%, 97%, 98%, 99% or 100% identical to SEQ ID NO:49, and a polypeptide sequence that is at least about 95%, 96%, 97%, 98%, 99% or 100% identical to SEQ ID NO: 51.

In one embodiment the T cell activating bispecific antigen binding molecule additionally comprises (iii) a third antigen binding moiety capable of specific binding to FolR1.

In one embodiment, the third antigen binding moiety is a conventional Fab molecule. In one embodiment, the second antigen binding moiety is a crossover Fab molecule.

In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety.

In one embodiment the T cell activating bispecific antigen binding molecule comprises (i) a first antigen binding moiety which is a crossover Fab molecule capable of specific binding to CD3, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33, SEQ ID NO: 34;

(ii) a second antigen binding moiety capable of specific binding to Folate Receptor 1 (FolR1) comprising at least one heavy chain complementarity determining region (CDR) selected from the group consisting of SEQ ID NO: 8, SEQ ID NO: 9 and SEQ ID NO: 49 and at least one light chain CDR selected from the group of SEQ ID NO: 52, SEQ ID NO: 53, SEQ ID NO: 54.

(iii) a third antigen binding moiety capable of specific binding to Folate Receptor 1 (FolR1) comprising at least one heavy chain complementarity determining region (CDR) selected from the group consisting of SEQ ID NO: 8, SEQ ID NO: 9 and SEQ ID NO: 50 and at least one light chain CDR selected from the group of SEQ ID NO: 52, SEQ ID NO: 53, SEQ ID NO: 54.

In one such embodiment the CD3 antigen binding moiety comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and the FolR1 antigen binding moiety comprises the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

In one embodiment, the second antigen binding moiety and the third antigen binding moiety are both a conventional Fab molecule.

In one embodiment the T cell activating bispecific antigen binding molecule comprises (i) a first antigen binding moiety which is a crossover Fab molecule capable of specific binding to CD3 comprising a variable heavy chain comprising an amino acid sequence of SEQ ID NO: 36 and a variable light chain comprising an amino acid sequence of SEQ ID NO: 31.

(ii) a second antigen binding moiety which is a Fab molecule capable of specific binding to Folate Receptor 1 (FolR1) comprising a variable heavy chain comprising an amino acid sequence of SEQ ID NO: 49 and a variable light chain comprising an amino acid sequence of SEQ ID NO: 51.

(iii) a third antigen binding moiety which is a Fab molecule capable of specific binding to Folate Receptor 1 (FolR1) comprising a variable heavy chain comprising an amino acid sequence of SEQ ID NO: 49 and a variable light chain comprising an amino acid sequence of SEQ ID NO: 51.

In one embodiment, the second antigen binding moiety and the third antigen binding moiety are both a conventional Fab molecule.

Thus, in one embodiment, the invention relates to bispecific molecules wherein two binding moieties confer specific binding to FolR1 and one binding moiety confers specificity to the T cell activating antigen CD3. One of the heavy chains is modified to ensure proper pairing of the heavy and light chains, thus eliminating the need for a common light chain approach. The presence of two FolR1 binding sites enables appropriate engagement with the target antigen FolR1 and the activation of T cells.

The components of the T cell activating bispecific antigen binding molecule can be fused to each other in a variety of configurations. Exemplary configurations are depicted in FIGS. 1A-I and are further described below.

In some embodiments, said T cell activating bispecific antigen binding molecule further comprises an Fc domain composed of a first and a second subunit capable of stable association. Below exemplary embodiments of T cell activating bispecific antigen binding molecule comprising an Fc domain are described.

T Cell Activating Bispecific Antigen Binding Molecule Formats

As depicted above and in FIGS. 1A-I, in one embodiment the T cell activating bispecific antigen binding molecules comprise at least two Fab fragments having identical light chains (VLCL) and having different heavy chains (VHCL) which confer the specificities to two different antigens, i.e. one Fab fragment is capable of specific binding to a T cell activating antigen CD3 and the other Fab fragment is capable of specific binding to the target cell antigen FolR1.

In another embodiment the T cell activating bispecific antigen binding molecule comprises at least two antigen binding moieties (Fab molecules), one of which is a crossover Fab molecule and one of which is a conventional Fab molecule. In one such embodiment the first antigen binding moiety capable of specific binding to CD3 is a crossover Fab molecule and the second antigen binding moiety capable of specific binding to FolR is a conventional Fab molecule.

These components of the T cell activating bispecific antigen binding molecule can be fused to each other in a variety of configurations. Exemplary configurations are depicted in FIGS. 1A-I.

In some embodiments, the first and second antigen binding moiety are each fused at the C-terminus of the Fab heavy chain to the N-terminus of the first or the second subunit of the Fc domain. In a specific such embodiment, the T cell activating bispecific antigen binding molecule essentially consists of a first and a second antigen binding moiety, an Fc domain composed of a first and a second subunit, and optionally one or more peptide linkers, wherein the first and second antigen binding moiety are each fused at the C-terminus of the Fab heavy chain to the N-terminus of the first or the second subunit of the Fc domain. In one such embodiment the first and second antigen binding moiety both are Fab fragments and have identical light chains (VLCL). In another such embodiment the first antigen binding moiety capable of specific binding to CD3 is a crossover Fab molecule and the second antigen binding moiety capable of specific binding to FolR is a conventional Fab molecule.

In one embodiment, the second antigen binding moiety is fused at the C-terminus of the Fab heavy chain to the N-terminus of the first or the second subunit of the Fc domain and the first antigen binding moiety is fused at the C-terminus of the Fab heavy chain to the N-terminus of the Fab heavy chain of the second antigen binding moiety. In a specific such embodiment, the T cell activating bispecific antigen binding molecule essentially consists of a first and a second antigen binding moiety, an Fc domain composed of a first and a second subunit, and optionally one or more peptide linkers, wherein the first antigen binding moiety is fused at the C-terminus of the Fab heavy chain to the N-terminus of the Fab heavy chain of the second antigen binding moiety, and the second antigen binding moiety is fused at the C-terminus of the Fab heavy chain to the N-terminus of the first or the second subunit of the Fc domain. In one such embodiment the first and second antigen binding moiety both are Fab fragments and have identical light chains (VLCL). In another such embodiment the first antigen binding moiety capable of specific binding to CD3 is a crossover Fab molecule and the second antigen binding moiety capable of specific binding to FolR is a conventional Fab molecule. Optionally, the Fab light chain of the first antigen binding moiety and the Fab light chain of the second antigen binding moiety may additionally be fused to each other.

In other embodiments, the first antigen binding moiety is fused at the C-terminus of the Fab heavy chain to the N-terminus of the first or second subunit of the Fc domain. In a particular such embodiment, the second antigen binding moiety is fused at the C-terminus of the Fab heavy chain to the N-terminus of the Fab heavy chain of the first antigen binding moiety. In a specific such embodiment, the T cell activating bispecific antigen binding molecule essentially consists of a first and a second antigen binding moiety, an Fc domain composed of a first and a second subunit, and optionally one or more peptide linkers, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first or the second subunit of the Fc domain. In one such embodiment the first and second antigen binding moiety both are Fab fragments and have identical light chains (VLCL). In another such embodiment the first antigen binding moiety capable of specific binding to CD3 is a crossover Fab molecule and the second antigen binding moiety capable of specific binding to FolR is a conventional Fab molecule. Optionally, the Fab light chain of the first antigen binding moiety and the Fab light chain of the second antigen binding moiety may additionally be fused to each other.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$ (SEQ ID NO: 300), $(SG_4)_n$ (SEQ ID NO: 301), $(G_4S)_n$ (SEQ ID NO: 300) or $G_4(SG_4)_n$ (SEQ ID NO: 302) peptide linkers. "n" is generally a number between 1 and 10, typically between 2 and 4. A particularly suitable peptide linker for fusing the Fab light chains of the first and the second antigen binding moiety to each other is $(G_4S)_2$ (SEQ ID NO: 303). An exemplary peptide linker suitable for connecting the Fab heavy chains of the first and the second antigen binding moiety is EPKSC (D)-$(G_4S)_2$ (SEQ ID NOS 304 and 305). Additionally, linkers may comprise (a portion of) an immunoglobulin hinge region. Particularly where an antigen binding moiety is fused to the N-terminus of an Fc domain subunit, it may be fused via an immunoglobulin hinge region or a portion thereof, with or without an additional peptide linker.

It has been found by the inventors of the present invention that T cell activating bispecific antigen binding molecule comprising two binding moieties specific for the target cell antigen FolR have superior characteristics compared to T cell activating bispecific antigen binding molecule comprising only one binding moiety specific for the target cell antigen FolR.

Accordingly, in certain embodiments, the T cell activating bispecific antigen binding molecule of the invention further comprises a third antigen binding moiety which is a Fab molecule capable of specific binding to FolR. In one such embodiment the second and third antigen binding moiety capable of specific binding to FolR1 comprise identical heavy chain complementarity determining region (CDR) and light chain CDR sequences. In one such embodiment the third antigen binding moiety is identical to the second antigen binding moiety (i.e. they comprise the same amino acid sequences).

In one embodiment, the first and second antigen binding moiety are each fused at the C-terminus of the Fab heavy chain to the N-terminus of the first or second subunit of the Fc domain and the third antigen binding moiety is fused at the C-terminus of the Fab heavy chain to the N-terminus to the N-terminus of the Fab heavy chain of the first antigen binding moiety. In a specific such embodiment, the T cell activating bispecific antigen binding molecule essentially consists of a first, a second and a third antigen binding moiety, an Fc domain composed of a first and a second subunit, and optionally one or more peptide linkers, wherein the first and second antigen binding moiety are each fused at the C-terminus of the Fab heavy chain to the N-terminus of the first subunit of the Fc domain and the third antigen binding moiety is fused at the C-terminus of the Fab heavy chain to the N-terminus of the Fab heavy chain of the first antigen binding moiety. In one such embodiment the first, second and third antigen binding moiety are conventional Fab fragments and have identical light chains (VLCL). In another such embodiment the first antigen binding moiety capable of specific binding to CD3 is a crossover Fab molecule and the second and third antigen binding moiety capable of specific binding to FolR is a conventional Fab molecule. Optionally, the Fab light chain of the first antigen binding moiety and the Fab light chain of the third antigen binding moiety may additionally be fused to each other.

Accordingly, in certain embodiments, the T cell activating bispecific antigen binding molecule of the invention comprises five polypeptide chains that form a first, a second and a third antigen binding moiety wherein the first antigen binding moiety is capable of binding CD3 and the second and the third antigen binding moiety each are capable of binding Folate Receptor 1 (FolR1). The first and the second polypeptide chain comprise, in amino (N)-terminal to carboxyl (C)-terminal direction, a first light chain variable domain (VLD1) and a first light chain constant domain (CLD1). The third polypeptide chain comprises, in N-terminal to C-terminal direction, second light chain variable domain (VLD2) and a second heavy chain constant domain 1 (CH1D2). The fourth polypeptide chain comprises, in N-terminal to C-terminal direction, a first heavy chain variable domain (VHD1), a first heavy chain constant domain 1 (CH1D1), a first heavy chain constant domain 2 (CH2D1) and a first heavy chain constant domain 3 (CH3D1). The fifth polypeptide chain comprises VHD1, CH1D1, a second heavy chain variable domain (VHD2), a second light chain constant domain (CLD2), a second heavy chain constant domain 2 (CH2D2) and a second heavy chain constant domain 3 (CH3D2). The third polypeptide chain and VHD2 and CLD2 of the fifth polypeptide chain form the first antigen binding moiety capable of binding CD3. The second polypeptide chain and VHD1 and CH of the fifth polypeptide chain form the third binding moiety capable of binding to FolR1. The first polypeptide chain and VHD1 and CH1D1 of the fourth polypeptide chain form the second binding moiety capable of binding to FolR1.

In another embodiment, the second and the third antigen binding moiety are each fused at the C-terminus of the Fab heavy chain to the N-terminus of the first or second subunit of the Fc domain, and the first antigen binding moiety is fused at the C-terminus of the Fab heavy chain to the N-terminus of the Fab heavy chain of the second antigen binding moiety. In a specific such embodiment, the T cell activating bispecific antigen binding molecule essentially consists of a first, a second and a third antigen binding moiety, an Fc domain composed of a first and a second subunit, and optionally one or more peptide linkers, wherein the second and third antigen binding moiety are each fused at the C-terminus of the Fab heavy chain to the N-terminus of the first subunit of the Fc domain and the first antigen binding moiety is fused at the C-terminus of the Fab heavy chain to the N-terminus of the Fab heavy chain of the third antigen binding moiety. In one such embodiment the first, second and third antigen binding moiety are conventional Fab fragments and have identical light chains (VLCL). In another such embodiment the first antigen binding moiety capable of specific binding to CD3 is a crossover Fab molecule and the second and third antigen binding moiety capable of specific binding to FolR is a conventional Fab molecule. Optionally, the Fab light chain of the first antigen binding moiety and the Fab light chain of the second antigen binding moiety may additionally be fused to each other.

The antigen binding moieties may be fused to the Fc domain directly or through a peptide linker. In a particular embodiment the antigen binding moieties are each fused to the Fc domain through an immunoglobulin hinge region. In a specific embodiment, the immunoglobulin hinge region is a human IgG$_1$ hinge region.

In one embodiment the first and the second antigen binding moiety and the Fc domain are part of an immunoglobulin molecule. In a particular embodiment the immunoglobulin molecule is an IgG class immunoglobulin. In an even more particular embodiment the immunoglobulin is an IgG$_1$ subclass immunoglobulin. In another embodiment the immunoglobulin is an IgG$_4$ subclass immunoglobulin. In a further particular embodiment the immunoglobulin is a human immunoglobulin. In other embodiments the immunoglobulin is a chimeric immunoglobulin or a humanized immunoglobulin.

In a particular embodiment said T cell activating bispecific antigen binding molecule the first and the second antigen binding moiety and the Fc domain are part of an immunoglobulin molecule, and the third antigen binding moiety is fused at the C-terminus of the Fab heavy chain to the N-terminus of the Fab heavy chain of the first antigen binding moiety, wherein the first, second and third antigen binding moiety are conventional Fab fragments and have identical light chains (VLCL), wherein the first antigen binding moiety capable of specific binding to CD3 comprises at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33 and SEQ ID NO: 34; and the second and the third antigen binding moiety capable of specific binding to FolR1 comprise at least one heavy chain complementarity determining region (CDR) selected from the group consisting of SEQ ID NO: 16, SEQ ID NO: 17 and SEQ ID NO: 18 and at least one light chain CDR selected from the group of SEQ ID NO: 32, SEQ ID NO: 33 and SEQ ID NO: 34.

In a particular embodiment said T cell activating bispecific antigen binding molecule the first and the second antigen binding moiety and the Fc domain are part of an immunoglobulin molecule, and the third antigen binding moiety is fused at the C-terminus of the Fab heavy chain to the N-terminus of the Fab heavy chain of the first antigen binding moiety, wherein the first, second and third antigen binding moiety are conventional Fab fragments and have identical light chains (VLCL), wherein the first antigen binding moiety capable of specific binding to CD3 comprises a variable heavy chain comprising a sequence of SEQ ID NO: 36, a variable light chain comprising a sequence of SEQ ID NO: 31; and the second and the third antigen binding moiety capable of specific binding to FolR1 comprise a variable heavy chain comprising a sequence of SEQ ID NO: 15, a variable light chain comprising a sequence of SEQ ID NO: 31.

In a particular embodiment said T cell activating bispecific antigen binding molecule the first and the second antigen binding moiety and the Fc domain are part of an immunoglobulin molecule, and the third antigen binding moiety is fused at the C-terminus of the Fab heavy chain to the N-terminus of the Fab heavy chain of the first antigen binding moiety and the first antigen binding moiety capable of specific binding to CD3 is a crossover Fab molecule wherein either the variable or the constant regions of the Fab light chain and the Fab heavy chain are exchanged, comprising at least one heavy chain complementarity determining region (CDR) selected from the group consisting of SEQ ID NO: 37, SEQ ID NO: 38 and SEQ ID NO: 39 and at least one light chain CDR selected from the group of SEQ ID NO: 32, SEQ ID NO: 33 and SEQ ID NO: 34; and the second and the third antigen binding moiety capable of specific binding to FolR1 comprise at least one heavy chain complementarity determining region (CDR) selected from the group consisting of SEQ ID NO: 8, SEQ ID NO: 56 and SEQ ID NO: 57 and at least one light chain CDR selected from the group of SEQ ID NO: 59, SEQ ID NO: 60 and SEQ ID NO: 65.

In a particular embodiment said T cell activating bispecific antigen binding molecule the first and the second antigen binding moiety and the Fc domain are part of an immunoglobulin molecule, and the third antigen binding moiety is fused at the C-terminus of the Fab heavy chain to the N-terminus of the Fab heavy chain of the first antigen binding moiety and the first antigen binding moiety capable of specific binding to CD3 is a crossover Fab molecule wherein either the variable or the constant regions of the Fab light chain and the Fab heavy chain are exchanged, wherein the first antigen binding moiety capable of specific binding to CD3 comprises a variable heavy chain comprising a sequence of SEQ ID NO: 36, a variable light chain comprising a sequence of SEQ ID NO: 31; and the second and the third antigen binding moiety capable of specific binding to FolR1 comprise a variable heavy chain comprising a sequence of SEQ ID NO: 55, a variable light chain comprising a sequence of SEQ ID NO: 65.

In one embodiment the T cell activating bispecific antigen binding molecule is monovalent for each antigen. In a particular embodiment the T cell activating bispecific antigen binding molecule can bind to human CD3 and human folate receptor alpha (FolR1) and was made without employing a hetero-dimerization approach, such as, e.g., knob-into-hole technology. For example, the molecule can be produced by employing a common light chain library and CrossMab technology. In a particular embodiment, The variable region of the CD3 binder is fused to the CH1 domain of a standard human IgG1 antibody to form the VLVH crossed molecule (fused to Fc) which is common for both specificities. To generate the crossed counterparts (VHCL), a CD3 specific variable heavy chain domain is fused to a constant human λ light chain whereas a variable heavy chain domain specific for human FolR1 (e.g., isolated from a common light chain library) is fused to a constant human κ light chain. The resulting desired molecule with correctly paired chains comprises both kappa and lambda light chains or fragments thereof. Consequently, this desired bispecific molecule species can be purified from mispaired or homodimeric species with sequential purification steps selecting for kappa and lambda light chain, in either sequence. In one particular embodiment, purification of the desired bispecific antibody employs subsequent purification steps with KappaSelect and LambdaFabSelect columns (GE Healthcare) to remove undesired homodimeric antibodies.

Fc Domain

The Fc domain of the T cell activating bispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the T cell activating bispecific antigen binding molecule of the invention comprises not more than one Fc domain.

In one embodiment according the invention the Fc domain of the T cell activating bispecific antigen binding molecule is an IgG Fc domain. In a particular embodiment the Fc domain is an IgG$_1$ Fc domain. In another embodiment the Fc domain is an IgG$_4$ Fc domain. In a more specific embodiment, the Fc domain is an IgG$_4$ Fc domain comprising an amino acid substitution at position S228 (Kabat numbering), particularly the amino acid substitution S228P. This amino acid substitution reduces in vivo Fab arm exchange of IgG$_4$ antibodies (see Stubenrauch et al., Drug Metabolism and Disposition 38, 84-91 (2010)). In a further particular embodiment the Fc domain is human. An exemplary sequence of a human IgG$_1$ Fc region is given in SEQ ID NO:245.

Fc Domain Modifications Promoting Heterodimerization

T cell activating bispecific antigen binding molecules according to the invention comprise different antigen binding moieties, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of T cell activating bispecific antigen binding molecules in recombinant production, it will thus be advantageous to introduce in the Fc domain of the T cell activating bispecific antigen binding molecule a modification promoting the association of the desired polypeptides.

Accordingly, in particular embodiments the Fc domain of the T cell activating bispecific antigen binding molecule according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment said modification is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). Accordingly, in a particular embodiment, in the CH3 domain of the first subunit of the Fc domain of the T cell activating bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C).

Introduction of these two cysteine residues results in formation of a disulfide bridge between the two subunits of the Fc domain, thus further stabilizing the dimer (Carter, J Immunol Methods 248, 7-15 (2001)).

In a particular embodiment the antigen binding moiety capable of binding to CD3 is fused (optionally via the antigen binding moiety capable of binding to FolR1 on a target cell antigen) to the first subunit of the Fc domain (comprising the "knob" modification). Without wishing to be bound by theory, fusion of the antigen binding moiety capable of binding to CD3 to the knob-containing subunit of the Fc domain will (further) minimize the generation of antigen binding molecules comprising two antigen binding moieties capable of binding to CD3 (steric clash of two knob-containing polypeptides).

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Fc Domain Modifications Abolishing Fc Receptor Binding and/or Effector Function

The Fc domain confers to the T cell activating bispecific antigen binding molecule favorable pharmacokinetic properties, including a long serum half-life which contributes to good accumulation in the target tissue and a favorable tissue-blood distribution ratio. At the same time it may, however, lead to undesirable targeting of the T cell activating bispecific antigen binding molecule to cells expressing Fc receptors rather than to the preferred antigen-bearing cells. Moreover, the co-activation of Fc receptor signaling pathways may lead to cytokine release which, in combination with the T cell activating properties and the long half-life of the antigen binding molecule, results in excessive activation of cytokine receptors and severe side effects upon systemic administration. Activation of (Fc receptor-bearing) immune cells other than T cells may even reduce efficacy of the T cell activating bispecific antigen binding molecule due to the potential destruction of T cells e.g. by NK cells.

Accordingly, in particular embodiments the Fc domain of the T cell activating bispecific antigen binding molecules according to the invention exhibits reduced binding affinity to an Fc receptor and/or reduced effector function, as compared to a native $IgG_1$ Fc domain. In one such embodiment the Fc domain (or the T cell activating bispecific antigen binding molecule comprising said Fc domain) exhibits less than 50%, preferably less than 20%, more preferably less than 10% and most preferably less than 5% of the binding affinity to an Fc receptor, as compared to a native $IgG_1$ Fc domain (or a T cell activating bispecific antigen binding molecule comprising a native $IgG_1$ Fc domain), and/or less than 50%, preferably less than 20%, more preferably less than 10% and most preferably less than 5% of the effector function, as compared to a native $IgG_1$ Fc domain (or a T cell activating bispecific antigen binding molecule comprising a native $IgG_1$ Fc domain). In one embodiment, the Fc domain (or the T cell activating bispecific antigen binding molecule comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain exhibits substantially similar binding affinity to neonatal Fc receptor (FcRn), as compared to a native $IgG_1$ Fc domain. Substantially similar binding to FcRn is achieved when the Fc domain (or the T cell activating bispecific antigen binding molecule comprising said Fc domain) exhibits greater than about 70%, particularly greater than about 80%, more particularly greater than about 90% of the binding affinity of a native $IgG_1$ Fc domain (or the T cell activating bispecific antigen binding molecule comprising a native $IgG_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the T cell activating bispecific antigen binding molecule comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the T cell activating bispecific antigen binding molecule comprising an engineered Fc domain exhibits less than 20%, particularly less than 10%, more particularly less than 5% of the binding affinity to an Fc receptor as compared to a T cell activating bispecific antigen binding molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the T cell activating bispecific antigen binding molecule comprising said Fc domain) exhibits greater than about 70% of the binding affinity of a non-engineered form of the Fc domain (or the T cell activating bispecific antigen binding molecule comprising said non-engineered form of the Fc domain) to FcRn. The Fc domain, or T cell activating bispecific antigen binding molecules of the invention comprising said Fc domain, may exhibit greater than about 80% and even greater than about 90% of such affinity. In certain embodiments the Fc domain of the T cell activating bispecific antigen binding molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a T cell activating bispecific antigen binding molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329. In a more specific embodiment the Fc domain comprises an amino acid substitution at a position selected from the group of L234, L235 and P329. In some embodiments the Fc domain comprises the amino acid substitutions L234A and L235A. In one such embodiment, the Fc domain is an IgG$_1$ Fc domain, particularly a human IgG$_1$ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In more particular embodiments the Fc domain comprises the amino acid mutations L234A, L235A and P329G ("P329G LALA"). In one such embodiment, the Fc domain is an IgG$_1$ Fc domain, particularly a human IgG$_1$ Fc domain. The "P329G LALA" combination of amino acid substitutions almost completely abolishes Fcγ receptor binding of a human IgG$_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some embodiments the Fc domain of the T cell activating bispecific antigen binding molecules of the invention is an IgG$_4$ Fc domain, particularly a human IgG$_4$ Fc domain. In one embodiment the IgG$_4$ Fc domain comprises amino acid substitutions at position S228, specifically the amino acid substitution S228P. To further reduce its binding affinity to an Fc receptor and/or its effector function, in one embodiment the IgG$_4$ Fc domain comprises an amino acid substitution at position L235, specifically the amino acid substitution L235E. In another embodiment, the IgG$_4$ Fc domain comprises an amino acid substitution at position P329, specifically the amino acid substitution P329G. In a particular embodiment, the IgG$_4$ Fc domain comprises amino acid substitutions at positions S228, L235 and P329, specifically amino acid substitutions S228P, L235E and P329G. Such IgG$_4$ Fc domain mutants and their Fcγ receptor binding properties are described in PCT publication no. WO 2012/130831, incorporated herein by reference in its entirety.

In a particular embodiment the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G. In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or a T cell activating bispecific antigen binding molecule comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998). In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the T cell activating bispecific antigen binding molecule is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Biological Properties and Functional Characteristics of T Cell Activating Bispecific Antigen Binding Molecules One of skill in the art can appreciate the advantageous efficiency of a molecule that selectively distinguishes between cancerous and non-cancerous, healthy cells. One way to accomplish this goal is by appropriate target selection. Markers expressed exclusively on tumor cells can be employed to selectively target effector molecules or cells to tumor cells while sparing normal cells that do not express such marker. However, in some instances, so called tumor cell markers are also expressed in normal tissue, albeit at lower levels. This expression in normal tissue raises the possibility of toxicity. Thus, there was a need in the art for molecules that can more selectively target tumor cells. The invention described herein provides for T cell activating bispecific antigen binding molecules that selectively target FolR1-positive tumor cells and not normal, non-cancerous cells that express FolR1 at low levels or not at all. In one embodiment, the T cell activating bispecific antigen binding molecule comprises at least two, preferably two, FolR1 binding moieties of relatively low affinity that confer an avidity effect which allows for differentiation between high and low FolR1 expressing cells. Because tumor cells express FolR1 at high or intermediate levels, this embodiment of the invention selectively binds to, and/or induces killing of, tumor cells and not normal, non-cancerous cells that express FolR1 at low levels or not at all. In one embodiment, the T cell activating bispecific antigen binding molecule is in the 2+1 inverted format. In one embodiment, the T cell activating bispecific antigen binding molecule induces T cell mediated killing of FolR1-positive tumor cells and not non-tumor cells and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

In one specific embodiment, the T cell activating bispecific antigen binding molecule does not induce killing of a normal cells having less than about 1000 copies of FolR1 its surface.

In addition to the above advantageous characteristics, one embodiment of the invention does not require chemical cross linking or a hybrid approach to be produced. Accordingly, in one embodiment, the invention provides for T cell activating bispecific antigen binding molecule capable of production in CHO cells. In one embodiment, the T cell activating bispecific antigen binding molecule comprises humanized and human polypeptides. In one embodiment, the T cell activating bispecific antigen binding molecule does not cause FcgR crosslinking. In one such embodiment, the T cell activating bispecific antigen binding molecule is capable of production in CHO cells and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

As noted above, some embodiments contemplated herein include T cell activating bispecific antigen binding molecules having two binding moieties that confer specific binding to FolR1 and one binding moiety that confers specificity to the T cell activating antigen CD3, wherein each individual FolR1 binding moiety engages the antigen with low affinity. Because the molecule comprises two antigen binding moieties that confer binding to FolR1, the overall avidity of the molecule, nevertheless, provides effective binding to FolR1-expressing target cells and activation of T cells to induce T cell effector function. Considering that while FolR1 is expressed at various level on tumor cells, it is also expressed at very low levels (e.g., less than about 1000 copies on the cell surface) in certain normal cells, one of skill in the art can readily recognize the advantageous efficiency of such a molecule for use as a therapeutic agent. Such molecule selectively targets tumor cells over normal cells. Such molecule, thus, can be administered to an individual in need thereof with significantly less concern about toxicity resulting from FolR1 positive normal cells compared to molecules that bind to FolR1 with high affinity to induce effector function. In a preferred embodiment, the T cell activating bispecific antigen binding molecules have a monovalent binding affinity to huFolR1 in the micromolar range and an avidity to huFolR1 in the nanomolar range.

In one embodiment, the T cell activating bispecific antigen binding molecule binds human FolR1 with an apparent $K_D$ of about 10 nM to about 40 nM. In one embodiment, the T cell activating bispecific antigen binding molecule binds human FolR1 with an apparent $K_D$ of about 10 nM. In one embodiment, the T cell activating bispecific antigen binding molecule binds human and cynomolgus FolR1 with an apparent $K_D$ of about 10 nM and about 30 nM, respectively. In one embodiment, the T cell activating bispecific antigen binding molecule binds human FolR1 with a monovalent binding $K_D$ of at least about 1000 nM. In one embodiment, the T cell activating bispecific antigen binding molecule binds human FolR1 with a monovalent binding $K_D$ of about 1400 nM. In one embodiment, the T cell activating bispecific antigen binding molecule binds human FolR1 with a monovalent binding $K_D$ of about 1400 nM and to cynomolgus FolR1 with a monovalent binding $K_D$ of about 5600 nM. In one embodiment, the T cell activating bispecific antigen binding molecule binds human FolR1 with an apparent $K_D$ of about 10 nM and with a monovalent binding $K_D$ of about 1400 nM.

In one embodiment, the T cell activating bispecific antigen binding molecule binds human FolR1 with an apparent $K_D$ of about 5.36 pM to about 4 nM. In one embodiment, the T cell activating bispecific antigen binding molecule binds human and cynomolgus FolR1 with an apparent $K_D$ of about 4 nM. In one embodiment, the T cell activating bispecific antigen binding molecule binds murine FolR1 with an apparent $K_D$ of about 1.5 nM. In one embodiment, the T cell activating bispecific antigen binding molecule binds human FolR1 with a monovalent binding $K_D$ of at least about 1000 nM. In a specific embodiment, the T cell activating bispecific antigen binding molecule binds human and cynomolgus FolR1 with an apparent $K_D$ of about 4 nM, binds murine FolR1 with an apparent $K_D$ of about 1.5 nM, and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54. In one embodiment, the T cell activating bispecific antigen binding molecule binds human FolR1 with a monovalent binding $K_D$ of at least about 1000 nM and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

As described above, the T cell activating bispecific antigen binding molecules contemplated herein can induce T cell effector function, e.g., cell surface marker expression, cytokine production, T cell mediated killing. In one embodiment, the T cell activating bispecific antigen binding molecule induces T cell mediated killing of the FolR1-expressing target cell, such as a human tumor cell, in vitro. In one embodiment, the T cell is a CD8 positive T cell. Examples of FolR1-expressing human tumor cells include but are not limited to Hela, Skov-3, HT-29, and HRCEpiC cells. Other FolR1 positive human cancer cells that can be used for in vitro testing are readily available to the skilled artisan. In one embodiment, the T cell activating bispecific antigen binding molecule induces T cell mediated killing of the FolR1-expressing human tumor cell in vitro with an EC50 of between about 36 pM and about 39573 pM after 24 hours. Specifically contemplated are T cell activating bispecific antigen binding molecules that induce T cell mediated killing of the FolR1-expressing tumor cell in vitro with an EC50 of about 36 pM after 24 hours. In one embodiment, the T cell activating bispecific antigen binding molecule induces T cell mediated killing of the FolR1-expressing tumor cell in vitro with an EC50 of about 178.4 pM after 24 hours. In one embodiment, the T cell activating bispecific antigen binding molecule induces T cell mediated killing of the FolR1-expressing tumor cell in vitro with an EC50 of about 134.5 pM or greater after 48 hours. The EC50 can be measure by methods known in the art, for example by methods disclosed herein by the examples.

In one embodiment, the T cell activating bispecific antigen binding molecule of any of the above embodiments induces upregulation of cell surface expression of at least one of CD25 and CD69 on the T cell as measured by flow cytometry. In one embodiment, the T cell is a CD4 positive T cell or a CD8 positive T cell.

In one embodiment, the T cell activating bispecific antigen binding molecule of any of the above embodiments binds to FolR1 expressed on a human tumor cell. In one embodiment, the T cell activating bispecific antigen binding molecule of any of the above embodiments binds to a conformational epitope on human FolR1. In one embodiment, the T cell activating bispecific antigen binding molecule of any of the above embodiments does not bind to human Folate Receptor 2 (FolR2) or to human Folate Receptor 3 (FolR3). In one embodiment of the T cell activating bispecific antigen binding molecule of any of the above embodiments, the antigen binding moiety binds to a FolR1 polypeptide comprising the amino acids 25 to 234 of human FolR1 (SEQ ID NO:227). In one embodiment of the T cell activating bispecific antigen binding molecule of any of the above embodiments, the FolR1 antigen binding moiety binds to a FolR1 polypeptide comprising the amino acid sequence of SEQ ID NO:227, to a FolR1 polypeptide comprising the amino acid sequence of SEQ ID NO:230 and to a FolR1 polypeptide comprising the amino acid sequence of SEQ ID NO:231, and wherein the FolR1 antigen binding moiety does not bind to a FolR polypeptide comprising the amino acid sequence of SEQ ID NOs:228 or 229. In one specific embodiment, the T cell activating bispecific antigen binding molecule comprises a FolR1 antigen binding moiety that binds to a FolR1 polypeptide comprising the amino acid sequence of SEQ ID NOs:227, 230 and 231, and wherein the FolR1 antigen binding moiety does not bind to a FolR polypeptide comprising the amino acid sequence of SEQ ID NOs:228 or 229, and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 8, the heavy chain CDR2 of SEQ ID NO: 9, the heavy chain CDR3 of SEQ ID NO:50, the light chain CDR1 of SEQ ID NO: 52, the light chain CDR2 of SEQ ID NO: 53, and the light chain CDR3 of SEQ ID NO:54.

In one embodiment of the T cell activating bispecific antigen binding molecule of any of the above embodiments, the FolR1 antigen binding moiety binds to a FolR1 polypeptide comprising the amino acid sequence of SEQ ID NO:227 and to a FolR1 polypeptide comprising the amino acid sequence of SEQ ID NO:231, and wherein the FolR1 antigen binding moiety does not bind to a FolR polypeptide comprising the amino acid sequence of SEQ ID NOs:228, 229 or 230. In one specific embodiment, the T cell activating bispecific antigen binding molecule comprises a FolR1 antigen binding moiety that binds to a FolR1 polypeptide comprising the amino acid sequence of SEQ ID NO:227 and to a FolR1 polypeptide comprising the amino acid sequence of SEQ ID NO:231, and wherein the FolR1 antigen binding moiety does not bind to a FolR polypeptide comprising the amino acid sequence of SEQ ID NOs:228, 229 or 230, and comprises a CD3 antigen binding moiety that comprises the heavy chain CDR1 of SEQ ID NO: 37, the heavy chain CDR2 of SEQ ID NO: 38, the heavy chain CDR3 of SEQ ID NO:39, the light chain CDR1 of SEQ ID NO: 32, the light chain CDR2 of SEQ ID NO: 33, and the light chain CDR3 of SEQ ID NO:34 and two FolR1 antigen binding moieties that each comprise the heavy chain CDR1 of SEQ ID NO: 16, the heavy chain CDR2 of SEQ ID NO: 275, the heavy chain CDR3 of SEQ ID NO:315, the light chain CDR1 of SEQ ID NO: 32, the light chain CDR2 of SEQ ID NO: 33, and the light chain CDR3 of SEQ ID NO:34.

With respect to the FolR1, the T cell activating bispecific antigen binding molecules contemplated herein can have agonist, antagonist or neutral effect. Examples of agonist effect include induction or enhancement of signaling through the FolR1 upon engagement by the FolR1 binding moiety with the FolR1 receptor on the target cell. Examples of antagonist activity include abrogation or reduction of signaling through the FolR1 upon engagement by the FolR1 binding moiety with the FolR1 receptor on the target cell. This can, for example, occur by blocking or reducing the interaction between folate with FolR1. Sequence variants of the embodiments disclosed herein having lower affinity while retaining the above described biological properties are specifically contemplated.

Immunoconjugates

The invention also pertains to immunoconjugates comprising a T cell activating bispecific antigen binding molecule conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Polynucleotides

The invention further provides isolated polynucleotides encoding a T cell activating bispecific antigen binding molecule as described herein or a fragment thereof.

Polynucleotides of the invention include those that are at least about 80%, 85%, 90%, 95%, 96%, 97%, 98%, 99%, or 100% identical to the sequences set forth in SEQ ID NOs: 151-226 including functional fragments or variants thereof.

The polynucleotides encoding T cell activating bispecific antigen binding molecules of the invention may be expressed as a single polynucleotide that encodes the entire T cell activating bispecific antigen binding molecule or as multiple (e.g., two or more) polynucleotides that are co-expressed. Polypeptides encoded by polynucleotides that are co-expressed may associate through, e.g., disulfide bonds or other means to form a functional T cell activating bispecific antigen binding molecule. For example, the light chain portion of an antigen binding moiety may be encoded by a separate polynucleotide from the portion of the T cell activating bispecific antigen binding molecule comprising the heavy chain portion of the antigen binding moiety, an Fc domain subunit and optionally (part of) another antigen binding moiety. When co-expressed, the heavy chain polypeptides will associate with the light chain polypeptides to form the antigen binding moiety. In another example, the portion of the T cell activating bispecific antigen binding molecule comprising one of the two Fc domain subunits and optionally (part of) one or more antigen binding moieties could be encoded by a separate polynucleotide from the portion of the T cell activating bispecific antigen binding molecule comprising the other of the two Fc domain subunits and optionally (part of) an antigen binding moiety. When co-expressed, the Fc domain subunits will associate to form the Fc domain.

In some embodiments, the isolated polynucleotide encodes the entire T cell activating bispecific antigen binding molecule according to the invention as described herein. In other embodiments, the isolated polynucleotide encodes a polypeptides comprised in the T cell activating bispecific antigen binding molecule according to the invention as described herein.

In another embodiment, the present invention is directed to an isolated polynucleotide encoding a T cell activating bispecific antigen binding molecule of the invention or a fragment thereof, wherein the polynucleotide comprises a sequence that encodes a variable region sequence as shown in SEQ ID NOs 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 and 205, 206, 207, 208, 209, 210, 211, 212, 213, 214, 215, 216, 217, 218, 219, 220, 221, 222, 223. In another embodiment, the present invention is directed to an isolated polynucleotide encoding a T cell activating bispecific antigen binding molecule or fragment thereof, wherein the polynucleotide comprises a sequence that encodes a polypeptide sequence as shown in SEQ ID NOs:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 1, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111,112, 113, 114, 115, 116, 117, 118, 119, 120, 121, 122, 123, 124, 125, 126, 127, 128, 129, 130, 131, 132, 133, 134, 135, 136, 137, 138, 227, 228, 229, 230, 231, 232, 233, 234, 235, 236, 237, 238, 239, 240, 241, 242, 243, 244. In another embodiment, the invention is further directed to an isolated polynucleotide encoding a T cell activating bispecific antigen binding molecule of the invention or a fragment thereof, wherein the polynucleotide comprises a sequence that is at least about 80%, 85%, 90%, 95%, 96%, 97%, 98%, or 99% identical to a nucleotide sequence shown in SEQ ID NOs 97, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 189, 190, 191, 192, 193, 194, 195, 196, 197, 198, 199, 200, 201, 202, 203, 204, 205, 206, 207, 208, 209, 210, 211, 12, 213, 214, 215, 216, 217, 218, 219, 220, 221, 222, 223, 224, 225, 226, 246, 247. In another embodiment, the invention is directed to an isolated polynucleotide encoding a T cell activating bispecific antigen binding molecule of the invention or a fragment thereof, wherein the polynucleotide comprises a nucleic acid sequence shown in SEQ ID NOs 97, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 189, 190, 191, 192, 193, 194, 195, 196, 197, 198, 199, 200, 201, 202, 203, 204, 205, 206, 207, 208, 209, 210, 211, 12, 213, 214, 215, 216, 217, 218, 219, 220, 221, 222, 223, 224, 225, 226, 246, 247. In another embodiment, the invention is directed to an isolated polynucleotide encoding a T cell activating bispecific antigen binding molecule of the invention or a fragment thereof, wherein the polynucleotide comprises a sequence that encodes a variable region sequence that is at least about 80%, 85%, 90%, 95%, 96%, 97%, 98%, or 99% identical to an amino acid sequence in SEQ ID NOs 1, 2, 3, 4, 5, 6, 7, 11, 13, 15, 19, 21, 12, 25, 27, 29, 31, 36, 41, 45, 49, 51, 55, 58, 62, 64, 66, 68, 70, 72, 74, 76, 78, 82, 113, 114, 115, 116, 117, 118, 119, 12, 121, 122, 123, 124, 125, 126, 127, 128, 129, 130, 131, 132, 133, 134, 135. In another embodiment, the invention is directed to an isolated polynucleotide encoding a T cell activating bispecific antigen binding molecule or fragment thereof, wherein the polynucleotide comprises a sequence that encodes a polypeptide comprising one or more sequences that are at least 80%, 85%, 90%, 95%, 96%, 97%, 98%, or 99% identical to an amino acid sequence in SEQ ID NOs: 8, 9, 50, 37, 38, and 39. The invention encompasses an isolated polynucleotide encoding a T cell activating bispecific antigen binding molecule of the invention or a fragment thereof, wherein the polynucleotide comprises a sequence that encodes the variable region sequence of SEQ ID NOs 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 and 205, 206, 207, 208, 209, 210, 211, 212, 213, 214, 215, 216, 217, 218, 219, 220, 221, 222, 223 with conservative amino acid substitutions. The invention also encompasses an isolated polynucleotide encoding a T cell activating bispecific antigen binding molecule of the invention or fragment thereof, wherein the polynucleotide comprises a sequence that encodes the polypeptide sequence of SEQ ID NOs 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 1, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111,112, 113, 114, 115, 116, 117, 118, 119, 120, 121, 122, 123, 124, 125, 126, 127, 128, 129, 130, 131, 132, 133, 134, 135, 136, 137, 138 and 227, 228, 229, 230, 231, 232, 233, 234, 235, 236, 237, 238, 239, 240, 241, 242, 243, 244 with conservative amino acid substitutions.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

T cell activating bispecific antigen binding molecules of the invention may be obtained, for example, by solid-state peptide synthesis (e.g. Merrifield solid phase synthesis) or recombinant production. For recombinant production one or more polynucleotide encoding the T cell activating bispecific antigen binding molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a T cell activating bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the T cell activating bispecific antigen binding molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the T cell activating bispecific antigen binding molecule (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit a-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the T cell activating bispecific antigen binding molecule is desired, DNA encoding a signal sequence may be placed upstream of the nucleic acid encoding a T cell activating bispecific antigen binding molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the T cell activating bispecific antigen binding molecule may be included within or at the ends of the T cell activating bispecific antigen binding molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a T cell activating bispecific antigen binding molecule of the invention. As used herein, the term "host cell" refers to any kind of cellular system which can be engineered to generate the T cell activating bispecific antigen binding molecules of the invention or fragments thereof. Host cells suitable for replicating and for supporting expression of T cell activating bispecific antigen binding molecules are well known in the art. Such cells may be transfected or transduced as appropriate with the particular expression vector and large quantities of vector containing cells can be grown for seeding large scale fermenters to obtain sufficient quantities of the T cell activating bispecific antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a T cell activating bispecific antigen binding molecule according to the invention is provided, wherein the method comprises culturing a host cell comprising a polynucleotide encoding the T cell activating bispecific antigen binding molecule, as provided herein, under conditions suitable for expression of the T cell activating bispecific antigen binding molecule, and recovering the T cell activating bispecific antigen binding molecule from the host cell (or host cell culture medium).

The components of the T cell activating bispecific antigen binding molecule are genetically fused to each other. T cell activating bispecific antigen binding molecule can be designed such that its components are fused directly to each other or indirectly through a linker sequence. The composition and length of the linker may be determined in accordance with methods well known in the art and may be tested for efficacy. Examples of linker sequences between different components of T cell activating bispecific antigen binding molecules are found in the sequences provided herein. Additional sequences may also be included to incorporate a cleavage site to separate the individual components of the fusion if desired, for example an endopeptidase recognition sequence.

In certain embodiments the one or more antigen binding moieties of the T cell activating bispecific antigen binding molecules comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108, McCafferty).

Any animal species of antibody, antibody fragment, antigen binding domain or variable region can be used in the T cell activating bispecific antigen binding molecules of the invention. Non-limiting antibodies, antibody fragments, antigen binding domains or variable regions useful in the present invention can be of murine, primate, or human origin. If the T cell activating bispecific antigen binding molecule is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, NJ, 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the T cell activating bispecific antigen binding molecule of the invention to bind to a specific antigenic determinant can be measured either through an enzyme-linked immunosorbent assay (ELISA) or other techniques familiar to one of skill in the art, e.g. surface plasmon resonance technique (analyzed on a BIA-CORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the V9 antibody for binding to CD3. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, NJ). In an exemplary competition assay, immobilized antigen (e.g. CD3) is incubated in a solution comprising a first labeled antibody that binds to the antigen (e.g. V9 antibody, described in U.S. Pat. No. 6,054,297) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, NY).

Figure 2A:
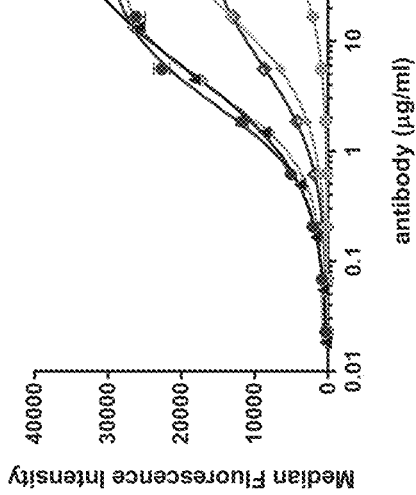
FIGS. 2A-C depict graphs summarizing Binding of FoLR1 IgG binders to HeLa cells. Binding of newly generated FolR1 binders to FolR1 expressed on HeLa cells were determined by flow cytometry. Bound antibodies were detected with a fluorescently labeled anti-human secondary antibody.
Figure 2B:
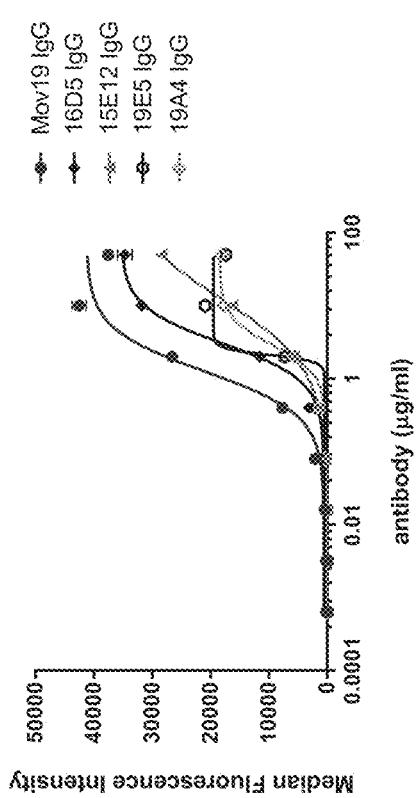
Figure 2C:
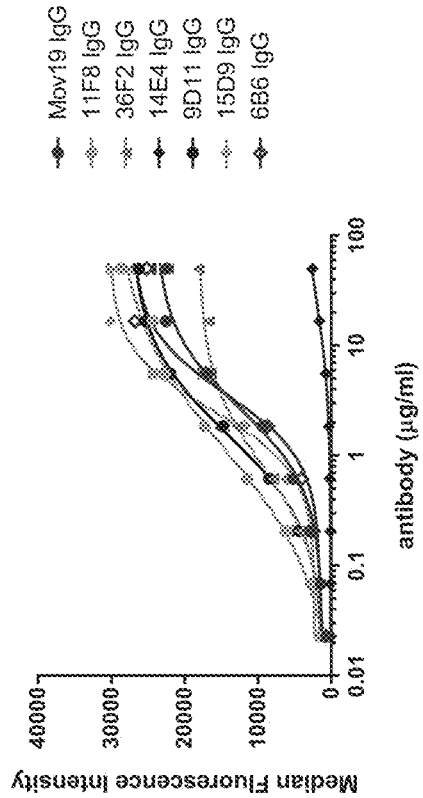

T cell activating bispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the T cell activating bispecific antigen binding molecule binds. For example, for affinity chromatography purification of T cell activating bispecific antigen binding molecules of the invention, a matrix with protein A or protein G may be used. Sequential Protein A or G affinity chromatography and size exclusion chromatography can be used to isolate a T cell activating bispecific antigen binding molecule essentially as described in the Examples. The purity of the T cell activating bispecific antigen binding molecule can be determined by any of a variety of well known analytical methods including gel electrophoresis, high pressure liquid chromatography, and the like. For example, the heavy chain fusion proteins expressed as described in the Examples were shown to be intact and properly assembled as demonstrated by reducing SDS-PAGE (see e.g. FIG. 2). Three bands were resolved at approximately Mr 25,000, Mr 50,000 and Mr 75,000, corresponding to the predicted molecular weights of the T cell activating bispecific antigen binding molecule light chain, heavy chain and heavy chain/light chain fusion protein.

Assays

T cell activating bispecific antigen binding molecules provided herein may be identified, screened for, or characterized for their physical/chemical properties and/or biological activities by various assays known in the art.

Affinity Assays

The affinity of the T cell activating bispecific antigen binding molecule for an Fc receptor or a target antigen can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of T cell activating bispecific antigen binding molecules for different receptors or target antigens may be evaluated using cell lines expressing the particular receptor or target antigen, for example by flow cytometry (FACS). A specific illustrative and exemplary embodiment for measuring binding affinity is described in the following and in the Examples below. According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody ("Penta His" disclosed as SEQ ID NO: 306) (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody ("Penta-His" disclosed as SEQ ID NO: 306) is diluted with 10 mM sodium acetate, pH 5.0, to 40 μg/ml before injection at a flow rate of 5 μl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 μl/min for 120 s.

To determine the affinity to the target antigen, bispecific constructs are captured by an anti human Fab specific antibody (GE Healthcare) that is immobilized on an activated CM5-sensor chip surface as described for the anti Penta-His antibody ("Penta-His" disclosed as SEQ ID NO: 306). The final amount of coupled protein is approximately 12000 RU. The bispecific constructs are captured for 90 s at 300 nM. The target antigens are passed through the flow cells for 180 s at a concentration range from 250 to 1000 nM with a flowrate of 30 μl/min. The dissociation is monitored for 180 s. Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the T cell activating bispecific antigen binding molecules of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

Compositions, Formulations, and Routes of Administration

In a further aspect, the invention provides pharmaceutical compositions comprising any of the T cell activating bispecific antigen binding molecules provided herein, e.g., for use in any of the below therapeutic methods. In one embodiment, a pharmaceutical composition comprises any of the T cell activating bispecific antigen binding molecules provided herein and a pharmaceutically acceptable carrier. In another embodiment, a pharmaceutical composition comprises any of the T cell activating bispecific antigen binding molecules provided herein and at least one additional therapeutic agent, e.g., as described below.

Further provided is a method of producing a T cell activating bispecific antigen binding molecule of the invention in a form suitable for administration in vivo, the method comprising (a) obtaining a T cell activating bispecific antigen binding molecule according to the invention, and (b) formulating the T cell activating bispecific antigen binding molecule with at least one pharmaceutically acceptable carrier, whereby a preparation of T cell activating bispecific antigen binding molecule is formulated for administration in vivo.

Pharmaceutical compositions of the present invention comprise a therapeutically effective amount of one or more T cell activating bispecific antigen binding molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one T cell activating bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. T cell activating bispecific antigen binding molecules of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularlly, mucosally, intrapericardially, intraumbilically, intraocularally, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the T cell activating bispecific antigen binding molecules of the invention.

Parenteral compositions include those designed for administration by injection, e.g. subcutaneous, intradermal, intralesional, intravenous, intraarterial intramuscular, intrathecal or intraperitoneal injection. For injection, the T cell activating bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the T cell activating bispecific antigen binding molecules may be in powder form for constitution with a suitable vehicle, e.g., sterile pyrogen-free water, before use. Sterile injectable solutions are prepared by incorporating the T cell activating bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the T cell activating bispecific antigen binding molecules may also be formulated as a depot preparation. Such long acting formulations may be administered by implantation (for example subcutaneously or intramuscularly) or by intramuscular injection. Thus, for example, the T cell activating bispecific antigen binding molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the T cell activating bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The T cell activating bispecific antigen binding molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the T cell activating bispecific antigen binding molecules provided herein may be used in therapeutic methods. T cell activating bispecific antigen binding molecules of the invention can be used as immunotherapeutic agents, for example in the treatment of cancers.

For use in therapeutic methods, T cell activating bispecific antigen binding molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, T cell activating bispecific antigen binding molecules of the invention for use as a medicament are provided. In further aspects, T cell activating bispecific antigen binding molecules of the invention for use in treating a disease are provided. In certain embodiments, T cell activating bispecific antigen binding molecules of the invention for use in a method of treatment are provided. In one embodiment, the invention provides a T cell activating bispecific antigen binding molecule as described herein for use in the treatment of a disease in an individual in need thereof. In certain embodiments, the invention provides a T cell activating bispecific antigen binding molecule for use in a method of treating an individual having a disease comprising administering to the individual a therapeutically effective amount of the T cell activating bispecific antigen binding molecule. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides a T cell activating bispecific antigen binding molecule as described herein for use in inducing lysis of a target cell, particularly a tumor cell. In certain embodiments, the invention provides a T cell activating bispecific antigen binding molecule for use in a method of inducing lysis of a target cell, particularly a tumor cell, in an individual comprising administering to the individual an effective amount of the T cell activating bispecific antigen binding molecule to induce lysis of a target cell. An "individual" according to any of the above embodiments is a mammal, preferably a human.

In a further aspect, the invention provides for the use of a T cell activating bispecific antigen binding molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of a T cell activating bispecific antigen binding molecule of the invention. In one embodiment a composition is administered to said individual, comprising the T cell activating bispecific antigen binding molecule of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with a T cell activating bispecific antigen binding molecule of the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of a T cell activating bispecific antigen binding molecule to induce lysis of a target cell. In one embodiment, an "individual" is a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a T cell activating bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the T cell activating bispecific antigen binding molecule may not provide a cure but may only provide partial benefit. In some embodiments, a physiological change having some benefit is also considered therapeutically beneficial. Thus, in some embodiments, an amount of T cell activating bispecific antigen binding molecule that provides a physiological change is considered an "effective amount" or a "therapeutically effective amount". The subject, patient, or individual in need of treatment is typically a mammal, more specifically a human.

In some embodiments, an effective amount of a T cell activating bispecific antigen binding molecule of the invention is administered to a cell. In other embodiments, a therapeutically effective amount of a T cell activating bispecific antigen binding molecule of the invention is administered to an individual for the treatment of disease.

For the prevention or treatment of disease, the appropriate dosage of a T cell activating bispecific antigen binding molecule of the invention (when used alone or in combination with one or more other additional therapeutic agents) will depend on the type of disease to be treated, the route of administration, the body weight of the patient, the type of T cell activating bispecific antigen binding molecule, the severity and course of the disease, whether the T cell activating bispecific antigen binding molecule is administered for preventive or therapeutic purposes, previous or concurrent therapeutic interventions, the patient's clinical history and response to the T cell activating bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The T cell activating bispecific antigen binding molecule is suitably administered to the patient at one time or over a series of treatments. Depending on the type and severity of the disease, about 1 μg/kg to 15 mg/kg (e.g. 0.1 mg/kg-10 mg/kg) of T cell activating bispecific antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the T cell activating bispecific antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the T cell activating bispecific antigen binding molecule). An initial higher loading dose, followed by one or more lower doses may be administered. However, other dosage regimens may be useful. The progress of this therapy is easily monitored by conventional techniques and assays.

The T cell activating bispecific antigen binding molecules of the invention will generally be used in an amount effective to achieve the intended purpose. For use to treat or prevent a disease condition, the T cell activating bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the T cell activating bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC. In cases of local administration or selective uptake, the effective local concentration of the T cell activating bispecific antigen binding molecules may not be related to plasma concentration. One having skill in the art will be able to optimize therapeutically effective local dosages without undue experimentation.

A therapeutically effective dose of the T cell activating bispecific antigen binding molecules described herein will generally provide therapeutic benefit without causing substantial toxicity. Toxicity and therapeutic efficacy of a T cell activating bispecific antigen binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. T cell activating bispecific antigen binding molecules that exhibit large therapeutic indices are preferred. In one embodiment, the T cell activating bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety). The attending physician for patients treated with T cell activating bispecific antigen binding molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The T cell activating bispecific antigen binding molecules of the invention may be administered in combination with one or more other agents in therapy. For instance, a T cell activating bispecific antigen binding molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anticancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of T cell activating bispecific antigen binding molecule used, the type of disorder or treatment, and other factors discussed above. The T cell activating bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the T cell activating bispecific antigen binding molecule of the invention can occur prior to, simultaneously, and/or following, administration of the additional therapeutic agent and/or adjuvant. T cell activating bispecific antigen binding molecules of the invention can also be used in combination with radiation therapy.

In another aspect, the invention provides for a bispecific antibody comprising a) a first antigen-binding site that comprises a variable heavy chain domain (VH) of SEQ ID NO: 274 and a variable light chain domain of SEQ ID NO: 31; and b) a second antigen-binding site that comprises a variable heavy chain domain (VH) of SEQ ID NO: 36 and a variable light chain domain of SEQ ID NO: 31 for use in combination with an antibody to PD-L1 or FAP-4-1BBL. In one embodiment, the bispecific antibody further comprises a third antigen-binding site that comprises a variable heavy chain domain (VH) of SEQ ID NO: 274 and a variable light chain domain of SEQ ID NO: 31.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a T cell activating bispecific antigen binding molecule of the invention. The label or package insert indicates that the composition is used for treating the condition of choice. Moreover, the article of manufacture may comprise (a) a first container with a composition contained therein, wherein the composition comprises a T cell activating bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

General Methods

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturers' instructions. General information regarding the nucleotide sequences of human immunoglobulins light and heavy chains is given in: Kabat, E. A. et al., (1991) Sequences of Proteins of Immunological Interest, 5$^{th}$ ed., NIH Publication No. 91-3242.
DNA Sequencing DNA sequences were determined by standard double strand sequencing at Synergene (Schlieren).
Gene Synthesis Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.
Isolation of Primary Human Pan T Cells from PBMCs Peripheral blood mononuclear cells (PBMCs) were prepared by Histopaque density centrifugation from enriched lymphocyte preparations (buffy coats) obtained from local blood banks or from fresh blood from healthy human donors. Briefly, blood was diluted with sterile PBS and carefully layered over a Histopaque gradient (Sigma, H8889). After centrifugation for 30 minutes at 450×g at room temperature (brake switched off), part of the plasma above the PBMC containing interphase was discarded. The PBMCs were transferred into new 50 ml Falcon tubes and tubes were filled up with PBS to a total volume of 50 ml. The mixture was centrifuged at room temperature for 10 minutes at 400×g (brake switched on). The supernatant was discarded and the PBMC pellet washed twice with sterile PBS (centrifugation steps at 4° C. for 10 minutes at 350×g). The resulting PBMC population was counted automatically (Vi-Cell) and stored in RPMI1640 medium, containing 10% FCS and 1% L-alanyl-L-glutamine (Biochrom, K0302) at 37° C., 5% $CO_2$ in the incubator until assay start. T cell enrichment from PBMCs was performed using the Pan T Cell Isolation Kit II (Miltenyi Biotec #130-091-156), according to the manufacturer's instructions. Briefly, the cell pellets were diluted in 40 µl cold buffer per 10 million cells (PBS with 0.5% BSA, 2 mM EDTA, sterile filtered) and incubated with 10 µl Biotin-Antibody Cocktail per 10 million cells for 10 min at 4° C. 30 µl cold buffer and 20 µl Anti-Biotin magnetic beads per 10 million cells were added, and the mixture incubated for another 15 min at 4° C. Cells were washed by adding 10-20× the current volume and a subsequent centrifugation step at 300×g for 10 min. Up to 100 million cells were resuspended in 500 µl buffer. Magnetic separation of unlabeled human pan T cells was performed using LS columns (Miltenyi Biotec #130-042-401) according to the manufacturer's instructions. The resulting T cell population was counted automatically (ViCell) and stored in AIM-V medium at 37° C., 5% $CO_2$ in the incubator until assay start (not longer than 24 h).
Isolation of Primary Human Naive T Cells from PBMCs Peripheral blood mononuclar cells (PBMCs) were prepared by Histopaque density centrifugation from enriched lymphocyte preparations (buffy coats) obtained from local blood banks or from fresh blood from healthy human donors. T-cell enrichment from PBMCs was performed using the Naive CD8$^+$ T cell isolation Kit from Miltenyi Biotec (#130-093-244), according to the manufacturer's instructions, but skipping the last isolation step of CD8$^+$ T cells (also see description for the isolation of primary human pan T cells).
Isolation of Murine Pan T Cells from Splenocytes Spleens were isolated from C57BL/6 mice, transferred into a GentleMACS C-tube (Miltenyi Biotech #130-093-237) containing MACS buffer (PBS+0.5% BSA+2 mM EDTA) and dissociated with the GentleMACS Dissociator to obtain single-cell suspensions according to the manufacturer's instructions. The cell suspension was passed through a pre-separation filter to remove remaining undissociated tissue particles. After centrifugation at 400×g for 4 min at 4°

C., ACK Lysis Buffer was added to lyse red blood cells (incubation for 5 min at room temperature). The remaining cells were washed with MACS buffer twice, counted and used for the isolation of murine pan T cells. The negative (magnetic) selection was performed using the Pan T Cell Isolation Kit from Miltenyi Biotec (#130-090-861), following the manufacturer's instructions. The resulting T cell population was automatically counted (ViCell) and immediately used for further assays.

Isolation of Primary Cynomolgus PBMCs from Heparinized Blood

Peripheral blood mononuclear cells (PBMCs) were prepared by density centrifugation from fresh blood from healthy cynomolgus donors, as follows: Heparinized blood was diluted 1:3 with sterile PBS, and Lymphoprep medium (Axon Lab #1114545) was diluted to 90% with sterile PBS. Two volumes of the diluted blood were layered over one volume of the diluted density gradient and the PBMC fraction was separated by centrifugation for 30 min at 520×g, without brake, at room temperature. The PBMC band was transferred into a fresh 50 ml Falcon tube and washed with sterile PBS by centrifugation for 10 min at 400×g at 4° C. One low-speed centrifugation was performed to remove the platelets (15 min at 150×g, 4° C.), and the resulting PBMC population was automatically counted (ViCell) and immediately used for further assays.

Example 1

Purification of Biotinylated Folate Receptor-Fc Fusions

To generate new antibodies against human FolR1 the following antigens and screening tools were generated as monovalent Fc fusion proteins (the extracellular domain of the antigen linked to the hinge region of Fc-knob which is co-expressed with an Fc-hole molecule). The antigen genes were synthesized (Geneart, Regensburg, Germany) based on sequences obtained from GenBank or SwissProt and inserted into expression vectors to generate fusion proteins with Fc-knob with a C-terminal Avi-tag for in vivo or in vitro biotinylation. In vivo biotinylation was achieved by co-expression of the bacterial birA gene encoding a bacterial biotin ligase during production. Expression of all genes was under control of a chimeric MPSV promoter on a plasmid containing an oriP element for stable maintenance of the plasmids in EBNA containing cell lines.

For preparation of the biotinylated monomeric antigen/Fc fusion molecules, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 9.5:9.5:1 ratio ("antigen ECD-Fc knob-avi tag":"Fc hole":"BirA").

For protein production in 500 ml shake flasks, 400 million HEK293 EBNA cells were seeded 24 hours before transfection. For transfection cells were centrifuged for 5 minutes at 210 g, and supernatant was replaced by pre-warmed CD CHO medium. Expression vectors were resuspended in 20 mL of CD CHO medium containing 200 μg of vector DNA. After addition of 540 μL of polyethylenimine (PEI), the solution was mixed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection, 1 mM valproic acid and 7% Feed 1 (Lonza) were added to the culture. The production medium was also supplemented with 100 μM biotin. After 7 days of culturing, the cell supernatant was collected by spinning down cells for 15 min at 210 g. The solution was sterile filtered (0.22 μm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HiTrap ProteinA HP column (CV=5 mL, GE Healthcare) equilibrated with 40 mL 20 mM sodium phosphate, 20 mM sodium citrate pH 7.5. Unbound protein was removed by washing with at least 10 column volumes of 20 mM sodium phosphate, 20 mM sodium citrate pH 7.5. The bound protein was eluted using a linear pH-gradient created over 20 column volumes of 20 mM sodium citrate, 100 mM sodium chloride, 100 mM glycine, pH 3.0. The column was then washed with 10 column volumes of 20 mM sodium citrate, 100 mM sodium chloride, 100 mM glycine, pH 3.0.

pH of collected fractions was adjusted by adding 1/10 (v/v) of 0.5 M sodium phosphate, pH 8.0. The protein was concentrated and filtered prior to loading on a HiLoad Superdex 200 column (GE Healthcare) equilibrated with 20 mM histidine, 140 mM sodium chloride, pH 6.0.

The protein concentration was determined by measuring the optical density (OD) at 280 nm, using the molar extinction coefficient calculated on the basis of the amino acid sequence. Purity and molecular weight of the FolR1-Fc-fusion was analyzed by SDS capillary electrophoresis in the presence and absence of a reducing agent following the manufacturer instructions (instrument Caliper LabChipGX, Perkin Elmer). The aggregate content of samples was analyzed using a TSKgel G3000 SW XL analytical size-exclusion column (Tosoh) equilibrated in 25 mM K2HPO4, 125 mM NaCl, 200 mM L-arginine monohydrochloride, 0.02% (w/v) NaN3, pH 6.7 running buffer at 25° C. Purified antigen-Fc-fusion proteins were analyzed by surface plasmon resonance assays using commercially available antibodies to confirm correct and natural conformation of the antigens (data not shown).

TABLE 1

Antigens produced for isolation, selection and counter selection of human FolR1 antibodies

| Antigen | ECD (aa) | Accession number | Sequence | Seq ID No |
|---------|----------|------------------|----------|-----------|
| human FolR1 | 25-234 | P15328 | RIAWARTELLNVCMNAKHHKEKPGPEDKLHEQCRPWR KNACCSTNTSQEAHKDVSYLYRFNWNHCGEMAPACKR HFIQDTCLYECSPNLGPWIQQVDQSWRKERVLNVPLC | 227 |

TABLE 1-continued

Antigens produced for isolation, selection and counter selection of human FolR1 antibodies

| Antigen | ECD (aa) | Accession number | Sequence | Seq ID No |
|---|---|---|---|---|
| | | | KEDCEQWWEDCRTSYTCKSNWHKGWNWTSGFNKCAVG AACQPFHFYFPTPTVLCNEIWTHSYKVSNYSRGSGRC IQMWFDPAQGNPNEEVARFYAAAM | |
| human FolR2 | 17-230 | P14207 | TMCSAQDRTDLLNVCMDAKHHKTKPGPEDKLHDQCSP WKKNACCTASTSQELHKDTSRLYNFNWDHCGKMEPAC KRHFIQDTCLYECSPNLGPWIQQVNQSWRKERFLDVP LCKEDCQRWWEDCHTSHTCKSNWHRGWDWTSGVNKCP AGALCRTFESYFPTPAALCEGLWSHSYKVSNYSRGSG RCIQMWFDSAQGNPNEEVARFYAAAMHVN | 228 |
| human FolR3 | 24-243 | P41439 | SARARTDLLNVCMNAKHHKTQPSPEDELYGQCSPWKK NACCTASTSQELHKDTSRLYNFNWDHCGKMEPTCKRH FIQDSCLYECSPNLGPWIRQVNQSWRKERILNVPLCK EDCERWWEDCRTSYTCKSNWHKGWNWTSGINECPAGA LCSTFESYFPTPAALCEGLWSHSFKVSNYSRGSGRCI QMWFDSAQGNPNEEVAKFYAAAMNAGAPSRGIIDS | 229 |
| murine FolR1 | 25-232 | P35846 | TRARTELLNVCMDAKHHKEKPGPEDNLHDQCSPWKTN SCCSTNTSQEAHKDISYLYRFNWNHCGTMTSECKRHF IQDTCLYECSPNLGPWIQQVDQSWRKERILDVPLCKE DCQQWWEDCQSSFTCKSNWHKGWNWSSGHNECPVGAS CHPFTFYFPTSAALCEEIWSHSYKLSNYSRGSGRCIQ MWFDPAQGNPNEEVARFYAEAMS | 230 |
| cynomolgus FolR1 | 25-234 | G7PR14 | EAQTRTARARTELLNVCMNAKHHKEKPGPEDKLHEQC RPWKKNACCSTNTSQEAHKDVSYLYRFNWNHCGEMAP ACKRHFIQDTCLYECSPNLGPWIQQVDQSWRKERVLN VPLCKEDCERWWEDCRTSYCKSNWHKGWNWTSGFNKC PVGAACQPFHFYFPTPTVLCNEIWTYSYKVSNYSRGS GRCIQMWFDPAQGNPNEEVARFYAAAMS | 231 |

TABLE 2

Summary of the yield and final monomer content of the FolR-Fc-fusions.

| Antigen | Monomer [%] (SEC) | Yield |
|---|---|---|
| huFolR1 | 100 | 30 mg/L |
| cyFolR1 | 100 | 32 mg/L |
| muFolR1 | 100 | 31 mg/L |
| huFolR2 | 100 | 16 mg/L |
| huFolR3 | 95 | 38 mg/L |

Example 2

Generation of Common Light Chain with CD3ε Specificity

The T cell activating bispecific molecules described herein comprise at least one CD3 binding moiety. This moiety can be generated by immunizing laboratory animals, screening phage library or using known anti-CD3 antibodies. The common light chain with CD3ε specificity was generated by humanizing the light chain of a murine parental anti-CD3ε antibody (CH2527). For humanization of an antibody of non-human origin, the CDR residues from the non-human antibody (donor) have to be transplanted onto the framework of a human (acceptor) antibody. Generally, acceptor framework sequences are selected by aligning the sequence of the donor to a collection of potential acceptor sequences and choosing one that has either reasonable homology to the donor, or shows similar amino acids at some positions critical for structure and activity. In the present case, the search for the antibody acceptor framework was performed by aligning the mouse VL-domain sequence of the parental antibody to a collection of human germline sequences and choosing the human sequence that showed high sequence identity. Surprisingly, a good match in terms of framework sequence homology was found in a rather infrequent human light chain belonging to the V-domain family 7 of the lambda type, more precisely, hVL_7_46 (IMGT nomenclature, GenBank Acc No. Z73674). This infrequent human light chain was subsequently chosen as acceptor framework for humanization of the light chain of CH2527. The three complementarity determining regions (CDRs) of the mouse light chain variable domain were grafted onto this acceptor framework. Since the framework 4 region is not part of the variable region of the germline V-gene, the alignment for this region (J-element) was done individually. Hence the IGLJ3-02 sequence was chosen for humanization of this light chain.

Thirteen humanized variants were generated (CH2527-VL7_46-1 to VL7_46-10, VL7_46-12 to VL7_46-14). These differ in framework residues (and combinations thereof) that were back-mutated to the murine V-domain sequence or in CDR-residues (Kabat definition) that could be kept identical to the human germline sequence. The following framework residues outside the CDRs were back-mutated to the murine residues in the final humanized VL-domain variant VL7_46-13 (murine residues listed): V36, E38, F44, G46, G49, and G57, respectively. The human J-element IGLJ3-02 was 100% identical to the J-element of the murine parental antibody.

Example 3

SPR Assessment of Humanized Variants with CD3ε Specificity

Humanized VL variants were assessed as chimera in a 2+1 classical format (FIG. 1D), i.e. humanized light chain V-domains were paired with murine heavy chain V-domains. SPR assessment was carried out on a ProteOn XPR36 instrument (Bio-Rad). More precisely, the variants were captured directly from the culture supernatant on an anti-Fab derivatized GLM sensorchip (Goat Anti-Human IgG, F(ab')2 Fragment Specific, Jackson ImmunoResearch) in vertical orientation. The following analytes were subsequently injected horizontally as single concentrations to assess binding to human and cynomolgus CD3ε: 3 µM hu CD3ε(–1-26)-Fc (knob)-avi (ID807) and 2.5 µM cy CD3ε-(–1-26)-Fc(knob)-Avi-Fc(hole) (ID873), respectively. Binding responses were qualitatively compared to binding of the murine control construct and graded+(comparable binding observed), +/– (reduced binding observed) and–(no binding observed). The capture antibody was regenerated after each cycle of ligand capture and analyte binding and the murine construct was re-injected at the end of the study to confirm the activity of the capture surface. The results are summarized in Table 3.

TABLE 3

Qualitative binding assessment based on SPR for the humanized light chain variants combined with the murine heavy chain of CH2527.

| humanized VL variant | binding to CD3ε |
|---|---|
| murine_CH2527_VL | + |
| CH2527-VL7_46-1 | – |
| CH2527-VL7_46-2 | – |
| CH2527-VL7_46-3 | – |
| CH2527-VL7_46-4 | – |
| CH2527-VL7_46-5 | – |
| CH2527-VL7_46-6 | – |
| CH2527-VL7_46-7 | – |
| CH2527-VL7_46-8 | – |
| CH2527-VL7_46-9 | – |
| CH2527-VL7_46-10 | – |
| CH2527-VL7_46-12 | +/– |
| CH2527-VL7_46-13 | + |
| CH2527-VL7_46-14 | – |

Only the humanized light chain variant that was finally chosen, CH2527-VL7_46-13, highlighted in bold letters, exhibited comparable binding to human and cynomolgus CD3ε.

Example 4

Properties of Humanized Common Light Chain with CD3ε Specificity

The light chain V-domain variant that was chosen for the humanized lead molecule is VL7_46-13. The degree of humanness, i.e. the sequence homology of the humanized V-domain to the human germline V-domain sequence was determined. For VL7_46-13, the overall sequence identity with the closest human germline homolog is 65% before humanization and 80% afterwards. Omitting the CDR regions, the sequence identity is 92% to the closest human germline homolog. As can be seen from Table 3, VL7_46-13 is the only humanized VL variant out of a panel of 13 variants that showed comparable binding to the parental murine antibody and also retained its cross-reactivity to cynomolgus CD3ε. This result indicates that it was not trivial to humanize the murine VL-domain without losing binding affinity to CD3ε which required several back-mutations to murine framework residues (in particular G46) while retaining G24 in CDR1. In addition, this result shows that the VL-domain plays a crucial role in target recognition. Importantly, the humanized VL-domain VL7_46-13 based on an infrequent human germline belonging to the V-domain family 7 of the lambda type and retaining affinity and specificity for CD3ε, is also suitable to be used as a common light chain in phage-displayed antibody libraries of the Fab-format and enables successful selection for novel specificities which greatly facilitates the generation and production of bispecific molecules binding to CD3ε and e.g. a tumor target and sharing the same 'common' light chain.

Example 5

Generation of a Phage Displayed Antibody Library Using a Human Germ-Line Common Light Chain Derived from HVK1-39

Several approaches to generate bispecific antibodies that resemble full length human IgG utilize modifications in the Fc region that induce heterodimerization of two distinct heavy chains. Such examples include knobs-into-holes (Merchant et al., Nat Biotechnol. 1998 July; 16(7):677-81) SEED (Davis et al., Protein Eng Des Sel. 2010 April; 23(4):195-202) and electrostatic steering technologies (Gunasekaran et al., J Biol Chem. 2010 Jun. 18; 285(25):19637-46). Although these approaches enable effective heterodimerization of two distinct heavy chains, appropriate pairing of cognate light and heavy chains remains a problem. Usage of a common light chain (LC) can solve this issue (Merchant, et al. Nat Biotech 16, 677-681 (1998)).

Here, we describe the generation of an antibody library for the display on a M13 phage. Essentially, we designed a multi framework library for the heavy chain with one constant (or "common") light chain. This library is designed for generating multispecific antibodies without the need to use sophisticated technologies to avoid light chain mispairing.

By using a common light chain the production of these molecules can be facilitated as no mispairing occurs any longer and the isolation of a highly pure bispecific antibody is facilitated. As compared to other formats the use of Fab fragments as building blocks as opposed to e.g. the use of scFv fragments results in higher thermal stability and the lack of scFv aggregation and intermolecular scFv formation.

Library Generation

In the following the generation of an antibody library for the display on M13 phage is described. Essentially, we designed a multi framework library for the heavy chain with one constant (or "common") light chain.

We used these heavy chains in the library (GenBank Accession Numbers in brackets):
IGHV1-46*01 (X92343) (SEQ ID NO:104),
IGHV1-69*06 (L22583), (SEQ ID NO:105)
IGHV3-15*01 (X92216), (SEQ ID NO:106)
IGHV3-23*01 (M99660), (SEQ ID NO:107)
IGHV4-59*01 (AB019438), (SEQ ID NO:108)
IGHV5-51*01 (M99686), (SEQ ID NO:109)

All heavy chains use the IGHJ2 as J-element, except the IGHV1-69*06 which uses IGHJ6 sequence. The design of the randomization included the CDR-H1, CDR-H2, and CDR-H3. For CDR-H1 and CDR-H2 a "soft" randomization strategy was chosen, and the randomization oligonucleotides were such that the codon for the amino acid of the germ-line sequence was present at 50%. All other amino acids, except cysteine, were summing up for the remaining 50%. In CDR-H3, where no germ-line amino acid is present due to the presence of the genetic D-element, oligonucleotides were designed that allow for the usage of randomized inserts between the V-element and the J-element of 4 to 9 amino acids in length. Those oligonucleotides contained in their randomized part e.g. The three amino acids G/Y/S are present to 15% each, those amino acids A/D/T/R/P/L/V/N/W/F/I/E are present to 4,6% each.

Exemplary methods for generation of antibody libraries are described in Hoogenboom et al., Nucleic Acids Res. 1991, 19, 4133-413; Lee et., al J. Mol. Biol. (2004) 340, 1073-1093.

The light chain is derived from the human sequence hVK1-39, and is used in an unmodified and non-randomized fashion. This will ensure that the same light chain can be used for other projects without additional modifications.

Exemplary Library Selection:

Selections with all affinity maturation libraries are carried out in solution according to the following procedure using a monomeric and biotinylated extracellular domain of a target antigen X. $1.10^{12}$ phagemid particles of each library are bound to 100 nM biotinylated soluble antigen for 0.5 h in a total volume of 1 ml. 2. Biotinylated antigen is captured and specifically bound phage particles are isolated by addition of ~$5 \times 10^{7}$ streptavidin-coated magnetic beads for 10 min. 3. Beads are washed using 5-10×1 ml PBS/Tween20 and 5-10×1 ml PBS. 4. Elution of phage particles is done by addition of 1 ml 100 mM TEA (triethylamine) for 10 min and neutralization by addition of 500 ul 1M Tris/HCl pH 7.4 and 5. Re-infection of exponentially growing E. coli TG1 bacteria, infection with helper phage VCSM13 and subsequent PEG/NaCl precipitation of phagemid particles is applied in subsequent selection rounds. Selections are carried out over 3-5 rounds using either constant or decreasing (from $10^{-7}M$ to $2 \times 10^{-9}M$) antigen concentrations. In round 2, capture of antigen/phage complexes is performed using neutravidin plates instead of streptavidin beads. All binding reactions are supplemented either with 100 nM bovine serum albumin, or with non-fat milk powder in order to compete for unwanted clones arising from mere sticky binding of the antibodies to the plastic support.

Selections are being carried out over three or four rounds using decreasing antigen concentrations of the antigen starting from 100 nM and going down to 5 nM in the final selection round. Specific binders are defined as signals ca. 5× higher than background and are identified by ELISA. Specific binders are identified by ELISA as follows: 100 µl of 10 nM biotinylated antigen per well are coated on neutravidin plates. Fab-containing bacterial supernatants are added and binding Fabs are detected via their Flag-tags by using an anti-Flag/HRP secondary antibody. ELISA-positive clones are bacterially expressed as soluble Fab fragments in 96-well format and supernatants are subjected to a kinetic screening experiment by SPR-analysis using ProteOn XPR36 (BioRad). Clones expressing Fabs with the highest affinity constants are identified and the corresponding phagemids are sequenced. For further characterization, the Fab sequences are amplified via PCR from the phagemid and cloned via appropriate restriction sites into human IgG1 expression vectors for mammalian production.

Generation of a Phage Displayed Antibody Library Using a Humanized CD3ε Specific Common Light Chain Here, the generation of an antibody library for the display on M13 phage is described. Essentially, we designed a multi framework library for the heavy chain with one constant (or "common") light chain. This library was designed for the generation of Fc-containing, but FcgR binding inactive T cell bispecific antibodies of IgG1 P329G LALA or IgG4 SPLE PG isotype in which one or two Fab recognize a tumor surface antigen expressed on a tumor cell whereas the remaining Fab arm of the antibody recognizes CD3e on a T cell.

Library Generation

In the following the generation of an antibody library for the display on M13 phage is described. Essentially, we designed a multi framework library for the heavy chain with one constant (or "common") light chain. This library is designed solely for the generation of Fc-containing, but FcgR binding inactive T cell bispecific antibodies of IgG1 P329G LALA or IgG4 SPLE PG isotype. Diversity was introduced via randomization oligonucleotides only in the CDR3 of the different heavy chains. Methods for generation of antibody libraries are well known in the art and are described in (Hoogenboom et al., Nucleic Acids Res. 1991, 19, 4133-413; or in: Lee et., al J. Mol. Biol. (2004) 340, 1073-1093).

We used these heavy chains in the library:
IGHV1-46*01 (X92343), (SEQ ID NO:104)
IGHV1-69*06 (L22583), (SEQ ID NO:105)
IGHV3-15*01 (X92216), (SEQ ID NO:106)
IGHV3-23*01 (M99660), (SEQ ID NO:107)
IGHV4-59*01 (AB019438), (SEQ ID NO:108)
IGHV5-51*01 (M99686), (SEQ ID NO:109)

We used the light chain derived from the humanized human and Cynomolgus CD3 c specific antibody CH2527 in the library: (VL7_46-13; SEQ ID NO:112). This light chain was not randomized and used without any further modifications in order to ensure compatibility with different bispecific binders.

All heavy chains use the IGHJ2 as J-element, except the IGHV1-69*06 which uses IGHJ6 sequence. The design of the randomization focused on the CDR-H3 only, and PCR oligonucleotides were designed that allow for the usage of randomized inserts between the V-element and the J-element of 4 to 9 amino acids in length.

Example 6

Selection of Antibody Fragments from Common Light Chain Libraries (Comprising Light Chain with CD3ε Specificity) to FolR1

The antibodies 16A3, 15A1, 18D3, 19E5, 19A4, 15H7, 15B6, 16D5, 15E12, 21D1, 16F12, 21A5, 21G8, 19H3, 20G6, and 20H7 comprising the common light chain VL7_46-13 with CD3ε specificity were obtained by phage display selections against different species (human, cynomolgus and murine) of FolR1. Clones 16A3, 15A1, 18D3, 19E5, 19A4, 15H7, 15B6, 21D1, 16F12, 19H3, 20G6, and 20H7 were selected from a sub-library in which the common light chain was paired with a heavy chain repertoire based on the human germline VH1_46. In this sub-library, CDR3 of VH1_46 has been randomized based on 6 different CDR3 lengths. Clones 16D5, 15E12, 21A5, and 21G8 were selected from a sub-library in which the common light chain was paired with a heavy chain repertoire based on the human germline VH3_15. In this sub-library, CDR3 of VH3_15 has been randomized based on 6 different CDR3 lengths. In order to obtain species cross-reactive (or murine FolR1-reactive) antibodies, the different species of FolR1 were alternated (or kept constant) in different ways over 3 rounds of biopanning: 16A3 and 15A1 (human—cynomolgus—human FolR1); 18D3 (cynomolgus—human—murine FolR1); 19E5 and 19A4 (3 rounds against murine FolR1); 15H7, 15B6, 16D5, 15E12, 21D1, 16F12, 21A5, 21G8 (human—cynomolgus—human FolR1); 19H3, 20G6, and 20H7 (3 rounds against murine FolR1).

Human, murine and cynomolgus FolR1 as antigens for the phage display selections as well as ELISA- and SPR-based screenings were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). In order to assess the specificity to FolR1, two related receptors, human FolR2 and FolR3 were generated in the same way.

Selection rounds (biopanning) were performed in solution according to the following pattern:
1. Pre-clearing of ~$10^{12}$ phagemid particles on maxisorp plates coated with 10 ug/ml of an unrelated human IgG to deplete the libraries of antibodies recognizing the Fc-portion of the antigen.
2. Incubating the non-Fc-binding phagemid particles with 100 nM biotinylated human, cynomolgus, or murine FolR1 for 0.5h in the presence of 100 nM unrelated non-biotinylated Fc knob-into-hole construct for further depletion of Fc-binders in a total volume of 1 ml.
3. Capturing the biotinylated FolR1 and attached specifically binding phage by transfer to 4 wells of a neutravidin pre-coated microtiter plate for 10 min (in rounds 1 & 3).
4. Washing the respective wells using 5×PBS/Tween20 and 5×PBS.
5. Eluting the phage particles by addition of 250 ul 100 mM TEA (triethylamine) per well for 10 min and neutralization by addition of 500 ul 1 M Tris/HCl pH 7.4 to the pooled eluates from 4 wells.
6. Post-clearing of neutralized eluates by incubation on neutravidin pre-coated microtiter plate with 100 nM biotin-captured FolR2 or FolR3 for final removal of Fc- and unspecific binders.
7. Re-infection of log-phase E. coli TG1 cells with the supernatant of eluted phage particles, infection with helperphage VCSM13, incubation on a shaker at 30° C. over night and subsequent PEG/NaCl precipitation of phagemid particles to be used in the next selection round.

Selections were carried out over 3 rounds using constant antigen concentrations of 100 nM. In round 2, in order to avoid enrichment of binders to neutravidin, capture of antigen: phage complexes was performed by addition of $5.4 \times 10^7$ streptavidin-coated magnetic beads. Specific binders were identified by ELISA as follows: 100 ul of 25 nM biotinylated human, cynomolgus, or murine FolR1 and 10 ug/ml of human IgG were coated on neutravidin plates and maxisorp plates, respectively. Fab-containing bacterial supernatants were added and binding Fabs were detected via their Flag-tags using an anti-Flag/HRP secondary antibody. Clones exhibiting signals on human FolR1 and being negative on human IgG were short-listed for further analyses and were also tested in a similar fashion against the remaining two species of FolR1. They were bacterially expressed in a 0.5 liter culture volume, affinity purified and further characterized by SPR-analysis using BioRad's ProteOn XPR36 biosensor.

Affinities ($K_D$) of selected clones were measured by surface plasmon resonance (SPR) using a ProteOn XPR36 instrument (Biorad) at 25° C. with biotinylated human, cynomolgus, and murine FolR1 as well as human FolR2 and FolR3 (negative controls) immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10 µg/ml, then injected at 30 µl/minute in vertical orientation. Injection of analytes: For 'one-shot kinetics' measurements, injection direction was changed to horizontal orientation, two-fold dilution series of purified Fab (varying concentration ranges) were injected simultaneously along separate channels 1-5, with association times of 200 s, and dissociation times of 600 s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Table 4 lists the equilibrium dissociation constants ($K_D$) of the selected clones specific for FolR1.

TABLE 4

Equilibrium dissociation constants (KD) for anti-FolR1 antibodies (Fab-format) selected by phage display from common light chain sub-libraries comprising VL7_46-13, a humanized light chain specific for CD3ε.

| Clone | huFolR1 [nM] | cyFolR1 [nM] | muFolR1 [nM] | huFolR2 [nM] | huFolR3 [nM] |
|---|---|---|---|---|---|
| 16A3 | 21.7 | 18 | very weak | no binding | no binding |
| 15A1 | 30.9 | 17.3 | very weak | no binding | no binding |
| 18D3 | 93.6 | 40.2 | very weak | no binding | no binding |
| 19E5 | 522 | 276 | 19.4 | no binding | no binding |
| 19A4 | 2050 | 4250 | 43.1 | no binding | no binding |
| 15H7 | 13.4 | 72.5 | no binding | no binding | no binding |
| 15B6 | 19.1 | 13.9 | no binding | no binding | no binding |
| 16D5 | 39.5 | 114 | no binding | no binding | no binding |
| 15E12 | 55.7 | 137 | no binding | no binding | no binding |
| 21D1 | 62.6 | 32.1 | no binding | no binding | no binding |
| 16F12 | 68 | 90.9 | no binding | no binding | no binding |
| 21A5 | 68.8 | 131 | no binding | no binding | no binding |
| 21G8 | 130 | 261 | no binding | no binding | no binding |
| 19H3 | no binding | no binding | 89.7 | no binding | no binding |
| 20G6 | no binding | no binding | 78.5 | no binding | no binding |

KD in nM.

Example 7

Selection of Antibody Fragments from Generic Multi-Framework Libraries to FolR1

The antibodies 11F8, 36F2, 9D11, 5D9, 6B6, and 14E4 were obtained by phage display selections based on generic multi-framework sub-libraries against different species (human, cynomolgus and murine) of FolR1. In these multi-framework sub-libraries, different VL-domains with randomized CDR3 (3 different lengths) are paired with different VH-domains with randomized CDR3 (6 different lengths). The selected clones are of the following VL/VH pairings: 11F8 (Vk_1_5/VH_1_69), 36F2 (Vk_3_20/VH_1_46), 9D11 (Vk2D_28/VH1_46), 5D9 (Vk3_20/VH1_46), 6B6 (Vk3_20/VH1_46), and 14E4 (Vk3_20/VH3_23). In order to obtain species cross-reactive (or murine FolR1-reactive) antibodies, the different species of FolR1 were alternated (or kept constant) in different ways over 3 or 4 rounds of biopanning: 11F8 (cynomolgus—murine—human FolR1); 36F2 (human—murine—cynomolgus—murine FolR1); 9D11 (cynomolgus—human—cynomolgus FolR1); 5D9 (human—cynomolgus—human FolR1); 6B6 (human—cynomolgus—human FolR1) and 14E4 (3 rounds against murine FolR1).

Human, murine and cynomolgus FolR1 as antigens for the phage display selections as well as ELISA- and SPR-based screenings were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). In order to assess the specificity to FolR1, two related receptors, human FolR2 and FolR3 were generated in the same way.

Selection rounds (biopanning) were performed in solution according to the following pattern:
1. Pre-clearing of ~$10^{12}$ phagemid particles on maxisorp plates coated with 10 ug/ml of an unrelated human IgG to deplete the libraries of antibodies recognizing the Fc-portion of the antigen.
2. Incubating the non-Fc-binding phagemid particles with 100 nM biotinylated human, cynomolgus, or murine FolR1 for 0.5h in the presence of 100 nM unrelated non-biotinylated Fc knob-into-hole construct for further depletion of Fc-binders in a total volume of 1 ml.
3. Capturing the biotinylated FolR1 and attached specifically binding phage by transfer to 4 wells of a neutravidin pre-coated microtiter plate for 10 min (in rounds 1 & 3).
4. Washing the respective wells using 5×PBS/Tween20 and 5×PBS.
5. Eluting the phage particles by addition of 250 ul 100 mM TEA (triethylamine) per well for 10 min and neutralization by addition of 500 ul 1 M Tris/HCl pH 7.4 to the pooled eluates from 4 wells.
6. Post-clearing of neutralized eluates by incubation on neutravidin pre-coated microtiter plate with 100 nM biotin-captured FolR2 or FolR3 for final removal of Fc- and unspecific binders.
7. Re-infection of log-phase E. coli TG1 cells with the supernatant of eluted phage particles, infection with helperphage VCSM13, incubation on a shaker at 30° C. over night and subsequent PEG/NaCl precipitation of phagemid particles to be used in the next selection round.

Selections were carried out over 3 rounds using constant antigen concentrations of 100 nM. In round 2 and 4, in order to avoid enrichment of binders to neutravidin, capture of antigen: phage complexes was performed by addition of 5.4×$10^7$ streptavidin-coated magnetic beads. Specific binders were identified by ELISA as follows: 100 ul of 25 nM biotinylated human, cynomolgus, or murine FolR1 and 10 ug/ml of human IgG were coated on neutravidin plates and maxisorp plates, respectively.

Fab-containing bacterial supernatants were added and binding Fabs were detected via their Flag-tags using an anti-Flag/HRP secondary antibody. Clones exhibiting signals on human FolR1 and being negative on human IgG were short-listed for further analyses and were also tested in a similar fashion against the remaining two species of FolR1. They were bacterially expressed in a 0.5 liter culture volume, affinity purified and further characterized by SPR-analysis using BioRad's ProteOn XPR36 biosensor.

Affinities ($K_D$) of selected clones were measured by surface plasmon resonance (SPR) using a ProteOn XPR36 instrument (Biorad) at 25° C. with biotinylated human, cynomolgus, and murine FolR1 as well as human FolR2 and FolR3 (negative controls) immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10 µg/ml, then injected at 30 µl/minute in vertical orientation. Injection of analytes: For 'one-shot kinetics' measurements, injection direction was changed to horizontal orientation, two-fold dilution series of purified Fab (varying concentration ranges) were injected simultaneously along separate channels 1-5, with association times of 150 or 200 s, and dissociation times of 200 or 600 s, respectively. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Table 5 lists the equilibrium dissociation constants ($K_D$) of the selected clones specific for FolR1.

TABLE 5

Equilibrium dissociation constants ($K_D$) for anti-FolR1 antibodies (Fab-format) selected by phage display from generic multi-framework sub-libraries.

| | KD (nM) | | | | |
|---|---|---|---|---|---|
| Clone | huFolR1 | cyFolR1 | muFolR1 | huFolR2 | huFolR3 |
| 11F8 | 632 | 794 | 1200 | no binding | no binding |
| 36F2 | 1810 | 1640 | 737 | no binding | no binding |
| 9D11 | 8.64 | 5.29 | no binding | no binding | no binding |

TABLE 5-continued

Equilibrium dissociation constants ($K_D$) for anti-FolR1 antibodies (Fab-format) selected by phage display from generic multi-framework sub-libraries.

| Clone | KD (nM) | | | | |
| --- | --- | --- | --- | --- | --- |
| | huFolR1 | cyFolR1 | muFolR1 | huFolR2 | huFolR3 |
| 5D9 | 8.6 | 5.9 | no binding | no binding | no binding |
| 6B6 | 14.5 | 9.4 | no binding | no binding | no binding |
| 14E4 | no binding | no binding | 6.09 | no binding | no binding |

$K_D$ in nM.

Example 8

Production and Purification of Novel FolR1 Binders in IgG and T-Cell Bispecific Formats To identify FolR1 binders which are able to induce T-cell dependent killing of selected target cells the antibodies isolated from a common light chain- or Fab-library were converted into the corresponding human IgG1 format. In brief, the variable heavy and variable light chains of unique FolR1 binders from phage display were amplified by standard PCR reactions using the Fab clones as the template. The PCR products were purified and inserted (either by restriction endonuclease and ligase based cloning, or by 'recombineering' using the InFusion kit from Invitrogen) into suitable expression vectors in which they are fused to the appropriate human constant heavy or human constant light chain. The expression cassettes in these vectors consist of a chimeric MPSV promoter and a synthetic polyadenylation site. In addition, the plasmids contain the oriP region from the Epstein Barr virus for the stable maintenance of the plasmids in HEK293 cells harboring the EBV nuclear antigen (EBNA). After PEI mediated transfection the antibodies were transiently produced in HEK293 EBNA cells and purified by standard ProteinA affinity chromatography followed by size exclusion chromatography as described:

Transient Transfection and Production

All (bispecific) antibodies (if not obtained from a commercial source) used herein were transiently produced in HEK293 EBNA cells using a PEI mediated transfection procedure for the required vectors as described below. HEK293 EBNA cells are cultivated in suspension serum free in CD CHO culture medium. For the production in 500 ml shake flask 400 million HEK293 EBNA cells are seeded 24 hours before transfection (for alternative scales all amounts were adjusted accordingly). For transfection cells are centrifuged for 5 min by 210×g, supernatant is replaced by pre-warmed 20 ml CD CHO medium. Expression vectors are mixed in 20 ml CD CHO medium to a final amount of 200m DNA. After addition of 540 µl PEI solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% CO2 atmosphere. After incubation time 160 ml F17 medium is added and cell are cultivated for 24 hours. One day after transfection 1 mM valporic acid and 7% Feed 1 is added. After 7 days cultivation supernatant is collected for purification by centrifugation for 15 min at 210×g, the solution is sterile filtered (0.22 µm filter) and sodium azide in a final concentration of 0.01% w/v is added, and kept at 4° C. After production the supernatants were harvested and the antibody containing supernatants were filtered through 0.22 µm sterile filters and stored at 4° C. until purification.

Antibody Purification

All molecules were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to HiTrap PA FF (GE Healthcare, column volume (cv)=5 ml) equilibrated with 8 column volumes (cv) buffer A (20 mM sodium phosphate, 20 mM sodium citrate, pH 7.5). After washing with 10 cv of buffer A, the protein was eluted using a pH gradient to buffer B (20 mM sodium citrate pH 3, 100 mM NaCl, 100 mM glycine) over 12 cv. Fractions containing the protein of interest were pooled and the pH of the solution was gently adjusted to pH 6.0 (using 0.5 M $Na_2HPO_4$ pH 8.0). Samples were concentrated to 2 ml using ultra-concentrators (Vivaspin 15R 30.000 MWCO HY, Sartorius) and subsequently applied to a HiLoad™ 16/60 Superdex™ 200 preparative grade (GE Healthcare) equilibrated with 20 mM Histidine, pH 6.0, 140 mM NaCl, 0.01% Tween-20. The aggregate content of eluted fractions was analyzed by analytical size exclusion chromatography. Therefore, 30 µl of each fraction was applied to a TSKgel G3000 SW XL analytical size-exclusion column (Tosoh) equilibrated in 25 mM $K_2HPO_4$, 125 mM NaCl, 200 mM L-arginine monohydrochloride, 0.02% (w/v) $NaN_3$, pH 6.7 running buffer at 25° C. Fractions containing less than 2% oligomers were pooled and concentrated to final concentration of 1-1.5 mg/ml using ultra concentrators (Vivaspin 15R 30.000 MWCO HY, Sartorius). The protein concentration was determined by measuring the optical density (OD) at 280 nm, using the molar extinction coefficient calculated on the basis of the amino acid sequence. Purity and molecular weight of the constructs were analyzed by SDS capillary electrophoresis in the presence and absence of a reducing agent following the manufacturer instructions (instrument Caliper LabChipGX, Perkin Elmer). Purified proteins were frozen in liquid $N_2$ and stored at −80° C.

Based on in vitro characterization results selected binders were converted into a T-cell bispecific format. In these molecules the FolR1:CD3 binding moieties are arranged in a 2:1 order with the FolR1 Fabs being located at the N-terminus. For clones isolated from the standard Fab library the CD3 binding part was generated as a CrossFab (CHICK crossing) while for the clones from the common light chain library no crossing was necessary. These bispecific molecules were produced and purified analogously to the IgGs.

TABLE 6

Yield and monomer content of novel FolR1 binders in IgG and TCB format, respectively

|   |   |   | IgG | | TCB | |
|---|---|---|---|---|---|---|
| # | Clone | Library | Yield [mg/L] | Monomer [%] | Yield [mg/L] | Monomer [%] |
| 1 | 11F8 | Fab | 8.03 | 96.26 | — | — |
| 2 | 14E4 | Fab | 8.90 | 98.12 | — | — |
| 3 | 1586 | CLC | 7.72 | 100.00 | — | — |
| 4 | 15E12 | CLC | 6.19 | 100.00 | — | — |
| 5 | 15H7 | CLC | 8.94 | 100.00 | — | — |
| 6 | 16A3 | CLC | 0.60 | n.d. | — | — |
| 7 | 16D5 | CLC | 36.50 | 96.96 | 4.36 | 97.19 |
| 8 | 16F12 | CLC | 5.73 | 97.17 | — | — |
| 9 | 18D3 | CLC | 0.90 | n.d. | — | — |
| 10 | 19A4 | CLC | 38.32 | 100.00 | 37.50 | 100.00 |
| 11 | 19E5 | CLC | 46.09 | 100.00 | — | — |
| 12 | 19H3 | CLC | 7.64 | 100.00 | — | — |
| 13 | 20G6 | CLC | 24.00 | 100.00 | — | — |
| 14 | 20H7 | CLC | 45.39 | 100.00 | — | — |
| 15 | 21A5 | CLC | 1.38 | 98.56 | 47.31 | 95.08 |
| 16 | 21D1 | CLC | 5.47 | 100.00 | — | — |
| 17 | 21G8 | CLC | 6.14 | 97.28 | 9.27 | 100.00 |
| 18 | 36F2 | Fab | 11.22 | 100.00 | 18.00 | 100.00 |
| 19 | 5D9 | Fab | 20.50 | 100.00 | 0.93 | 97.32 |
| 20 | 6B6 | Fab | 3.83 | 100.00 | 4.17 | 91.53 |
| 21 | 9D11 | Fab | 14.61 | 100.00 | 2.63 | 100.00 |

CLC: Common light chain

Example 9

2+1 and 1+1 T-Cell Bispecific Formats

Four different T-cell bispecific formats were prepared for one common light chain binder (16D5) and three formats for one binder from the Fab library (9D11) to compare their killing properties in vitro.

The standard format is the 2+1 inverted format as already described (FolR1:CD3 binding moieties arranged in a 2:1 order with the FolR1 Fabs located at the N-terminus). In the 2+1 classical format the FolR1:CD3 binding moieties are arranged in a 2:1 order with the CD3 Fab being located at the N-terminus. Two monovalent formats were also prepared. The 1+1 head-to-tail has the FolR1:CD3 binding moieties arranged in a 1:1 order on the same arm of the molecule with the FolR1 Fab located at the N-terminus. In the 1+1 classical format the FolR1:CD3 binding moieties are present once, each on one arm of the molecule. For the 9D11 clone isolated from the standard Fab library the CD3 binding part was generated as a CrossFab (CH1Cκ crossing) while for the 16D5 from the common light chain library no crossing was necessary. These bispecific molecules were produced and purified analogously to the standard inverted T-cell bispecific format.

TABLE 7

Summary of the yield and final monomer content of the different T-cell bispecific formats.

| Construct | Monomer [%] (SEC) | Yield |
|---|---|---|
| 16D5 FolR1 TCB 2 + 1 (inverted) | 96% | 5.4 mg/L |
| 16D5 FolR1 TCB 2 + 1 (classical) | 90% | 4.6 mg/L |
| 16D5 FolR1 TCB 1 + 1 (head-to-tail) | 100% | 5.4 mg/L |
| 16D5 FolR1 TCB 1 + 1 (classical) | 100% | 0.7 mg/L |
| 9D11 FolR1 TCB 2 + 1 (inverted) | 100% | 2.6 mg/L |
| 9D11 FolR1 TCB 1 + 1 (head-to-tail) | 100% | 6.1 mg/L |
| 9D11 FolR1 TCB 1 + 1 (classical) | 96% | 1.3 mg/L |
| Mov19 FolR1 TCB 2 + 1 (inverted) | 98% | 3 mg/L |
| Mov19 FolR1 TCB 1 + 1 (head-to-tail) | 100% | 5.2 mg/L |

Example 10

Biochemical Characterization of FolR1 Binders by Surface Plasmon Resonance

Binding of FolR1 binders as IgG or in the T-cell bispecific format to different recombinant folate receptors (human FolR1, 2 and 3, murine FolR1 and cynomolgus FolR1; all as Fc fusions) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

Single Injections

First the anti-FolR1 IgGs were analyzed by single injections (Table 1) to characterize their crossreactivity (to human, murine and cyno FolR1) and specificity (to human FolR1, human FolR2, human FolR3). Recombinant biotinylated monomeric Fc fusions of human, cynomolgus and murine Folate Receptor 1 (FolR1-Fc) or human Folate Receptor 2 and 3 (FolR2-Fc, FolR3-Fc) were directly coupled on a SA chip using the standard coupling instruction (Biacore, Freiburg/Germany). The immobilization level was about 300-400 RU. The IgGs were injected for 60 seconds at a concentration of 500 nM. IgGs binding to huFolR2 and huFolR3 were rejected for lack of specificity. Most of the binders are only crossreactive between human and cyno FolR1, additional crossreactivity to murine FolR1 went most of the time hand in hand with loss of specificity.

TABLE 8

Crossreactivity and specificity of 25 new folate receptor 1 binders (as IgGs) as well as of two control IgGs (Mov19 and Farletuzumab).

| Clone name | Binding to huFolR1 | Binding to cyFolR1 | Binding to muFolR1 | Binding to huFolR2 | Binding to huFolR3 |
|---|---|---|---|---|---|
| Mov19 | + | + | − | − | − |
| Farletuzumab | + | + | − | − | − |
| 16A3 | + | + | +/− | − | − |
| 18D3 | + | + | − | − | − |
| 19E5 | + | + | + | + | + |
| 19A4 | − | − | + | + | + |
| 15H7 | + | + | + | − | − |
| 15B6 | + | + | − | − | − |
| 16D5 | + | + | − | − | − |
| 15E12 | + | + | +/− | + | + |
| 21D1 | + | + | +/− | − | − |
| 16F12 | + | + | − | − | − |
| 21A5 | + | + | − | − | +/− |
| 21G8 | + | + | − | + | + |
| 19H3 | − | − | + | − | − |
| 20G6 | − | − | + | − | − |
| 20H7 | − | − | + | − | − |

TABLE 8-continued

Crossreactivity and specificity of 25 new folate receptor 1 binders (as IgGs) as well as of two control IgGs (Mov19 and Farletuzumab).

| Clone name | Binding to huFolR1 | Binding to cyFolR1 | Binding to muFolR1 | Binding to huFolR2 | Binding to huFolR3 |
|---|---|---|---|---|---|
| 9D11 | + | + | − | − | − |
| 5D9 | + | + | − | + | + |
| 6B6 | + | + | − | + | + |
| 11F8 | + | + | + | + | + |
| 36F2 | + | + | + | − | − |
| 14E4 | − | − | + | − | − |

+ means binding, − means no binding, +/− means weak binding.

Avidity to Folate Receptor 1

The avidity of the interaction between the anti-FolR1 IgGs or T cell bispecifics and the recombinant folate receptors was determined as described below (Table 9).

Recombinant biotinylated monomeric Fc fusions of human, cynomolgus and murine Folate Receptor 1 (FolR1-Fc) were directly coupled on a SA chip using the standard coupling instruction (Biacore, Freiburg/Germany). The immobilization level was about 300-400 RU. The anti-FolR1 IgGs or T cell bispecifics were passed at a concentration range from 2.1 to 500 nM with a flow of 30 µL/minutes through the flow cells over 180 seconds. The dissociation was monitored for 600 seconds. Bulk refractive index differences were corrected for by subtracting the response obtained on reference flow cell immobilized with recombinant biotinylated IL2 receptor Fc fusion. For the analysis of the interaction of 19H3 IgG and murine folate receptor 1, folate (Sigma F7876) was added in the HBS-EP running buffer at a concentration of 2.3 µM. The binding curves resulting from the bivalent binding of the IgGs or T cell bispecifics were approximated to a 1:1 Langmuir binding and fitted with that model (which is not correct, but gives an idea of the avidity). The apparent avidity constants for the interactions were derived from the rate constants of the fitting using the Bia Evaluation software (GE Healthcare).

TABLE 9

Bivalent binding (avidity with apparent KD) of selected FolR1 binders as IgGs or as T-cell bispecifics (TCB) on human and cyno FolRl.

| Analyte | Ligand | ka (1/Ms) | kd (1/s) | Apparent KD (M) |
|---|---|---|---|---|
| 16D5 TCB | huFolR1 | 8.31E+04 | 3.53E−04 | 4.24E−09 |
|  | cyFolR1 | 1.07E+05 | 3.70E−04 | 3.45E−09 |
| 9D11 TCB | huFolR1 | 1.83E+05 | 9.83E−05 | 5.36E−10 |
|  | cyFolR1 | 2.90E+05 | 6.80E−05 | 2.35E−10 |
| 21A5 TCB | huFolR1 | 2.43E+05 | 2.64E−04 | 1.09E−09 |
|  | cyFolR1 | 2.96E+05 | 2.76E−04 | 9.32E−10 |
| 36F2 IgG | huFolR1 | 2.62E+06 | 1.51E−02 | 5.74E−9 |
|  | cyFolR1 | 3.02E+06 | 1.60E−02 | 5.31E−9 |
|  | muFolR1 | 3.7E+05 | 6.03E−04 | 1.63E−9 |
| Mov19 IgG | huFolR1 | 8.61E+05 | 1.21E−04 | 1.4E−10 |
|  | cyFolR1 | 1.29E+06 | 1.39E−04 | 1.08E−10 |
| Farletuzumab | huFolR1 | 1.23E+06 | 9E−04 | 7.3E−10 |
|  | cyFolR1 | 1.33E+06 | 8.68E−04 | 6.5E−10 |
| 19H3 IgG | muFolR1 | 7.1E+05 | 1.1E−03 | 1.55E−09 |

1. Affinity to Folate Receptor 1

The affinity of the interaction between the anti-FolR1 IgGs or the T cell bispecifics and the recombinant folate receptors was determined as described below (Table 10).

For affinity measurement, direct coupling of around 6000-7000 resonance units (RU) of the anti-human Fab specific antibody (Fab capture kit, GE Healthcare) was performed on a CM5 chip at pH 5.0 using the standard amine coupling kit (GE Healthcare). Anti-FolR1 IgGs or T cell bispecifics were captured at 20 nM with a flow rate of 10 µl/min for 20 or 40 sec, the reference flow cell was left without capture. Dilution series (6.17 to 500 nM or 12.35 to 3000 nM) of human or cyno Folate Receptor 1 Fc fusion were passed on all flow cells at 30 µl/min for 120 or 240 sec to record the association phase. The dissociation phase was monitored for 240 s and triggered by switching from the sample solution to HBS-EP. The chip surface was regenerated after every cycle using a double injection of 60 sec 10 mM Glycine-HCl pH 2.1 or pH 1.5. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 10

Monovalent binding (affinity) of selected FolR1 binders as IgGs or as T-cell bispecifics (TCB) on human and cyno FolRl.

| Ligand | Analyte | ka (1/Ms) | kd (1/s) | KD (M) |
|---|---|---|---|---|
| 16D5 TCB | huFolR1 | 1.53E+04 | 6.88E−04 | 4.49E−08 |
|  | cyFolR1 | 1.32E+04 | 1.59E−03 | 1.21E−07 |
| 9D11 TCB | huFolR1 | 3.69E+04 | 3.00E−04 | 8.13E−09 |
|  | cyFolR1 | 3.54E+04 | 2.06E−04 | 5.82E−09 |
| 21A5 TCB | huFolR1 | 1.79E+04 | 1.1E−03 | 6.16E−08 |
|  | cyFolR1 | 1.48E+04 | 2.06E−03 | 1.4E−07 |
| Mov19 IgG | huFolR1 | 2.89E+05 | 1.59E−04 | 5.5E−10 |
|  | cyFolR1 | 2.97E+05 | 1.93E−04 | 6.5E−10 |
| Farletuzumab | huFolR1 | 4.17E+05 | 2.30E−02 | 5.53E−08 |
|  | cyFolR1 | 5.53E+05 | 3.73E−02 | 6.73E−08 |

2. Affinity to CD3

The affinity of the interaction between the anti-FolR1 T cell bispecifics and the recombinant human CD3εδ-Fc was determined as described below (Table 11).

For affinity measurement, direct coupling of around 9000 resonance units (RU) of the anti-human Fab specific antibody (Fab capture kit, GE Healthcare) was performed on a CM5 chip at pH 5.0 using the standard amine coupling kit (GE Healthcare). Anti-FolR1 T cell bispecifics were captured at 20 nM with a flow rate of 10 µl/min for 40 sec, the reference flow cell was left without capture. Dilution series (6.17 to 500 nM) of human CD3εδ-Fc fusion were passed on all flow cells at 30 µl/min for 240 sec to record the association phase. The dissociation phase was monitored for 240 s and triggered by switching from the sample solution to HBS-EP. The chip surface was regenerated after every cycle using a double injection of 60 sec 10 mM Glycine-HCl pH 2.1. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 11

Monovalent binding (affinity) of selected FolR1 T-cell bispecifics (TCB) on human CD3-Fc.

| Ligand | Analyte | ka (1/Ms) | kd (1/s) | KD (M) |
|---|---|---|---|---|
| 16D5 TCB | huCD3 | 4.25E+04 | 3.46E−03 | 8.14E−08 |
| 21A5 TCB | huCD3 | 3.72E+04 | 3.29E−03 | 8.8E−08 |

The CD3 binding part is identical for all constructs and the affinity is similar for the measured T cell bispecifics (KD range between 60 and 90 nM).

Example 11

Simultaneous Binding T Cell Bispecifics on Folate Receptor 1 and CD3

Simultaneous binding of the anti-FolR1 T cell bispecifics on recombinant Folate Receptor 1 and recombinant human CD3εδ-Fc was determined by surface plasmon resonance as described below. Recombinant biotinylated monomeric Fc fusions of human, cynomolgus and murine Folate Receptor 1 (FolR1-Fc) were directly coupled on a SA chip using the standard coupling instruction (Biacore, Freiburg/Germany). The immobilization level was about 300-400 RU. The anti-FolR1 T cell bispecifics were injected for 60 s at 500 nM with a flow of 30 μL/minutes through the flow cells, followed by an injection of hu CDεδ-Fc for 60 s at 500 nM. Bulk refractive index differences were corrected for by subtracting the response obtained on reference flow cell immobilized with recombinant biotinylated IL2 receptor Fc fusion. The four T cell bispecifics tested (16D5 TCB, 21A5 TCB, 51C7 TCB and 45D2 TCB) were able to bind simultaneously to Folate Receptor 1 and human CD3 as expected.

Example 12

Epitope Binning

For epitope binning, the anti-FolR1 IgGs or T cell bispecifics were directly immobilized on a CM5 chip at pH 5.0 using the standard amine coupling kit (GE Healthcare), with a final response around 700 RU. 500 nM huFolR1-Fc was then captured for 60 s, followed by 500 nM of the different binders for 30 s. The surface was regenerated with two injections of 10 mM glycine pH 2 for 30 s each. It is assessed if the different binders can bind to huFolR1 captured on immobilized binders (Table 12).

TABLE 12

Epitope characterization of selected FolR1 binders as IgGs or as T-cell bispecifics (TCB) on human FolRl.

| | | Analytes in solution | | | | | |
|---|---|---|---|---|---|---|---|
| | On huFolR1 | 16D5 TCB | 21A5 TCB | 9D11 TCB | 36F2 IgG | Mov19 IgG | Farletuzumab |
| Immo-bilized | 16D5 TCB | − | − | − | + | + | + |
| | 21A5 TCB | − | − | − | + | + | + |
| | 9D11 TCB | No additional binding on FolR1 possible once captured on 9D11 | | | | | |
| | 36F2 IgG | Measure not possible, huFolR1 dissociates too rapidly | | | | | |
| | Mov19 IgG | + | + | +/− | − | − | − |

+ means binding, − means no binding, +/− means weak binding

Based on these results and additional data with simultaneous binding on immobilized huFolR1, the binders were separated in three groups. It is not clear if 9D11 has a separate epitope because it displaces all the other binders. 16D5 and 21A5 seem to be in the same group and Mov19, Farletuzumab (Coney et al., Cancer Res. 1991 Nov. 15; 51(22):6125-32; Kalli et al., Curr Opin Investig Drugs. 2007 December; 8(12):1067-73) and 36F2 in another (Table 13). However, 36F2 binds to a different epitope than Mov 19 and Farletuzumab as it binds to human, cynomous and murine FolR1.

TABLE 13

Epitope grouping of selected FolR1 binders as IgGs or as T-cell bispecifics (TCB) on human FolR1

| Epitope 1 | Epitope 2 | Epitope 3 |
|---|---|---|
| 16D5 | 9D11 | Mov19 |
| 21A5 | | Farletuzumab |
| | | 36F2 |

Example 13

Selection of Binders

FolR1 binders in the IgG formats were screened by surface plasmon resonance (SPR) and by in vitro assay on cells to select the best candidates.

The anti-FolR1 IgGs were analyzed by SPR to characterize their crossreactivity (to human, murine and cynomolgus FolR1) and specificity (to human FolR1, human FolR2, human FolR3). Unspecific binding to human FolR2 and 3 was considered an exclusion factor. Binding and specificity to human FolR1 was confirmed on cells. Some binders did not bind on cells expressing FolR1 even though they recognized the recombinant human FolR1 in SPR. Aggregation temperature was determined but was not an exclusion factor because the selected binders were all stable. Selected binders were tested in a polyreactivity ELISA to check for unspecific binding, which led to the exclusion of four binders. This process resulted in an initial selection of three binders: 36F2 (Fab library), 9D11 (Fab library) and 16D5 (common light chain). 36F2 dissociated rapidly from huFolR1 and was, therefore, initially not favored.

Example 14

Figure 4A:
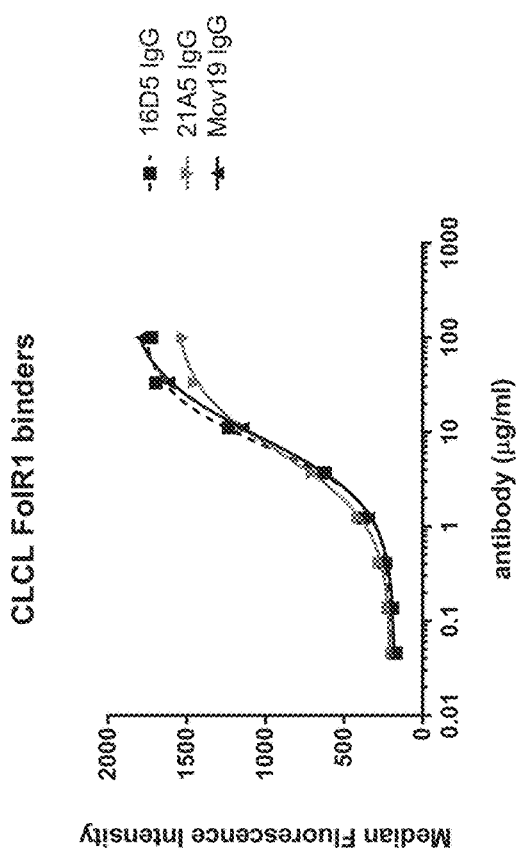
FIGS. 4A-B depict graphs summarizing cross-reactivity of FolR1 binders to cyFoLR1. Cross-reactivity of the FolR1 antibodies to cyno FolR1 was addressed on HEK cells transiently transfected with cyFolR1 by flow cytometry. The antibodies were detected with a fluorescently labeled anti-human secondary antibody.
Figure 4B:
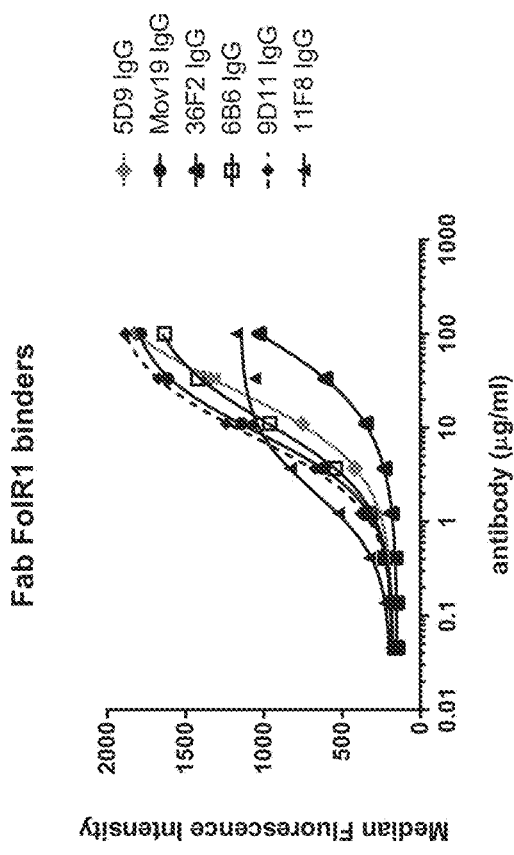
Figure 5:
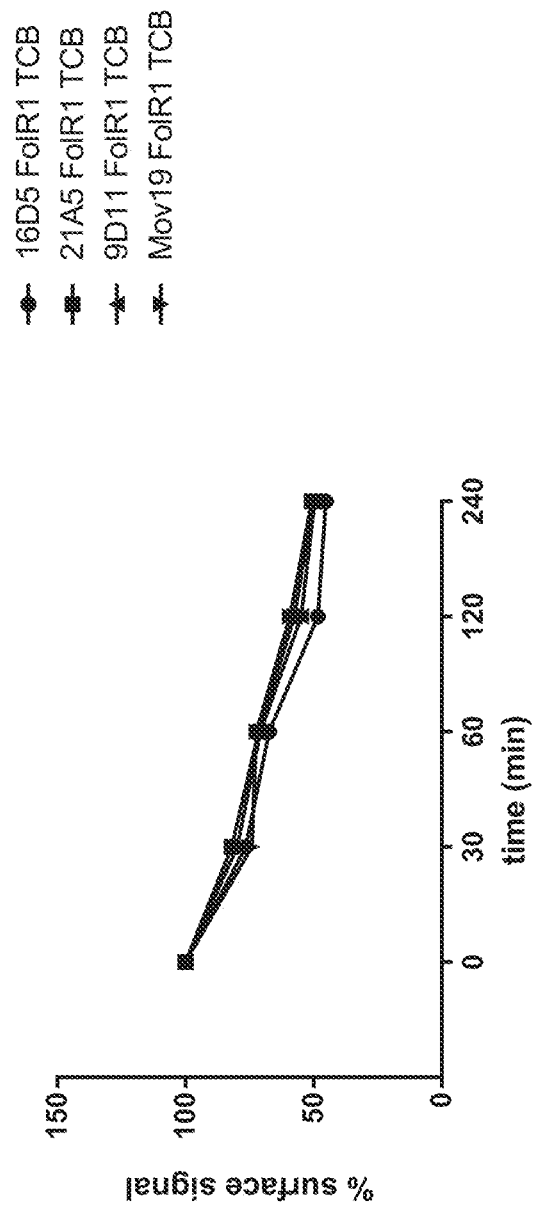
FIG. 5 depicts a graph illustrating internalization of FolR1 TCBs after binding. Internalization of the four FolR1 TCBs after binding to FolR1 was tested on HeLa cells. Remaining FolR1 TCBs on the surface were detected with a fluorescently labeled anti-human secondary antibody after indicated time points of incubation at 37° C. Percentage of internalization was calculated.
Figure 7E:
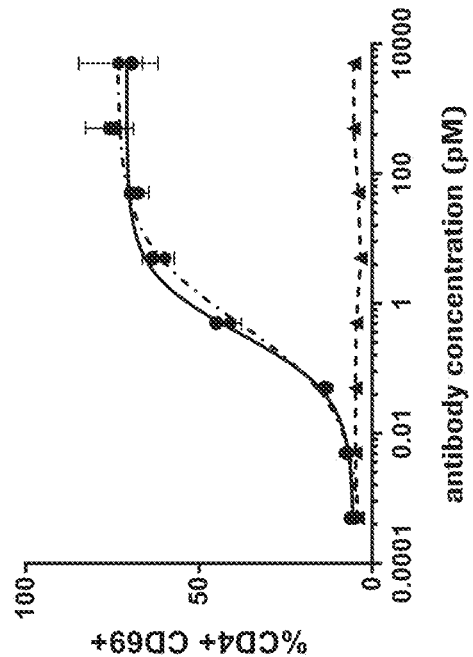
Figure 7F:
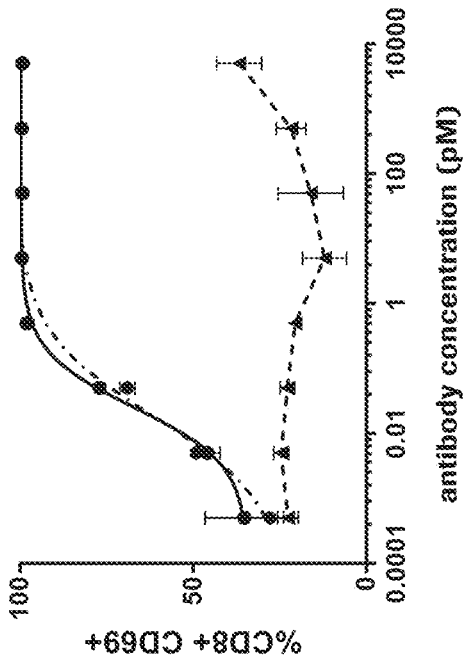
Figure 7G:
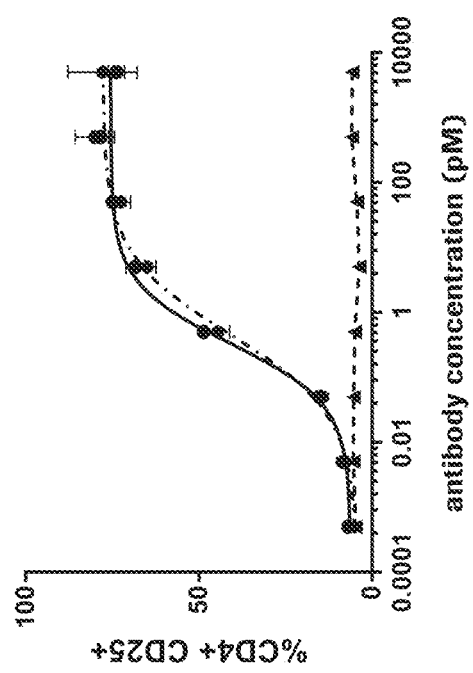
Figure 7H:
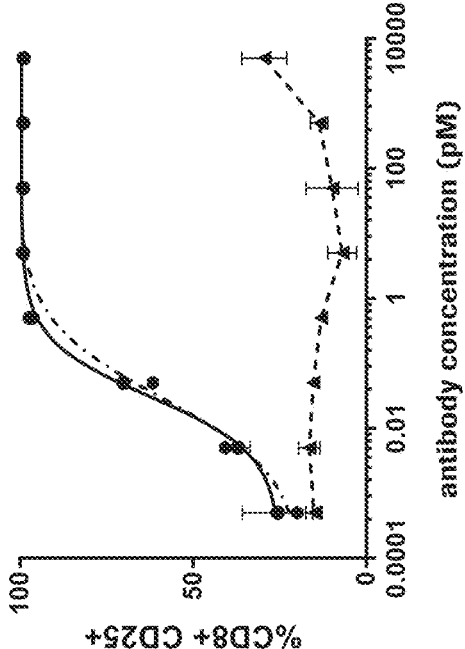

Specific Binding of Newly Generated FolR1 Binders to Human FolR1 Positive Tumor Cells New FolR1 binders were generated via Phage Display using either a Fab library or a common light chain library using the CD3 light chain. The identified binders were converted into a human IgG1 format and binding to FolR1 high expressing HeLa cells was addressed. As reference molecule the human FolR1 binder Mov19 was included. Most of the binders tested in this assay showed intermediate to good binding to FolR1 with some clones binding equally well as Mov19 (see FIG. 2). The clones 16A3, 18D3, 15H7, 15B6, 21D1, 14E4 and 16F12 were excluded because binding to FolR1 on cells could not be confirmed by flow cytometry. In a next step the selected clones were tested for specificity to human FolR1 by excluding binding to the closely related human FolR2. HEK cells were transiently transfected with either human FolR1 or human FolR2 to address specificity. The clones 36F2 and 9D11 derived from the Fab library and the clones 16D5 and 21A5 derived from the CLC library bind specifically to human FolR1 and not to human FolR2 (see FIGS. 3A-B). All the other tested clones showed at least some binding to human FolR2 (see FIGS. 3A-B). Therefore these clones were excluded from further characterization. In parallel cross-reactivity of the FolR1 clones to cyno FolR1 was addressed by performing binding studies to HEK cells transiently transfected with cyno FolR1. All tested clones were able to bind cyno FolR1 and the four selected human FoLR1 specific clones 36F2, 9D11, 16D5 and 21A5 bind comparably well human and cyno FolR1 (FIG. 4). Subsequently three human FolR1 specific cyno cross-reactive binders were converted into TCB format and tested for induction of T cell killing and T cell activation. These clones were 9D11 from the Fab library and 16D5 and 21A5 from the CLC library. As reference molecule Mov19 FolR1 TCB was included in all studies. These FolR1 TCBs were then used to compare induction of internalization after binding to FolR1 on HeLa cells. All three tested clones are internalized upon binding to FolR1 comparable to internalization upon binding of Mov19 FolR1 TCB (FIG. 5). 21A5 FolR1 TCB was discontinued due to signs of polyreactivity.

Example 15

T Cell-Mediated Killing of FolR1-Expressing Tumor Target Cells Induced by FolR1 TCB Antibodies The FolR1 TCBs were used to determine T cell mediated killing of tumor cells expressing FoLR1. A panel of potential target cell lines was used to determine FoLR1 binding sites by Qifikit analysis. The used panel of tumor cells contains FolR1 high, intermediate and low expressing tumor cells and a FolR1 negative cell line.

TABLE 14

FolR1 binding sites on tumor cells

| Cell line | Origin | FolR1 binding sites |
| --- | --- | --- |
| Hela | Cervix adenocarcinoma | 2,240,716 |
| Skov3 | Ovarian adenocarcinoma | 91,510 |
| OVCAR5 | Ovarian adenocarcinoma | 22,077 |
| HT29 | Colorectal adenocarcinoma | 10,135 |
| MKN45 | Gastric adenocarcinoma | 54 |

Binding of the three different FoLR1 TCBs (containing 9D11, 16D5 and Mov19 binders) to this panel of tumor cell lines was determined showing that the FoLR1 TCBs bind specifically to FolR1 expressing tumor cells and not to a FoLR1 negative tumor cell line. The amount of bound construct is proportional to the FoLR1 expression level and there is still good binding of the constructs to the FoLR1 low cell line HT-29 detectable. In addition there is no binding of the negative control DP47 TCB to any of the used cell lines (FIGS. 6A-E).

The intermediate expressing cell line SKOV3 and the low expressing cell line HT-29 were further on used to test T cell mediated killing and T cell activation using 16D5 TCB and 9D11 TCB; DP47 TCB was included as negative control. Both cell lines were killed in the presence of already very low levels of 16D5 TCB and 9D11 TCB and there was no difference in activity between both TCBs even though 9D11 TCB binds stronger to FolR1 than 16D5 TCB. Overall killing of SKOV3 cells was higher compared to HT-29 which reflects the higher expression levels of FolR1 on SKOV3 cells (FIGS. 7A-D). In line with this, a strong upregulation of the activation marker CD25 and CD69 on CD4$^+$ T cells and CD8$^+$ T cells was detected. Activation of T cells was very similar in the presence of SKOV3 cells and HT-29 cells. The negative control DP47 TCB does not induce any killing at the used concentrations and there was no significant upregulation of CD25 and CD69 on T cells.

TABLE 15

EC50 values of tumor cell killing and T cell activation with SKOV3 cells

| Construct | Killing 24 h (pM) | Killing 48 h (pM) | CD4 + CD69 + (%) | CD4 + CD25 + (%) | CD8 + CD69 + (%) | CD8 + CD25 + (%) |
| --- | --- | --- | --- | --- | --- | --- |
| 9D11 FolR1 TCB | 1.1 | 0.03 | 0.51 | 0.46 | 0.019 | 0.03 |
| 16D5 FolR1 TCB | 0.7 | 0.04 | 0.34 | 0.33 | 0.025 | 0.031 |

TABLE 16

EC50 values of tumor cell killing and T cell activation with HT-29 cells

| Construct | Killing 24 h (pM) | Killing 48 h (pM) | CD4 + CD69 + (%) | CD4 + CD25 + (%) | CD8 + CD69 + (%) | CD8 + CD25 + (%) |
| --- | --- | --- | --- | --- | --- | --- |
| 9D11 FolR1 TCB | 2.3 | 0.1 | 1.22 | 1.11 | 0.071 | 0.084 |
| 16D5 FolR1 TCB | 2.8 | 0.1 | 0.69 | 0.62 | 0.021 | 0.028 |

Example 16

Binding to Erythrocytes and T Cell Activation in Whole Blood

Figure 8:
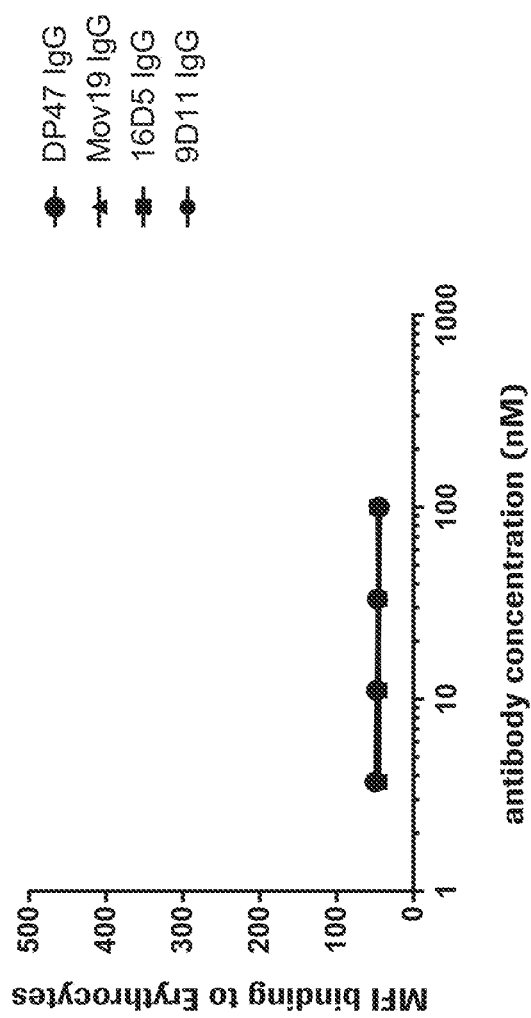
FIG. 8 depicts a graph showing absence of anti-FolR1 binding to erythrocytes. Erythrocytes were gated as CD235a positive population and binding of 9D11 IgG, 16D5 IgG, Mov19 IgG and DP47 IgG to this population was determined by flow cytometry. The antibodies were detected with a fluorescently labeled anti-human secondary antibody.
Figure 9A:
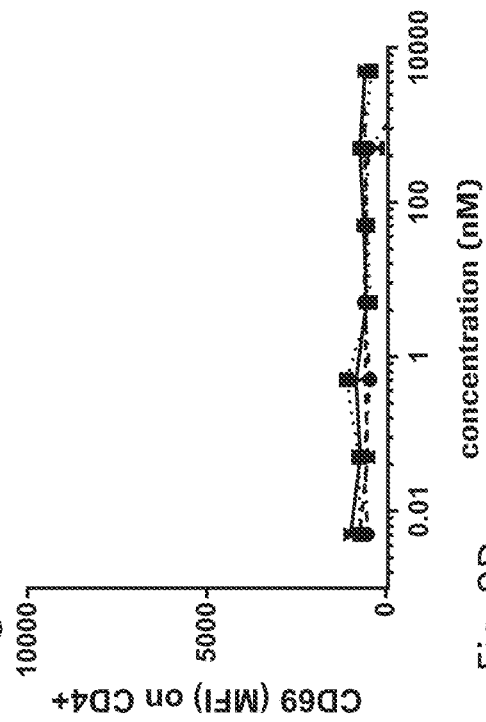
FIGS. 9A-D depict graphs summarizing activation marker upregulation in whole blood. CD25 and CD69 activation marker upregulation of CD4 T cells and CD8 T cells 24 h after addition of 9D11 FolR1 TCB, 16D5 FolR1 TCB, Mov19 FolR1 TCB and DP47 TCB was analyzed by flow cytometry.
Figure 9B:
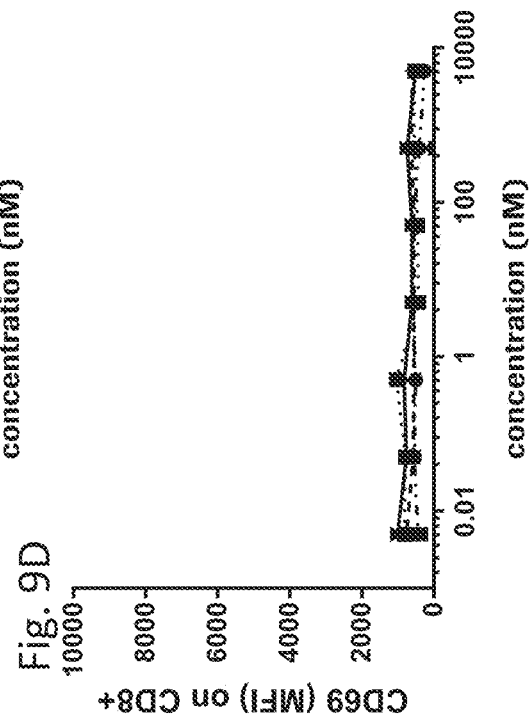
Figure 9C:
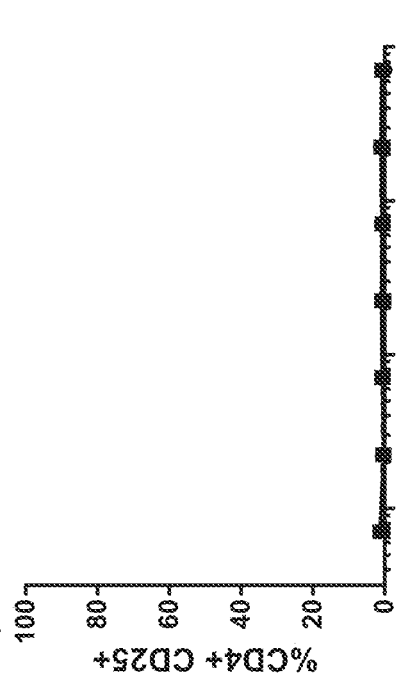
Figure 9D:
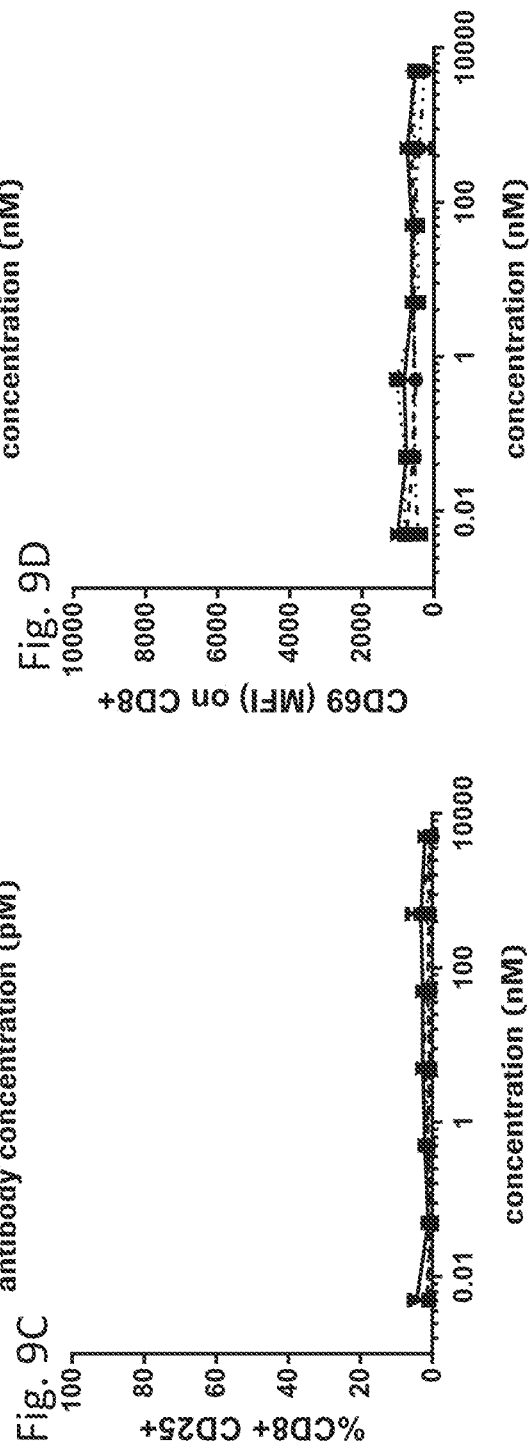

To prove that there is no spontaneous activation in the absence of FoLR1 expressing tumor cells we tested if there is binding of the FolR1 clones to erythrocytes which might potentially express FolR1. We could not observe any specific binding of 9D11 IgG, 16D5 IgG and Mov19 IgG to erythrocytes, as negative control DP47 IgG was included (FIG. 8).

To exclude any further unspecific binding to blood cells or unspecific activation via FoLR1 TCB, 9D11 TCB, 16D5 TCB and Mov19 TCB were added into whole blood and upregulation of CD25 and CD69 on CD4$^+$ T cells and CD8$^+$ T cells was analyzed by flow cytometry. DP47 TCB was included as negative control. No activation of T cells with any of the tested constructs could be observed by analyzing upregulation of CD25 and CD69 on CD4$^+$ T cells and CD8$^+$ T cells (FIG. 9).

Example 17

Removal of the N-Glycosylation Site in 9D11 Light Chain

During analysis of the different FolR1 binders to identify potential sequence hot spots, at the end of CDR L3 of the clone 9D11 a putative N-glycosylation site was identified. Usually the consensus motif for N-glycosylation is defined as N-X-S/T-X (where X is not P). The sequence of CDR L3 (MQASIMNRT) (SEQ ID NO: 61) perfectly matches this consensus motif having the sequence N-R-T. Since glycosylation might not be completely reproducible among different production batches this could have an impact on FolR1 binding, if the glycosylation in CDR L3 contributes to antigen binding. To evaluate if this N-glycosylation site is important for FolR1 binding, or could be replaced without impairing binding, different variants of the 9D11 light chain were generated in which the N-glycosylation site was exchanged by site specific mutagenesis.

1. Transient Transfection and Production

The four T cell bispecifics were transiently produced in HEK293 EBNA cells using a PEI mediated transfection procedure for the required vectors as described below. HEK293 EBNA cells were cultivated in suspension serum free in CD CHO culture medium. For the production in 500 ml shake flask 400 million HEK293 EBNA cells were seeded 24 hours before transfection (for alternative scales all amounts were adjusted accordingly). For transfection cells were centrifuged for 5 min by 210×g, supernatant was replaced by pre-warmed 20 ml CD CHO medium. Expression vectors were mixed in 20 ml CD CHO medium to a final amount of 200m DNA. After addition of 540 ml PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 was added. After 7 days cultivation supernatant was collected for purification by centrifugation for 15 min at 210×g, the solution is sterile filtered (0.22 μm filter) and sodium azide in a final concentration of 0.01% w/v was added, and kept at 4° C. After production the supernatants were harvested and the antibody containing supernatants were filtered through 0.22 μm sterile filters and stored at 4° C. until purification.

2. Antibody Purification

All molecules were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to HiTrap PA HP (GE Healthcare, column volume (cv)=5 ml) equilibrated with 8 column volumes (cv) buffer A (20 mM sodium phosphate, 20 mM sodium citrate, 0.5 M NaCl, 0.01% Tween-20, pH 7.5). After washing with 10 cv of buffer A, the protein was eluted using a pH gradient to buffer B (20 mM sodium citrate pH 2.5, 0.5 M NaCl, 0.01% Tween-20) over 20 cv. Fractions containing the protein of interest were pooled and the pH of the solution was gently adjusted to pH 6.0 (using 2 M Tris pH 8.0). Samples were concentrated to 1 ml using ultra-concentrators (Vivaspin 15R 30.000 MWCO HY, Sartorius) and subsequently applied to a Superdex™ 200 10/300 GL (GE Healthcare) equilibrated with 20 mM Histidine, pH 6.0, 140 mM NaCl, 0.01% Tween-20. The aggregate content of eluted fractions was analyzed by analytical size exclusion chromatography. Therefore, 30 μl of each fraction was applied to a TSKgel G3000 SW XL analytical size-exclusion column (Tosoh) equilibrated in 25 mM K₂HPO₄, 125 mM NaCl, 200 mM L-arginine monohydrochloride, 0.02% (w/v) NaN₃, pH 6.7 running buffer at 25° C. Fractions containing less than 2% oligomers were pooled and concentrated to final concentration of 1-1.5 mg/ml using ultra concentrators (Vivaspin 15R 30.000 MWCO HY, Sartorius). The protein concentration was determined by measuring the optical density (OD) at 280 nm, using the molar extinction coefficient calculated on the basis of the amino acid sequence. Purity and molecular weight of the constructs were analyzed by SDS capillary electrophoresis in the presence and absence of a reducing agent following the manufacturer instructions (instrument Caliper LabChipGX, Perkin Elmer). Purified proteins were frozen in liquid N₂ and stored at −80° C.

3. Aggregation Temperature

Stability of the four constructs was tested on an Optim1000 (Avacta, PALL Corporation) by a gradient heating from 25° to 80° at 0.1° C./min. The temperature at onset of aggregation is recorded.

TABLE 34

Yield, monomer content and aggregation temperature of four N-glycosylation site knock-out mutant of the 9D11 binder in the 2 + 1 inverted T-cell bispecific format.

| Clone | Mutation | Yield [mg/L] | Monomer [%] | Aggregation temperature |
|-------|----------|--------------|-------------|-------------------------|
| 9D11  | T102N    | 1.34         | 97          | 56°                     |
| 9D11  | T102A    | 1.29         | 100         | 56°                     |
| 9D11  | N100Q    | 2.5          | 100         | 56°                     |
| 9D11  | N100S    | 2.05         | 100         | 56°                     |
| 9D11  | —        | 2.6          | 100         | 57°                     |

All four mutants behaved similarly to the wild-type 9D11 binder

The following variants were generated: N100S (N95S); N100Q (N95Q), T102A (T97A) and T102N (T97N) (Kabat numbering indicated in parenthesis) and converted into the T-cell bispecific format. After transient production in HEK293 EBNA cells and purification the different variants were analyzed for target binding and cell killing activity in comparison to the original 9D11 clone.

TABLE 17

Primers used for removal of N-glycosylation site in CDR L3 of 9D11 (sequences see below)

| # | Amino acid exchange | Mutagenesis primer |
|---|---------------------|--------------------|
| 1 | N95S                | GAB-7735           |
| 2 | N95Q                | GAB-7734           |
| 3 | T97A                | GAB7736            |
| 4 | T97N                | GAB-7737           |

Example 18

Binding and T Cell Mediated Killing with 9D11 a-Glyco Variants

Figure 10:
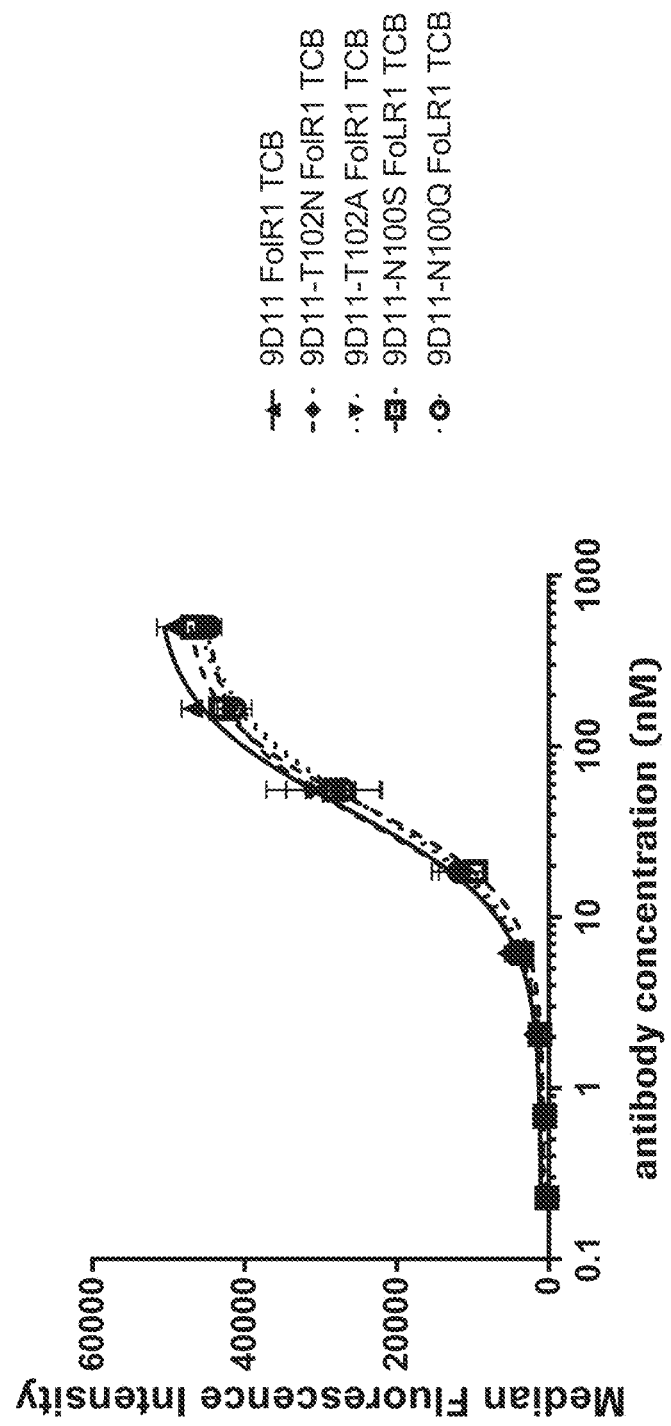
FIG. 10 Binding of 9D11 TCB a-glyco variants to HeLa cells. Binding of 9D11 FolR1 TCB a-glyco variants to Hela cells was compared to binding of the original 9D11 TCB on HeLa cells. The antibodies were detected with a fluorescently labeled anti-human secondary antibody and binding was determined by flow cytometry.

Due to a glycosylation site in the CDRs four different 9D11 variants were produced with a mutation removing the glycosylation site (Example 17). These four variants were tested in comparison to the original 9D11 for binding to FolR1 on HeLa cells (FIG. 10) and induction of tumor cell killing on SKOV3 and HT-29 (FIG. 11A-B, E-F). None of the variants showed differences in binding or induction of tumor cell killing. In parallel unspecific killing of the FolR1 negative cell lines MKN-45 was addressed (FIGS. 11C-D). Also, no differences between the variants and the original binder could be observed. None of the constructs induced unspecific killing on FoLR1 negative tumor cells.

Example 19

FolR1 Expression on Primary Epithelial Cells

FolR1 is expressed at low levels on primary epithelial cells. Here we wanted to test if these levels are sufficient to induce T cell mediated killing in the presence of the FolR1

TCBs. To test this we used primary human bronchial epithelial cells, primary human choroid plexus epithelial cell, primary human renal cortical epithelial cells and primary human retinal pigment epithelial cells. As positive control either FolR1 positive SKOV3 cells or HT-29 cells were included. First we verified FolR1 expression on the used primary cells and determined the amount of FolR1 binding sites on these cells. Bronchial epithelial cells, renal cortical epithelial cells and retinal pigment epithelial cells express very low but significant levels of FolR1 compared to the levels expressed on tumor cells. The choroid plexus epithelial cells do not express significant levels of FolR1.

TABLE 18

FolR1 binding sites on primary epithelial cells

| Cell line | Binding sites |
|---|---|
| Bronchial epithelium | 492 |
| Choroid plexus epithelium | 104 |
| Renal cortical epithelium | 312 |
| Retinal pigment epithelium | 822 |
| Skov3 | 69,890 |

Figure 12I:
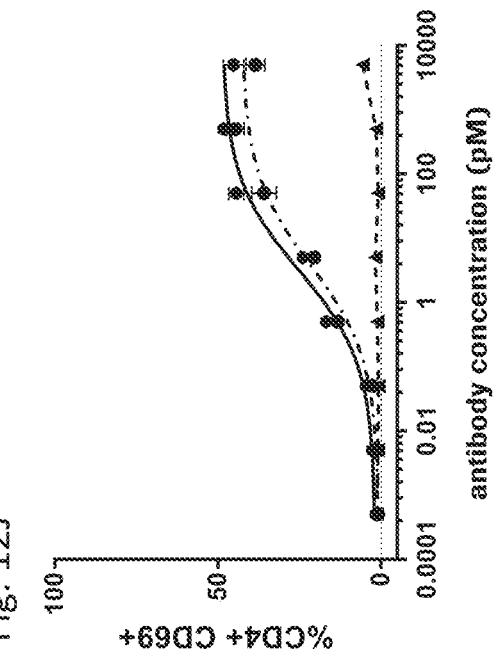
Figure 12K:
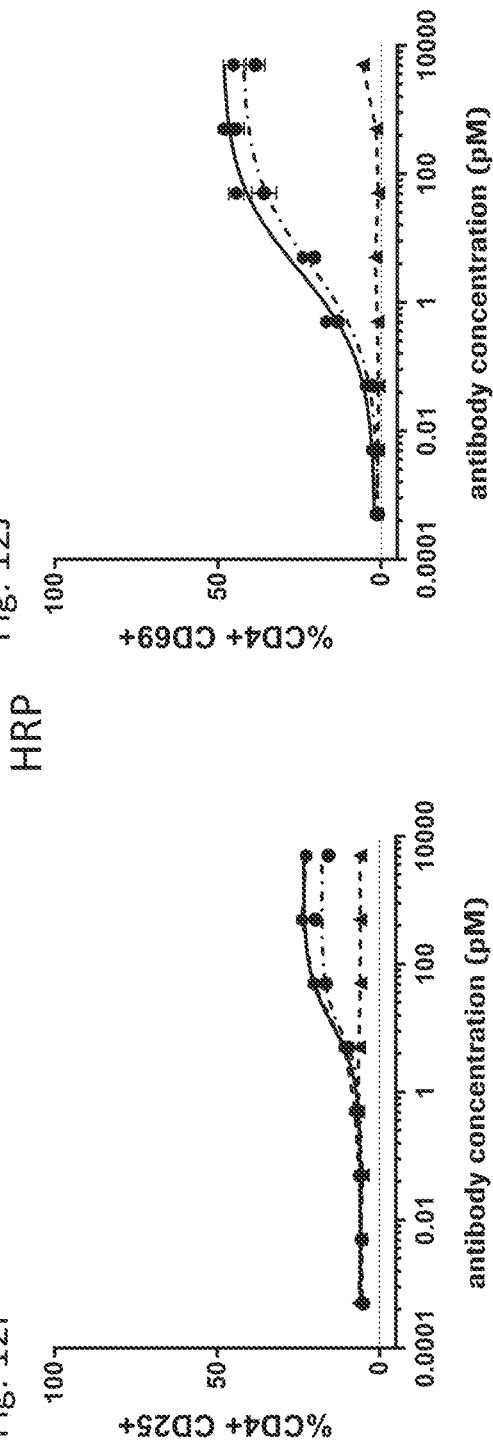
Figure 12J:
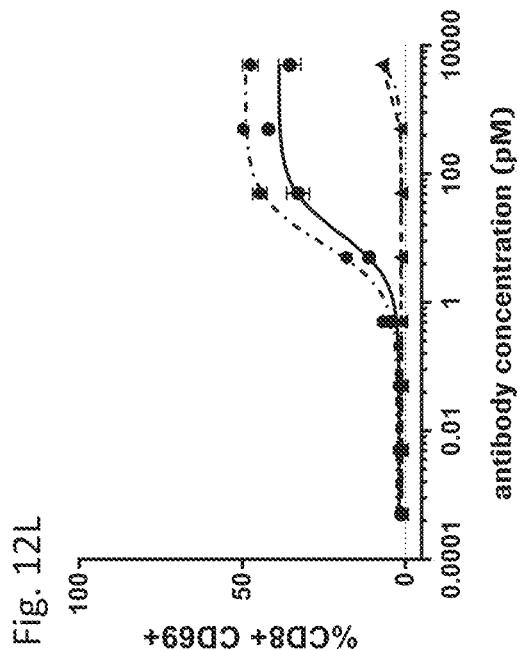
Figure 12L:
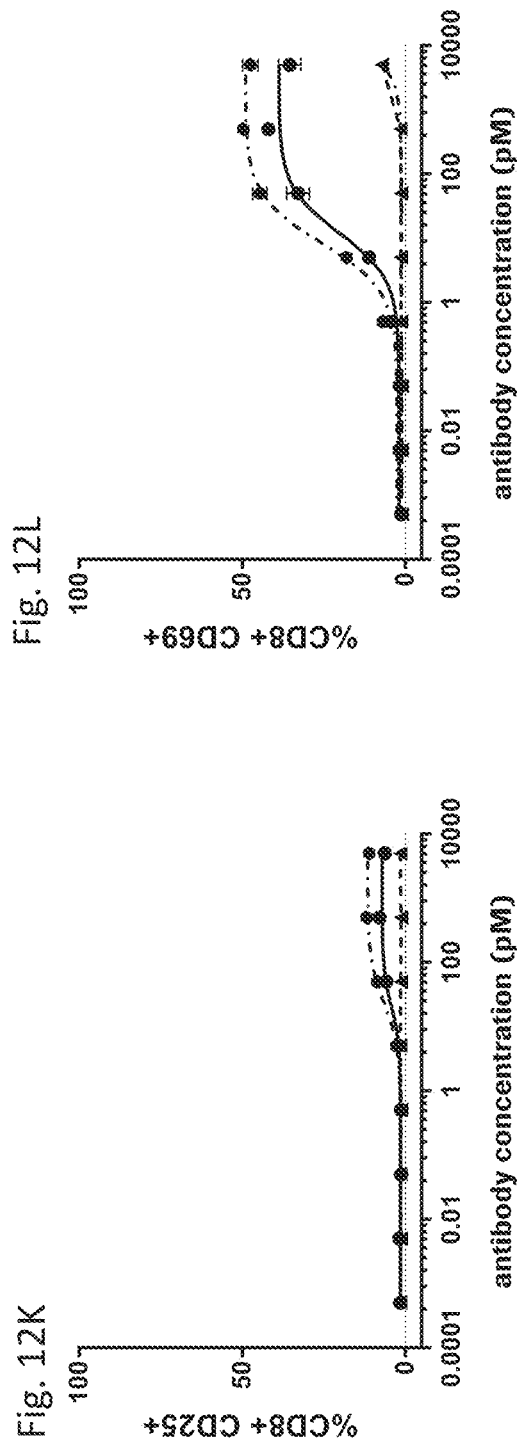
Figure 12M:
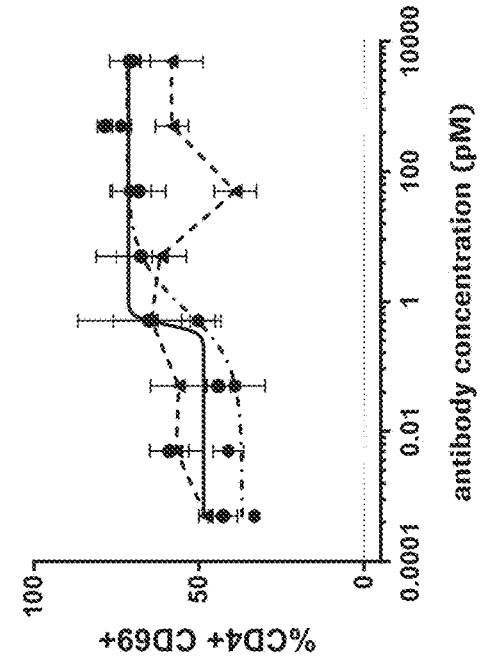
Figure 12N:
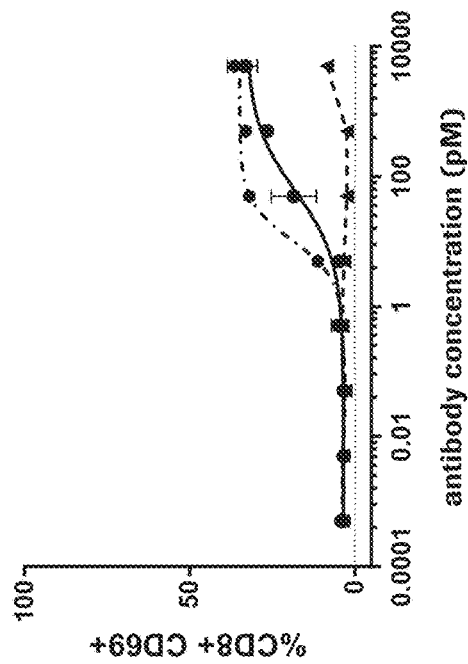
Figure 12O:
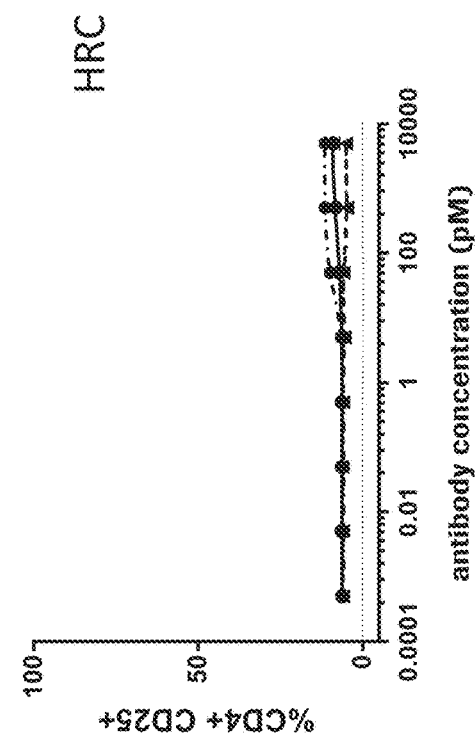
Figure 12P:
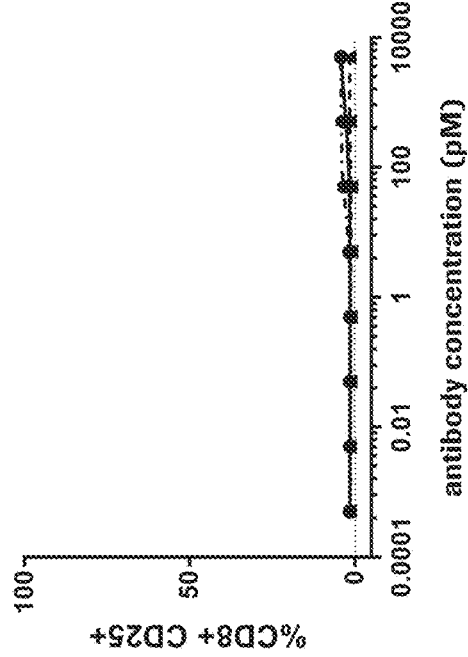
Figure 12U:
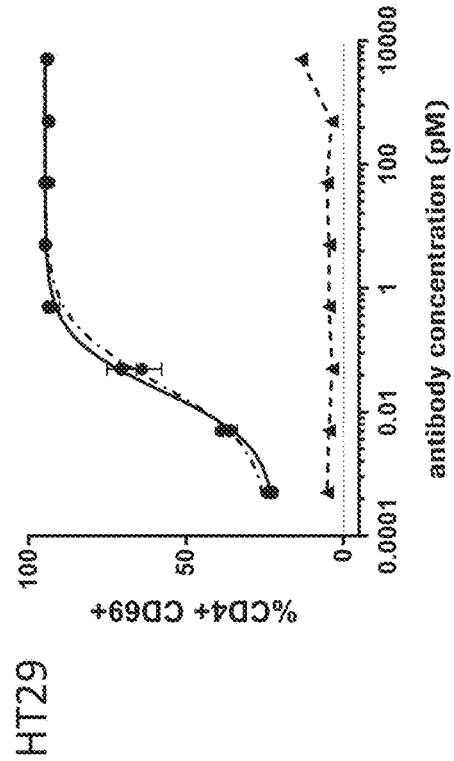
Figure 12V:
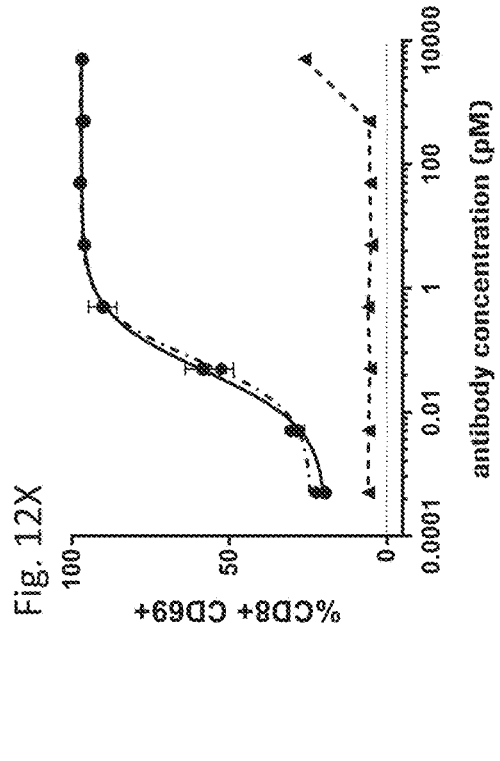
Figure 12W:
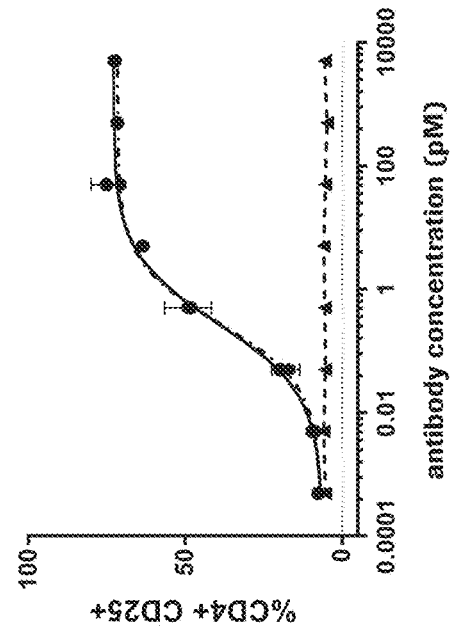
Figure 12X:
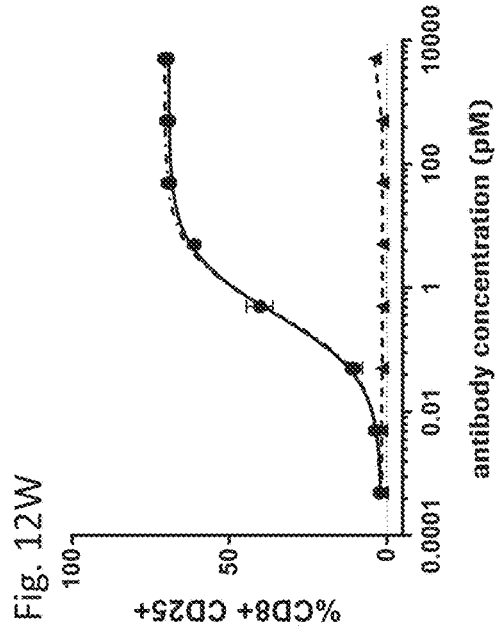
Figure 13B:
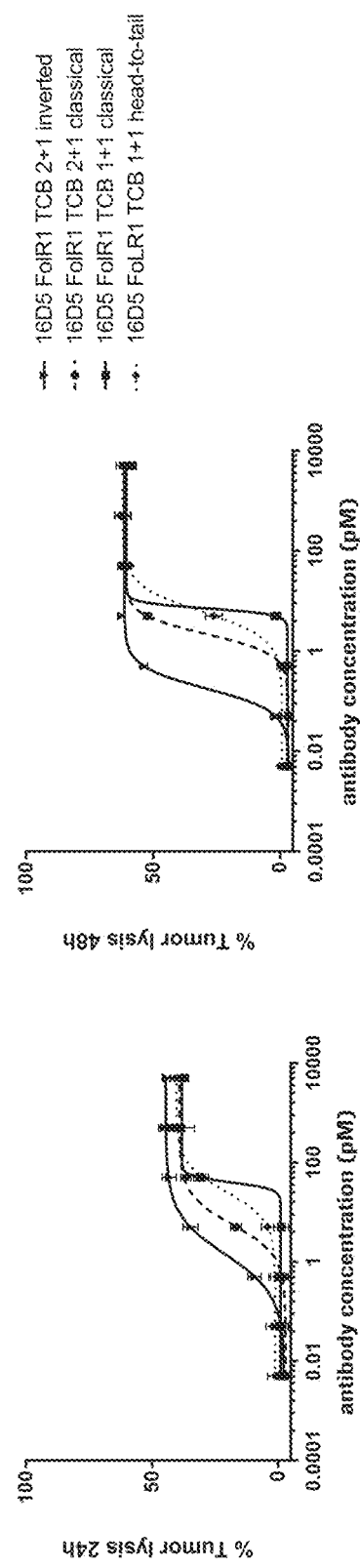
Figure 14B:
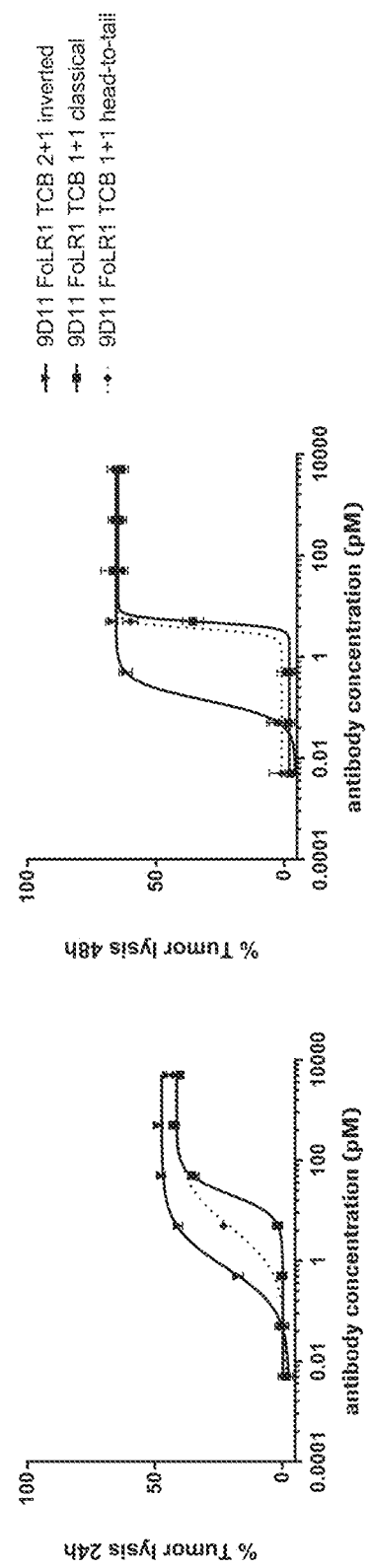

The primary epithelial cells that demonstrated FolR1 expression on the surface were used to address the question if these cells can be killed by T cells in the presence of FolR1 TCBs. No significant levels of killing could be measured but induction of T cell activation in the presence of retinal pigment epithelial cells, bronchial epithelial cells and renal cortical cells resulting in upregulation of CD25 and CD69 was detected. The strongest activation is seen with retinal pigment epithelial cells resulting in upregulation of CD25 and CD69 both on CD4$^+$ T cells and CD8$^+$ T cells. In the presence of bronchial epithelial cells lower activation of T cells is induced with upregulation of CD69 on CD4$^+$ T cells and CD8$^+$ T cells but very low upregulation of CD25 only on CD4$^+$ T cells but not on CD8$^+$ T cells. The lowest activation of T cells is obtained in the presence of renal epithelial cells with no upregulation of CD25 on CD4 T$^+$ cells and CD8$^+$ T cells and CD69 been only upregulated on CD8$^+$ T cells (FIGS. 12A-X).

Example 20

Comparison of Different TCB Formats Containing Either 16D5 or 9D11 Binder

To determine if the TCB 2+1 inverted format is the most active format with the selected FolR1 binder, different formats containing either 16D5 or 9D11 were produced and compared in target cell binding, T cell mediated killing and T cell activation. The 16D5 binder was tested in the TCB 2+1 inverted (FIG. 1A), TCB 2+1 classical (FIG. 1D), TCB 1+1 classical (FIG. 1C) and TCB 1+1 head-to-tail (FIG. 1B) format; the 9D11 binder was tested in the TCB 2+1 inverted (FIG. 1A), TCB 1+1 classical (FIG. 1C) and TCB 1+1 head-to-tail (FIG. 1B) format.

All constructs were tested for binding to FolR1 on HeLa cells. The molecules bivalent for binding to FolR1 bind stronger compared to the monovalent constructs due to avidity. The difference between the bivalent vs. monovalent constructs is more pronounced for 16D5. The reason might be that due to the lower affinity of 16D5 the avidity effect for this binder is stronger. Between the two 1+1 TCBs there is no significant difference in binding but there is a difference between the two 2+1 constructs. The inverted 2+1 construct binds stronger to FolR1 than the classical 2+1 construct. This indicates that in the classical 2+1 construct the binding to FoLR1 is influenced by the presence of the CD3 Fab whereas in the inverted construct binding is less influenced.

By testing T cell mediated killing with these constructs we could show that stronger binding of the 2+1 inverted TCB in converted into stronger tumor cell killing and T cell activation compared to the 2+1 classical TCB. The 16D5 FoLR1 TCB 2+1 classical is only a little bit more active than the respective 1+1 head-to-tail construct. The 1+1 head-to-tail construct is significantly more active than the 1+1 classical construct. This does not reflect the situation seen in binding and might be due to better crosslinking with the head-to-tail construct. Overall tumor cell killing and T cell activation is comparable with all tested constructs, the differences in potency seen with the differences are only in terms of EC50 values. In general it can be concluded that the FolR1 TCB 2+1 inverted independent of the used binder is the preferred format to induce T cell mediated tumor cell killing and T cell activation (see FIG. 13A-C and FIG. 14A-C).

TABLE 19

EC50 values of target cell binding and T cell mediated killing with different TCB formats

| Construct | Binding EC50 (nM) | Killing 24 h (pM) | Killing 48 h (pM) |
|---|---|---|---|
| 16D5 FolR1 TCB 2 + 1 inverted | 11.03 | 1.43 | 0.18 |
| 16D5 FolR1 TCB 2 + 1 classical | 17.07 | 5.60 | 2.18 |
| 16D5 FolR1 TCB 1 + 1 classical | 107.3 | n.d. | n.d. |
| 16D5 FolR1 TCB 1 + 1 head-to-tail | 102.6 | 26.24 | 6.06 |
| 9D11 FoLR1 TCB 2 + 1 inverted | 17.52 | 0.74 | 0.14 |
| 9D11 FoLR1 TCB 1 + 1 classical | 38.57 | 20.92 | n.d. |
| 9D11 FoLR1 TCB 1 + 1 head-to-tail | 44.20 | 4.73 | n.d. |

TABLE 20

EC50 values of T cell activation in the presence of SKOV3 cells with different TCB formats

| Construct | CD4 + CD25 + (%) | CD4 + CD69 + (%) | CD8 + CD25 + (%) | CD8 + CD69 + (%) |
|---|---|---|---|---|
| 16D5 FolR1 TCB 2 + 1 inverted | 1.96 | 0.33 | 2.10 | n.d. |
| 16D5 FolR1 TCB 2 + 1 classical | 13.83 | 3.67 | 12.88 | 4.47 |
| 16D5 FolR1 TCB 1 + 1 classical | 38.54 | n.d. | n.d. | n.d. |
| 16D5 FoLR1 TCB 1 + 1 head-to-tail | 17.14 | 7.47 | 25.15 | n.d. |
| 9D11 FoLR1 TCB 2 + 1 inverted | 1.41 | 0.27 | 1.24 | 0.35 |
| 9D11 FoLR1 TCB 1 + 1 classical | 34.01 | n.d. | 34.39 | 7.40 |
| 9D11 FoLR1 TCB 1 + 1 head-to-tail | 3.73 | 2.47 | 4.98 | 2.89 |

Example 21

Tumor Cell Lines and Primary Cells

HeLa cells (CCL-2) were obtained from ATCC and cultured in DMEM with 10% FCS and 2 mM Glutamine, SKOV3 (HTB-77) were obtained from ATCC and cultured in RPMI with 10% FCS and 2 mM Glutamine, OVCAR5 were obtained from NCI and cultured in RPMI with 10% FCS and 2 mM Glutamine, HT-29 (ACC-299) were obtained from DSMZ and cultured in McCoy's 5A medium with 10% FCS and 2 mM Glutamine, MKN-45 (ACC-409) were obtained from DSMZ and cultured in RPMI with 10% FCS and 2 mM Glutamine.

All tested primary epithelial cells were obtained from ScienCell Research Laboratories. Human Bronchial Epithelium Cells (HBEpiC, Catalog Number 3210 were cultured in Bronchial Epithelial Cell Medium (BEpiCM, Cat. No. 3211, ScienCell). Human Colonic Epithelial Cells (HCoEpiC), Catalog Number 2950 were cultured in Colonic Epithelial Cell Medium (CoEpiCM, Cat. No. 2951, ScienCell). Human Retinal Pigment Epithelial Cells (HRPEpiC), Catalog Number 6540 were cultured in Epithelial Cell Medium (EpiCM, Cat. No. 4101, ScienCell). Human Renal Cortical Epithelial Cells (HRCEpiC), Catalog Number 4110, were cultured in Epithelial Cell Medium (EpiCM, Cat. No. 4101, ScienCell). Human Choroid Plexus Epithelial Cells (HCPEpiC), Catalog Number 1310 were cultured in Epithelial Cell Medium (EpiCM, Cat. No. 4101, ScienCell).

Example 22

Target Binding by Flow Cytometry

Target cells as indicated were harvested with Cell Dissociation Buffer, washed with PBS and resuspended in FACS buffer. The antibody staining was performed in a 96 well round bottom plate. Therefore 200,000 cells were seeded per well. The plate was centrifuged for 4 min at 400 g and the supernatant was removed. The test antibodies were diluted in FACS buffer and 20 µl of the antibody solution were added to the cells for 30 min at 4° C. To remove unbound antibody the cells were washed twice with FACS buffer before addition of the diluted secondary antibody (FITC conjugated AffiniPure F(ab')2 fragment goat anti-human IgG, Fcg Fragment, Jackson ImmunoResearch #109-096-098 or PE-conjugated AffiniPure F(ab')2 Fragment goat anti-human IgG Fcg Fragment Specific, Jackson ImmunoResearch #109-116-170. After 30 min incubation on 4° C. unbound secondary antibody was washed away. Before measurement the cells were resuspended in 200 µl FACS buffer and analyzed by flow cytometry using BD Canto II or BD Fortessa.

Example 23

Internalization

The cells were harvested and the viability was determined. The cells were re-suspended in fresh cold medium at 2 Mio cells per ml and the cell suspension was transferred in a 15 ml falcon tube for each antibody. The antibodies that should be tested for internalization were added with a final concentration of 20 µg per ml to the cells. The tubes were incubated for 45 min in the cold room on a shaker. After incubation the cells were washed three times with cold PBS to remove unbound antibodies. 0.2 Mio cells per well were transfer to the FACS plate as time point zero. The labeled cells were re-suspended in warm medium and incubated at 37° C. At the indicated time-points 0.2 Mio cells per well were transferred in cold PBS, washed in plated on the FACS plate. To detect the constructs that remain on the surface the cells were stained with PE-labeled anti-human Fc secondary antibody. Therefore 20 µl of the diluted antibody were added per well and the plate was incubated for 30 min at 4° C. Then the cells were washed twice to remove unbound antibodies and then fixed with 1% PFA to prevent any further internalization. The fluorescence was measured using BD FACS CantoII.

Example 24

QIFIKIT® Analysis

QIFIKIT® contains a series of beads, 10 µm in diameter and coated with different, but well-defined quantities of mouse Mab molecules (high-affinity anti-human CD5, Clone CRIS-1, isotype IgG2a). The beads mimic cells with different antigen densities which have been labeled with a primary mouse Mab, isotype IgG. Briefly, cells were labeled with primary mouse monoclonal antibody directed against the antigen of interest. In a separate test well, cells were labeled with irrelevant mouse monoclonal antibody (isotype control). Then, cells, Set-Up Beads and Calibration Beads were labeled with a fluorescein-conjugated anti-mouse secondary antibody included in the kit. The primary antibody used for labeling of the cells has to be used at saturating concentration. The primary antibody may be of any mouse IgG isotype. Under these conditions, the number of bound primary antibody molecules corresponds to the number of antigenic sites present on the cell surface. The secondary antibody is also used at saturating concentration. Consequently, the fluorescence is correlated with the number of bound primary antibody molecules on the cells and on the beads.

Example 25

T Cell Mediated Tumor Cell Killing and T Cell Activation

Target cells were harvested with Trypsin/EDTA, counted and viability was checked. The cells were resuspended in their respective medium with a final concentration of 300,000 cells per ml. Then 100 µl of the target cell suspension was transferred into each well of a 96-flat bottom plate. The plate was incubated overnight at 37° C. in the incubator to allow adherence of the cells to the plate. On the next day PBMCs were isolated from whole blood from healthy donors. The blood was diluted 2:1 with PBS and overlayed on 15 ml Histopaque-1077 (#10771, Sigma-Aldrich) in Leucosep tubes and centrifuged for 30 min at 450 g without break. After centrifugation the band containing the cells was collected with a 10 ml pipette and transferred into 50 ml tubes. The tubes were filled up with PBS until 50 ml and centrifuged (400 g, 10 min, room temperature). The supernatant was removed and the pellet resuspended in PBS. After centrifugation (300 g, 10 min, room temperature), supernatants were discarded, 2 tubes were pooled and the washing step was repeated (this time centrifugation 350×g, 10 min, room temperature). Afterwards the cells were resuspended and the pellets pooled in 50 ml PBS for cell counting. After counting cells were centrifuged (350 g, 10 min, room temperature) and resuspended at 6 Mio cells per ml in RPMI with 2% FCS and 2 nM Glutamine. Medium was removed from plated target cells and the test antibodies diluted in RPMI with 2% FCS and 2 nM Glutamine were added as well as. 300,000 cells of the effector cell solution were transferred to each well resulting in a E:T ratio of 10:1. To determine the maximal release target cells were lysed with Triton X-100.

LDH release was determined after 24 h and 48 h using Cytotoxicity Detection Kit (#1644793, Roche Applied Science). Activation marker upregulation on T cells after tumor cell killing was measured by flow cytometry. Briefly PBMCs were harvested, transferred into a 96 well round bottom plate and stained with CD4 PE-Cy7 (#3557852, BD Bioscience), CD8 FITC (#555634, BD Bioscience), CD25 APC (#555434, BD Bioscience), CD69 PE (#310906, BioLegend) antibodies diluted in FACS buffer. After 30 min incubation at 4° C. the cells were washed twice with FACS buffer. Before measuring the fluorescence using BD Canto II the cells were resuspended in 200 µl FACS buffer.

Example 26

T Cell Activation in Whole Blood

280 µl of fresh blood were added into a 96 well conical deep well plate. Then 20 µl of the diluted TCBs were added to the blood and mixed well by shaking the plate. After 24 h incubation at 37° C. in an incubator the blood was mixed and 35 µl were transferred to a 96 well round bottom plate. Then 20 µl of the antibody staining mix were added consisting of CD4 PE-Cy7 (#3557852, BD Bioscience), CD8 FITC (#555634, BD Bioscience), CD25 APC (#555434, BD Bioscience), CD69 PE (#310906, BioLegend) and CD45 V500 (#560777, BD Horizon) and incubated for 15 min in the dark at room temperature. Before measuring 200 µl of the freshly prepared BD FACS lysing solution (#349202, BD FCAS) was added to the blood. After 15 min incubation at room temperature the cells were measured with BD Fortessa.

Example 27

SDPK (Single Dose Pharmacokinetics) Study of Humanized FOLR1 TCB (Clone 16D5) in Immunodeficient NOD/Shi-Scid/IL-2RγNull (NOG) Mice Female NOD/Shi-scid/IL-2Rγnull (NOG) mice, age 6-7 weeks at start of the experiment (bred at Taconic, Denmark) were maintained under specific-pathogen-free condition with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis.

Mice were injected i.v. with 10/1/0.1 µg/mouse of the FOLR1 TCB whereas 3 mice were bled per group and time point. All mice were injected with a total volume of 200 µl of the appropriate solution. To obtain the proper amount of the FOLR1 TCB per 200 µl, the stock solutions were diluted with PBS when necessary. Serum samples were collected 5 min, 1h, 3h, 8h, 24 h, 48h, 72h, 96h and 168h after therapy injection.

Figure 15:
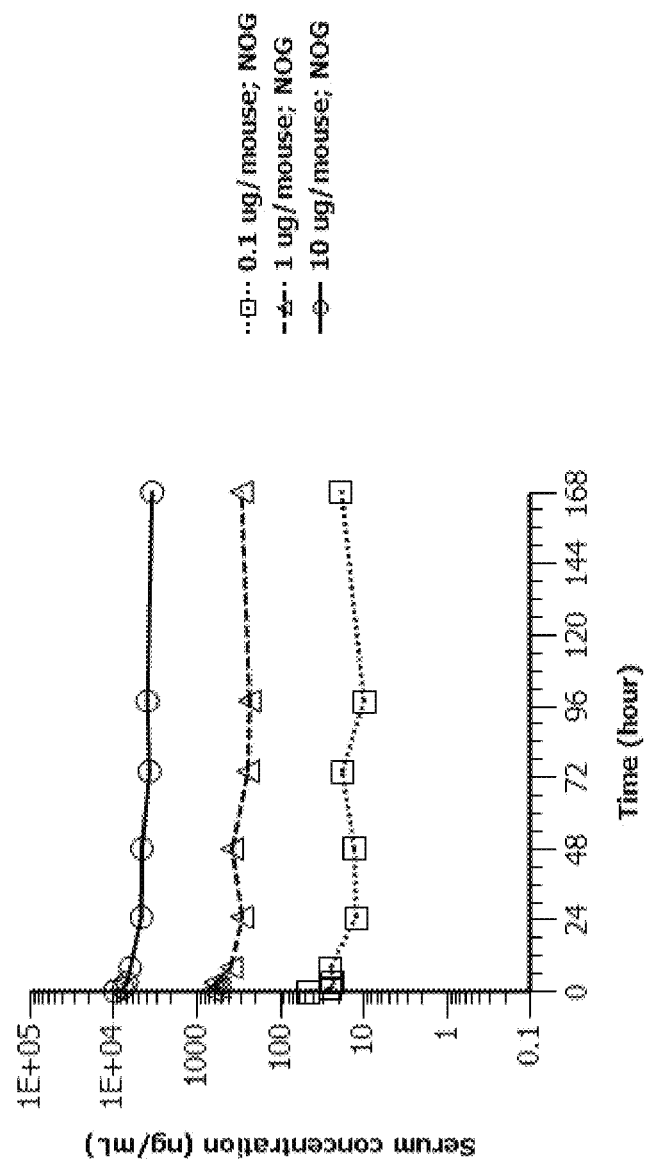
FIG. 15 depicts a PK-profile of FOLR1 TCB in NOG mice for three different doses.

FIG. 15 shows that the 16D5 FOLR1 TCB shows typical and dose proportional IgG-like PK properties in NOG mice with slow clearance.

TABLE 21

Experimental conditions.

| Compound | Dose | Formulation buffer | Concentration (mg/mL) |
|---|---|---|---|
| FOLR1 TCB (16D5) | 10 µg (corresponding to ca. 0.5 mg/kg) | 20 mM Histidine, 140 mM NaCl, pH 6.0 | 5.43 (= stock solution) |
| FOLR1 TCB (16D5) | 1 µg (corresponding to ca. 0.05 mg/kg) | 20 mM Histidine, 140 mM NaCl, pH 6.0 | 5.43 (= stock solution) |
| FOLR1 TCB (16D5) | 0.1 µg (corresponding to ca. 0.005 mg/kg) | 20mM Histidine, 140 mM NaCl, pH6.0 | 5.43 (= stock solution) |

Example 28

In Vivo Efficacy of FOLR1 TCB (Clone 16D5) after Human PBMC Transfer in Skov3-Bearing NOG Mice The FOLR1 TCB was tested in the human ovarian carcinoma cell line Skov3, injected s.c. into PBMC engrafted NOG mice.

The Skov3 ovarian carcinoma cells were obtained from ATCC (HTB-77). The tumor cell line was cultured in RPMI containing 10% FCS (Gibco) at 37° C. in a water-saturated atmosphere at 5% $CO_2$. Passage 35 was used for transplantation, at a viability >95%. $5 \times 10^6$ cells per animal were injected s.c. into the right flank of the animals in a total of 100 µl of RPMI cell culture medium (Gibco).

Female NOD/Shi-scid/IL-2Rγnull (NOG) mice, age 6-7 weeks at start of the experiment (bred at Taconic, Denmark) were maintained under specific-pathogen-free condition with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis.

Figure 16:
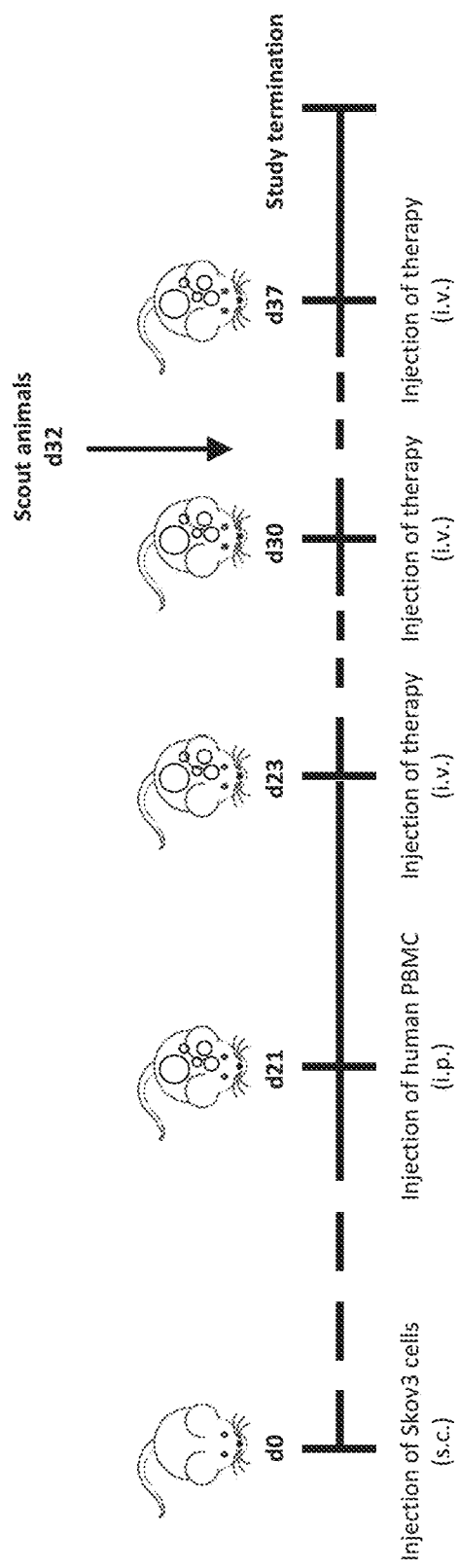
FIG. 16 illustrates an experimental protocol for efficacy study with FOLR1 TCB.

According to the protocol (FIG. 16), mice were injected s.c. on study day 0 with $5 \times 10^6$ of the Skov3. At study day 21, human PBMC of a healthy donor were isolated via the Ficoll method and $10 \times 10^6$ cells were injected i.p. into the tumor-bearing mice. Two days after, mice were randomized and equally distributed in five treatment groups (n=12) followed by i.v. injection with either 10/1/0.1 µg/mouse of the FOLR1 TCB or 10 µg/mouse of the DP47 control TCB once weekly for three weeks. All mice were injected i.v. with 200 µl of the appropriate solution. The mice in the vehicle group were injected with PBS. To obtain the proper amount of TCB per 200 µl, the stock solutions were diluted with PBS when necessary. Tumor growth was measured once weekly using a caliper (FIG. 17) and tumor volume was calculated as followed:

$T_v : (W^2/2) \times L$ (W: Width, L: Length)

Figure 17A:
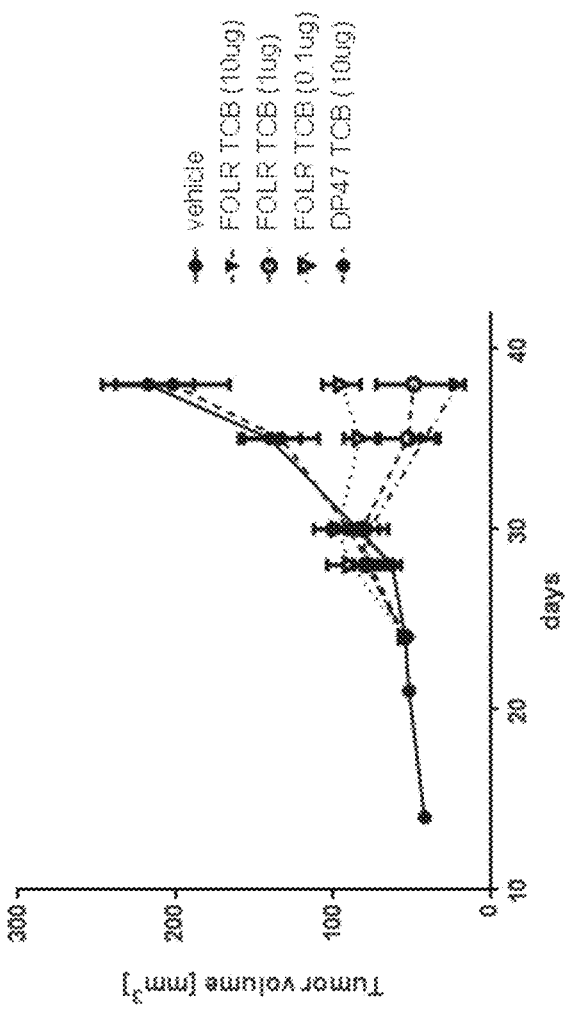
FIGS. 17A-B depict tumor growth curves.
Figure 17B:
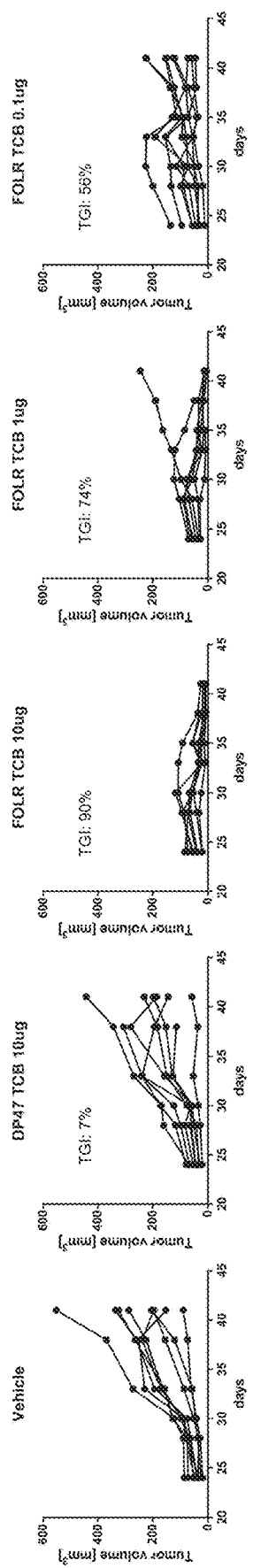

The once weekly injection of the FOLR1 TCB resulted in a dose-dependent anti-tumoral effect. Whereas a dose of 10 µg/mouse and 1 µg/mouse induced tumor shrinkage and 0.1 µg/mouse a tumor stasis (FIG. 17, Table 22). Maximal tumor shrinkage was achieved at a dose of 10 µg/mouse as compared to a non-targeted control DP47 TCB.

TABLE 22

In vivo efficacy.

| Compound | Dose | Tumor growth inhibition |
| --- | --- | --- |
| DP47 TCB control TCB | 10 µg (corresponding to ca. 0.5 mg/kg) | 7% |
| FOLR1 TCB (16D5) | 10 µg (corresponding to ca. 0.5 mg/kg) | 90% |
| FOLR1 TCB (16D5) | 1 µg (corresponding to ca. 0.05 mg/kg) | 74% |
| FOLR1 TCB (16D5) | 0.1 µg (corresponding to ca. 0.005 mg/kg) | 56% |

Figure 19B:
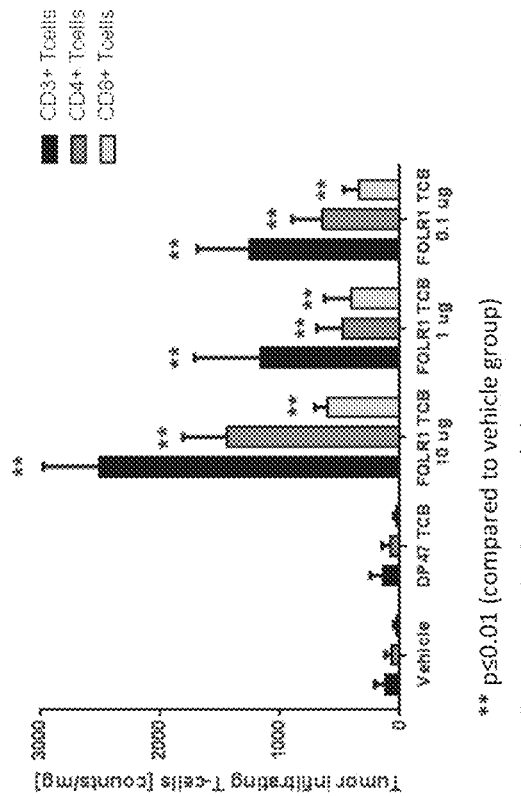
FIGS. 19A-B show FACS analysis of tumor infiltrating T-cells at study day 32.
Figure 19A:
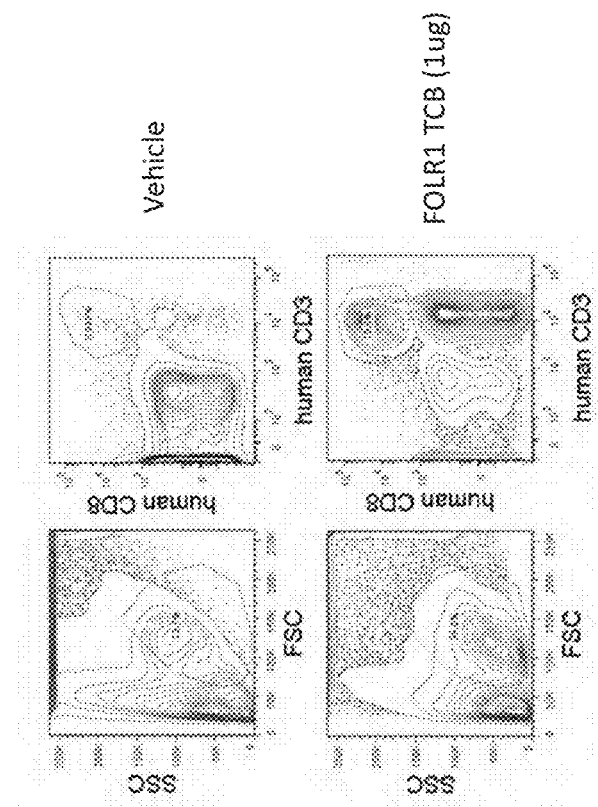

For PD read-outs, three mice per treatment group were sacrificed at study day 32, tumors were removed and single cell suspensions were prepared through an enzymatic digestion with Collagenase V, Dispase II and DNAse for subsequent FACS-analysis (FIGS. 19 and 20). Single cells where either used directly for staining of extracellular antigens and activation markers or were re-stimulated using 5 ng/ml PMA and 500 ng/ml Ionomycin in the presence of a protein transport inhibitor Monensin for 5h in normal culture medium. After re-stimulation, cells were stained for surface antigens, followed by a fixation and permeabilization step. Fix samples were then stained intracellulary for TNF-α, IFN-γ, IL-10 and IL-2 and analyzed by flow cytometry. Same procedure was used for the degranulation of cells, but an anti-CD107a antibody was added during the restimulation period and fixed samples were staining for intracellular perforin and granzyme-B contents. The FACS analysis revealed statistically higher number of infiltrating CD4$^+$ and CD8$^+$ T-cells in the tumor tissue upon treatment with FOLR1 TCB compared to vehicle and untargeted control TCB. Furthermore, higher numbers of TNF-α, IFN-γ and IL-2 producing as well as perforin$^+$/granzym-B$^+$ CD4$^+$ and CD8$^+$ T-cells were detected in FOLR1 TCB treated tumors. Tumor infiltrating T-cells treated with FOLR1 TCB also showed higher degranulation rates compared to control groups.

At study termination day 38, all animals were sacrificed; tumors were removed and weight (FIG. 18). The weight of the tumors treated with 10 and 1 µg/mouse of the FOLR1 TCB showed a statistically significant difference compared to the control groups.

TABLE 23

Experimental conditions.

| Compound | Dose | Formulation buffer | Concentration (mg/mL) |
| --- | --- | --- | --- |
| PBS | | | |
| FOLR1 TCB (16D5) | 10 µg | 20 mM Histidine, 140 mM NaCl, pH6.0 | 3.88 (= stock solution) |
| FOLR1 TCB (16D5) | 1 µg | 20 mM Histidine, 140 mM NaCl, pH6.0 | 3.88 (= stock solution) |
| FOLR1 TCB (16D5) | 0.1 µg | 20 mM Histidine, 140 mM NaCl, pH6.0 | 3.88 (= stock solution) |
| DP47 TCB | 10 µg | 20 mM Histidine, 140 mM NaCl, pH6.0 | 4.35 (= stock solution) |

Example 29

Generation of a Bispecific FolR1/CD3– Kappa—Lambda Antibody

To generate a bispecific antibody (monovalent for each antigen) that simultaneously can bind to human CD3 and human folate receptor alpha (FolR1) without using any hetero-dimerization approach (e.g. knob-into-hole technology), a combination of a common light chain library with the so-called CrossMab technology was applied: The variable region of the humanized CD3 binder (CH2527_VL7_46/13) was fused to the CH1 domain of a standard human IgG1 antibody to form the VLVH crossed molecule (fused to Fc) which is common for both specificities. To generate the crossed counterparts (VHCL), a CD3 specific variable heavy chain domain (CH2527_VH_23/12) was fused to a constant human λ light chain whereas a variable heavy chain domain specific for human FolR1 (clone 16D5, isolated from common light chain library) was fused to a constant human κ light chain. This enables the purification of the desired bispecific antibody by applying subsequent purification steps with KappaSelect and LambdaFabSelect columns (GE Healthcare) to remove undesired homodimeric antibodies.

All antibody expression vectors were generated using standard recombinant DNA technology as described in Sambrook, J. et al., Molecular cloning: A laboratory manual; Cold Spring Harbor Laboratory Press, Cold Spring Harbor, New York, 1989. Molecular biological reagents were used according the manufacturer's recommendations. Genes or gene fragments were either amplified by polymerase chain reaction (PCR) or generated from synthetic oligonucleotides at Geneart AG (Regensburg, Germany) by automated gene synthesis. PCR-amplified or subcloned DNA fragments were confirmed by DNA sequencing (Synergene GmbH, Switzerland). Plasmid DNA was transformed into and amplified in suitable E. coli host strains for preparation of transfection-grade plasmid DNA using standard Maxiprep kits (Qiagen). For production of the bispecific molecules HEK293 EBNA cells were transfected with plasmids encoding the respective genes using a standard polyethlenimine (PEI) based method. The used plasmid ratio of the three expression vectors was 1:1:1. Transfected cells were cultivated for 7 days before supernatants were harvested for purification. The bispecific FolR1/CD3– kappa—lambda antibodies were produced and purified as follows.

1. Transient Transfection and Production

The kappa-lambda bispecific antibody was transiently produced in HEK293 EBNA cells using a PEI mediated transfection procedure for the required vectors as described below. HEK293 EBNA cells were cultivated in suspension serum free in CD CHO culture medium. For the production in 500 ml shake flask 400 million HEK293 EBNA cells were seeded 24 hours before transfection (for alternative scales all amounts were adjusted accordingly). For transfection cells were centrifuged for 5 min by 210×g, supernatant is replaced by pre-warmed 20 ml CD CHO medium. Expression vectors were mixed in 20 ml CD CHO medium to a final amount of 200m DNA. After addition of 540 µl PEI solution is vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 was added. After 7 days cultivation supernatant was collected for purification by centrifugation for 15 min at 210×g, the solution is sterile filtered (0.22 µm filter) and sodium azide in a final concentration of 0.01% w/v was added, and kept at 4° C.

2. Purification

The kappa-lambda bispecific antibody was purified in three steps, using an affinity step specific for kappa light chains, followed by an affinity step specific for lambda light chains and finally by a size exclusion chromatography step for removal of aggregates. The supernatant obtained from transient production was adjusted to pH 8.0 (using 2 M TRIS pH 8.0) and applied to Capture Select kappa affinity matrix, or HiTrap KappaSelect, GE Healthcare, column volume (cv)=1 ml, equilibrated with 5 column volumes (cv) buffer A (50 mM Tris, 100 mM glycine, 150 mM NaCl, pH 8.0). After washing with 15 cv of buffer A, the protein was eluted using a pH gradient to buffer B (50 mM Tris, 100 mM glycine, 150 mM NaCl, pH 2.0) over 25 cv. Fractions containing the protein of interest were pooled and the pH of the solution was adjusted to pH 8.0 (using 2 M Tris pH 8.0). The neutralized pooled fractions were applied to Capture Select lambda affinity matrix (now: HiTrap LambdaFabSelect, GE Healthcare, column volume (cv)=1 ml) equilibrated with 5 column volumes (cv) buffer A (50 mM Tris, 100 mM glycine, 150 mM NaCl, pH 8.0). After washing with 15 cv of buffer A, the protein was eluted using a pH gradient to buffer B (50 mM Tris, 100 mM glycine, 150 mM NaCl, pH 2.0) over 25 cv. Fractions containing the protein of interest were pooled and the pH of the solution was adjusted to pH 8.0 (using 2 M Tris pH 8.0). This solution was concentrated using ultra-concentrators (Vivaspin 15R 30.000 MWCO HY, Sartorius) and subsequently applied to a Superdex™ 200 10/300 GL (GE Healthcare) equilibrated with 20 mM Histidine, pH 6.0, 140 mM NaCl, 0.01% Tween-20. The pooled fractions after size exclusion were again concentrated using ultra-concentrators (Vivaspin 15R 30.000 MWCO HY, Sartorius).

The protein concentration was determined by measuring the optical density (OD) at 280 nm, using the molar extinction coefficient calculated on the basis of the amino acid sequence. Purity and molecular weight of the constructs were analyzed by SDS capillary electrophoresis in the presence and absence of a reducing agent following the manufacturer instructions (instrument Caliper LabChipGX, Perkin Elmer). Only small amounts of protein could be purified with a final yield of 0.17 mg/L.

Example 30

T Cell Mediated Killing with Bispecific FolR1/CD3- Kappa—Lambda Antibody

Activity of kappa lambda FolR1 TCB was tested on SKOV3 cells in the presence of freshly isolated PBMCs. As negative control DP47 TCB was included. T cell mediated killing of SKOV3 cells was determined after 24 h and 48 h by LDH release. After 48 h the T cells were harvested and CD69 and CD25 upregulation on CD4 T cells and CD8 T cells was measured by flow cytometry. The kappa lambda FolR1 construct induces killing of SKOV3 cells in a concentration dependent manner which is accompanied by CD69 and CD25 upregulation both on CD4 T cells and on CD8 T cells.

SKOV3 cells were incubated with PBMCs in the presence of either kappa lambda FoLR1 TCB or DP47 TCB. After 24 h and 48 h killing of tumor cells was determined by measuring LDH release (FIG. 21). SKOV3 cells were incubated with PBMCs in the presence of either kappa lambda FoLR1 TCB or DP47 TCB. After 48 h CD25 and CD69 upregulation on CD4 T cells and CD8 T cells was measured by flow cytometry (FIG. 22).

Example 31

Biochemical Characterization of 16D5 and 36F2 FolR1 Binders by Surface Plasmon Resonance Binding of anti-FolR1 16D5 in different monovalent or bivalent T-cell bispecific formats and of anti-FolR1 36F2 as IgG or as T-cell bispecific to recombinant human, cynomolgus and murine folate receptor 1 (all as Fc fusions) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, GE Healthcare).

1. Molecules Tested

The molecules used for affinity and avidity determination are described in Table 24.

TABLE 24

Name and description of the 6 constructs used in SPR analysis

| Name | Description |
|---|---|
| 16D5 TCB | 2 + 1 T-cell bispecific, inverted format (common light chain) |
| 16D5 TCB classical | 2 + 1 T-cell bispecific, classical format (common light chain) |
| 16D5 TCB 1 + 1 | 1 + 1 T-cell bispecific (common light chain) |
| 16D5 TCB 1 + 1 HT | 1 + 1 T-cell bispecific head-to-tail (common light chain) |
| 36F2 IgG | Human IgG1 with P329G LALA |
| 36F2 TCB | 2 + 1 T-cell bispecific, inverted format, crossfab |

2. Avidity to Folate Receptor 1

The avidity of the interaction between the anti-FolR1 IgG or T cell bispecifics and the recombinant folate receptors was determined as described below (Table 25).

Recombinant biotinylated monomeric Fc fusions of human, cynomolgus and murine Folate Receptor 1 (FolR1-Fc) were directly coupled on a SA chip using the standard coupling instruction (Biacore, GE Healthcare). The immobilization level was about 300-400 RU. The anti-FolR1 IgGs or T cell bispecifics were passed at a concentration range from 3.7 to 900 nM with a flow of 30 µL/minutes through the flow cells over 180 seconds. The dissociation was monitored for 240 or 600 seconds. The chip surface was regenerated after every cycle using a double injection of 30 sec 10 mM Glycine-HCl pH 2. Bulk refractive index differences were corrected for by subtracting the response obtained on reference flow cell immobilized with recombinant biotinylated murine CD134 Fc fusion. The binding curves resulting from the bivalent binding of the IgG or T cell bispecifics were approximated to a 1:1 Langmuir binding (even though it is a 1:2 binding) and fitted with that model to get an apparent KD representing the avidity of the bivalent binding. The apparent avidity constants for the interactions were derived from the rate constants of the fitting using the Bia Evaluation software (GE Healthcare). For the 1+1 T cell bispecifics format the interaction is a real 1:1 and the KD represents affinity since there is only one FolR1 binder in this construct.

TABLE 25

Bivalent binding (avidity with apparent KD) of anti-FolR1 16D5 and 36F2 as IgG or as T-cell bispecifics (TCB) on human, cyno and murine FolR1.

| Analyte | Ligand | ka (1/Ms) | kd (1/s) | Apparent KD |
|---|---|---|---|---|
| 36F2 IgG | huFolR1 | 2.07E+06 | 1.3E-02 | 6 nM |
|  | cyFolR1 | 2.78E+06 | 1.75E-02 | 6 nM |
|  | muFolR1 | 4.28E+05 | 8.23E-04 | 2 nM |
| 36F2 TCB | huFolR1 | 2.45E+06 | 9.120E-03 | 4 nM |
|  | cyFolR1 | 4.31E+06 | 1.45E-02 | 3 nM |
|  | muFolR1 | 6.97E+05 | 9.51E-04 | 1 nM |
| 16D5 TCB | huFolR1 | 1.57E+05 | 3.92E-04 | 3 nM |
|  | cyFolR1 | 2.01E+05 | 3.81E-04 | 2 nM |
| 16D5 TCB classical | huFolR1 | 2.04E+05 | 1.84E-04 | 0.9 nM |
|  | cyFolR1 | 2.50E+05 | 3.05E-04 | 1 nM |
| 16D5 TCB 1 + 1 HT | huFolR1 | 5.00E+04 | 2.25E-03 | 45 nM |
|  | cyFolR1 | 5.75E+04 | 4.10E-03 | 70 nM |
| 16D5 TCB 1 + 1 | huFolR1 | 3.65E+04 | 2.04E-03 | 56 nM |
|  | cyFolR1 | 4.09E+04 | 3.60E-03 | 90 nM |

3. Affinity to Folate Receptor 1

The affinity of the interaction between the anti-FolR1 IgG or T cell bispecifics and the recombinant folate receptors was determined as described below (Table 26).

For affinity measurement, direct coupling of around 12000 resonance units (RU) of the anti-human Fab specific antibody (Fab capture kit, GE Healthcare) was performed on a CM5 chip at pH 5.0 using the standard amine coupling kit (GE Healthcare). Anti-FolR1 IgG or T cell bispecifics were captured at 20 nM with a flow rate of 10 μl/min for 40 sec, the reference flow cell was left without capture. Dilution series (12.3 to 3000 nM) of human, cyno or murine Folate Receptor 1 Fc fusion were passed on all flow cells at 30 μl/min for 240 sec to record the association phase. The dissociation phase was monitored for 300 s and triggered by switching from the sample solution to HBS-EP. The chip surface was regenerated after every cycle using a double injection of 60 sec 10 mM Glycine-HCl pH 1.5. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 26

Monovalent binding (affinity) of anti-FolR1 16D5 and 36F2 as IgG or as T-cell bispecifics (TCB) on human, cyno and murine FolR1.

| Analyte | Ligand | ka (1/Ms) | kd (1/s) | KD |
|---|---|---|---|---|
| 36F2 IgG | huFolR1 | 9.10E+04 | 6.65E-02 | 730 nM |
|  | cyFolR1 | 1.02E+05 | 5.78E-02 | 570 nM |
|  | muFolR1 | 8.32E+04 | 1.78E-02 | 210 nM |
| 36F2 TCB | huFolR1 | 5.94E+04 | 6.13E-02 | 1000 nM |
|  | cyFolR1 | 6.29E+04 | 5.42E-02 | 860 nM |
|  | muFolR1 | 5.68E+04 | 1.75E-02 | 300 nM |
| 16D5 TCB | huFolR1 | 2.23E+04 | 7.33E-04 | 33 nM |
|  | cyFolR1 | 1.57E+04 | 1.60E-03 | 100 nM |
| 16D5 TCB classical | huFolR1 | 1.03E+04 | 7.59E-04 | 74 nM |
|  | cyFolR1 | 9.18E+03 | 1.61E-03 | 175 nM |
| 16D5 TCB 1 + 1 HT | huFolR1 | 2.05E+04 | 7.08E-04 | 35 nM |
|  | cyFolR1 | 1.67E+04 | 1.53E-03 | 92 nM |
| 16D5 TCB 1 + 1 | huFolR1 | 1.43E+04 | 9.91E-04 | 69 nM |
|  | cyFolR1 | 1.20E+04 | 1.80E-03 | 150 nM |

The affinity (monovalent binding) to human and cyno FolR1-Fc of 36F2 TCB is similar and around 1000 nM for both, whereas the affinity to murine FolR1-Fc is slightly better and around 300 nM. The 36F2 can be used in murine and primate models, there is no need for a surrogate.

The avidity (apparent $K_D$) of 36F2 TCB to human FolR1 is around 30 times lower than the affinity of the 16D5 TCB to human FolR1. In the bivalent format, 36F2 TCB is in the low nanomolar range, whereas 16D5 TCB is in the low picomolar range (1000 fold difference).

FolR1 is expressed on tumor cells overexpressed, at intermittent and high levels, on the surface of cancer cells in a spectrum of epithelial malignancies, including ovarian, breast, renal, colorectal, lung and other solid cancers and is also expressed on the apical surface of a limited subset of polarized epithelial cells in normal tissue. These non-tumorous, normal cells express FolR1 only at low levels, and include, e.g., bronchiolal epithelial cells on alveolar surface, renal cortical luminal border of tubular cells, retinal pigment epithelium (basolateral membrane) and choroid plexus. 16D5 TCB binds to normal tissues cells expressing low amounts of FolR1 which results in their T cell mediated killing. This might, at least in part, account for limited tolerance observed at 10 μg/kg in cynomolgus monkeys. The inventors wanted to determine if lowering the affinity of the T cell bispecific molecule could increase the differentiation between high and low target density tissues and, thereby, lower toxicity by making use of bivalent binding and avidity. Low affinity binders are ordinarily not selected as suitable candidates for further analysis because low affinity is often associated with low potency and efficacy. Nevertheless, the low affinity FolR1 binder 36F2 was developed in several formats and characterized for its biological properties. For the 36F2 used in the bivalent T cell bispecific format the avidity effect (difference between monovalent and bivalent binding) is around 250 fold (1000 nM versus 4 nM). At low target density the affinity defined the interaction and with 1000 nM led to a low potency of the TCB. However, at high target density the molecule's avidity comes into play and with 4 nM led to a high activity of the TCB (see Example 32).

In an alternatively approach, the inventors generated monovalent formats of 16D5 and low affinity variant of 16D5 (affinity about 10-40 nM) in a bivalent format. The 16D5 binder used in a monovalent format (1+1) has an affinity of about 50 nM. The differentiation between high and low target density tissues can be better achieved by taking advantage of the avidity effect.

Example 32

T-Cell Killing of SKov-3 Cells Induced by 36F2 TCB, Mov19 TCB and 21A5 TCB

T-cell killing mediated by 36F2 TCB, Mov19 TCB and 21A5 TCB was assessed on SKov-3 cells (medium FolR1). Human PBMCs were used as effectors and the killing was detected at 24 h and 48 h of incubation with the bispecific antibodies. Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% CO2 in cell incubator until further use (no longer than 24 h). For the killing assay, the antibody was added at the indicated concentrations (range of 0.005 pM-5 nM in triplicates). PBMCs were added to target cells at final E:T ratio of 10:1. Target cell killing was assessed after 24 h and 48 h of incubation at 37° C., 5% CO2 by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 23A:
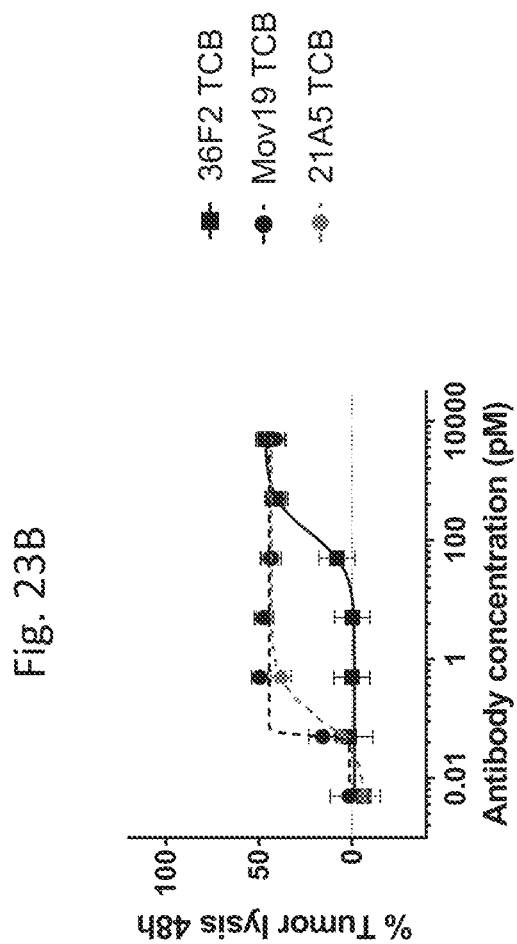
FIGS. 23A-B show percent tumor lysis. T-cell killing of SKov-3 cells (medium FolR1) induced by 36F2 TCB, Mov19 TCB and 21A5 TCB after 24h (FIG. 23A) and 48 h (FIG. 23B) of incubation (E:T=10:1, effectors human PBMCs).
Figure 23B:
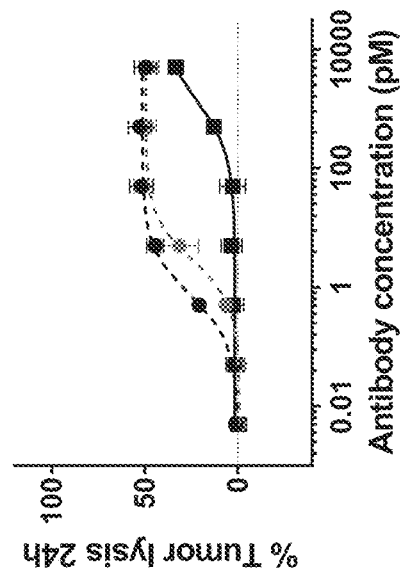

The results show that the killing induced by 36F2 is strongly reduced in comparison to Mov19 TCB and 21A5 TCB (FIGS. 23A-B). The EC50 values related to killing assays, calculated using GraphPadPrism6 are summarized in Table 27.

TABLE 27

EC50 values (pM) for T-cell mediated killing of FolR1-expressing SKov-3 cells induced by 36F2 TCB, Mov19 TCB and 21A5 TCB.

| Antibody | EC50 [pM] | |
| --- | --- | --- |
| | 24 h | 48 h |
| 36F2 TCB | 1406.07* | 134.5 |
| Mov19 TCB | 0.75 | 0.05 |
| 21A5 TCB | 2.83 | 0.10 |

*curve did not reach saturation, value is hypothetical

Example 33

T-Cell Killing Induced by 36F2 TCB and 16D5 TCB in Different Monovalent and Bivalent T-Cell Bispecific Formats T-cell killing mediated by 36F2 TCB, 16D5 TCB, 16D5 TCB classical, 16D5 TCB 1+1 and 16D5 TCB HT antibodies of Hela (high FolR1, about 2 million copies, Table 14, FIG. 27), Skov-3 (medium FolR1, about 70000-90000 copies, Table 14, FIG. 27) and HT-29 (low FolR1, about 10000, Table 14, FIG. 27) human tumor cells was assessed. DP47 TCB antibody was included as negative control. Human PBMCs were used as effectors and the killing was detected at 24 h of incubation with the bispecific antibody. Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% CO2 in cell incubator until further use (no longer than 24 h). For the killing assay, the antibody was added at the indicated concentrations (range of 0.01 pM-100 nM in triplicates). PBMCs were added to target cells at final E:T ratio of 10:1. Target cell killing was assessed after 24 h of incubation at 37° C., 5% CO2 by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 26B:
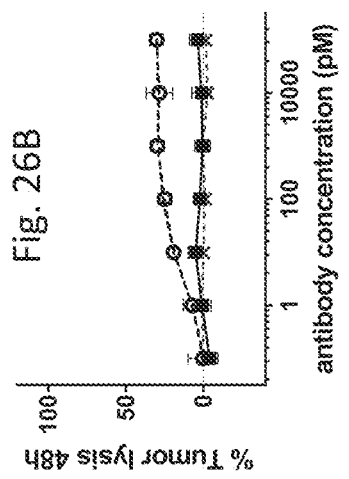
FIGS. 26A-F show T-cell killing induced by 36F2 TCB, 16D5 TCB and DP47 TCB of human Renal Cortical Epithelial Cells (FIG. 26A, B), human Retinal Pigment Epithelial Cells (FIG. 26C, D) and HT-29 cells (FIG. 26E, F) cells after 24h (FIG. 26A, C, E) and 48 h (FIG. 26B, D, F) of incubation (E:T=10:1, effectors human PBMCs).
Figure 26D:
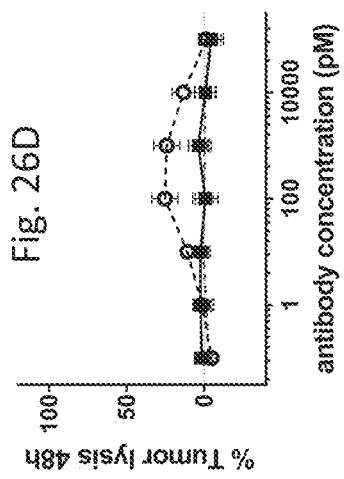
Figure 26F:
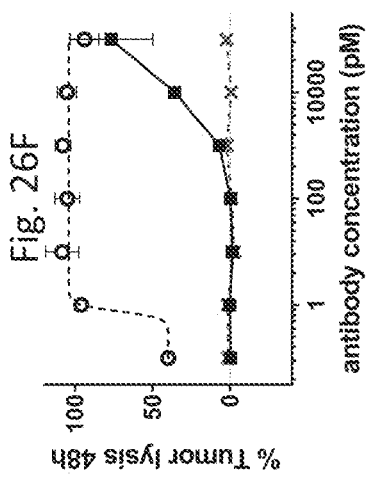
Figure 26A:
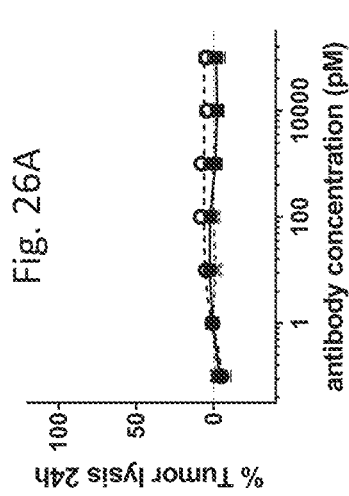
Figure 26C:
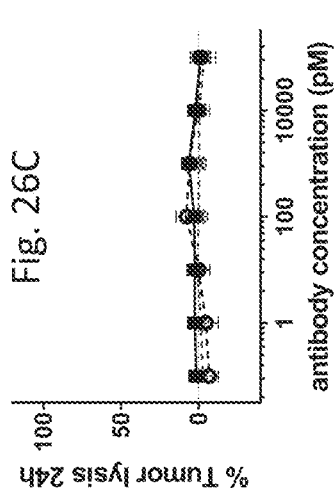

The results show that target-specific killing of all three FolR1+ target cell lines induced by 36F2 TCB is much weaker compared to the killing induced by 16D5 TCB (FIGS. 24A-C, Table 29). Target-specific killing induced by the monovalent 16D5 TCBs (16D5 HT and 16D5 1+1) is worse compared to the bivalent 16D5 TCBs (16D5 TCB and 16D5 TCB classical). The EC50 values related to killing assays, calculated using GraphPadPrism6, are summarized in Table 28. Importantly, this data shows that using the 36F2 FolR1 binder in the bivalent 2+1 TCB format widens the therapeutic window compared to the 16D5 FOLR1 TCB (FIG. 24A-C). Whereas the potency reduction between 16D5 and 36F2 FOLR1 TCB is approximately 45-fold for Hela cells (high FOLR1 expression, see Table 28: 16D5 TCB=0.8 versus 36F2 TCB 36.0) and approximately 297-fold for Skov3 cells (medium FOLR1 expression, see Table 28: 16D5 TCB=0.6 versus 36F2 TCB 178.4), this reduction is almost 7000-fold for HT29 with low FOLR1 expression (see Table 28: 16D5 TCB=5.7 versus 36F2 TCB 39573). Thus, the 36F2 FOLR1 TCB differentiates between high and low expressing cells which is of special importance to reduce toxicity as the cells of some normal, non-tumorous tissues express very low levels of FolR1 (approximately less than 1000 copies per cell). Consistent with this observation, the results discussed in Example 35 below show that 36F2 TCB does not induce T-cell killing of primary cells (FIGS. 26A-D) whereas for 16D5 TCB some killing can be observed on HRCEpiC and HRPEpiC cells after 48 h of incubation (FIGS. 26B and C). This important characteristic of 36F2 TCB allows for dosing for the treatment of FolR1-positive tumors so that it mediates potent killing of tumor tissues with high or medium FOLR1 expression, but not of normal tissues with low (partially polarized) expression. Notably, this characteristic appears to be mediated by the avidity of 36F2 TCB in the bivalent 2+1 inverted format, as it was not observed when using the 1+1 monovalent formats carrying the same low affinity 36F2 binder.

Stated another way, 36F2 TCB in the bivalent 2+1 format comprises FolR1 binding moieties of relatively low affinity but it possesses an avidity effect which allows for differentiation between high and low FolR1 expressing cells. Because tumor cells express FolR1 at high or intermediate levels, this TCB selectively binds to tumor cells and not normal, non-cancerous cells that express FolR1 at low levels or not at all.

In addition to the above advantageous characteristics, the 36F2 TCB in the bivalent 2+1 inverted format also has the advantage that it does not require chemical cross linking or other hybrid approach. This makes it suitable for manufacture of a medicament to treat patients, for example patients having FolR1-positive cancerous tumors. The 36F2 TCB in the bivalent 2+1 inverted format can be produced using standard CHO processes with low aggregates. Further, the 36F2 TCB in the bivalent 2+1 comprises human and humanized sequences making it superior to molecules that employ rat and murine polypeptides that are highly immunogenic when administered to humans. Furthermore, the 36F2 TCB in the bivalent 2+1 format was engineered to abolish FcgR binding and, as such, does not cause FcgR crosslinking and infusion reactions, further enhancing its safety when administered to patients.

As demonstrated by the results described above, its head-to-tail geometry make the 36F2 TCB in the bivalent 2+1 inverted format a highly potent molecule that induces absolute target cell killing. Its bivalency enhance avidity and potency, but also allow for differentiation between high and low expressing cells. Its preference for high or medium target expressing cells due to its avidity affect reduce toxicity resulting from T cell mediated killing of normal cells that express FolR1 at low levels.

A further advantage of the 36F2 TCB in the bivalent 2+1 format and other embodiments disclosed herein is that their clinical development does not require the use of surrogate molecules as they bind to human, cynomous and murine FolR1. As such, the molecules disclosed herein recognize a different epitope than antibodies to FolR1 previously described that do not recognize FolR1 from all three species.

TABLE 28

EC50 values (pM) for T-cell mediated killing of FolR1-expressing tumor cells induced by 36F2 TCB and 16D5 TCB in different monovalent and bivalent T-cell bispecific formats after 24 h of incubation.

| Antibody | Hela (FolR1 high) | Skov-3 (FolR1 medium) | HT-29 (FolR1 low) |
|---|---|---|---|
| 16D5 TCB | 0.8 | 0.6 | 5.7 |
| 16D5 TCB classical | 4.6 | 2.0 | 13.0 |
| 16D5 TCB HT | 11.6 | 12.3 | 15.1 |
| 16D5 TCB 1 + 1 | 23.8 | 48.9 | 883.8* |
| 36F2 TCB | 36.0 | 178.4 | 39573.0* |

*curve did not reach saturation, only hypothetical value

Table 29 shows a comparison of EC50 values of 16D5 TCB and 36F2 TCB on the different cell lines tested. Out of the obtained EC50 values the delta (EC50 of 16D5 TCB minus EC50 of 36F2 TCB) and the x-fold difference (EC50 of 16D5 TCB divided by the EC50 of 36F2 TCB) was calculated.

TABLE 29

Comparison of EC50 values of 16D5 TCB and 36F2 TCB.

| Antibody | Hela (FolR1 high) | Skov-3 (FolR1 medium) | HT-29 (FolR1 low) |
|---|---|---|---|
| 16D5 TCB | 0.82 | 0.63 | 5.73 |
| 36F2 TCB | 35.99 | 178.40 | 39573.00* |
| Δ | 35.17 | 177.77 | 39567.27 |
| x-fold | 43.83 | 284.61 | 6906.58 |

*curve did not reach saturation, only hypothetical value

The calculated EC50 values clearly show that the difference between 36F2 TCB and 16D5 TCB gets larger the lower the FolR1 expression on the target cells is.

The same calculations as done for the comparison of the EC50 values of 16D5 TCB and 36F2 TCB were done for 16D5 TCB and the two monovalent 16D5 TCBs (16D5 TCB HT and 16D5 1+1). Tables 30 and 31 show the comparisons of the EC50 values of 16D5 TCB vs 16D5 TCB HT (Table 30) and 16D5 TCB vs 16D5 TCB 1+1 (Table 31) as well as the corresponding deltas (EC50 of 16D5 TCB minus EC50 of 16D5 TCB HT/1+1) and the x-fold differences (EC50 of 16D5 TCB divided by the EC50 of 16D5 TCB HT/1+1).

TABLE 30

Comparison of EC50 values of 16D5 TCB (2 + 1 inverted) and 16D5 TCB HT.

| Antibody | Hela (FolR1 high) | Skov-3 (FolR1 medium) | HT-29 (FolR1 low) |
|---|---|---|---|
| 16D5 TCB | 0.82 | 0.63 | 5.73 |
| 16D5 TCB HT | 11.61 | 12.27 | 15.11 |
| Δ | 10.79 | 11.65 | 9.38 |
| x-fold | 14.14 | 19.58 | 2.64 |

TABLE 31

Comparison of EC50 values of 16D5 TCB and 16D5 TCB 1 + 1.

| Antibody | Hela (FolR1 high) | Skov-3 (FolR1 medium) | HT-29 (FolR1 low) |
|---|---|---|---|
| 16D5 TCB | 0.82 | 0.63 | 5.73 |
| 16D5 TCB 1 + 1 | 23.84 | 48.86 | 883.78* |
| Δ | 23.02 | 48.24 | 878.05 |
| x-fold | 29.03 | 77.95 | 154.24 |

*curve did not reach saturation, only hypothetical value

The comparison of the EC50 values of 16D5 TCB and 36F2 TCB (Table 29) shows that the difference in the EC50 values gets larger the lower the FolR1 expression on the target cells is. This effect cannot be seen in the comparison of 16D5 TCB and the monovalent 16D5 TCBs (Table 29 and Table 30). For 16D5 TCB 1+1 (Table 31) there is also a slight increase in the difference between the EC50 of 16D5 TCB and 16D5 TCB 1+1 with decreasing FolR1 expression but by far not as pronounced as can be seen in the comparison of 16D5 TCB vs 36F2 TCB.

Example 34

CD25 and CD69 Upregulation on CD8+ and CD4+ Effector Cells after T Cell-Killing of FolR1-Expressing Tumor Cells Induced by 36F2 TCB and 16D5 TCB Antibody Activation of $CD8^+$ and $CD4^+$ T cells after T-cell killing of FolR1-expressing Hela, SKov-3 and HT-29 tumor cells mediated by 36F2 TCB and 16D5 TCB was assessed by FACS analysis using antibodies recognizing the T cell activation markers CD25 (late activation marker) and CD69 (early activation marker). DP47 TCB was included as non-binding control. The antibody and the killing assay conditions were essentially as described above (Example 32) using the same antibody concentration range (0.01 pM-100 nM in triplicates), E:T ratio 10:1 and an incubation time of 48h.

Figure 25A:
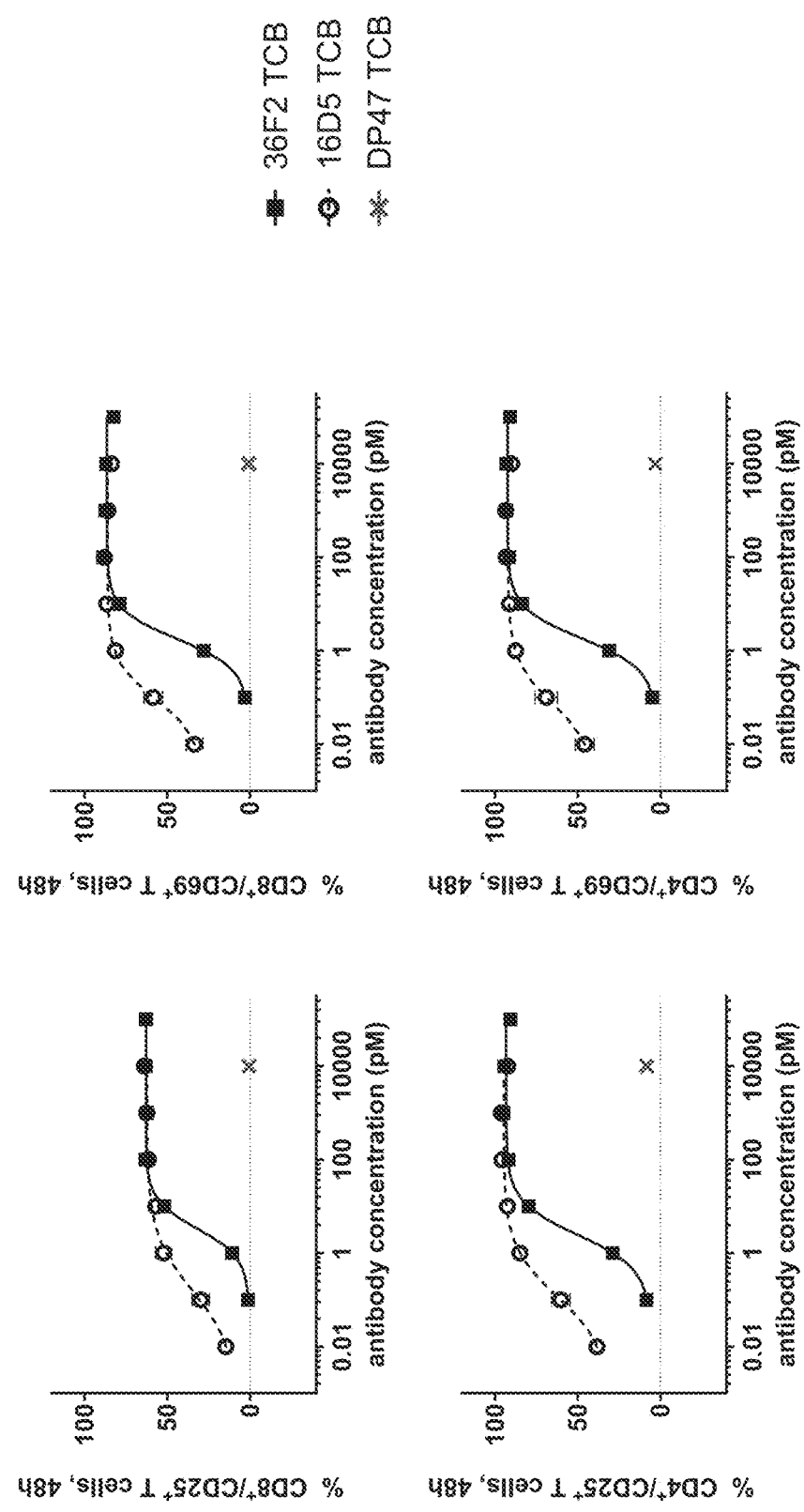
FIGS. 25A-C show upregulation of CD25 and CD69 on human CD8+(FIG. 25A, B) and CD4+(FIG. 25C), T cells after T cell-mediated killing of Hela cells (high FolR1) (FIG. 25A), SKov-3 cells (medium FolR1) (FIG. 25B) and HT-29 cells (low FolR1) (FIG. 25C) (E:T=10:1, 48 h incubation) induced by 36F2 TCB, 16D5 TCB and DP47 TCB (non-binding control).
Figure 25B:
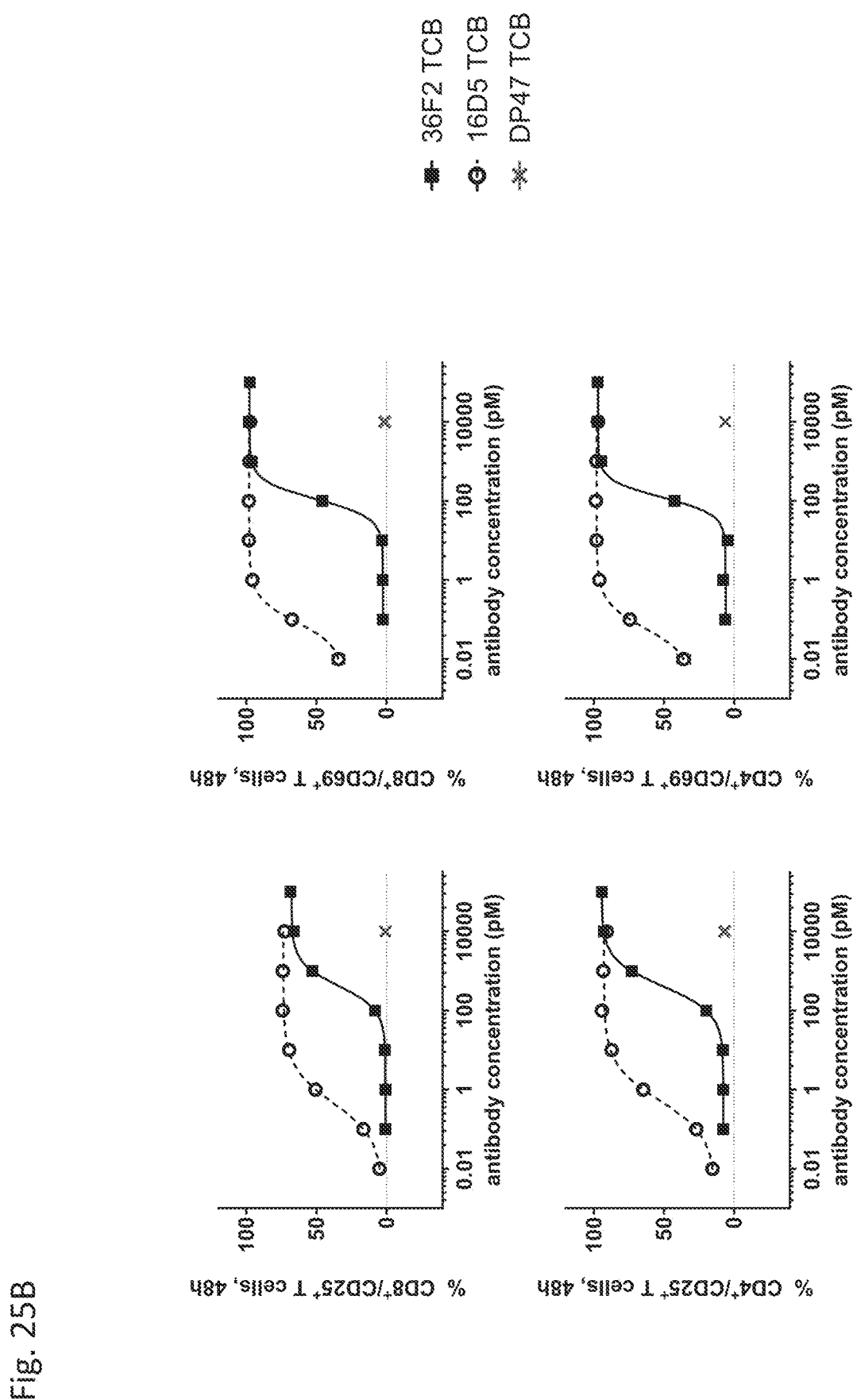

After the incubation, PBMCs were transferred to a round-bottom 96-well plate, centrifuged at 400× g for 4 min and washed twice with PBS containing 0.1% BSA. Surface staining for CD8 (PE anti-human CD8, BD #555635), CD4 (Brilliant Violet 421™ anti-human CD4, Biolegend #300532), CD69 (FITC anti-human CD69, BD #555530) and CD25 (APC anti-human CD25 BD #555434) was performed according to the manufacturer's instructions. Cells were washed twice with 150 μl/well PBS containing 0.1% BSA. After centrifugation, the samples were resuspended in 200 µl/well PBS 0.1% for the FACS measurement. Samples were analyzed at BD FACS Canto II. 36F2 TCB induced a target-specific up-regulation of activation markers (CD25, CD69) on CD8+ and CD4+ T cells after killing of Hela (FIG. 25A) and SKov-3 (FIG. 25B) cells. In comparison to 16D5 TCB the up-regulation of CD25 and CD69 on CD8+ and CD4+ T cells induced by 36F2 is much weaker.

Figure 25C:
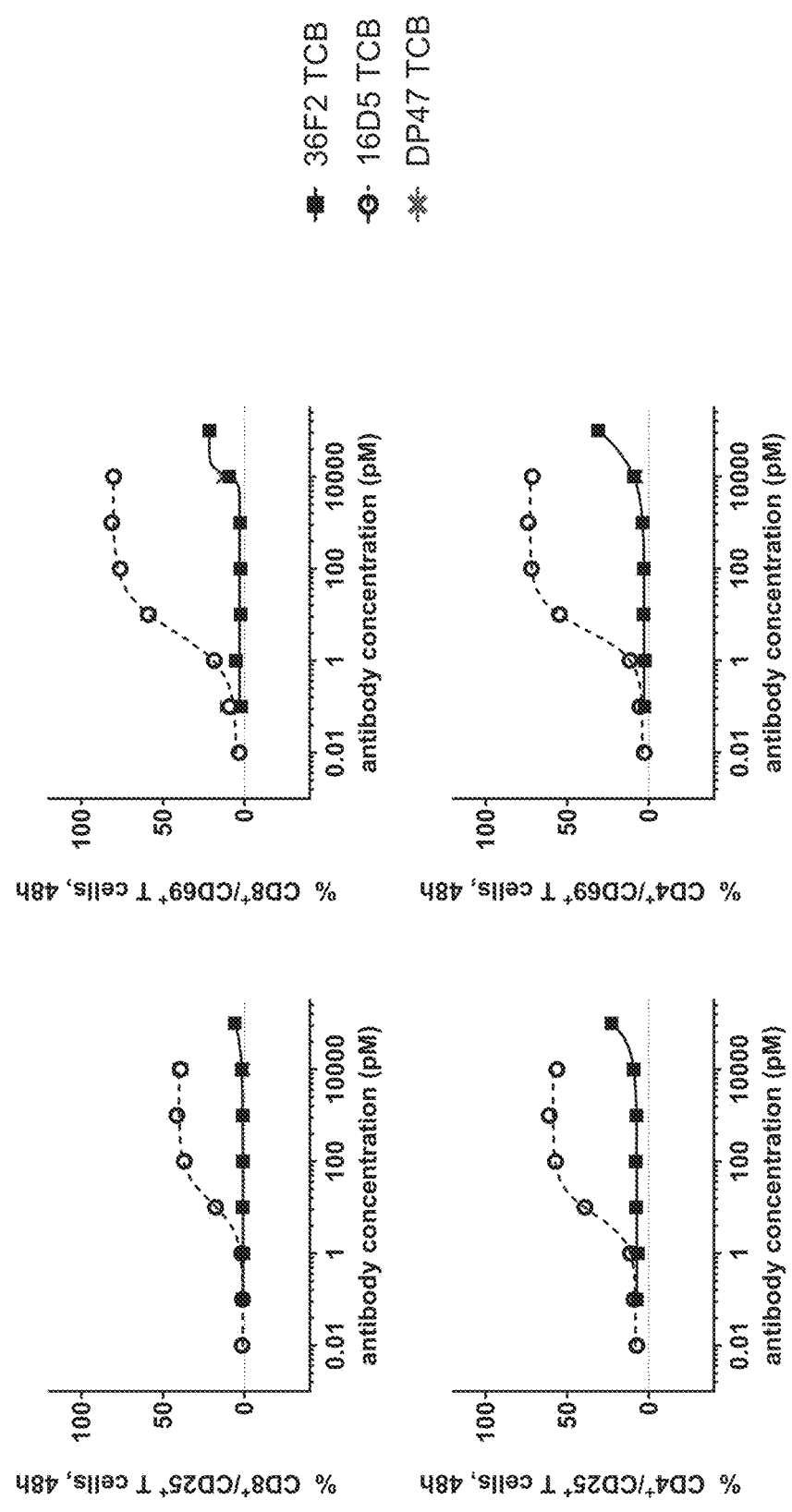

On HT-29 (low FolR1) an up-regulation of activation markers can only be seen at the highest concentration of 36F2 TCB. In contrast, with 16D5 TCB up-regulation of CD25 and CD69 can be seen already at much lower antibody concentrations (FIG. 25C).

As seen as well in the tumor lysis experiment, the analysis of activation markers (CD25 and CD69) on T cells (CD4+ and CD8+) after killing clearly shows that the difference between 16D5 TCB and 36F2 TCB becomes larger the lower the FolR1 expression level on the target cells is.

Example 35

T-Cell Killing of Primary Cells Induced by 36F2 TCB and 16D5 TCB

T-cell killing mediated by 36F2 TCB and 16D5 TCB was assessed on primary cells (Human Renal Cortical Epithelial Cells (HRCEpiC) (ScienCell Research Laboratories; Cat No 4110) and Human Retinal Pigment Epithelial Cells (HRPEpiC) (ScienCell Research Laboratories; Cat No 6540)). HT-29 cells (low FolR1) were included as control cell line. DP47 TCB served as non-binding control. Human PBMCs were used as effectors and the killing was detected at 24 h and 48 h of incubation with the bispecific antibodies. Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% CO2 in cell incubator until further use (no longer than 24 h). For the killing assay, the antibody was added at the indicated concentrations (range of 0.01 pM-10 nM in triplicates). PBMCs were added to target cells at final E:T ratio of 10:1. Target cell killing was assessed after 24 h and 48 h of incubation at 37° C., 5% CO2 by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

The results show that 36F2 TCB does not induce T-cell killing of primary cells (FIG. 26A—D) whereas for 16D5 TCB some killing can be observed on HRCEpiC and HRPEpiC cells after 48 h of incubation (FIGS. 26B and D).

Figure 26E:
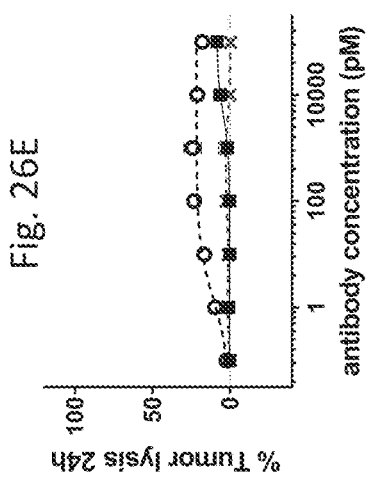

As described above, a strong difference in T-cell killing between of HT-29 cells was observed between 16D5 TCB and 36F2 TCB (FIG. 26E, F).

Example 36

Preparation of DP47 GS TCB (2+1 Crossfab-IgG P329G LALA Inverted="Untargeted TCB")

The "untargeted TCB" was used as a control in the above experiments. The bispecific antibody engages CD3e but does not bind to any other antigen and therefore cannot crosslink T cells to any target cells (and subsequently cannot induce any killing). It was therefore used as negative control in the assays to monitor any unspecific T cell activation. This untargeted TCB was prepared as described in WO2014/131712. In brief, the variable region of heavy and light chain DNA sequences have been subcloned in frame with either the constant heavy chain or the constant light chain pre-inserted into the respective recipient mammalian expression vector. The antibody expression was driven by an MPSV promoter and carries a synthetic polyA signal sequence at the 3' end of the CDS. In addition each vector contains an EBV OriP sequence.

The molecule was produced by co-transfecting HEK293-EBNA cells with the mammalian expression vectors using polyethylenimine. The cells were transfected with the corresponding expression vectors in a 1:2:1:1 ratio ("vector heavy chain Fc(hole)": "vector light chain": "vector light chain Crossfab": "vector heavy chain Fc(knob)-FabCrossfab").

For transfection HEK293 EBNA cells were cultivated in suspension serum free in CD CHO culture medium. For the production in 500 ml shake flask 400 million HEK293 EBNA cells were seeded 24 hours before transfection. For transfection cells were centrifuged for 5 min by 210×g, supernatant is replaced by pre-warmed 20 ml CD CHO medium. Expression vectors were mixed in 20 ml CD CHO medium to a final amount of 200 g DNA. After addition of 540 µl PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 was added. After 7 days cultivation supernatant was collected for purification by centrifugation for 15 min at 210×g, the solution was sterile filtered (0.22 µm filter) and sodium azide in a final concentration of 0.01% w/v was added, and kept at 4° C.

The secreted protein was purified from cell culture supernatants by affinity chromatography using ProteinA. Supernatant was loaded on a HiTrap ProteinA HP column (CV=5 mL, GE Healthcare) equilibrated with 40 ml 20 mM sodium phosphate, 20 mM sodium citrate, 0.5 M sodium chloride, pH 7.5. Unbound protein was removed by washing with at least 10 column volume 20 mM sodium phosphate, 20 mM sodium citrate, 0.5 M sodium chloride, pH 7.5. Target protein was eluted during a gradient over 20 column volume from 20 mM sodium citrate, 0.5 M sodium chloride, pH 7.5 to 20 mM sodium citrate, 0.5 M sodium chloride, pH 2.5. Protein solution was neutralized by adding ⅒ of 0.5 M sodium phosphate, pH 8. Target protein was concentrated and filtrated prior loading on a HiLoad Superdex 200 column (GE Healthcare) equilibrated with 20 mM Histidine, 140 mM sodium chloride solution of pH 6.0.

The protein concentration of purified protein samples was determined by measuring the optical density (OD) at 280 nm, using the molar extinction coefficient calculated on the basis of the amino acid sequence.

Purity and molecular weight of molecules were analyzed by CE-SDS analyses in the presence and absence of a reducing agent. The Caliper LabChip GXII system (Caliper lifescience) was used according to the manufacturer's instruction. 2 ug sample is used for analyses.

The aggregate content of antibody samples was analyzed using a TSKgel G3000 SW XL analytical size-exclusion column (Tosoh) in 25 mM K2HPO4, 125 mM NaCl, 200 mM L-Arginine Monohydrocloride, 0.02% (w/v) NaN3, pH 6.7 running buffer at 25° C.

TABLE 32

Summary production and purification of DP47 GS TCB.

| Construct | Titer [mg/l] | Yield [mg/l] | Aggregate after 1$^{st}$ purification step [%] | HMW [%] | LMW [%] | Monomer [%] |
|---|---|---|---|---|---|---|
| DP47 GS TCB | 103.7 | 8.04 | 8 | 2.3 | 6.9 | 91.8 |

TABLE 33

CE-SDS analyses of DP47 GS TCB.

| | Peak | kDa | Corresponding Chain |
|---|---|---|---|
| DP47 GS TCB non reduced (A) | 1 | 165.22 | Molecule with 2 missing light chains |
| | 2 | 181.35 | Molecule with 1 missing light chain |
| | 3 | 190.58 | Correct molecule without N-linked glycosylation |
| | 4 | 198.98 | Correct molecule |
| DP47 GS TCB reduced (B) | 1 | 27.86 | Light chain DP47 GS |
| | 2 | 35.74 | Light chain huCH2527 |
| | 3 | 63.57 | Fc (hole) |
| | 4 | 93.02 | Fc (knob) |

Example 37

Figure 28A:
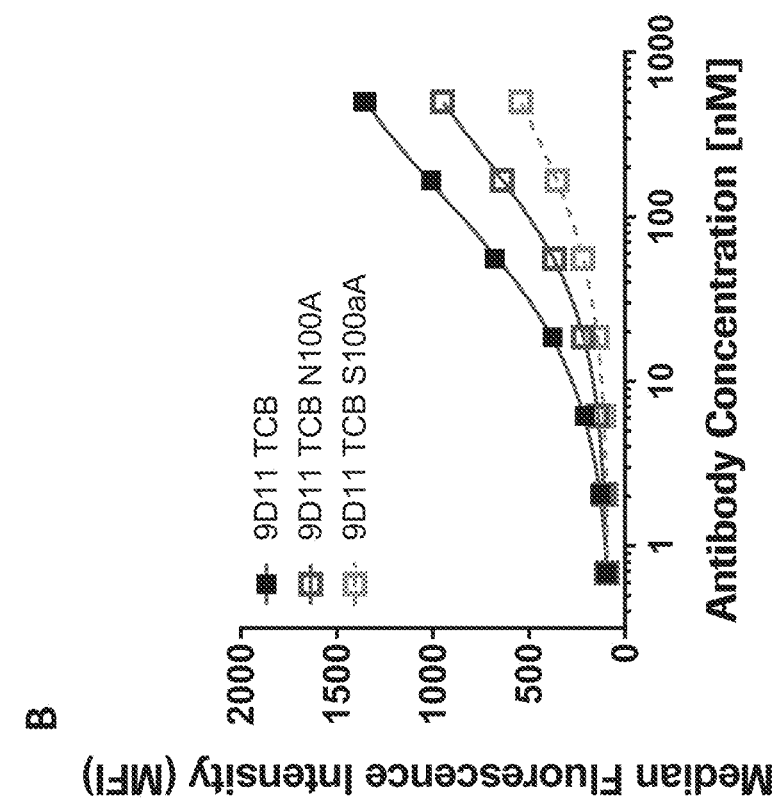
FIGS. 28A-B show binding of 16D5 TCB and its corresponding CD3 deamidation variants 16D5 TCB N100A and 16D5 TCB S100aA and 9D11 TCB and its demidation variants 9D11 TCB N100A and 9D11 TCB S100aA to human CD3 expressed on Jurkat cells.

Binding of 16D5 TCB and 9D11 TCB and their Corresponding CD3 Deamidation Variants N100A and S100aA to CD3-Expressing Jurkat Cells The binding of 16D5 TCB and the corresponding CD3 deamidation variants 16D5 TCB N100A and 16D5 TCB S100aA and 9D11 TCB and the demidation variants 9D11 TCB N100A and 9D11 TCB S100aA to human CD3 was assessed on a CD3-expressing immortalized T lymphocyte line (Jurkat). Briefly, cells were harvested, counted, checked for viability and resuspended at 2×10$^6$ cells/ml in FACS buffer (100 µl PBS 0.1% BSA). 100 µl of cell suspension (containing 0.2×10$^6$ cells) was incubated in round-bottom 96-well plates for 30 min at 4° C. with different concentrations of the bispecific antibodies (686 pM-500 nM). After two washing steps with cold PBS 0.1% BSA, samples were re-incubated for further 30 min at 4° C. with a PE-conjugated AffiniPure F(ab')2 Fragment goat anti-human IgG Fcg Fragment Specific secondary antibody (Jackson Immuno Research Lab PE #109-116-170). After washing the samples twice with cold PBS 0.1% BSA they were immediately analyzed by FACS using a FACS CantoII (Software FACS Diva). Binding curves were obtained using GraphPadPrism6 (FIG. 28A-B).

Figure 28B:
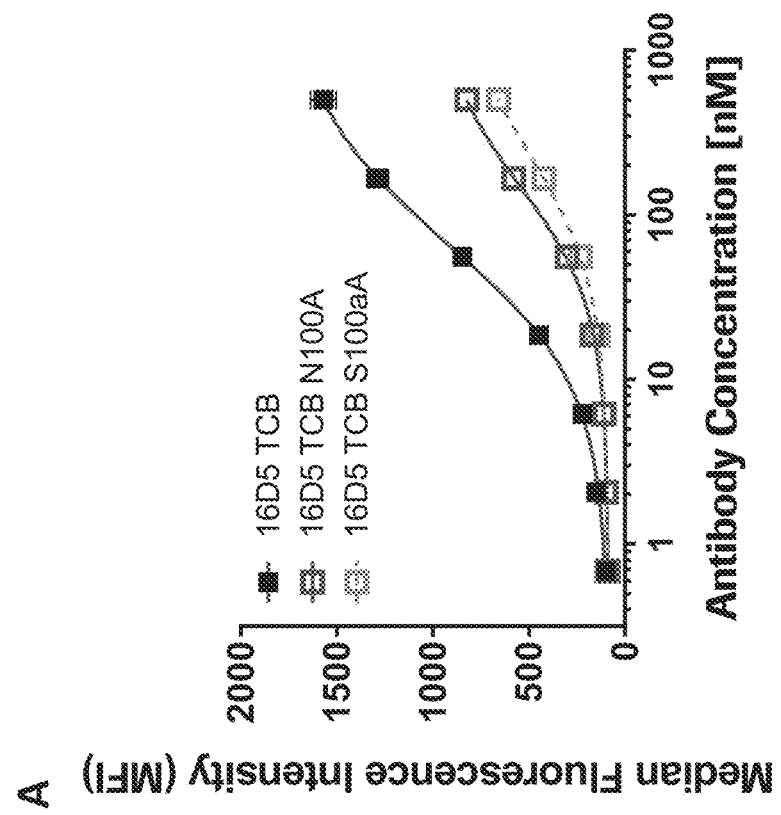

The results show reduced binding of the deamidation variants N100A and S100aA to CD3 compared to the parental antibodies 16D5 TCB (FIG. 28A) and 9D11 TCB (FIG. 28B).

Example 38

T-Cell Killing of SKov-3 and HT-29 Cells Induced by 16D5 TCB and 9D11 TCB and their CD3 Deamidation Variants N100A and S100aA T-cell killing mediated by 16D5 TCB and the corresponding CD3 deamidation variants 16D5 TCB N100A and 16D5 TCB S100aA and 9D11 TCB and the demidation variants 9D11 TCB N100A and 9D11 TCB S100aA was assessed on SKov-3 (medium FolR1) and HT-29 (low FolR1) cells. Human PBMCs were used as effectors and the killing was detected at 24 h of incubation with the bispecific antibodies. Briefly, target cells were harvested with Trypsin/EDTA, washed, and plated at a density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% CO2 in cell incubator until further use (no longer than 24 h). For the killing assay, the antibody was added at the indicated concentrations (range of 0.01 pM-10 nM in triplicates). PBMCs were added to target cells at final E:T ratio of 10:1. Target cell killing was assessed after 24 h of incubation at 37° C., 5% CO2 by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 29A:
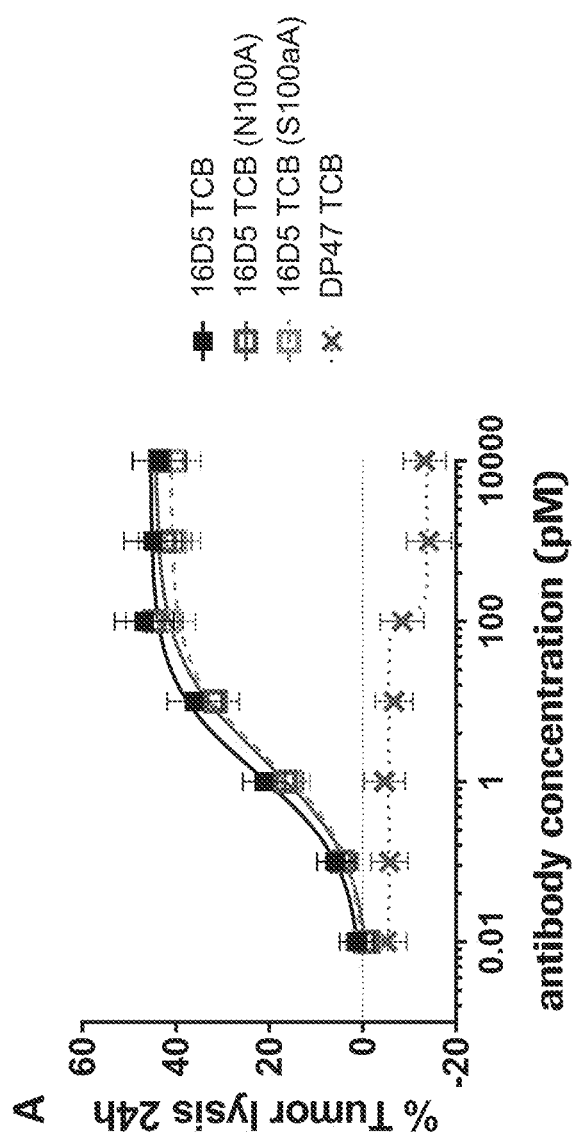
FIGS. 29A-B show T-cell killing of SKov-3 (medium FolR1) human tumor cells induced by 16D5 TCB and its corresponding CD3 deamidation variants 16D5 TCB N100A and 16D5 TCB S100aA (FIG. 29A) and 9D11 TCB and its demidation variants 9D11 TCB N100A and 9D11 TCB S100aA (FIG. 29B) (E:T=10:1, effectors human PBMCs, incubation time 24 h). DP47 TCB was included as non-binding control.
Figure 29B:
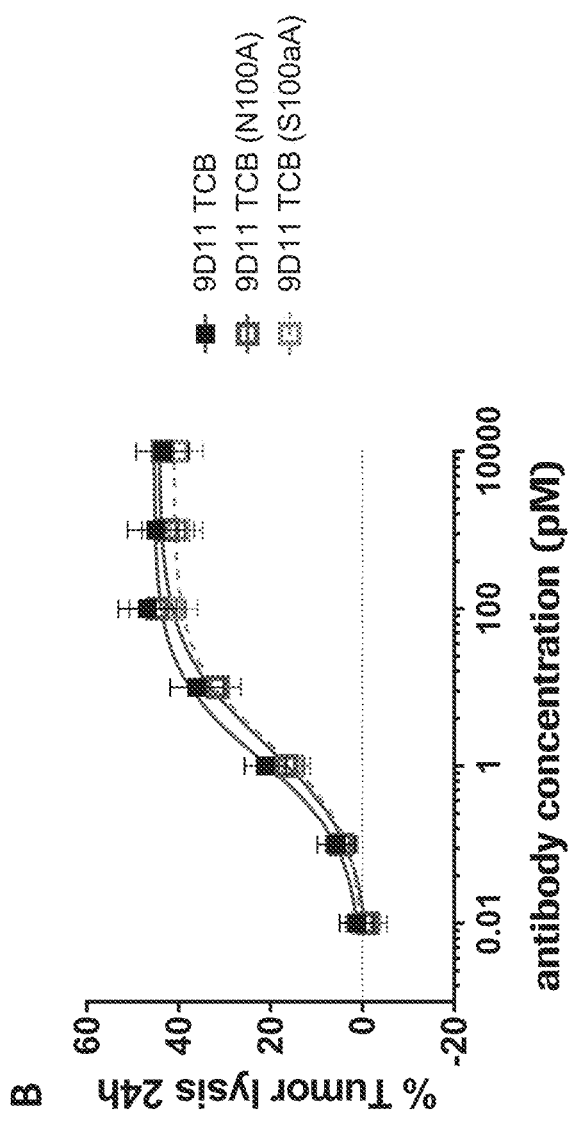
Figure 32A:
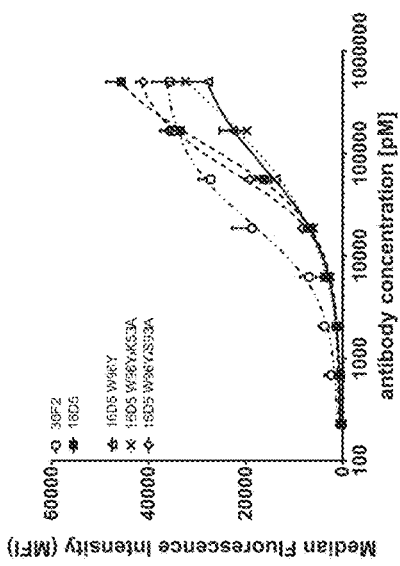
FIGS. 32A-E shows binding of 36F2 TCB, 16D5 TCB and 16D5 HC/LC variants to human FolR1 expressed on Hela cells.
Figure 32B:
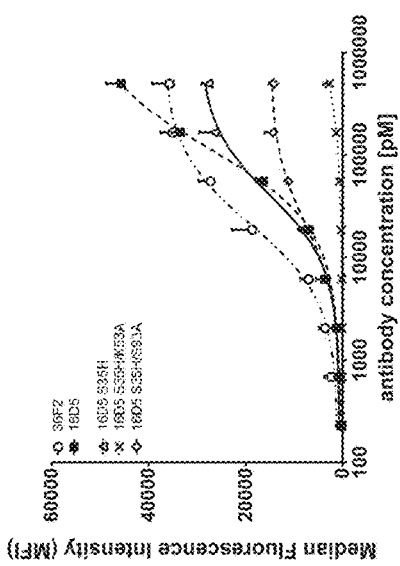
Figure 32C:
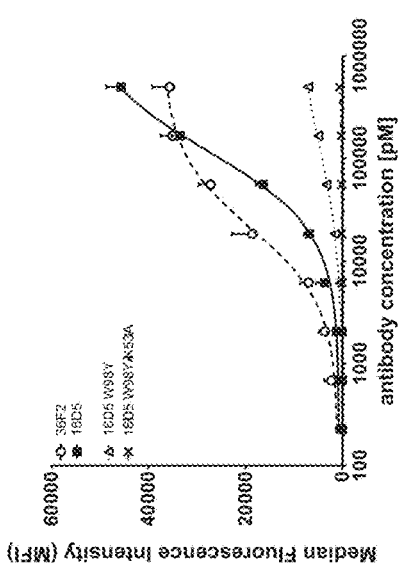
Figure 32D:
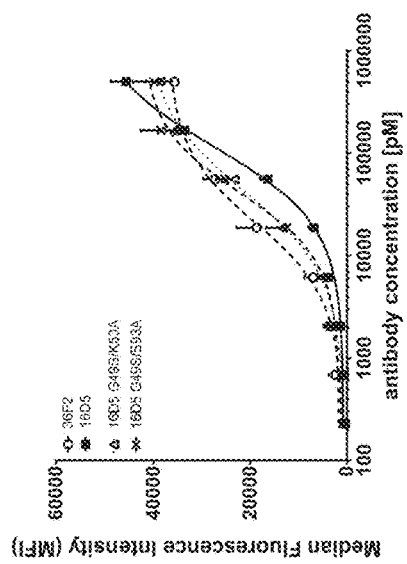
Figure 32E:
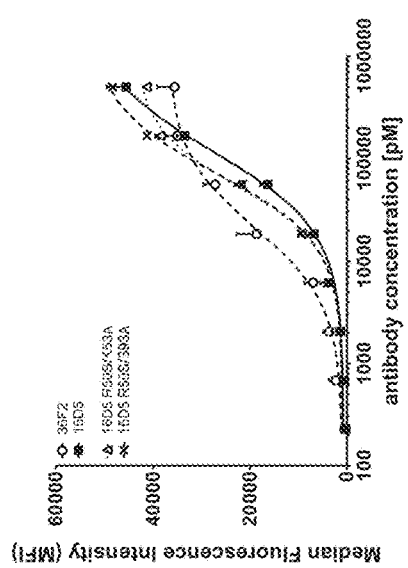

The results show that on SKov-3 cells the killing induced by the CD3 deamidation variants 16D5 TCB N100A and 16D5 S100aA is comparable to the one induced by 16D5 TCB (FIG. 29A). The same is true for 9D11 TCB and its variants 9D11 TCB N100A and 9D11 TCB S100aA (FIG. 29B). On FolR1 low expressing HT-29 cells the S100aA variant shows an impaired killing efficiency which is the case for 16D5 TCB (FIG. 30A) as well as for 9D11 TCB (FIG. 30B). The EC50 values related to killing assays, calculated using GraphPadPrism6 are given in Table 35.

TABLE 35

EC50 values (pM) for T-cell mediated killing of FolR1-expressing SKov-3 and HT-29 cells induced by 16D5 TCB and 9D11 TCB and their deamidation variants N100A and A100aA.

| Antibody | EC50 [pM] | |
| --- | --- | --- |
| | SKov-3 | HT-29 |
| 16D5 TCB | 1.283 | 56.67 |
| 16D5 TCB N100A | 1.886 | 91.95 |
| 16D5 TCB S100aA | 1.939 | 165.6 |
| 9D11 TCB | 1.283 | 2.827 |
| 9D11 TCB N100A | 1.886 | 37.72 |
| 9D11 TCB S100aA | 1.939 | n.d.* |

*not determined

Example 39

Biochemical Characterization by Surface Plasmon Resonance as TCBs of Two CD3 Binder Variants (N100A and S100aA) to Remove a Deamidation Site Binding of two 16D5 TCBs with CD3 binder variants (N100A or S100aA) to human recombinant CD3 (CD3epsilon-CD3delta heterodimer as Fc fusion) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

Affinity to CD3ed-Fc

The affinity of the interaction between the anti-FolR1 T cell bispecifics and the recombinant CD3 epsilon-delta heterodimer was determined as described below (Table 36).

For affinity measurement, direct coupling of around 6000 resonance units (RU) of the anti-human Fab specific antibody (Fab capture kit, GE Healthcare) was performed on a CM5 chip at pH 5.0 using the standard amine coupling kit (GE Healthcare). Anti-FolR1 T cell bispecifics were captured at 200 nM with a flow rate of 20 µl/min for 60 sec, the reference flow cell was left without capture. Dilution series (4.1 to 3000 nM) of human and cyno Folate Receptor 1 Fc fusion were passed on all flow cells at 30 µl/min for 240 sec to record the association phase. The dissociation phase was monitored for 240 s and triggered by switching from the sample solution to HBS-EP. The chip surface was regenerated after every cycle using a double injection of 60 sec 10 mM Glycine-HCl pH 1.5. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 36

Monovalent binding (affinity) of two 16D5 CD3 deamidation variants as TCBs on human CD3ed-Fc.

| Ligand | Analyte | ka (1/Ms) | kd (1/s) | KD |
| --- | --- | --- | --- | --- |
| 16D5 TCB N100A | huCD3 | 1.23E+04 | 4.67E-03 | 380 nM |
| 16D5 TCB S100aA | huCD3 | 1.21E+04 | 5.49E-03 | 460 nM |
| 16D5 TCB | huCD3 | 2.03E+04 | 4.41E-03 | 220 nM |

The two CD3 deamidation variants have a slightly reduced affinity compared to the wild-type CD3 binder (CH2527), but the difference is not grave.

Example 40

Production and Purification of Two Variants of the 16D5 T-Cell Bispecific with Mutations to Remove the Deamidation Site in the CD3 Binder: 16D5 TCB N100A, 16D5 TCB S100aA Transient Transfection and Production The two deamidation variants 16D5 TCBs were transiently produced in HEK293 EBNA cells using a PEI mediated transfection procedure for the required vectors as described below. HEK293 EBNA cells are cultivated in suspension serum free in CD CHO culture medium. For the production in 500 ml shake flask 400 million HEK293 EBNA cells are seeded 24 hours before transfection (for alternative scales all amounts were adjusted accordingly). For transfection cells are centrifuged for 5 min by 210×g, supernatant is replaced by pre-warmed 20 ml CD CHO medium. Expression vectors are mixed in 20 ml CD CHO medium to a final amount of 200m DNA. After addition of 540 µl PEI solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% CO2 atmosphere. After incubation time 160 ml F17 medium is added and cell are cultivated for 24 hours. One day after transfection 1 mM valporic acid and 7% Feed 1 is added. After 7 days cultivation supernatant is collected for purification by centrifugation for 15 min at 210×g, the solution is sterile filtered (0.22 µm filter) and sodium azide in a final concentration of 0.01% w/v is added, and kept at 4° C. After production the supernatant was harvested, filtered through 0.22 µm sterile filters and stored at 4° C. until purification.

Purification

The two deamidation variants 16D5 TCBs were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to MabSelect SuRe (GE Healthcare, column volume (cv)=2 ml) equilibrated with 8 column volumes (cv) buffer A (20 mM sodium phosphate pH 7.5, 20 mM sodium citrate). After washing with 10 cv of buffer A, the protein was eluted using a pH gradient to buffer B (20 mM sodium citrate pH 3.0, 100 mM NaCl, 100 mM glycine) over 20 cv. Fractions containing the protein of interest were pooled and the pH of the solution was gently adjusted to pH 6.0 (using 0.5 M Na$_2$HPO$_4$ pH 8.0). Samples were concentrated to 1 ml using ultra-concentrators (Amicon Ultra-15, 30.000 MWCO, Millipore) and subsequently applied to a HiLoad™ 16/60 Superdex™ 200 preparative grade (GE Healthcare) equilibrated with 20 mM Histidine, pH 6.0, 140 mM NaCl. The aggregate content of eluted fractions was analyzed by analytical size exclusion chromatography. Therefore, 30 µl of each fraction was applied to a TSKgel G3000 SW XL analytical size-exclusion column (Tosoh) equilibrated in 25 mM $K_2HPO_4$, 125 mM NaCl, 200 mM L-arginine monohydrochloride, 0.02% (w/v) $NaN_3$, pH 6.7 running buffer at 25° C. Fractions containing less than 2% oligomers were pooled. The protein concentration was determined by measuring the optical density (OD) at 280 nm, using the molar extinction coefficient calculated on the basis of the amino acid sequence. Purity and molecular weight of the constructs were analyzed by SDS capillary electrophoresis (CE-SDS) in the presence and absence of a reducing agent following the manufacturer instructions (instrument Caliper LabChipGX, Perkin Elmer). Purified proteins were frozen in liquid N2 and stored at −80° C.

TABLE 36

Yield, monomer content and purity by CE-SDS of the two 16D5 deamidation variants in the T cell bispecific format.

| Name | Mutation in the CD3 binder | Yield [mg/L] | Monomer [%] | Purity by CE-SDS [%] |
|---|---|---|---|---|
| 16D5 TCB | N100A | 9 | 100 | 89 |
| 16D5 TCB | S100aA | 23 | 100 | 83 |
| 16D5 TCB | Wild-type | 9 | 100 | 93 |

Both TCBs were produced in good quality, similar to the construct with the wild-type CD3 binder.

Example 41

Production and Purification of Two 16D5 Binder Variants (D52dE and D52dQ) as IgGs to Remove a Hotspot in the CDR Transient Transfection and Production The two IgGs were transiently produced in HEK293 EBNA cells using a PEI mediated transfection procedure for the required vectors as described below. HEK293 EBNA cells are cultivated in suspension serum free in CD CHO culture medium. For the production in 500 ml shake flask 400 million HEK293 EBNA cells are seeded 24 hours before transfection (for alternative scales all amounts were adjusted accordingly). For transfection cells are centrifuged for 5 min by 210×g, supernatant is replaced by pre-warmed 20 ml CD CHO medium. Expression vectors are mixed in 20 ml CD CHO medium to a final amount of 200m DNA. After addition of 540 μl PEI solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% CO2 atmosphere. After incubation time 160 ml F17 medium is added and cell are cultivated for 24 hours. One day after transfection 1 mM valporic acid and 7% Feed 1 is added. After 7 days cultivation supernatant is collected for purification by centrifugation for 15 min at 210×g, the solution is sterile filtered (0.22 μm filter) and sodium azide in a final concentration of 0.01% w/v is added, and kept at 4° C. After production the supernatants were harvested and the antibody containing supernatants were filtered through 0.22 μm sterile filters and stored at 4° C. until purification.

Antibody Purification

The two IgGs were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to POROS MabCapture A (Applied Biosystems, column volume (cv)=1 ml) equilibrated with 8 column volumes (cv) buffer A (20 mM sodium phosphate, 20 mM sodium citrate, pH 7.5). After washing with 10 cv of buffer A, the protein was eluted using a pH step to buffer B (20 mM sodium citrate pH 3.0, 100 mM NaCl, 100 mM glycine) over 5 cv. The 5 ml containing the protein of interest are stored in a loop on the Äkta Explorer and subsequently applied to a HiLoad 16/60 Superdex™ 200 (GE Healthcare) equilibrated with 20 mM Histidine, pH 6.0, 140 mM NaCl (no TWEEn was used). Fractions containing the IgGs were pooled and concentrated using ultra concentrators (Amicon Ultra-15, 30.000 MWCO, Millipore). The aggregate content of the final pool was analyzed by analytical size exclusion chromatography. Therefore, 30 μl were applied to a TSKgel G3000 SW XL analytical size-exclusion column (Tosoh) equilibrated in 25 mM $K_2HPO_4$, 125 mM NaCl, 200 mM L-arginine monohydrochloride, 0.02% (w/v) $NaN_3$, pH 6.7 running buffer at 25° C. The protein concentration was determined by measuring the optical density (OD) at 280 nm, using the molar extinction coefficient calculated on the basis of the amino acid sequence. Purity and molecular weight of the constructs were analyzed by SDS capillary electrophoresis (CE-SDS) in the presence and absence of a reducing agent following the manufacturer instructions (instrument Caliper LabChipGX, Perkin Elmer). Purified proteins were stored at 4° C.

TABLE 37

Yield, monomer content and purity by CE-SDS of two 16D5 IgG hotspot variants.

| Clone | Mutation HC/LC | Yield [mg/L} | Monomer [%] | Purity by CE-SDS [%] |
|---|---|---|---|---|
| 16D5 | D52dE | 24 | 100 | 96 |
| 16D5 | D52dQ | 20 | 100 | 96 |

Both IgGs produced well and in good quality.

Example 42

Biochemical Characterization by Surface Plasmon Resonance of Two 16D5 Binder Variants (D52dE and D52dQ) as IgGs to Remove a Hotspot in the CDR Binding of two 16D5 binder variants (D52dE and D52dQ) as IgGs to human and cyno recombinant folate receptor 1 (both as Fc fusions) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

1. Avidity to Folate Receptor 1

The avidity of the interaction between the anti-FolR1 IgGs or T cell bispecifics and the recombinant folate receptors was determined as described below (Table 38).

Recombinant biotinylated monomeric Fc fusions of human, cynomolgus and murine Folate Receptor 1 (FolR1-Fc) were directly coupled on a SA chip using the standard coupling instruction (Biacore, Freiburg/Germany). The immobilization level was about 160. The anti-FolR1 IgGs or T cell bispecifics were passed at a concentration range from 3.7 to 900 nM with a flow of 30 μL/minutes through the flow cells over 180 seconds. The dissociation was monitored for 600 seconds. Bulk refractive index differences were corrected for by subtracting the response obtained on reference flow cell immobilized with recombinant biotinylated murine IL2 receptor Fc fusion. The binding curves resulting from the bivalent binding of the IgG or T cell bispecifics were approximated to a 1:1 Langmuir binding (even though it is a 1:2 binding) and fitted with that model to get an apparent KD representing the avidity of the bivalent binding. The apparent avidity constants for the interactions were derived from the rate constants of the fitting using the Bia Evaluation software (GE Healthcare).

TABLE 38

Bivalent binding (avidity with apparent KD) of two 16D5 hot spot variants as IgGs on human, murine and cyno FolR1 (no binding on muFolR1 as expected).

| Analyte | Ligand | ka (1/Ms) | kd (1/s) | Apparent KD |
|---|---|---|---|---|
| 16D5 D52dE IgG | huFolR1 | 1.62E+05 | 5.45E−04 | 3.4 nM |
|  | cyFolR1 | 2.98E+06 | 7.47E−03 | 2.5 nM |
| 16D5 D52dQ IgG | huFolR1 | 8.40E+04 | 7.75E−04 | 9.2 nM |
|  | cyFolR1 | 4.12E+05 | 2.04E−03 | 5 nM |
| 16D5 TCB | huFolR1 | 2.25E+05 | 5.00E−04 | 2.2 nM |
|  | cyFolR1 | 2.71E+05 | 6.63E−04 | 2.5 nM |

2. Affinity to Folate Receptor 1

The affinity of the interaction between the anti-FolR1 IgGs or the T cell bispecifics and the recombinant folate receptors was determined as described below (Table 39).

For affinity measurement, direct coupling of around 10000 resonance units (RU) of the anti-human Fab specific antibody (Fab capture kit, GE Healthcare) was performed on a CM5 chip at pH 5.0 using the standard amine coupling kit (GE Healthcare). Anti-FolR1 IgGs or T cell bispecifics were captured at 20 nM with a flow rate of 10 μl/min for 40 sec, the reference flow cell was left without capture. Dilution series (12.35 to 3000 nM) of human and cyno Folate Receptor 1 Fc fusion were passed on all flow cells at 30 μl/min for 240 sec to record the association phase. The dissociation phase was monitored for 300 s and triggered by switching from the sample solution to HBS-EP. The chip surface was regenerated after every cycle using a double injection of 60 sec 10 mM Glycine-HCl pH 1.5. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 39

Monovalent binding (affinity) of two 16D5 hot spot variants as IgGs on human and cyno FolR1.

| Ligand | Analyte | ka (1/Ms) | kd (1/s) | KD |
|---|---|---|---|---|
| 16D5 D52dE IgG | huFolR1 | 2.40E+04 | 2.27E−03 | 95 nM |
|  | cyFolR1 | 2.25E+04 | 1.20E−02 | 530 nM |
| 16D5 D52dQ IgG | huFolR1 | 6.97E+03 | 1.62E−03 | 230 nM |
|  | cyFolR1 | 8.20E+03 | 3.32E−03 | 410 nM |
| 16D5 TCB | huFolR1 | 2.05E+04 | 7.05E−04 | 35 nM |
|  | cyFolR1 | 1.72E+04 | 1.62E−03 | 90 nM |

The two 16D5 hot spot variants have similar avidity (bivalent binding) than the wild-type 16D5 binder. The avidity is slightly decreased for the D52dQ variant and this difference is even more visible in affinity (monovalent binding).

Example 43

Production and Purification as IgGs of Twelve Variants of the 16D5 Binder with Mutations in the Heavy and Light Chain to Reduce Affinity to FolR1

Transient Transfection and Production

The twelve IgGs were transiently produced in HEK293 EBNA cells using a PEI mediated transfection procedure for the required vectors as described below. HEK293 EBNA cells are cultivated in suspension serum free in CD CHO culture medium. For the production in 500 ml shake flask 400 million HEK293 EBNA cells are seeded 24 hours before transfection (for alternative scales all amounts were adjusted accordingly). For transfection cells are centrifuged for 5 min by 210×g, supernatant is replaced by pre-warmed 20 ml CD CHO medium. Expression vectors are mixed in 20 ml CD CHO medium to a final amount of 200m DNA. After addition of 540 μl PEI solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% CO2 atmosphere. After incubation time 160 ml F17 medium is added and cell are cultivated for 24 hours. One day after transfection 1 mM valporic acid and 7% Feed 1 is added. After 7 days cultivation supernatant is collected for purification by centrifugation for 15 min at 210×g, the solution is sterile filtered (0.22 μm filter) and sodium azide in a final concentration of 0.01% w/v is added, and kept at 4° C. After production the supernatants were harvested and the antibody containing supernatants were filtered through 0.22 μm sterile filters and stored at 4° C. until purification.

Antibody Purification

All molecules were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to POROS MabCapture A (Applied Biosystems, column volume (cv)=1 ml) equilibrated with 8 column volumes (cv) buffer A (20 mM sodium phosphate, 20 mM sodium citrate, pH 7.5). After washing with 10 cv of buffer A, the protein was eluted using a pH step to buffer B (20 mM sodium citrate pH 3.0, 100 mM NaCl, 100 mM glycine) over 5 cv. The 5 ml containing the protein of interest are stored in a loop on the Äkta Explorer and subsequently applied to a HiLoad 16/60 Superdex™ 200 (GE Healthcare) equilibrated with 20 mM Histidine, pH 6.0, 140 mM NaCl, 0.01% Tween-20. Fractions containing the IgGs were pooled and concentrated using ultra concentrators (Amicon Ultra-15, 30.000 MWCO, Millipore). The aggregate content of the final pool was analyzed by analytical size exclusion chromatography. Therefore, 30 μl were applied to a TSKgel G3000 SW XL analytical size-exclusion column (Tosoh) equilibrated in 25 mM $K_2HPO_4$, 125 mM NaCl, 200 mM L-arginine monohydrochloride, 0.02% (w/v) $NaN_3$, pH 6.7 running buffer at 25° C. The protein concentration was determined by measuring the optical density (OD) at 280 nm, using the molar extinction coefficient calculated on the basis of the amino acid sequence. Purity and molecular weight of the constructs were analyzed by SDS capillary electrophoresis (CE-SDS) in the presence and absence of a reducing agent following the manufacturer instructions (instrument Caliper LabChipGX, Perkin Elmer). Purified proteins were stored at 4° C.

TABLE 40

Yield, monomer content and purity by CE-SDS of twelve 16D5 IgG variants

| Clone | Mutation HC/LC | Yield [mg/L] | Monomer [%] | Purity by CE-SDS [%] |
|---|---|---|---|---|
| 16D5 | W98Y/wt | 32 | 100 | 100 |
| 16D5 | W98Y/K53A | 24 | 100 | 100 |
| 16D5 | S35H/wt | 21 | 100 | 100 |
| 16D5 | S35H/K53A | 18 | 100 | 100 |
| 16D5 | S35H/S93A | 18 | 100 | 100 |
| 16D5 | W96Y/wt | 40 | 100 | 100 |
| 16D5 | W96Y/K53A | 21 | 100 | 100 |
| 16D5 | W96Y/S93A | 25 | 98 | 100 |
| 16D5 | R50S/K53A | 10 | 98 | 100 |
| 16D5 | R50S/S93A | 7 | 100 | 100 |
| 16D5 | G49S/K53A | 42 | 100 | 100 |
| 16D5 | G49S/S93A | 45 | 100 | 100 |

All twelve IgGs produced well and in good quality.

Example 44

Biochemical Characterization of 16D5 Heavy and Light Chain Combination Variants as IgG by Surface Plasmon Resonance Binding of FolR1 16D5 heavy and light chain combination variants binders as IgG to different recombinant folate receptors (human, murine and cynomolgus FolR1; all as Fc fusions) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

Avidity to Folate Receptor 1

The avidity of the interaction between the anti-FolR1 IgGs or T cell bispecifics and the recombinant folate receptors was determined as described below (Table 41).

Recombinant biotinylated monomeric Fc fusions of human, cynomolgus and murine Folate Receptor 1 (FolR1-Fc) were directly coupled on a SA chip using the standard coupling instruction (Biacore, Freiburg/Germany). The immobilization level was about 300. The anti-FolR1 IgGs or T cell bispecifics were passed at a concentration range from 11.1 to 900 nM with a flow of 30 µL/minutes through the flow cells over 180 seconds. The dissociation was monitored for 240 or 600 seconds. Bulk refractive index differences were corrected for by subtracting the response obtained on reference flow cell immobilized with recombinant biotinylated murine IL2 receptor Fc fusion. The binding curves resulting from the bivalent binding of the IgG or T cell bispecifics were approximated to a 1:1 Langmuir binding (even though it is a 1:2 binding) and fitted with that model to get an apparent KD representing the avidity of the bivalent binding. The apparent avidity constants for the interactions were derived from the rate constants of the fitting using the Bia Evaluation software (GE Healthcare). For low affinity kinetics with association and dissociation phases too fast to be fitted by the 1:1 Langmuir binding model, the steady state analysis model was applied using the Bia Evaluation software (GE Healthcare). The steady state analysis gives the KD of the binding reaction at equilibrium.

TABLE 41

Bivalent binding (avidity with apparent KD) of twelve 16D5 variants binders as IgGs on human, murine and cyno FolR1.

| Analyte HC variant/LC variant | Ligand | ka (1/Ms) | kd (1/s) | Apparent KD |
|---|---|---|---|---|
| W98Y/K53A | huFolR1 | | | Weak binding |
| | cyFolR1 | | | Weak binding |
| S35H/K53A | huFolR1 | 2.10E+04 | 2.91E-02 | 1400 nM |
| | cyFolR1 | 3.47E+04 | 4.04E-02 | 1100 nM |
| W96Y/K53A | huFolR1 | | | 580 nM (steady state) |
| | cyFolR1 | | | 660 nM (steady state) |
| W98Y/wt | huFolR1 | 1.36E+05 | 3.28E-02 | 240 nM |
| | cyFolR1 | 1.71E+05 | 3.61E-02 | 200 nM |
| S35H/S93A | huFolR1 | 2.43E+05 | 2.20E-02 | 90 nM |
| | cyFolR1 | 6.12E+05 | 6.77E-02 | 110 nM |
| G49S/K53A | huFolR1 | 1.90E+05 | 1.15E-02 | 60 nM |
| | cyFolR1 | 3.93E+05 | 3.28E-02 | 80 nM |
| R50S/K53A | huFolR1 | 3.28E+05 | 1.97E-02 | 60 nM |
| | cyFolR1 | 5.50E+05 | 4.55E-02 | 80 nM |
| S35H/wt | huFolR1 | 1.32E+05 | 5.68E-03 | 40 nM |
| | cyFolR1 | 2.23E+05 | 1.24E-02 | 55 nM |
| R50S/S93A | huFolR1 | 1.25E+05 | 3.23E-03 | 30 nM |
| | cyFolR1 | 4.39E+05 | 7.80E-03 | 20 nM |
| W96Y/S93A | huFolR1 | 6.55E+05 | 1.89E-02 | 30 nM |
| | cyFolR1 | 6.25E+05 | 1.74E-02 | 30 nM |
| G49S/S93A | huFolR1 | 1.52E+05 | 3.06E-02 | 20 nM |
| | cyFolR1 | 3.58E+05 | 6.22E-03 | 20 nM |
| W96Y/wt | huFolR1 | 1.29E+05 | 2.13E-03 | 20 nM |
| | cyFolR1 | 1.73E+05 | 2.11E-03 | 10 nM |
| 36F2 TCB | huFolR1 | 2.44E+06 | 1.37E-02 | 6 nM |
| | cyFolR1 | 4.12E+06 | 2.15E-02 | 5 nM |
| | muFolR1 | 4.86E+05 | 1.20E-03 | 2.5 nM |
| 16D5 TCB | huFolR1 | 1.41E+05 | 4.25E-04 | 3 nM |
| | cyFolR1 | 1.78E+05 | 6.39E-04 | 3.5 nM |

Affinity to Folate Receptor 1

The affinity of the interaction between the anti-FolR1 IgGs or the T cell bispecifics and the recombinant folate receptors was determined as described below (Table 42).

For affinity measurement, direct coupling of around 10000 resonance units (RU) of the anti-human Fab specific antibody (Fab capture kit, GE Healthcare) was performed on a CM5 chip at pH 5.0 using the standard amine coupling kit (GE Healthcare). Anti-FolR1 IgGs or T cell bispecifics were captured at 200 nM with a flow rate of 10 ul/min for 40 sec, the reference flow cell was left without capture. Dilution series (12.35 to 3000 nM) of human Folate Receptor 1 Fc fusion were passed on all flow cells at 30 µl/min for 240 sec to record the association phase. The dissociation phase was monitored for 300 s and triggered by switching from the sample solution to HBS-EP. The chip surface was regenerated after every cycle using a double injection of 60 sec 10 mM Glycine-HCl pH 1.5. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 42

Monovalent binding (affinity) of twelve 16D5 variants FolR1 binders as IgGs on human, cyno and murine FolR1.

| Ligand HC variant/LC variant | Analyte | ka (1/Ms) | kd (1/s) | KD |
|---|---|---|---|---|
| W98Y/K53A | huFolR1 | | | No binding |
| S35H/K53A | huFolR1 | | | Weak binding |

TABLE 42-continued

Monovalent binding (affinity) of twelve 16D5 variants FolR1 binders as IgGs on human, cyno and murine FolR1.

| Ligand HC variant/LC variant | Analyte | ka (1/Ms) | kd (1/s) | KD |
|---|---|---|---|---|
| W96Y/K53A | huFolR1 | | | Weak binding |
| W98Y/wt | huFolR1 | | | 5400 nM (steady state) |
| G49S/K53A | huFolR1 | 9.19E+03 | 1.74E−02 | 1900 nM |
| R50S/K53A | huFolR1 | 1.35E+04 | 2.45E−02 | 1800 nM |
| 36F2 TCB | huFolR1 | 5.00E+04 | 8.57E−02 | 1700 nM |
| S35H/S93A | huFolR1 | 8.43E+03 | 1.12E−02 | 1300 nM |
| S35H/wt | huFolR1 | 8.96E+03 | 1.13E−02 | 1200 nM |
| R50S/S93A | huFolR1 | 1.57E+04 | 1.23E−02 | 780 nM |
| G49S/S93A | huFolR1 | 1.05E+04 | 7.99E−03 | 760 nM |
| W96Y/wt | huFolR1 | 9.95E+03 | 5.44E−03 | 550 nM |
| W96Y/S93A | huFolR1 | 4.05E+04 | 1.72E−02 | 420 nM |
| 16D5 TCB | huFolR1 | 1.18E+04 | 7.22E−04 | 60 nM |

Twelve "affinity reduced" variants of the 16D5 FolR1 binder were analyzed by surface plasmon resonance in comparison to the 16D5 wild-type binder and the 36F2 binder. The goal was to find a 16D5 variant with an affinity and an avidity comparable to 36F2. When measuring monovalent binding (affinity) there were variants with a higher and variants with a lower affinity than 36F2. However in the bivalent binding (avidity) all the variants have a higher apparent KD value than 36F2. This is mainly due to the fast association rate (ka) of 36F2 that results in a small apparent KD for 36F2. The big avidity effect when 36F2 binds bivalently seems to be unique to this binder. As noted above, 36F2 was the only human, murine and cyno crossreactive binder that could be identified.

Example 45

Binding of 16D5 HC/LC Variants to Human FolR1 Expressed on Hela Cells

The binding of 36F2 TCB, 16D5 TCB and various HC/LC variants of 16D5 to human FolR1 was assessed on Hela cells. Briefly, cells were harvested, counted, checked for viability and resuspended at $2 \times 10^6$ cells/ml in FACS buffer (100 µl PBS 0.1% BSA). 100 µl of cell suspension (containing $0.2 \times 10^6$ cells) was incubated in round-bottom 96-well plates for 30 min at 4° C. with different concentrations of the bispecific antibodies (229 pM-500 nM). After two washing steps with cold PBS 0.1% BSA, samples were re-incubated for further 30 min at 4° C. with a PE-conjugated AffiniPure F(ab')2 Fragment goat anti-human IgG Fcg Fragment Specific secondary antibody (Jackson Immuno Research Lab PE #109-116-170). After washing the samples twice with cold PBS 0.1% BSA they were fixed with 1% PFA overnight. Afterwards samples were centrifuged, resuspended in PBS 0.1% BSA and analyzed by FACS using a FACS CantoII (Software FACS Diva). Binding curves were obtained using GraphPadPrism6 (FIG. 32A-E). The 36F2 TCB bound FolR2, was not well tolerated in mice, and did not demonstrate the desired efficacy.

Example 46

Production and Purification of Four Variants of the 16D5 T-Cell Bispecific with Mutations to Reduce the Affinity to Human and Cynomolgus FolR1: 16D5 TCB G49S/S93A, G49S/K53A, W96Y, W96Y/D52E Transient Transfection and Production Four additional variants of 16D5 TCBs having reduced affinity to FolR1 were transiently produced in HEK293 EBNA cells using a PEI mediated transfection procedure for the required vectors as described below. For transfection HEK293 EBNA cells are cultivated in suspension serum free in Excell culture medium containing 6 mM L-Glutamine and 250 mg/l G418 culture medium. For the production in 600 ml tubespin flask (max. working volume 400 mL) 600 million HEK293 EBNA cells are seeded 24 hours before transfection. For transfection cells are centrifuged for 5 min by 210× g, supernatant is replaced by pre-warmed 20 ml CD CHO medium. Expression vectors are mixed in 20 ml CD CHO medium to a final amount of 400 µg DNA. After addition of 1080 µl PEI solution (2.7 µg/ml) is vortexed for 15 s and subsequently incubated for 10 min at room temperature. Afterwards cells are mixed with the DNA/PEI solution, transferred to a 600 ml tubespin flask and incubated for 3 hours by 37° C. in an incubator with a 5% CO2 atmosphere. After incubation time 360 ml Excell+6 mM L-Glutamine+5 g/L Pepsoy+1.0 mM VPA medium is added and cells are cultivated for 24 hours. One day after transfection 7% Feed 7 is added. After 7 days cultivation supernatant is collected for purification by centrifugation for 20-30 min at 3600×g (Sigma 8K centrifuge), the solution is sterile filtered (0.22 mm filter) and sodium azide in a final concentration of 0.01% w/v is added, and kept at 4° C.

Purification

The reduced affinity variants 16D5 TCBs were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to HiTrap Protein A (GE Healthcare, column volume (cv)=5 ml) equilibrated with 8 column volumes (cv) buffer A (20 mM sodium phosphate pH 7.5, 20 mM sodium citrate). After washing with 10 cv of buffer A, the protein was eluted using a pH gradient to buffer B (20 mM sodium citrate pH 3.0, 100 mM NaCl, 100 mM glycine) over 20 cv. Fractions containing the protein of interest were pooled and the pH of the solution was gently adjusted to pH 6.0 (using 0.5 M $Na_2HPO_4$ pH 8.0). Samples were concentrated to 1 ml using ultra-concentrators (Amicon Ultra-15, 30.000 MWCO, Millipore) and subsequently applied to a HiLoad™ 16/60 Superdex™ 200 preparative grade (GE Healthcare) equilibrated with 20 mM Histidine, pH 6.0, 140 mM NaCl, 0.01% Tween 20. The aggregate content of eluted fractions was analyzed by analytical size exclusion chromatography. Therefore, 30 µl of each fraction was applied to a TSKgel G3000 SW XL analytical size-exclusion column (Tosoh) equilibrated in 25 mM $K_2HPO_4$, 125 mM NaCl, 200 mM L-arginine monohydrochloride, 0.02% (w/v) $NaN_3$, pH 6.7 running buffer at 25° C. Fractions containing less than 2% oligomers were pooled. The protein concentration was determined by measuring the optical density (OD) at 280 nm, using the molar extinction coefficient calculated on the basis of the amino acid sequence. Purity and molecular weight of the constructs were analyzed by SDS capillary electrophoresis (CE-SDS) in the presence and absence of a reducing agent following the manufacturer instructions (instrument Caliper LabChipGX, Perkin Elmer). Purified proteins were frozen in liquid N2 and stored at −80° C.

TABLE 43

Yield, monomer content and purity by CE-SDS of the reduced affinity 16D5 variants in the T cell bispecific format.

| Name | Mutations to reduce affinity | Yield [mg/L] | Monomer [%] | Purity by CE-SDS [%] |
|---|---|---|---|---|
| 16D5 TCB | G49S S93A | 10.3 | 100 | 88 |
| 16D5 TCB | G49S K53A | 22.3 | 98.5 | 96 |
| 16D5 TCB | W96Y | 15.2 | 98.7 | 92.5 |
| 16D5 TCB | W96Y D52E | 9.9 | 99.3 | 92.9 |
| 16D5 TCB | Wild-type | 5.4 | 96 | 91.6 |

All variants with reduced affinity could be produced in good quality.

Example 47

Figure 33:
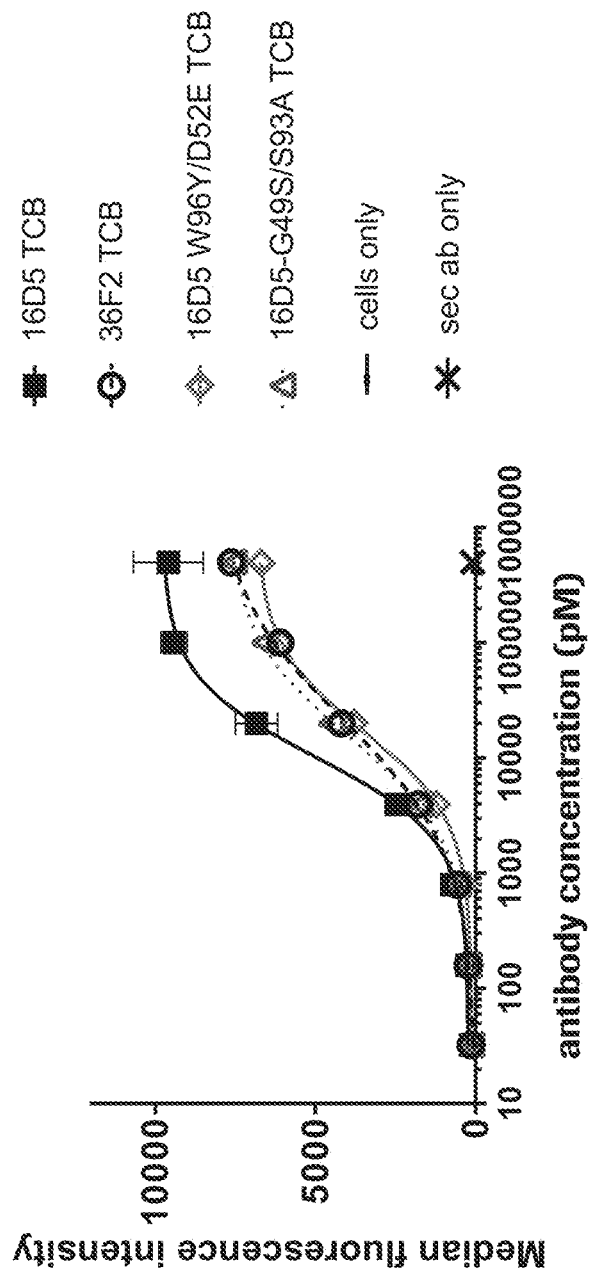
FIG. 33 shows binding of 36F2 TCB, 16D5 TCB and the two 16D5 affinity reduced variants 16D5 W96Y/D52E TCB and 16D5 G49S/S93A TCB to human FolR1 on Hela cells.
Figure 34A:
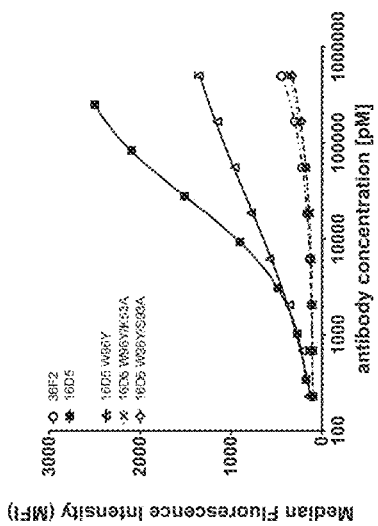
FIGS. 34A-E show binding of 36F2 TCB, 16D5 TCB and 16D5 HC/LC variants to human FolR1 expressed on HT-29 cells.
Figure 34B:
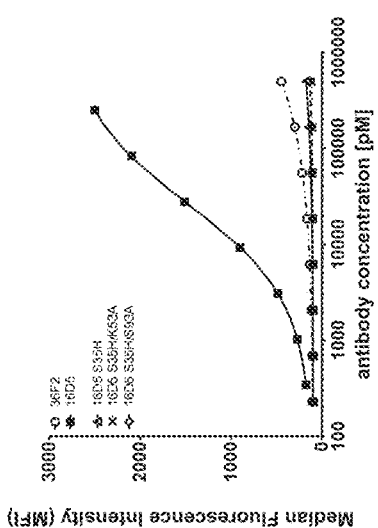
Figure 34C:
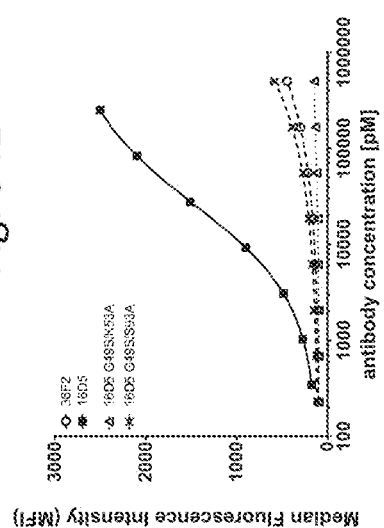
Figure 34D:
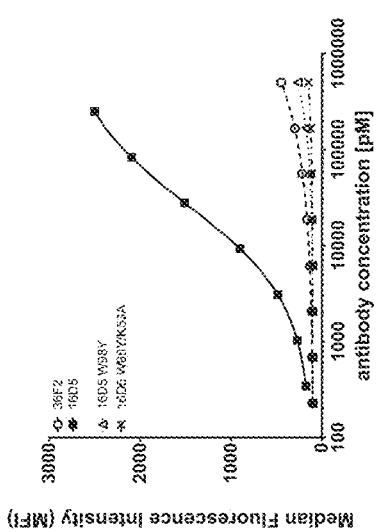
Figure 34E:
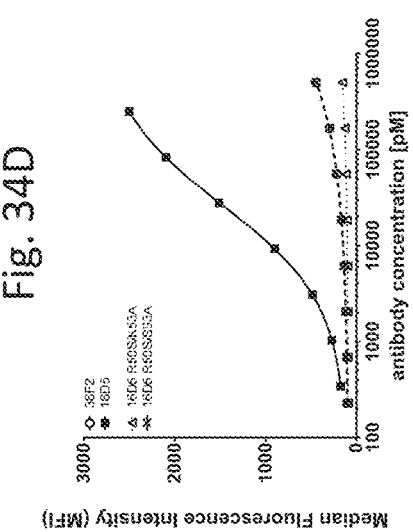

Binding of 36F2 TCB, 16D5 TCB and the Two 16D5 Affinity Reduced Variants 16D5 W96Y/D52E TCB and 16D5 G49S/S93A TCB to Human FolR1 Expressed on Hela Cells The binding of 36F2 TCB, 16D5 TCB and the two 16D5 affinity reduced variants 16D5 W96Y/D52E TCB and 16D5 G49S/S93A TCB to human FolR1 was assessed on Hela cells. Briefly, cells were harvested, counted, checked for viability and resuspended at $2 \times 10^6$ cells/ml in FACS buffer (100 μl PBS 0.1% BSA). 100 μl of cell suspension (containing $0.2 \times 10^6$ cells) was incubated in round-bottom 96-well plates for 30 min at 4° C. with different concentrations of the bispecific antibodies (30 pM-500 nM). After two washing steps with cold PBS 0.1% BSA, samples were re-incubated for further 30 min at 4° C. with a FITC-conjugated AffiniPure F(ab')2 Fragment goat anti-human IgG Fcg Fragment Specific secondary antibody (Jackson Immuno Research Lab PE #109-096-098). After washing the samples twice with cold PBS 0.1% BSA samples were centrifuged, resuspended in PBS 0.1% BSA and analyzed by FACS using a FACS CantoII (Software FACS Diva). Binding curves were obtained using GraphPadPrism6 (FIG. 33).

Example 48

Production and Purification of Three T-Cell Bispecifics with Intermediate Affinity to Human and Cynomolgus FolR1: 14B1, 6E10, 2C7

Transient Transfection and Production

The intermediate affinity TCBs were transiently produced in HEK293 EBNA cells using a PEI mediated transfection procedure for the required vectors as described below. For transfection HEK293 EBNA cells are cultivated in suspension serum free in Excell culture medium containing 6 mM L-Glutamine and 250 mg/l G418 culture medium. For the production in 600 ml tubespin flask (max. working volume 400 mL) 600 million HEK293 EBNA cells are seeded 24 hours before transfection. For transfection cells are centrifuged for 5 min by 210×g, supernatant is replaced by pre-warmed 20 ml CD CHO medium. Expression vectors are mixed in 20 ml CD CHO medium to a final amount of 400 μg DNA. After addition of 1080 μl PEI solution (2.7 μg/ml) is vortexed for 15 s and subsequently incubated for 10 min at room temperature. Afterwards cells are mixed with the DNA/PEI solution, transferred to a 600 ml tubespin flask and incubated for 3 hours by 37° C. in an incubator with a 5% CO2 atmosphere. After incubation time 360 ml Excell+6 mM L-Glutamine+5 g/L Pepsoy+1.0 mM VPA medium is added and cells are cultivated for 24 hours. One day after transfection 7% Feed 7 is added. After 7 days cultivation supernatant is collected for purification by centrifugation for 20-30 min at 3600×g (Sigma 8K centrifuge), the solution is sterile filtered (0.22 μm filter) and sodium azide in a final concentration of 0.01% w/v is added, and kept at 4° C.

Purification

The intermediate affinity TCBs were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to HiTrap Protein A (GE Healthcare, column volume (cv)=5 ml) equilibrated with 8 column volumes (cv) buffer A (20 mM sodium phosphate pH 7.5, 20 mM sodium citrate). After washing with 10 cv of buffer A, the protein was eluted using a pH gradient to buffer B (20 mM sodium citrate pH 3.0, 100 mM NaCl, 100 mM glycine) over 20 cv. Fractions containing the protein of interest were pooled and the pH of the solution was gently adjusted to pH 6.0 (using 0.5 M $Na_2HPO_4$ pH 8.0). Samples were concentrated to 1 ml using ultra-concentrators (Amicon Ultra-15, 30.000 MWCO, Millipore) and subsequently applied to a HiLoad™ 16/60 Superdex™ 200 preparative grade (GE Healthcare) equilibrated with 20 mM Histidine, pH 6.0, 140 mM NaCl, 0.01% Tween 20. The aggregate content of eluted fractions was analyzed by analytical size exclusion chromatography. Therefore, 30 μl of each fraction was applied to a TSKgel G3000 SW XL analytical size-exclusion column (Toso h) equilibrated in 25 mM $K_2HPO_4$, 125 mM NaCl, 200 mM L-arginine monohydrochloride, 0.02% (w/v) $NaN_3$, pH 6.7 running buffer at 25° C. Fractions containing less than 2% oligomers were pooled. The protein concentration was determined by measuring the optical density (OD) at 280 nm, using the molar extinction coefficient calculated on the basis of the amino acid sequence. Purity and molecular weight of the constructs were analyzed by SDS capillary electrophoresis (CE-SDS) in the presence and absence of a reducing agent following the manufacturer instructions (instrument Caliper LabChipGX, Perkin Elmer). Purified proteins were frozen in liquid N2 and stored at −80° C.

TABLE 44

Yield, monomer content and purity by CE-SDS of the intermediate affinity TCBs.

| Name | Yield [mg/L] | Monomer [%] | Purity by CE-SDS [%] |
|---|---|---|---|
| 6E10 TCB | 2.3 | 93 | 95 |
| 14B1 TCB | 1.8 | 94 | 70 |
| 9C7 TCB | 3.4 | 98 | 99 |

All intermediate affinity T cell bispecifics could be produced. The yields are not high. The quality is good for 9C7 and acceptable for 14B1 and 6E10.

Example 49

Binding of 16D5 HC/LC Variants to Human FolR1 Expressed on HT-29 Cells

The binding of 36F2 TCB, 16D5 TCB and various HC/LC variants (FIG. 34A-E) of 16D5 to human FolR1 was assessed on HT-29 cells. Briefly, cells were harvested, counted, checked for viability and resuspended at $2 \times 10^6$ cells/ml in FACS buffer (100 μl PBS 0.1% BSA). 100 μl of cell suspension (containing $0.2 \times 10^6$ cells) was incubated in round-bottom 96-well plates for 30 min at 4° C. with different concentrations of the bispecific antibodies (229 pM-500 nM). After two washing steps with cold PBS 0.1% BSA, samples were re-incubated for further 30 min at 4° C. with a PE-conjugated AffiniPure F(ab')2 Fragment goat anti-human IgG Fcg Fragment Specific secondary antibody (Jackson Immuno Research Lab PE #109-116-170). After washing the samples twice with cold PBS 0.1% BSA they were fixed with 1% PFA overnight. Afterwards samples were centrifuged, resuspended in PBS 0.1% BSA and analyzed by FACS using a FACS CantoII (Software FACS Diva). Binding curves were obtained using GraphPadPrism6 (FIG. 34A-E).

Example 50

Binding of Intermediate FolR1 Binders to Human and Mouse FolR1 and FolR2

Cross-reactivity of the intermediate FolR1 binders (6E10 TCB, 14B1 TCB and 9C7 TCB), as well as 16D5 TCB and 36F2 TCB to human and mouse FolR1 and FolR2 was assessed in a FACS binding assay on transfected HEK293T cells.

Briefly, cells were harvested, counted, checked for viability and resuspended at $2\times10^6$ cells/ml in FACS buffer (100 µl PBS 0.1% BSA). 100 µl of cell suspension (containing $0.2\times10^6$ cells) was incubated in round-bottom 96-well plates for 30 min at 4° C. with 100 nM of the bispecific antibodies. After two washing steps with cold PBS 0.1% BSA, samples were re-incubated for further 30 min at 4° C. with a Fluorescein (FITC) AffiniPure F(ab')$_2$ Fragment Goat Anti-Human IgG, Fcγ Fragment Specific secondary antibody (Jackson Immuno Research Lab PE #109-096-098). After washing the samples twice with cold PBS 0.1% BSA they were fixed with 1% PFA overnight. Afterwards samples were centrifuged, resuspended in PBS 0.1% BSA and analyzed by FACS using a FACS CantoII (Software FACS Diva). Graphs were obtained using GraphPadPrism6 (FIG. 35A-D). The results show that 36F2 TCB and 14B1 TCB are cross-reactive to mouse FolR1 and human and mouse FolR2. For 6E10 TCB a weak binding to human FolR2 can be observed. 16D5 TCB and 9C7 TCB are specific for human FolR1 and show no cross-reactivity to mouse FolR1 or human and mouse FolR2.

Example 51

Biochemical Characterization by Surface Plasmon Resonance of 16D5 Reduced Affinity Variants and Additional Intermediate Affinity Binders in the T-Cell Bispecific Format Binding of anti-FolR1 16D5 reduced affinity variants and additional intermediate affinity binders in the bivalent T-cell bispecific format to recombinant human, cynomolgus and murine folate receptor 1 (all as Fc fusions) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, GE Healthcare). The molecules used for affinity and avidity determination are described in Table 45.

TABLE 45

Name, description and figure reference of the nine constructs used in SPR analysis.

Figure 1F:
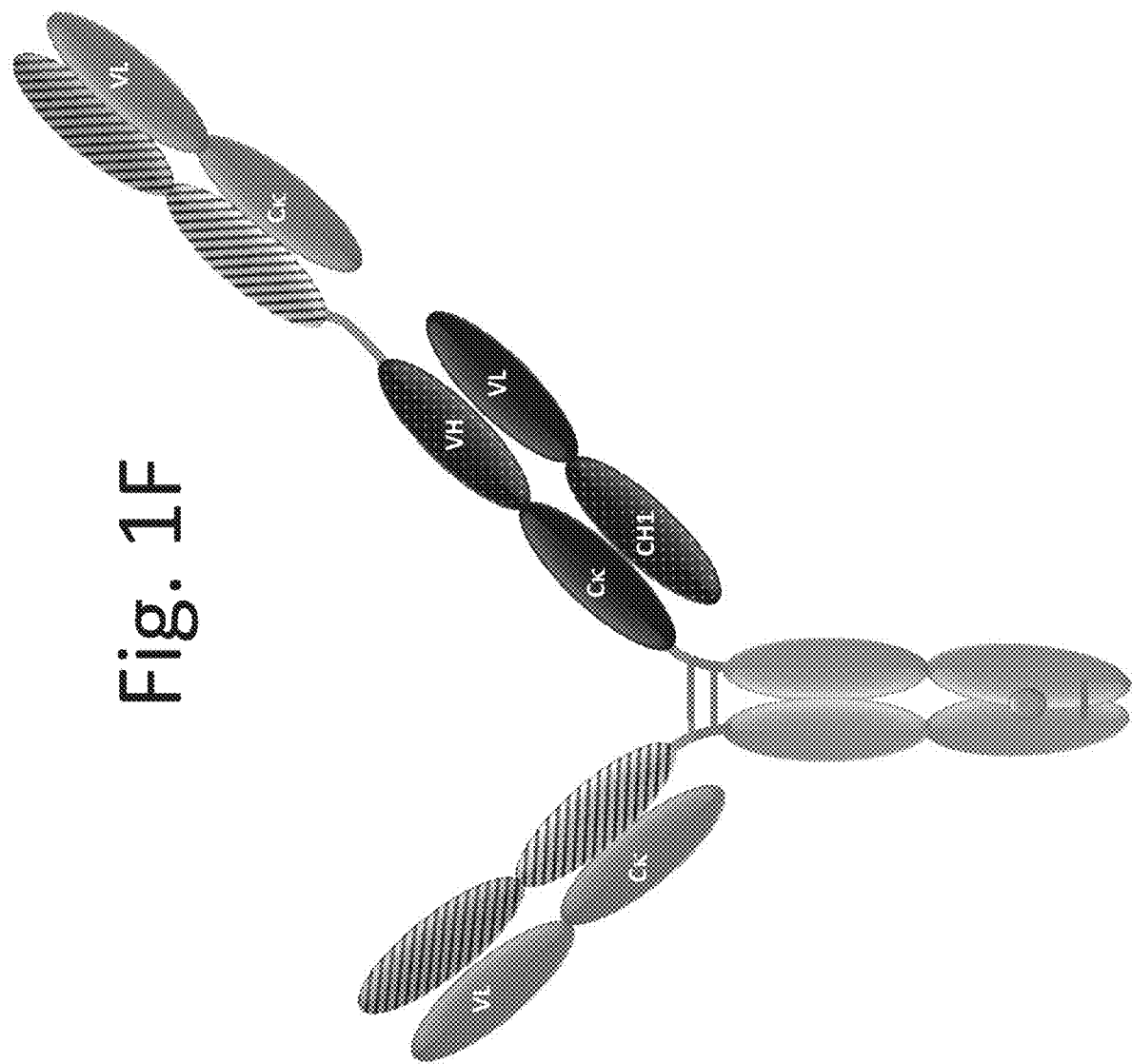
Figure 1G:
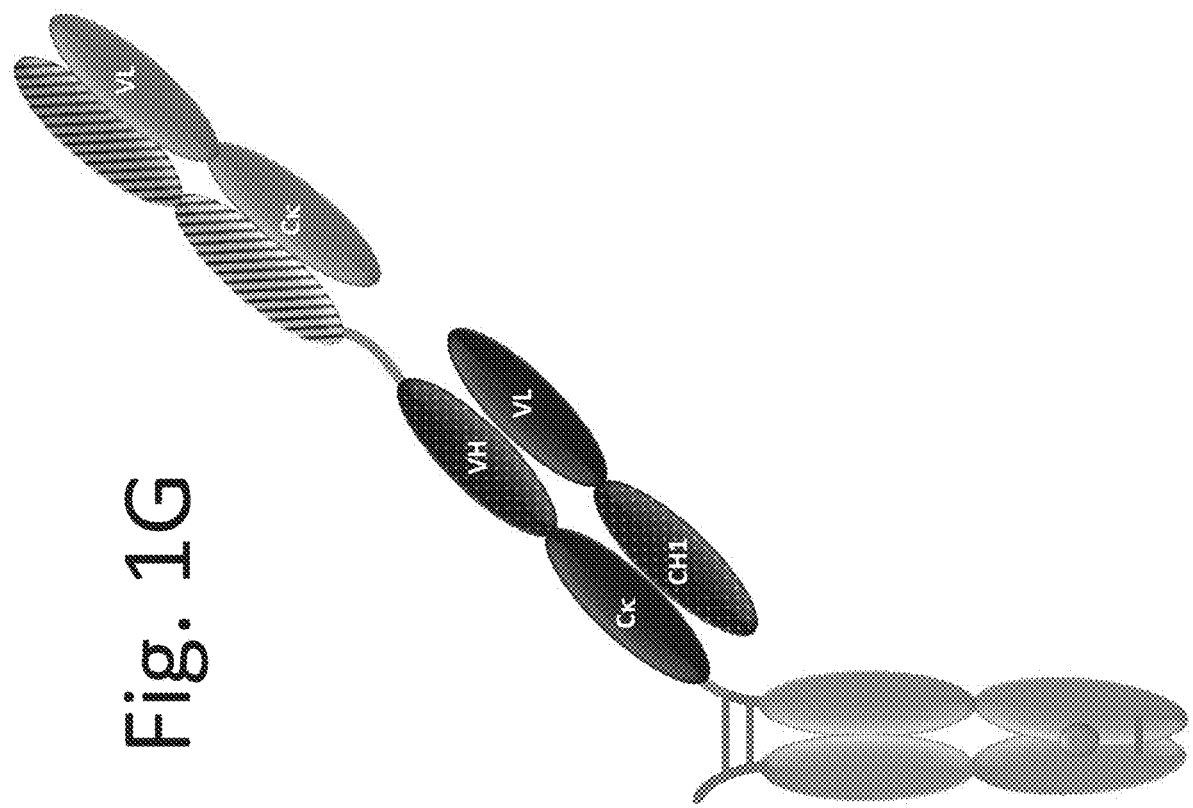
Figure 1H:
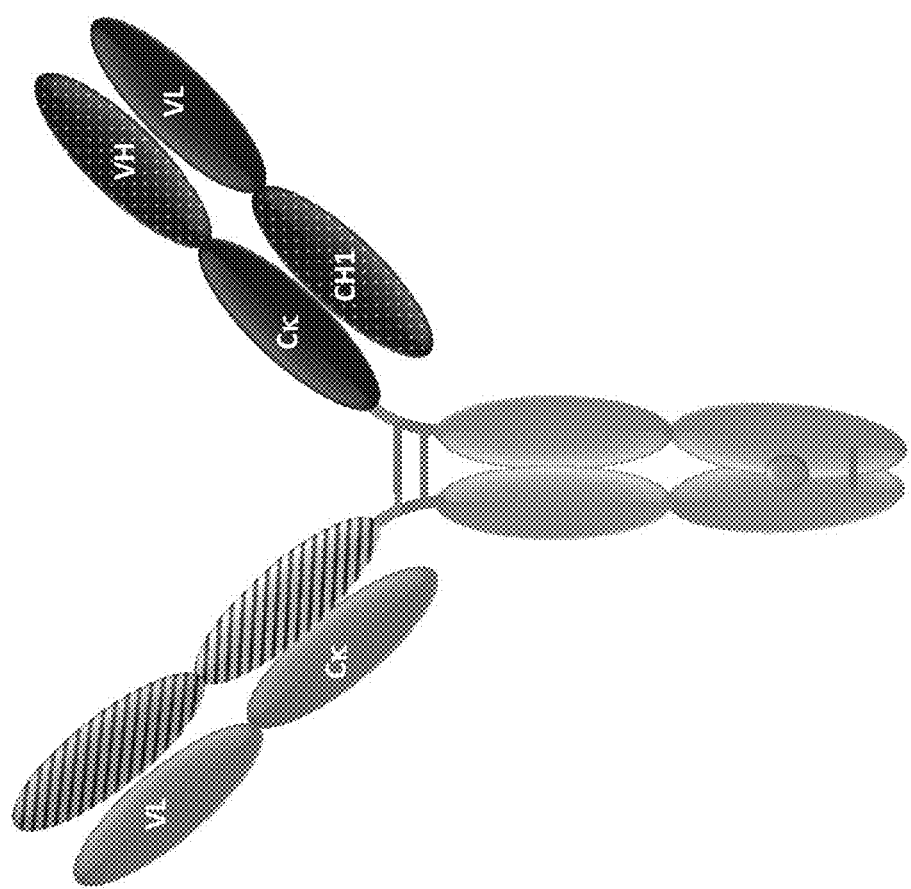
Figure 1I:
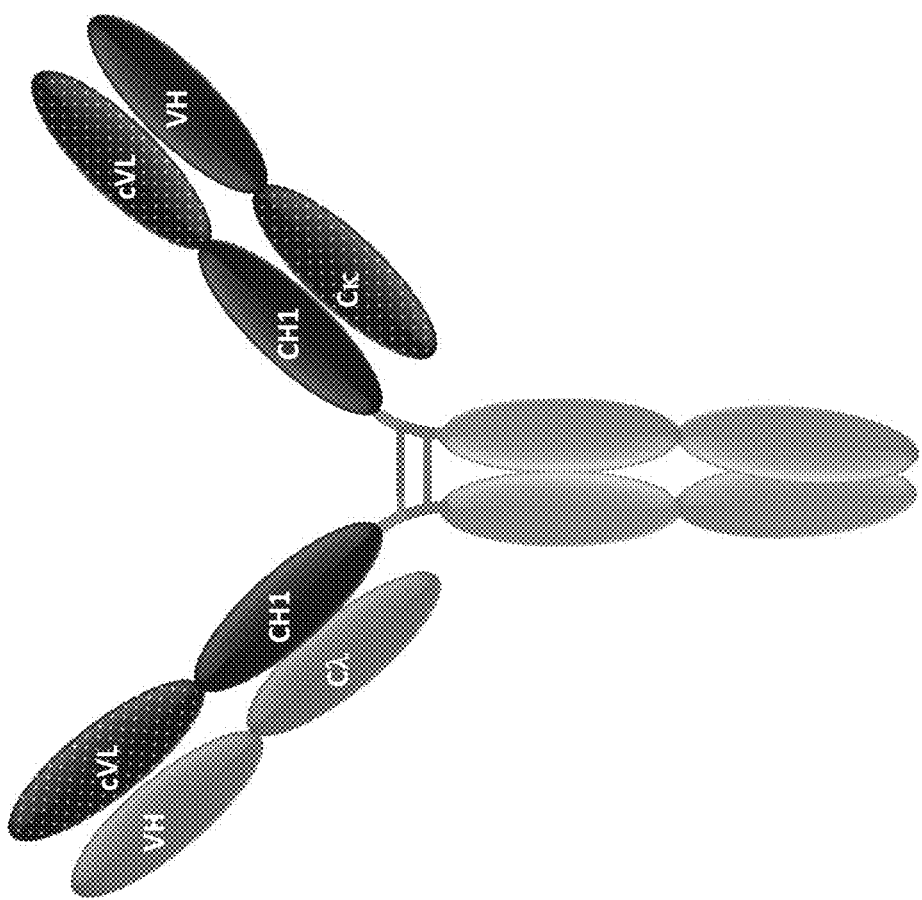

| Name | Description | Figure reference |
| --- | --- | --- |
| 16D5 reduced affinity variants<br>16D5 TCB<br>16D5 G49S/S93A TCB<br>16D5 G49S/K53A TCB<br>16D5 W96Y TCB<br>16D5 W96Y/D52E TCB | 2 + 1 T-cell bispecific, inverted format (common light chain) | FIG. 1A |
| Intermediate affinity binders<br>36F2 TCB<br>6E10 TCB<br>14B1 TCB<br>9C7 TCB | 2 + 1 T-cell bispecific, inverted format, crossfab | FIG. 1F |

Single Injections

First the anti-FolR1 TCBs were analyzed by single injections (Table 46) to characterize their crossreactivity (to human, murine and cyno FolR1) and specificity (to human FolR1, human FolR2, human FolR3). Recombinant biotinylated monomeric Fc fusions of human, cynomolgus and murine Folate Receptor 1 (FolR1-Fc) or human Folate Receptor 2 and 3 (FolR2-Fc, FolR3-Fc) were directly coupled on a SA chip using the standard coupling instruction (Biacore, Freiburg/Germany). The immobilization level was about 300-400 RU. The TCBs were injected for 60 seconds at a concentration of 500 nM.

TABLE 46

Crossreactivity and specificity of 7 folate receptor 1 T cell bispecifics.
+ means binding, − means no binding, +/− means weak binding.

| Clone name | Binding to huFolR1 | Binding to cyFolR1 | Binding to muFolR1 | Binding to huFolR2 | Binding to huFolR3 |
| --- | --- | --- | --- | --- | --- |
| 16D5 TCB | + | + | − | − | − |
| 16D5 G49S/S93A TCB | + | + | − | − | − |
| 16D5 W96Y/D52E TCB | + | + | − | − | − |
| 36F2 TCB | + | + | + | +/− | − |
| 6E10 TCB | + | + | − | − | − |
| 14B1 TCB | + | + | + | +/− | − |
| 9C7 TCB | + | + | − | − | − |

Avidity to Folate Receptor 1

The avidity of the interaction between the anti-FolR1 T cell bispecifics and the recombinant folate receptors was determined as described below (Table 47).

Recombinant biotinylated monomeric Fc fusions of human, cynomolgus and murine Folate Receptor 1 (FolR1-Fc) were directly coupled on a SA chip using the standard coupling instruction (Biacore, GE Healthcare). The immobilization level was about 200-300 RU. The anti-FolR1 T cell bispecifics were passed at a concentration range from 11.1 to 900 nM (for the 16D5 reduced affinity variants) or 0.2 to 500 nM (for the additional intermediate affinity binders and 36F2) with a flow of 30 µL/minutes through the flow cells over 180 seconds. The dissociation was monitored for 240 or 600 seconds. The chip surface was regenerated after every cycle using a double injection of 30 sec 10 mM Glycine-HCl pH 1.5. Bulk refractive index differences were corrected for by subtracting the response obtained on reference flow cell immobilized with recombinant biotinylated murine IL2R Fc fusion (unrelated Fc fused receptor). The binding curves resulting from the bivalent binding of the T cell bispecifics were approximated to a 1:1 Langmuir binding (even though it is a 1:2 binding) and fitted with that model to get an apparent KD representing the avidity of the bivalent binding. The apparent avidity constants for the interactions were derived from the rate constants of the fitting using the Bia Evaluation software (GE Healthcare).

TABLE 47

Bivalent binding (avidity with apparent KD) of anti-FolR1 T-cell bispecifics (TCB) on human, cyno and murine FolRl.

| Analyte | Ligand | ka (1/Ms) | kd (1/s) | Apparent KD |
|---|---|---|---|---|
| 16D5 TCB | huFolR1 | 1.68E+05 | 4.33E−04 | 3 nM |
|  | cyFolR1 | 2.08E+05 | 6.95E−04 | 3 nM |
| 16D5 G49S/S93A TCB | huFolR1 | 1.49E+05 | 2.09E−03 | 10 nM |
|  | cyFolR1 | 4.54E+05 | 7.84E−03 | 20 nM |
| 16D5 G49S/K53A TCB | huFolR1 | 1.32E+05 | 5.86E−03 | 40 nM |
|  | cyFolR1 | 3.73E+05 | 2.56E−02 | 70 nM |
| 16D5 W96Y TCB | huFolR1 | 1.15E+05 | 1.44E−03 | 10 nM |
|  | cyFolR1 | 1.37E+05 | 1.68E−03 | 10 nM |
| 16D5 W96Y/D52E TCB | huFolR1 | 1.24E+05 | 1.40E−03 | 10 nM |
|  | cyFolR1 | 5.17E+05 | 1.41E−02 | 30 nM |
| 36F2 TCB | huFolR1 | 1.12E+06 | 7.90E−03 | 7 nM |
|  | cyFolR1 | 1.97E+06 | 1.10E−02 | 6 nM |
|  | muFolR1 | 5.54E+05 | 1.47E−03 | 3 nM |
| 6E10 TCB | huFolR1 | 7.93E+06 | 8.74E−03 | 1 nM |
|  | cyFolR1 | 5.56E+06 | 5.72E−03 | 1 nM |
| 14B1 TCB | huFolR1 | 1.12E+06 | 1.40E−03 | 1 nM |
|  | cyFolR1 | 1.02E+06 | 1.66E−03 | 2 nM |
|  | muFolR1 | 8.03E+06 | 8.20E−04 | 0.1 nM |
| 9C7 TCB | huFolR1 | 1.18E+06 | 1.42E−03 | 1 nM |
|  | cyFolR1 | 4.98E+06 | 4.82E−03 | 1 nM |

3. Affinity to Folate Receptor 1

The affinity of the interaction between the anti-FolR1 T cell bispecifics and the recombinant folate receptors was determined as described below (Table 48).

For affinity measurement, direct coupling of around 12000 resonance units (RU) of the anti-human Fab specific antibody (Fab capture kit, GE Healthcare) was performed on a CM5 chip at pH 5.0 using the standard amine coupling kit (GE Healthcare). Anti-FolR1 T cell bispecifics were captured at 20 nM with a flow rate of 10 μl/min for 40 sec, the reference flow cell was left without capture. Dilution series (12.3 to 3000 nM) of human, cyno or murine Folate Receptor 1 Fc fusion were passed on all flow cells at 30 μl/min for 240 sec to record the association phase. The dissociation phase was monitored for 300 s and triggered by switching from the sample solution to HBS-EP. The chip surface was regenerated after every cycle using a double injection of 60 sec 10 mM Glycine-HCl pH 2.1. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare). For low affinity kinetics with association and dissociation phases too fast to be fitted by the 1:1 Langmuir binding model, the steady state analysis model was applied using the Bia Evaluation software (GE Healthcare). The steady state analysis gives the $K_D$ of the binding reaction at equilibrium.

TABLE 48

Monovalent binding (affinity) of anti-FolR1 T-cell bispecifics (TCB) on human, cyno and murine FolR1.

| Analyte | Ligand | ka (1/Ms) | kd (1/s) | KD |
|---|---|---|---|---|
| 16D5 TCB | huFolR1 | 1.22E+04 | 7.02E−04 | 57 nM |
|  | cyFolR1 | 1.29E+04 | 1.71E−03 | 130 nM |
| 16D5 G49S/S93A TCB | huFolR1 | 1.01E+04 | 8.37E−03 | 830 nM |
|  | cyFolR1 | 2.05E+04 | 8.60E−03 | 420 nM |
| 16D5 G49S/K53A TCB | huFolR1 | 9.17E+03 | 1.59E−02 | 1700 nM |
|  | cyFolR1 |  |  | 1900 nM (steady state analysis) |
| 16D5 W96Y TCB | huFolR1 | 1.11E+04 | 4.05E−03 | 370 nM |
|  | cyFolR1 | 1.17E+04 | 5.16E−03 | 440 nM |
| 16D5 W96Y/D52E TCB | huFolR1 |  |  | 1400 nM (steady state analysis) |
|  | cyFolR1 |  |  | 5600 nM (steady state analysis) |
| 36F2 TCB | huFolR1 |  |  | 1400 nM (steady state analysis) |
|  | cyFolR1 |  |  | 1500 nM (steady state analysis) |
| 6E10 TCB | muFolR1 | 3.50E+04 | 1.73E−02 | 490 nM |
|  | huFolR1 |  |  | 1200 nM (steady state analysis) |
|  | cyFolR1 |  |  | 1500 nM (steady state analysis) |
| 14B1 TCB | huFolR1 | 6.16E+04 | 3.03E−02 | 490 nM |
|  | cyFolR1 |  |  | 1200 nM (steady state analysis) |
| 9C7 TCB | muFolR1 | 7.03E+04 | 2.28E−03 | 30 nM |
|  | huFolR1 |  |  | 840 nM (steady state analysis) |
|  | cyFolR1 |  |  | 1400 nM (steady state analysis) |

The mutations introduced into the 16D5 binders reduce its affinity to human and cynomolgus FolR1 as determined by surface plasmon resonance. The ranking with decreasing affinity is 16D5 WT (57 nM)>W96Y (6.5 fold lower)>G49S/S93A (14.5 fold lower)>W96Y/D52E (24.5 fold lower) >G49S/K53A (30 fold lower). The same ranking is visible in the avidity values, however the fold differences are smaller 16D5 WT (3 nM)>W96Y, G49S/S93A, W96Y/D52E (3 fold lower)>G49S/K53A (13 fold lower).

The intermediate affinity binders have following ranking in affinity 16D5 (57 nM)>14B1 (8.5 fold lower)>9C7 (15 fold lower) >6E10 (21 fold lower)>36F2 (24.5 fold lower). These differences however disappear in the avidity measurement 14B1, 9C7, 6E10 (1 nM)>16D5 (3 nM) >36F2 (7 nM).

16D5 W96Y/D52E TCB addresses the problems observed with previous candidates. 16D5 W96Y/D52E TCB is based on the common light chain 16D5 binder and has two point mutations on the heavy chain with respect to the parental 16D5 binder. The W96Y mutation reduces the affinity of the binder to FolR1 compared to the parental binder and the D52E mutation removes a deamidation site and also contributes to the reduction in affinity. 16D5 W96Y/D52E TCB binds to human and cynomolgus FolR1, but not to murine FolR1. It is specific for FolR1 and does not bind to recombinant human FolR2 or human FolR3. The affinity (monovalent binding) of 16D5 W96Y/D52E is around 1.4 μM for human FolR1 (24.5 fold lower than the parental 16D5 binder) and the avidity (bivalent binding) is around 10 nM (3 fold lower than the parental 16D5 binder).

Example 52

T-Cell Killing of Hela, SKov-3 and HT-29 Cells Induced by Intermediate FolR1 TCBs T-cell killing mediated by intermediate FolR1 binders (6E10 TCB, 14B1 TCB and 9C7 TCB), was assessed on Hela (high FolR1), SKov-3 (medium FolR1) and HT-29 (low FolR1) cells. 16D5 TCB and 36F2 TCB were included as benchmarks. Human PBMCs were used as effectors and the killing was detected at 24 h and 48 h of incubation with the bispecific antibodies. Briefly, target cells were harvested with Trypsin/EDTA, washed, and plated at a density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% CO2 in cell incubator until further use (no longer than 24 h). For the killing assay, the antibody was added at the indicated concentrations (range of 0.01 pM-10 nM in triplicates). PBMCs were added to target cells at final E:T ratio of 10:1. Target cell killing was assessed after 24 h and 48 h of incubation at 37° C., 5% CO2 by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

The results show that tumor lysis induced by the intermediate FolR1 binders (6E10 TCB, 14B1 TCB and 9C7 TCB) ranges between the one obtained for the high affinity 16D5 TCB and the low affinity 36F2 TCB (FIG. 36A-F). Among the intermediate FolR1 binders, 14B1 TCB shows the strongest killing as can be seen after 48 h of incubation (FIG. 36D-F). The EC50 values related to killing assays after 24 h and 48 h of incubation, calculated using GraphPadPrism6, are given in Table 49 and Table 50.

TABLE 49

EC50 values (pM) for T-cell mediated killing of Hela, SKov-3 and HT-29 cells induced by intermediate FolR1 TCBs after 24 h of incubation.

| Antibody | EC50 [pM] | | |
|---|---|---|---|
| | Hela | SKov-3 | HT-29 |
| 6E10 TCB | 6.5 | n.d. | *n.d. |
| 14B1 TCB | 8.5 | 30.1 | *n.d. |
| 9C7 TCB | 2.8 | 741.4 | *n.d. |

TABLE 49-continued

EC50 values (pM) for T-cell mediated killing of Hela, SKov-3 and HT-29 cells induced by intermediate FolR1 TCBs after 24 h of incubation.

| Antibody | EC50 [pM] | | |
|---|---|---|---|
| | Hela | SKov-3 | HT-29 |
| 16D5 TCB | 2.2 | 1.5 | *n.d. |
| 36F2 TCB | 31.1 | *n.d. | *n.d. |

*not determined

TABLE 50

EC50 values (pM) for T-cell mediated killing of Hela, SKov-3 and HT-29 cells induced by intermediate FolR1 TCBs after 48 h of incubation.

| Antibody | EC50 [pM] | | |
|---|---|---|---|
| | Hela | SKov-3 | HT-29 |
| 6E10 TCB | 2.1 | 2164.0 | *n.d. |
| 14B1 TCB | 5.5 | 4.7 | 397.7 |
| 9C7 TCB | 4.3 | 519.6 | *n.d. |
| 16D5 TCB | 2.3 | *n.d. | 4.9 |
| 36F2 TCB | 10.5 | *n.d. | n.d. |

*not determined

Example 53

T-Cell Killing of Hela, SKov-3 and HT-29 Cells Induced by Affinity Reduced 16D5 Variants T-cell killing mediated by affinity reduced 16D5 variants (16D5-G49S/S93A TCB, 16D5-G49S/K53A TCB, 16D5 W96Y TCB, 16D5 W96Y/D52E TCB) was assessed on Hela (high FolR1), SKov-3 (medium FolR1) and HT-29 (low FolR1) cells. 16D5 TCB and 36F2 TCB were included as benchmarks. The assay was performed as described above (Example 52).

The results show that tumor lysis induced by affinity reduced 16D5 variants (16D5-G49S/S93A TCB, 16D5-G49S/K53A TCB, 16D5 W96Y TCB, 16D5 W96Y/D52E TCB), ranges between the one obtained for the high affinity 16D5 TCB and the low affinity 36F2 TCB. The EC50 values related to killing assays after 24 h and 48 h of incubation, calculated using GraphPadPrism6, are given in Table 51 and Table 52 (FIG. 37A-F).

TABLE 51

EC50 values (pM) for T-cell mediated killing of FolR1-expressing Hela, SKov-3 and HT-29 cells induced by 16D5 TCB and its affinity reduced variants after 24 h of incubation.

| Antibody | EC5 [pM] | | |
|---|---|---|---|
| | Hela | SKov-3 | HT-29 |
| 16D5 TCB | 2.2 | 1.5 | *n.d. |
| 16D5-G49S/S93A TCB | 2.3 | 430.4 | *n.d. |
| 16D5-G49S/K53A TCB | 4.4 | 1701.9 | *n.d. |
| 16D5 W96Y TCB | 3.0 | 164.5 | *n.d. |

TABLE 51-continued

EC50 values (pM) for T-cell mediated killing
of FolR1-expressing Hela, SKov-3 and HT-
29 cells induced by 16D5 TCB and its affinity
reduced variants after 24 h of incubation.

| Antibody | EC5 [pM] | | |
|---|---|---|---|
| | Hela | SKov-3 | HT-29 |
| 16D5 W96Y/D52E TCB | 1.3 | 235.4 | *n.d. |
| 36F2 TCB | 31.1 | *n.d. | *n.d. |

*not determined

TABLE 52

EC50 values (pM) for T-cell mediated killing
of FolR1-expressing Hela, SKov-3
and HT-29 cells induced by 16D5 TCB and its
affinity reduced variants after 48 h of incubation.

| Antibody | EC50 [pM] | | |
|---|---|---|---|
| | Hela | SKov-3 | HT-29 |
| 16D5 TCB | 2.3 | 0.1 | 4.9 |
| 16D5-G49S/S93A TCB | 0.9 | 95.9 | 99.3 |
| 16D5-G49S/K53A TCB | 0.5 | 950.4 | 1790.7 |
| 16D5 W96Y TCB | 1.8 | 24.7 | 99.3 |
| 16D5 W96Y/D52E TCB | 0.9 | 93.0 | 399.4 |
| 36F2 TCB | 10.5 | 968.5 | *n.d. |

*not determined

Thus, as with 36F2 FOLR1 TCB described above, the 16D5 W96Y/D52E TCB differentiates between high and low expressing cells which is of special importance to reduce toxicity as the cells of some normal, non-tumorous tissues express very low levels of FolR1 (approximately less than 1000 copies per cell). Consistent with this observation, the results discussed in Example 54 below show that 16D5 W96Y/D52E TCB induces much lower levels of T-cell-mediated killing of primary cells (FIG. 38A-F) compared to the parental 16D5 TCB. As such, 16D5 W96Y/D52E TCB mediates potent killing of tumor tissues with high or medium FOLR1 expression, but not of normal tissues with low expression. 16D5 W96Y/D52E TCB in the bivalent 2+1 format comprises FolR1 binding moieties of relatively low affinity but it possesses an avidity effect which allows for differentiation between high and low FolR1 expressing cells. Because tumor cells express FolR1 at high or intermediate levels, this TCB selectively binds to tumor cells and not normal, non-cancerous cells that express FolR1 at low levels or not at all. As an additional advantage over the 36F2 FOLR1 TCB described above, the 16D5 W96Y/D52E TCB binds specifically to FolR1 and not to FolR2 or FolR3, further enhancing its safety for in vivo treatment.

In addition to the above advantageous characteristics, the 16D5 W96Y/D52E TCB in the bivalent 2+1 inverted format also has the advantage that it does not require chemical cross linking or other hybrid approach. This makes it suitable for manufacture of a medicament to treat patients, for example patients having FolR1-positive cancerous tumors. The 16D5 W96Y/D52E TCB in the bivalent 2+1 inverted format can be produced using standard CHO processes with low aggregates. Further, the 16D5 W96Y/D52E TCB in the bivalent 2+1 comprises human and humanized sequences making it superior to molecules that employ rat and murine polypeptides that are highly immunogenic when administered to humans. Furthermore, the 16D5 W96Y/D52E TCB in the bivalent 2+1 format was engineered to abolish FcgR binding and, as such, does not cause FcgR crosslinking and infusion reactions, further enhancing its safety when administered to patients.

As demonstrated by the results described above, its head-to-tail geometry make the 16D5 W96Y/D52E TCB in the bivalent 2+1 inverted format a highly potent molecule that induces absolute target cell killing. Its bivalency enhance avidity and potency, but also allow for differentiation between high and low expressing cells. Its preference for high or medium target expressing cells due to its avidity affect reduce toxicity resulting from T cell mediated killing of normal cells that express FolR1 at low levels.

Figure 41:
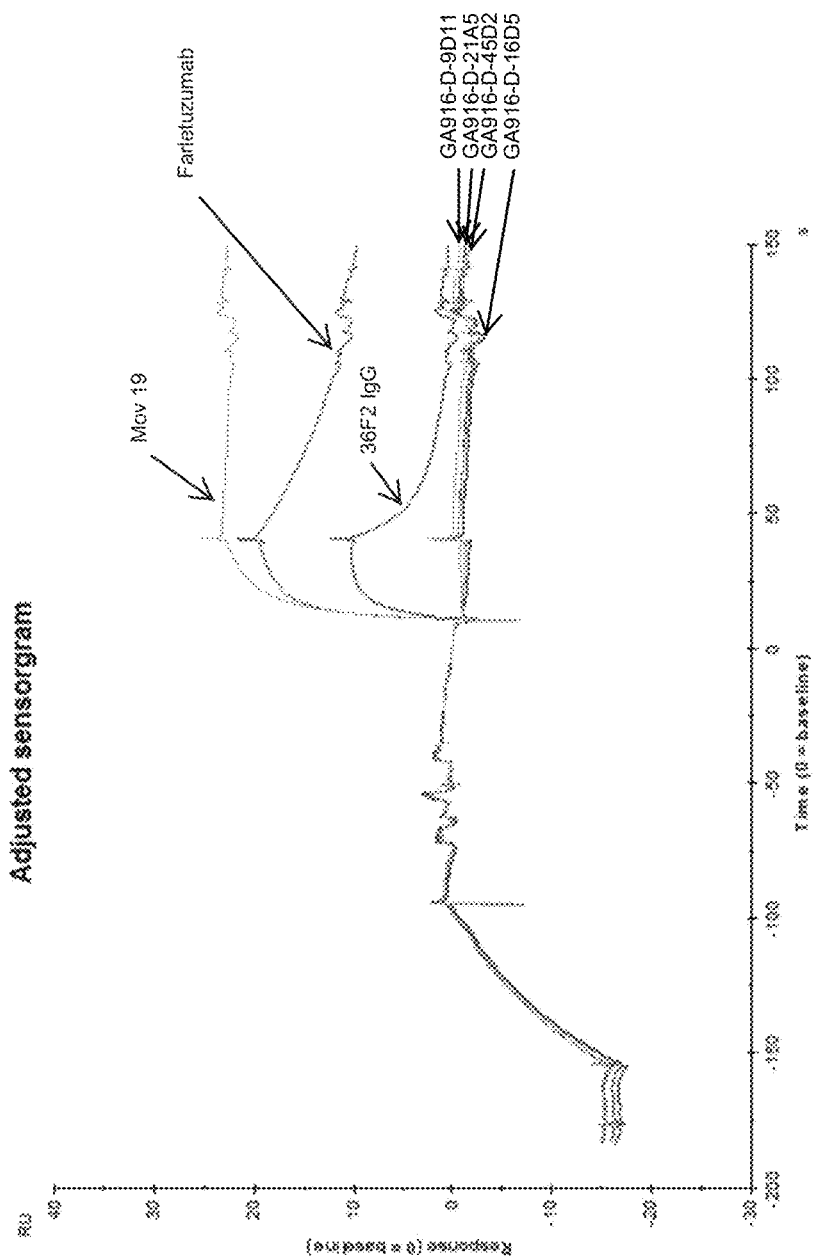
FIG. 41 shows that Farletuzumab (dark green, second from the top) and Mov19 (grey, top) are able to bind on huFolR1 that is captured on 16D5, demonstrating that the 16D5 series binders recognize an epitope distinct from that recognized by either Farletuzumab or Mov19.

A further advantage of the 16D5 W96Y/D52E TCB in the bivalent 2+1 format and other embodiments disclosed herein is that their clinical development does not require the use of surrogate molecules as they bind to human and cynomous FolR1. As such, the molecules disclosed herein recognize a different epitope than antibodies to FolR1 previously described that do not recognize FolR1 from both species (see also FIG. 41).

Example 54

T-Cell Killing of Primary Cells Induced by Affinity Reduced 16D5 Variants and Intermediate FolR1 TCBs T-cell killing mediated by affinity reduced 16D5 variants (16D5-G49S/S93A TCB, 16D5 W96Y/D52E TCB) and the intermediate FolR1 binder 14B1 TCB was assessed on primary cells (Human Renal Cortical Epithelial Cells (HR-CEpiC) (ScienCell Research Laboratories; Cat No 4110) and Human Retinal Pigment Epithelial Cells (HRPEpiC) (ScienCell Research Laboratories; Cat No 6540)). HT-29 cells (low FolR1) were included as control cell line. 16D5 TCB and 36F2 TCB were included as benchmarks and DP47 TCB served as non-binding control.

The assay was performed as described in Example 52, with a concentration range of the antibodies of 0.1 pM-100 nM (in triplicates).

When human primary cells are used as targets, the overall lysis is much lower due to a lower expression rate of FolR1 on these cells (FIG. 38A-F). For the high affinity FolR1 binder 16D5 TCB a T-cell mediated lysis can be observed on both primary cell types used. As observed previously when tumor cell lines were used as targets, lysis induced by the intermediate FolR1 binder 14B1 TCB and the affinity reduced 16D5 variants (16D5-G49S/S93A TCB, 16D5 W96Y/D52E TCB), ranges between the one obtained for the high affinity 16D5 TCB and the low affinity 36F2 TCB. The significantly reduced lysis of cells that express FolR1 at low levels is consistent with low off target activity and the affinity reduced 16D5 variants 16D5-G49S/S93A TCB and 16D5 W96Y/D52E TCB are, thus, expected to be well tolerated in vivo.

Example 55

Single Dose PK of FOLR1 TCB Constructs in Female NOG Mice

Female NOD/Shi-scid/IL-2Rγnull (NOG) mice at an average ager of 8-10 weeks at start of experiment (purchased from Taconic, SOPF facility) were maintained under specific-pathogen-free condition with daily cycles of 12 h light/12 h darkness according to committed guidelines (GV-Solas; Felasa; TierschG). Experimental study protocol was reviewed and approved by local government (ZH193/2014). After arrival animals were maintained for one week to get accustomed to new environment and for observation. Continuous health monitoring was carried out on regular basis.

A single dose pharmacokinetic study (SDPK) was performed to evaluate exposure of FOLR1 TCB constructs (36F2, 16D5, 16D5 G49S/S93A and 16D5 W96Y/D52E). An i.v. bolus administration of 0.5 mg/kg was administered to NOG mice and blood samples were taken at selected time points for pharmacokinetic evaluation. Mouse serum samples were analyzed by ELISA. Biotinylated a-huCD3-CDR (mAb<ID-mAb<CD3>>M-4.25.93-IgG-Bi), test samples, Digoxygenin labelled a-huFc antibody (mAb<H-FC pan>M-R10Z8E9-IgG-Dig) and anti-Digoxygenin detection antibody (POD) were added stepwise to a 96-well streptavidin-coated microtiter plate and incubated after every step for 1h at room temperature. The plate is washed three times after each step to remove unbound substances. Finally, the peroxidase-bound complex is visualized by adding ABTS substrate solution to form a colored reaction product. The reaction product intensity, which is photometrically determined at 405 nm (with reference wavelength at 490 nm), is proportional to the analyte concentration in the serum sample. The calibration range of the standard curve for the constructs is was 0.078 to 5 ng/ml, where 1.5 ng/ml is the lower limit of quantification (LLOQ).

Figures 39A, 39B:
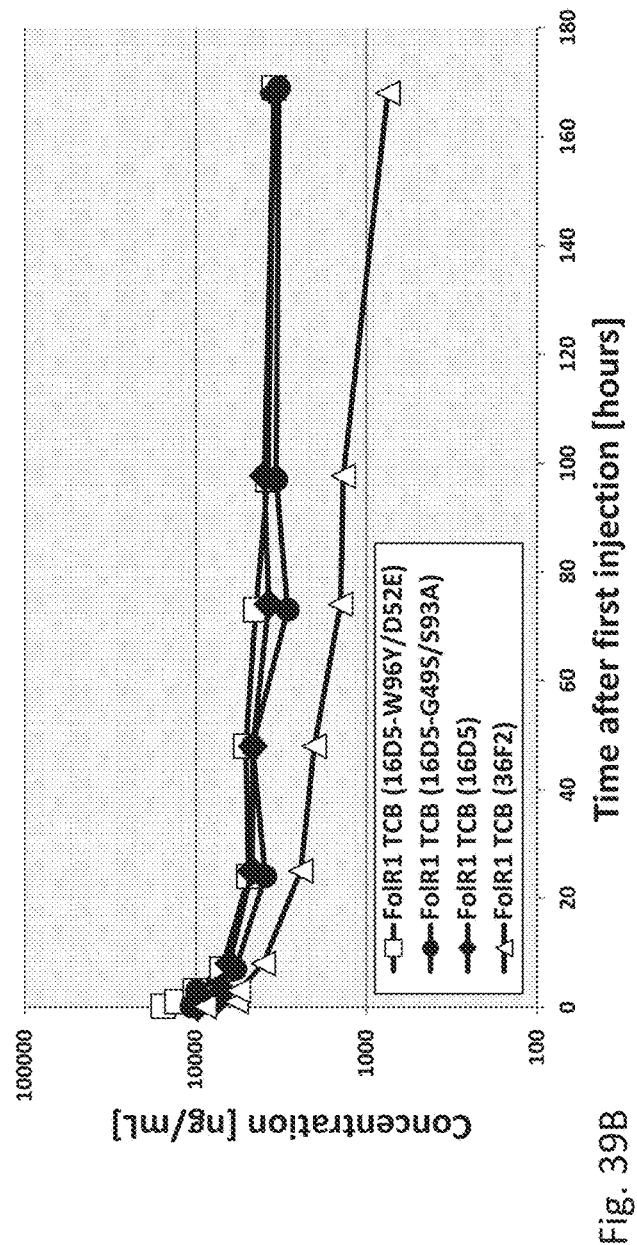
FIGS. 39A-B show single dose PK of FOLR1 TCB constructs in female NOG mice.

The SDPK study revealed an IgG-like PK-profile for the 16D5, 16D5 W96Y/D52E and 16D5 G49S/S93A constructs (FIG. 39A-B). Because of that, a once per weeks scheduling was chosen for the efficacy study (FIG. 40B). The half-life for 36F2 is lower as compared to the other clones. 36F2 is the only out of the four molecules tested that is cross-reactive to mouse FOLR1, which might explain the lower half-life for this molecule and indicates a TMDD (Target Mediated Drug Disposition).

Example 56

In Vivo Efficacy of FOLR1 TCB Constructs (16D5, 16D5 G49S/S93A and 16D5 W96Y/D52E) after Human PBMC Transfer in Hela-Bearing NOG Mice The FOLR1 TCB constructs were tested in the FOLR1-expressing human cervical cancer cell line Hela, injected s.c. into PBMC engrafted NOG mice.

Hela cells were originally obtained from ATCC (CCL2) and after expansion deposited in the Roche-Glycart internal cell bank. The tumor cell line was routinely cultured in RPMI containing 10% FCS (Gibco) at 37° C. in a water-saturated atmosphere at 5% CO2. Passage 13 was used for transplantation, at a viability >95%. 1×106 cells per animal were injected s.c. into the right flank of the animals in a total of 100 µl of RPMI cell culture medium (Gibco).

60 female NOG mice, age 8-10 weeks at start of the experiment (bred at Taconic, Denmark) were maintained under specific-pathogen-free condition with daily cycles of 12 h light/12 h darkness according to committed guidelines (GV-Solas; Felasa; TierschG). The experimental study protocol was reviewed and approved by local government (ZH193/2014). After arrival, animals were maintained for one week to get accustomed to the new environment and for observation. Continuous health monitoring was carried out on a regular basis.

According to the study protocol (FIG. 40B), mice were injected s.c. on study day 0 with 1×106 Hela cells. At study day 30, when tumor reached a size of app. 150 mm3, human PBMC of a healthy donor were isolated via the Ficoll method and 10×106 cells were injected i.v. into the tumor-bearing mice. Two days after (day 32), mice were randomized and equally distributed in six treatment groups (n=10) followed by i.v. injection with either 16D5 (0.5 mg/kg), 16D5 G49S/S93A (2.5 or 0.5 mg/kg) and 16D5 W96Y/D52E (2.5 or 0.5 mg/kg). All treatments group were injected once weekly for three weeks in total. Mice were injected i.v. with 200 µl of the appropriate solution. The mice in the vehicle group were injected with PBS. To obtain the proper amount of TCB per 200 µl, the stock solutions were diluted with PBS when necessary. Tumor growth was measured once weekly using a caliper (FIG. 40C-E) and tumor volume was calculated as followed:

$Tv:(W2/2) \times L$ (W: Width, L: Length)

Figures 40C, 40D, 40E:
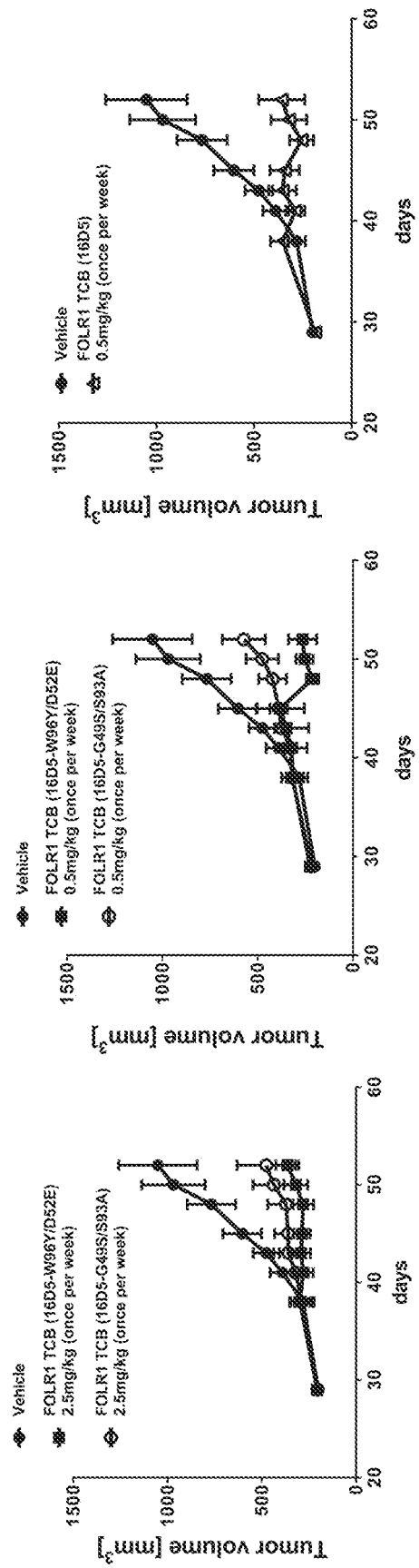
Figure 40G:
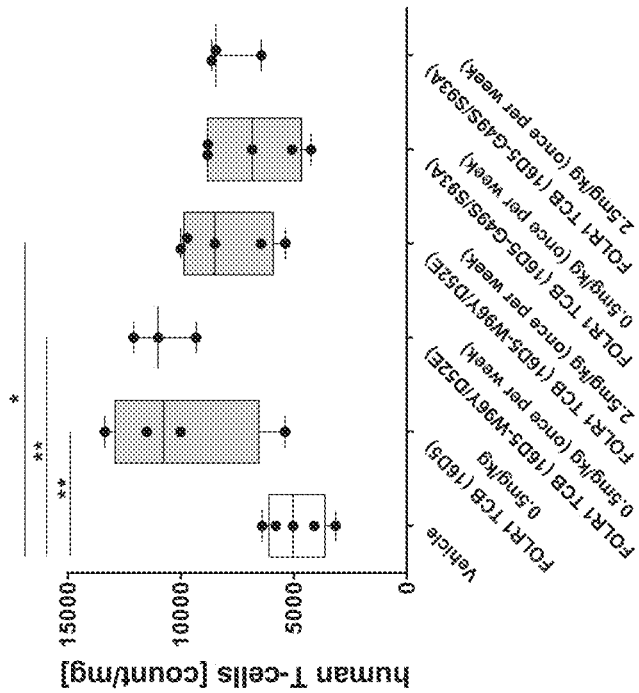
Figure 40F:
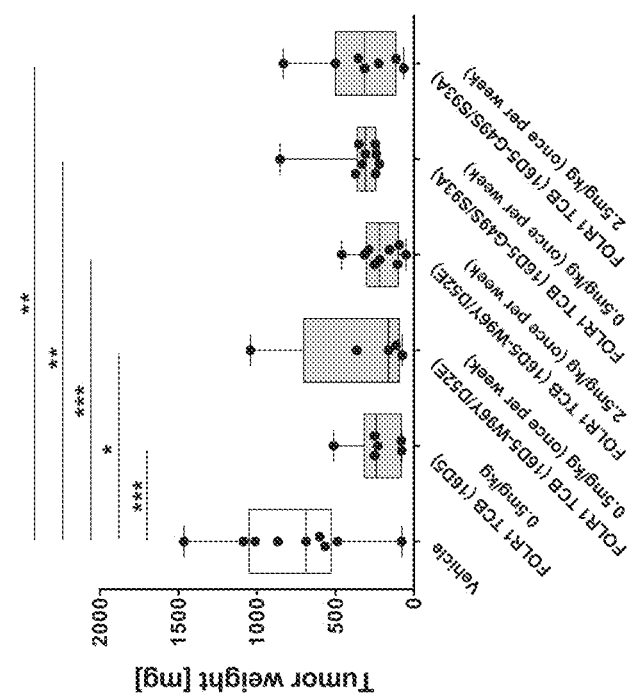

The once weekly injection of the FOLR1 TCB constructs resulted in significant tumor regression (FIG. 40C-E). The efficacy of 16D5 (0.5 mg/kg) and 16D5 W96Y/D52E16D5 (0.5 mg/kg) was comparable, whereas 16D5 G49S/S93A (0.5 mg/kg) showed slight less potency. The higher doses of 2.5 mg/kg of 16D5 W96Y/D52E16D5 and 16D5 G49S/S93A didn't show increased efficacy compared to 0.5 mg/kg doses. For PD read-outs, mice were sacrificed at study day 52, tumors were removed, weighted and single cell suspensions were prepared through an enzymatic digestion with Collagenase V, Dispase II and DNAse for subsequent FACS-analysis. Explanted tumors of all treatment groups showed significant lower tumor weight at study termination as compared to vehicle control tumors (FIG. 40F). Single cell suspensions from tumors where stained for huCD45 and huCD3 and DAPI for dead cell exclusion and were analyzed at the BD Fortessa. The FACS analysis revealed statistically higher numbers of infiltrated CD3-positive human T-cells in the tumor tissue upon treatment with 16D5 as well as 16D5 W96Y/D52E16D5 compared to vehicle control tumors (FIG. 40C).

Example 57

Toxicity Study in Cynomolgus Monkey

A pharmacokinetic (PK), pharmacodynamic (PD) and tolerability study is performed to investigate the tolerability, PK and PD effects of a single intravenous dose of affinity reduced 16D5 variant TCBs (e.g., 16D5-G49S/S93A TCB, 16D5 W96Y/D52E TCB) in cynomolgus monkeys. In this study, naïve cynomolgus monkeys, (1 male and 1 female monkey/group), receive a single intravenous dose of affinity reduced 16D5 variant TCBs, including 16D5 W96Y/D52E TCB, following a dose escalating protocol. Exemplary dose levels include 0.003, 0.03, and 0.09 mg/kg. Standard toxicity parameters (clinical signs, body weights, hematology & clinical chemistry) and the kinetics of T cell numbers and activation status in blood and the kinetics of cytokine release are assessed. Blood samples are also taken for PK for a period of 28 days for the measurement of affinity reduced 16D5 variant TCBs, including 16D5 W96Y/D52E TCB, and of anti-drug antibodies.

Amino Acid Sequences of Exemplary Embodiments
1) FolR binders useful in common light chain format, variable heavy chain

| Description | Sequence | Seq ID No |
|---|---|---|
| 16A3 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARNYYAGVTPFDYWGQGTLVTVSS | 1 |
| 18D3 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARNYYTGGSSAFDYWGQGTLVTVS | 2 |
| 15H7 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARNYYLFSTSFDYWGQGTLVTVSS | 3 |
| 15B6 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARNYYIGIVPFDYWGQGTLVTVSS | 4 |
| 21D1 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARNYYVGVSPFDYWGQGTLVTVSS | 5 |
| 16F12 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARNFTVLRVPFDYWGQGTLVTVSS | 6 |
| 15A1 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARNYYIGVVTFDYWGQGTLVTVSS | 7 |
| 15A1_CDR1 | SYYMH | 8 |
| 15A1_CDR2 | IINPSGGSTSYAQKFQG | 9 |
| 15A1_CDR3 | NYYIGVVTFDY | 10 |
| 19E5 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARGEWRRYTSFDYWGQGTLVTVSS | 11 |
| 19E5_CDR1 | SYYMH | 8 |
| 19E5_CDR2 | IINPSGGSTSYAQKFQG | 9 |
| 19E5_CDR3 | GEWRRYTSFDY | 12 |
| 19A4 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARGGWIRWEHFDYWGQGTLVTVSS | 13 |
| 19A4_CDR1 | SYYMH | 8 |
| 19A4_CDR2 | IINPSGGSTSYAQKFQG | 9 |
| 19A4_CDR3 | GGWIRWEHFDY | 14 |
| 16D5 | EVQLVESGGGLVKPGGSLRLSCAASGFTFSNAWMSWVRQAPGKGLE WVGRIKSKTDGGTTDYAAPVKGRFTISRDDSKNTLYLQMNSLKTED TAVYYCTTPWEWSWYDYWGQGTLVTVSS | 15 |
| 16D5_CDR1 | NAWMS | 16 |
| 16D5_CDR2 | RIKSKTDGGTTDYAAPVKG | 17 |
| 16D5_CDR3 | PWEWSWYDY | 18 |
| 15E12 | EVQLVESGGGLVKPGGSLRLSCAASGFTFSNAWMSWVRQAPGKGLE WVGRIKSKTDGGTTDYAAPVKGRFTISRDDSKNTLYLQMNSLKTED TAVYYCTTPWEWSYFDYWGQGTLVTVSS | 19 |
| 15E12_CDR1 | NAWMS | 16 |
| 15E12_CDR2 | RIKSKTDGGTTDYAAPVKG | 17 |
| 15E12_CDR3 | PWEWSYFDY | 20 |

| Description | Sequence | Seq ID No |
|---|---|---|
| 21A5 | EVQLVESGGGLVKPGGSLRLSCAASGFTFSNAWMSWVRQAPGKGLE WVGRIKSKTDGGTTDYAAPVKGRFTISRDDSKNTLYLQMNSLKTED TAVYYCTTPWEWAWFDYWGQGTLVTVSS | 21 |
| 21A5_CDR1 | NAWMS | 16 |
| 21A5_CDR2 | RIKSKTDGGTTDYAAPVKG | 17 |
| 21A5_CDR3 | PWEWAWFDY | 22 |
| 21G8 | EVQLVESGGGLVKPGGSLRLSCAASGFTFSNAWMSWVRQAPGKGLE WVGRIKSKTDGGTTDYAAPVKGRFTISRDDSKNTLYLQMNSLKTED TAVYYCTTPWEWAYFDYWGQGTLVTVSS | 23 |
| 21G8_CDR1 | NAWMS | 16 |
| 21G8_CDR2 | RIKSKTDGGTTDYAAPVKG | 17 |
| 21G8_CDR3 | PWEWAYFDY | 24 |
| 19H3 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARTGWSRWGYMDYWGQGTLVTVSS | 25 |
| 19H3_CDR1 | SYYMH | 8 |
| 19H3_CDR2 | IINPSGGSTSYAQKFQG | 9 |
| 19H3_CDR3 | TGWSRWGYMDY | 26 |
| 20G6 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARGEWIRYYHFDYWGQGTLVTVSS | 27 |
| 20G6_CDR1 | SYYMH | 8 |
| 20G6_CDR2 | IINPSGGSTSYAQKFQG | 9 |
| 20G6_CDR3 | GEWIRYYHFDY | 28 |
| 20H7 | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARVGWYRWGYMDYWGQGTLVTVSS | 29 |
| 20H7_CDR1 | SYYMH | 8 |
| 20H7_CDR2 | IINPSGGSTSYAQKFQG | 9 |
| 20H7_CDR3 | VGWYRWGYMDY | 30 |

2) CD3 binder common light chain (CLC)

| Description | Sequence | Seq ID No |
|---|---|---|
| common CD3 light chain (VL) | QAVVTQEPSLTVSPGGTVTLTCGSSTGAVT TSNYANWVQEKPGQAFRGLIGGTNKRAPGT PARFSGSLLGGKAALTLSGAQPEDEAEYYC ALWYSNLWVFGGGTKLTVL | 31 |
| common CD3 light chain_CDR1 | GSSTGAVTTSNYAN | 32 |
| common CD3 light chain_CDR2 | GTNKRAP | 33 |
| common CD3 light chain_CDR3 | ALWYSNLWV | 34 |
| common CD3 light chain (VLCL) | QAVVTQEPSLTVSPGGTVTLTCGSSTGAVT TSNYANWVQEKPGQAFRGLIGGTNKRAPGT PARFSGSLLGGKAALTLSGAQPEDEAEYYC ALWYSNLWVFGGGTKLTVLGQPKAAPSVTL FPPSSEELQANKATLVCLISDFYPGAVTVA WKADSSPVKAGVETTTPSKQSNNKYAASSY LSLTPEQWKSHRSYSCQVTHEGSTVEKTVA PTECS | 35 |

3) CD3 binder, heavy chain

| Description | Sequence | Seq ID No |
|---|---|---|
| CD3 variable heavy chain (VH) | EVQLLESGGGLVQPGGSLRLSCAAS GFTFSTYAMNWVRQAPGKGLEWVSR IRSKYNNYATYYADSVKGRFTISRD DSKNTLYLQMNSLRAEDTAVYYCVR HGNFGNSYVSWFAYWGQGTLVTVSS | 36 |
| CD3 heavy chain (VH)_CDR1 | TYAMN | 37 |
| CD3 heavy chain (VH)_CDR2 | RIRSKYNNYATYYADSVKG | 38 |
| CD3 heavy chain (VH)_CDR3 | HGNFGNSYVSWFAY | 39 |
| CD3 full heavy chain (VHCH1) | EVQLLESGGGLVQPGGSLRLSCAAS GFTFSTYAMNWVRQAPGKGLEWVSR IRSKYNNYATYYADSVKGRFTISRD DSKNTLYLQMNSLRAEDTAVYYCVR HGNFGNSYVSWFAYWGQGTLVTVSS ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSC | 40 |
| CD3 constant heavy chain CH1 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSC | 84 |

4) FolR binders useful for crossfab Format

| Description | Sequence | Seq ID No |
|---|---|---|
| 11F8_VH | QVQLVQSGAEVKKPGSSVKVSCKASGGTFSSYAISWVRQAPGQGLE WMGGIIPIFGTANYAQKFQGRVTITADKSTSTAYMELSSLRSEDTA VYYCARAVFYRAWYSFDYWGQGTTVTVSS | 41 |
| 11F8_VH_CDR1 | SYAIS | 42 |
| 11F8_VH_CDR2 | GIIPIFGTANYAQKFQG | 43 |
| 11F8_VH_CDR3 | AVFYRAWYSFDY | 44 |
| 11F8_VL | DIQMTQSPSTLSASVGDRVTITCRASQSISSWLAWYQQKPGKAPKL LIYDASSLESGVPSRFSGSGSGTEFTLTISSLQPDDFATYYCQQYT SPPPTFGQGTKVEIK | 45 |
| 11F8_VL_CDR1 | RASQSISSWLA | 46 |
| 11F8_VL_CDR2 | DASSLES | 47 |
| 11F8_VL_CDR3 | QQYTSPPPT | 48 |
| 36F2_VH | QVQLVQSGAEVKKPGASVKVSCKASGYTFTSYYMHWVRQAPGQGLE WMGIINPSGGSTSYAQKFQGRVTMTHDTSTSTVYMELSSLRSEDTA VYYCARSFFTGFHLDYWGQGTLVTVSS | 49 |
| 36F2_VH_CDR1 | SYYMH | 8 |
| 36F2_VH_CDR2 | IINPSGGSTSYAQKFQG | 9 |
| 36F2_VH_CDR3 | SFFTGFHLDY | 50 |
| 36F2_VL | EIVLTQSPGTLSLSPGERATLSCRASQSVSSSYLAWYQQKPGQAPR LLIYGASSRATGIPDRFSGSGSGTDFTLTISRLEPEDFAVYYCQQY TNEHYYTFGQGTKVEIK | 51 |
| 36F2_VL_CDR1 | RASQSVSSSYLA | 52 |
| 36F2_VL_CDR2 | GASSRAT | 53 |
| 36F2_VL_CDR3 | QQYTNEHYYT | 54 |
| 9D11_VH | QVQLVQSGAEVKKPGASVKVSCKASGYTFTSYYMHWVRQAPGQGLE WMGIINPSGGPTSYAQKFQGRVTMTRDTSTSTVYMELSSLRSEDTA VYYCARGDFAWLDYWGQGTLVTVSS | 55 |
| 9D11_VH_CDR1 | SYYMH | 8 |
| 9D11_VH_CDR2 | IINPSGGPTSYAQKFQG | 56 |

| Description | Sequence | Seq ID No |
|---|---|---|
| 9D11_VH_CDR3 | GDFAWLDY | 57 |
| 9D11_VL | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQASIMNRTFGQGTKVEIK | 58 |
| 9D11_VL_CDR1 | RSSQSLLHSNGYNYLD | 59 |
| 9D11_VL_CDR2 | LGSNRAS | 60 |
| 9D11_VL_CDR3 | MQASIMNRT | 61 |
| 9D11_VL N95S | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQASIMSRTFGQGTKVEIK | 62 |
| 9D11_VL N95S_CDR3 | MQASIMSRT | 63 |
| 9D11_VL N95Q | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQASIMQRTFGQGTKVEIK | 64 |
| 9D11_VL N95Q_CDR3 | MQASIMQRT | 65 |
| 9D11_VL T97A | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQASIMNRAFGQGTKVEIK | 66 |
| 9D11_VL T97A | MQASIMNRA | 67 |
| 9D11_VL T97N | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQASIMNRNFGQGTKVEIK | 68 |
| 9D11_VL T97N_CDR3 | MQASIMNRN | 69 |
| 5D9_VH | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARSYIDMDYWGQGTLVTVSS | 70 |
| 5D9_VH_CDR1 | SYYMH | 8 |
| 5D9_VH_CDR2 | IINPSGGSTSYAQKFQG | 9 |
| 5D9_VH_CDR3 | SYIDMDY | 71 |
| 5D9_VL | EIVLTQSPGTLSLSPGERATLSCRASQSVSSSYLAWYQQKPGQAPR LLIYGASSRATGIPDRFSGSGSGTDFTLTISRLEPEDFAVYYCQQD NWSPTFGQGTKVEIK | 72 |
| 5D9_VL_CDR1 | RASQSVSSSYLA | 52 |
| 5D9_VL_CDR2 | GASSRAT | 53 |
| 5D9_VL_CDR3 | QQDNWSPT | 73 |
| 6B6_VH | QVQLVQSGAEVKKPGASVKVSCKASGYTFTSYYMHWVRQAPGQGLE WMGIINPSGGSTSYAQKFQGRVTMTRDTSTSTVYMELSSLRSEDTA VYYCARSYVDMDYWGQGTLVTVSS | 74 |
| 6B6_VH_CDR1 | SYYMH | 8 |
| 6B6_VH_CDR2 | IINPSGGSTSYAQKFQG | 9 |
| 6B6_VH_CDR3 | SYVDMDY | 75 |
| 6B6_VL | EIVLTQSPGTLSLSPGERATLSCRASQSVSSSYLAWYQQKPGQAPR LLIYGASSRATGIPDRFSGSGSGTDFTLTISRLEPEDFAVYYCQQD IWSPTFGQGTKVEIK | 76 |
| 6B6_VL_CDR1 | RASQSVSSSYLA | 52 |

-continued

| Description | Sequence | Seq ID No |
|---|---|---|
| 6B6_VL_CDR2 | GASSRAT | 53 |
| 6B6_VL_CDR3 | QQDIWSPT | 77 |
| 14E4_VH | EVQLLESGGGLVQPGGSLRLSCAASGFTFSSYAMSWVRQAPGKGLE WVSAISGSGGSTYYADSVKGRFTISRDNSKNTLYLQMNSLRAEDTA VYYCAKDSSYVEWYAFDYWGQGTLVTVSS | 78 |
| 14E4_VH_CDR1 | SYAMS | 79 |
| 14E4_VH_CDR2 | AISGSGGSTYYADSVKG | 80 |
| 14E4_VH_CDR3 | DSSYVEWYAFDY | 81 |
| 14E4_VL | EIVLTQSPGTLSLSPGERATLSCRASQSVSSSYLAWYQQKPGQAPR LLIYGASSRATGIPDRFSGSGSGTDSTLTISRLEPEDFAVYYCQQP TSSPITFG QGTKVEIK | 82 |
| 14E4_VL_CDR1 | RASQSVSSSYLA | 52 |
| 14E4_VL_CDR2 | GASSRAT | 53 |
| 14E4_VL_CDR3 | QQPTSSPIT | 83 |

5) CD3 binder useful in crossfab Format

| Description | Sequence | Seq ID No |
|---|---|---|
| CD3 heavy chain (VH) | EVQLLESGGGLVQPGGSLRLSCAASGFTFSTYAMNWVRQAPG KGLEWVSRIRSKYNNYATYYADSVKGRFTISRDDSKNTLYLQ MNSLRAEDTAVYYCVRHGNFGNSYVSWFAYWGQGTLVTVSS | 36 |
| CD3 heavy chain (VH)_CDR1 | TYAMN | 37 |
| CD3 heavy chain (VH)_CDR2 | RIRSKYNNYATYYADSVKG | 38 |
| CD3 heavy chain (VH)_CDR3 | HGNFGNSYVSWFAY | 39 |
| CD3 light chain (VL) | QAVVTQEPSLTVSPGGTVTLTCGSSTGAVTTSNYANWVQEKP GQAFRGLIGGTNKRAPGTPARFSGSLLGGKAALTLSGAQPED EAEYYCALWYSNLWVFGGGTKLTVL | 31 |
| CD3 light chain_CDR1 | GSSTGAVTTSNYAN | 32 |
| CD3 light chain_CDR2 | GTNKRAP | 33 |
| CD3 light chain_CDR3 | ALWYSNLWV | 34 |
| pETR12940: crossed common CD3 light chain (VLCH1) | QAVVTQEPSLTVSPGGTVTLTCGSSTGAVTTSNYANWVQEKP GQAFRGLIGGTNKRAPGTPARFSGSLLGGKAALTLSGAQPED EAEYYCALWYSNLWVFGGGTKLTVLSSASTKGPSVFPLAPSS KSTSGGTAALGCLVKDYFPEPVTVSWNSGALTSGVHTFPAVL QSSGLYSLSSVVTVPSSSLGTQTYICNVNHKPSNTKVDKKVE PKSC | 86 |
| Crossed CD3 heavy chain (VHCκ); e.g. in | EVQLLESGGGLVQPGGSLRLSCAASGFTFSTYAMNWVRQAPG KGLEWVSRIRSKYNNYATYYADSVKGRFTISRDDSKNTLYLQ MNSLRAEDTAVYYCVRHGNFGNSYVSWFAYWGQGTLVTVSSA SVAAPSVFIFPPSDEQLKSGTASVVCLLNNFYPREAKVQWKV DNALQSGNSQESVTEQDSKDSTYSLSSTLTLSKADYEKHKVY | 87 |

-continued

| Description | Sequence | Seq ID No |
|---|---|---|
| pCON1057 | ACEVTHQGLSSPVTKSFNRGEC | |
| CD3-CH1 | ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSC | 85 |
| CD3-ckappa | VAAPSVFIFPPSDEQLKSGTASVVCLLNNFYPREAKVQWKVD NALQSGNSQESVTEQDSKDSTYSLSSTLTLSKADYEKHKVYA CEVTHQGLSSPVTKSFNRGEC | 88 |

6)—Exemplary amino acid sequences of CD3-FolR bispecific antibodies 2+1 inverted crossmab format

| Description | Sequence | Seq ID No |
|---|---|---|
| VHCH1[9D 11]_VHCL[ CD3]_Fckn ob_PGLALA pCON1057 | QVQLVQSGAEVKKPGASVKVSCKASGYTFTSYYMHWVRQAPGQGLE WMGIINPSGGPTSYAQKFQGRVTMTRDTSTSTVYMELSSLRSEDTA VYYCARGDFAWLDYWGQGTLVTVSSASTKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKKVEPKSCDGGGSGGGG SEVQLLESGGGLVQPGGSLRLSCAASGFTFSTYAMNWVRQAPGKGL EWVSRIRSKYNNYATYYADSVKGRFTISRDDSKNTLYLQMNSLRAE DTAVYYCVRHGNFGNSYVSWFAYWGQGTLVTVSSASVAAPSVFIFP PSDEQLKSGTASVVCLLNNFYPREAKVQWKVDNALQSGNSQESVTE QDSKDSTYSLSSTLTLSKADYEKHKVYACEVTHQGLSSPVTKSFNR GECDKTHTCPPCPAPEAAGGPSVFLFPPKPKDTLMISRTPEVTCVV VDVSHEDPEVKFNWYVDGVEVHNAKTKPREEQYNSTYRVVSVLTVL HQDWLNGKEYKCKVSNKALGAPIEKTISKAKGQPREPQVYTLPPCR DELTKNQVSLWCLVKGFYPSDIAVEWESNGQPENNYKTTPPVLDSD GSFFLYSKLTVDKSRWQQGNVFSCSVMHEALHNHYTQKSLSLSPGK | 94 |
| 9D11_Fcho le_PGLALA_ HYRF | QVQLVQSGAEVKKPGASVKVSCKASGYTFTSYYMHWVRQAPGQGLE WMGIINPSGGPTSYAQKFQGRVTMTRDTSTSTVYMELSSLRSEDTA VYYCARGDFAWLDYWGQGTLVTVSSASTKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKKVEPKSCDKTHTCPPCP APEAAGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALGAPIEKTISKAKGQPREPQVCTLPPSRDELTKNQVSLSCA VKGFYPSDIAVEWESNGQPENNYKTTPPVLDSDGSFFLVSKLTVDK SRWQQGNVFSCSVMHEALHNHYTQKSLSLSPGK | 95 |
| 9D11_LC pCON1063 | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQASIMNRTFGQGTKVEIKRTVAAPSVFIFPPSDEQLKSGTASVV CLLNNFYPREAKVQWKVDNALQSGNSQESVTEQDSKDSTYSLSSTL TLSKADYEKHKVYACEVTHQGLSSPVTKSFNRGEC | 96 |
| VLCH1[CD 3] pETR12940 | QAVVTQEPSLTVSPGGTVTLTCGSSTGAVTTSNYANWVQEKPGQAF RGLIGGTNKRAPGTPARFSGSLLGGKAALTLSGAQPEDEAEYYCAL WYSNLWVFGGGTKLTVLSSASTKGPSVFPLAPSSKSTSGGTAALGC LVKDYFPEPVTVSWNSGALTSGVHTFPAVLQSSGLYSLSSVVTVPS SSLGTQTYICNVNHKPSNTKVDKKVEPKSC | 86 |
| CH1 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCD | 307 |
| VHCH1[36 F2]_VHCL[ CD3_Fc knob_PGLA LA pCON1056 | QVQLVQSGAEVKKPGASVKVSCKASGYTFTSYYMHWVRQAPGQGLE WMGIINPSGGSTSYAQKFQGRVTMTHDTSTSTVYMELSSLRSEDTA VYYCARSFFTGFHLDYWGQGTLVTVSSASTKGPSVFPLAPSSKSTS GGTAALGCLVKDYFPEPVTVSWNSGALTSGVHTFPAVLQSSGLYSL SSVVTVPSSSLGTQTYICNVNHKPSNTKVDKKVEPKSCDGGGSGG GGSEVQLLESGGGLVQPGGSLRLSCAASGFTFSTYAMNWVRQAPGK GLEWVSRIRSKYNNYATYYADSVKGRFTISRDDSKNTLYLQMNSLR AEDTAVYYCVRHGNFGNSYVSWFAYWGQGTLVTVSSASVAAPSVFI FPPSDEQLKSGTASVVCLLNNFYPREAKVQWKVDNALQSGNSQESV TEQDSKDSTYSLSSTLTLSKADYEKHKVYACEVTHQGLSSPVTKSF | 308 |

| Description | Sequence | Seq ID No |
|---|---|---|
| | NRGECDKTHTCPPCPAPEAAGGPSVFLFPPKPKDTLMISRTPEVTC<br>VVVDVSHEDPEVKFNWYVDGVEVHNAKTKPREEQYNSTYRVVSVLT<br>VLHQDWLNGKEYKCKVSNKALGAPIEKTISKAKGQPREPQVYTLPP<br>CRDELTKNQVSLWCLVKGFYPSDIAVEWESNGQPENNYKTTPPVLD<br>SDGSFFLYSKLTVDKSRWQQGNVFSCSVMHEALHNHYTQKSLSLSP<br>GK | |
| 36F2-Fc<br>hole<br>PGLALA<br>pCON1050 | QVQLVQSGAEVKKPGASVKVSCKASGYTFTSYYMHWVRQAPGQGLE<br>WMGIINPSGGSTSYAQKFQGRVTMTHDTSTSTVYMELSSLRSEDTA<br>VYYCARSFFTGFHLDYWGQGTLVTVSSASTKGPSVFPLAPSSKSTS<br>GGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPP<br>CPAPEAAGGPSVFLFPPKPKDTLMISRTPEVTCVVVDVSHEDPEVK<br>FNWYVDGVEVHNAKTKPREEQYNSTYRVVSVLTVLHQDWLNGKEYK<br>CKVSNKALGAPIEKTISKAKGQPREPQVCTLPPSRDELTKNQVSLS<br>CAVKGFYPSDIAVEWESNGQPENNYKTTPPVLDSDGSFFLVSKLTV<br>DKSRWQQGNVFSCSVMHEALHNHYTQKSLSLSPGK | 309 |
| 36F2 LC<br>pCON1062 | EIVLTQSPGTLSLSPGERATLSCRASQSVSSSYLAWYQQKPGQAPR<br>LLIYGASSRATGIPDRFSGSGSGTDFTLTISRLEPEDFAVYYCQQY<br>TNEHYYTFGQGTKVEIKRTVAAPSVFIFPPSDEQLKSGTASVVCLL<br>NNFYPREAKVQWKVDNALQSGNSQESVTEQDSKDSTYSLSSTLTLS<br>KADYEKHKVYACEVTHXGLSSPVTKSFNRGEC | 310 |
| CD3 VLCH1<br>pETR12940 | QAVVTQEPSLTVSPGGTVTLTCGSSTGAVTTSNYANWVQEKPGQAF<br>RGLIGGTNKRAPGTPARFSGSLLGGKAALTLSGAQPEDEAEYYCAL<br>WYSNLWVFGGGTKLTVLSSASTKGPSVFPLAPSSKSTSGGTAALGC<br>LVKDYFPEPVTVSWNSGALTSGVHTFPAVLQSSGLYSLSSVVTVPS<br>SSLGTQTYICNVNHKPSNTKVDKKVEPKSC | 86 |

7) Exemplary amino acid sequences of CD3-FolR bispecific antibodies with common light chain

| Description | Sequence | Seq ID No |
|---|---|---|
| VHCH1[16D<br>5]VHCH1[<br>CD-3]_Fcknob<br>pCON999 | EVQLVESGGGLVKPGGSLRLSCAASGFTFSNAWMSWVRQAPGKGLEWVG<br>RIKSKTDGGTTDYAAPVKGRFTISRDDSKNTLYLQMNSLKTEDTAVYYC<br>TTPWEWSWYDYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKKVEPKSCDGGGSGGGGSGGGGSEVQLLESGGGL<br>VQPGGSLRLSCAASGFTFSTYAMNWVRQAPGKGLEWVSRIRSKYNNYAT<br>YYADSVKGRFTISRDDSKNTLYLQMNSLRAEDTAVYYCVRHGNFGNSYV<br>SWFAYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYI<br>CNVNHKPSNTKVDKKVEPKSCDKTHTCPPCPAPEAAGGPSVFLFPPKPK<br>DTLMISRTPEVTCVVVDVSHEDPEVKFNWYVDGVEVHNAKTKPREEQYN<br>STYRVVSVLTVLHQDWLNGKEYKCKVSNKALGAPIEKTISKAKGQPREP<br>QVYTLPPCRDELTKNQVSLWCLVKGFYPSDIAVEWESNGQPENNYKTTP<br>PVLDSDGSFFLYSKLTVDKSRWQQGNVFSCSVMHEALHNHYTQKSLSLS<br>PGK | 89 |
| VHCH1[16D<br>5]_Fchole<br>pCON983 | EVQLVESGGGLVKPGGSLRLSCAASGFTFSNAWMSWVRQAPGKGLEWVG<br>RIKSKTDGGTTDYAAPVKGRFTISRDDSKNTLYLQMNSLKTEDTAVYYC<br>TTPWEWSWYDYWGQGTLVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKKVEPKSCDKTHTCPPCPAPEAAGGPSVFL<br>FPPKPKDTLMISRTPEVTCVVVDVSHEDPEVKFNWYVDGVEVHNAKTKP<br>REEQYNSTYRVVSVLTVLHQDWLNGKEYKCKVSNKALGAPIEKTISKAK<br>GQPREPQVCTLPPSRDELTKNQVSLSCAVKGFYPSDIAVEWESNGQPEN<br>NYKTTPPVLDSDGSFFLVSKLTVDKSRWQQGNVFSCSVMHEALHNRFTQ<br>KSLSLSPGK | 90 |
| CD3 comm<br>on light<br>chain<br>pETR13197 | QAVVTQEPSLTVSPGGTVTLTCGSSTGAVTTSNYANWVQEKPGQAFRGL<br>IGGTNKRAPGTPARFSGSLLGGKAALTLSGAQPEDEAEYYCALWYSNLW<br>VFGGGTKLTVLGQPKAAPSVTLFPPSSEELQANKATLVCLISDFYPGAV<br>TVAWKADSSPVKAGVETTTPSKQSNNKYAASSYLSLTPEQWKSHRSYSC<br>QVTHEGSTVEKTVAPTECS | 35 |
| VHCH1[CD3<br>]_VHCH1[1<br>6D5]_Fckno<br>b_PGLALA<br>pETR13932 | EVQLLESGGGLVQPGGSLRLSCAASGFTFSTYAMNWVRQAPGKGLEWVS<br>RIRSKYNNYATYYADSVKGRFTISRDDSKNTLYLQMNSLRAEDTAVYYC<br>VRHGNFGNSYVSWFAYWGQGTLVTVSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSCDGGGSGGGGSEVQLVE<br>SGGGLVKPGGSLRLSCAASGFTFSNAWMSWVRQAPGKGLEWVGRIKSKT<br>DGGTTDYAAPVKGRFTISRDDSKNTLYLQMNSLKTEDTAVYYCTTPWEW<br>SWYDYWGQGTLVTVSSASTKGPSVFPLAPSSKSTSGGTAALGCLVKDYF | 91 |

| | | |
|---|---|---|
| | PEPVTVSWNSGALTSGVHTFPAVLQSSGLYSLSSVVTVPSSSLGTQTYI CNVNHKPSNTKVDKKVEPKSCDKTHTCPPCPAPEAAGGPSVFLFPPKPK DTLMISRTPEVTCVVVDVSHEDPEVKFNWYVDGVEVHNAKTKPREEQYN STYRVVSVLTVLHQDWLNGKEYKCKVSNKALGAPIEKTISKAKGQPREP QVYTLPPCRDELTKNQVSLWCLVKGFYPSDIAVEWESNGQPENNYKTTP PVLDSDGSFFLYSKLTVDKSRWQQGNVFSCSVMHEALHNHYTQKSLSLS PGK | |
| CD3_Fcknob_PGLALA pETR13917 | EVQLLESGGGLVQPGGSLRLSCAASGFTFSTYAMNWVRQAPGKGLEWVS RIRSKYNNYATYYADSVKGRFTISRDDSKNTLYLQMNSLRAEDTAVYYC VRHGNFGNSYVSWFAYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPEAAGG PSVFLFPPKPKDTLMISRTPEVTCVVVDVSHEDPEVKFNWYVDGVEVHN AKTKPREEQYNSTYRVVSVLTVLHQDWLNGKEYKCKVSNKALGAPIEKT ISKAKGQPREPQVYTLPPCRDELTKNQVSLWCLVKGFYPSDIAVEWESN GQPENNYKTTPPVLDSDGSFFLYSKLTVDKSRWQQGNVFSCSVMHEALH NHYTQKSLSLSPGK | 92 |
| Fc_hole_PGLALA_HYRF pETR10755 | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVCTLPPSRDELTKNQVSLSC AVKGFYPSDIAVEWESNGQPENNYKTTPPVLDSDGSFFLVSKLTVDKSR WQQGNVFSCSVMHEALHNRFTQKSLSLSPGK | 93 |
| VHCL[CD3]_Fcknob_PGLALA pETR13378 | EVQLLESGGGLVQPGGSLRLSCAASGFTFSTYAMNWVRQAPGKGLEWVS RIRSKYNNYATYYADSVKGRFTISRDDSKNTLYLQMNSLRAEDTAVYYC VRHGNFGNSYVSWFAYWGQGTLVTVSSASVAAPSVFIFPPSDEQLKSGT ASVVCLLNNFYPREAKVQWKVDNALQSGNSQESVTEQDSKDSTYSLSST LTLSKADYEKHKVYACEVTHQGLSSPVTKSFNRGECDKTHTCPPCPAPE AAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALGAP IEKTISKAKGQPREPQVYTLPPCRDELTKNQVSLWCLVKGFYPSDIAVE WESNGQPENNYKTTPPVLDSDGSFFLYSKLTVDKSRWQQGNVFSCSVMH EALHNHYTQKSLSLSPGK | 98 |
| 16D5 inverted 2 + with N100A in CDR H3 pETR14096 | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYC TTPWEWSWYDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDGGGSGGGGSEVQLLESGGGGL VQPGGSLRLSCAASGFTFSTYAMNWVRQAPGKGLEWVSRIRSKYNNYAT YYADSVKGRFTISRDDSKNTLYLQMNSLRAEDTAVYYCVRHGNGASYV SWFAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYI CNVNHKPSNTKVDKKVEPKSCDKTHTCPPCPAPEAAGGPSVFLFPPKPK DTLMISRTPEVTCVVVDVSHEDPEVKFNWYVDGVEVHNAKTKPREEQYN STYRVVSVLTVLHQDWLNGKEYKCKVSNKALGAPIEKTISKAKGQPREP QVYTLPPCRDELTKNQVSLWCLVKGFYPSDIAVEWESNGQPENNYKTTP PVLDSDGSFFLYSKLTVDKSRWQQGNVFSCSVMHEALHNHYTQKSLSLS PGK | 99 |
| 16D5 inverted 2 + 1 with S100aA in CDR H3 pETR14097 | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYC TTPWEWSWYDYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDGGGSGGGGSEVQLLESGGGGL VQPGGSLRLSCAASGFTFSTYAMNWVRQAPGKGLEWVSRIRSKYNNYAT YYADSVKGRFTISRDDSKNTLYLQMNSLRAEDTAVYYCVRHGNFGNAYV SWFAYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYI CNVNHKPSNTKVDKKVEPKSCDKTHTCPPCPAPEAAGGPSVFLFPPKPK DTLMISRTPEVTCVVVDVSHEDPEVKFNWYVDGVEVHNAKTKPREEQYN STYRVVSVLTVLHQDWLNGKEYKCKVSNKALGAPIEKTISKAKGQPREP QVYTLPPCRDELTKNQVSLWCLVKGFYPSDIAVEWESNGQPENNYKTTP PVLDSDGSFFLYSKLTVDKSRWQQGNVFSCSVMHEALHNHYTQKSLSLS PGK | 100 |
| CD3 light chain fused to CH1; Fc_PGLALA; pETR13862 | QAVVTQEPSLTVSPGGTVTLTCGSSTGAVTTSNYANWVQEKPGQAFRGL IGGTNKRAPGTPARFSGSLLGGKAALTLSGAQPEDEAEYYCALWYSNLW VFGGGTKLTVLSSASTKGPSVFPLAPSSKSTSGGTAALGCLVKDYFPEP VTVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALGAPIEKTISKAKGQPREPQVY TLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 101 |

| | | |
|---|---|---|
| 16D5 VH fused to constant kappa chain; pETR13859 | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYC TTPWEWSWYDYWGQGTLVTVSSASVAAPSVFIFPPSDEQLKSGTASVVC LLNNFYPREAKVQWKVDNALQSGNSQESVTEQDSKDSTYSLSSTLTLSK ADYEKHKVYACEVTHQGLSSPVTKSFNRGEC | 102 |
| CD3 VH fused to constant lambda chain; pETR13860 | EVQLLESGGGLVQPGGSLRLSCAASGFTFSTYAMNWVRQAPGKGLEWVS RIRSKYNNYATYYADSVKGRFTISRDNSKNTLYLQMNSLRAEDTAVYYC VRHGNFGNSYVSWFAYWGQGTLVTVSSASPKAAPSVTLFPPSSEELQAN KATLVCLISDFYPGAVTVAWKADSSPVKAGVETTTPSKQSNNKYAASSY LSLTPEQWKSHRSYSCQVTHEGSTVEKTVAPTECS | 103 |
| IGHV1-46*01 (X92343), plus JH4 element | QVQLVQSGAEVKKPGASVKVSCKASGYTFTSYYMHWVRQAPGQGLEWMG IINPSGGSTSYAQKFQGRVTMTRDTSTSTVYMELSSLRSEDTAVYYCAR GGSGGSFDYWGQGTLVTVSS | 104 |
| IGHV1-69*06 (L22583), plus JH6 element | QVQLVQSGAEVKKPGSSVKVSCKASGGTFSSYAISWVRQAPGQGLEWMG GIIPIFGTANYAQKFQGRVTITADKSTSTAYMELSSLRSEDTAVYYCAR GGSGGSMDAWGQGTTVTVSS | 105 |
| IGHV3-15*01 (X92216), plus JH4 element | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYC TTGGSGGSFDYWGQGTLVTVSS | 106 |
| IGHV3-23*01 (M99660), plus JH4 element | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCAK GGSGGSFDYWGQGTLVTVSS | 107 |
| IGHV4-59*01 (AB019438), plus JH4 element | QVQLQESGPGLVKPSETLSLTCTVSGGSISSYYWSWIRQPPGKGLEWIG YIYYSGSTNYNPSLKSRVTISVDTSKNQFSLKLSSVTAADTAVYYCARG GSGGSFDYWGQGTLVTVSS | 108 |
| IGHV5-51*01 (M99686), plus JH4 element | EVQLVQSGAEVKKPGESLKISCKGSGYSFTSYWIGWVRQMPGKGLEWMG IIYPGDSDTRYSPSFQGQVTISADKSISTAYLQWSSLKASDTAMYYCAR GGSGGSFDYWGQGTLVTVSS | 109 |
| CD3 specific antibody based on humanized CH2527 light chain | QTVVTQEPSLTVSPGGTVTLTCGSSTGAVTTSNYANWVQEKPGQAFRGL IGGTNKRAPGTPARFSGSLLGGKAALTLSGAQPEDEAEYYCALWYSNLW VFGGGTKLTVL | 110 |
| hVK1-39 (JK4 J-element) | DIQMTQSPSSLSASVGDRVTITCRASQSISSYLNWYQQKPGKAPKLLIY AASSLQSGVPSRFSGSGSGTDFTLTISSLQPEDFATYYCQQSYSTPLTF GGGTKVEIK | 111 |
| VL7_46-13 (humanized anti-CD3 antibody light chain) | QAVVTQEPSLTVSPGGTVTLTCGSSTGAVTTSNYANWVQEKPGQAFRGL IGGTNKRAPGTPARFSGSLLGGKAALTLSGAQPEDEAEYYCALWYSNLW VFGGGTKLTVL | 112 |

8) Exemplary 16D5 variants with reduced affinity
   a. Exemplary light chain variants with reduced affinity

| Name | Sequence | Seq ID No |
|---|---|---|
| K53A aa | QTVVTQEPSLTVSPGGTVTLTCGSSTGAVTTSNYANWVQQKPGQAPRGLIGG TNARAPGTPARFSGSLLGGKAALTLSGVQPEDEAEYYCALWYSNLWVFGGGT KLTVL | 113 |
| K53A_VL_CDR1 | GSSTGAVTTSNYAN | 32 |
| K53A_VL_CDR2 | GTNARAP | 311 |
| K53A_VL_CDR3 | ALWYSNLWV | 34 |
| S93A aa | QTVVTQEPSLTVSPGGTVTLTCGSSTGAVTTSNYANWVQQKPGQAPRGLIGG TNKRAPGTPARFSGSLLGGKAALTLSGVQPEDEAEYYCALWYANLWVFGGGT KLTVL | 114 |
| S93A_VL_CDR1 | GSSTGAVTTSNYAN | 32 |
| S93A_VL_CDR2 | GTNKRAP | 33 |
| S93A_VL_CDR3 | ALWYANLWV | 312 | b. Exemplary heavy chain variants with reduced affinity

| Name | Sequence | Seq ID No |
|---|---|---|
| S35H aa | EVQLVESGGGLVKPGGSLRLSCAASGFTFSNAWMHWVRQAPGKGLEWVGRIK SKTDGGTTDYAAPVKGRFTISRDDSKNTLYLQMNSLKTEDTAVYYCTTPWEW SWYDYWGQGTLVTVSSAS | 115 |
| S35H_VH_CDR1 | NAWMH | 313 |
| S35H_VH_CDR2 | RIKSKTDGGTTDYAAPVKG | 17 |
| S35H_VH_CDR3 | PWEWSWYDY | 18 |
| G49S aa | EVQLVESGGGLVKPGGSLRLSCAASGFTFSNAWMSWVRQAPGKGLEWVSRIK SKTDGGTTDYAAPVKGRFTISRDDSKNTLYLQMNSLKTEDTAVYYCTTPWEW SWYDYWGQGTLVTVSSAS | 116 |
| G49S_VH_CDR1 | NAWMS | 16 |
| G49S_VH_CDR2 | RIKSKTDGGTTDYAAPVKG | 17 |
| G49S_VH_CDR3 | PWEWSWYDY | 18 |
| R50S aa | EVQLVESGGGLVKPGGSLRLSCAASGFTFSNAWMSWVRQAPGKGLEWVGSIK SKTDGGTTDYAAPVKGRFTISRDDSKNTLYLQMNSLKTEDTAVYYCTTPWEW SWYDYWGQGTLVTVSSAS | 117 |
| R50S_VH_CDR1 | NAWMS | 16 |
| R50S_VH_CDR2 | SIKSKTDGGTTDYAAPVKG | 314 |
| R50S_VH_CDR3 | PWEWSWYDY | 18 |
| W96Y aa | EVQLVESGGGLVKPGGSLRLSCAASGFTFSNAWMSWVRQAPGKGLEWVGRIK SKTDGGTTDYAAPVKGRFTISRDDSKNTLYLQMNSLKTEDTAVYYCTTPYEW SWYDYWGQGTLVTVSSAS | 118 |

-continued

| Name | Sequence | Seq ID No |
|---|---|---|
| W96Y_VH_CDR1 | NAWMS | 16 |
| W96Y_VH-CDR2 | RIKSKTDGGTTDYAAPVKG | 17 |
| W96Y_VH_CDR3 | PYEWSWYDY | 315 |
| W98Y aa | EVQLVESGGGLVKPGGSLRLSCAASGFTFSNAWMSWVRQAPGKGLEWVGRIK SKTDGGTTDYAAPVKGRFTISRDDSKNTLYLQMNSLKTEDTAVYYCTTPWEY SWYDYWGQGTLVTVSSAS | 119 |
| W98Y_VH_CDR1 | NAWMS | 16 |
| W98Y_VH_CDR2 | RIKSKTDGGTTDYAAPVKG | 17 |
| W98Y_VH_CDR3 | PWEYSWYDY | 232 |

9) Additional exemplary embodiments generated from a phage display library (CDRs underlined)

| Name | Sequence | Seq ID No |
|---|---|---|
| 90D7 aa | QVQLVQSGAEVKKPGASVKVSCKASGYTFTSYYMHWVRQAPGQGLEWMGIIN PSGGSTSYAQKFQGRVTMTRDTSTSTVYMELSSLRSEDTAVYYCARNYTIVV SPFDYWGQGTLVTVSSAS | 120 |
| 90D7_VH_CDR1 | SYYMH | 8 |
| 90D7_VH_CDR2 | IINPSGGSTSYAQKFQG | 9 |
| 90D7_VH_CDR3 | NYTIVVSPFDY | 233 |
| 90C1 aa | QVQLVQSGAEVKKPGASVKVSCKASGYTFTSYYMHWVRQAPGQGLEWMGIIN PSGGSTSYAQKFQGRVTMTRDTSTSTVYMELSSLRSEDTAVYYCARNYFIGS VAMDYWGQGTLVTVSSAS | 121 |
| 90C1_VH_CDR1 | SYYMH | 8 |
| 90C1_VH_CDR2 | IINPSGGSTSYAQKFQG | 9 |
| 90C1_VH_CDR3 | NYFIGSVAMDY | 234 |
| 5E8 VH aa | QVQLVQSGAEVKKPGASVKVSCKASGYTFTSYYMHWVRQAPGQGLEWMGIIN PSGGSTSYAQKFQGRVTMTRDTSTSTVYMELSSLRSEDTAVYYCARGLTYSM DYWGQGTLVTVSSAS | 122 |
| 5E8_VH_CDR1 | SYYMH | 8 |
| 5E8_VH_CDR2 | IINPSGGSTSYAQKFQG | 9 |
| 5E8_VH_CDR3 | GLTYSMDY | 235 |
| 5E8 VL aa | DIVMTQSPLSLPVTPGEPASISCRSSQSLLHSNGYNYLDWYLQKPGQSPQLL IYLGSNRASGVPDRFSGSGSGTDFTLKISRVEAEDVGVYYCMQALQIPNTFG QGTKVEIKRT | 123 |
| 5E8_VL_CDR1 | RSSQSLLHSNGYNYLD | 59 |

| Name | Sequence | Seq ID No |
|---|---|---|
| 5E8_VL_CDR2 | LGSNRAS | 60 |
| 5E8_VL_CDR3 | MQALQIPNT | 236 |
| 12A4_VH aa | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKYAYALDYWGQGTLVTVSSAS | 124 |
| 12A4_VH_CDR1 | SYAMS | 79 |
| 12A4_VH_CDR2 | AISGSGGSTYYADSVKG | 80 |
| 12A4_VH_CDR3 | YAYALDY | 237 |
| 12A4_VL aa | EIVLTQSPGTLSLSPGERATLSCRASQSVSSSYLAWYQQKPGQAPRLLIYGASSRATGIPDRFSGSGSGTDFTLTISRLEPEDFAVYYCQQHGSSSTFGQGTKVEIKRT | 125 |
| 12A4_VL_CDR1 | RASQSVSSSYLA | 52 |
| 12A4_VL_CDR2 | GASSRAT | 53 |
| 12A4_VL_CDR3 | QQHGSSST | 238 |
| 7A3_VH aa | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGDFSAGGDFSAGRLMDYWGQGTLVTVSSAS | 126 |
| 7A3_VH_CDR1 | SYYMH | 8 |
| 7A3_VH_CDR2 | IINPSGGSTSYAQKFQG | 9 |
| 7A3_VH_CDR3 | GDFSAGRLMDY | 239 |
| 7A3_VL aa | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPPITGQGTKVEIKRT | 127 |
| 7A3_VL_CDR1 | RSSQSLLHSNGYNYLD | 59 |
| 7A3_VL_CDR2 | LGSNRAS | 60 |
| 7A3_VL_CDR3 | MQALQTPPIT | 240 |
| 6E10_VH aa | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGDYNAFDYWGHGTLVTVSSAS | 128 |
| 6E10_VH_CDR1 | SYYMH | 8 |
| 6E10_VH_CDR2 | IINPSGGSTSYAQKFQG | 9 |
| 6E10_VH_CDR3 | GDYNAFDY | 241 |
| 6E10_VL aa | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQAWHSPTFGQGTKVEIKRT | 129 |
| 6E10_VL_CDR1 | RSSQSLLHSNGYNYLD | 59 |

| Name | Sequence | Seq ID No |
|---|---|---|
| 6E10_VL_CDR2 | LGSNRAS | 60 |
| 6E10_VL_CDR3 | MQAWHSPT | 242 |
| 12F9 VH aa | QVQLVQSGAEVKKPGASVKVSCKASGYTFTSYYMHWVRQAPGQGLEWMGIIN PSGGSTSYAQKFQGRVTMTRDTSTSTVYMELSSLRSEDTAVYYCARGATYTM DYWGQGTLVTVSSAS | 130 |
| 12F9_VH_CDR1 | SYYMH | 8 |
| 12F9_VH_CDR2 | IINPSGGSTSYAQKFQG | 9 |
| 12F9_VH_CDR3 | GATYTMDY | 243 |
| 12F9 VL aa | DIVMTQSPLSLPVTPGEPASISCRSSQSLLHSNGYNYLDWYLQKPGQSPQLL IYLGSNRASGVPDRFSGSGSGTDFTLKISRVEAEDVGVYYCMQALQTPITFG QGTKVEIKRT | 131 |
| 12F9_VL_CDR1 | RSSQSLLHSNGYNYLD | 59 |
| 12F9_VL_CDR2 | LGSNRAS | 60 |
| 12F9_VL_CDR3 | MQALQTPIT | 244 |

10) 9D11 Glycosite variants: variable light chain of exemplary embodiments (CDRs underlined)

| Variant | Sequence | Seq ID No |
|---|---|---|
| N95S | DIVMTQSPLSLPVTPGEPASISC<u>RSSQSLLHSNGYNYLD</u>WYLQKPGQSPQLL IY<u>LGSNRAS</u>GVPDRFSGSGSGTDFTLKISRVEAEDVGVYYC<u>MQASIMSRT</u>FG QGTKVEIK | 132 |
| 12F9_VL_CDR1 | RSSQSLLHSNGYNYLD | 59 |
| 12F9_VL_CDR2 | LGSNRAS | 60 |
| 12F9_VL_CDR3 | MQASIMSRT | 63 |
| N95Q | DIVMTQSPLSLPVTPGEPASISC<u>RSSQSLLHSNGYNYLD</u>WYLQKPGQSPQLL IY<u>LGSNRAS</u>GVPDRFSGSGSGTDFTLKISRVEAEDVGVYYC<u>MQASIMQRT</u>FG QGTKVEIK | 133 |
| N95Q_VL_CDR1 | RSSQSLLHSNGYNYLD | 59 |
| N95Q_VL_CDR2 | LGSNRAS | 60 |
| N95Q_VL_CDR3 | MQASIMQRT | 65 |
| T97A | DIVMTQSPLSLPVTPGEPASISC<u>RSSQSLLHSNGYNYLD</u>WYLQKPGQSPQLL IY<u>LGSNRAS</u>GVPDRFSGSGSGTDFTLKISRVEAEDVGVYYC<u>MQASIMNRA</u>FG QGTKVEIK | 134 |
| T97A_VL_CDR1 | RSSQSLLHSNGYNYLD | 59 |
| T97A_VL_CDR2 | LGSNRAS | 60 |

| Variant | Sequence | Seq ID No |
|---|---|---|
| T97A_VL_CDR3 | MQASIMNRA | 67 |
| T97N | DIVMTQSPLSLPVTPGEPASISCRSSQSLLHSNGYNYLDWYLQKPGQSPQLL IYLGSNRASGVPDRFSGSGSGTDFTLKISRVEAEDVGVYYCMQASIMNRNFG QGTKVEIK | 135 |
| T97N_VL_CDR1 | RSSQSLLHSNGYNYLD | 59 |
| T97N_VL_CDR2 | LGSNRAS | 60 |
| T97N_VL_CDR3 | MQASIMNRN | 69 |

11) Deamination Variants

| Variant | Sequence | Seq ID No |
|---|---|---|
| 16D5 VH_D52d E | EVQLVESGGGLVKPGGSLRLSCAASGFTFSNAWMSWVRQAPGKGLEWVGRIK SKTEGGTTDYAAPVKGRFTISRDDSKNTLYLQMNSLKTEDTAVYYCTTPWEW SWYDYWGQGTLVTVSS | 248 |
| 16D5 VH_D52d Q | EVQLVESGGGLVKPGGSLRLSCAASGFTFSNAWMSWVRQAPGKGLEWVGRIK SKTQGGTTDYAAPVKGRFTISRDDSKNTLYLQMNSLKTEDTAVYYCTTPWEW SWYDYWGQGTLVTVSS | 249 |
| CD3_VH N100A | EVQLLESGGGLVQPGGSLRLSCAASGFTFSTYAMNWVRQAPGKGLEWVSRIR SKYNNYATYYADSVKGRFTISRDDSKNTLYLQMNSLRAEDTAVYYCVRHGNF GASYVSWFAYWGQGTLVTVSS | 250 |
| CD3_VH S100aA | EVQLLESGGGLVQPGGSLRLSCAASGFTFSTYAMNWVRQAPGKGLEWVSRIR SKYNNYATYYADSVKGRFTISRDDSKNTLYLQMNSLRAEDTAVYYCVRHGNF GNAYVSWFAYWGQGTLVTVSS | 251 |
| 16D5 [VHCH1]-CD3[VHCH1-N100A]-Fcknob_P GLALA | EVQLVESGGGLVKPGGSLRLSCAASGFTFSNAWMSWVRQAPGKGLEWVGRIK SKTDGGTTDYAAPVKGRFTISRDDSKNTLYLQMNSLKTEDTAVYYCTTPWEW SWYDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHK PSNTKVDKKVEPKSCDGGGGSGGGGSEVQLLESGGGLVQPGGSLRLSCAASG FTFSTYAMNWVRQAPGKGLEWVSRIRSKYNNYATYYADSVKGRFTISRDDSK NTLYLQMNSLRAEDTAVYYCVRHGNFGASYVSWFAYWGQGTLVTVSSASTKG PSVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCDKTHTC PPCPAPEAAGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALGA PIEKTISKAKGQPREPQVYTLPPCRDELTKNQVSLWCLVKGFYPSDIAVEWE SNGQPENNYKTTPPVLDSDGSFFLYSKLTVDKSRWQQGNVFSCSVMHEALHN HYTQKSLSLSPGK | 252 |
| 16D5-Fchole-PGLALA | EVQLVESGGGLVKPGGSLRLSCAASGFTFSNAWMSWVRQAPGKGLEWVGRIK SKTDGGTTDYAAPVKGRFTISRDDSKNTLYLQMNSLKTEDTAVYYCTTPWEW SWYDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHK PSNTKVDKKVEPKSCDKTHTCPPCPAPEAAGGPSVFLFPPKPKDTLMISRTP EVTCVVVDVSHEDPEVKFNWYVDGVEVHNAKTKPREEQYNSTYRVVSVLTVL HQDWLNGKEYKCKVSNKALGAPIEKTISKAKGQPREPQVCTLPPSRDELTKN QVSLSCAVKGFYPSDIAVEWESNGQPENNYKTTPPVLDSDGSFFLVSKLTVD KSRWQQGNVFSCSVMHEALHNRFTQKSLSLSPGK | 253 |
| CD3-CLC | QAVVTQEPSLTVSPGGTVTLTCGSSTGAVTTSNYANWVQEKPGQAFRGLIGG TNKRAPGTPARFSGSLLGGKAALTLSGAQPEDEAEYYCALWYSNLWVFGGGT KLTVLGQPKAAPSVTLFPPSSEELQANKATLVCLISDFYPGAVTVAWKADSS PVKAGVETTTPSKQSNNKYAASSYLSLTPEQWKSHRSYSCQVTHEGSTVEKT VAPTECS | 254 |
| 16D5 [VHCH1]-CD3[VHCH1-S100aA]-Fcknob_P GLALA | EVQLVESGGGLVKPGGSLRLSCAASGFTFSNAWMSWVRQAPGKGLEWVGRIK SKTDGGTTDYAAPVKGRFTISRDDSKNTLYLQMNSLKTEDTAVYYCTTPWEW SWYDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHK PSNTKVDKKVEPKSCDGGGGSGG GGSEVQLLESGGGLVQPGGSLRLSCAASGFTFSTYAMNWVRQAPGKGLEWVS RIRSKYNNYATYYADSVKGRFTISRDDSKNTLYLQMNSLRAEDTAVYYCVRH | 255 |

| Variant | Sequence | Seq ID No |
|---|---|---|
|  | GNFGNAYVSWFAYWGQGTLVTVSSASTKGPSVFPLAPSSKSTSGGTAALGCL VKDYFPEPVTVSWNSGALTSGVHTFPAVLQSSGLYSLSSVVTVPSSSLGTQT YICNVNHKPSNTKVDKKVEPKSCDKTHTCPPCPAPEAAGGPSVFLFPPKPKD TLMISRTPEVTCVVVDVSHEDPEVKFNWYVDGVEVHNAKTKPREEQYNSTYR VVSVLTVLHQDWLNGKEYKCKVSNKALGAPIEKTISKAKGQPREPQVYTLPP CRDELTKNQVSLWCLVKGFYPSDIAVEWESNGQPENNYKTTPPVLDSDGSFF LYSKLTVDKSRWQQGNVFSCSVMHEALHNHYTQKSLSLSPGK |  |
| 9D11 [VHCH1]- CD3[VHC L- N100A]- Fcknob_P GLALA | QVQLVQSGAEVKKPGASVKVSCKASGYTFTSYYMHWVRQAPGQGLEWMGIIN PSGGPTSYAQKFQGRVTMTRDTSTSTVYMELSSLRSEDTAVYYCARGDFAWL DYWGQGTLVTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSN TKVDKKVEPKSCDGGGGSGGGGSEVQLLESGGGLVQPGGSLRLSCAASGFTF STYAMNWVRQAPGKGLEWVSRIRSKYNNYATYYADSVKGRFTISRDDSKNTL YLQMNSLRAEDTAVYYCVRHGNFGASYVSWFAYWGQGTLVTVSSASVAAPSV FIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGECDKTHT CPPCPAPEAAGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALG APIEKTISKAKGQPREPQVYTLPPCRDELTKNQVSLWCLVKGFYPSDIAVEW ESNGQPENNYKTTPPVLDSDGSFFLYSKLTVDKSRWQQGNVFSCSVMHEALH NHYTQKSLSLSPGK | 256 |
| 9D11- Fchole | QVQLVQSGAEVKKPGASVKVSCKASGYTFTSYYMHWVRQAPGQGLEWMGIIN PSGGPTSYAQKFQGRVTMTRDTSTSTVYMELSSLRSEDTAVYYCARGDFAWL DYWGQGTLVTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSN TKVDKKVEPKSCDKTHTCPPCPAPEAAGGPSVFLFPPKPKDTLMISRTPEVT CVVVDVSHEDPEVKFNWYVDGVEVHNAKTKPREEQYNSTYRVVSVLTVLHQD WLNGKEYKCKVSNKALGAPIEKTISKAKGQPREPQVCTLPPSRDELTKNQVS LSCAVKGFYPSDIAVEWESNGQPENNYKTTPPVLDSDGSFFLVSKLTVDKSR WQQGNVFSCSVMHEALHNHYTQKSLSLSPGK | 257 |
| 9D11_LC [N95Q] | DIVMTQSPLSLPVTPGEPASISCRSSQSLLHSNGYNYLDWYLQKPGQSPQLL IYLGSNRASGVPDRFSGSGSGTDFTLKISRVEAEDVGVYYCMQASIMQRTFG QGTKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGLSS PVTKSFNRGEC | 258 |
| CD3_VLC H1 | QAVVTQEPSLTVSPGGTVTLTCGSSTGAVTTSNYANWVQEKPGQAFRGLIGG TNKRAPGTPARFSGSLLGGKAALTLSGAQPEDEAEYYCALWYSNLWVFGGGT KLTVLSSASTKGPSVFPLAPSSKSTSGGTAALGCLVKDYFPEPVTVSWNSGA LTSGVHTFPAVLQSSGLYSLSSVVTVPSSSLGTQTYICNVNHKPSNTKVDKK VEPKSC | 259 |
| 9D11 [VHCH1]- CD3[VHC H1- S100aA]- Fcknob_P GLALA | QVQLVQSGAEVKKPGASVKVSCKASGYTFTSYYMHWVRQAPGQGLEWMGIIN PSGGPTSYAQKFQGRVTMTRDTSTSTVYMELSSLRSEDTAVYYCARGDFAWL DYWGQGTLVTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSN TKVDKKVEPKSCDGGGGSGGGGSEVQLLESGGGLVQPGGSLRLSCAASGFTF STYAMNWVRQAPGKGLEWVSRIRSKYNNYATYYADSVKGRFTISRDDSKNTL YLQMNSLRAEDTAVYYCVRHGNFGNAYVSWFAYWGQGTLVTVSSASVAAPSV FIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGECDKTHT CPPCPAPEAAGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALG APIEKTISKAKGQPREPQVYTLPPCRDELTKNQVSLWCLVKGFYPSDIAVEW ESNGQPENNYKTTPPVLDSDGSFFLYSKLTVDKSRWQQGNVFSCSVMHEALH NHYTQKSLSLSPGK | 260 |

12) Mov19 based TCBs of exemplary embodiments (CDRs underlined)

| Name | Sequence | Seq ID No |
|---|---|---|
| pETR116 46 Mov19 VH-CH1- Fchole PG/LALA | QVQLQQSGAELVKPGASVKISCKASGYSFTGYFMNWVKQSHGKSLEWIGRIH PYDGDTFYNQNFKDKATLTVDKSSNTAHMELLSLTSEDFAVYYCTRYDGSRA MDYWGQGTTVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPS NTKVDKKVEPKSCDKTHTCPPCPAPEAAGGPSVFLFPPKPKDTLMISRTPEV TCVVVDVSHEDPEVKFNWYVDGVEVHNAKTKPREEQYNSTYRVVSVLTVLHQ DWLNGKEYKCKVSNKALGAPIEKTISKAKGQPREPQVCTLPPSRDELTKNQV SLSCAVKGFYPSDIAVEWESNGQPENNYKTTPPVLDSDGSFFLVSKLTVDKS RWQQGNVFSCSVMHEALHNHYTQKSLSLSPGK | 136 |

| Name | Sequence | Seq ID No |
|---|---|---|
| pETR116<br>47<br>Mov19<br>VH-CH1-<br>CD3 VH-<br>CL-<br>Fcknob<br>PG/LALA | QVQLQQSGAELVKPGASVKISCKASGYSFTGYFMNWVKQSHGKSLEWIGRIH<br>PYDGDTFYNQNFKDKATLTVDKSSNTAHMELLSLTSEDFAVYYCTRYDGSRA<br>MDYWGQGTTVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPS<br>NTKVDKKVEPKSCDGGGSGGGGSEVQLVESGGGLVQPKGSLKLSCAASGFT<br>FNTYAMNWVRQAPGKGLEWVARIRSKYNNYATYYADSVKDRFTISRDDSQSI<br>LYLQMNNLKTEDTAMYYCVRHGNFGNSYVSWFAYWGQGTLVTVSAASVAAP<br>VFIFPPSDEQLKSGTASVVCLLNNFYPREAKVQWKVDNALQSGNSQESVTEQ<br>DSKDSTYSLSSTLTLSKADYEKHKVYACEVTHQGLSSPVTKSFNRGECDKTH<br>TCPPCPAPEAAGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKAL<br>GAPIEKTISKAKGQPREPQVYTLPPCRDELTKNQVSLWCLVKGFYPSDIAVE<br>WESNGQPENNYKTTPPVLDSDGSFFLYSKLTVDKSRWQQGNVFSCSVMHEAL<br>HNHYTQKSLSLSPGK | 137<br>S |
| pETR116<br>44<br>Mov19 LC | DIELTQSPASLAVSLGQRAIISCKASQSVSFAGTSLMHWYHQKPGQQPKLLI<br>YRASNLEAGVPTRFSGSGSKTDFTLN IHPVEEEDAATYYCQQSREYPYTFGG<br>GTKLEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC | 138 |
| Hu IgG1<br>Fc | DKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVS<br>NKALPAPIEKTISKAKGQPREPQVYTLPPSRDELTKNQVSLTCLVKGFYPSD<br>IAVEWESNGQPENNYKTTPPVLDSDGSFFLYSKLTVDKSRWQQGNVFSCSVM<br>HEALHNHYTQKSLSLSPGK | 245 |

13) Additional FolR1 TCBs with intermediate affinity binders (CDRs according to Kabat, underlined):

| Name | Sequence | Seq ID No |
|---|---|---|
| 16D5<br>variant<br>W96Y/D52E<br>VH | EVQLVESGGGLVKPGGSLRLSCAASGFTFS<u>NAWMS</u>WVRQAPGKGLEWVG<u>RIKSK<br>TEGGTTDYAAPVKG</u>RFTISRDDSKNTLYLQMNSLKTEDTAVYYCTT<u>PYEWSWYD<br>Y</u>WGQGTLVTVSS | 274 |
| W96Y/D52E<br>_VH CDR1 | NAWMS | 16 |
| W96Y/D52E<br>_VH CDR2 | RIKSKTEGGTTDYAAPVKG | 275 |
| W96Y/D52E<br>_VH CDR3 | PYEWSWYDY | 315 |
| 16D5<br>variant<br>W96Y/D52E<br>VL | QAVVTQEPSLTVSPGGTVTLTC<u>GSSTGAVTTSNYAN</u>WVQEKPGQA<br>FRGLIGG<u>TNKRAP</u>GTPARFSGSLLGGKAALTLSGAQPEDEAEYYC<br><u>ALWYSNLWV</u>FGGGTKLTVL | 31 |
| W96Y/D52<br>E_CD3-<br>VHCH1_Fc-<br>knob_PGLA<br>LA<br>pETR1494<br>5 | EVQLVESGGGLVKPGGSLRLSCAASGFTFSNAWMSWVRQAPGKGLEWVGRIKSK<br>TEGGTTDYAAPVKGRFTISRDDSKNTLYLQMNSLKTEDTAVYYCTTPYEWSWYD<br>YWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDK<br>KVEPKSCDGGGSGGGGSEVQLLESGGGLVQPGGSLRLSCAASGFTFSTYAMNW<br>VRQAPGKGLEWVSRIRSKYNNYATYYADSVKGRFTISRDDSKNTLYLQMNSLRA<br>EDTAVYYCVRHGNFGNSYVSWFAYWGQGTLVTVSSASTKGPSVFPLAPSSKSTS<br>GGTAALGCLVKDYFPEPVTVSWNSGALTSGVHTFPAVLQSSGLYSLSSVVTVPS<br>SSLGTQTYICNVNHKPSNTKVDKKVEPKSCDKTHTCPPCPAPEAAGGPSVFLFP<br>PKPKDTLMISRTPEVTCVVVDVSHEDPEVKFNWYVDGVEVHNAKTKPREEQYNS<br>TYRVVSVLTVLHQDWLNGKEYKCKVSNKALGAPIEKTISKAKGQPREPQVYTLP<br>PCRDELTKNQVSLWCLVKGFYPSDIAVEWESNGQPENNYKTTPPVLDSDGSFFL<br>YSKLTVDKSRWQQGNVFSCSVMHEALHNHYTQKSLSLSPGK | 276 |

-continued

| Name | Sequence | Seq ID No |
|---|---|---|
| W96Y/D52E_Fc-hole_PGLALA_HYRF pETR14946 | EVQLVESGGGLVKPGGSLRLSCAASGFTFSNAWMSWVRQAPGKGLEWVGRIKSK TEGGTTDYAAPVKGRFTISRDDSKNTLYLQMNSLKTEDTAVYYCTTPYEWSWYD YWGQGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDK KVEPKSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGKEYKC KVSNKALGAPIEKTISKAKGQPREPQVCTLPPSRDELTKNQVSLSCAVKGFYPS DIAVEWESNGQPENNYKTTPPVLDSDGSFFLVSKLTVDKSRWQQGNVFSCSVMH EALHNRFTQKSLSLSPGK | 277 |
| 14B1 VH | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCARGDYRYRYFDY WGQGTLVTVSS | 278 |
| 14B1 VL | SSELTQDPAVSVALGQTVRITCQGDSLRSYYASWYQQKPGQAPVLVIYGKNNRP SGIPDRFSGSSSGNTASLTITGAQAEDEADYYCNSRESPPTGLVVFGGGTKLTV L | 279 |
| 14B1[EE]_CD3[FLCH1]_Fc-knob_PGLALA pETR14976 | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCARGDYRYRYFDY WGQGTLVTVSSASTKGPSVFPLAPSSKSTSGGTAALGCLVEDYFPEPVTVSWNS GALTSGVHTFPAVLQSSGLYSLSSVVTVPSSSLGTQTYICNVNHKPSNTKVDEK VEPKSCDGGGGSGGGGSQAVVTQEPSLTVSPGGTVTLTCGSSTGAVTTSNYANW VQEKPGQAFRGLIGGTNKRAPGTPARFSGSLLGGKAALTLSGAQPEDEAEYYCA LWYSNLWVFGGGTKLTVLSSASTKGPSVFPLAPSSKSTSGGTAALGCLVKDYFP EPVTVSWNSGALTSGVHTFPAVLQSSGLYSLSSVVTVPSSSLGTQTYICNVNHK PSNTKVDKKVEPKSCDKTHTCPPCPAPEAAGGPSVFLFPPKPKDTLMISRTPEV TCVVVDVSHEDPEVKFNWYVDGVEVHNAKTKPREEQYNSTYRVVSVLTVLHQDW LNGKEYKCKVSNKALGAPIEKTISKAKGQPREPQVYTLPPCRDELTKNQVSLWC LVKGFYPSDIAVEWESNGQPENNYKTTPPVLDSDGSFFLYSKLTVDKSRWQQGN VFSCSVMHEALHNHYTQKSLSLSPGK | 280 |
| 14B1[EE]_Fc-hole_PGLALA pETR14977 | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCARGDYRYRYFDY WGQGTLVTVSSASTKGPSVFPLAPSSKSTSGGTAALGCLVEDYFPEPVTVSWNS GALTSGVHTFPAVLQSSGLYSLSSVVTVPSSSLGTQTYICNVNHKPSNTKVDEK VEPKSCDKTHTCPPCPAPEAAGGPSVFLFPPKPKDTLMISRTPEVTCVVVDVSH EDPEVKFNWYVDGVEVHNAKTKPREEQYNSTYRVVSVLTVLHQDWLNGKEYKCK VSNKALGAPIEKTISKAKGQPREPQVCTLPPSRDELTKNQVSLSCAVKGFYPSD IAVEWESNGQPENNYKTTPPVLDSDGSFELVSKLTVDKSRWQQGNVFSCSVMHE ALHNHYTQKSLSLSPGK | 281 |
| 14B1 LC [KK] Constant lambda pETR14979 | SSELTQDPAVSVALGQTVRITCQGDSLRSYYASWYQQKPGQAPVLVIYGKNNRP SGIPDRFSGSSSGNTASLTITGAQAEDEADYYCNSRESPPTGLVVFGGGTKLTV LGQPKAAPSVTLFPPSSKKLQANKATLVCLISDFYPGAVTVAWKADSSPVKAGV ETTTPSKQSNNKYAASSYLSLTPEQWKSHRSYSCQVTHEGSTVEKTVAPTECS | 282 |
| 9C7 VH | QVQLVQSGAEVKKPGASVKVSCKASGYTFTSYYMHWVRQAPGQGLEWMGIINPS GGSTSYAQKFQGRVTMTRDTSTSTVYMELSSLRSEDTAVYYCARGDWSYYMDW GQGTLVTVSS | 283 |
| 9C7 VL | DIVMTQSPLSLPVTPGEPASISCRSSQSLLHSNGYNYLD WYLQKPGQSPQLLIY LGSNRASGVPDRFSGSGSGTDFTLKISRVEAEDVGVYYCMQARQTPTFGQGTKV EIK | 284 |
| 9C7[EE]_CD3[VLCH1]_Fc-knob_PGLALA pETR14974 | QVQLVQSGAEVKKPGASVKVSCKASGYTFTSYYMHWVRQAPGQGLEWMGIINPS GGSTSYAQKFQGRVTMTRDTSTSTVYMELSSLRSEDTAVYYCARGDWSYYMDYW GQGTLVTVSSASTKGPSVFPLAPSSKSTSGGTAALGCLVEDYFPEPVTVSWNSG ALTSGVHTFPAVLQSSGLYSLSSVVTVPSSSLGTQTYICNVNHKPSNTKVDEKV EPKSCDGGGGSGGGGSQAVVTQEPSLTVSPGGTVTLTCGSSTGAVTTSNYANWV QEKPGQAFRGLIGGTNKRAPGTPARFSGSLLGGKAALTLSGAQPEDEAEYYCAL WYSNLWVFGGGTKLTVLSSASTKGPSVFPLAPSSKSTSGGTAALGCLVKDYFPE PVTVSWNSGALTSGVHTFPAVLQSSGLYSLSSVVTVPSSSLGTQTYICNVNHKP SNTKVDKKVEPKSCDKTHTCPPCPAPEAAGGPSVFLFPPKPKDTLMISRTPEVT CVVVDVSHEDPEVKFNWYVDGVEVHNAKTKPREEQYNSTYRVVSVLTVLHQDWL NGKEYKCKVSNKALGAPIEKTISKAKGQPREPQVYTLPPCRDELTKNQVSLWCL VKGFYPSDIAVEWESNGQPENNYKTTPPVLDSDGSFFLYSKLTVDKSRWQQGNV FSCSVMHEALHNHYTQKSLSLSPGK | 285 |
| 9C7[EE]_LFc-hole_PGLALA pETR14975 | QVQLVQSGAEVKKPGASVKVSCKASGYTFTSYYMHWVRQAPGQGLEWMGIINPS GGSTSYAQKFQGRVTMTRDTSTSTVYMELSSLRSEDTAVYYCARGDWSYYMDYW GQGTLVTVSSASTKGPSVFPLAPSSKSTSGGTAALGCLVEDYFPEPVTVSWNSG ALTSGVHTFPAVLQSSGLYSLSSVVTVPSSSLGTQTYICNVNHKPSNTKVDEKV EPKSCDKTHTCPPCPAPEAAGGPSVFLFPPKPKDTLMISRTPEVTCVVVDVSHE DPEVKFNWYVDGVEVHNAKTKPREEQYNSTYRVVSVLTVLHQDWLNGKEYKCKV | 286 |

-continued

| Name | Sequence | Seq ID No |
|---|---|---|
| | SNKALGAPIEKTISKAKGQPREPQVCTLPPSRDELTKNQVSLSCAVKGFYPSDI AVEWESNGQPENNYKTTPPVLDSDGSFFLVSKLTVDKSRWQQGNVFSCSVMHEA LHNHYTQKSLSLSPGK | |
| 9C7 LC [RK] pETR14980 | DIVMTQSPLSLPVTPGEPASISCRSSQSLLHSNGYNYLDWYLQKPGQSPQLLIY LGSNRASGVPDRFSGSGSGTDFTLKISRVEAEDVGVYYCMQARQTPTFGQGTKV EIKRTVAAPSVFIFPPSDRKLKSGTASVVCLLNNFYPREAKVQWKVDNALQSGN SQESVTEQDSKDSTYSLSSTLTLSKADYEKHKVYACEVTHQGLSSPVTKSFNRG EC | 316 |

14) Antigen Sequences

| Antigen | Sequence | Seq ID No |
|---|---|---|
| hu FolR1 | MAQRMTTQLLLLLVWVAVVGEAQTRIAWARTELLNVCMNAKHHKEKPGPEDKL HEQCRPWRKNACCSTNTSQEAHKDVSYLYRFNWNHCGEMAPACKRHFIQDTCL YECSPNLGPWIQQVDQSWRKERVLNVPLCKEDCEQWWEDCRTSYTCKSNWHKG WNWTSGFNKCAVGAACQPFHFYFPTPTVLCNEIWTHSYKVSNYSRGSGRCIQM WFDPAQGNPNEEVARFYAAAMSGAGPWAAWPFLLSLALMLLWLLS | 139 |
| huFolR1 ECD-AcTev-Fcknob-Avi tag | RIAWARTELLNVCMNAKHHKEKPGPEDKLHEQCRPWRKNACCSTNTSQEAHKD VSYLYRFNWNHCGEMAPACKRHFIQDTCLYECSPNLGPWIQQVDQSWRKERVL NVPLCKEDCEQWWEDCRTSYTCKSNWHKGWNWTSGFNKCAVGAACQPFHFYFP TPTVLCNEIWTHSYKVSNYSRGSGRCIQMWFDPAQGNPNEEVARFYAAAMVDE QLYFQGGSPKSADKTHTCPPCPAPELLGGPSVFLFPPKPKDTLMISRTPEVTC VVVDVSHEDPEVKFNWYVDGVEVHNAKTKPREEQYNSTYRVVSVLTVLHQDWL NGKEYKCKVSNKALPAPIEKTISKAKGQPREPQVYTLPPCRDELTKNQVSLWC LVKGFYPSDIAVEWESNGQPENNYKTTPPVLDSDGSFFLYSKLTVDKSRWQQG NVFSCSVMHEALHNHYTQKSLSLSPGKSGGLNDIFEAQKIEWHE | 140 |
| Fchole | DKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVCTLPPSRDELTKNQVSLCAVKGFYPSDIAV EWESNGQPENNYKTTPPVLDSDGSFFLVSKLTVDKSRWQQGNVFSCSVMHEAL HNRFTQKSLSLSPGK | 141 |
| mu FolR1 | MAHLMTVQLLLLVMWMAECAQSRATRARTELLNVCMDAKHHKEKPGPEDNLHD QCSPWKTNSCCSTNTSQEAHKDISYLYRFNWNHCGTMTSECKRHFIQDTCLYE CSPNLGPWIQQVDQSWRKERILDVPLCKEDCQQWWEDCQSSFTCKSNWHKGWN WSSGHNECPVGASCHPFTFYFPTSAALCEEIWSHSYKLSNYSRGSGRCIQMWF DPAQGNPNEEVARFYAEAMSGAGLHGTWPLLCSLSLVLLWVIS | 142 |
| mu FolR1 ECD-AcTev-Fcknob-Avitag | TRARTELLNVCMDAKHHKEKPGPEDNLHDQCSPWKTNSCCSTNTSQEAHKDIS YLYRFNWNHCGTMTSECKRHFIQDTCLYECSPNLGPWIQQVDQSWRKERILDV PLCKEDCQQWWEDCQSSFTCKSNWHKGWNWSSGHNECPVGASCHPFTFYFPTS AALCEEIWSHSYKLSNYSRGSGRCIQMWFDPAQGNPNEEVARFYAEAMEQL YFQGGSPKSADKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPCRDELTKNQVSLWCLV KGFYPSDIAVEWESNGQPENNYKTTPPVLDSDGSFFLYSKLTVDKSRWQQGNV FSCSVMHEALHNHYTQKSLSLSPGKSGGLNDIFEAQKIEWHE | 143 |
| cy FolR1 | MAQRMTTQLLLLLVWVAVVGEAQTRTARARTELLNVCMNAKHHKEKPGPEDKL HEQCRPWKKNACCSTNTSQEAHKDVSYLYRFNWNHCGEMAPACKRHFIQDTCL YECSPNLGPWIQQVDQSWRKERVLNVPLCKEDCERWWEDCRTSYTCKSNWHKG WNWTSGFNKCPVGAACQPFHFYFPTPTVLCNEIWTYSYKVSNYSRGSGRCIQM WFDPAQGNPNEEVARFYAAAMSGAGPWAAWPLLLSLALTLLWLLS | 144 |
| cy FolR1 ECD-AcTev-Fcknob-Avi tag | RTARARTELLNVCMNAKHHKEKPGPEDKLHEQCRPWKKNACCSTNTSQEAHKD VSYLYRFNWNHCGEMAPACKRHFIQDTCLYECSPNLGPWIQQVDQSWRKERVL NVPLCKEDCEQWWEDCRTSYTCKSNWHKGWNWTSGFNKCPVGAACQPFHFYFP TPTVLCNEIWTYSYKVSNYSRGSGRCIQMWFDPAQGNPNEEVARFYAAAMVDE QLYFQGGSPKSADKTHTCPPCPAPELLGGPSVFLFPPKPKDTLMISRTPEVTC VVVDVSHEDPEVKFNWYVDGVEVHNAKTKPREEQYNSTYRVVSVLTVLHQDWL NGKEYKCKVSNKALPAPIEKTISKAKGQPREPQVYTLPPCRDELTKNQVSLWC LVKGFYPSDIAVEWESNGQPENNYKTTPPVLDSDGSFFLYSKLTVDKSRWQQG NVFSCSVMHEALHNHYTQKSLSLSPGKSGLNDIFEAQKIEWHE | 145 |
| hu FolR2 | MVWKWMPLLLLLVCVATMCSAQDRTDLLNVCMDAKHHKTKPGPEDKLHDQCSP WKKNACCTASTSQELHKDTSRLYNFNWDHCGKMEPACKRHFIQDTCLYECSPN LGPWIQQVNQSWRKERFLDVPLCKEDCQRWWEDCHTSHTCKSNWHRGWDWTSG VNKCPAGALCRTFESYFPTPAALCEGLWSHSYKVSNYSRGSGRCIQMWFDSAQ GNPNEEVARFYAAAMHVNAGEMLHGTGGLLLSLALMLQLWLLG | 146 |

-continued

| Antigen | Sequence | Seq ID No |
|---|---|---|
| hu FolR2 ECD-AcTev-Fcknob-Avi tag | TMCSAQDRTDLLNVCMDAKHHKTKPGPEDKLHDQCSPWKKNACCTASTSQELH KDTSRLYNFNWDHCGKMEPACKRHFIQDTCLYECSPNLGPWIQQVNQSWRKER FLDVPLCKEDCQRWWEDCHTSHTCKSNWHRGWDWTSGVNKCPAGALCRTFESY FPTPAALCEGLWSHSYKVSNYSRGSGRCIQMWFDSAQGNPNEEVARFYAAAMH VVDEQLYFQGGSPKSADKTHTCPPCPAPELLGGPSVFLFPPKPKDTLMISRTP EVTCVVVDVSHEDPEVKFNWYVDGVEVHNAKTKPREEQYNSTYRVVSVLTVLH QDWLNGKEYKCKVSNKALPAPIEKTISKAKGQPREPQVYTLPPCRDELTKNQV SLWCLVKGFYPSDIAVEWESNGQPENNYKTTPPVLDSDGSFFLYSKLTVDKSR WQQGNVFSCSVMHEALHNHYTQKSLSLSPGKSGGLNDIFEAQKIEWHE | 147 |
| hu FolR3 | MAWQMMQLLLLALVTAAGSAQPRSARARTDLLNVCMNAKHHKTQPSPEDELYG QCSPWKKNACCTASTSQELHKDTSRLYNFNWDHCGKMEPTCKRHFIQDSCLYE CSPNLGPWIRQVNQSWRKERILNVPLCKEDCERWWEDCRTSYTCKSNWHKGWN WTSGINECPAGALCSTFESYFPTPAALCEGLWSHSFKVSNYSRGSGRCIQMWF DSAQGNPNEEVAKFYAAAMNAGAPSRGIIDS SARARTDLLNVCMNAKHHKTQPSPEDELYGQCSPWKKNACCTASTSQELHKDT | 148 |
| hu FolR3 ECD-AcTev-Fcknob-Avi tag | SRLYNFNWDHCGKMEPTCKRHFIQDSCLYECSPNLGPWIRQVNQSWRKERILN VPLCKEDCERWWEDCRTSYTCKSNWHKGWNWTSGINECPAGALCSTFESYFPT PAALCEGLWSHSFKVSNYSRGSGRCIQMWFDSAQGNPNEEVAKFYAAAMNAGA PSRGIIDSVDEQLYFQGGSPKSADKTHTCPPCPAPELLGGPSVFLFPPKPKDT LMISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPCRD ELTKNQVSLWCLVKGFYPSDIAVEWESNGQPENNYKTTPPVLDSDGSFFLYSK LTVDKSRWQQGNVFSCSVMHEALHNHYTQKSLSLSPGKSGGLNDIFEAQKIEW HE | 149 |
| hu CD3ε | MQSGTHWRVLGLCLLSVGVWGQDGNEEMGGITQTPYKVSISGTTVILTCPQYP GSEILWQHNDKNIGGDEDDKNIGSDEDHLSLKEFSELEQSGYYVCYPRGSKPE DANFYLYLRARVCENCMEMDVMSVATIVIVDICITGGLLLLVYYWSKNRKAKA KPVTRGAGAGGRQRGQNKERPPPVPNPDYEPIRKGQRDLYSGLNQRRI | 150 |

15) Nucleotide sequences of exemplary embodiments

| Description | Sequence | Seq ID No |
|---|---|---|
| 16A3 | CAGGTGCAATTGGTTCAATCTGGTGCTGAAGTAAAAAAACCGGGCG CTTCCGTTAAAGTGAGCTGCAAAGCATCCGGATACACCTTCACTTC CTATTACATGCACTGGGTTCGTCAAGCCCCGGGCCAGGGTCTGGAA TGGATGGGCATCATTAACCCAAGCGGTGGCTCTACCTCCTACGCGC AGAAATTCCAGGGTCGCGTCACGATGACCCGTGACACTAGCACCTC TACCGTTTATATGGAGCTGTCCAGCCTGCGTTCTGAAGATACTGCA GTGTACTACTGTGCACGCAACTACTACGCTGGTGTTACTCCGTTCG ACTATTGGGGTCAAGGCACCCTCGTAACGGTTTCTTCT | 151 |
| 15A1 | CAGGTGCAATTGGTTCAATCTGGTGCTGAAGTAAAAAAACCGGGCG CTTCCGTTAAAGTGAGCTGCAAAGCATCCGGATACACCTTCACTTC CTATTACATGCACTGGGTTCGTCAAGCCCCGGGCCAGGGTCTGGAA TGGATGGGCATCATTAACCCAAGCGGTGGCTCTACCTCCTACGCGC AGAAATTCCAGGGTCGCGTCACGATGACCCGTGACACTAGCACCTC TACCGTTTATATGGAGCTGTCCAGCCTGCGTTCTGAAGATACTGCA GTGTACTACTGTGCACGCAACTACTACATCGGTGTTGTTACTTTCG ACTATTGGGGTCAAGGCACCCTCGTAACGGTTTCTTCT | 152 |
| 18D3 | CAGGTGCAATTGGTTCAATCTGGTGCTGAAGTAAAAAAACCGGGCG CTTCCGTTAAAGTGAGCTGCAAAGCATCCGGATACACCTTCACTTC CTATTACATGCACTGGGTTCGTCAAGCCCCGGGCCAGGGTCTGGAA TGGATGGGCATCATTAACCCAAGCGGTGGCTCTACCTCCTACGCGC AGAAATTCCAGGGTCGCGTCACGATGACCCGTGACACTAGCACCTC TACCGTTTATATGGAGCTGTCCAGCCTGCGTTCTGAAGATACTGCA GTGTACTACTGTGCACGCAACTACTACACTGGTGGTTCTTCTGCTT TCGACTATTGGGGTCAAGGCACCCTCGTAACGGTTTCTTCT | 153 |
| 19E5 | CAGGTGCAATTGGTTCAATCTGGTGCTGAAGTAAAAAAACCGGGCG NTTCCGTTAAAGTGAGCTGCAAAGCATCCGGATACACCTTCACTTC CTATTACATGCACTGGGTTCGTCAAGCCCCGGGCCAGGGTCTGGAA TGGATGGGCATCATTAACCCAAGCGGTGGCTCTACCTCCTACGCGC AGAAATTCCAGGGTCGCGTCACGATGACCCGTGACACTAGCACCTC TACCGTTTATATGGAGCTGTCCAGCCTGCGTTCTGAAGATACTGCA GTGTACTACTGTGCACGCGGTAATGGCGTCGTTACACTTCTTTCG ACTATTGGGGTCAAGGCACCCTCGTAACGGTTTCTTCT | 154 |
| 19A4 | CAGGTGCAATTGGTTCAATCTGGTGCTGAAGTAAAAAAACCGGGCG CTTCCGTTAAAGTGAGCTGCAAAGCATCCGGATACACCTTCACTTC | 155 |

| Description | Sequence | Seq ID No |
|---|---|---|
| | CTATTACATGCACTGGGTTCGTCAAGCCCCGGGCCAGGGTCTGGAA<br>TGGATGGGCATCATTAACCCAAGCGGTGGCTCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCGGTGGTTGGATCCGTTGGGAACATTTCG<br>ACTATTGGGGTCAAGGCACCCTCGTAACGGTTTCTTCT | |
| 15H7 | CAGGTGCAATTGGTTCAATCTGGTGCTGAAGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCTCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCAACTACTACCTGTTCTCTACTTCTTTCG<br>ACTATTGGGGTCAAGGCACCCTCGTAACGGTTTCTTCT | 156 |
| 15I36 | CAGGTGCAATTGGTTCAATCTGGTGCTGAGGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCTCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCAACTACTACATCGGTATCGTTCCGTTCG<br>ACTATTGGGGTCAAGGCACCCTCGTAACGGTTTCTTCT | 157 |
| 16D5 | GAGGTGCAATTGGTTGAATCTGGTGGTGGTCTGGTAAAACCGGGCG<br>GTTCCCTGCGTCTGAGCTGCGCGGCTTCCGGATTCACCTTCTCCAA<br>CGCGTGGATGAGCTGGGTTCGCCAGGCCCCGGGCAAAGGCCTCGAG<br>TGGGTTGGTCGTATCAAGTCTAAAACTGACGGTGGCACCACGGATT<br>ACGCGGCTCCAGTTAAAGGTCGTTTTACCATTTCCCGCGACGATAG<br>CAAAAACACTCTGTATCTGCAGATGAACTCTCTGAAAACTGAAGAC<br>ACCGCAGTCTACTACTGTACTACCCCGTGGGAATGGTCTTGGTACG<br>ATTATTGGGGCCAGGGCACGCTGGTTACGGTGTCTTCC | 158 |
| 15E12 | GAGGTGCAATTGGTTGAATCTGGTGGTGGTCTGGTAAAACCGGGCG<br>GTTCCCNGCGTCTGAGCTGCGCGGCTTCCGGATTCACCTTCTCCAA<br>CGCGTGGATGAGCTGGGTTCGCCAGGCCCCGGGCAAAGGCCTCGAG<br>TGGGTTGGTCGTATCAAGTCTAAAACTGACGGTGGCACCACGGATT<br>ACGCGGCTCCAGTTAAAGGTCGTTTTACCATTTCCCGCGACGATAG<br>CAAAAACACTCTGTATCTGCAGATGAACTCTCTGAAAACCGAAGAC<br>ACCGCAGTCTACTACTGTACTACCCCGTGGGAATGGTCTTACTTCG<br>ATTATTGGGGCCAGGGCACGCTGGTTACGGTGTCTTCC | 159 |
| 21D1 | CAGGTGCAATTGGTTCAATCTGGTGCTGAAGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCTCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCAACTACTACGTTGGTGTTTCTCCGTTCG<br>ACTATTGGGGTCAAGGCACCCTCGTAACGGTTTCTTCT | 160 |
| 16F12 | CAGGTGCAATTGGTTCAATCTGGTGCTGAAGTAAAAAAACCGGGCG<br>NTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCTCTACCTCNTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCAACTTCACTGTTCTGCGTGTTCCGTTCG<br>ACTATTGGGGTCAAGGCACCCTCGTAACGGTTTCTTCT | 161 |
| 21A5 | GAGGTGCAATTGGTTGAATCTGGTGGTGGTCTGGTAAAACCGGGCG<br>GTTCCCTGCGTCTGAGCTGCGCGGCTTCCGGATTCACCTTCTCCAA<br>CGCGTGGATGAGCTGGGTTCGCCAGGCCCCGGGCAAAGGCCTCGAG<br>TGGGTTGGTCGTATCAAGTCTAAAACTGACGGTGGCACCACGGATT<br>ACGCGGCTCCAGTTAAAGGTCGTTTTACCATTTCCCGCGACGATAG<br>CAAAAACACTCTGTATCTGCAGATGAACTCTCTGAAAACTGAAGAC<br>ACCGCAGTCTACTACTGTACTACCCCGTGGGAATGGGCTTGGTTCG<br>ATTATTGGGGCCAGGGCACGCTGGTTACGGTGTCTTCC | 162 |

| Description | Sequence | Seq ID No |
|---|---|---|
| 21G8 | GAGGTGCAATTGGTTGAATCTGGTGGTGGTCTGGTAAAACCGGGCG<br>GTTCCCTGCGTCTGAGCTGCGCGGCTTCCGGATTCACCTTCTCCAA<br>CGCGTGGATGAGCTGGGTTCGCCAGGCCCCGGGCAAAGGCCTCGAG<br>TGGGTTGGTCGTATCAAGTCTAAAACTGACGGTGGCACCACGGATT<br>ACGCGGCTCCAGTTAAAGGTCGTTTTACCATTTCCCGCGACGATAG<br>CAAAAACACTCTGTATCTGCAGATGAACTCTCTGAAAACCGAAGAC<br>ACCGCAGTCTACTACTGTACTACCCCTTGGGAATGGGCTTACTTCG<br>ATTATTGGGGCCAGGGCACGCTGGTTACGGTGTCTTCC | 163 |
| 19H3 | CAGGTGCAATTGGTTCAATCTGGTGCTGAAGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCTCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCACTGGTTGGTCTCGTTGGGGTTACATGG<br>ACTATTGGGGCCAAGGCACCCTCGTAACGGTTTCTTCT | 164 |
| 20G6 | CAGGTGCAATTGGTTCAATCTGGTGCTGAAGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCTCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCGGTAATGGATCCGTTACTACCATTTCG<br>ACTATTGGGTCAAGGCACCCTCGTAACGGTTTCTTCT | 165 |
| 20H7 | CAGGTGCAATTGGTTCAATCTGGTGCTGAAGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCTCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCGTTGGTTGGTACCGTTGGGGTTACATGG<br>ACTATTGGGTCAAGGCACCCTCGTAACGGTTTCTTCT | 166 |
| 11F8_VH | CAGGTGCAATTGGTGCAGTCTGGGGCTGAGGTGAAGAAGCCTGGGT<br>CCTCGGTGAAGGTCTCCTGCAAGGCCTCCGGAGGCACATTCAGCAG<br>CTACGCTATAAGCTGGGTGCGACAGGCCCCTGGACAAGGGCTCGAG<br>TGGATGGGAGGGATCATCCCTATCTTTGGTACAGCAAACTACGCAC<br>AGAAGTTCCAGGGCAGGGTAACCATTACTGCAGACAAATCCACGAG<br>CACAGCCTACATGGAGCTGAGCAGCCTGAGATCTGAGGACACCGCC<br>GTGTATTACTGTGCGAGAGCTGTTTTCTACCGTGCTTGGTACTCTT<br>TCGACTACTGGGGCCAAGGGACCACCGTGACCGTCTCCTCA | 167 |
| 11F8_VL | GACATCCAGATGACCCAGTCTCCTTCCACCCTGTCTGCATCTGTAG<br>GAGACCGTGTCACCATCACTTGCCGTGCCAGTCAGAGTATTAGTAG<br>CTGGTTGGCCTGGTATCAGCAGAAACCAGGGAAAGCCCCTAAGCTC<br>CTGATCTATGATGCCTCCAGTTTGGAAAGTGGGGTCCCATCACGTT<br>TCAGCGGCAGTGGATCCGGGACAGAATTCACTCTCACCATCAGCAG<br>CTTGCAGCCTGATGATTTTGCAACTTATTACTGCCAACAGTATACC<br>AGCCCACCACCAACGTTTGGCCAGGGCACCAAAGTCGAGATCAAG | 168 |
| 36F2_VH | CAGGTGCAATTGGTTCAATCTGGTGCTGAAGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCTCTACCTCCTACGCGC<br>AGAAATTCCAGGGTCGCGTCACGATGACCCATGACACTAGCACCTC<br>TACCGTTTATATGGAGCTGTCCAGCCTGCGTTCTGAAGATACTGCA<br>GTGTACTACTGTGCACGCTCTTTCTTCACTGGTTTCCATCTGGACT<br>ATTGGGGTCAAGGCACCCTCGTAACGGTTTCTTCT | 169 |
| 36F2_VL | GAAATCGTGTTAACGCAGTCTCCAGGCACCCTGTCTTTGTCTCCAG<br>GGGAAAGAGCCACCCTCTCTTGCAGGGCCAGTCAGAGTGTTAGCAG<br>CAGCTACTTAGCCTGGTACCAGCAGAAACCTGGCCAGGCTCCCAGG<br>CTCCTCATCTATGGAGCATCCAGCAGGGCCACTGGCATCCCAGACA<br>GGTTCAGTGGCAGTGGATCCGGGACAGACTTCACTCTCACCATCAG<br>CAGACTGGAGCCTGAAGATTTTGCAGTGTATTACTGTCAGCAGTAT<br>ACCAACGAACATTATTATACGTTCGGCCAGGGGACCAAAGTGGAAA<br>TCAAA | 170 |
| 9D11_VH | CAGGTGCAATTGGTTCAATCTGGTGCTGAAGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCCCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA | 171 |

| Description | Sequence | Seq ID No |
|---|---|---|
| | GTGTACTACTGTGCACGCGGTGACTTCGCTTGGCTGGACTATTGGG GTCAAGGCACCCTCGTAACGGTTTCTTCT | |
| 9D11_VL | GATATTGTTATGACTCAATCTCCACTGTCTCTGCCGGTGACTCCAG GCGAACCGGCGAGCATTTCTTGCCGTTCCAGCCAGTCTCTGCTGCA CTCCAACGGCTACAACTATCTCGATTGGTACCTGCAAAAACCGGGT CAGAGCCCTCAGCTGCTGATCTACCTGGGCTCTAACCGCGCTTCCG GTGTACCGGACCGTTTCAGCGGCTCTGGATCCGGCACCGATTTCAC GTTGAAAATCAGCCGTGTTGAAGCAGAAGACGTGGGCGTTTATTAC TGTATGCAGGCAAGCATTATGAACCGGACTTTTGGTCAAGGCACCA AGGTCGAAATTAAA | 172 |
| 9D11_VL N95S | GATATTGTTATGACTCAATCTCCACTGTCTCTGCCGGTGACTCCAG GCGAACCGGCGAGCATTTCTTGCCGTTCCAGCCAGTCTCTGCTGCA CTCCAACGGCTACAACTATCTCGATTGGTACCTGCAAAAACCGGGT CAGAGCCCTCAGCTGCTGATCTACCTGGGCTCTAACCGCGCTTCCG GTGTACCGGACCGTTTCAGCGGCTCTGGATCCGGCACCGATTTCAC GTTGAAAATCAGCCGTGTTGAAGCAGAAGACGTGGGCGTTTATTAC TGTATGCAGGCAAGCATTATGAGCCGGACTTTTGGTCAAGGCACCA AGGTCGAAATTAAA | 173 |
| 9D11_VL N95Q | GATATTGTTATGACTCAATCTCCACTGTCTCTGCCGGTGACTCCAG GCGAACCGGCGAGCATTTCTTGCCGTTCCAGCCAGTCTCTGCTGCA CTCCAACGGCTACAACTATCTCGATTGGTACCTGCAAAAACCGGGT CAGAGCCCTCAGCTGCTGATCTACCTGGGCTCTAACCGCGCTTCCG GTGTACCGGACCGTTTCAGCGGCTCTGGATCCGGCACCGATTTCAC GTTGAAAATCAGCCGTGTTGAAGCAGAAGACGTGGGCGTTTATTAC TGTATGCAGGCAAGCATTATGCAGCGGACTTTTGGTCAAGGCACCA AGGTCGAAATTAAA | 174 |
| 9D11_VL T97A | GATATTGTTATGACTCAATCTCCACTGTCTCTGCCGGTGACTCCAG GCGAACCGGCGAGCATTTCTTGCCGTTCCAGCCAGTCTCTGCTGCA CTCCAACGGCTACAACTATCTCGATTGGTACCTGCAAAAACCGGGT CAGAGCCCTCAGCTGCTGATCTACCTGGGCTCTAACCGCGCTTCCG GTGTACCGGACCGTTTCAGCGGCTCTGGATCCGGCACCGATTTCAC GTTGAAAATCAGCCGTGTTGAAGCAGAAGACGTGGGCGTTTATTAC TGTATGCAGGCAAGCATTATGAACCGGGCTTTTGGTCAAGGCACCA AGGTCGAAATTAAA | 175 |
| 9D11_VL T97N | GATATTGTTATGACTCAATCTCCACTGTCTCTGCCGGTGACTCCAG GCGAACCGGCGAGCATTTCTTGCCGTTCCAGCCAGTCTCTGCTGCA CTCCAACGGCTACAACTATCTCGATTGGTACCTGCAAAAACCGGGT CAGAGCCCTCAGCTGCTGATCTACCTGGGCTCTAACCGCGCTTCCG GTGTACCGGACCGTTTCAGCGGCTCTGGATCCGGCACCGATTTCAC GTTGAAAATCAGCCGTGTTGAAGCAGAAGACGTGGGCGTTTATTAC TGTATGCAGGCAAGCATTATGAACCGGAATTTTGGTCAAGGCACCA AGGTCGAAATTAAA | 176 |
| 5D9_VH | CAGGTGCAATTGGTTCAATCTGGTGCTGAAGTAAAAAAACCGGGCG CTTCCGTTAAAGTGAGCTGCAAAGCATCCGGATACACCTTCACTTC CTATTACATGCACTGGGTTCGTCAAGCCCCGGGCCAGGGTCTGGAA TGGATGGGCATCATTAACCCAAGCGGTGGCTCTACCTCCTACGCGC AGAAATTCCAGGGTCGCGTCACGATGACCCGTGACACTAGCACCTC TACCGTTTATATGGAGCTGTCCAGCCTGCGTTCTGAAGATACTGCA GTGTACTACTGTGCACGCTCTTACATCGACATGGACTATTGGGGTC AAGGCACCCTCGTAACGGTTTCTTCT | 177 |
| 5D9_VL | GAAATCGTGTTAACGCAGTCTCCAGGCACCCTGTCTTTGTCTCCAG GGGAAAGAGCCACCCTCTCTTGCAGGGCCAGTCAGAGTGTTAGCAG CAGCTACTTAGCCTGGTACCAGCAGAAACCTGGCCAGGCTCCCAGG CTCCTCATCTATGGAGCATCCAGCAGGGCCACTGGCATCCCAGACA GGTTCAGTGGCAGTGGATCCGGGACAGACTTCACTCTCACCATCAG CAGACTGGAGCCTGAAGATTTTGCAGTGTATTACTGTCAGCAGGAT AACTGGAGCCCAACGTTCGGCCAGGGGACCAAAGTGGAAATCAAA | 178 |
| 6B6_VH | CAGGTGCAATTGGTTCAATCTGGTGCTGAAGTAAAAAAACCGGGCG CTTCCGTTAAAGTGAGCTGCAAAGCATCCGGATACACCTTCACTTC CTATTACATGCACTGGGTTCGTCAAGCCCCGGGCCAGGGTCTGGAA TGGATGGGCATCATTAACCCAAGCGGTGGCTCTACCTCCTACGCGC AGAAATTCCAGGGTCGCGTCACGATGACCCGTGACACTAGCACCTC TACCGTTTATATGGAGCTGTCCAGCCTGCGTTCTGAAGATACTGCA GTGTACTACTGTGCACGCTCTTACGTTGACATGGACTATTGGGGTC AAGGCACCCTCGTAACGGTTTCTTCT | 179 |
| 6B6_VL | GAAATCGTGTTAACGCAGTCTCCAGGCACCCTGTCTTTGTCTCCAG GGGAAAGAGCCACCCTCTCTTGCAGGGCCAGTCAGAGTGTTAGCAG CAGCTACCTAGCCTGGTACCAGCAGAAACCTGGCCAGGCTCCCAGG | 180 |

| Description | Sequence | Seq ID No |
|---|---|---|
| | CTCCTCATCTATGGAGCATCCAGCAGGGCCACTGGCATCCCAGACA<br>GGTTCAGTGGCAGTGGATCCGGGACAGACTTCACTCTCACCATCAG<br>CAGACTGGAGCCTGAAGATTTTGCAGTGTATTACTGTCAGCAGGAT<br>ATTTGGAGCCCAACGTTCGGCCAGGGGACCAAAGTGGAAATCAAA | |
| 14E4_VH | GAGGTGCAATTGTTGGAGTCTGGGGGAGGCTTGGTACAGCCTGGGG<br>GGTCCCTGAGACTCTCCTGTGCAGCCTCCGGATTCACCTTTAGCAG<br>TTATGCCATGAGCTGGGTCCGCCAGGCTCCAGGGAAGGGGCTGGAG<br>TGGGTCTCAGCTATTAGTGGTAGTGGTGGTAGCACATACTACGCAG<br>ACTCCGTGAAGGGCCGGTTCACCATCTCCAGAGACAATTCCAAGAA<br>CACGCTGTATCTGCAGATGAACAGCCTGAGAGCCGAGGACACGGCC<br>GTATATTACTGTGCGAAAGACTCTTCTTACGTTGAATGGTACGCTT<br>TCGACTACTGGGGCCAAGGAACCCTGGTCACCGTCTCGAGT | 181 |
| 14E4_VL | GAAATCGTGTTAACGCAGTCTCCAGGCACCCTGTCTTTGTCTCCAG<br>GGGAAAGAGCCACCCTCTCTTGCAGGGCCAGTCAGAGTGTTAGCAG<br>CAGCTACTTAGCCTGGTACCAGCAGAAACCTGGCCAGGCTCCCAGG<br>CTCCTCATCTATGGAGCATCCAGCAGGGCCACTGGCATCCCAGACA<br>GGTTCAGTGGCAGTGGATCCGGGACAGACTCCACTCTCACCATCAG<br>CAGACTGGAGCCTGAAGATTTTGCAGTGTATTACTGTCAGCAGCCA<br>ACCAGCAGCCCAATTACGTTCGGCCAGGGGACCAAAGTGGAAATCA<br>AA | 182 |
| CD3 heavy<br>chain<br>(VHCH1) | GAGGTGCAGCTGCTGGAATCTGGCGGCGGACTGGTGCAGCCT<br>GGCGGATCTCTGAGACTGAGCTGTGCCGCCAGCGGCTTCACC<br>TTCAGCACCTACGCCATGAACTGGGTGCGCCAGGCCCCTGGC<br>AAAGGCCTGGAATGGGTGTCCCGGATCAGAAGCAAGTACAAC<br>AACTACGCCACCTACTACGCCGACAGCGTGAAGGGCCGGTTC<br>ACCATCAGCCGGGACGACAGCAAGAACACCCTGTACCTGCAG<br>ATGAACAGCCTGCGGGCCGAGGACACCGCCGTGTACTATTGT<br>GTGCGGCACGGCAACTTCGGCAACAGCTATGTGTCTTGGTTT<br>GCCTACTGGGGCCAGGGCACCCTCGTGACCGTGTCAAGCGCT<br>AGTACCAAGGGCCCCAGCGTGTTCCCCCTGGCACCCAGCAGC<br>AAGAGCACATCTGGCGGAACAGCCGCTCTGGGCTGTCTGGTG<br>AAAGACTACTTCCCCGAGCCCGTGACCGTGTCTTGGAACTCT<br>GGCGCCCTGACCAGCGGCGTGCACACCTTTCCAGCCGTGCTG<br>CAGAGCAGCGGCCTGTACTCCCTGTCCTCCGTGGTCACCGTG<br>CCCTCTAGCTCCCTGGGAACACAGACATATATCTGTAATGTC<br>AATCACAAGCCTTCCAACACCAAAGTCGATAAGAAAGTCGAG<br>CCCAAGAGCTGC | 183 |
| Crossed<br>CD3 heavy<br>chain<br>(VHCκ) | GAGGTGCAGCTGCTGGAATCTGGCGGCGGACTGGTGCAGCCTGGCG<br>GATCTCTGAGACTGAGCTGTGCCGCCAGCGGCTTCACCTTCAGCAC<br>CTACGCCATGAACTGGGTGCGCCAGGCCCCTGGCAAAGGCCTGGAA<br>TGGGTGTCCCGGATCAGAAGCAAGTACAACAACTACGCCACCTACT<br>ACGCCGACAGCGTGAAGGGCCGGTTCACCATCAGCCGGGACGACAG<br>CAAGAACACCCTGTACCTGCAGATGAACAGCCTGCGGGCCGAGGAC<br>ACCGCCGTGTACTATTGTGTGCGGCACGGCAACTTCGGCAACAGCT<br>ATGTGTCTTGGTTTGCCTACTGGGGCCAGGGCACCCTCGTGACCGT<br>GTCAAGCGCTAGTGTGGCCGCTCCCTCCGTGTTTATCTTTCCCCCA<br>TCCGATGAACAGCTGAAAAGCGGCACCGCCTCCGTCGTGTGTCTGC<br>TGAACAATTTTTACCCTAGGGAAGCTAAAGTGCAGTGGAAAGTGGA<br>TAACGCACTGCAGTCCGGCAACTCCCAGGAATCTGTGACAGAACAG<br>GACTCCAAGGACAGCACCTACTCCCTGTCCTCCACCCTGACACTGT<br>CTAAGGCTGATTATGAGAAACACAAAGTCTACGCCTGCGAAGTCAC<br>CCATCAGGGCCTGAGCTCGCCCGTCACAAAGAGCTTCAACAGGGGA<br>GAGTGT | 184 |
| Mutagenesis<br>primer<br>GAB7734<br>N95Q | GCAGGCAAGCATTATGCAGCGGACTTTTGGTCAAGG | 185 |
| Mutagenesis<br>primer<br>GAB7735<br>N95S | CAGGCAAGCATTATGAGCCGGACTTTTGGTCAAGG | 186 |
| Mutagenesis<br>primer<br>GAB7736<br>T97A | CATTATGAACCGGGCTTTTGGTCAAGGCACCAAGGTC | 187 |
| Mutagenesis<br>primer<br>GAB7737<br>T97N | CATTATGAACCGGAATTTTGGTCAAGGCACCAAGGTC | 188 |

| Description | Sequence | Seq ID No |
|---|---|---|
| VHCH1[16D5]_VHCH1[CD3]_Fcknob_PGLALA pCON999 (Inverted TCB with 16D5 2 + 1: pCON999 + pCON983 + pETR13197) | GAGGTGCAATTGGTTGAATCTGGTGGTGGTCTGGTAAAACCGGGCG GTTCCCTGCGTCTGAGCTGCGCGGCTTCCGGATTCACCTTCTCCAA CGCGTGGATGAGCTGGGTTCGCCAGGCCCCGGGCAAAGGCCTCGAG TGGGTTGGTCGTATCAAGTCTAAAACTGACGGTGGCACCACGGATT ACGCGGCTCCAGTTAAAGGTCGTTTTACCATTTCCCGCGACGATAG CAAAAACACTCTGTATCTGCAGATGAACTCTCTGAAAACTGAAGAC ACCGCAGTCTACTACTGTACTACCCCGTGGGAATGGTCTTGGTACG ATTATTGGGGCCAGGGCACGCTGGTTACGGTGTCTTCCGCTAGCAC AAAGGGCCCTAGCGTGTTCCCTCTGGCCCCCAGCAGCAAGAGCACA AGCGGCGGAACAGCCGCCCTGGGCTGCCTCGTGAAGGACTACTTCC CCGAGCCCGTGACAGTGTCTTGGAACAGCGGAGCCCTGACAAGCGG CGTGCACACTTTCCCTGCCGTCTGCAGAGCAGCGGCCTGTACTCC CTGAGCAGCGTGGTCACCGTGCCTAGCAGCAGCCTGGGCACCCAGA CCTACATCTGCAACGTGAACCACAAGCCCAGCAACACCAAAGTGGA CAAGAAGGTGGAGCCCAAGAGCTGTGATGGCGGAGGAGGGTCCGGA GGCGGAGGATCCGAGGTGCAGCTGCTGGAATCTGGCGGCGGACTGG TGCAGCCTGGCGGATCTCTGAGACTGAGCTGTGCCGCCAGCGGCTT CACCTTCAGCACCTACGCCATGAACTGGGTGCGCCAGGCCCCTGGC AAAGGCCTGGAATGGGTGTCCCGGATCAGAAGCAAGTACAACAACT ACGCCACCTACTACGCCGACAGCGTGAAGGGCCGGTTCACCATCAG CCGGGACGACAGCAAGAACACCCTGTACCTGCAGATGAACAGCCTG CGGGCCGAGGACACCGCCGTGTACTATTGTGTGCGGCACGGCAACT TCGGCAACAGCTATGTGTCTTGGTTTGCCTACTGGGGCCAGGGCAC CCTCGTGACCGTGTCAAGCGCTAGTACCAAGGGCCCCAGCGTGTTC CCCCTGGCACCCAGCAGCAAGAGCACATCTGGCGGAACAGCCGCTC TGGGCTGTCTGGTGAAAGACTACTTCCCCGAGCCCGTGACCGTGTC TTGGAACTCTGGCGCCCTGACCAGCGGCGTGCACACCTTTCCAGCC GTGCTGCAGAGCAGCGGCCTGTACTCCCTGTCCTCCGTGGTCACCG TGCCCTCTAGCTCCCTGGGAACACAGACATATATCTGTAATGTCAA TCACAAGCCTTCCAACACCAAAGTCGATAAGAAAGTCGAGCCCAAG AGCTGCGACAAAACTCACACATGCCCACCGTGCCCAGCACCTGAAG CTGCAGGGGGACCGTCAGTCTTCCTCTTCCCCCCAAAACCCAAGGA CACCCTCATGATCTCCCGGACCCCTGAGGTCACATGCGTGGTGGTG GACGTGAGCCACGAAGACCCTGAGGTCAAGTTCAACTGGTACGTGG ACGGCGTGGAGGTGCATAATGCCAAGACAAAGCCGCGGGAGGAGCA GTACAACAGCACGTACCGTGTGGTCAGCGTCCTCACCGTCCTGCAC CAGGACTGGCTGAATGGCAAGGAGTACAAGTGCAAGGTCTCCAACA AAGCCCTCGGCGCCCCCATCGAGAAAACCATCTCCAAAGCCAAAGG GCAGCCCCGAGAACCACAGGTGTACACCCTGCCCCCATGCCGGGAT GAGCTGACCAAGAACCAGGTCAGCCTGTGTGCTGGTCAAAGGCT TCTATCCCAGCGACATCGCCGTGGAGTGGGAGAGCAATGGGCAGCC GGAGAACAACTACAAGACCACGCCTCCCGTGCTGGACTCCGACGGC TCCTTCTTCCTCTACAGCAAGCTCACCGTGGACAAGAGCAGGTGGC AGCAGGGGAACGTCTTCTCATGCTCCGTGATGCATGAGGCTCTGCA CAACCACTACACGCAGAAGAGCCTCTCCCTGTCTCCGGGTAAA | 189 |
| VHCH1 [16D5]_Fchole_PGLALA_HYRF pCON983 | GAGGTGCAATTGGTTGAATCTGGTGGTGGTCTGGTAAAACCGGGCG GTTCCCTGCGTCTGAGCTGCGCGGCTTCCGGATTCACCTTCTCCAA CGCGTGGATGAGCTGGGTTCGCCAGGCCCCGGGCAAAGGCCTCGAG TGGGTTGGTCGTATCAAGTCTAAAACTGACGGTGGCACCACGGATT ACGCGGCTCCAGTTAAAGGTCGTTTTACCATTTCCCGCGACGATAG CAAAAACACTCTGTATCTGCAGATGAACTCTCTGAAAACTGAAGAC ACCGCAGTCTACTACTGTACTACCCCGTGGGAATGGTCTTGGTACG ATTATTGGGGCCAGGGCACGCTGGTTACGGTGTCTTCCGCTAGCAC CAAGGGCCCCTCCGTGTTCCCCCTGGCCCCCAGCAGCAAGAGCACC AGCGGCGGCACAGCCGCTCTGGGCTGCCTGGTCAAGGACTACTTCC CCGAGCCCGTGACCGTGTCCTGGAACAGCGGAGCCCTGACCTCCGG CGTGCACACCTTCCCCGCCGTGCTGCAGAGTTCTGGCCTGTATAGC CTGAGCAGCGTGGTCACCGTGCCTTCTAGCAGCCTGGGCACCCAGA CCTACATCTGCAACGTGAACCACAAGCCCAGCAACACCAAGGTGGA CAAGAAGGTGGAGCCCAAGAGCTGCGACAAAACTCACACATGCCCA CCGTGCCCAGCACCTGAAGCTGCAGGGGGACCGTCAGTCTTCCTCT TCCCCCCAAAACCCAAGGACACCCTCATGATCTCCCGGACCCCTGA GGTCACATGCGTGGTGGTGGACGTGAGCCACGAAGACCCTGAGGTC AAGTTCAACTGGTACGTGGACGGCGTGGAGGTGCATAATGCCAAGA CAAAGCCGCGGGAGGAGCAGTACAACAGCACGTACCGTGTGGTCAG CGTCCTCACCGTCCTGCACCAGGACTGGCTGAATGGCAAGGAGTAC AAGTGCAAGGTCTCCAACAAAGCCCTCGGCGCCCCCATCGAGAAAA CCATCTCCAAAGCCAAAGGGCAGCCCCGAGAACCACAGGTGTGCAC CCTGCCCCCATCCCGGGATGAGCTGACCAAGAACCAGGTCAGCCTC TCGTGCGCAGTCAAAGGCTTCTATCCCAGCGACATCGCCGTGGAGT GGGAGAGCAATGGGCAGCCGGAGAACAACTACAAGACCACGCCTCC CGTGCTGGACTCCGACGGCTCCTTCTTCCTCGTGAGCAAGCTCACC GTGGACAAGAGCAGGTGGCAGCAGGGGAACGTCTTCTCATGCTCCG TGATGCATGAGGCTCTGCACAACCGCTTCACGCAGAAGAGCCTCTC CCTGTCTCCGGGTAAA | 190 |

| Description | Sequence | Seq ID No |
|---|---|---|
| CD3_common light chain pETR1319 7 | CAGGCCGTCGTGACCCAGGAACCCAGCCTGACAGTGTCTCCTGGCG<br>GCACCGTGACCCTGACATGTGGCAGTTCTACAGGCGCCGTGACCAC<br>CAGCAACTACGCCAACTGGGTGCAGGAAAAGCCCGGCCAGGCCTTC<br>AGAGGACTGATCGGCGGCACCAACAAGAGAGCCCCTGGCACCCCTG<br>CCAGATTCAGCGGATCTCTGCTGGGAGGAAAGGCCGCCCTGACACT<br>GTCTGGCGCCCAGCCAGAAGATGAGGCCGAGTACTACTGCGCCCTG<br>TGGTACAGCAACCTGTGGGTGTTCGGCGGAGGCACCAAGCTGACAG<br>TCCTAGGTCAACCCAAGGCTGCCCCCAGCGTGACCCTGTTCCCCCC<br>CAGCAGCGAGGAACTGCAGGCCAACAAGGCCACCCTGGTCTGCCTG<br>ATCAGCGACTTCTACCCAGGCGCCGTGACCGTGGCCTGGAAGGCCG<br>ACAGCAGCCCCGTGAAGGCCGGCGTGGAGACCACCACCCCCAGCAA<br>GCAGAGCAACAACAAGTACGCCGCCAGCAGCTACCTGAGCCTGACC<br>CCCGAGCAGTGGAAGAGCCACAGGTCCTACAGCTGCCAGGTGACCC<br>ACGAGGGCAGCACCGTGGAGAAAACCGTGGCCCCCACCGAGTGCAG<br>C | 191 |
| VHCH1[CD 3]_VHCH1 [16D5]_Fck nob_PGLAL A pETR1393 2 (Classical TCB with 16D5; 2 + 1: pETR13932 + pCON983 + pETR13197) | GAGGTGCAGCTGCTGGAATCTGGCGGCGGACTGGTGCAGCCTGGCG<br>GATCTCTGAGACTGAGCTGTGCCGCCAGCGGCTTCACCTTCAGCAC<br>CTACGCCATGAACTGGGTGCGCCAGGCCCCTGGCAAAGGCCTGGAA<br>TGGGTGTCCCGGATCAGAAGCAAGTACAACAACTACGCCACCTACT<br>ACGCCGACAGCGTGAAGGGCCGGTTCACCATCAGCCGGGACGACAG<br>CAAGAACACCCTGTACCTGCAGATGAACAGCCTGCGGGCCGAGGAC<br>ACCGCCGTGTACTATTGTGTGCGGCACGGCAACTTCGGCAACAGCT<br>ATGTGTCTTGGTTTGCCTACTGGGGCCAGGGCACCCTCGTGACCGT<br>GTCATCTGCTAGCACAAAGGGCCCTAGCGTGTTCCCTCTGGCCCCC<br>AGCAGCAAGAGCACAAGCGGCGGAACAGCCGCCCTGGGCTGCCTCG<br>TGAAGGACTACTTCCCCGAGCCCGTGACAGTGTCTTGGAACAGCGG<br>AGCCCTGACAAGCGGCGTGCACACCTTCCCTGCCGTGCTGCAGAGC<br>AGCGGCCTGTACTCCCTGAGCAGCGTGGTCACCGTGCCTAGCAGCA<br>GCCTGGGCACCCAGACCTACATCTGCAACGTGAACCACAAGCCCAG<br>CAACACCAAAGTGGACAAGAAGGTGGAGCCCAAGAGCTGTGATGC<br>GGAGGAGGGTCCGGAGGCGGAGGATCCGAGGTGCAATTGGTTGAAT<br>CTGGTGGTGGTCTGGTAAAACCGGGCGGTTCCCTGCGTCTGAGCTG<br>CGCGGCTTCCGGATTCACCTTCTCCAACGCGTGGATGAGCTGGGTT<br>CGCCAGGCCCCGGGCAAAGGCCTCGAGTGGGTTGGTCGTATCAAGT<br>CTAAAACTGACGGTGGCACCACGGATTACGCGGCTCCAGTTAAAGG<br>TCGTTTTACCATTTCCCGCGACGATAGCAAAAACACTCTGTATCTG<br>CAGATGAACTCTCTGAAAACTGAAGACACCGCAGTCTACTACTGTA<br>CTACCCCGTGGGAATGGTCTTGGTACGATTATTGGGGCCAGGGCAC<br>GCTGGTTACGGTGTCTAGCGCTAGTACCAAGGGCCCCAGCGTGTTC<br>CCCCTGGCACCCAGCAGCAAGAGCACATCTGGCGGAACAGCCGCTC<br>TGGGCTGTCTGGTGAAAGACTACTTCCCCGAGCCCGTGACCGTGTC<br>TTGGAACTCTGGCGCCCTGACCAGCGGCGTGCACACCTTTCCAGCC<br>GTGCTGCAGAGCAGCGGCCTGTACTCCCTGTCCTCCGTGGTCACCG<br>TGCCCTCTAGCTCCCTGGGAACACAGACATATATCTGTAATGTCAA<br>TCACAAGCCTTCCAACACCAAAGTCGATAAGAAAGTCGAGCCCAAG<br>AGCTGCGACAAAACTCACACATGCCCACCGTGCCCAGCACCTGAAG<br>CTGCAGGGGGACCGTCAGTCTTCCTCTTCCCCCCAAAACCCAAGGA<br>CACCCTCATGATCTCCCGGACCCCTGAGGTCACATGCGTGGTGGTG<br>GACGTGAGCCACGAAGACCCTGAGGTCAAGTTCAACTGGTACGTGG<br>ACGGCGTGGAGGTGCATAATGCCAAGACAAAGCCGCGGGAGGAGCA<br>GTACAACAGCACGTACCGTGTGGTCAGCGTCCTCACCGTCCTGCAC<br>CAGGACTGGCTGAATGGCAAGGAGTACAAGTGCAAGGTCTCCAACA<br>AAGCCCTCGGCGCCCCCATCGAGAAAACCATCTCCAAAGCCAAAGG<br>GCAGCCCCGAGAACCACAGGTGTACACCCTGCCCCCATGCCGGGAT<br>GAGCTGACCAAGAACCAGGTCAGCCTGTGTGGTGCCTGGTCAAAGGCT<br>TCTATCCCAGCGACATCGCCGTGGAGTGGGAGAGCAATGGGCAGCC<br>GGAGAACAACTACAAGACCACGCCTCCCGTGCTGGACTCCGACGGC<br>TCCTTCTTCCTCTACAGCAAGCTCACCGTGGACAAGAGCAGGTGGC<br>AGCAGGGGAACGTCTTCTCATGCTCCGTGATGCATGAGGCTCTGCA<br>CAACCACTACACGCAGAAGAGCCTCTCCCTGTCTCCGGGTAAA | 192 |
| VHCH 1 [CD 3]_Fcknob_ PGLALA pETR1371 9 (16D5 IgG format, 1 + 1: pETR13719 + pCON983 + pETR13197) | GAGGTGCAGCTGCTGGAATCTGGCGGCGGACTGGTGCAGCCTGGCG<br>GATCTCTGAGACTGAGCTGTGCCGCCAGCGGCTTCACCTTCAGCAC<br>CTACGCCATGAACTGGGTGCGCCAGGCCCCTGGCAAAGGCCTGGAA<br>TGGGTGTCCCGGATCAGAAGCAAGTACAACAACTACGCCACCTACT<br>ACGCCGACAGCGTGAAGGGCCGGTTCACCATCAGCCGGGACGACAG<br>CAAGAACACCCTGTACCTGCAGATGAACAGCCTGCGGGCCGAGGAC<br>ACCGCCGTGTACTATTGTGTGCGGCACGGCAACTTCGGCAACAGCT<br>ATGTGTCTTGGTTTGCCTACTGGGGCCAGGGCACCCTCGTGACCGT<br>GTCATCTGCTAGCACCAAGGGCCCATCGGTCTTCCCCCTGGCACCC<br>TCCTCCAAGAGCACCTCTGGGGGCACAGCGGCCCTGGGCTGCCTGG<br>TCAAGGACTACTTCCCCGAACCGGTGACGGTGTCGTGGAACTCAGG<br>CGCCCTGACCAGCGGCGTGCACACCTTCCCGGCTGTCCTACAGTCC<br>TCAGGACTCTACTCCCTCAGCAGCGTGGTGACCGTGCCCTCCAGCA<br>GCTTGGGCACCCAGACCTACATCTGCAACGTGAATCACAAGCCCAG | 193 |

-continued

| Description | Sequence | Seq ID No |
|---|---|---|
| | CAACACCAAGGTGGACAAGAAAGTTGAGCCCAAATCTTGTGACAAA<br>ACTCACACATGCCCACCGTGCCCAGCACCTGAAGCTGCAGGGGGAC<br>CGTCAGTCTTCCTCTTCCCCCCAAAACCCAAGGACACCCTCATGAT<br>CTCCCGGACCCCTGAGGTCACATGCGTGGTGGTGGACGTGAGCCAC<br>GAAGACCCTGAGGTCAAGTTCAACTGGTACGTGGACGGCGTGGAGG<br>TGCATAATGCCAAGACAAAGCCGCGGGAGGAGCAGTACAACAGCAC<br>GTACCGTGTGGTCAGCGTCCTCACCGTCCTGCACCAGGACTGGCTG<br>AATGGCAAGGAGTACAAGTGCAAGGTCTCCAACAAAGCCCTCGGCG<br>CCCCCATCGAGAAAACCATCTCCAAAGCCAAAGGGCAGCCCCGAGA<br>ACCACAGGTGTACACCCTGCCCCCATGCCGGGATGAGCTGACCAAG<br>AACCAGGTCAGCCTGTGGTGCCTGGTCAAAGGCTTCTATCCCAGCG<br>ACATCGCCGTGGAGTGGGAGAGCAATGGGCAGCCGGAGAACAACTA<br>CAAGACCACGCCTCCCGTGCTGGACTCCGACGGCTCCTTCTTCCTC<br>TACAGCAAGCTCACCGTGGACAAGAGCAGGTGGCAGCAGGGGAACG<br>TCTTCTCATGCTCCGTGATGCATGAGGCTCTGCACAACCACTACAC<br>GCAGAAGAGCCTCTCCCTGTCTCCGGGTAAA | |
| Fc_hole_PG<br>LALA_HYR<br>F<br>pETR1075<br>5<br>(16D5 Head-<br>to-tail, 1 + 1:<br>pCON999 +<br>pETR10755 +<br>pETR13197) | GACAAAACTCACACATGCCCACCGTGCCCAGCACCTGAACTCCTGG<br>GGGGACCGTCAGTCTTCCTCTTCCCCCCAAAACCCAAGGACACCCT<br>CATGATCTCCCGGACCCCTGAGGTCACATGCGTGGTGGTGGACGTG<br>AGCCACGAAGACCCTGAGGTCAAGTTCAACTGGTACGTGGACGGCG<br>TGGAGGTGCATAATGCCAAGACAAAGCCGCGGGAGGAGCAGTACAA<br>CAGCACGTACCGTGTGGTCAGCGTCCTCACCGTCCTGCACCAGGAC<br>TGGCTGAATGGCAAGGAGTACAAGTGCAAGGTCTCCAACAAAGCCC<br>TCCCAGCCCCCATCGAGAAAACCATCTCCAAAGCCAAAGGGCAGCC<br>CCGAGAACCACAGGTGTGCACCCTGCCCCCATCCCGGGATGAGCTG<br>ACCAAGAACCAGGTCAGCCTCTCGTGCGCAGTCAAAGGCTTCTATC<br>CCAGCGACATCGCCGTGGAGTGGGAGAGCAATGGGCAGCCGGAGAA<br>CAACTACAAGACCACGCCTCCCGTGCTGGACTCCGACGGCTCCTTC<br>TTCCTCGTGAGCAAGCTCACCGTGGACAAGAGCAGGTGGCAGCAGG<br>GGAACGTCTTCTCATGCTCCGTGATGCATGAGGCTCTGCACAACCG<br>CTTCACGCAGAAGAGCCTCTCCCTGTCTCCGGGTAAA | 194 |
| VHCH1[9D<br>11]_VHCL[<br>CD3]_Fckn<br>ob_PGLALA<br>pCON1057<br>(9D11<br>inverted<br>format, 2 + 1:<br>pCON1057 +<br>pCON1051 +<br>pCON1063 +<br>pETR12940) | CAGGTGCAATTGGTTCAATCTGGTGCTGAAGTAAAAAAACCGGGCG<br>CTTCCGTTAAAGTGAGCTGCAAAGCATCCGGATACACCTTCACTTC<br>CTATTACATGCACTGGGTCGTCAAGCCCCGGGCCAGGGTCTGGAA<br>TGGATGGGCATCATTAACCCAAGCGGTGGCCCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCGGTGACTTCGCTTGGCTGGACTATTGGG<br>GTCAAGGCACCCTCGTAACGGTTTCTTCTGCTAGCACAAAGGGCCC<br>CAGCGTGTTCCCTCTGGCCCCTAGCAGCAAGAGCACATCGGCGGA<br>ACAGCCGCCCTGGGCTGCCTCGTGAAGGACTACTTTCCCGAGCCTG<br>TGACCGTGTCCTGGAACTCTGGCGCCCTGACAAGCGGCGTGCACAC<br>CTTTCCAGCCGTGCTGCAGAGCAGCGGCCTGTACTCTCTGAGCAGC<br>GTGGTCACCGTGCCTAGCAGCAGCCTGGGCACCCAGACCTACATCT<br>GCAACGTGAACCACAAGCCCAGCAACACCAAAGTGGACAAGAAGGT<br>GGAGCCCAAGAGCTGTGATGGCGGAGGAGGGTCCGGAGGCGGAGGA<br>TCCGAGGTGCAGCTGCTGGAATCTGGCGGCGGACTGGTGCAGCCTG<br>GCGGATCTCTGAGACTGAGCTGTGCCGCCAGCGGCTTCACCTTCAG<br>CACCTACGCCATGAACTGGGTGCGCCAGGCCCCTGGCAAAGGCCTG<br>GAATGGGTGTCCCGGATCAGAAGCAAGTACAACAACTACGCCACCT<br>ACTACGCCGACAGCGTGAAGGGCCGGTTCACCATCAGCCGGGACGA<br>CAGCAAGAACACCCTGTACCTGCAGATGAACAGCCTGCGGGCCGAG<br>GACACCGCCGTGTACTATTGTGCGGCACGGCAACTTCGGCAACA<br>GCTATGTGTCTTGGTTTGCCTACTGGGGCCAGGGCACCCTCGTGAC<br>CGTGTCAAGCGCTAGTGTGGCCGCTCCCTCCGTGTTTATCTTTCCC<br>CCATCCGATGAACAGCTGAAAAGCGGCACCGCCTCCGTCGTGTGTC<br>TGCTGAACAATTTTTACCCTAGGGAAGCTAAAGTGCAGTGGAAAGT<br>GGATAACGCACTGCAGTCCGGCAACTCCCAGGAATCTGTGACAGAA<br>CAGGACTCCAAGGACAGCACCTACTCCCTGTCCTCCACCCTGACAC<br>TGTCTAAGGCTGATTATGAGAAACACAAAGTCTACGCCTGCGAAGT<br>CACCCATCAGGGCCTGAGCTCGCCCGTCACAAAGAGCTTCAACAGG<br>GGAGAGTGTGACAAGACCCACACCTGTCCCCTTGTCCTGCCCCTG<br>AAGCTGCTGGCGGCCCTTCTGTGTTCCTGTTCCCCCCAAAGCCCAA<br>GGACACCCTGATGATCAGCCGGACCCCCGAAGTGACCTGCGTGGTG<br>GTGGATGTGTCCCACGAGGACCCTGAAGTGAAGTTCAATTGGTACG<br>TGGACGGCGTGGAAGTGCACAACGCCAAGACAAAGCCGCGGGAGGA<br>GCAGTACAACAGCACGTACCGTGTGGTCAGCGTCCTCACCGTCCTG<br>CACCAGGACTGGCTGAATGGCAAGGAGTACAAGTGCAAGGTCTCCA<br>ACAAAGCCCTCGGCGCCCCCATCGAGAAAACCATCTCCAAAGCCAA<br>AGGGCAGCCCCGAGAACCACAGGTGTACACCCTGCCCCCATGCCGG<br>GATGAGCTGACCAAGAACCAGGTCAGCCTGTGGTGCCTGGTCAAAG | 195 |

| Description | Sequence | Seq ID No |
|---|---|---|
| | GCTTCTATCCCAGCGACATCGCCGTGGAGTGGGAGAGCAATGGGCA<br>GCCGGAGAACAACTACAAGACCACGCCTCCCGTGCTGGACTCCGAC<br>GGCTCCTTCTTCCTCTACAGCAAGCTCACCGTGGACAAGAGCAGGT<br>GGCAGCAGGGGAACGTCTTCTCATGCTCCGTGATGCATGAGGCTCT<br>GCACAACCACTACACGCAGAAGAGCCTCTCCCTGTCTCCGGGTAAA | |
| 9D11_Fcho<br>le_PGLALA_<br>HYRF<br>PCON1051 | CAGGTGCAATTGGTTCAATCTGGTGCTGAAGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGAA<br>TGGATGGGCATCATTAACCCAAGCGGTGGCCCTACCTCCTACGCGC<br>AGAAATTCCAGGGTCGCGTCACGATGACCCGTGACACTAGCACCTC<br>TACCGTTTATATGGAGCTGTCCAGCCTGCGTTCTGAAGATACTGCA<br>GTGTACTACTGTGCACGCGGTGACTTCGCTTGGCTGGACTATTGGG<br>GTCAAGGCACCCTCGTAACGGTTTCTTCTGCTAGCACCAAGGGCCC<br>CTCCGTGTTCCCCCTGGCCCCCAGCAGCAAGAGCACCAGCGGCGGC<br>ACAGCCGCTCTGGGCTGCCTGGTCAAGGACTACTTCCCCGAGCCCG<br>TGACCGTGTCCTGGAACAGCGGAGCCCTGACCTCCGGCGTGCACAC<br>CTTCCCCGCCGTGCTGCAGAGTTCTGGCCTGTATAGCCTGAGCAGC<br>GTGGTCACCGTGCCTTCTAGCAGCCTGGGCACCCAGACCTACATCT<br>GCAACGTGAACCACAAGCCCAGCAACACCAAGGTGGACAAGAAGGT<br>GGAGCCCAAGAGCTGCGACAAAACTCACACATGCCCACCGTGCCCA<br>GCACCTGAAGCTGCAGGGGGACCGTCAGTCTTCCTCTTCCCCCCAA<br>AACCCAAGGACACCCTCATGATCTCCCGGACCCCTGAGGTCACATG<br>CGTGGTGGTGGACGTGAGCCACGAAGACCCTGAGGTCAAGTTCAAC<br>TGGTACGTGGACGGCGTGGAGGTGCATAATGCCAAGACAAAGCCGC<br>GGGAGGAGCAGTACAACAGCACGTACCGTGTGGTCAGCGTCCTCAC<br>CGTCCTGCACCAGGACTGGCTGAATGGCAAGGAGTACAAGTGCAAG<br>GTCTCCAACAAAGCCCTCGGCGCCCCCATCGAGAAAACCATCTCCA<br>AAGCCAAAGGGCAGCCCCGAGAACCACAGGTGTGCACCCTGCCCCC<br>ATCCCGGGATGAGCTGACCAAGAACCAGGTCAGCCTCTCGTGCGCA<br>GTCAAAGGCTTCTATCCCAGCGACATCGCCGTGGAGTGGGAGAGCA<br>ATGGGCAGCCGGAGAACAACTACAAGACCACGCCTCCCGTGCTGGA<br>CTCCGACGGCTCCTTCTTCCTCGTGAGCAAGCTCACCGTGGACAAG<br>AGCAGGTGGCAGCAGGGGAACGTCTTCTCATGCTCCGTGATGCATG<br>AGGCTCTGCACAACCACTACACGCAGAAGAGCCTCTCCCTGTCTCC<br>GGGTAAA | 196 |
| 9D11_LC<br>pCON1063 | GATATTGTTATGACTCAATCTCCACTGTCTCTGCCGGTGACTCCAG<br>GCGAACCGGCGAGCATTTCTTGCCGTTCCAGCCAGTCTCTGCTGCA<br>CTCCAACGGCTACAACTATCTCGATTGGTACCTGCAAAAACCGGGT<br>CAGAGCCCTCAGCTGCTGATCTACCTGGGCTCTAACCGCGCTTCCG<br>GTGTACCGGACCGTTTCAGCGGCTCTGGATCCGGCACCGATTTCAC<br>GTTGAAAATCAGCCGTGTTGAAGCAGAAGACGTGGGCGTTTATTAC<br>TGTATGCAGGCAAGCATTATGAACCGGACTTTTGGTCAAGGCACCA<br>AGGTCGAAATTAAACGTACGGTGGCTGCCACCATCTGTCTTCATCTT<br>CCCGCCATCTGATGAGCAGTTGAAATCTGGAACTGCCTCTGTTGTG<br>TGCCTGCTGAATAACTTCTATCCCAGAGAGGCCAAAGTACAGTGGA<br>AGGTGGATAACGCCCTCCAATCGGGTAACTCCCAGGAGAGTGTCAC<br>AGAGCAGGACAGCAAGGACAGCACCTACAGCCTCAGCAGCACCCTG<br>ACGCTGAGCAAAGCAGACTACGAGAAACACAAAGTCTACGCCTGCG<br>AAGTCACCCATCAGGGCCTGAGCTCGCCCGTCACAAAGAGCTTCAA<br>CAGGGGAGAGTGT | 197 |
| VLCH1[CD<br>3]<br>nETR12940 | CAGGCCGTCGTGACCCAGGAACCCAGCCTGACAGTGTCTCCTGGCG<br>GCACCGTGACCCTGACATGTGGCAGTTCTACAGGCGCCGTGACCAC<br>CAGCAACTACGCCAACTGGGTGCAGGAAAAGCCCGGCCAGGCCTTC<br>AGAGGACTGATCGGCGGCACCAACAAGAGAGCCCCTGGCACCCCTG<br>CCAGATTCAGCGGATCTCTGCTGGGAGGAAAGGCCGCCCTGACACT<br>GTCTGGCGCCCAGCCAGAAGATGAGGCCGAGTACTACTGCGCCCTG<br>TGGTACAGCAACCTGTGGGTGTTCGGCGGAGGCACCAAGCTGACAG<br>TGCTGAGCAGCGCTTCCACCAAAGGCCCTTCCGTGTTTCCTCTGGC<br>TCCTAGCTCCAAGTCCACCTCTGGAGGCACCGCTGCTCTCGGATGC<br>CTCGTGAAGGATTATTTTCCTGAGCCTGTGACAGTGTCCTGGAATA<br>GCGGAGCACTGACCTCTGGAGTGCATACTTTCCCCGCTGTGCTGCA<br>GTCCTCTGGACTGTACAGCCTGAGCAGCGTGGTGACAGTGCCCAGC<br>AGCAGCCTGGGCACCCAGACCTACATCTGCAACGTGAACCACAAGC<br>CCAGCAACACCAAGGTGGACAAGAAGGTGGAACCCAAGTCTTGT | 198 |
| VHCL[CD3]<br>_Fcknob_P<br>GLALA<br>pETR1337<br>8 (9D11<br>CrossMab<br>format, 1 + 1:<br>pETR13378 +<br>pCON1051 + | GAGGTGCAGCTGCTGGAATCTGGCGGCGGACTGGTGCAGCCTGGCG<br>GATCTCTGAGACTGAGCTGTGCCGCCAGCGGCTTCACCTTCAGCAC<br>CTACGCCATGAACTGGGTGCGCCAGGCCCCTGGCAAAGGCCTGGAA<br>TGGGTGTCCCGGATCAGAAGCAAGTACAACAACTACGCCACCTACT<br>ACGCCGACAGCGTGAAGGGCCGGTTCACCATCAGCCGGGACGACAG<br>CAAGAACACCCTGTACCTGCAGATGAACAGCCTGCGGGCCGAGGAC<br>ACCGCCGTGTACTATTGTGTGCGGCACGGCAACTTCGGCAACAGCT<br>ATGTGTCTTGGTTTGCCTACTGGGGCCAGGGCACCCTCGTGACCGT<br>GTCATCTGCTAGCGTGGCCGCTCCCTCCGTGTTTATCTTTCCCCCA | 199 |

| Description | Sequence | Seq ID No |
|---|---|---|
| pCON1063 + pETR12940) | TCCGATGAACAGCTGAAAAGCGGCACCGCCTCCGTCGTGTGTCTGC<br>TGAACAATTTTTACCCTAGGGAAGCTAAAGTGCAGTGGAAAGTGGA<br>TAACGCACTGCAGTCCGGCAACTCCCAGGAATCTGTGACAGAACAG<br>GACTCCAAGGACAGCACCTACTCCCTGTCCTCCACCCTGACACTGT<br>CTAAGGCTGATTATGAGAAACACAAAGTCTACGCCTGCGAAGTCAC<br>CCATCAGGGCCTGAGCTCGCCCGTCACAAAGAGCTTCAACAGGGGA<br>GAGTGTGACAAGACCCACACCTGTCCCCCTTGTCCTGCCCCTGAAG<br>CTGCTGGCGGCCCTTCTGTGTTCCTGTTCCCCCCAAAGCCCAAGGA<br>CACCCTGATGATCAGCCGGACCCCCGAAGTGACCTGCGTGGTGGTG<br>GATGTGTCCCACGAGGACCCTGAAGTGAAGTTCAATTGGTACGTGG<br>ACGGCGTGGAAGTGCACAACGCCAAGACAAAGCCGCGGGAGGAGCA<br>GTACAACAGCACGTACCGTGTGGTCAGCGTCCTCACCGTCCTGCAC<br>CAGGACTGGCTGAATGGCAAGGAGTACAAGTGCAAGGTCTCCAACA<br>AAGCCCTCGGCGCCCCCATCGAGAAAACCATCTCCAAAGCCAAAGG<br>GCAGCCCCGAGAACCACAGGTGTACACCCTGCCCCCATGCCGGGAT<br>GAGCTGACCAAGAACCAGGTCAGCCTGTGGTGCCTGGTCAAAGGCT<br>TCTATCCCAGCGACATCGCCGTGGAGTGGGAGAGCAATGGGCAGCC<br>GGAGAACAACTACAAGACCACGCCTCCCGTGCTGGACTCCGACGGC<br>TCCTTCTTCCTCTACAGCAAGCTCACCGTGGACAAGAGCAGGTGGC<br>AGCAGGGGAACGTCTTCTCATGCTCCGTGATGCATGAGGCTCTGCA<br>CAACCACTACACGCAGAAGAGCCTCTCCCTGTCTCCGGGTAAA | |
| 16D5 inverted 2 + 1 with N100A in CDR H3 pETR14096 (pETR14096 + pCON983 + pETR13197) | GAGGTGCAATTGGTTGAATCTGGTGGTGGTCTGGTAAAACCGGGCG<br>GTTCCCTGCGTCTGAGCTGCGCGGCTTCCGGATTCACCTTCTCCAA<br>CGCGTGGATGAGCTGGGTTCGCCAGGCCCCGGGCAAAGGCCTCGAG<br>TGGGTTGGTCGTATCAAGTCTAAAACTGACGGTGGCACCACGGATT<br>ACGCGGCTCCAGTTAAAGGTCGTTTTACCATTTCCCGCGACGATAG<br>CAAAAACACTCTGTATCTGCAGATGAACTCTCTGAAAACTGAAGAC<br>ACCGCAGTCTACTACTGTACTACCCCGTGGGAATGGTCTTGGTACG<br>ATTATTGGGGCCAGGGCACGCTGGTTACGGTGTCTTCCGCTAGCAC<br>AAAGGGCCCTAGCGTGTTCCCTCTGGCCCCCAGCAGCAAGAGCACA<br>AGCGGCGGAACAGCCGCCCTGGGCTGCCTCGTGAAGGACTACTTCC<br>CCGAGCCCGTGACAGTGTCTTGGAACAGCGGAGCCCTGACAAGCGG<br>CGTGCACACTTTCCCTGCCGTGCTGCAGAGCAGCGGCCTGTACTCC<br>CTGAGCAGCGTGGTCACCGTGCCTAGCAGCAGCCTGGGCACCCAGA<br>CCTACATCTGCAACGTGAACCACAAGCCCAGCAACACCAAAGTGGA<br>CAAGAAGGTGGAGCCCAAGAGCTGTGATGGCGGAGGAGGGTCCGGA<br>GGCGGAGGATCCGAGGTGCAGCTGCTGGAATCTGGCGGCGGACTGG<br>TGCAGCCTGGCGGATCTCTGAGACTGAGCTGTGCCGCCAGCGGCTT<br>CACCTTCAGCACCTACGCCATGAACTGGGTGCGCCAGGCCCCTGGC<br>AAAGGCCTGGAATGGGTGTCCCGGATCAGAAGCAAGTACAACAACT<br>ACGCCACCTACTACGCCGACAGCGTGAAGGGCCGGTTCACCATCAG<br>CCGGGACGACAGCAAGAACACCCTGTACCTGCAGATGAACAGCCTG<br>CGGGCCGAGGACACCGCCGTGTACTATTGTGTGCGGCACGGCAACT<br>TCGGCGCCAGCTATGTGTCTTGGTTTGCCTACTGGGGCCAGGGCAC<br>CCTCGTGACCGTGTCAAGCGCTAGTACCAAGGGCCCCAGCGTGTTC<br>CCCCTGGCACCCAGCAGCAAGAGCACATCTGGCGGAACAGCCGCTC<br>TGGGCTGTCTGGTGAAAGACTACTTCCCCGAGCCCGTGACCGTGTC<br>TTGGAACTCTGGCGCCCTGACCAGCGGCGTGCACACCTTTCCAGCC<br>GTGCTGCAGAGCAGCGGCCTGTACTCCCTGTCCTCCGTGGTCACCG<br>TGCCCTCTAGCTCCCTGGGAACACAGACATATATCTGTAATGTCAA<br>TCACAAGCCTTCCAACACCAAAGTGCGATAAGAAAGTCGAGCCCAAG<br>AGCTGCGACAAAACTCACACATGCCCACCGTGCCCAGCACCTGAAG<br>CTGCAGGGGGACCGTCAGTCTTCCTCTTCCCCCCAAAACCCAAGGA<br>CACCCTCATGATCTCCCGGACCCCTGAGGTCACATGCGTGGTGGTG<br>GACGTGAGCCACGAAGACCCTGAGGTCAAGTTCAACTGGTACGTGG<br>ACGGCGTGGAGGTGCATAATGCCAAGACAAAGCCGCGGGAGGAGCA<br>GTACAACAGCACGTACCGTGTGGTCAGCGTCCTCACCGTCCTGCAC<br>CAGGACTGGCTGAATGGCAAGGAGTACAAGTGCAAGGTCTCCAACA<br>AAGCCCTCGGCGCCCCCATCGAGAAAACCATCTCCAAAGCCAAAGG<br>GCAGCCCCGAGAACCACAGGTGTACACCCTGCCCCCATGCCGGGAT<br>GAGCTGACCAAGAACCAGGTCAGCCTGTGGTGCCTGGTCAAAGGCT<br>TCTATCCCAGCGACATCGCCGTGGAGTGGGAGAGCAATGGGCAGCC<br>GGAGAACAACTACAAGACCACGCCTCCCGTGCTGGACTCCGACGGC<br>TCCTTCTTCCTCTACAGCAAGCTCACCGTGGACAAGAGCAGGTGGC<br>AGCAGGGGAACGTCTTCTCATGCTCCGTGATGCATGAGGCTCTGCA<br>CAACCACTACACGCAGAAGAGCCTCTCCCTGTCTCCGGGTAAA | 200 |
| 16D5 inverted 2 + 1 with S100aA in CDR H3 pETR14097 (pETR14097 + pCON983 + | GAGGTGCAATTGGTTGAATCTGGTGGTGGTCTGGTAAAACCGGGCG<br>GTTCCCTGCGTCTGAGCTGCGCGGCTTCCGGATTCACCTTCTCCAA<br>CGCGTGGATGAGCTGGGTTCGCCAGGCCCCGGGCAAAGGCCTCGAG<br>TGGGTTGGTCGTATCAAGTCTAAAACTGACGGTGGCACCACGGATT<br>ACGCGGCTCCAGTTAAAGGTCGTTTTACCATTTCCCGCGACGATAG<br>CAAAAACACTCTGTATCTGCAGATGAACTCTCTGAAAACTGAAGAC<br>ACCGCAGTCTACTACTGTACTACCCCGTGGGAATGGTCTTGGTACG<br>ATTATTGGGGCCAGGGCACGCTGGTTACGGTGTCTTCCGCTAGCAC<br>AAAGGGCCCTAGCGTGTTCCCTCTGGCCCCCAGCAGCAAGAGCACA | 201 |

| Description | Sequence | Seq ID No |
|---|---|---|
| pETR13197) | AGCGGCGGAACAGCCGCCCTGGGCTGCCTCGTGAAGGACTACTTCC<br>CCGAGCCCGTGACAGTGTCTTGGAACAGCGGAGCCCTGACAAGCGG<br>CGTGCACACTTTCCCTGCCGTGCTGCAGAGCAGCGGCCTGTACTCC<br>CTGAGCAGCGTGGTCACCGTGCCTAGCAGCAGCCTGGGCACCCAGA<br>CCTACATCTGCAACGTGAACCACAAGCCCAGCAACACCAAAGTGGA<br>CAAGAAGGTGGAGCCCAAGAGCTGTGATGGCGGAGGAGGGTCCGGA<br>GGCGGAGGATCCGAGGTGCAGCTGCTGGAATCTGGCGGCGGACTGG<br>TGCAGCCTGGCGGATCTCTGAGACTGAGCTGTGCCGCCAGCGGCTT<br>CACCTTCAGCACCTACGCCATGAACTGGGTGCGCCAGGCCCCTGGC<br>AAAGGCCTGGAATGGGTGTCCCGGATCAGAAGCAAGTACAACAACT<br>ACGCCACCTACTACGCCGACAGCGTGAAGGGCCGGTTCACCATCAG<br>CCGGGACGACAGCAAGAACACCCTGTACCTGCAGATGAACAGCCTG<br>CGGGCCGAGGACACCGCCGTGTACTATTGTGTGCGGCACGGCAACT<br>TCGGCAACGCCTATGTGTCTTGGTTTGCCTACTGGGGCCAGGGCAC<br>CCTCGTGACCGTGTCAAGCGCTAGTACCAAGGGCCCCAGCGTGTTC<br>CCCCTGGCACCCAGCAGCAAGAGCACATCTGGCGGAACAGCCGCTC<br>TGGGCTGTCTGGTGAAAGACTACTTCCCCGAGCCCGTGACCGTGTC<br>TTGGAACTCTGGCGCCCTGACCAGCGGCGTGCACACCTTTCCAGCC<br>GTGCTGCAGAGCAGCGGCCTGTACTCCCTGTCCTCCGTGGTCACCG<br>TGCCCTCTAGCTCCCTGGGAACACAGACATATATCTGTAATGTCAA<br>TCACAAGCCTTCCAACACCAAAGTCGATAAGAAAGTCGAGCCCAAG<br>AGCTGCGACAAAACTCACACATGCCCACCGTGCCCAGCACCTGAAG<br>CTGCAGGGGACCGTCAGTCTTCCTCTTCCCCCCAAAACCCAAGGA<br>CACCCTCATGATCTCCCGGACCCCTGAGGTCACATGCGTGGTGGTG<br>GACGTGAGCCACGAAGACCCTGAGGTCAAGTTCAACTGGTACGTGG<br>ACGGCGTGGAGGTGCATAATGCCAAGACAAAGCCGCGGGAGGAGCA<br>GTACAACAGCACGTACCGTGTGGTCAGCGTCCTCACCGTCCTGCAC<br>CAGGACTGGCTGAATGGCAAGGAGTACAAGTGCAAGGTCTCCAACA<br>AAGCCCTCGGCGCCCCCATCGAGAAAACCATCTCCAAAGCCAAAGG<br>GCAGCCCCGAGAACCACAGGTGTACACCCTGCCCCCATGCCGGGAT<br>GAGCTGACCAAGAACCAGGTCAGCCTGACCTGCCTGGTCAAAGGCT<br>TCTATCCCAGCGACATCGCCGTGGAGTGGGAGAGCAATGGGCAGCC<br>GGAGAACAACTACAAGACCACGCCTCCCGTGCTGGACTCCGACGGC<br>TCCTTCTTCCTCTACAGCAAGCTCACCGTGGACAAGAGCAGGTGGC<br>AGCAGGGGAACGTCTTCTCATGCTCCGTGATGCATGAGGCTCTGCA<br>CAACCACTACACGCAGAAGAGCCTCTCCCTGTCTCCGGGTAAA | |
| CD3 light chain fused to CH1; Fc_PGLALA; pETR1386 2 (Kappa-lambda antibody with CD3 common light chain fused to CH1 + Fc_PGLALA. VHs fused to kappa or lambda constant chain pETR13859 + pETR13860 + pETR13862) | CAGGCCGTCGTGACCCAGGAACCCAGCCTGACAGTGTCTCCTGGCG<br>GCACCGTGACCCTGACATGTGGCAGTTCTACAGGCGCCGTGACCAC<br>CAGCAACTACGCCAACTGGGTGCAGGAAAAGCCCGGCCAGGCCTTC<br>AGAGGACTGATCGGCGGCACCAACAAGAGAGCCCCTGGCACCCCTG<br>CCAGATTCAGCGGATCTCTGCTGGGAGGAAAGGCCGCCCTGACACT<br>GTCTGGCGCCCAGCCAGAAGATGAGGCCGAGTACTACTGCGCCCTG<br>TGGTACAGCAACCTGTGGGTGTTCGGCGGAGGCACCAAGCTGACAG<br>TGCTGAGCGCGCTAGCACCAAGGGCCCATCGGTCTTCCCCCTGGC<br>ACCCTCCTCCAAGAGCACCTCTGGGGGCACAGCGGCCCTGGGCTGC<br>CTGGTCAAGGACTACTTCCCCGAACCGGTGACGGTGTCGTGGAACT<br>CAGGCGCCCTGACCAGCGGCGTGCACACCTTCCCGGCTGTCCTACA<br>GTCCTCAGGACTCTACTCCCTCAGCAGCGTGGTGACCGTGCCCTCC<br>AGCAGCTTGGGCACCCAGACCTACATCTGCAACGTGAATCACAAGC<br>CCAGCAACACCAAGGTGGACAAGAAAGTTGAGCCCAAATCTTGTGA<br>CAAAACTCACACATGCCCACCGTGCCCAGCACCTGAAGCTGCAGGG<br>GGACCGTCAGTCTTCCTCTTCCCCCCAAAACCCAAGGACACCCTCA<br>TGATCTCCCGGACCCCTGAGGTCACATGCGTGGTGGTGGACGTGAG<br>CCACGAAGACCCTGAGGTCAAGTTCAACTGGTACGTGGACGGCGTG<br>GAGGTGCATAATGCCAAGACAAAGCCGCGGGAGGAGCAGTACAACA<br>GCACGTACCGTGTGGTCAGCGTCCTCACCGTCCTGCACCAGGACTG<br>GCTGAATGGCAAGGAGTACAAGTGCAAGGTCTCCAACAAAGCCCTC<br>GGCGCCCCCATCGAGAAAACCATCTCCAAAGCCAAAGGGCAGCCCC<br>GAGAACCA<br>CAGGTGTACACCCTGCCCCCATCCCGGGATGAGCTGACCAAGAACC<br>AGGTCAGCCTGACCTGCCTGGTCAAAGGCTTCTATCCCAGCGACAT<br>CGCCGTGGAGTGGGAGAGCAATGGGCAGCCGGAGAACAACTACAAG<br>ACCACGCCTCCCGTGCTGGACTCCGACGGCTCCTTCTTCCTCTACA<br>GCAAGCTCACCGTGGACAAGAGCAGGTGGCAGCAGGGGAACGTCTT<br>CTCATGCTCCGTGATGCATGAGGCTCTGCACAACCACTACACGCAG<br>AAGAGCCTCTCCCTGTCTCCGGGTAAA | 202 |
| 16D5 VH fused to constant kappa chain; pETR1385 9 | GAGGTGCAATTGGTTGAATCTGGTGGTGGTCTGGTAAAACCGGGCG<br>GTTCCCTGCGTCTGAGCTGCGCGGCTTCCGGATTCACCTTCTCCAA<br>CGCGTGGATGAGCTGGGTTCGCCAGGCCCCGGGCAAAGGCCTGGAA<br>TGGGTTGGTCGTATCAAGTCTAAAACTGACGGTGGCACCACGGATT<br>ACGCGGCTCCAGTTAAAGGTCGTTTTACCATTTCCCGCGACGATAG<br>CAAAAACACTCTGTATCTGCAGATGAACTCTCTGAAACTGAAGAC<br>ACCGCAGTCTACTACTGTACTACCCCGTGGGAATGGTCTTGGTACG<br>ATTATTGGGGCCAGGGCACGCTGGTTACGGTGTCTTCCGCTAGCGT<br>GGCCGCTCCCTCCGTGTTCATCTTCCCACCTTCCGACGAGCAGCTG | 203 |

| Description | Sequence | Seq ID No |
|---|---|---|
| | AAGTCCGGCACCGCTTCTGTCGTGTGCCTGCTGAACAACTTCTACC<br>CCCGCGAGGCCAAGGTGCAGTGGAAGGTGGACAACGCCCTGCAGTC<br>CGGCAACAGCCAGGAATCCGTGACCGAGCAGGACTCCAAGGACAGC<br>ACCTACTCCCTGTCCTCCACCCTGACCCTGTCCAAGGCCGACTACG<br>AGAAGCACAAGGTGTACGCCTGCGAAGTGACCCACCAGGGCCTGTC<br>TAGCCCCGTGACCAAGTCTTTCAACCGGGGCGAGTGC | |
| CD3 VH fused to constant lambda chain; pETR1386 0 | GAAGTGCAGCTGCTGGAATCCGGCGGAGGACTGGTGCAGCCTGGCG<br>GATCTCTGAGACTGTCTTGTGCCGCCTCCGGCTTCACCTTCTCCAC<br>CTACGCCATGAACTGGGTGCGACAGGCTCCTGGCAAGGGCCTGGAA<br>TGGGTGTCCCGGATCAGATCCAAGTACAACAACTACGCCACCTACT<br>ACGCCGACTCCGTGAAGGGCCGGTTCACCATCTCTCGGGACGACTC<br>CAAGAACACCCTGTACCTGCAGATGAACTCCCTGCGGGCCGAGGAC<br>ACCGCCGTGTACTATTGTGTGCGGCACGGCAACTTCGGCAACTCCT<br>ATGTGTCTTGGTTTGCCTACTGGGGCCAGGGCACCCTCGTGACCGT<br>GTCATCTGCTAGCCCCAAGGCTGCCCCCAGCGTGACCCTGTTTCCC<br>CCCAGCAGCGAGGAACTGCAGGCCAACAAGGCCACCCTGGTCTGCC<br>TGATCAGCGACTTCTACCCAGGCGCCGTGACCGTGGCCTGGAAGGC<br>CGACAGCAGCCCCGTGAAGGCCGGCGTGGAGACCACCACCCCCAGC<br>AAGCAGAGCAACAACAAGTACGCCGCCAGCAGCTACCTGAGCCTGA<br>CCCCCGAGCAGTGGAAGAGCCACAGGTCCTACAGCTGCCAGGTGAC<br>CCACGAGGGCAGCACC<br>GTGGAGAAAACCGTGGCCCCCACCGAGTGCAGC | 204 |
| VHCH1[36 F2]_VHCL[ CD3]_Fc knob_PGLA LA pCON1056 | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCCAAGCGGTGGCTCTACCTCCTACGCGCAGAAATTCCAGGGTCGCGTC<br>ACGATGACCCATGACACTAGCACCTCTACCGTTTATATGGAGCTGTCCAGC<br>CTGCGTTCTGAAGATACTGCAGTGTACTACTGTGCACGCTCTTTCTTCACT<br>GGTTTCCATCTGGACTATTGGGGTCAAGGCACCCTCGTAACGGTTTCTTCT<br>GCTAGCACAAAGGGCCCCAGCGTGTTCCCTCTGGCCCCTAGCAGCAAGAGC<br>ACATCTGGCGGAACAGCCGCCCTGGGCTGCCTCGTGAAGGACTACTTTCCC<br>GAGCCTGTGACCGTGTCCTGGAACTCTGGCGCCCTGACAAGCGGCGTGCAC<br>ACCTTTCCAGCCGTGCTGCAGAGCAGCGGCCTGTACTCTCTGAGCAGCGTG<br>GTCACCGTGCCTAGCAGCAGCCTGGGCACCCAGACCTACATCTGCAACGTG<br>AACCACAAGCCCAGCAACACCAAAGTGGACAAGAAGGTGGAGCCCAAG<br>AGCTGTGATGGCGGAGGAGGGTCCGGAGGCGGAGGATCCGAGGTGCAGCTG<br>CTGGAATCTGGCGGCGGACTGGTGCAGCCTGGCGGATCTCTGAGACTGAGC<br>TGTGCCGCCAGCGGCTTCACCTTCAGCACCTACGCCATGAACTGGGTGCGC<br>CAGGCCCCTGGCAAAGGCCTGGAATGGGTGTCCCGGATCAGAAGCAAGTAC<br>AACAACTACGCCACCTACTACGCCGACAGCGTGAAGGGCCGGTTCACCATC<br>AGCCGGGACGACAGCAAGAACACCCTGTACCTGCAGATGAACAGCCTGCGG<br>GCCGAGGACACCGCCGTGTACTATTGTGTGCGGCACGGCAACTTCGGCAAC<br>AGCTATGTGTCTTGGTTTGCCTACTGGGGCCAGGGCACCCTCGTGACCGTG<br>TCAAGCGCTAGTGTGGCCGCTCCCTCCGTGTTTATCTTTCCCCCATCCGAT<br>GAACAGCTGAAAAGCGGCACCGCCTCCGTCGTGTGTCTGCTGAACAATTTT<br>TACCCTAGGGAAGCTAAAGTGCAGTGGAAAGTGGATAACGCACTGCAGTCC<br>GGCAACTCCCAGGAATCTGTGACAGAACAGGACTCCAAGGACAGCACCTAC<br>TCCCTGTCCTCCACCCTGACACTGTCTAAGGCTGATTATGAGAAACAC<br>AAAGTCTACGCCTGCGAAGTCACCCATCAGGGCCTGAGCTCGCCCGTCACA<br>AAGAGCTTCAACAGGGGAGAGTGTGACAAGACCCACACCTGTCCCCCTTGT<br>CCTGCCCCTGAAGCTGCTGGCGGCCCTTCTGTGTTCCTGTTCCCCCCAAAG<br>CCCAAGGACACCCTGATGATCAGCCGGACCCCCGAAGTGACCTGCGTGGTG<br>GTGGATGTGTCCCACGAGGACCCTGAAGTGAAGTTCAATTGGTACGTGGAC<br>GGCGTGGAAGTGCACAACGCCAAGACAAAGCCGCGGGAGGAGCAGTACAAC<br>AGCACGTACCGTGTGGTCAGCGTCCTCACCGTCCTGCACCAGGACTGGCTG<br>AATGGCAAGGAGTACAAGTGCAAGGTCTCCAACAAAGCCCTCGGCGCCCCC<br>ATCGAGAAAACCATCTCCAAAGCCAAAGGGCAGCCCCGAGAACCACAGGTG<br>TACACCCTGCCCCCATGCCGGGATGAGCTGACCAAGAACCAGGTCAGCCTG<br>TGGTGCCTGGTCAAAGGCTTCTATCCCAGCGACATCGCCGTGGAGTGGGAG<br>AGCAATGGGCAGCCGGAGAACAACTACAAGACCACGCCTCCCGTGCTGGAC<br>TCCGACGGCTCCTTCTTCCTCTACAGCAAGCTCACCGTGGACAAGAGC<br>AGGTGGCAGCAGGGGAACGTCTTCTCATGCTCCGTGATGCATGAGGCTCTG<br>CACAACCACTACACGCAGAAGAGCCTCTCCCTGTCTCCGGGTAAA | 246 |
| 36F2-Fc hole PGLALA pCON1050 | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCCAAGCGGTGGCTCTACCTCCTACGCGCAGAAATTCCAGGGTCGCGTC<br>ACGATGACCCATGACACTAGCACCTCTACCGTTTATATGGAGCTGTCCAGC<br>CTGCGTTCTGAAGATACTGCAGTGTACTACTGTGCACGCTCTTTCTTCACT<br>GGTTTCCATCTGGACTATTGGGGTCAAGGCACCCTCGTAACGGTTTCTTCT<br>GCTAGCACCAAGGGCCCCTCCGTGTTCCCCCTGGCCCCCAGCAGCAAGAGC<br>ACCAGCGGCGGCACAGCCGCTCTGGGCTGCCTGGTCAAGGACTACTTCCCC<br>GAGCCCGTGACCGTGTCCTGGAACAGCGGAGCCCTGACCTCCGGCGTGCAC<br>ACCTTCCCCGCCGTGCTGCAGAGTTCTGGCCTGTATAGCCTGAGCAGCGTG | 247 |

| Description | Sequence | Seq ID No |
| --- | --- | --- |
| | GTCACCGTGCCTTCTAGCAGCCTGGGCACCCAGACCTACATCTGCAACGTG<br>AACCACAAGCCCAGCAACACCAAGGTGGACAAGAAGGTGGAGCCCAAG<br>AGCTGCGACAAAACTCACACATGCCCACCGTGCCCAGCACCTGAAGCTGCA<br>GGGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGAA<br>GACCCTGAGGTCAAGTTCAACTGGTACGTGGACGGCGTGGAGGTGCATAAT<br>GCCAAGACAAAGCCGCGGGAGGAGCAGTACAACAGCACGTACCGTGTGGTC<br>AGCGTCCTCACCGTCCTGCACCAGGACTGGCTGAATGGCAAGGAGTACAAG<br>TGCAAGGTCTCCAACAAAGCCCTCGGCGCCCCCATCGAGAAAACCATCTCC<br>AAAGCCAAAGGGCAGCCCCGAGAACCACAGGTGTGCACCCTGCCCCCATCC<br>CGGGATGAGCTGACCAAGAACCAGGTCAGCCTCTCGTGCGCAGTCAAAGGC<br>TTCTATCCCAGCGACATCGCCGTGGAGTGGGAGAGCAATGGGCAGCCGGAG<br>AACAACTACAAGACCACGCCTCCCGTGCTGGACTCCGACGGCTCCTTCTTC<br>CTCGTGAGCAAGCTCACCGTGGACAAGAGCAGGTGGCAGCAGGGGAACGTC<br>TTCTCATGCTCCGTGATGCATGAGGCTCTGCACAACCACTACACGCAG<br>AAGAGCCTCTCCCTGTCTCCGGGTAAA | |
| 36F2 LC<br>pCON1062 | GAAATCGTGTTAACGCAGTCTCCAGGCACCCTGTCTTTGTCTCCAGGGGAA<br>AGAGCCACCCTCTCTTGCAGGGCCAGTCAGAGTGTTAGCAGCAGCTACTTA<br>GCCTGGTACCAGCAGAAACCTGGCCAGGCTCCCAGGCTCCTCATCTATGGA<br>GCATCCAGCAGGGCCACTGGCATCCCnAGACAGGTTCAGTGGCAGTGGATC<br>CGGGACAGACTTCACTCTCACCATCAGCAGACTGGAGCCTGAAGATTTTGC<br>AGTGTATTACTGTCAGCAGTATACCAACGAACATTATTATACGTTCGGCCA<br>GGGGACCAAAGTGGAAATCAAACGTACGGTGGCTGCACCATCTGTCTTCAT<br>CTTCCCGCCATCTGATGAGCAGTTGAAATCTGGAACTGCCTCTGTTGTGTG<br>CCTGCTGAATAACTTCTATCCCAGAGAGGCCAAAGTACAGTGGAAGGTGGA<br>TAACGCCCTCCAATCGGGTAACTCCCAGGAGAGTGTCACAGAGCAGGACAG<br>CAAGGACAGCACCTACAGCCTCAGCAGCACCCTGACGCTGAGCAAAGCAGA<br>CTACGAGAAACAAAGTCTACGCCTGCGAAGTCACCCATCANGGCCTGAG<br>CTCGCCCGTCACAAAGAGCTTCAACAGGGGAGAGTGT | 97 |
| CD3 VLCH1<br>pETR12940 | CAGGCCGTCGTGACCCAGGAACCCAGCCTGACAGTGTCTCCTGGCGGCACC<br>GTGACCCTGACATGTGGCAGTTCTACAGGCGCCGTGACCACCAGCAACTAC<br>GCCAACTGGGTGCAGGAAAAGCCCGGCCAGGCCTTCAGAGGACTGATCGGC<br>GGCACCAACAAGAGAGCCCCTGGCACCCCTGCCAGATTCAGCGGATCTCTG<br>CTGGGAGGAAAGGCCGCCCTGACACTGTCTGGCGCCCAGCCAGAAGATGAG<br>GCCGAGTACTACTGCGCCCTGTGGTACAGCAACCTGTGGGTGTTCGGCGGA<br>GGCACCAAGCTGACAGTGCTGAGCAGCGCTTCCACCAAAGGCCCTTCCGTG<br>TTTCCTCTGGCTCCTAGCTCCAAGTCCACCTCTGGAGGCACCGCTGCTCTC<br>GGATGCCTCGTGAAGGATTATTTTCCTGAGCCTGTGACAGTGTCCTGGAAT<br>AGCGGAGCACTGACCTCTGGAGTGCATACTTTCCCCGCTGTGCTGCAGTCC<br>TCTGGACTGTACAGCCTGAGCAGCGTGGTGACAGTGCCCAGCAGCAGCCTG<br>GGCACCCAGACCTACATCTGCAACGTGAACCACAAGCCCAGCAACACCAAG<br>GTGGACAAGAAGGTGGAACCCAAGTCTTGT | 198 |
| K53A<br>nt | CAGACCGTCGTGACCCAGGAACCCAGCCTGACAGTGTCTCCTGGCGGCACC<br>GTGACCCTGACATGTGGCAGTTCTACAGGCGCCGTGACCACCAGCAACTAC<br>GCCAACTGGGTGCAGCAGAAGCCAGGCCAGGCTCCCAGAGGACTGATCGGC<br>GGCACCAACGCCAGAGCCCCTGGCACCCCTGCCAGATTCAGCGGATCTCTG<br>CTGGGAGGAAAGGCCGCCCTGACACTGTCTGGCGTGCAGCCTGAAGATGAG<br>GCCGAGTACTACTGCGCCCTGTGGTACAGCAACCTGTGGGTGTTCGGCGGA<br>GGCACCAAGCTGACAGTCCTA | 205 |
| S93A<br>nt | CAGACCGTCGTGACCCAGGAACCCAGCCTGACAGTGTCTCCTGGCGGCACC<br>GTGACCCTGACATGTGGCAGTTCTACAGGCGCCGTGACCACCAGCAACTAC<br>GCCAACTGGGTGCAGCAGAAGCCAGGCCAGGCTCCCAGAGGACTGATCGGC<br>GGCACCAACAAGAGAGCCCCTGGCACCCCTGCCAGATTCAGCGGATCTCTG<br>CTGGGAGGAAAGGCCGCCCTGACACTGTCTGGCGTGCAGCCTGAAGATGAG<br>GCCGAGTACTACTGCGCCCTGTGGTACGCCAACCTGTGGGTGTTCGGCGGA<br>GGCACCAAGCTGACAGTCCTA | 206 |
| S35H<br>nt | GAGGTGCAATTGGTGGAAAGCGGAGGCGGCCTCGTGAAGCCTGGCGGATCT<br>CTGAGACTGAGCTGTGCCGCCAGCGGCTTCACCTTCAGCAACGCCTGGATG<br>CACTGGGTGCGCCAGGCCCCTGGAAAAGGACTCGAGTGGGTGGGACGGATC<br>AAGAGCAAGACCGATGGCGGCACCACCGACTATGCCGCCCCTGTGAAGGGC<br>CGGTTCACCATCAGCAGGGACGACAGCAAGAACACCCTGTACCTGCAGATG<br>AACAGCCTGAAAACCGAGGACACCGCCGTGTACTACTGCACCACCCCTGG<br>GAGTGGTCTTGGTACGACTATTGGGGCCAGGGCACCCTCGTGACCGTGTCC<br>TCTGCTAGC | 207 |

| Description | Sequence | Seq ID No |
|---|---|---|
| G49S nt | GAGGTGCAATTGGTGGAAAGCGGAGGCGGCCTCGTGAAGCCTGGCGGATCT CTGAGACTGAGCTGTGCCGCCAGCGGCTTCACCTTCAGCAACGCCTGGATG AGCTGGGTGCGCCAGGCCCCTGGAAAAGGACTCGAGTGGGTGTCCCGGATC AAGAGCAAGACCGATGGCGGCACCACCGACTATGCCGCCCCTGTGAAGGGC CGGTTCACCATCAGCAGGGACGACAGCAAGAACACCCTGTACCTGCAGATG AACAGCCTGAAAACCGAGGACACCGCCGTGTACTACTGCACCACCCCCTGG GAGTGGTCTTGGTACGACTATTGGGGCCAGGGCACCCTCGTGACCGTGTCC TCTGCTAGC | 208 |
| R50S nt | GAGGTGCAATTGGTGGAAAGCGGAGGCGGCCTCGTGAAGCCTGGCGGATCT CTGAGACTGAGCTGTGCCGCCAGCGGCTTCACCTTCAGCAACGCCTGGATG AGCTGGGTGCGCCAGGCCCCTGGAAAAGGACTCGAGTGGGTGGGATCTATC AAGAGCAAGACCGACGGCGGCACCACCGACTATGCCGCCCCTGTGAAGGGC CGGTTCACCATCAGCAGGGACGACAGCAAGAACACCCTGTACCTGCAGATG AACAGCCTGAAAACCGAGGACACCGCCGTGTACTACTGCACCACCCCCTGG GAGTGGTCTTGGTACGACTATTGGGGCCAGGGCACCCTCGTGACCGTGTCC TCT GCTAGC | 209 |
| W96Y nt | GAGGTGCAATTGGTGGAAAGCGGAGGCGGCCTCGTGAAGCCTGGCGGATCT CTGAGACTGAGCTGTGCCGCCAGCGGCTTCACCTTCAGCAACGCCTGGATG AGCTGGGTGCGCCAGGCCCCTGGAAAAGGACTCGAGTGGGTGGGACGGATC AAGAGCAAGACCGATGGCGGCACCACCGACTATGCCGCCCCTGTGAAGGGC CGGTTCACCATCAGCAGGGACGACAGCAAGAACACCCTGTACCTGCAGATG AACAGCCTGAAAACCGAGGACACCGCCGTGTACTACTGCACCACCCCCTAC GAGTGGTCTTGGTACGACTACTGGGGCCAGGGCACCCTCGTGACCGTGTCA TCT GCTAGC | 210 |
| W98Y nt | GAGGTGCAATTGGTGGAAAGCGGAGGCGGCCTCGTGAAGCCTGGCGGATCT CTGAGACTGAGCTGTGCCGCCAGCGGCTTCACCTTCAGCAACGCCTGGATG AGCTGGGTGCGCCAGGCCCCTGGAAAAGGACTCGAGTGGGTGGGACGGATC AAGAGCAAGACCGATGGCGGCACCACCGACTATGCCGCCCCTGTGAAGGGC CGGTTCACCATCAGCAGGGACGACAGCAAGAACACCCTGTACCTGCAGATG AACAGCCTGAAAACCGAGGACACCGCCGTGTACTACTGCACCACCCCCTGG GAGTACTCTTGGTACGACTACTGGGGCCAGGGCACCCTCGTGACCGTGTCA TCT GCTAGC | 211 |
| 90D7 nt | CAGGTGCAATTGGTTCAATCTGGTGCTGAAGTAAAAAAACCGGGCGCTTCC GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTACACTATC GTTGTTTCTCCGTTCGACTATTGGGGTCAAGGCACCCTCGTAACGGTTTCT TCTGCTAGC | 212 |
| 90C1 nt | CAGGTGCAATTGGTTCAATCTGGTGCTGAAGTAAAAAAACCGGGCGCTTCC GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCAACTACTTCATC GGTTCTGTTGCTATGGACTATTGGGGTCAAGGCACCCTCGTAACGGTTTCT TCTGCTAGC | 213 |
| 5E8 VH nt | CAGGTGCAATTGGTTCAATCTGGTGCTGAAGTAAAAAAACCGGGCGCTTCC GTTAAAGTGAGCTGCAAAGCATCCGGATACACCTTCACTTCCTATTACATG CACTGGGTTCGTCAAGCCCCGGGCCAGGGTCTGGAATGGATGGGCATCATT AACCCAAGCGGTGGCTCTACCTCCTACGCGCAGAAATTCCAGGGTCGCGTC ACGATGACCCGTGACACTAGCACCTCTACCGTTTATATGGAGCTGTCCAGC CTGCGTTCTGAAGATACTGCAGTGTACTACTGTGCACGCGGTCTGACTTAC TCTATGGACTATTGGGGTCAAGGCACCCTCGTAACGGTTTCTTCTGCTAGC | 214 |
| 5E8 VL nt | GATATTGTTATGACTCAATCTCCACTGTCTCTGCCGGTGACTCCAGGCGAA CCGGCGAGCATTTCTTGCCGTTCCAGCCAGTCTCTGCTGCACTCCAACGGC TACAACTATCTCGATTGGTACCTGCAAAAACCGGGTCAGAGCCCTCAGCTG CTGATCTACCTGGGCTCTAACCGCGCTTCCGGTGTACCGGACCGTTTCAGC GGCTCTGGATCCGGCACCGATTTCACGTTGAAAATCAGCCGTGTTGAAGCA GAAGACGTGGGCGTTTATTACTGTATGCAGGCACTGCAGATTCCAAACACT TTTGGTCAAGGCACCAAGGTCGAAATTAAACGTACG | 215 |
| 12A4 VH nt | GAGGTGCAATTGTTGGAGTCTGGGGGAGGCTTGGTACAGCCTGGGGGGTCC CTGAGACTCTCCTGTGCAGCCTCCGGATTCACCTTTAGCAGTTATGCCATG AGCTGGGTCCGCCAGGCTCCAGGGAAGGGGCTGGAGTGGGTCTCAGCTATT AGTGGTAGTGGTGGTAGCACATACTACGCAGACTCCGTGAAGGGCCGGTTC | 216 |

| Description | Sequence | Seq ID No |
|---|---|---|
| | ACCATCTCCAGAGACAATTCCAAGAACACGCTGTATCTGCAGATGAACAGC<br>CTGAGAGCCGAGGACACGGCCGTATATTACTGTGCGAAATACGCTTACGCT<br>CTGGACTACTGGGGCCAAGGAACCCTGGTCACCGTCTCGAGTGCTAGC | |
| 12A4 VL<br>nt | GAAATCGTGTTAACGCAGTCTCCAGGCACCCTGTCTTTGTCTCCAGGGGAA<br>AGAGCCACCCTCTCTTGCAGGGCCAGTCAGAGTGTTAGCAGCAGCTACTTA<br>GCCTGGTACCAGCAGAAACCTGGCCAGGCTCCCAGGCTCCTCATCTATGGA<br>GCATCCAGCAGGGCCACTGGCATCCCAGACAGGTTCAGTGGCAGTGGATCC<br>GGGACAGACTTCACTCTCACCATCAGCAGACTGGAGCCTGAAGATTTTGCA<br>GTGTATTACTGTCAGCAGCATGGCAGCAGCAGCACGTTCGGCCAGGGGACC<br>AAAGTGGAAATCAAACGTACG | 217 |
| 7A3 VH<br>nt | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGGTGACTTCTCT<br>GCTGGTCGTCTGATGGACTATTGGGGTCAAGGCACCCTCGTAACGGTTTCT<br>TCTGCTAGC | 218 |
| 7A3 VL<br>nt | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACCGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCACTGCAGACCCCACCAATT<br>ACCTTTGGTCAAGGCACCAAGGTCGAAATTAAACGTACG | 219 |
| 6E10 VH<br>nt | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGGTGACTACAAC<br>GCTTTCGACTATTGGGGTCACGGCACCCTCGTAACGGTTTCTTCTGCTAGC | 220 |
| 6E10 VL<br>nt | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACCGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCATGGCATAGCCCAACTTTT<br>GGTCAAGGCACCAAGGTCGAAATTAAACGTACG | 221 |
| 12F9 VH<br>nt | CAGGTGCAATTGGTTCAATCTGGTGCTGAAGTAAAAAAACCGGGCGCTTCC<br>GTTAAAGTGAGCTGCAAAGCATCCGGATACACCTTCACTTCCTATTACATG<br>CACTGGGTTCGTCAAGCCCCGGGCCAGGGTCTGGAATGGATGGGCATCATT<br>AACCCAAGCGGTGGCTCTACCTCCTACGCGCAGAAATTCCAGGGTCGCGTC<br>ACGATGACCCGTGACACTAGCACCTCTACCGTTTATATGGAGCTGTCCAGC<br>CTGCGTTCTGAAGATACTGCAGTGTACTACTGTGCACGCGGTGCTACTTAC<br>ACTATGGACTATTGGGGTCAAGGCACCCTCGTAACGGTTTCTTCTGCTAGC | 222 |
| 12F9 VL<br>nt | GATATTGTTATGACTCAATCTCCACTGTCTCTGCCGGTGACTCCAGGCGAA<br>CCGGCGAGCATTTCTTGCCGTTCCAGCCAGTCTCTGCTGCACTCCAACGGC<br>TACAACTATCTCGATTGGTACCTGCAAAAACCGGGTCAGAGCCCTCAGCTG<br>CTGATCTACCTGGGCTCTAACCGCGCTTCCGGTGTACCGGACCGTTTCAGC<br>GGCTCTGGATCCGGCACCGATTTCACGTTGAAAATCAGCCGTGTTGAAGCA<br>GAAGACGTGGGCGTTTATTACTGTATGCAGGCACTGCAGACCCCAATTACT<br>TTTGGTCAAGGCACCAAGGTCGAAATTAAACGTACG | 223 |
| pETR1164<br>6<br>Mov19 VH-<br>CH1-Fchole<br>PG/LALA | CAGGTGCAGCTGCAGCAGTCTGGCGCCGAGCTCGTGAAACCTGGCGCCTCC<br>GTGAAGATCAGCTGCAAGGCCAGCGGCTACAGCTTCACCGGCTACTTCATG<br>AACTGGGTCAAGCAGAGCCACGGCAAGAGCCTGGAATGGATCGGCAGAATC<br>CACCCCTACGACGGCGACACCTTCTACAACCAGAACTTCAAGGACAAGGCC<br>ACCCTGACCGTGGACAAGAGCAGCAACACCGCCCACATGGAACTGCTGAGC<br>CTGACCAGCGAGGACTTCGCCGTGTACTACTGCACCAGATACGACGGCAGC<br>CGGGCCATGGATTATTGGGGCCAGGGCACCACCGTGACAGTGTCCAGCGCT<br>AGCACCAAGGGCCCCTCCGTGTTCCCCCTGGCCCCCAGCAGCAAGAGCACC<br>AGCGGCGGCACAGCCGCTCTGGGCTGCCTGGTCAAGGACTACTTCCCCGAG<br>CCCGTGACCGTGTCCTGGAACAGCGGAGCCCTGACCTCCGGCGTGCACACC<br>TTCCCCGCCGTGCTGCAGAGTTCTGGCCTGTATAGCCTGAGCAGCGTGGTC<br>ACCGTGCCTTCTAGCAGCCTGGGCACCCAGACCTACATCTGCAACGTGAAC<br>CACAAGCCCAGCAACACCAAGGTGGACAAGAAGGTGGAGCCCAAGAGCTGC<br>GACAAAACTCACACATGCCCACCGTGCCCAGCACCTGAAGCTGCAGGGGGA<br>CCGTCAGTCTTCCTCTTCCCCCCAAAACCCAAGGACACCCTCATGATCTCC<br>CGGACCCCTGAGGTCACATGCGTGGTGGTGGACGTGAGCCACGAAGACCCT | 224 |

| Description | Sequence | Seq ID No |
|---|---|---|
| | GAGGTCAAGTTCAACTGGTACGTGGACGGCGTGGAGGTGCATAATGCCAAG<br>ACAAAGCCGCGGGAGGAGCAGTACAACAGCACGTACCGTGTGGTCAGCGTC<br>CTCACCGTCCTGCACCAGGACTGGCTGAATGGCAAGGAGTACAAGTGCAAG<br>GTCTCCAACAAAGCCCTCGGCGCCCCCATCGAGAAAACCATCTCCAAAGCC<br>AAAGGGCAGCCCCGAGAACCACAGGTGTGCACCCTGCCCCCATCCCGGGAT<br>GAGCTGACCAAGAACCAGGTCAGCCTCTCGTGCGCAGTCAAAGGCTTCTAT<br>CCCAGCGACATCGCCGTGGAGTGGGAGAGCAATGGGCAGCCGGAGAACAAC<br>TACAAGACCACGCCTCCCGTGCTGGACTCCGACGGCTCCTTCTTCCTCGTG<br>AGCAAGCTCACCGTGGACAAGAGCAGGTGGCAGCAGGGGAACGTCTTCTCA<br>TGCTCCGTGATGCATGAGGCTCTGCACAACCACTACACGCAGAAGAGCCTC<br>TCCCTGTCTCCGGGTAAA | |
| pETR1164<br>7<br>Mov19 VH-<br>CH1-CD3<br>VH-CL-<br>Fcknob<br>PG/LALA | CAGGTGCAGCTGCAGCAGTCTGGCGCCGAGCTCGTGAAACCTGGCGCCTCC<br>GTGAAGATCAGCTGCAAGGCCAGCGGCTACAGCTTCACCGGCTACTTCATG<br>AACTGGGTCAAGCAGAGCCACGGCAAGAGCCTGGAATGGATCGGCAGAATC<br>CACCCCTACGACGGCGACACCTTCTACAACCAGAACTTCAAGGACAAGGCC<br>ACCCTGACCGTGGACAAGAGCAGCAACACCGCCCACATGGAACTGCTGAGC<br>CTGACCAGCGAGGACTTCGCCGTGTACTACTGCACCAGATACGACGGCAGC<br>CGGGCCATGGATTATTGGGGCCAGGGCACCACCGTGACAGTGTCCAGCGCT<br>AGCACAAAGGGCCCCAGCGTGTTCCCTCTGGCCCCTAGCAGCAAGAGCACA<br>TCTGGCGGAACAGCCGCCCTGGGCTGCCTCGTGAAGGACTACTTTCCCGAG<br>CCTGTGACCGTGTCCTGGAACTCTGGCGCCCTGACAAGCGGCGTGCACACC<br>TTTCCAGCCGTGCTGCAGAGCAGCGGCCTGTACTCTCTGAGCAGCGTGGTC<br>ACCGTGCCTAGCAGCAGCCTGGGCACCCAGACCTACATCTGCAACGTGAAC<br>CACAAGCCCAGCAACACCAAAGTGGACAAGAAGGTGGAGCCCAAGAGCTGT<br>GATGGCGAGGAGGGTCCGGAGGCGGAGGATCCGAAGTGCAGCTGGTGGAA<br>AGCGGCGGAGGCCTGGTGCAGCCTAAGGGCTCTCTGAAGCTGAGCTGTGCC<br>GCCAGCGGCTTCACCTTCAACACCTACGCCATGAACTGGGTGCGCCAGGCC<br>CCTGGCAAAGGCCTGGAATGGGTGGCCCGGATCAGAAGCAAGTACAACAAT<br>TACGCCACCTACTACGCCGACAGCGTGAAGGACCGGTTCACCATCAGCCGG<br>GACGACAGCCAGAGCATCCTGTACCTGCAGATGAACAACCTGAAAACCGAG<br>GACACCGCCATGTACTGCGTGCGGCACGGCAACTTCGGCAACAGCTAT<br>GTGTCTTGGTTTGCCTACTGGGGCCAGGGCACCCTCGTGACAGTGTCTGCT<br>GCTAGCGTGGCCGCTCCCTCCGTGTTTATCTTTCCCCCATCCGATGAACAG<br>CTGAAAAGCGGCACCGCCTCCGTCGTGTGTCTGCTGAACAATTTTTACCCT<br>AGGGAAGCTAAAGTGCAGTGGAAAGTGGATAACGCACTGCAGTCCGGCAAC<br>TCCCAGGAATCTGTGACAGAACAGGACTCCAAGGACAGCACCTACTCCCTG<br>TCCTCCACCCTGACACTGTCTAAGGCTGATTATGAGAAACACAAAGTCTAC<br>GCCTGCGAAGTCACCCATCAGGGCCTGAGCTCGCCCGTCACAAAGAGCTTC<br>AACAGGGGAGAGTGTGACAAGACCCACACCTGTCCCCCTTGTCCTGCCCCT<br>GAAGCTGCTGGCGGCCCCTTCTGTGTTCCTGTTCCCCCCAAAGCCCAAGGAC<br>ACCCTGATGATCAGCCGGACCCCCGAAGTGACCTGCGTGGTGGTGGATGTG<br>TCCCACGAGGACCCTGAAGTGAAGTTCAATTGGTACGTGGACGGCGTGGAA<br>GTGCACAACGCCAAGACAAAGCCGCGGGAGGAGCAGTACAACAGCACGTAC<br>CGTGTGGTCAGCGTCCTCACCGTCCTGCACCAGGACTGGCTGAATGGCAAG<br>GAGTACAAGTGCAAGGTCTCCAACAAAGCCCTCGGCGCCCCCATCGAGAAA<br>ACCATCTCCAAAGCCAAAGGGCAGCCCCGAGAACCACAGGTGTACACCCTG<br>CCCCCATGCCGGGATGAGCTGACCAAGAACCAGGTCAGCCTGTGGTGCCTG<br>GTCAAAGGCTTCTATCCCAGCGACATCGCCGTGGAGTGGGAGAGCAATGGG<br>CAGCCGGAGAACAACTACAAGACCACGCCTCCCGTGCTGGACTCCGACGGC<br>TCCTTCTTCCTCTACAGCAAGCTCACCGTGGACAAGAGCAGGTGGCAGCAG<br>GGGAACGTCTTCTCATGCTCCGTGATGCATGAGGCTCTGCACAACCACTAC<br>ACGCAGAAGAGCCTCTCCCTGTCTCCGGGTAAA | 225 |
| pETR1164<br>4<br>Mov19 LC | GACATCGAGCTGACCCAGAGCCCTGCCTCTCTGGCCGTGTCTCTGGGACAG<br>AGAGCCATCATCAGCTGCAAGGCCAGCCAGAGCGTGTCCTTTGCCGGCACC<br>TCTCTGATGCACTGGTATCACCAGAAGCCCGGCCAGCAGCCCAAGCTGCTG<br>ATCTACAGAGCCAGCAACCTGGAAGCCGGCGTGCCCACAAGATTTTCCGGC<br>AGCGGCAGCAAGACCGACTTCACCCTGAACATCCACCCCGTGGAAGAAGAG<br>GACGCCGCCACCTACTACTGCCAGCAGAGCAGAGAGTACCCCTACACCTTC<br>GGCGGAGGCACCAAGCTGGAAATCAAGCGTACGGTGGCTGCACCATCTGTC<br>TTCATCTTCCCGCCATCTGATGAGCAGTTGAAATCTGGAACTGCCTCTGTT<br>GTGTGCCTGCTGAATAACTTCTATCCCAGAGAGGCCAAAGTACAGTGGAAG<br>GTGGATAACGCCCTCCAATCGGGTAACTCCCAGGAGAGTGTCACAGAGCAG<br>GACAGCAAGGACAGCACCTACAGCCTCAGCAGCACCCTGACGCTGAGCAAA<br>GCAGACTACGAGAAACACAAAGTCTACGCCTGCGAAGTCACCCATCAGGGC<br>CTGAGCTCGCCCGTCACAAAGAGCTTCAACAGGGGAGAGTGT | 226 |
| 16D5<br>VH_D52d<br>E | GAGGTGCAATTGGTTGAATCTGGTGGTGGTCTGGTAAAACCGGGCGGTTCCC<br>TGCGTCTGAGCTGCGCGGCTTCCGGATTCACCTTCTCCAACGCGTGGATGAG<br>CTGGGTTCGCCAGGCCCCGGGCAAAGGCCTCGAGTGGGTTGGTCGTATCAAG<br>TCTAAAACTGAGGGTGGCACCACGGATTACGCGGCTCCAGTTAAAGGTCGTT<br>TTACCATTTCCCGCGACGATAGCAAAAACACTCTGTATCTGCAGATGAACTC<br>TCTGAAACTGAAGACACCGCAGTCTACTACTGTACTACCCCGTGGGAATGG<br>TCTTGGTACGATTATTGGGGCCAGGGCACGCTGGTTACGGTGTCTTCC | 261 |

| Description | Sequence | Seq ID No |
|---|---|---|
| 16D5 VH_D52d Q | GAGGTGCAATTGGTTGAATCTGGTGGTGGTCTGGTAAAACCGGGCGGTTCCC TGCGTCTGAGCTGCGCGGCTTCCGGATTCACCTTCTCCAACGCGTGGATGAG CTGGGTTCGCCAGGCCCCGGGCAAAGGCCTCGAGTGGGTTGGTCGTATCAAG TCTAAAACTCAGGGTGGCACCACGGATTACGCGGCTCCAGTTAAAGGTCGTT TTACCATTTCCCGCGACGATAGCAAAAACACTCTGTATCTGCAGATGAACTC TCTGAAAACTGAAGACACCGCAGTCTACTACTGTACTACCCCGTGGGAATGG TCTTGGTACGATTATTGGGGCCAGGGCACGCTGGTTACGGTGTCTTCC | 262 |
| CD3_VH N100A | GAGGTGCAGCTGCTGGAATCTGGCGGCGGACTGGTGCAGCCTGGCGGATCTC TGAGACTGAGCTGTGCCGCCAGCGGCTTCACCTTCAGCACCTACGCCATGAA CTGGGTGCGCCAGGCCCCTGGCAAAGGCCTGGAATGGGTGTCCCGGATCAGA AGCAAGTACAACAACTACGCCACCTACTACGCCGACAGCGTGAAGGGCCGGT TCACCATCAGCCGGGACGACAGCAAGAACACCCTGTACCTGCAGATGAACAG CCTGCGGGCCGAGGACACCGCCGTGTACTATTGTGCGCGGCACGGCAACTTC GGCGCCAGCTATGTGTCTTGGTTTGCCTACTGGGGCCAGGGCACCCTCGTGA CCGTGTCAAGC | 263 |
| CD3_VH S100aA | GAGGTGCAGCTGCTGGAATCTGGCGGCGGACTGGTGCAGCCTGGCGGATCTC TGAGACTGAGCTGTGCCGCCAGCGGCTTCACCTTCAGCACCTACGCCATGAA CTGGGTGCGCCAGGCCCCTGGCAAAGGCCTGGAATGGGTGTCCCGGATCAGA AGCAAGTACAACAACTACGCCACCTACTACGCCGACAGCGTGAAGGGCCGGT TCACCATCAGCCGGGACGACAGCAAGAACACCCTGTACCTGCAGATGAACAG CCTGCGGGCCGAGGACACCGCCGTGTACTATTGTGCGCGGCACGGCAACTTC GGCAACGCCTATGTGTCTTGGTTTGCCTACTGGGGCCAGGGCACCCTCGTGA CCGTGTCAAGC | 264 |
| 16D5 [VHCH11] CD3[VHC H1- N100A]- Fcknob_P GLALA | GAGGTGCAATTGGTTGAATCTGGTGGTGGTCTGGTAAAACCGGGCGGTTCCC TGCGTCTGAGCTGCGCGGCTTCCGGATTCACCTTCTCCAACGCGTGGATGAG CTGGGTTCGCCAGGCCCCGGGCAAAGGCCTCGAGTGGGTTGGTCGTATCAAG TCTAAAACTGACGGTGGCACCACGGATTACGCGGCTCCAGTTAAAGGTCGTT TTACCATTTCCCGCGACGATAGCAAAAACACTCTGTATCTGCAGATGAACTC TCTGAAAACTGAAGACACCGCAGTCTACTACTGTACTACCCCGTGGGAATGG TCTTGGTACGATTATTGGGGCCAGGGCACGCTGGTTACGGTGTCTTCCGCTA GCACAAAGGGCCCTAGCGTGTTCCCTCTGGCCCCCAGCAGCAAGAGCACAAG CGGCGGAACAGCCGCCCTGGGCTGCCTCGTGAAGGACTACTTCCCCGAGCCC GTGACAGTGTCTTGGAACAGCGGAGCCCTGACAAGCGGCGTGCACACTTTCC CTGCCGTGCTGCAGAGCAGCGGCCTGTACTCCCTGAGCAGCGTGGTCACCGT GCCTAGCAGCAGCCTGGGCACCCAGACCTACATCTGCAACGTGAACCACAAG CCCAGCAACACCAAAGTGGACAAGAAGGTGGAGCCCAAGAGCTGTGATGGCG GAGGAGGGTCCGGAGGCGGAGGATCCGAGGTGCAGCTGCTGGAATCTGGCGG CGGACTGGTGCAGCCTGGCGGATCTCTGAGACTGAGCTGTGCCGCCAGCGGC TTCACCTTCAGCACCTACGCCATGAACTGGGTGCGCCAGGCCCCTGGCAAAG GCCTGGAATGGGTGTCCCGGATCAGAAGCAAGTACAACAACTACGCCACCTA CTACGCCGACAGCGTGAAGGGCCGGTTCACCATCAGCCGGGACGACAGCAAG AACACCCTGTACCTGCAGATGAACAGCCTGCGGGCCGAGGACACCGCCGTGT ACTATTGTGCGCGGCACGGCAACTTCGGCGCCAGCTATGTGTCTTGGTTTGC CTACTGGGGCCAGGGCACCCTCGTGACCGTGTCAAGCGCTAGTACCAAGGGC CCCAGCGTGTTCCCCCTGGCACCCAGCAGCAAGAGCACATCTGGCGGAACAG CCGCTCTGGGCTGTCTCGTGAAAGACTACTTCCCCGAGCCCGTGACCGTGTC TTGGAACTCTGGCGCCCTGACCAGCGGCGTGCACACCTTTCCAGCCGTGCTG CAGAGCAGCGGCCTGTACTCCCTGTCCTCCGTGGTCACCGTGCCCTCTAGCT CCCTGGGAACACAGACATATATCTGTAATGTCAATCACAAGCCTTCCAACAC CAAAGTCGATAAGAAAGTCGAGCCCAAGAGCTGCGACAAAACTCACACATGC CCACCGTGCCCAGCACCTGAAGCTGCAGGGGACCGTCAGTCTTCCTCTTCC CCCCAAAACCCAAGGACACCCTCATGATCTCCCGGACCCCTGAGGTCACATG CGTGGTGGTGGACGTGAGCCACGAAGACCCTGAGGTCAAGTTCAACTGGTAC GTGGACGGCGTGGAGGTGCATAATGCCAAGACAAAGCCGCGGGAGGAGCAGT ACAACAGCACGTACCGTGTGGTCAGCGTCCTCACCGTCCTGCACCAGGACTG GCTGAATGGCAAGGAGTACAAGTGCAAGGTCTCCAACAAAGCCCTCGGCGCC CCCATCGAGAAAACCATCTCCAAAGCCAAAGGGCAGCCCCGAGAACCACAGG TGTACACCCTGCCCCCATGCCGGGATGAGCTGACCAAGAACCAGGTCAGCCT GTGGTGCCTGGTCAAAGGCTTCTATCCCAGCGACATCGCCGTGGAGTGGGAG AGCAATGGGCAGCCGGAGAACAACTACAAGACCACGCCTCCCGTGCTGGACT CCGACGGCTCCTTCTTCCTCTACAGCAAGCTCACCGTGGACAAGAGCAGGTG GCAGCAGGGGAACGTCTTCTCATGCTCCGTGATGCATGAGGCTCTGCACAAC CACTACACGCAGAAGAGCCTCTCCCTGTCTCCGGGTAAA | 265 |
| 16D5- Fchole- PGLALA | GAGGTGCAATTGGTTGAATCTGGTGGTGGTCTGGTAAAACCGGGCGGTTCCC TGCGTCTGAGCTGCGCGGCTTCCGGATTCACCTTCTCCAACGCGTGGATGAG CTGGGTTCGCCAGGCCCCGGGCAAAGGCCTCGAGTGGGTTGGTCGTATCAAG TCTAAAACTGACGGTGGCACCACGGATTACGCGGCTCCAGTTAAAGGTCGTT TTACCATTTCCCGCGACGATAGCAAAAACACTCTGTATCTGCAGATGAACTC TCTGAAAACTGAAGACACCGCAGTCTACTACTGTACTACCCCGTGGGAATGG TCTTGGTACGATTATTGGGGCCAGGGCACGCTGGTTACGGTGTCTTCCGCTA GCACCAAGGGCCCCTCCGTGTTCCCCCTGGCCCCCAGCAGCAAGAGCACCAG CGGCGGCACAGCCGCTCTGGGCTGCCTGGTCAAGGACTACTTCCCCGAGCCC GTGACCGTGTCCTGGAACAGCGGAGCCCTGACCTCCGGCGTGCACACCTTCC | 266 |

| Description | Sequence | Seq ID No |
|---|---|---|
| | CCGCCGTGCTGCAGAGTTCTGGCCTGTATAGCCTGAGCAGCGTGGTCACCGT<br>GCCTTCTAGCAGCCTGGGCACCCAGACCTACATCTGCAACGTGAACCACAAG<br>CCCAGCAACACCAAGGTGGACAAGAAGGTGGAGCCCAAGAGCTGCGACAAAA<br>CTCACACATGCCCACCGTGCCCAGCACCTGAAGCTGCAGGGGACCGTCAGT<br>CTTCCTCTTCCCCCCAAAACCCAAGGACACCCTCATGATCTCCCGGACCCCT<br>GAGGTCACATGCGTGGTGGTGGACGTGAGCCACGAAGACCCTGAGGTCAAGT<br>TCAACTGGTACGTGGACGGCGTGGAGGTGCATAATGCCAAGACAAAGCCGCG<br>GGAGGAGCAGTACAACAGCACGTACCGTGTGGTCAGCGTCCTCACCGTCCTG<br>CACCAGGACTGGCTGAATGGCAAGGAGTACAAGTGCAAGGTCTCCAACAAAG<br>CCCTCGGCGCCCCATCGAGAAAACCATCTCCAAAGCCAAAGGGCAGCCCCG<br>AGAACCACAGGTGTGCACCCTGCCCCCATCCCGGGATGAGCTGACCAAGAAC<br>CAGGTCAGCCTCTCGTGCGCAGTCAAAGGCTTCTATCCCAGCGACATCGCCG<br>TGGAGTGGGAGAGCAATGGGCAGCCGGAGAACAACTACAAGACCACGCCTCC<br>CGTGCTGGACTCCGACGGCTCCTTCTTCCTCGTGAGCAAGCTCACCGTGGAC<br>AAGAGCAGGTGGCAGCAGGGGAACGTCTTCTCATGCTCCGTGATGCATGAGG<br>CTCTGCACAACCGCTTCACGCAGAAGAGCCTCTCCCTGTCTCCGGGTAAA | |
| CD3-CLC | CAGGCCGTCGTGACCCAGGAACCCAGCCTGACAGTGTCTCCTGGCGGCACCG<br>TGACCCTGACATGTGGCAGTTCTACAGGCGCCGTGACCACCAGCAACTACGC<br>CAACTGGGTGCAGGAAAAGCCCGGCCAGGCCTTCAGAGGACTGATCGGCGGC<br>ACCAACAAGAGAGCCCCTGGCACCCCTGCCAGATTCAGCGGATCTCTGCTGG<br>GAGGAAAGGCCGCCCTGACACTGTCTGGCGCCCAGCCAGAAGATGAGGCCGA<br>GTACTACTGCGCCCTGTGGTACAGCAACCTGTGGGTGTTCGGCGGAGGCACC<br>AAGCTGACAGTCCTAGGTCAACCCAAGGCTGCCCCCAGCGTGACCCTGTTCC<br>CCCCCAGCAGCGAGGAACTGCAGGCCAACAAGGCCACCCTGGTCTGCCTGAT<br>CAGCGACTTCTACCCAGGCGCCGTGACCGTGGCCTGGAAGGCCGACAGCAGC<br>CCCGTGAAGGCCGGCGTGGAGACCACCACCCCCAGCAAGCAGAGCAACAACA<br>AGTACGCCGCCAGCAGCTACCTGAGCCTGACCCCCGAGCAGTGGAAGAGCCA<br>CAGGTCCTACAGCTGCCAGGTGACCCACGAGGGCAGCACCGTGGAGAAAACC<br>GTGGCCCCCACCGAGTGCAGC | 267 |
| 16D5<br>[VHCH1]-<br>CD3[VHC<br>H1-<br>S100aA]<br>Fcknob_P<br>GLALA | GAGGTGCAATTGGTTGAATCTGGTGGTGGTCTGGTAAAACCGGGCGGTTCCC<br>TGCGTCTGAGCTGCGCGGCTTCCGGATTCACCTTCTCCAACGCGTGGATGAG<br>CTGGGTTCGCCAGGCCCCGGGCAAAGGCCTCGAGTGGGTTGGTCGTATCAAG<br>TCTAAAACTGACGGTGGCACCACGGATTACGCGGCTCCAGTTAAAGGTCGTT<br>TTACCATTTCCCGCGACGATAGCAAAAACACTCTGTATCTGCAGATGAACTC<br>TCTGAAAACTGAAGACACCGCAGTCTACTACTGTACTACCCCGTGGGAATGG<br>TCTGGTACGATTATTGGGGCCAGGGCACGCTGGTTACGGTGTCTTCCGCTA<br>GCACAAAGGGCCCTAGCGTGTTCCCTCTGGCCCCCAGCAGCAAGAGCACAAG<br>CGGCGGAACAGCCGCCCTGGGCTGCCTCGTGAAGGACTACTTCCCCGAGCCC<br>GTGACAGTGTCTTGGAACAGCGGAGCCCTGACAAGCGGCGTGCACACTTTCC<br>CTGCCGTGCTGCAGAGCAGCGGCCTGTACTCCCTGAGCAGCGTGGTCACCGT<br>GCCTAGCAGCAGCCTGGGCACCCAGACCTACATCTGCAACGTGAACCACAAG<br>CCCAGCAACACCAAAGTGGACAAGAAGGTGGAGCCCAAGAGCTGTGATGGCG<br>GAGGAGGGTCCGGAGGCGGAGGATCCGAGGTGCAGCTGCTGGAATCTGGCGG<br>CGGACTGGTGCAGCCTGGCGGATCTCTGAGACTGAGCTGTGCCGCCAGCGGC<br>TTCACCTTCAGCACCTACGCCATGAACTGGGTGCGCCAGGCCCCTGGCAAAG<br>GCCTGGAATGGGTGTCCCGGATCAGAAGCAAGTACAACAACTACGCCACCTA<br>CTACGCCGACAGCGTGAAGGGCCGGTTCACCATCAGCCGGGACGACAGCAAG<br>AACACCCTGTACCTGCAGATGAACAGCCTGCGGGCCGAGGACACCGCCGTGT<br>ACTATTGTGTGCGGCACGGCAACTTCGGCAACGCCTATGTGTCTTGGTTTGC<br>CTACTGGGGCCAGGGCACCCTCGTGACCGTGTCAAGCGCTAGTACCAAGGGC<br>CCCAGCGTGTTCCCCCTGGCACCCAGCAGCAAGAGCACATCTGGCGGAACAG<br>CCGCTCTGGGCTGTCTGGTGAAAGACTACTTCCCCGAGCCCGTGACCGTGTC<br>TTGGAACTCTGGCGCCCTGACCAGCGGCGTGCACACCTTTCCAGCCGTGCTG<br>CAGAGCAGCGGCCTGTACTCCCTGTCCTCCGTGGTCACCGTGCCCTCTAGCT<br>CCCTGGGAACACAGACATATATCTGTAATGTCAATCACAAGCCTTCCAACAC<br>CAAAGTCGATAAGAAAGTCGAGCCCAAGAGCTGCGACAAAACTCACACATGC<br>CCACCGTGCCCAGCACCTGAAGCTGCAGGGGACCGTCAGTCTTCCTCTTCC<br>CCCCAAAACCCAAGGACACCCTCATGATCTCCCGGACCCCTGAGGTCACATG<br>CGTGGTGGTGGACGTGAGCCACGAAGACCCTGAGGTCAAGTTCAACTGGTAC<br>GTGGACGGCGTGGAGGTGCATAATGCCAAGACAAAGCCGCGGGAGGAGCAGT<br>ACAACAGCACGTACCGTGTGGTCAGCGTCCTCACCGTCCTGCACCAGGACTG<br>GCTGAATGGCAAGGAGTACAAGTGCAAGGTCTCCAACAAAGCCCTCGGCGCC<br>CCCATCGAGAAAACCATCTCCAAAGCCAAAGGGCAGCCCCGAGAACCACAGG<br>TGTACACCCTGCCCCCATGCCCGGGATGAGCTGACCAAGAACCAGGTCAGCCT<br>GTGGTGCCTGGTCAAAGGCTTCTATCCCAGCGACATCGCCGTGGAGTGGGAG<br>AGCAATGGGCAGCCGGAGAACAACTACAAGACCACGCCTCCCGTGCTGGACT<br>CCGACGGCTCCTTCTTCCTCTACAGCAAGCTCACCGTGGACAAGAGCAGGTG<br>GCAGCAGGGGAACGTCTTCTCATGCTCCGTGATGCATGAGGCTCTGCACAAC<br>CACTACACGCAGAAGAGCCTCTCCCTGTCTCCGGGTAAA | 268 |
| 9D11<br>[VHCH1]-<br>CD3[VHC<br>L-<br>N100A] | CAGGTGCAATTGGTTCAATCTGGTGCTGAAGTAAAAAAACCGGGCGCTTCCG<br>TTAAAGTGAGCTGCAAAGCATCCGGATACACCTTCACTTCCTATTACATGCA<br>CTGGGTTCGTCAAGCCCCGGGCCAGGGTCTGGAATGGATGGGCATCATTAAC<br>CCAAGCGGTGGCCCTACCTCCTACGCGCAGAAATTCCAGGGTCGCGTCACGA<br>TGACCCGTGACACTAGCACCTCTACCGTTTATATGGAGCTGTCCAGCCTGCG | 269 |

| Description | Sequence | Seq ID No |
|---|---|---|
| Fcknob_P GLALA | TTCTGAAGATACTGCAGTGTACTACTGTGCACGCGGTGACTTCGCTTGGCTG<br>GACTATTGGGTCAAGGCACCCTCGTAACGGTTTCTTCTGCTAGCACAAAGG<br>GCCCCAGCGTGTTCCCTCTGGCCCCTAGCAGCAAGAGCACATCTGGCGGAAC<br>AGCCGCCCTGGGCTGCCTCGTGAAGGACTACTTTCCCGAGCCTGTGACCGTG<br>TCCTGGAACTCTGGCGCCCTGACAAGCGGCGTGCACACCTTTCCAGCCGTGC<br>TGCAGAGCAGCGGCCTGTACTCTCTGAGCAGCGTGGTCACCGTGCCTAGCAG<br>CAGCCTGGGCACCCAGACCTACATCTGCAACGTGAACCACAAGCCCAGCAAC<br>ACCAAAGTGGACAAGAAGGTGGAGCCCAAGAGCTGTGATGGCGGAGGAGGGT<br>CCGGAGGCGGAGGATCCGAGGTGCAGCTGCTGGAATCTGGCGGCGGACTGGT<br>GCAGCCTGGCGGATCTCTGAGACTGAGCTGTGCCGCCAGCGGCTTCACCTTC<br>AGCACCTACGCCATGAACTGGGTGCGCCAGGCCCCTGGCAAAGGCCTGGAAT<br>GGGTGTCCCGGATCAGAAGCAAGTACAACAACTACGCCACCTACTACGCCGA<br>CAGCGTGAAGGGCCGGTTCACCATCAGCCGGGACGACAGCAAGAACACCCTG<br>TACCTGCAGATGAACAGCCTGCGGGCCGAGGACACCGCCGTGTACTATTGTG<br>TGCGGCACGGCAACTTCGGCGCCAGCTATGTGTCTTGGTTTGCCTACTGGGG<br>CCAGGGCACCCTCGTGACCGTGTCAAGCGCTAGTGTGGCCGCTCCCTCCGTG<br>TTTATCTTTCCCCCATCCGATGAACAGCTGAAAAGCGGCACCGCCTCCGTCG<br>TGTGTCTGCTGAACAATTTTTACCCTAGGGAAGCTAAAGTGCAGTGGAAAGT<br>GGATAACGCACTGCAGTCCGGCAACTCCCAGGAATCTGTGACAGAACAGGAC<br>TCCAAGGACAGCACCTACTCCCTGTCCTCCACCCTGACACTGTCTAAGGCTG<br>ATTATGAGAAACACAAAGTCTACGCCTGCGAAGTCACCCATCAGGGCCTGAG<br>CTCGCCCGTCACAAAGAGCTTCAACAGGGGAGAGTGTGACAAGACCCACACC<br>TGTCCCCCTTGTCCTGCCCCTGAAGCTGCTGGCGGCCCTTCTGTGTTCCTGT<br>TCCCCCCAAAGCCCAAGGACACCCTGATGATCAGCCGGACCCCCGAAGTGAC<br>CTGCGTGGTGGTGGATGTGTCCCACGAGGACCCTGAAGTGAAGTTCAATTGG<br>TACGTGGACGGCGTGGAAGTGCACAACGCCAAGACAAAGCCGCGGGAGGAGC<br>AGTACAACAGCACGTACCGTGTGGTCAGCGTCCTCACCGTCCTGCACCAGGA<br>CTGGCTGAATGGCAAGGAGTACAAGTGCAAGGTCTCCAACAAAGCCCTCGGC<br>GCCCCCATCGAGAAAACCATCTCCAAAGCCAAAGGGCAGCCCCGAGAACCAC<br>AGGTGTACACCCTGCCCCCATGCCGGGATGAGCTGACCAAGAACCAGGTCAG<br>CCTGTGGTGCCTGGTCAAAGGCTTCTATCCCAGCGACATCGCCGTGGAGTGG<br>GAGAGCAATGGGCAGCCGGAGAACAACTACAAGACCACGCCTCCCGTGCTGG<br>ACTCCGACGGCTCCTTCTTCCTCTACAGCAAGCTCACCGTGGACAAGAGCAG<br>GTGGCAGCAGGGGAACGTCTTCTCATGCTCCGTGATGCATGAGGCTCTGCAC<br>AACCACTACACGCAGAAGAGCCTCTCCCTGTCTCCGGGTAAA | |
| 9D11-Fchole | CAGGTGCAATTGGTTCAATCTGGTGCTGAAGTAAAAAAACCGGGCGCTTCCG<br>TTAAAGTGAGCTGCAAAGCATCCGGATACACCTTCACTTCCTATTACATGCA<br>CTGGGTTCGTCAAGCCCCGGGCCAGGGTCTGGAATGGATGGGCATCATTAAC<br>CCAAGCGGTGGCCCTACCTCCTACGCGCAGAAATTCCAGGGTCGCGTCACGA<br>TGACCCGTGACACTAGCACCTCTACCGTTTATATGGAGCTGTCCAGCCTGCG<br>TTCTGAAGATACTGCAGTGTACTACTGTGCACGCGGTGACTTCGCTTGGCTG<br>GACTATTGGGTCAAGGCACCCTCGTAACGGTTTCTTCTGCTAGCACCAAGG<br>GCCCCTCCGTGTTCCCCCTGGCCCCCAGCAGCAAGAGCACCAGCGGCGGCAC<br>AGCCGCTCTGGGCTGCCTGGTCAAGGACTACTTCCCCGAGCCCGTGACCGTG<br>TCCTGGAACAGCGGAGCCCTGACCTCCGGCGTGCACACCTTCCCCGCCGTGC<br>TGCAGAGTTCTGGCCTGTATAGCCTGAGCAGCGTGGTCACCGTGCCTTCTAG<br>CAGCCTGGGCACCCAGACCTACATCTGCAACGTGAACCACAAGCCCAGCAAC<br>ACCAAGGTGGACAAGAAGGTGGAGCCCAAGAGCTGCGACAAAACTCACACAT<br>GCCCACCGTGCCCAGCACCTGAAGCTGCAGGGGGACCGTCAGTCTTCCTCTT<br>CCCCCCAAAACCCAAGGACACCCTCATGATCTCCCGGACCCCTGAGGTCACA<br>TGCGTGGTGGTGGACGTGAGCCACGAAGACCCTGAGGTCAAGTTCAACTGGT<br>ACGTGGACGGCGTGGAGGTGCATAATGCCAAGACAAAGCCGCGGGAGGAGCA<br>GTACAACAGCACGTACCGTGTGGTCAGCGTCCTCACCGTCCTGCACCAGGAC<br>TGGCTGAATGGCAAGGAGTACAAGTGCAAGGTCTCCAACAAAGCCCTCGGCG<br>CCCCCATCGAGAAAACCATCTCCAAAGCCAAAGGGCAGCCCCGAGAACCACA<br>GGTGTGCACCCTGCCCCCATCCCGGGATGAGCTGACCAAGAACCAGGTCAGC<br>CTCTCGTGCGCAGTCAAAGGCTTCTATCCCAGCGACATCGCCGTGGAGTGGG<br>AGAGCAATGGGCAGCCGGAGAACAACTACAAGACCACGCCTCCCGTGCTGGA<br>CTCCGACGGCTCCTTCTTCCTCGTGAGCAAGCTCACCGTGGACAAGAGCAGG<br>TGGCAGCAGGGGAACGTCTTCTCATGCTCCGTGATGCATGAGGCTCTGCACA<br>ACCACTACACGCAGAAGAGCCTCTCCCTGTCTCCGGGTAAA | 270 |
| 9D11_LC [N95Q] | GATATTGTTATGACTCAATCTCCACTGTCTCTGCCGGTGACTCCAGGCGAAC<br>CGGCGAGCATTTCTTGCCGTTCCAGCCAGTCTCTGCTGCACTCCAACGGCTA<br>CAACTATCTCGATTGGTACCTGCAAAAACCGGGTCAGAGCCCTCAGCTGCTG<br>ATCTACCTGGGCTCTAACCGCGCTTCCGGTGTACCGGACCGTTTCAGCGGCT<br>CTGGATCCGGCACCGATTTCACGTTGAAAATCAGCCGTGTTGAAGCAGAAGA<br>CGTGGGCGTTTATTACTGTATGCAGGCAAGCATTATGCAGCGGACTTTTGGT<br>CAAGGCACCAAGGTCGAAATTAAACGTACGGTGGCTGCACCATCTGTCTTCA<br>TCTTCCCGCCATCTGATGAGCAGTTGAAATCTGGAACTGCCTCTGTTGTGTG<br>CCTGCTGAATAACTTCTATCCCAGAGAGGCAAAGTACAGTGGAAGGTGGAT<br>AACGCCCTCCAATCGGGTAACTCCCAGGAGAGTGTCACAGAGCAGGACAGCA<br>AGGACAGCACCTACAGCCTCAGCAGCACCCTGACGCTGAGCAAAGCAGACTA<br>CGAGAAACACAAAGTCTACGCCTGCGAAGTCACCCATCAGGGCCTGAGCTCG<br>CCCGTCACAAAGAGCTTCAACAGGGGAGAGTGT | 271 |

-continued

| Description | Sequence | Seq ID No |
|---|---|---|
| CD3_VLC H1 | CAGGCCGTCGTGACCCAGGAACCCAGCCTGACAGTGTCTCCTGGCGGCACCG TGACCCTGACATGTGGCAGTTCTACAGGCGCCGTGACCACCAGCAACTACGC CAACTGGGTGCAGGAAAAGCCCGGCCAGGCCTTCAGAGGACTGATCGGCGGC ACCAACAAGAGAGCCCCTGGCACCCCTGCCAGATTCAGCGGATCTCTGCTGG GAGGAAAGGCCGCCCTGACACTGTCTGGCGCCCAGCCAGAAGATGAGGCCGA GTACTACTGCGCCCTGTGGTACAGCAACCTGTGGGTGTTCGGCGGAGGCACC AAGCTGACAGTGCTGAGCAGCGCTTCCACCAAAGGCCCTTCCGTGTTTCCTC TGGCTCCTAGCTCCAAGTCCACCTCTGGAGGCACCGCTGCTCTCGGATGCCT CGTGAAGGATTATTTTCCTGAGCCTGTGACAGTGTCCTGGAATAGCGGAGCA CTGACCTCTGGAGTGCATACTTTCCCCGCTGTGCTGCAGTCCTCTGGACTGT ACAGCCTGAGCAGCGTGGTGACAGTGCCCAGCAGCAGCCTGGGCACCCAGAC CTACATCTGCAACGTGAACCACAAGCCCAGCAACACCAAGGTGGACAAGAAG GTGGAACCCAAGTCTTGT | 272 |
| 9D11 [VHCH1]- CD3[VHC H1- S100aA]- Fcknob_P GLALA | CAGGTGCAATTGGTTCAATCTGGTGCTGAAGTAAAAAAACCGGGCGCTTCCG TTAAAGTGAGCTGCAAAGCATCCGGATACACCTTCACTTCCTATTACATGCA CTGGGTTCGTCAAGCCCCGGGCAGGGTCTGGAATGGATGGGCATCATTAAC CCAAGCGGTGGCCCTACCTCCTACGCGCAGAAATTCCAGGGTCGCGTCACGA TGACCCGTGACACTAGCACCTCTACCGTTTATATGGAGCTGTCCAGCCTGCG TTCTGAAGATACTGCAGTGTACTACTGTGCACGCGGTGACTTCGCTTGGCTG GACTATTGGGGTCAAGGCACCCTCGTAACGGTTTCTTCTGCTAGCACAAAGG GCCCCAGCGTGTTCCCTCTGGCCCCTAGCAGCAAGAGCACATCTGGCGGAAC AGCCGCCCTGGGCTGCCTCGTGAAGGACTACTTTCCCGAGCCTGTGACCGTG TCCTGGAACTCTGGCGCCCTGACAAGCGGCGTGCACACCTTTCCAGCCGTGC TGCAGAGCAGCGGCCTGTACTCTCTGAGCAGCGTGGTCACCGTGCCTAGCAG CAGCCTGGGCACCCAGACCTACATCTGCAACGTGAACCACAAGCCCAGCAAC ACCAAAGTGGACAAGAAGGTGGAGCCCAAGAGCTGTGATGGCGGAGGAGGGT CCGGAGGCGGAGGATCCGAGGTGCAGCTGCTGGAATCTGGCGGCGGACTGGT GCAGCCTGGCGGATCTCTGAGACTGAGCTGTGCCGCCAGCGGCTTCACCTTC AGCACCTACGCCATGAACTGGGTGCGCCAGGCCCCTGGCAAAGGCCTGGAAT GGGTGTCCCGGATCAGAAGCAAGTACAACAACTACGCCACCTACTACGCCGA CAGCGTGAAGGGCCGGTTCACCATCAGCCGGGACGACAGCAAGAACACCCTG TACCTGCAGATGAACAGCCTGCGGGCCGAGGACACCGCCGTGTACTATTGTG TGCGGCACGGCAACTTCGGCAACGCCTATGTCTTGGTTTGCCTACTGGGG CCAGGGCACCCTCGTGACCGTGTCAAGCGCTAGTGTGGCCGCTCCCTCCGTG TTTATCTTTCCCCCATCCGATGAACAGCTGAAAAGCGGCACCGCCTCCGTCG TGTGTCTGCTGAACAATTTTTACCCTAGGGAAGCTAAAGTGCAGTGGAAAGT GGATAACGCACTGCAGTCCGGCAACTCCCAGGAATCTGTGACAGAACAGGAC TCCAAGGACAGCACCTACTCCCTGTCCTCCACCCTGACACTGTCTAAGGCTG ATTATGAGAAACACAAAGTCTACGCCTGCGAAGTCACCCATCAGGGCCTGAG CTCGCCCGTCACAAAGAGCTTCAACAGGGGAGAGTGTGACAAGACCCACACC TGTCCCCCTTGTCCTGCCCCTGAAGCTGCTGGCGGACCCTTCTGTGTTCCTGT TCCCCCCAAAGCCCAAGGACACCCTGATGATCAGCCGGACCCCCGAAGTGAC CTGCGTGGTGGTGGATGTGTCCCACGAGGACCCTGAAGTGAAGTTCAATTGG TACGTGGACGGCGTGGAAGTGCACAACGCCAAGACAAAGCCGCGGGAGGAGC AGTACAACAGCACGTACCGTGTGGTCAGCGTCCTCACCGTCCTGCACCAGGA CTGGCTGAATGGCAAGGAGTACAAGTGCAAGGTCTCCAACAAAGCCCTCGGC GCCCCCATCGAGAAAACCATCTCCAAAGCCAAAGGGCAGCCCCGAGAACCAC AGGTGTACACCCTGCCCCCATGCCGGGATGAGCTGACCAAGAACCAGGTCAG CCTGTGGTGCCTGGTCAAAGGCTTCTATCCCAGCGACATCGCCGTGGAGTGG GAGAGCAATGGGCAGCCGGAGAACAACTACAAGACCACGCCTCCCGTGCTGG ACTCCGACGGCTCCTTCTTCCTCTACAGCAAGCTCACCGTGGACAAGAGCAG GTGGCAGCAGGGGAACGTCTTCTCATGCTCCGTGATGCATGAGGCTCTGCAC AACCACTACACGCAGAAGAGCCTCTCCCTGTCTCCGGGTAAA | 273 |
| 16D5 variant W96Y/D52 E VH | GAGGTGCAATTGGTGGAAAGCGGAGGCGGCCTCGTGAAGCCTGGCGGATCTCTG AGACTGAGCTGTGCCGCCAGCGGCTTCACCTTCAGCAACGCCTGGATGAGCTGG GTGCGCCAGGCCCCTGGAAAAGGACTCGAGTGGGTGGGACGGATCAAGAGCAAG ACCGAGGGCGGCACCACCGACTATGCCGCCCCTGTGAAGGGCCGGTTCACCATC AGCAGGGACGACAGCAAGAACACCCTGTACCTGCAGATGAACAGCCTGAAAACC GAGGACACCGCCGTGTACTACTGCACCACCCCCTACGAGTGGTCTTGGTACGAC TACTGGGGCCAGGGCACCCTCGTGACCGTGTCATCT | 287 |
| W96Y/D5 2E CD3- VHCH1_Fc knob_PGL ALA pETR1494 5 | GAGGTGCAATTGGTGGAAAGCGGAGGCGGCCTCGTGAAGCCTGGCGGATCTCTG AGACTGAGCTGTGCCGCCAGCGGCTTCACCTTCAGCAACGCCTGGATGAGCTGG GTGCGCCAGGCCCCTGGAAAAGGACTCGAGTGGGTGGGACGGATCAAGAGCAAG ACCGAGGGCGGCACCACCGACTATGCCGCCCCTGTGAAGGGCCGGTTCACCATC AGCAGGGACGACAGCAAGAACACCCTGTACCTGCAGATGAACAGCCTGAAAACC GAGGACACCGCCGTGTACTACTGCACCACCCCCTACGAGTGGTCTTGGTACGAC TACTGGGGCCAGGGCACCCTCGTGACCGTGTCATCTGCTAGCACAAAGGGCCCT AGCGTGTTCCCTCTGGCCCCCAGCAGCAAGAGCACAAGCGGCGGAACCGCCGCC CTGGGCTGCCTCGTGAAGGACTACTTCCCCGAGCCCGTGACAGTGTCTTGGAAC AGCGGAGCCCTGACAAGCGGCGTGCACACCTTCCCTGCCGTGCTGCAGAGCAGC GGCCTGTACTCCCTGAGCAGCGTGGTCACCGTGCCTAGCAGCAGCCTGGGCACC CAGACCTACATCTGCAACGTGAACCACAAGCCCAGCAACACCAAAGTGGACAAG AAGGTGGAGCCCAAGAGCTGTGATGGCGGAGGAGGGTCCGGAGGCGGAGGATCC GAGGTGCAGCTGCTGGAATCTGGCGGCGGACTGGTGCAGCCTGGCGGATCTCTG | 288 |

-continued

| Description | Sequence | Seq ID No |
|---|---|---|
| | AGACTGAGCTGTGCCGCCAGCGGCTTCACCTTCAGCACCTACGCCATGAACTGG<br>GTGCGCCAGGCCCCTGGCAAAGGCCTGGAATGGGTGTCCCGGATCAGAAGCAAG<br>TACAACAACTACGCCACCTACTACGCCGACAGCGTGAAGGGCCGGTTCACCATC<br>AGCCGGGACGACAGCAAGAACACCCTGTACCTGCAGATGAACAGCCTGCGGGCC<br>GAGGACACCGCCGTGTACTATTGTGTGCGGCACGGCAACTTCGGCAACAGCTAT<br>GTGTCTTGGTTTGCCTACTGGGGCCAGGGCACCCTCGTGACCGTGTCAAGCGCT<br>AGTACCAAGGGCCCCAGCGTGTTCCCCCTGGCACCCAGCAGCAAGAGCACATCT<br>GGCGGAACAGCCGCTCTGGGCTGTCTGGTGAAAGACTACTTCCCCGAGCCCGTG<br>ACCGTGTCTTGGAACTCTGGCGCCCTGACCAGCGGCGTGCACACCTTTCCAGCC<br>GTGCTGCAGAGCAGCGGCCTGTACTCCCTGTCCTCCGTGGTCACCGTGCCCTCT<br>AGCTCCCTGGGAACACAGACATATATCTGTAATGTCAATCACAAGCCTTCCAAC<br>ACCAAAGTCGATAAGAAAGTCGAGCCCAAGAGCTGCGACAAAACTCACACATGC<br>CCACCGTGCCCAGCACCTGAAGCTGCAGGGGGACCGTCAGTCTTCCTCTTCCCC<br>CCAAAACCCAAGGACACCCTCATGATCTCCCGGACCCCTGAGGTCACATGCGTG<br>GTGGTGGACGTGAGCCACGAAGACCCTGAGGTCAAGTTCAACTGGTACGTGGAC<br>GGCGTGGAGGTGCATAATGCCAAGACAAAGCCGCGGGAGGAGCAGTACAACAGC<br>ACGTACCGTGTGGTCAGCGTCCTCACCGTCCTGCACCAGGACTGGCTGAATGGC<br>AAGGAGTACAAGTGCAAGGTCTCCAACAAAGCCCTCGGCGCCCCCATCGAGAAA<br>ACCATCTCCAAAGCCAAAGGGCAGCCCCGAGAACCACAGGTGTACACCCTGCCC<br>CCATGCCGGGATGAGCTGACCAAGAACCAGGTCAGCCTGTGGTGCCTGGTCAAA<br>GGCTTCTATCCCAGCGACATCGCCGTGGAGTGGGAGAGCAATGGGCAGCCGGAG<br>AACAACTACAAGACCACGCCTCCCGTGCTGGACTCCGACGGCTCCTTCTTCCTC<br>TACAGCAAGCTCACCGTGGACAAGAGCAGGTGGCAGCAGGGGAACGTCTTCTCA<br>TGCTCCGTGATGCATGAGGCTCTGCACAACCACTACACGCAGAAGAGCCTCTCC<br>CTGTCTCCGGGTAAA | |
| W96Y/D5<br>2E_Fc-<br>hole_PGLA<br>LA_HYRF<br>pETR1494<br>6 | GAGGTGCAATTGGTGGAAAGCGGAGGCGGCCTCGTGAAGCCTGGCGGATCTCTG<br>AGACTGAGCTGTGCCGCCAGCGGCTTCACCTTCAGCAACGCCTGGATGAGCTGG<br>GTGCGCCAGGCCCCTGGAAAAGGACTCGAGTGGGTGGGACGGATCAAGAGCAAG<br>ACCGAGGGCGGCACCACCGACTATGCCGCCCCTGTGAAGGGCCGGTTCACCATC<br>AGCAGGGACGACAGCAAGAACACCCTGTACCTGCAGATGAACAGCCTGAAAACC<br>GAGGACACCGCCGTGTACTACTGCACCACCCCCTACGAGTGGTCTTGGTACGAC<br>TACTGGGGCCAGGGCACCCTCGTGACCGTGTCATCTGCTAGCACCAAGGGCCCC<br>TCCGTGTTCCCCCTGGCCCCCAGCAGCAAGAGCACCAGCGGCGGCACAGCCGCT<br>CTGGGCTGCCTGGTCAAGGACTACTTCCCCGAGCCCGTGACCGTGTCCTGGAAC<br>AGCGGAGCCCTGACCTCCGGCGTGCACACCTTCCCCGCCGTGCTGCAGAGTTCT<br>GGCCTGTATAGCCTGAGCAGCGTGGTCACCGTGCCTTCTAGCAGCCTGGGCACC<br>CAGACCTACATCTGCAACGTGAACCACAAGCCCAGCAACACCAAGGTGGACAAG<br>AAGGTGGAGCCCAAGAGCTGCGACAAAACTCACACATGCCCACCGTGCCCAGCA<br>CCTGAAGCTGCAGGGGGACCGTCAGTCTTCCTCTTCCCCCCAAAACCCAAGGAC<br>ACCCTCATGATCTCCCGGACCCCTGAGGTCACATGCGTGGTGGTGGACGTGAGC<br>CACGAAGACCCTGAGGTCAAGTTCAACTGGTACGTGGACGGCGTGGAGGTGCAT<br>AATGCCAAGACAAAGCCGCGGGAGGAGCAGTACAACAGCACGTACCGTGTGGTC<br>AGCGTCCTCACCGTCCTGCACCAGGACTGGCTGAATGGCAAGGAGTACAAGTGC<br>AAGGTCTCCAACAAAGCCCTCGGCGCCCCCATCGAGAAAACCATCTCCAAAGCC<br>AAAGGGCAGCCCCGAGAACCACAGGTGTGCACCCTGCCCCCATCCCGGGATGAG<br>CTGACCAAGAACCAGGTCAGCCTCTCGTGCGCAGTCAAAGGCTTCTATCCCAGC<br>GACATCGCCGTGGAGTGGGAGAGCAATGGGCAGCCGGAGAACAACTACAAGACC<br>ACGCCTCCCGTGCTGGACTCCGACGGCTCCTTCTTCCTCGTGAGCAAGCTCACC<br>GTGGACAAGAGCAGGTGGCAGCAGGGGAACGTCTTCTCATGCTCCGTGATGCAT<br>GAGGCTCTGCACAACCGCTTCACGCAGAAGAGCCTCTCCCTGTCTCCGGGTAAA | 289 |
| 14B1<br>VH | GAGGTGCAATTGTTGGAGTCTGGGGGAGGCTTGGTACAGCCTGGGGGGTCCCTG<br>AGACTCTCCTGTGCAGCCTCCGGATTCACCTTTAGCAGTTATGCCATGAGCTGG<br>GTCCGCCAGGCTCCAGGGAAGGGGCTGGAGTGGGTCTCAGCTATTAGTGGTAGT<br>GGTGGTAGCACATACTACGCAGACTCCGTGAAGGGCCGGTTCACCATCTCCAGA<br>GACAATTCCAAGAACACGCTGTATCTGCAGATGAACAGCCTGAGAGCCGAGGAC<br>ACGGCCGTATATTACTGTGCGCGTGGTGACTACCGTTACCGTTACTTCGACTAC<br>TGGGGCCAAGGAACCCTGGTCACCGTCTCGAGT | 290 |
| 14B1<br>VL | TCTTCTGAACTGACTCAAGATCCAGCTGTTAGCGTGGCTCTGGGTCAGACTGTA<br>CGTATCACCTGCCAAGGCGATTCTCTGCGCTCCTACTACGCAAGCTGGTACCAG<br>CAGAAACCGGGTCAGGCCCCAGTTCTGGTGATTTACGGCAAAAACAACCGTCCG<br>TCTGGGATCCCGGACCGTTTCTCCGGCAGCTCTTCCGGTAACACGGCGAGCCTC<br>ACCATCACTGGCGCTCAAGCAGAAGACGAGGCCGACTATTACTGTAACTCTCGG<br>GAAAGCCCACCAACCGGCCTGGTTGTCTTCGGTGGCGGTACCAAGCTGACCGTC<br>CTA | 291 |
| 14B1[EE]_<br>CD3[VLCH<br>1]_Fc-<br>knob_PGL<br>ALA<br>pETR1497<br>6 | GAGGTGCAATTGTTGGAGTCTGGGGGAGGCTTGGTACAGCCTGGGGGGTCCCTG<br>AGACTCTCCTGTGCAGCCTCCGGATTCACCTTTAGCAGTTATGCCATGAGCTGG<br>GTCCGCCAGGCTCCAGGGAAGGGGCTGGAGTGGGTCTCAGCTATTAGTGGTAGT<br>GGTGGTAGCACATACTACGCAGACTCCGTGAAGGGCCGGTTCACCATCTCCAGA<br>GACAATTCCAAGAACACGCTGTATCTGCAGATGAACAGCCTGAGAGCCGAGGAC<br>ACGGCCGTATATTACTGTGCGCGTGGTGACTACCGTTACCGTTACTTCGACTAC<br>TGGGGCCAAGGAACCCTGGTCACCGTCTCGAGTGCTAGCACCAAGGGCCCCTCC<br>GTGTTTCCTCTGGCCCCTTCCAGCAAGTCCACCTCTGGCGGAACTGCCGCTCTG<br>GGCTGCCTGGTGGAAGATTACTTCCCCGAGCCCGTGACCGTGTCCTGGAATTCT | 292 |

| Description | Sequence | Seq ID No |
|---|---|---|
| | GGCGCTCTGACCTCCGGCGTGCACACCTTTCCAGCTGTGCTGCAGTCCTCCGGC<br>CTGTACTCCCTGTCCTCCGTCGTGACAGTGCCCTCCAGCTCTCTGGGCACCCAG<br>ACCTACATCTGCAACGTGAACCACAAGCCCTCCAACACCAAGGTGGACAAGAAA<br>GTGGAACCCAAGTCCTGCGACGGTGGCGGAGGTTCCGGAGGCGGAGGATCCCAG<br>GCTGTCGTGACCCAGGAACCCTCCCTGACAGTGTCTCCTGGCGGCACCGTGACC<br>CTGACCTGTGGATCTTCTACCGGCGCTGTGACCACTCCAACTACGCCAATTGG<br>GTGCAGGAAAAGCCCGGCCAGGCCTTCAGAGGACTGATCGGCGGCACCAACAAG<br>AGAGCCCCTGGCACCCCTGCCAGATTCTCCGGTTCTCTGCTGGGCGGCAAGGCT<br>GCCCTGACTCTGTCTGGTGCTCAGCCTGAGGACGAGGCCGAGTACTACTGCGCC<br>CTGTGGTACTCCAACCTGTGGGTGTTCGGCGGAGGCACCAAGCTGACCGTGCTG<br>TCCAGCGCTTCCACCAAGGGACCCAGTGTGTTCCCCCTGGCCCCCAGCTCCAAG<br>TCTACATCCGGTGGCACAGCTGCCCTGGGATGTCTCGTGAAGGACTACTTTCCT<br>GAGCCTGTGACAGTGTCTTGGAACAGCGGAGCCCTGACCAGCGGAGTGCACACA<br>TTCCCTGCAGTGCTGCAGAGCAGCGGCCTGTATAGCCTGAGCAGCGTCGTGACC<br>GTGCCTTCCTCTAGCCTGGGAACACAGACATATATCTGTAATGTGAATCATAAG<br>CCCAGTAATACCAAAGTGGATAAGAAAGTGGAACCTAAGAGCTGCGATAAGACC<br>CACACCTGTCCCCCCTGCCCTGCTCCTGAAGCTGCTGGTGGCCCTAGCGTGTTC<br>CTGTTCCCCCCAAAGCCCAAGGACACCCTGATGATCTCCCGGACCCCCGAAGTG<br>ACCTGCGTGGTGGTGGATGTGTCCCACGAGGACCCTGAAGTGAAGTTCAATTGG<br>TACGTGGACGGCGTGGAAGTGCACAACGCCAAGACCAAGCCTAGAGAGGAACAG<br>TACAACTCCACCTACCGGGTGGTGTCCGTGCTGACAGTGCTGCACCAGGACTGG<br>CTGAACGGCAAAGAGTACAAGTGCAAGGTGTCCAACAAGGCCCTGGGCGCTCCC<br>ATCGAAAAGACCATCTCCAAGGCCAAGGGCCAGCCCCGGGAACCCCAGGTGTAC<br>ACCCTGCCCCCATGCCGGGATGAGCTGACCAAGAACCAGGTCAGCCTGTGGTGC<br>CTGGTCAAAGGCTTCTATCCCAGCGACATCGCCGTGGAGTGGGAGAGCAATGGG<br>CAGCCGGAGAACAACTACAAGACCACGCCTCCCGTGCTGGACTCCGACGGCTCC<br>TTCTTCCTCTACAGCAAGCTCACCGTGGACAAGAGCAGGTGGCAGCAGGGGAAC<br>GTCTTCTCATGCTCCGTGATGCATGAGGCTCTGCACAACCACTACACGCAGAAG<br>AGCCTCTCCCTGTCTCCGGGTAAA | |
| 14B1[EE]_<br>Fc-<br>hole_PGLA<br>LA<br>pETR1497<br>7 | GAGGTGCAATTGTTGGAGTCTGGGGGAGGCTTGGTACAGCCTGGGGGGTCCCTG<br>AGACTCTCCTGTGCAGCCTCCGGATTCACCTTTAGCAGTTATGCCATGAGCTGG<br>GTCCGCCAGGCTCCAGGGAAGGGGCTGGAGTGGGTCTCAGCTATTAGTGGTAGT<br>GGTGGTAGCACATACTACGCAGACTCCGTGAAGGGCCGGTTCACCATCTCCAGA<br>GACAATTCCAAGAACACGCTGTATCTGCAGATGAACAGCCTGAGAGCCGAGGAC<br>ACGGCCGTATATTACTGTGCGCGTGGTGACTACCGTTACCGTTACTTCGACTAC<br>TGGGGCCAAGGAACCCTGGTCACCGTCTCGAGTGCTAGCACCAAGGGCCCCTCC<br>GTGTTCCCCCTGGCCCCCAGCAGCAAGAGCACCAGCGGCGGCACAGCCGCTCTG<br>GGCTGCCTGGTCGAGGACTACTTCCCCGAGCCCGTGACCGTGTCCTGGAACAGC<br>GGAGCCCTGACCTCCGGCGTGCACACCTTCCCGGCCGTGCTGCAGAGTTCTGGC<br>CTGTATAGCCTGAGCAGCGTGGTCACCGTGCCCTTCTAGCAGCCTGGGCACCCAG<br>ACCTACATCTGCAACGTGAACCACAAGCCCAGCAACACCAAGGTGGACGAGAAG<br>GTGGAGCCCAAGAGCTGCGACAAAACTCACACATGCCCACCGTGCCCAGCACCT<br>GAAGCTGCAGGGGGACCGTCAGTCTTCCTCTTCCCCCCAAAACCCAAGGACACC<br>CTCATGATCTCCCGGACCCCTGAGGTCACATGCGTGGTGGTGGACGTGAGCCAC<br>GAAGACCCTGAGGTCAAGTTCAACTGGTACGTGGACGGCGTGGAGGTGCATAAT<br>GCCAAGACAAAGCCGCGGGAGGAGCAGTACAACAGCACGTACCGTGTGGTCAGC<br>GTCCTCACCGTCCTGCACCAGGACTGGCTGAATGGCAAGGAGTACAAGTGCAAG<br>GTCTCCAACAAAGCCCTCGGCGCCCCCATCGAGAAAACCATCTCCAAAGCCAAA<br>GGGCAGCCCCGAGAACCACAGGTGTGCACCCTGCCCCCATCCCGGGATGAGCTG<br>ACCAAGAACCAGGTCAGCCTCTCGTGCGCAGTCAAAGGCTTCTATCCCAGCGAC<br>ATCGCCGTGGAGTGGGAGAGCAATGGGCAGCCGGAGAACAACTACAAGACCACG<br>CCTCCCGTGCTGGACTCCGACGGCTCCTTCTTCCTCGTGAGCAAGCTCACCGTG<br>GACAAGAGCAGGTGGCAGCAGGGGAACGTCTTCTCATGCTCCGTGATGCATGAG<br>GCTCTGCACAACCACTACACGCAGAAGAGCCTCTCCCTGTCTCCGGGTAAA | 293 |
| 14B1 LC<br>[KK]<br>Constant<br>lambda<br>pETR1497<br>9 | TCTTCTGAACTGACTCAAGATCCAGCTGTTAGCGTGGCTCTGGGTCAGACTGTA<br>CGTATCACCTGCCAAGGCGATTCTCTGCGCTCCTACTACGCAAGCTGGTACCAG<br>CAGAAACCGGGTCAGGCCCCAGTTCTGGTGATTTACGGCAAAAACAACCGTCCG<br>TCTGGGATCCCGGACCGTTTCTCCGGCAGCTCTTCCGGTAACACGGCGAGCCTC<br>ACCATCACTGGCGCTCAAGCAGAAGACGAGGCCGACTATTACTGTAACTCTCGG<br>GAAAGCCCACCAACCGGCCTGGTTGTCTTCGGTGGCGGTACCAAGCTGACCGTC<br>CTAGGTCAACCCAAGGCTGCCCCCAGCGTGACCCTGTTCCCCCCCAGCAGCAAG<br>AAACTGCAGGCCAACAAGGCCACCCTGGTCTGCCTGATCAGCGACTTCTACCCA<br>GGCGCCGTGACCGTGGCCTGGAAGGCCGACAGCAGCCCCGTGAAGGCCGGCGTG<br>GAGACCACCACCCCCAGCAAGCAGAGCAACAACAAGTACGCCGCCAGCCTAC<br>CTGAGCCTGACCCCCGAGCAGTGGAAGAGCCACAGGTCCTACAGCTGCCAGGTG<br>ACCCACGAGGGCAGCACCGTGGAGAAAACCGTGGCCCCCACCGAGTGCAGC | 294 |
| 9C7 VH | CAGGTGCAATTGGTTCAATCTGGTGCTGAAGTAAAAAAACCGGGCGCTTCCGTT<br>AAAGTGAGCTGCAAAGCATCCGGATACACCTTCACTTCCTATTACATGCACTGG<br>GTTCGTCAAGCCCCGGGCCAGGGTCTGGAATGGATGGGCATCATTAACCCAAGC<br>GGTGGCTCTACCTCCTACGCGCAGAAATTCCAGGGTCGCGTCACGATGACCCGT<br>GACACTAGCACCTCTACCGTTTATATGGAGCTGTCCAGCCTGCGTTCTGAAGAT<br>ACTGCAGTGTACTACTGTGCACGCGGTGACTGGTCTTACTACATGGACTATTGG<br>GGTCAAGGCACCCTCGTAACGGTTTCTTCT | 295 |

| Description | Sequence | Seq ID No |
|---|---|---|
| 9C7 VL | GATATTGTTATGACTCAATCTCCACTGTCTCTGCCGGTGACTCCAGGCGAACCG<br>GCGAGCATTTCTTGCCGTTCCAGCCAGTCTCTGCTGCACTCCAACGGCTACAAC<br>TATCTCGATTGGTACCTGCAAAAACGGGTCAGAGCCCTCAGCTGCTGATCTAC<br>CTGGGCTCTAACCGCGCTTCCGGTGTACCGGACCGTTTCAGCGGCTCTGGATCC<br>GGCACCGATTTCACGTTGAAAATCAGCCGTGTTGAAGCAGAAGACGTGGGCGTT<br>TATTACTGTATGCAGGCACGGCAGACCCCAACTTTTGGTCAAGGCACCAAGGTC<br>GAAATTAAA | 296 |
| 9C7[EE]_C<br>D3[VLCH1<br>]_Fc-<br>knob_PGL<br>ALA<br>pETR1497<br>4 | CAGGTGCAATTGGTTCAATCTGGTGCTGAAGTAAAAAAACCGGGCGCTTCCGTT<br>AAAGTGAGCTGCAAAGCATCCGGATACACCTTCACTTCCTATTACATGCACTGG<br>GTTCGTCAAGCCCCGGGCCAGGGTCTGGAATGGATGGGCATCATTAACCCAAGC<br>GGTGGCTCTACCTCCTACGCGCAGAAATTCCAGGGTCGCGTCACGATGACCCGT<br>GACACTAGCACCTCTACCGTTTATATGGAGCTGTCCAGCCTGCGTTCTGAAGAT<br>ACTGCAGTGTACTACTGTGCACGCGGTGACTGGTCTTACTACATGGACTATTGG<br>GGTCAAGGCACCCTCGTAACGGTTTCTTCTGCTAGCACCAAGGGCCCCTCCGTG<br>TTTCCTCTGGCCCCTTCCAGCAAGTCCACCTCTGGCGGAACTGCCGCTCTGGGC<br>TGCCTGGTGGAAGATTACTTCCCCGAGCCCGTGACCGTGTCCTGGAATTCTGGC<br>GCTCTGACCTCCGGCGTGCACACCTTTCCAGCTGTGCTGCAGTCCTCCGGCCTG<br>TACTCCCTGTCCTCCGTCGTGACAGTGCCCTCCAGCTCTCTGGGCACCCAGACC<br>TACATCTGCAACGTGAACCACAAGCCCTCCAACACCAAGGTGGACGAGAAGGTG<br>GAACCCAAGTCCTGCGACGGTGGCGGAGGTTCCGGAGGCGGAGGATCCCAGGCT<br>GTCGTGACCCAGGAACCCTCCCTGACAGTGTCTCCTGGCGGCACCGTGACCCTG<br>ACCTGTGGATCTTCTACCGGCGCTGTGACCACCTCCAACTACGCCAATTGGGTG<br>CAGGAAAAGCCCGGCCAGGCCTTCAGAGGACTGATCGGCGGCACCAACAAGAGA<br>GCCCCTGGCACCCCTGCCAGATTCTCCGGTTCTCTGCTGGGCGGCAAGGCTGCC<br>CTGACTCTGTCTGGTGCTCAGCCTGAGGACGAGGCCGAGTACTACTGCGCCCTG<br>TGGTACTCCAACCTGTGGGTGTTCGGCGGAGGCACCAAGCTGACCGTGCTGTCC<br>AGCGCTTCCACCAAGGGACCCAGTGTGTTCCCCCTGGCCCCCAGCTCCAAGTCT<br>ACATCCGGTGGCACAGCTGCCCTGGGATGTCTCGTGAAGGACTACTTTCCTGAG<br>CCTGTGACAGTGTCTTGGAACAGCGGAGCCCTGACCAGCGGAGTGCACACATTC<br>CCTGCAGTGCTGCAGAGCAGCGGCCTGTATAGCCTGAGCAGCGTCGTGACCGTG<br>CCTTCCTCTAGCCTGGGAACACAGACATATATCTGTAATGTGAATCATAAGCCC<br>AGTAATACCAAAGTGGATAAGAAAGTGGAACCTAAGAGCTGCGATAAGACCCAC<br>ACCTGTCCCCCCTGCCCTGCTCCTGAAGCTGCTGGTGGCCCTAGCGTGTTCCTG<br>TTCCCCCCAAAGCCCAAGGACACCCTGATGATCTCCCGGACCCCCGAAGTGACC<br>TGCGTGGTGGTGGATGTGTCCCACGAGGACCCTGAAGTGAAGTTCAATTGGTAC<br>GTGGACGGCGTGGAAGTGCACAACGCCAAGACCAAGCCTAGAGAGGAACAGTAC<br>AACTCCACCTACCGGGTGGTGTCCGTGCTGACAGTGCTGCACCAGGACTGGCTG<br>AACGGCAAGGAGTACAAGTGCAAGGTGTCCAACAAGGCCCTGGGCGCTCCCATC<br>GAAAAGACCATCTCCAAGGCCAAGGGCCAGCCCCGGGAACCCCAGGTGTACACC<br>CTGCCCCCATGCCGGGATGAGCTGACCAAGAACCAGGTCAGCCTGTGGTGCCTG<br>GTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTC<br>TTCCTCTACAGCAAGCTCACCGTGGACAAGAGCAGGTGGCAGCAGGGGAACGTC<br>TTCTCATGCTCCGTGATGCATGAGGCTCTGCACAACCACTACACGCAGAAGAGC<br>CTCTCCCTGTCTCCGGGTAAA | 297 |
| 9C7[EE]_F<br>c-<br>hole_PGLA<br>LA<br>pETR1497<br>5 | CAGGTGCAATTGGTTCAATCTGGTGCTGAAGTAAAAAAACCGGGCGCTTCCGTT<br>AAAGTGAGCTGCAAAGCATCCGGATACACCTTCACTTCCTATTACATGCACTGG<br>GTTCGTCAAGCCCCGGGCCAGGGTCTGGAATGGATGGGCATCATTAACCCAAGC<br>GGTGGCTCTACCTCCTACGCGCAGAAATTCCAGGGTCGCGTCACGATGACCCGT<br>GACACTAGCACCTCTACCGTTTATATGGAGCTGTCCAGCCTGCGTTCTGAAGAT<br>ACTGCAGTGTACTACTGTGCACGCGGTGACTGGTCTTACTACATGGACTATTGG<br>GGTCAAGGCACCCTCGTAACGGTTTCTTCTGCTAGCACCAAGGGCCCCTCCGTG<br>TTCCCCCTGGCCCCCAGCAGCAAGAGCACCAGCGGCGGCACAGCCGCTCTGGGC<br>TGCCTGGTCGAGGACTACTTCCCCGAGCCCGTGACCGTGTCCTGGAACAGCGGA<br>GCCCTGACCTCCGGCGTGCACACCTTCCCCGCCGTGCTGCAGAGTTCTGGCCTG<br>TATAGCCTGAGCAGCGTGGTCACCGTGCCTTCTAGCAGCCTGGGCACCCAGACC<br>TACATCTGCAACGTGAACCACAAGCCCAGCAACACCAAGGTGGACGAGAAGGTG<br>GAGCCCAAGAGCTGCGACAAAACTCACACATGCCCACCGTGCCCAGCACCTGAA<br>GCTGCAGGGGGACCGTCAGTCTTCCTCTTCCCCCCAAAACCCAAGGACACCCTC<br>ATGATCTCCCGGACCCCTGAGGTCACATGCGTGGTGGTGGACGTGAGCCACGAA<br>GACCCTGAGGTCAAGTTCAACTGGTACGTGGACGGCGTGGAGGTGCATAATGCC<br>AAGACAAAGCCGCGGGAGGAGCAGTACAACAGCACGTACCGTGTGGTCAGCGTC<br>CTCACCGTCCTGCACCAGGACTGGCTGAATGGCAAGGAGTACAAGTGCAAGGTC<br>TCCAACAAAGCCCTCGGCGCCCCCATCGAGAAAACCATCTCCAAAGCCAAAGGG<br>CAGCCCCGAGAACCACAGGTGTGCACCCTGCCCCCATCCCGGGATGAGCTGACC<br>AAGAACCAGGTCAGCCTCTCGTGCGCAGTCAAAGGCTTCTATCCCAGCGACATC<br>GCCGTGGAGTGGGAGAGCAATGGGCAGCCGGAGAACAACTACAAGACCACGCCT<br>CCCGTGCTGGACTCCGACGGCTCCTTCTTCCTCGTGAGCAAGCTCACCGTGGAC<br>AAGAGCAGGTGGCAGCAGGGGAACGTCTTCTCATGCTCCGTGATGCATGAGGCT<br>CTGCACAACCACTACACGCAGAAGAGCCTCTCCCTGTCTCCGGGTAAA | 298 |
| 9C7 LC<br>[RK]<br>pETR1498<br>0 | GATATTGTTATGACTCAATCTCCACTGTCTCTGCCGGTGACTCCAGGCGAACCG<br>GCGAGCATTTCTTGCCGTTCCAGCCAGTCTCTGCTGCACTCCAACGGCTACAAC<br>TATCTCGATTGGTACCTGCAAAAACGGGTCAGAGCCCTCAGCTGCTGATCTAC<br>CTGGGCTCTAACCGCGCTTCCGGTGTACCGGACCGTTTCAGCGGCTCTGGATCC | 299 |

| Description | Sequence | Seq ID No |
|---|---|---|
| | GGCACCGATTTCACGTTGAAAATCAGCCGTGTTGAAGCAGAAGACGTGGGCGTT<br>TATTACTGTATGCAGGCACGGCAGACCCCAACTTTTGGTCAAGGCACCAAGGTC<br>GAAATTAAACGTACGGTGGCTGCACCATCTGTCTTCATCTTCCCGCCATCTGAT<br>CGGAAGTTGAAATCTGGAACTGCCTCTGTTGTGTGCCTGCTGAATAACTTCTAT<br>CCCAGAGAGGCCAAAGTACAGTGGAAGGTGGATAACGCCCTCCAATCGGGTAAC<br>TCCCAGGAGAGTGTCACAGAGCAGGACAGCAAGGACAGCACCTACAGCCTCAGC<br>AGCACCCTGACGCTGAGCAAAGCAGACTACGAGAAACACAAAGTCTACGCCTGC<br>GAAGTCACCCATCAGGGCCTGAGCTCGCCCGTCACAAAGAGCTTCAACAGGGGA<br>GAGTGT | |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An antigen-binding molecule comprising a Folate Receptor 1 (FolR1) antigen-binding moiety that binds to FolR1, wherein the FolR1 antigen-binding moiety comprises a complementarity-determining region heavy chain 1 (CDR-H1) comprising the amino acid sequence of SEQ ID NO: 16, a complementarity-determining region heavy chain 2 (CDR-H2) comprising the amino acid sequence of SEQ ID NO: 275, a complementarity-determining region heavy chain 3 (CDR-H3) comprising the amino acid sequence of SEQ ID NO: 315, a complementarity-determining region light chain 1 (CDR-L1) comprising the amino acid sequence of SEQ ID NO: 32, a complementarity-determining region light chain 2 (CDR-L2) comprising the amino acid sequence of SEQ ID NO: 33, and a complementarity-determining region light chain 3 (CDR-L3) comprising the amino acid sequence of SEQ ID NO: 34.

2. The antigen-binding molecule of claim 1, wherein the FolR1 antigen-binding moiety comprises a variable heavy chain comprising the amino acid sequence of SEQ ID NO: 274 and a variable light chain comprising the amino acid sequence of SEQ ID NO: 31.

3. The antigen-binding molecule of claim 1, wherein the FolR1 antigen-binding moiety binds to human FolR1 and cynomolgus monkey FolR1.

4. The antigen-binding molecule of claim 1, wherein the FolR1 antigen-binding moiety binds to FolR1 expressed on a human tumor cell.

5. The antigen-binding molecule of claim 4, wherein the FolR1 antigen-binding moiety binds to a conformational epitope of human FolR1 expressed on the human tumor cell.

6. The antigen-binding molecule of claim 1, wherein the FolR1 antigen-binding moiety binds to a FolR1 polypeptide comprising amino acids 25 to 234 of human FolR1 (SEQ ID NO: 227).

7. The antigen-binding molecule of claim 6, wherein the FolR1 antigen-binding moiety:
   (a) binds to a FolR1 polypeptide comprising the amino acid sequence of SEQ ID NO: 230;
   (b) binds to a FolR1 polypeptide comprising the amino acid sequence of SEQ ID NO: 231;
   (c) does not bind to a FolR polypeptide comprising the amino acid sequence of SEQ ID NO: 228; and/or
   (d) does not bind to a FolR polypeptide comprising the amino acid sequence of SEQ ID NO: 229.

8. The antigen-binding molecule of claim 1, wherein the FolR1 antigen-binding moiety does not bind to human Folate Receptor 2 (FolR2) or to human Folate Receptor 3 (FolR3).

9. The antigen-binding molecule of claim 1, wherein the FolR1 antigen-binding moiety binds to human FolR1 with a monovalent binding KD of at least about 1,000 nM.

10. The antigen-binding molecule of claim 1, wherein the antigen-binding molecule additionally comprises an Fc domain composed of a first subunit and a second subunit capable of stable association.

11. The antigen-binding molecule of claim 10, wherein the Fc domain is an IgG class immunoglobulin Fc domain.

12. The antigen-binding molecule of claim 11, wherein the antigen-binding molecule is bivalent for FolR1.

13. The antigen-binding molecule of claim 1, wherein the antigen-binding molecule is a bispecific antigen-binding molecule.

14. The antigen-binding molecule of claim 13, wherein the bispecific antigen-binding molecule is a T cell activating bispecific antigen-binding molecule.

15. The antigen-binding molecule of claim 14, wherein the T cell activating bispecific antigen-binding molecule further comprises a CD3 antigen-binding moiety that binds to CD3.

16. The antigen-binding molecule of claim 15, wherein the FolR1 antigen-binding moiety and the CD3 antigen-binding moiety share a common light chain.

17. The antigen-binding molecule of claim 16, wherein the common light chain comprises the amino acid sequence of SEQ ID NO: 35.

18. The antigen-binding molecule of claim 15, wherein the CD3 antigen-binding moiety is a crossover Fab molecule, wherein either the variable or the constant regions of the Fab light chain and the Fab heavy chain are exchanged.

19. An antigen-binding molecule produced by a method comprising the steps of (a) culturing a host cell comprising an isolated polynucleotide encoding the antigen binding molecule of claim 1 under conditions suitable for the expression of the antigen-binding molecule and (b) recovering the antigen-binding molecule.

20. A pharmaceutical composition comprising the antigen-binding molecule of claim 1 and a pharmaceutical acceptable carrier.

* * * * *

SEQUENCE LISTING

<160> NUMBER OF SEQ ID NOS: 316

<210> SEQ ID NO 1
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Ala Gly Val Thr Pro Phe Asp Tyr Trp Gly Gln
            100                 105                 110

Gly Thr Leu Val Thr Val Ser Ser
        115                 120

<210> SEQ ID NO 2
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Thr Gly Gly Ser Ser Ala Phe Asp Tyr Trp Gly
            100                 105                 110

Gln Gly Thr Leu Val Thr Val Ser
            115                 120

<210> SEQ ID NO 3
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Leu Phe Ser Thr Ser Phe Asp Tyr Trp Gly Gln
            100                 105                 110

Gly Thr Leu Val Thr Val Ser Ser
            115                 120

<210> SEQ ID NO 4
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe

```
                50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asn Tyr Tyr Ile Gly Ile Val Pro Phe Asp Tyr Trp Gly Gln
            100                 105                 110

Gly Thr Leu Val Thr Val Ser Ser
            115                 120

<210> SEQ ID NO 5
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asn Tyr Tyr Val Gly Val Ser Pro Phe Asp Tyr Trp Gly Gln
            100                 105                 110

Gly Thr Leu Val Thr Val Ser Ser
            115                 120

<210> SEQ ID NO 6
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95
```

```
Ala Arg Asn Phe Thr Val Leu Arg Val Pro Phe Asp Tyr Trp Gly Gln
            100                 105                 110

Gly Thr Leu Val Thr Val Ser Ser
        115                 120

<210> SEQ ID NO 7
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Ile Gly Val Val Thr Phe Asp Tyr Trp Gly Gln
            100                 105                 110

Gly Thr Leu Val Thr Val Ser Ser
        115                 120

<210> SEQ ID NO 8
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ser Tyr Tyr Met His
1               5

<210> SEQ ID NO 9
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ile Ile Asn Pro Ser Gly Gly Ser Thr Ser Tyr Ala Gln Lys Phe Gln
1               5                   10                  15

Gly

<210> SEQ ID NO 10
<211> LENGTH: 11
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asn Tyr Tyr Ile Gly Val Val Thr Phe Asp Tyr
1               5                   10

<210> SEQ ID NO 11
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Trp Arg Arg Tyr Thr Ser Phe Asp Tyr Trp Gly Gln
            100                 105                 110

Gly Thr Leu Val Thr Val Ser Ser
        115                 120

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Glu Trp Arg Arg Tyr Thr Ser Phe Asp Tyr
1               5                   10

<210> SEQ ID NO 13
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Ile Arg Trp Glu His Phe Asp Tyr Trp Gly Gln
            100                 105                 110

Gly Thr Leu Val Thr Val Ser Ser
        115                 120

<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Gly Trp Ile Arg Trp Glu His Phe Asp Tyr
1               5                   10

<210> SEQ ID NO 15
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser
        115                 120

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 16

Asn Ala Trp Met Ser
1               5

<210> SEQ ID NO 17
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Arg Ile Lys Ser Lys Thr Asp Gly Gly Thr Thr Asp Tyr Ala Ala Pro
1               5                   10                  15

Val Lys Gly

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Pro Trp Glu Trp Ser Trp Tyr Asp Tyr
1               5

<210> SEQ ID NO 19
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser
        115                 120

<210> SEQ ID NO 20
<211> LENGTH: 9
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 20

Pro Trp Glu Trp Ser Tyr Phe Asp Tyr
1               5

<210> SEQ ID NO 21
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ala Trp Phe Asp Tyr Trp Gly Gln
            100                 105                 110

Gly Thr Leu Val Thr Val Ser Ser
        115                 120

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Pro Trp Glu Trp Ala Trp Phe Asp Tyr
1               5

<210> SEQ ID NO 23
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30
```

-continued

```
Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
65                   70                  75                  80

Leu Tyr Leu Gln Met Asn Ser Leu Lys Thr Glu Asp Thr Ala Val Tyr
                 85                  90                  95

Tyr Cys Thr Thr Pro Trp Glu Trp Ala Tyr Phe Asp Tyr Trp Gly Gln
            100                 105                 110

Gly Thr Leu Val Thr Val Ser Ser
        115                 120
```

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

```
Pro Trp Glu Trp Ala Tyr Phe Asp Tyr
1               5
```

<210> SEQ ID NO 25
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
65                   70                  75                  80

Met Glu Leu Ser Ser Leu Arg Ser Glu Asp Thr Ala Val Tyr Tyr Cys
                 85                  90                  95

Ala Arg Thr Gly Trp Ser Arg Trp Gly Tyr Met Asp Tyr Trp Gly Gln
            100                 105                 110

Gly Thr Leu Val Thr Val Ser Ser
        115                 120
```

<210> SEQ ID NO 26
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 26

Thr Gly Trp Ser Arg Trp Gly Tyr Met Asp Tyr
1               5                   10

<210> SEQ ID NO 27
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Trp Ile Arg Tyr Tyr His Phe Asp Tyr Trp Gly Gln
            100                 105                 110

Gly Thr Leu Val Thr Val Ser Ser
        115                 120

<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Glu Trp Ile Arg Tyr Tyr His Phe Asp Tyr
1               5                   10

<210> SEQ ID NO 29
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60
```

```
Gln Gly Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Val Gly Trp Tyr Arg Trp Gly Tyr Met Asp Tyr Trp Gly Gln
        100                 105                 110

Gly Thr Leu Val Thr Val Ser Ser
        115                 120

<210> SEQ ID NO 30
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Val Gly Trp Tyr Arg Trp Gly Tyr Met Asp Tyr
1               5                   10

<210> SEQ ID NO 31
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 32
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Ser Ser Thr Gly Ala Val Thr Thr Ser Asn Tyr Ala Asn
1               5                   10

<210> SEQ ID NO 33
<211> LENGTH: 7
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Thr Asn Lys Arg Ala Pro
1               5

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Leu Trp Tyr Ser Asn Leu Trp Val
1               5

<210> SEQ ID NO 35
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 36
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 37
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 37

Thr Tyr Ala Met Asn
1               5

<210> SEQ ID NO 38
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Arg Ile Arg Ser Lys Tyr Asn Asn Tyr Ala Thr Tyr Tyr Ala Asp Ser
1               5                   10                  15

Val Lys Gly

<210> SEQ ID NO 39
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 39

His Gly Asn Phe Gly Asn Ser Tyr Val Ser Trp Phe Ala Tyr
1               5                   10

<210> SEQ ID NO 40
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 41
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                 20                  25                  30
Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Val Phe Tyr Arg Ala Trp Tyr Ser Phe Asp Tyr Trp Gly
            100                 105                 110

Gln Gly Thr Thr Val Thr Val Ser Ser
        115                 120
```

<210> SEQ ID NO 42
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

```
Ser Tyr Ala Ile Ser
1               5
```

<210> SEQ ID NO 43
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

```
Gly Ile Ile Pro Ile Phe Gly Thr Ala Asn Tyr Ala Gln Lys Phe Gln
1               5                   10                  15

Gly
```

<210> SEQ ID NO 44
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

```
Ala Val Phe Tyr Arg Ala Trp Tyr Ser Phe Asp Tyr
1               5                   10
```

<210> SEQ ID NO 45
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Thr Ser Pro Pro Pro
                85                  90                  95

Thr Phe Gly Gln Gly Thr Lys Val Glu Ile Lys
            100                 105

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Arg Ala Ser Gln Ser Ile Ser Ser Trp Leu Ala
1               5                   10

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Asp Ala Ser Ser Leu Glu Ser
1               5

<210> SEQ ID NO 48
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gln Gln Tyr Thr Ser Pro Pro Pro Thr
1               5

<210> SEQ ID NO 49
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Ser Thr Ser Tyr Ala Gln Lys Phe
            50                  55                  60

Gln Gly Arg Val Thr Met Thr His Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Gly Phe His Leu Asp Tyr Trp Gly Gln Gly
                100                 105                 110

Thr Leu Val Thr Val Ser Ser
            115
```

<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 50

```
Ser Phe Phe Thr Gly Phe His Leu Asp Tyr
1               5                   10
```

<210> SEQ ID NO 51
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Thr Asn Glu His
                85                  90                  95

Tyr Tyr Thr Phe Gly Gln Gly Thr Lys Val Glu Ile Lys
                100                 105
```

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 52

Arg Ala Ser Gln Ser Val Ser Ser Ser Tyr Leu Ala
1               5                   10

<210> SEQ ID NO 53
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Ala Ser Ser Arg Ala Thr
1               5

<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gln Gln Tyr Thr Asn Glu His Tyr Tyr Thr
1               5                   10

<210> SEQ ID NO 55
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Pro Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Trp Leu Asp Tyr Trp Gly Gln Gly Thr Leu
            100                 105                 110

Val Thr Val Ser Ser
        115

<210> SEQ ID NO 56
<211> LENGTH: 17
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 56

Ile Ile Asn Pro Ser Gly Gly Pro Thr Ser Tyr Ala Gln Lys Phe Gln
1               5                   10                  15

Gly

<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gly Asp Phe Ala Trp Leu Asp Tyr
1               5

<210> SEQ ID NO 58
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Asn Arg Thr Phe Gly Gln Gly Thr Lys Val Glu Ile Lys
                100                 105                 110

<210> SEQ ID NO 59
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Arg Ser Ser Gln Ser Leu Leu His Ser Asn Gly Tyr Asn Tyr Leu Asp
1               5                   10                  15

<210> SEQ ID NO 60
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 60

Leu Gly Ser Asn Arg Ala Ser
1               5

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Met Gln Ala Ser Ile Met Asn Arg Thr
1               5

<210> SEQ ID NO 62
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Ser Arg Thr Phe Gly Gln Gly Thr Lys Val Glu Ile Lys
            100                 105                 110

<210> SEQ ID NO 63
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Met Gln Ala Ser Ile Met Ser Arg Thr
1               5

<210> SEQ ID NO 64
<211> LENGTH: 112
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic polypeptide"

<400> SEQUENCE: 64

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Gln Arg Thr Phe Gly Gln Gly Thr Lys Val Glu Ile Lys
            100                 105                 110
```

<210> SEQ ID NO 65
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 65

```
Met Gln Ala Ser Ile Met Gln Arg Thr
1               5
```

<210> SEQ ID NO 66
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Asn Arg Ala Phe Gly Gln Gly Thr Lys Val Glu Ile Lys
            100                 105                 110
```

<210> SEQ ID NO 67
<211> LENGTH: 9
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Met Gln Ala Ser Ile Met Asn Arg Ala
1               5

<210> SEQ ID NO 68
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Asn Arg Asn Phe Gly Gln Gly Thr Lys Val Glu Ile Lys
            100                 105                 110

<210> SEQ ID NO 69
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Met Gln Ala Ser Ile Met Asn Arg Asn
1               5

<210> SEQ ID NO 70
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45
```

```
Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Ile Asp Met Asp Tyr Trp Gly Gln Gly Thr Leu Val
                100                 105                 110

Thr Val Ser Ser
        115

<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ser Tyr Ile Asp Met Asp Tyr
1               5

<210> SEQ ID NO 72
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Asn Trp Ser Pro
                85                  90                  95

Thr Phe Gly Gln Gly Thr Lys Val Glu Ile Lys
            100                 105

<210> SEQ ID NO 73
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gln Gln Asp Asn Trp Ser Pro Thr
1               5
```

<210> SEQ ID NO 74
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Val Asp Met Asp Tyr Trp Gly Gln Gly Thr Leu Val
            100                 105                 110

Thr Val Ser Ser
        115

<210> SEQ ID NO 75
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ser Tyr Val Asp Met Asp Tyr
1               5

<210> SEQ ID NO 76
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Ile Trp Ser Pro

```
                85                  90                  95
Thr Phe Gly Gln Gly Thr Lys Val Glu Ile Lys
            100                 105

<210> SEQ ID NO 77
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Gln Gln Asp Ile Trp Ser Pro Thr
1               5

<210> SEQ ID NO 78
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Ser Tyr Val Glu Trp Tyr Ala Phe Asp Tyr Trp Gly
            100                 105                 110

Gln Gly Thr Leu Val Thr Val Ser Ser
        115                 120

<210> SEQ ID NO 79
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Ser Tyr Ala Met Ser
1               5

<210> SEQ ID NO 80
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                       Synthetic peptide"

<400> SEQUENCE: 80

Ala Ile Ser Gly Ser Gly Gly Ser Thr Tyr Tyr Ala Asp Ser Val Lys
1               5                   10                  15

Gly

<210> SEQ ID NO 81
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Asp Ser Ser Tyr Val Glu Trp Tyr Ala Phe Asp Tyr
1               5                   10

<210> SEQ ID NO 82
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Ser Thr Leu Thr Ile Ser Arg Leu Glu
65                  70                  75                  80

Pro Glu Asp Phe Ala Val Tyr Tyr Cys Gln Gln Pro Thr Ser Ser Pro
                85                  90                  95

Ile Thr Phe Gly Gln Gly Thr Lys Val Glu Ile Lys
            100                 105

<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gln Gln Pro Thr Ser Ser Pro Ile Thr
1               5

<210> SEQ ID NO 84
<211> LENGTH: 103
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 84

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 85
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 86
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

```
Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
 65              70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Ser Ser Ala
                100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
            130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
            195                 200                 205

Val Glu Pro Lys Ser Cys
            210

<210> SEQ ID NO 87
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
             20                  25                  30

Ala Met Asn Trp Val Arg Gln Ala Pro Gly Lys Gly Leu Glu Trp Val
             35                  40                  45

Ser Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
             85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
            115                 120                 125

Ala Ala Pro Ser Val Phe Ile Phe Pro Pro Ser Asp Glu Gln Leu Lys
            130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
            165                 170                 175
```

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
210                 215                 220

Lys Ser Phe Asn Arg Gly Glu Cys
225                 230

<210> SEQ ID NO 88
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 89
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val

```
                  115                 120                 125
Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                    180                 185                 190

Ser Ser Ser Leu Gly Thr Gln Thr Tyr Ile Cys Asn Val Asn His Lys
                    195                 200                 205

Pro Ser Asn Thr Lys Val Asp Lys Lys Val Glu Pro Lys Ser Cys Asp
210                 215                 220

Gly Gly Gly Gly Ser Gly Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                    245                 250                 255

Ala Ala Ser Gly Phe Thr Phe Ser Thr Tyr Ala Met Asn Trp Val Arg
                    260                 265                 270

Gln Ala Pro Gly Lys Gly Leu Glu Trp Val Ser Arg Ile Arg Ser Lys
                    275                 280                 285

Tyr Asn Asn Tyr Ala Thr Tyr Tyr Ala Asp Ser Val Lys Gly Arg Phe
                    290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
                    325                 330                 335

Asn Phe Gly Asn Ser Tyr Val Ser Trp Phe Ala Tyr Trp Gly Gln Gly
                    340                 345                 350

Thr Leu Val Thr Val Ser Ser Ala Ser Thr Lys Gly Pro Ser Val Phe
                    355                 360                 365

Pro Leu Ala Pro Ser Ser Lys Ser Thr Ser Gly Gly Thr Ala Ala Leu
370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                    405                 410                 415

Gln Ser Ser Gly Leu Tyr Ser Leu Ser Ser Val Val Thr Val Pro Ser
                    420                 425                 430

Ser Ser Leu Gly Thr Gln Thr Tyr Ile Cys Asn Val Asn His Lys Pro
                    435                 440                 445

Ser Asn Thr Lys Val Asp Lys Lys Val Glu Pro Lys Ser Cys Asp Lys
                    450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                    485                 490                 495

Arg Thr Pro Glu Val Thr Cys Val Val Val Asp Val Ser His Glu Asp
                    500                 505                 510

Pro Glu Val Lys Phe Asn Trp Tyr Val Asp Gly Val Glu Val His Asn
                    515                 520                 525

Ala Lys Thr Lys Pro Arg Glu Glu Gln Tyr Asn Ser Thr Tyr Arg Val
                    530                 535                 540
```

```
Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
            595                 600                 605

Cys Leu Val Lys Gly Phe Tyr Pro Ser Asp Ile Ala Val Glu Trp Glu
        610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys

<210> SEQ ID NO 90
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
                195                 200                 205
Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 91
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Gly Gly Gly Ser Gly Gly Gly Ser Glu
225                 230                 235                 240

Val Gln Leu Val Glu Ser Gly Gly Leu Val Lys Pro Gly Gly Ser
                245                 250                 255

Leu Arg Leu Ser Cys Ala Ala Ser Gly Phe Thr Phe Ser Asn Ala Trp
            260                 265                 270

Met Ser Trp Val Arg Gln Ala Pro Gly Lys Gly Leu Glu Trp Val Gly
        275                 280                 285

Arg Ile Lys Ser Lys Thr Asp Gly Gly Thr Thr Asp Tyr Ala Ala Pro
    290                 295                 300

Val Lys Gly Arg Phe Thr Ile Ser Arg Asp Asp Ser Lys Asn Thr Leu
305                 310                 315                 320

Tyr Leu Gln Met Asn Ser Leu Lys Thr Glu Asp Thr Ala Val Tyr Tyr
                325                 330                 335

Cys Thr Thr Pro Trp Glu Trp Ser Trp Tyr Asp Tyr Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
    370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
            420                 425                 430

Ser Ser Leu Gly Thr Gln Thr Tyr Ile Cys Asn Val Asn His Lys Pro
        435                 440                 445

Ser Asn Thr Lys Val Asp Lys Lys Val Glu Pro Lys Ser Cys Asp Lys
    450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510
```

```
Pro Glu Val Lys Phe Asn Trp Tyr Val Asp Gly Val Glu Val His Asn
            515                 520                 525

Ala Lys Thr Lys Pro Arg Glu Glu Gln Tyr Asn Ser Thr Tyr Arg Val
530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
            565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
            595                 600                 605

Cys Leu Val Lys Gly Phe Tyr Pro Ser Asp Ile Ala Val Glu Trp Glu
610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
            645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
            675                 680                 685

Lys

<210> SEQ ID NO 92
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

```
Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                    245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                    325                 330                 335

Gly Ala Pro Ile Glu Lys Thr Ile Ser Lys Ala Lys Gly Gln Pro Arg
            340                 345                 350

Glu Pro Gln Val Tyr Thr Leu Pro Pro Cys Arg Asp Glu Leu Thr Lys
            355                 360                 365

Asn Gln Val Ser Leu Trp Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 93
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

-continued

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Phe Thr Gln Lys Ser Leu Ser Leu Ser
    210                 215                 220

Pro Gly Lys
225

<210> SEQ ID NO 94
<211> LENGTH: 690
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Pro Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Asp Phe Ala Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser

```
                180             185             190
Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Gly Gly Gly
            210                 215                 220

Gly Ser Gly Gly Gly Ser Glu Val Gln Leu Leu Glu Ser Gly Gly
225                 230                 235                 240

Gly Leu Val Gln Pro Gly Gly Ser Leu Arg Leu Ser Cys Ala Ala Ser
                245                 250                 255

Gly Phe Thr Phe Ser Thr Tyr Ala Met Asn Trp Val Arg Gln Ala Pro
            260                 265                 270

Gly Lys Gly Leu Glu Trp Val Ser Arg Ile Arg Ser Lys Tyr Asn Asn
            275                 280                 285

Tyr Ala Thr Tyr Tyr Ala Asp Ser Val Lys Gly Arg Phe Thr Ile Ser
            290                 295                 300

Arg Asp Asp Ser Lys Asn Thr Leu Tyr Leu Gln Met Asn Ser Leu Arg
305                 310                 315                 320

Ala Glu Asp Thr Ala Val Tyr Tyr Cys Val Arg His Gly Asn Phe Gly
                325                 330                 335

Asn Ser Tyr Val Ser Trp Phe Ala Tyr Trp Gly Gln Gly Thr Leu Val
                340                 345                 350

Thr Val Ser Ser Ala Ser Val Ala Ala Pro Ser Val Phe Ile Phe Pro
            355                 360                 365

Pro Ser Asp Glu Gln Leu Lys Ser Gly Thr Ala Ser Val Val Cys Leu
            370                 375                 380

Leu Asn Asn Phe Tyr Pro Arg Glu Ala Lys Val Gln Trp Lys Val Asp
385                 390                 395                 400

Asn Ala Leu Gln Ser Gly Asn Ser Gln Glu Ser Val Thr Glu Gln Asp
                405                 410                 415

Ser Lys Asp Ser Thr Tyr Ser Leu Ser Ser Thr Leu Thr Leu Ser Lys
                420                 425                 430

Ala Asp Tyr Glu Lys His Lys Val Tyr Ala Cys Glu Val Thr His Gln
            435                 440                 445

Gly Leu Ser Ser Pro Val Thr Lys Ser Phe Asn Arg Gly Glu Cys Asp
            450                 455                 460

Lys Thr His Thr Cys Pro Pro Cys Pro Ala Pro Glu Ala Ala Gly Gly
465                 470                 475                 480

Pro Ser Val Phe Leu Phe Pro Pro Lys Pro Lys Asp Thr Leu Met Ile
                485                 490                 495

Ser Arg Thr Pro Glu Val Thr Cys Val Val Val Asp Val Ser His Glu
            500                 505                 510

Asp Pro Glu Val Lys Phe Asn Trp Tyr Val Asp Gly Val Glu Val His
            515                 520                 525

Asn Ala Lys Thr Lys Pro Arg Glu Glu Gln Tyr Asn Ser Thr Tyr Arg
            530                 535                 540

Val Val Ser Val Leu Thr Val Leu His Gln Asp Trp Leu Asn Gly Lys
545                 550                 555                 560

Glu Tyr Lys Cys Lys Val Ser Asn Lys Ala Leu Gly Ala Pro Ile Glu
                565                 570                 575

Lys Thr Ile Ser Lys Ala Lys Gly Gln Pro Arg Glu Pro Gln Val Tyr
            580                 585                 590

Thr Leu Pro Pro Cys Arg Asp Glu Leu Thr Lys Asn Gln Val Ser Leu
            595                 600                 605
```

-continued

```
Trp Cys Leu Val Lys Gly Phe Tyr Pro Ser Asp Ile Ala Val Glu Trp
            610                 615                 620
Glu Ser Asn Gly Gln Pro Glu Asn Asn Tyr Lys Thr Thr Pro Pro Val
625                 630                 635                 640
Leu Asp Ser Asp Gly Ser Phe Phe Leu Tyr Ser Lys Leu Thr Val Asp
                    645                 650                 655
Lys Ser Arg Trp Gln Gln Gly Asn Val Phe Ser Cys Ser Val Met His
                660                 665                 670
Glu Ala Leu His Asn His Tyr Thr Gln Lys Ser Leu Ser Leu Ser Pro
            675                 680                 685
Gly Lys
    690

<210> SEQ ID NO 95
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Tyr Met His Trp Val Arg Gln Ala Pro Gly Gln Gly Leu Glu Trp Met
            35                  40                  45
Gly Ile Ile Asn Pro Ser Gly Gly Pro Thr Ser Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Asp Phe Ala Trp Leu Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Ala Ala Gly Gly Pro Ser Val
225                 230                 235                 240
Phe Leu Phe Pro Pro Lys Pro Lys Asp Thr Leu Met Ile Ser Arg Thr
                245                 250                 255
```

-continued

Pro Glu Val Thr Cys Val Val Asp Val Ser His Glu Asp Pro Glu
              260                 265                 270

Val Lys Phe Asn Trp Tyr Val Asp Gly Val Glu Val His Asn Ala Lys
         275                 280                 285

Thr Lys Pro Arg Glu Glu Gln Tyr Asn Ser Thr Tyr Arg Val Val Ser
     290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                 325                 330                 335

Ser Lys Ala Lys Gly Gln Pro Arg Glu Pro Gln Val Cys Thr Leu Pro
             340                 345                 350

Pro Ser Arg Asp Glu Leu Thr Lys Asn Gln Val Ser Leu Ser Cys Ala
             355                 360                 365

Val Lys Gly Phe Tyr Pro Ser Asp Ile Ala Val Glu Trp Glu Ser Asn
         370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                 405                 410                 415

Trp Gln Gln Gly Asn Val Phe Ser Cys Ser Val Met His Glu Ala Leu
             420                 425                 430

His Asn His Tyr Thr Gln Lys Ser Leu Ser Leu Ser Pro Gly Lys
             435                 440                 445

<210> SEQ ID NO 96
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                 85                  90                  95

Ser Ile Met Asn Arg Thr Phe Gly Gln Gly Thr Lys Val Glu Ile Lys
             100                 105                 110

Arg Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
     130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser

```
                165                 170                 175
Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

<210> SEQ ID NO 97
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (603)..(603)
<223> OTHER INFORMATION: a, c, t, g, unknown or other

<400> SEQUENCE: 97

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagtatacca cgaacatta ttatacgttc      300
ggccagggga ccaaagtgga aatcaaacgt acggtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
canggcctga gctcgcccgt cacaaagagc ttcaacaggg gagagtgt               648
```

<210> SEQ ID NO 98
<211> LENGTH: 459
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 98

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys Asp Lys Thr His Thr Cys Pro Pro
225                 230                 235                 240

Cys Pro Ala Pro Glu Ala Ala Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Gly Ala Pro Ile Glu Lys Thr Ile Ser Lys Ala Lys
            340                 345                 350

Gly Gln Pro Arg Glu Pro Gln Val Tyr Thr Leu Pro Pro Cys Arg Asp
        355                 360                 365

Glu Leu Thr Lys Asn Gln Val Ser Leu Trp Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 99
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 99

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
            245                 250                 255

Ala Ala Ser Gly Phe Thr Phe Ser Thr Tyr Ala Met Asn Trp Val Arg
        260                 265                 270

Gln Ala Pro Gly Lys Gly Leu Glu Trp Val Ser Arg Ile Arg Ser Lys
    275                 280                 285

Tyr Asn Asn Tyr Ala Thr Tyr Tyr Ala Asp Ser Val Lys Gly Arg Phe
290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
            325                 330                 335

Asn Phe Gly Ala Ser Tyr Val Ser Trp Phe Ala Tyr Trp Gly Gln Gly
        340                 345                 350

Thr Leu Val Thr Val Ser Ser Ala Ser Thr Lys Gly Pro Ser Val Phe
    355                 360                 365

Pro Leu Ala Pro Ser Ser Lys Ser Thr Ser Gly Gly Thr Ala Ala Leu
370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
            405                 410                 415
```

Gln Ser Ser Gly Leu Tyr Ser Leu Ser Ser Val Val Thr Val Pro Ser
                420                 425                 430

Ser Ser Leu Gly Thr Gln Thr Tyr Ile Cys Asn Val Asn His Lys Pro
                435                 440                 445

Ser Asn Thr Lys Val Asp Lys Lys Val Glu Pro Lys Ser Cys Asp Lys
            450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
                500                 505                 510

Pro Glu Val Lys Phe Asn Trp Tyr Val Asp Gly Val Glu Val His Asn
            515                 520                 525

Ala Lys Thr Lys Pro Arg Glu Glu Gln Tyr Asn Ser Thr Tyr Arg Val
530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
                580                 585                 590

Leu Pro Pro Cys Arg Asp Glu Leu Thr Lys Asn Gln Val Ser Leu Trp
            595                 600                 605

Cys Leu Val Lys Gly Phe Tyr Pro Ser Asp Ile Ala Val Glu Trp Glu
610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
                660                 665                 670

Ala Leu His Asn His Tyr Thr Gln Lys Ser Leu Ser Leu Ser Pro Gly
            675                 680                 685

Lys

<210> SEQ ID NO 100
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 100

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr

```
            65                  70                  75                  80
Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
                100                 105                 110

Gly Thr Leu Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                245                 250                 255

Ala Ala Ser Gly Phe Thr Phe Ser Thr Tyr Ala Met Asn Trp Val Arg
                260                 265                 270

Gln Ala Pro Gly Lys Gly Leu Glu Trp Val Ser Arg Ile Arg Ser Lys
            275                 280                 285

Tyr Asn Asn Tyr Ala Thr Tyr Tyr Ala Asp Ser Val Lys Gly Arg Phe
            290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
                325                 330                 335

Asn Phe Gly Asn Ala Tyr Val Ser Trp Phe Ala Tyr Trp Gly Gln Gly
                340                 345                 350

Thr Leu Val Thr Val Ser Ser Ala Ser Thr Lys Gly Pro Ser Val Phe
                355                 360                 365

Pro Leu Ala Pro Ser Ser Lys Ser Thr Ser Gly Gly Thr Ala Ala Leu
    370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
                420                 425                 430

Ser Ser Leu Gly Thr Gln Thr Tyr Ile Cys Asn Val Asn His Lys Pro
            435                 440                 445

Ser Asn Thr Lys Val Asp Lys Lys Val Glu Pro Lys Ser Cys Asp Lys
    450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495
```

```
Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
            515                 520                 525

Ala Lys Thr Lys Pro Arg Glu Glu Gln Tyr Asn Ser Thr Tyr Arg Val
            530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
            565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
            595                 600                 605

Cys Leu Val Lys Gly Phe Tyr Pro Ser Asp Ile Ala Val Glu Trp Glu
            610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
            645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
            675                 680                 685

Lys

<210> SEQ ID NO 101
<211> LENGTH: 441
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
            50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
            85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
            130                 135                 140

Pro Glu Pro Val Thr Val Ser Trp Asn Ser Gly Ala Leu Thr Ser Gly
```

-continued

```
               145                 150                 155                 160
Val His Thr Phe Pro Ala Val Leu Gln Ser Ser Gly Leu Tyr Ser Leu
                    165                 170                 175

Ser Ser Val Thr Val Pro Ser Ser Leu Gly Thr Gln Thr Tyr
                180                 185                 190

Ile Cys Asn Val Asn His Lys Pro Ser Asn Thr Lys Val Asp Lys Lys
                195                 200                 205

Val Glu Pro Lys Ser Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
                275                 280                 285

Gln Tyr Asn Ser Thr Tyr Arg Val Val Ser Val Leu Thr Val Leu His
            290                 295                 300

Gln Asp Trp Leu Asn Gly Lys Glu Tyr Lys Cys Lys Val Ser Asn Lys
305                 310                 315                 320

Ala Leu Gly Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
                435                 440
```

<210> SEQ ID NO 102
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 102

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60
```

```
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Val Ala Ala Pro Ser Val
            115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
            195                 200                 205

Val Thr His Gln Gly Leu Ser Ser Pro Val Thr Lys Ser Phe Asn Arg
    210                 215                 220

Gly Glu Cys
225

<210> SEQ ID NO 103
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Pro
        115                 120                 125

Lys Ala Ala Pro Ser Val Thr Leu Phe Pro Pro Ser Ser Glu Glu Leu
    130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175
```

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
        195                 200                 205

Ser Tyr Ser Cys Gln Val Thr His Glu Gly Ser Thr Val Glu Lys Thr
        210                 215                 220

Val Ala Pro Thr Glu Cys Ser
225                 230

<210> SEQ ID NO 104
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Gly Gly Ser Phe Asp Tyr Trp Gly Gln Gly Thr
            100                 105                 110

Leu Val Thr Val Ser Ser
        115

<210> SEQ ID NO 105
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Gly Gly Ser Met Asp Ala Trp Gly Gln Gly Thr

Thr Val Thr Val Ser Ser
        115

<210> SEQ ID NO 106
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Ser Gly Gly Ser Phe Asp Tyr Trp Gly Gln
            100                 105                 110

Gly Thr Leu Val Thr Val Ser Ser
        115                 120

<210> SEQ ID NO 107
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ser Gly Gly Ser Phe Asp Tyr Trp Gly Gln Gly Thr
            100                 105                 110

Leu Val Thr Val Ser Ser
        115

<210> SEQ ID NO 108

<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 108

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Ser Gly Gly Ser Phe Asp Tyr Trp Gly Gln Gly Thr Leu
            100                 105                 110

Val Thr Val Ser Ser
        115

<210> SEQ ID NO 109
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Ser Gly Gly Ser Phe Asp Tyr Trp Gly Gln Gly Thr
            100                 105                 110

Leu Val Thr Val Ser Ser
        115

<210> SEQ ID NO 110
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 110

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 111
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 112
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe

```
                 50                  55                  60
Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu
                100                 105

<210> SEQ ID NO 113
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Gln Thr Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
                20                  25                  30

Asn Tyr Ala Asn Trp Val Gln Lys Pro Gly Gln Ala Pro Arg Gly
                 35                  40                  45

Leu Ile Gly Gly Thr Asn Ala Arg Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu
                100                 105

<210> SEQ ID NO 114
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Gln Thr Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
                20                  25                  30

Asn Tyr Ala Asn Trp Val Gln Lys Pro Gly Gln Ala Pro Arg Gly
                 35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ala Asn
                 85                  90                  95

Leu Trp Val Phe Gly Gly Gly Thr Lys Leu Thr Val Leu
                100                 105

<210> SEQ ID NO 115
```

<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 115

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser
        115                 120

<210> SEQ ID NO 116
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 116

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser
        115                 120

<210> SEQ ID NO 117
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 117

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Ser Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser
            115                 120

<210> SEQ ID NO 118
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Tyr Glu Trp Ser Trp Tyr Asp Tyr Trp Gly Gln
            100                 105                 110

Gly Thr Leu Val Thr Val Ser Ser Ala Ser
            115                 120

<210> SEQ ID NO 119
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala

```
                     20                  25                  30
Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Tyr Ser Trp Tyr Asp Tyr Trp Gly Gln
                100                 105                 110

Gly Thr Leu Val Thr Val Ser Ser Ala Ser
                115                 120

<210> SEQ ID NO 120
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Thr Ile Val Val Ser Pro Phe Asp Tyr Trp Gly Gln
                100                 105                 110

Gly Thr Leu Val Thr Val Ser Ser Ala Ser
                115                 120

<210> SEQ ID NO 121
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60
```

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asn Tyr Phe Ile Gly Ser Val Ala Met Asp Tyr Trp Gly Gln
            100                 105                 110

Gly Thr Leu Val Thr Val Ser Ser Ala Ser
        115                 120

<210> SEQ ID NO 122
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Leu Thr Tyr Ser Met Asp Tyr Trp Gly Gln Gly Thr Leu
            100                 105                 110

Val Thr Val Ser Ser Ala Ser
        115

<210> SEQ ID NO 123
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95
```

Leu Gln Ile Pro Asn Thr Phe Gly Gln Gly Thr Lys Val Glu Ile Lys
                100                 105                 110

Arg Thr

<210> SEQ ID NO 124
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Ala Tyr Ala Leu Asp Tyr Trp Gly Gln Gly Thr Leu Val
            100                 105                 110

Thr Val Ser Ser Ala Ser
        115

<210> SEQ ID NO 125
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Gly Ser Ser Ser
                85                  90                  95

Thr Phe Gly Gln Gly Thr Lys Val Glu Ile Lys Arg Thr
            100                 105

<210> SEQ ID NO 126
<211> LENGTH: 122
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ser Ala Gly Arg Leu Met Asp Tyr Trp Gly Gln
            100                 105                 110

Gly Thr Leu Val Thr Val Ser Ser Ala Ser
        115                 120

<210> SEQ ID NO 127
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Ile Thr Phe Gly Gln Gly Thr Lys Val Glu Ile
            100                 105                 110

Lys Arg Thr
        115

<210> SEQ ID NO 128
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128
```

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Asn Ala Phe Asp Tyr Trp Gly His Gly Thr Leu
            100                 105                 110

Val Thr Val Ser Ser Ala Ser
            115
```

<210> SEQ ID NO 129
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 129

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Trp His Ser Pro Thr Phe Gly Gln Gly Thr Lys Val Glu Ile Lys Arg
            100                 105                 110

Thr
```

<210> SEQ ID NO 130
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 130

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45
```

Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Thr Tyr Thr Met Asp Tyr Trp Gly Gln Gly Thr Leu
            100                 105                 110

Val Thr Val Ser Ser Ala Ser
        115

<210> SEQ ID NO 131
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Lys Val Glu Ile Lys
            100                 105                 110

Arg Thr

<210> SEQ ID NO 132
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala 85                  90                  95

Ser Ile Met Ser Arg Thr Phe Gly Gln Gly Thr Lys Val Glu Ile Lys
                100                 105                 110

<210> SEQ ID NO 133
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Gln Arg Thr Phe Gly Gln Gly Thr Lys Val Glu Ile Lys
                100                 105                 110

<210> SEQ ID NO 134
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Asn Arg Ala Phe Gly Gln Gly Thr Lys Val Glu Ile Lys
                100                 105                 110

<210> SEQ ID NO 135
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 135

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Asn Arg Asn Phe Gly Gln Gly Thr Lys Val Glu Ile Lys
            100                 105                 110

<210> SEQ ID NO 136
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile His Pro Tyr Asp Gly Asp Thr Phe Tyr Asn Gln Asn Phe
    50                  55                  60

Lys Asp Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 137
<211> LENGTH: 691
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile His Pro Tyr Asp Gly Asp Thr Phe Tyr Asn Gln Asn Phe
    50                  55                  60

Lys Asp Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly

```
                130             135             140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Gly Gly
210                 215                 220

Gly Gly Ser Gly Gly Gly Ser Glu Val Gln Leu Val Glu Ser Gly
225                 230                 235                 240

Gly Gly Leu Val Gln Pro Lys Gly Ser Leu Lys Leu Ser Cys Ala Ala
                245                 250                 255

Ser Gly Phe Thr Phe Asn Thr Tyr Ala Met Asn Trp Val Arg Gln Ala
                260                 265                 270

Pro Gly Lys Gly Leu Glu Trp Val Ala Arg Ile Arg Ser Lys Tyr Asn
                275                 280                 285

Asn Tyr Ala Thr Tyr Tyr Ala Asp Ser Val Lys Asp Arg Phe Thr Ile
                290                 295                 300

Ser Arg Asp Asp Ser Gln Ser Ile Leu Tyr Leu Gln Met Asn Asn Leu
305                 310                 315                 320

Lys Thr Glu Asp Thr Ala Met Tyr Tyr Cys Val Arg His Gly Asn Phe
                325                 330                 335

Gly Asn Ser Tyr Val Ser Trp Phe Ala Tyr Trp Gly Gln Gly Thr Leu
                340                 345                 350

Val Thr Val Ser Ala Ala Ser Val Ala Ala Pro Ser Val Phe Ile Phe
                355                 360                 365

Pro Pro Ser Asp Glu Gln Leu Lys Ser Gly Thr Ala Ser Val Val Cys
370                 375                 380

Leu Leu Asn Asn Phe Tyr Pro Arg Glu Ala Lys Val Gln Trp Lys Val
385                 390                 395                 400

Asp Asn Ala Leu Gln Ser Gly Asn Ser Gln Glu Ser Val Thr Glu Gln
                405                 410                 415

Asp Ser Lys Asp Ser Thr Tyr Ser Leu Ser Ser Thr Leu Thr Leu Ser
                420                 425                 430

Lys Ala Asp Tyr Glu Lys His Lys Val Tyr Ala Cys Glu Val Thr His
                435                 440                 445

Gln Gly Leu Ser Ser Pro Val Thr Lys Ser Phe Asn Arg Gly Glu Cys
450                 455                 460

Asp Lys Thr His Thr Cys Pro Pro Cys Pro Ala Pro Glu Ala Ala Gly
465                 470                 475                 480

Gly Pro Ser Val Phe Leu Phe Pro Pro Lys Pro Lys Asp Thr Leu Met
                485                 490                 495

Ile Ser Arg Thr Pro Glu Val Thr Cys Val Val Val Asp Val Ser His
                500                 505                 510

Glu Asp Pro Glu Val Lys Phe Asn Trp Tyr Val Asp Gly Val Glu Val
                515                 520                 525

His Asn Ala Lys Thr Lys Pro Arg Glu Glu Gln Tyr Asn Ser Thr Tyr
                530                 535                 540

Arg Val Val Ser Val Leu Thr Val Leu His Gln Asp Trp Leu Asn Gly
545                 550                 555                 560
```

```
Lys Glu Tyr Lys Cys Lys Val Ser Asn Lys Ala Leu Gly Ala Pro Ile
                565                 570                 575

Glu Lys Thr Ile Ser Lys Ala Lys Gly Gln Pro Arg Glu Pro Gln Val
            580                 585                 590

Tyr Thr Leu Pro Pro Cys Arg Asp Glu Leu Thr Lys Asn Gln Val Ser
            595                 600                 605

Leu Trp Cys Leu Val Lys Gly Phe Tyr Pro Ser Asp Ile Ala Val Glu
610                 615                 620

Trp Glu Ser Asn Gly Gln Pro Glu Asn Asn Tyr Lys Thr Thr Pro Pro
625                 630                 635                 640

Val Leu Asp Ser Asp Gly Ser Phe Phe Leu Tyr Ser Lys Leu Thr Val
            645                 650                 655

Asp Lys Ser Arg Trp Gln Gln Gly Asn Val Phe Ser Cys Ser Val Met
            660                 665                 670

His Glu Ala Leu His Asn His Tyr Thr Gln Lys Ser Leu Ser Leu Ser
            675                 680                 685

Pro Gly Lys
    690

<210> SEQ ID NO 138
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Asp Ile Glu Leu Thr Gln Ser Pro Ala Ser Leu Ala Val Ser Leu Gly
1               5                   10                  15

Gln Arg Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Lys Leu Leu Ile Tyr Arg Ala Ser Asn Leu Glu Ala Gly Val Pro Thr
50                  55                  60

Arg Phe Ser Gly Ser Gly Ser Lys Thr Asp Phe Thr Leu Asn Ile His
65                  70                  75                  80

Pro Val Glu Glu Glu Asp Ala Ala Thr Tyr Tyr Cys Gln Gln Ser Arg
            85                  90                  95

Glu Tyr Pro Tyr Thr Phe Gly Gly Gly Thr Lys Leu Glu Ile Lys Arg
        100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
            195                 200                 205
```

```
Val Thr Lys Ser Phe Asn Arg Gly Glu Cys
    210                 215
```

<210> SEQ ID NO 139
<211> LENGTH: 257
<212> TYPE: PRT
<213> ORGANISM: Homo sapiens

<400> SEQUENCE: 139

```
Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser
```

<210> SEQ ID NO 140
<211> LENGTH: 468
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 140

```
Arg Ile Ala Trp Ala Arg Thr Glu Leu Leu Asn Val Cys Met Asn Ala
1               5                   10                  15

Lys His Lys Glu Lys Pro Gly Pro Glu Asp Lys Leu His Glu Gln
            20                  25                  30
```

```
Cys Arg Pro Trp Arg Lys Asn Ala Cys Cys Ser Thr Asn Thr Ser Gln
         35                  40                  45

Glu Ala His Lys Asp Val Ser Tyr Leu Tyr Arg Phe Asn Trp Asn His
 50                  55                  60

Cys Gly Glu Met Ala Pro Ala Cys Lys Arg His Phe Ile Gln Asp Thr
 65                  70                  75                  80

Cys Leu Tyr Glu Cys Ser Pro Asn Leu Gly Pro Trp Ile Gln Gln Val
                 85                  90                  95

Asp Gln Ser Trp Arg Lys Glu Arg Val Leu Asn Val Pro Leu Cys Lys
            100                 105                 110

Glu Asp Cys Glu Gln Trp Trp Glu Asp Cys Arg Thr Ser Tyr Thr Cys
            115                 120                 125

Lys Ser Asn Trp His Lys Gly Trp Asn Trp Thr Ser Gly Phe Asn Lys
130                 135                 140

Cys Ala Val Gly Ala Ala Cys Gln Pro Phe His Phe Tyr Phe Pro Thr
145                 150                 155                 160

Pro Thr Val Leu Cys Asn Glu Ile Trp Thr His Ser Tyr Lys Val Ser
                165                 170                 175

Asn Tyr Ser Arg Gly Ser Gly Arg Cys Ile Gln Met Trp Phe Asp Pro
            180                 185                 190

Ala Gln Gly Asn Pro Asn Glu Glu Val Ala Arg Phe Tyr Ala Ala Ala
            195                 200                 205

Met Val Asp Glu Gln Leu Tyr Phe Gln Gly Gly Ser Pro Lys Ser Ala
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
            355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
435                 440                 445

Pro Gly Lys Ser Gly Gly Leu Asn Asp Ile Phe Glu Ala Gln Lys Ile
```

450                 455                 460

Glu Trp His Glu
465

<210> SEQ ID NO 141
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Phe Thr Gln Lys Ser Leu Ser Leu Ser
    210                 215                 220

Pro Gly Lys
225

<210> SEQ ID NO 142
<211> LENGTH: 255
<212> TYPE: PRT
<213> ORGANISM: Mus musculus

<400> SEQUENCE: 142

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu Leu Leu
            20                  25                  30

Asn Val Cys Met Asp Ala Lys His His Lys Glu Lys Pro Gly Pro Glu
        35                  40                  45

```
Asp Asn Leu His Asp Gln Cys Ser Pro Trp Lys Thr Asn Ser Cys Cys
 50                  55                  60

Ser Thr Asn Thr Ser Gln Glu Ala His Lys Asp Ile Ser Tyr Leu Tyr
 65                  70                  75                  80

Arg Phe Asn Trp Asn His Cys Gly Thr Met Thr Ser Glu Cys Lys Arg
                 85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Ile Leu
            115                 120                 125

Asp Val Pro Leu Cys Lys Glu Asp Cys Gln Gln Trp Trp Glu Asp Cys
130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
            180                 185                 190

His Ser Tyr Lys Leu Ser Asn Tyr Ser Arg Gly Ser Gly Arg Cys Ile
            195                 200                 205

Gln Met Trp Phe Asp Pro Ala Gln Gly Asn Pro Asn Glu Glu Val Ala
            210                 215                 220

Arg Phe Tyr Ala Glu Ala Met Ser Gly Ala Gly Leu His Gly Thr Trp
225                 230                 235                 240

Pro Leu Leu Cys Ser Leu Ser Leu Val Leu Leu Trp Val Ile Ser
                245                 250                 255

<210> SEQ ID NO 143
<211> LENGTH: 466
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Thr Arg Ala Arg Thr Glu Leu Leu Asn Val Cys Met Asp Ala Lys His
 1               5                  10                  15

His Lys Glu Lys Pro Gly Pro Glu Asp Asn Leu His Asp Gln Cys Ser
                 20                  25                  30

Pro Trp Lys Thr Asn Ser Cys Cys Ser Thr Asn Thr Ser Gln Glu Ala
             35                  40                  45

His Lys Asp Ile Ser Tyr Leu Tyr Arg Phe Asn Trp Asn His Cys Gly
 50                  55                  60

Thr Met Thr Ser Glu Cys Lys Arg His Phe Ile Gln Asp Thr Cys Leu
 65                  70                  75                  80

Tyr Glu Cys Ser Pro Asn Leu Gly Pro Trp Ile Gln Gln Val Asp Gln
                 85                  90                  95

Ser Trp Arg Lys Glu Arg Ile Leu Asp Val Pro Leu Cys Lys Glu Asp
            100                 105                 110

Cys Gln Gln Trp Trp Glu Asp Cys Gln Ser Ser Phe Thr Cys Lys Ser
            115                 120                 125

Asn Trp His Lys Gly Trp Asn Trp Ser Ser Gly His Asn Glu Cys Pro
        130                 135                 140

Val Gly Ala Ser Cys His Pro Phe Thr Phe Tyr Phe Pro Thr Ser Ala
```

```
                145                 150                 155                 160
Ala Leu Cys Glu Glu Ile Trp Ser His Ser Tyr Lys Leu Ser Asn Tyr
                165                 170                 175

Ser Arg Gly Ser Gly Arg Cys Ile Gln Met Trp Phe Asp Pro Ala Gln
                180                 185                 190

Gly Asn Pro Asn Glu Glu Val Ala Arg Phe Tyr Ala Glu Ala Met Val
                195                 200                 205

Asp Glu Gln Leu Tyr Phe Gln Gly Gly Ser Pro Lys Ser Ala Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Cys Arg Asp Glu Leu Thr Lys Asn Gln Val Ser Leu Trp
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys Ser Gly Gly Leu Asn Asp Ile Phe Glu Ala Gln Lys Ile Glu Trp
                450                 455                 460

His Glu
465

<210> SEQ ID NO 144
<211> LENGTH: 257
<212> TYPE: PRT
<213> ORGANISM: Macaca fascicularis

<400> SEQUENCE: 144

Met Ala Gln Arg Met Thr Thr Gln Leu Leu Leu Leu Val Trp Val
1               5                   10                  15

Ala Val Val Gly Glu Ala Gln Thr Arg Thr Ala Arg Ala Arg Thr Glu
                20                  25                  30

Leu Leu Asn Val Cys Met Asn Ala Lys His His Lys Glu Lys Pro Gly
                35                  40                  45
```

```
Pro Glu Asp Lys Leu His Glu Gln Cys Arg Pro Trp Lys Lys Asn Ala
 50                  55                  60
Cys Cys Ser Thr Asn Thr Ser Gln Glu Ala His Lys Asp Val Ser Tyr
 65                  70                  75                  80
Leu Tyr Arg Phe Asn Trp Asn His Cys Gly Glu Met Ala Pro Ala Cys
                 85                  90                  95
Lys Arg His Phe Ile Gln Asp Thr Cys Leu Tyr Glu Cys Ser Pro Asn
            100                 105                 110
Leu Gly Pro Trp Ile Gln Gln Val Asp Gln Ser Trp Arg Lys Glu Arg
            115                 120                 125
Val Leu Asn Val Pro Leu Cys Lys Glu Asp Cys Glu Arg Trp Trp Glu
130                 135                 140
Asp Cys Arg Thr Ser Tyr Thr Cys Lys Ser Asn Trp His Lys Gly Trp
145                 150                 155                 160
Asn Trp Thr Ser Gly Phe Asn Lys Cys Pro Val Gly Ala Ala Cys Gln
                165                 170                 175
Pro Phe His Phe Tyr Phe Pro Thr Pro Thr Val Leu Cys Asn Glu Ile
            180                 185                 190
Trp Thr Tyr Ser Tyr Lys Val Ser Asn Tyr Ser Arg Gly Ser Gly Arg
            195                 200                 205
Cys Ile Gln Met Trp Phe Asp Pro Ala Gln Gly Asn Pro Asn Glu Glu
210                 215                 220
Val Ala Arg Phe Tyr Ala Ala Met Ser Gly Ala Gly Pro Trp Ala
225                 230                 235                 240
Ala Trp Pro Leu Leu Leu Ser Leu Ala Leu Thr Leu Leu Trp Leu Leu
                245                 250                 255
Ser

<210> SEQ ID NO 145
<211> LENGTH: 468
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Arg Thr Ala Arg Ala Arg Thr Glu Leu Leu Asn Val Cys Met Asn Ala
1               5                  10                  15
Lys His His Lys Glu Lys Pro Gly Pro Glu Asp Lys Leu His Glu Gln
            20                  25                  30
Cys Arg Pro Trp Lys Lys Asn Ala Cys Cys Ser Thr Asn Thr Ser Gln
        35                  40                  45
Glu Ala His Lys Asp Val Ser Tyr Leu Tyr Arg Phe Asn Trp Asn His
 50                  55                  60
Cys Gly Glu Met Ala Pro Ala Cys Lys Arg His Phe Ile Gln Asp Thr
 65                  70                  75                  80
Cys Leu Tyr Glu Cys Ser Pro Asn Leu Gly Pro Trp Ile Gln Gln Val
                 85                  90                  95
Asp Gln Ser Trp Arg Lys Glu Arg Val Leu Asn Val Pro Leu Cys Lys
            100                 105                 110
Glu Asp Cys Glu Gln Trp Trp Glu Asp Cys Arg Thr Ser Tyr Thr Cys
            115                 120                 125
Lys Ser Asn Trp His Lys Gly Trp Asn Trp Thr Ser Gly Phe Asn Lys
            130                 135                 140
```

Cys Pro Val Gly Ala Ala Cys Gln Pro Phe His Phe Tyr Phe Pro Thr
145                 150                 155                 160

Pro Thr Val Leu Cys Asn Glu Ile Trp Thr Tyr Ser Tyr Lys Val Ser
            165                 170                 175

Asn Tyr Ser Arg Gly Ser Gly Arg Cys Ile Gln Met Trp Phe Asp Pro
        180                 185                 190

Ala Gln Gly Asn Pro Asn Glu Glu Val Ala Arg Phe Tyr Ala Ala Ala
    195                 200                 205

Met Val Asp Glu Gln Leu Tyr Phe Gln Gly Gly Ser Pro Lys Ser Ala
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Ser Gly Gly Leu Asn Asp Ile Phe Glu Ala Gln Lys Ile
    450                 455                 460

Glu Trp His Glu
465

<210> SEQ ID NO 146
<211> LENGTH: 255
<212> TYPE: PRT
<213> ORGANISM: Homo sapiens

<400> SEQUENCE: 146

Met Val Trp Lys Trp Met Pro Leu Leu Leu Leu Val Cys Val Ala
1               5                   10                  15

Thr Met Cys Ser Ala Gln Asp Arg Thr Asp Leu Leu Asn Val Cys Met
            20                  25                  30

Asp Ala Lys His His Lys Thr Lys Pro Gly Pro Glu Asp Lys Leu His

```
                35                  40                  45
Asp Gln Cys Ser Pro Trp Lys Lys Asn Ala Cys Cys Thr Ala Ser Thr
             50                  55                  60

Ser Gln Glu Leu His Lys Asp Thr Ser Arg Leu Tyr Asn Phe Asn Trp
 65                  70                  75                  80

Asp His Cys Gly Lys Met Glu Pro Ala Cys Lys Arg His Phe Ile Gln
                 85                  90                  95

Asp Thr Cys Leu Tyr Glu Cys Ser Pro Asn Leu Gly Pro Trp Ile Gln
            100                 105                 110

Gln Val Asn Gln Ser Trp Arg Lys Glu Arg Phe Leu Asp Val Pro Leu
        115                 120                 125

Cys Lys Glu Asp Cys Gln Arg Trp Trp Glu Asp Cys His Thr Ser His
    130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 147
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Thr Met Cys Ser Ala Gln Asp Arg Thr Asp Leu Leu Asn Val Cys Met
 1               5                  10                  15

Asp Ala Lys His His Lys Thr Lys Pro Gly Pro Glu Asp Lys Leu His
                20                  25                  30

Asp Gln Cys Ser Pro Trp Lys Lys Asn Ala Cys Cys Thr Ala Ser Thr
            35                  40                  45

Ser Gln Glu Leu His Lys Asp Thr Ser Arg Leu Tyr Asn Phe Asn Trp
         50                  55                  60

Asp His Cys Gly Lys Met Glu Pro Ala Cys Lys Arg His Phe Ile Gln
 65                  70                  75                  80

Asp Thr Cys Leu Tyr Glu Cys Ser Pro Asn Leu Gly Pro Trp Ile Gln
                85                  90                  95

Gln Val Asn Gln Ser Trp Arg Lys Glu Arg Phe Leu Asp Val Pro Leu
            100                 105                 110

Cys Lys Glu Asp Cys Gln Arg Trp Trp Glu Asp Cys His Thr Ser His
        115                 120                 125

Thr Cys Lys Ser Asn Trp His Arg Gly Trp Asp Trp Thr Ser Gly Val
    130                 135                 140
```

```
Asn Lys Cys Pro Ala Gly Ala Leu Cys Arg Thr Phe Glu Ser Tyr Phe
145                 150                 155                 160

Pro Thr Pro Ala Ala Leu Cys Glu Gly Leu Trp Ser His Ser Tyr Lys
                165                 170                 175

Val Ser Asn Tyr Ser Arg Gly Ser Gly Arg Cys Ile Gln Met Trp Phe
            180                 185                 190

Asp Ser Ala Gln Gly Asn Pro Asn Glu Glu Val Ala Arg Phe Tyr Ala
        195                 200                 205

Ala Ala Met His Val Val Asp Glu Gln Leu Tyr Phe Gln Gly Gly Ser
    210                 215                 220

Pro Lys Ser Ala Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Cys Arg Asp Glu Leu Thr Lys
        355                 360                 365

Asn Gln Val Ser Leu Trp Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Ser Gly Gly Leu Asn Asp Ile Phe Glu
    450                 455                 460

Ala Gln Lys Ile Glu Trp His Glu
465                 470

<210> SEQ ID NO 148
<211> LENGTH: 243
<212> TYPE: PRT
<213> ORGANISM: Homo sapiens

<400> SEQUENCE: 148

Met Ala Trp Gln Met Met Gln Leu Leu Leu Ala Leu Val Thr Ala
1               5                   10                  15

Ala Gly Ser Ala Gln Pro Arg Ser Ala Arg Ala Arg Thr Asp Leu Leu
            20                  25                  30

Asn Val Cys Met Asn Ala Lys His His Lys Thr Gln Pro Ser Pro Glu
```

```
              35                  40                  45
Asp Glu Leu Tyr Gly Gln Cys Ser Pro Trp Lys Lys Asn Ala Cys Cys
 50                  55                  60

Thr Ala Ser Thr Ser Gln Glu Leu His Lys Asp Thr Ser Arg Leu Tyr
 65                  70                  75                  80

Asn Phe Asn Trp Asp His Cys Gly Lys Met Glu Pro Thr Cys Lys Arg
                 85                  90                  95

His Phe Ile Gln Asp Ser Cys Leu Tyr Glu Cys Ser Pro Asn Leu Gly
            100                 105                 110

Pro Trp Ile Arg Gln Val Asn Gln Ser Trp Arg Lys Glu Arg Ile Leu
        115                 120                 125

Asn Val Pro Leu Cys Lys Glu Asp Cys Glu Arg Trp Trp Glu Asp Cys
130                 135                 140

Arg Thr Ser Tyr Thr Cys Lys Ser Asn Trp His Lys Gly Trp Asn Trp
145                 150                 155                 160

Thr Ser Gly Ile Asn Glu Cys Pro Ala Gly Leu Cys Ser Thr Phe
                165                 170                 175

Glu Ser Tyr Phe Pro Thr Pro Ala Ala Leu Cys Glu Gly Leu Trp Ser
            180                 185                 190

His Ser Phe Lys Val Ser Asn Tyr Ser Arg Gly Ser Gly Arg Cys Ile
        195                 200                 205

Gln Met Trp Phe Asp Ser Ala Gln Gly Asn Pro Asn Glu Val Ala
    210                 215                 220

Lys Phe Tyr Ala Ala Ala Met Asn Ala Gly Ala Pro Ser Arg Gly Ile
225                 230                 235                 240

Ile Asp Ser

<210> SEQ ID NO 149
<211> LENGTH: 479
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Ser Ala Arg Ala Arg Thr Asp Leu Leu Asn Val Cys Met Asn Ala Lys
 1               5                  10                  15

His His Lys Thr Gln Pro Ser Pro Glu Asp Glu Leu Tyr Gly Gln Cys
                20                  25                  30

Ser Pro Trp Lys Lys Asn Ala Cys Cys Thr Ala Ser Thr Ser Gln Glu
            35                  40                  45

Leu His Lys Asp Thr Ser Arg Leu Tyr Asn Phe Asn Trp Asp His Cys
 50                  55                  60

Gly Lys Met Glu Pro Thr Cys Lys Arg His Phe Ile Gln Asp Ser Cys
 65                  70                  75                  80

Leu Tyr Glu Cys Ser Pro Asn Leu Gly Pro Trp Ile Arg Gln Val Asn
                 85                  90                  95

Gln Ser Trp Arg Lys Glu Arg Ile Leu Asn Val Pro Leu Cys Lys Glu
            100                 105                 110

Asp Cys Glu Arg Trp Trp Glu Asp Cys Arg Thr Ser Tyr Thr Cys Lys
        115                 120                 125

Ser Asn Trp His Lys Gly Trp Asn Trp Thr Ser Gly Ile Asn Glu Cys
130                 135                 140
```

```
Pro Ala Gly Ala Leu Cys Ser Thr Phe Glu Ser Tyr Phe Pro Thr Pro
145                 150                 155                 160

Ala Ala Leu Cys Glu Gly Leu Trp Ser His Ser Phe Lys Val Ser Asn
                165                 170                 175

Tyr Ser Arg Gly Ser Gly Arg Cys Ile Gln Met Trp Phe Asp Ser Ala
            180                 185                 190

Gln Gly Asn Pro Asn Glu Glu Val Ala Lys Phe Tyr Ala Ala Ala Met
        195                 200                 205

Asn Ala Gly Ala Pro Ser Arg Gly Ile Ile Asp Ser Val Asp Glu Gln
210                 215                 220

Leu Tyr Phe Gln Gly Gly Ser Pro Lys Ser Ala Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Cys Arg Asp Glu Leu Thr Lys Asn Gln Val Ser Leu Trp Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Gly
450                 455                 460

Gly Leu Asn Asp Ile Phe Glu Ala Gln Lys Ile Glu Trp His Glu
465                 470                 475

<210> SEQ ID NO 150
<211> LENGTH: 207
<212> TYPE: PRT
<213> ORGANISM: Homo sapiens

<400> SEQUENCE: 150

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
            35                  40                  45
```

```
Cys Pro Gln Tyr Pro Gly Ser Glu Ile Leu Trp Gln His Asn Asp Lys
 50                  55                  60

Asn Ile Gly Gly Asp Glu Asp Lys Asn Ile Gly Ser Asp Glu Asp
 65                  70                  75                  80

His Leu Ser Leu Lys Glu Phe Ser Glu Leu Glu Gln Ser Gly Tyr Tyr
                 85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
            130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
                195                 200                 205
```

<210> SEQ ID NO 151
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 151

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacgctggtg ttactccgtt cgactattgg ggtcaaggca ccctcgtaac ggtttcttct     360
```

<210> SEQ ID NO 152
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 152

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacatcggtg ttgttacttt cgactattgg ggtcaaggca ccctcgtaac ggtttcttct     360
```

<210> SEQ ID NO 153
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 153
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacactggtg gttcttctgc tttcgactat ggggtcaag gcaccctcgt aacggtttct      360
tct                                                                   363

<210> SEQ ID NO 154
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (47)..(47)
<223> OTHER INFORMATION: a, c, t, g, unknown or other

<400> SEQUENCE: 154
caggtgcaat tggttcaatc tggtgctgaa gtaaaaaaac cgggcgnttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcggtgaa     300
tggcgtcgtt acacttcttt cgactattgg ggtcaaggca ccctcgtaac ggtttcttct     360

<210> SEQ ID NO 155
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 155
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcggtggt     300
tggatccgtt gggaacattt cgactattgg ggtcaaggca ccctcgtaac ggtttcttct     360

```
<210> SEQ ID NO 156
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacctgttct ctacttcttt cgactattgg ggtcaaggca ccctcgtaac ggtttcttct     360

<210> SEQ ID NO 157
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 157
caggtgcaat tggttcaatc tggtgctgag gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacatcggta tcgttccgtt cgactattgg ggtcaaggca ccctcgtaac ggtttcttct     360

<210> SEQ ID NO 158
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 158
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgacgg tggcaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360

<210> SEQ ID NO 159
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
```

```
       Synthetic polynucleotide"
<220> FEATURE:
<221> NAME/KEY: modified_base
<222> LOCATION: (53)..(53)
<223> OTHER INFORMATION: a, c, t, g, unknown or other

<400> SEQUENCE: 159
gaggtgcaat tggttgaatc tggtggtggt ctggtaaaac cgggcggttc ccngcgtctg      60
agctgcgcgg cttccggatt caccttctcc aacgcgtgga tgagctgggt tcgccaggcc     120
ccgggcaaag gcctcgagtg ggttggtcgt atcaagtcta aaactgacgg tggcaccacg     180
gattacgcgg ctccagttaa aggtcgtttt accatttccc gcgacgatag caaaaacact     240
ctgtatctgc agatgaactc tctgaaaacc gaagacaccg cagtctacta ctgtactacc     300
ccgtgggaat ggtcttactt cgattattgg ggccagggca cgctggttac ggtgtcttcc     360

<210> SEQ ID NO 160
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcgtggctc tacctcctac      180 gcgcagaaat tccagggtcg cgtcacgatg acccgtgaca ctagcacctc taccgtttat     240
atggagctgt ccagcctgcg ttctgaagat actgcagtgt actactgtgc acgcaactac     300
tacgttggtg tttctccgtt cgactattgg ggtcaaggca ccctcgtaac ggtttcttct     360

<210> SEQ ID NO 161
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (47)..(47)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other

<400> SEQUENCE: 161
caggtgcaat tggttcaatc tggtgctgaa gtaaaaaaac cgggcgnttc cgttaaagtg      60
agctgcaaag catccggata caccttcact tcctattaca tgcactgggt tcgtcaagcc     120
ccgggccagg gtctggaatg gatgggcatc attaacccaa gcgtggctc tacctcntac      180 gcgcagaaat tccagggtcg cgtcacgatg acccgtgaca ctagcacctc taccgtttat     240
atggagctgt ccagcctgcg ttctgaagat actgcagtgt actactgtgc acgcaacttc     300
actgttctgc gtgttccgtt cgactattgg ggtcaaggca ccctcgtaac ggtttcttct     360

<210> SEQ ID NO 162
<211> LENGTH: 360
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 162
gaggtgcaat tggttgaatc tggtggtggt ctggtaaaac cgggcggttc cctgcgtctg    60
agctgcgcgg cttccggatt caccttctcc aacgcgtgga tgagctgggt tcgccaggcc   120
ccgggcaaag gcctcgagtg ggttggtcgt atcaagtcta aaactgacgg tggcaccacg   180
gattacgcgg ctccagttaa aggtcgtttt accatttccc gcgacgatag caaaaacact   240
ctgtatctgc agatgaactc tctgaaaact gaagacaccg cagtctacta ctgtactacc   300
ccgtgggaat gggcttggtt cgattattgg ggccagggca cgctggttac ggtgtcttcc   360

<210> SEQ ID NO 163
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 163
gaggtgcaat tggttgaatc tggtggtggt ctggtaaaac cgggcggttc cctgcgtctg    60
agctgcgcgg cttccggatt caccttctcc aacgcgtgga tgagctgggt tcgccaggcc   120
ccgggcaaag gcctcgagtg ggttggtcgt atcaagtcta aaactgacgg tggcaccacg   180
gattacgcgg ctccagttaa aggtcgtttt accatttccc gcgacgatag caaaaacact   240
ctgtatctgc agatgaactc tctgaaaacc gaagacaccg cagtctacta ctgtactacc   300
ccttgggaat gggcttactt cgattattgg ggccagggca cgctggttac ggtgtcttcc   360

<210> SEQ ID NO 164
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcactggt   300
tggtctcgtt ggggttacat ggactattgg ggccaaggca ccctcgtaac ggtttcttct   360

<210> SEQ ID NO 165
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 165

| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcgtggctc tacctcctac | 180 |
| gcgcagaaat tccagggtcg cgtcacgatg acccgtgaca ctagcacctc taccgtttat | 240 |
| atggagctgt ccagcctgcg ttctgaagat actgcagtgt actactgtgc acgcggtgaa | 300 |
| tggatccgtt actaccattt cgactattgg ggtcaaggca ccctcgtaac ggtttcttct | 360 |

<210> SEQ ID NO 166
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 166

| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcgtggctc tacctcctac | 180 |
| gcgcagaaat tccagggtcg cgtcacgatg acccgtgaca ctagcacctc taccgtttat | 240 |
| atggagctgt ccagcctgcg ttctgaagat actgcagtgt actactgtgc acgcgttggt | 300 |
| tggtaccgtt ggggttacat ggactattgg ggtcaaggca ccctcgtaac ggtttcttct | 360 |

<210> SEQ ID NO 167
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 167

| caggtgcaat tggtgcagtc tggggctgag gtgaagaagc ctgggtcctc ggtgaaggtc | 60 |
| tcctgcaagg cctccggagg cacattcagc agctacgcta taagctgggt gcgacaggcc | 120 |
| cctggacaag gctcgagtg gatgggaggg atcatcccta tctttggtac agcaaactac | 180 |
| gcacagaagt tccagggcag ggtaaccatt actgcagaca atccacgag cacagcctac | 240 |
| atggagctga gcagcctgag atctgaggac accgccgtgt attactgtgc gagagctgtt | 300 |
| ttctaccgtg cttggtactc tttcgactac tggggccaag gaccaccgt gaccgtctcc | 360 |
| tca | 363 |

<210> SEQ ID NO 168
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 168

| gacatccaga tgacccagtc tccttccacc ctgtctgcat ctgtaggaga ccgtgtcacc | 60 |
| atcacttgcc gtgccagtca gagtattagt agctggttgg cctggtatca gcagaaacca | 120 |

```
gggaaagccc ctaagctcct gatctatgat gcctccagtt tggaaagtgg ggtcccatca      180
cgtttcagcg gcagtggatc cgggacagaa ttcactctca ccatcagcag cttgcagcct      240
gatgattttg caacttatta ctgccaacag tataccagcc caccaccaac gtttggccag      300
ggcaccaaag tcgagatcaa g                                                321
```

<210> SEQ ID NO 169
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 169

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccatgaca ctagcacctc taccgtttat     240
atggagctgt ccagcctgcg ttctgaagat actgcagtgt actactgtgc acgctctttc     300
ttcactggtt tccatctgga ctattggggt caaggcaccc tcgtaacggt tcttct        357
```

<210> SEQ ID NO 170
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 170

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagtatacca cgaacatta ttatacgttc      300 ggccagggga ccaaagtgga aatcaaa                                         327
```

<210> SEQ ID NO 171
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 171

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggccc tacctcctac     180
gcgcagaaat tccagggtcg cgtcacgatg acccgtgaca ctagcacctc taccgtttat     240
atggagctgt ccagcctgcg ttctgaagat actgcagtgt actactgtgc acgcggtgac     300
```
ttcgcttggc tggactattg gggtcaaggc accctcgtaa cggtttcttc t        351

<210> SEQ ID NO 172
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 172
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcaag cattatgaac   300 cggactttg gtcaaggcac caaggtcgaa attaaa                              336

<210> SEQ ID NO 173
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 173
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcaag cattatgagc   300 cggactttg gtcaaggcac caaggtcgaa attaaa                              336

<210> SEQ ID NO 174
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 174
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcaag cattatgcag   300 cggactttg gtcaaggcac caaggtcgaa attaaa                              336

<210> SEQ ID NO 175
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 175
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcaag cattatgaac   300
cgggcttttg gtcaaggcac caaggtcgaa attaaa                             336

<210> SEQ ID NO 176
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 176
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcaag cattatgaac   300
cggaattttg gtcaaggcac caaggtcgaa attaaa                             336

<210> SEQ ID NO 177
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 177
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg accgtgaca ctagcacctc taccgtttat    240
atggagctgt ccagcctgcg ttctgaagat actgcagtgt actactgtgc acgctcttac   300
atcgacatgg actattgggg tcaaggcacc ctcgtaacgg tttcttct                348

<210> SEQ ID NO 178
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 178

```
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag caggataact ggagcccaac gttcggccag   300
gggaccaaag tggaaatcaa a                                             321
```

<210> SEQ ID NO 179
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 179

```
caggtgcaat tggttcaatc tggtgctgaa gtaaaaaaac cgggcgcttc cgttaaagtg    60
agctgcaaag catccggata caccttcact cctattaca tgcactgggt tcgtcaagcc   120
ccgggccagg gtctggaatg gatgggcatc attaacccaa gcgtggctc tacctcctac   180 gcgcagaaat tccagggtcg cgtcacgatg acccgtgaca ctagcacctc taccgtttat   240
atggagctgt ccagcctgcg ttctgaagat actgcagtgt actactgtgc acgctcttac   300
gttgacatgg actattgggg tcaaggcacc ctcgtaacgg tttcttct                348
```

<210> SEQ ID NO 180
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 180

```
gaaatcgtgt taacgcagtc tccaggcacc ctgtctttgt ctccagggga aagagccacc    60
ctctcttgca gggccagtca gagtgttagc agcagctacc tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag caggatattt ggagcccaac gttcggccag   300
gggaccaaag tggaaatcaa a                                             321
```

<210> SEQ ID NO 181
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 181

```
gaggtgcaat tgttggagtc tgggggaggc ttggtacagc ctgggggggtc cctgagactc    60 tcctgtgcag cctccggatt caccttagc agttatgcca tgagctgggt ccgccaggct   120
ccagggaagg gctggagtg gtctcagct attagtggta gtggtggtag cacatactac   180
gcagactccg tgaagggccg gttcaccatc tccagagaca attccaagaa cacgctgtat   240
```

```
ctgcagatga acagcctgag agccgaggac acggccgtat attactgtgc gaaagactct    300
tcttacgttg aatggtacgc tttcgactac tggggccaag aaccctggt caccgtctcg    360 agt                                                                  363
```

<210> SEQ ID NO 182
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 182

```
gaaatcgtgt taacgcagtc tccaggcacc ctgtctttgt ctccagggga agagccacc     60 ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gactccactc tcaccatcag cagactggag   240
cctgaagatt ttgcagtgta ttactgtcag cagccaacca gcagcccaat tacgttcggc   300
caggggacca aagtggaaat caaa                                           324
```

<210> SEQ ID NO 183
<211> LENGTH: 684
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183

```
gaggtgcagc tgctggaatc tggcggcgga ctggtgcagc ctggcggatc tctgagactg    60
agctgtgccg ccagcggctt caccttcagc acctacgcca tgaactgggt cgcgcaggcc   120
cctggcaaag gcctggaatg ggtgtcccgg atcagaagca agtacaacaa ctacgccacc   180
tactacgccg acagcgtgaa gggccggttc accatcagcc gggacgacag caagaacacc   240
ctgtacctgc agatgaacag cctgcgggcc gaggacaccg ccgtgtacta ttgtgtgcgg   300
cacggcaact tcggcaacag ctatgtgtct tggtttgcct actggggcca gggcaccctc   360
gtgaccgtgt caagcgctag taccaagggc ccagcgtgt tccccctggc acccagcagc    420
aagagcacat ctgccggaac agccgctctg ggctgtctgg tgaaagacta cttccccgag   480
cccgtgaccg tgtcttggaa ctctggcgcc ctgaccagcg gcgtgcacac ctttccagcc   540
gtgctgcaga gcagcggcct gtactccctg tcctccgtgg tcaccgtgcc ctctagctcc   600
ctgggaacac agacatatat ctgtaatgtc aatcacaagc cttccaacac caaagtcgat   660
aagaaagtcg agcccaagag ctgc                                           684
```

<210> SEQ ID NO 184
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184

```
gaggtgcagc tgctggaatc tggcggcgga ctggtgcagc ctggcggatc tctgagactg      60
agctgtgccg ccagcggctt caccttcagc acctacgcca tgaactgggt gcgccaggcc     120
cctggcaaag gcctggaatg ggtgtcccgg atcagaagca agtacaacaa ctacgccacc     180
tactacgccg acagcgtgaa gggccggttc accatcagcc gggacgacag caagaacacc     240
ctgtacctgc agatgaacag cctgcgggcc gaggacaccg ccgtgtacta ttgtgtgcgg     300
cacggcaact tcggcaacag ctatgtgtct tggtttgcct actggggcca gggcaccctc     360
gtgaccgtgt caagcgctag tgtggccgct ccctccgtgt ttatctttcc cccatccgat     420
gaacagctga aaagcggcac cgcctccgtc gtgtgtctgc tgaacaattt ttacccgagg     480
gaagctaaag tgcagtggaa agtggataac gcactgcagt ccggcaactc ccaggaatct     540
gtgacagaac aggactccaa ggacagcacc tactccctgt cctccaccct gacactgtct     600
aaggctgatt atgagaaaca caaagtctac gcctgcgaag tcacccatca gggcctgagc     660
tcgcccgtca caaagagctt caacagggga gagtgt                               696
```

<210> SEQ ID NO 185
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 185

```
gcaggcaagc attatgcagc ggacttttgg tcaagg                                36
```

<210> SEQ ID NO 186
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 186

```
caggcaagca ttatgagccg gactttggt caagg                                  35
```

<210> SEQ ID NO 187
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 187

```
cattatgaac cgggcttttg gtcaaggcac caaggtc                               37
```

<210> SEQ ID NO 188
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 188

```
cattatgaac cggaattttg gtcaaggcac caaggtc                               37
```

<210> SEQ ID NO 189
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 189

```
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag cctcgagtg gttggtcgt atcaagtcta aaactgacgg tggcaccacg       180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacaa agggccctag cgtgttccct ctggccccca gcagcaagag cacaagcggc     420
ggaacagccg ccctgggctg cctcgtgaag gactacttcc ccgagcccgt gacagtgtct     480
tggaacagcg gagccctgac aagcggcgtg cacactttcc ctgccgtgct gcagagcagc     540
ggcctgtact ccctgagcag cgtggtcacc gtgcctagca gcagcctggg cacccagacc     600
tacatctgca acgtgaacca caagcccagc aacaccaaag tggacaagaa ggtggagccc     660
aagagctgtg atggcggagg agggtccgga ggcggaggat ccgaggtgca gctgctggaa     720
tctggcggcg gactggtgca gcctggcgga tctctgagac tgagctgtgc cgccagcggc     780
ttcaccttca gcacctacgc catgaactgg gtgcgccagg cccctggcaa aggcctggaa     840
tgggtgtccc ggatcagaag caagtacaac aactacgcca cctactacgc cgacagcgtg     900
aagggccggt tcaccatcag ccgggacgac agcaagaaca ccctgtacct gcagatgaac     960
agcctgcggg ccgaggacac cgccgtgtac tattgtgtgc ggcacggcaa cttcggcaac    1020
agctatgtgt cttggtttgc ctactggggc cagggcaccc tcgtgaccgt gtcaagcgct    1080
agtaccaagg gccccagcgt gttcccctg cacccagca gcaagagcac atctggcgga     1140
acagccgctc tgggctgtct ggtgaaagac tacttccccg agcccgtgac cgtgtcttgg    1200
aactctggcg ccctgaccag cggcgtgcac acctttccag ccgtgctgca gagcagcggc    1260
ctgtactccc tgtcctccgt ggtcaccgtg ccctctagct ccctgggaac acagacatat    1320
atctgtaatg tcaatcacaa gccttccaac accaaagtcg ataagaaagt cgagcccaag    1380
agctgcgaca aaactcacac atgcccaccg tgcccagcac ctgaagctgc aggggaccg     1440
tcagtcttcc tcttcccccc aaaacccaag gacaccctca tgatctcccg gacccctgag    1500
gtcacatgcg tggtggtgga cgtgagccac gaagaccctg aggtcaagtt caactggtac    1560
gtggacggcg tggaggtgca taatgccaag acaaagccgc gggaggagca gtacaacagc    1620
acgtaccgtg tggtcagcgt cctcaccgtc ctgcaccagg actggctgaa tggcaaggag    1680
tacaagtgca aggtctccaa caaagccctc ggcgccccca tcgagaaaac catctccaaa    1740
gccaaagggc agccccgaga accacaggtg tacaccctgc ccccatgccg ggatgagctg    1800
accaagaacc aggtcagcct gtggtgcctg gtcaaaggct tctatccag cgacatcgcc    1860
gtggagtggg agagcaatgg gcagccggag aacaactaca agaccacgcc tcccgtgctg    1920
gactccgacg gctccttctt cctctacagc aagctcaccg tggacaagag caggtggcag    1980
```

```
cagggggaacg tcttctcatg ctccgtgatg catgaggctc tgcacaacca ctacacgcag    2040
aagagcctct ccctgtctcc gggtaaa                                         2067
```

<210> SEQ ID NO 190
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 190

```
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgacgg tgcaccacg      180 gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacca agggcccctc cgtgttcccc ctggccccca gcagcaagag caccagcggc     420
ggcacagccg ctctgggctg cctggtcaag gactacttcc ccgagcccgt gaccgtgtcc     480
tggaacagcg gagccctgac ctccggcgtg cacaccttcc ccgccgtgct gcagagttct     540
ggcctgtata gcctgagcag cgtggtcacc gtgccttcta gcagcctggg cacccagacc     600
tacatctgca acgtgaacca caagcccagc aacaccaagg tggacaagaa ggtggagccc     660
aagagctgcg acaaaactca cacatgccca ccgtgcccag cacctgaagc tgcaggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcggcgccc ccatcgagaa aaccatctcc    1020
aaagccaaag gcagccccg agaaccacag gtgtgcaccc tgcccccatc ccgggatgag    1080
ctgaccaaga accaggtcag cctctcgtgc gcagtcaaag gcttctatcc cagcgacatc    1140
gccgtggagt gggagagcaa tgggcagccg gagaacaact acaagaccac gcctcccgtg    1200
ctggactccg acggctcctt cttcctcgtg agcaagctca ccgtggacaa gagcaggtgg    1260
cagcagggga acgtcttctc atgctccgtg atgcatgagg ctctgcacaa ccgcttcacg    1320
cagaagagcc tctccctgtc tccgggtaaa                                     1350
```

<210> SEQ ID NO 191
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 191

```
caggccgtcg tgacccagga acccagcctg acagtgtctc ctggcggcac cgtgaccctg      60
acatgtggca gttctacagg cgccgtgacc accagcaact acgccaactg ggtgcaggaa     120
aagcccggcc aggccttcag aggactgatc ggcggcacca caagagagc cctggcacc      180
```

| | |
|---|---|
| cctgccagat tcagcggatc tctgctggga ggaaaggccg ccctgacact gtctggcgcc | 240 |
| cagccagaag atgaggccga gtactactgc gccctgtggt acagcaacct gtgggtgttc | 300 |
| ggcggaggca ccaagctgac agtcctaggt caacccaagg ctgcccccag cgtgaccctg | 360 |
| ttcccccca gcagcgagga actgcaggcc aacaaggcca ccctggtctg cctgatcagc | 420 |
| gacttctacc caggcgccgt gaccgtggcc tggaaggccg acagcagccc cgtgaaggcc | 480 |
| ggcgtggaga ccaccacccc cagcaagcag agcaacaaca gtacgccgc cagcagctac | 540 |
| ctgagcctga ccccgagca gtggaagagc acaggtcct acagctgcca ggtgacccac | 600 |
| gagggcagca ccgtggagaa accgtggcc cccaccgagt gcagc | 645 |

<210> SEQ ID NO 192
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 192

| | |
|---|---|
| gaggtgcagc tgctggaatc tggcggcgga ctggtgcagc ctggcggatc tctgagactg | 60 |
| agctgtgccg ccagcggctt caccttcagc acctacgcca tgaactgggt gcgccaggcc | 120 |
| cctggcaaag gcctggaatg ggtgtcccgg atcagaagca agtacaacaa ctacgccacc | 180 |
| tactacgccg acagcgtgaa gggccggttc accatcagcc gggacgacag caagaacacc | 240 |
| ctgtacctgc agatgaacag cctgcgggcc gaggacaccg ccgtgtacta ttgtgtgcgg | 300 |
| cacggcaact tcggcaacag ctatgtgtct tggtttgcct actggggcca gggcacctc | 360 |
| gtgaccgtgt catctgctag cacaaagggc cctagcgtgt tccctctggc ccccagcagc | 420 |
| aagagcacaa gcggcggaac agccgccctg ggctgcctcg tgaaggacta cttccccgag | 480 |
| cccgtgacag tgtcttggaa cagcggagcc ctgacaagcg gcgtgcacac cttccctgcc | 540 |
| gtgctgcaga gcagcggcct gtactccctg agcagcgtgg tcaccgtgcc tagcagcagc | 600 |
| ctgggcaccc agacctacat ctgcaacgtg aaccacaagc ccagcaacac caaagtggac | 660 |
| aagaaggtgg agcccaagag ctgtgatggc ggaggagggt ccggaggcgg aggatccgag | 720 |
| gtgcaattgg ttgaatctgg tggtggtctg gtaaaaccgg gcggttccct gcgtctgagc | 780 |
| tgcgcggctt ccggattcac cttctccaac gcgtggatga gctgggttcg ccaggccccg | 840 |
| ggcaaaggcc tcgagtgggt tggtcgtatc aagtctaaaa ctgacggtgg caccacggat | 900 |
| tacgcggctc cagttaaagg tcgttttacc atttcccgcg acgatagcaa aaacactctg | 960 |
| tatctgcaga tgaactctct gaaaactgaa gacaccgcag tctactactg tactaccccg | 1020 |
| tgggaatggt cttggtacga ttattgggggc cagggcacgc tggttacggt gtctagcgct | 1080 |
| agtaccaagg gcccagcgt gttccccctg gcacccagca gcaagagcac atctggcgga | 1140 |
| acagccgctc tgggctgtct ggtgaaagac tacttccccg agcccgtgac cgtgtcttgg | 1200 |
| aactctggcg ccctgaccag cggcgtgcac acctttccag ccgtgctgca gagcagcggc | 1260 |
| ctgtactccc tgtcctccgt ggtcaccgtg ccctctagct ccctgggaac acagacatat | 1320 |
| atctgtaatg tcaatcacaa gccttccaac accaaagtcg ataagaaagt cgagcccaag | 1380 |
| agctgcgaca aaactcacac atgcccaccg tgcccagcac ctgaagctgc agggggaccg | 1440 |
| tcagtcttcc tcttcccccc aaaacccaag gacaccctca tgatctcccg gacccctgag | 1500 |

-continued

| | |
|---|---|
| gtcacatgcg tggtggtgga cgtgagccac gaagaccctg aggtcaagtt caactggtac | 1560 |
| gtggacggcg tggaggtgca taatgccaag acaaagccgc gggaggagca gtacaacagc | 1620 |
| acgtaccgtg tggtcagcgt cctcaccgtc ctgcaccagg actggctgaa tggcaaggag | 1680 |
| tacaagtgca aggtctccaa caaagccctc ggcgccccca tcgagaaaac catctccaaa | 1740 |
| gccaaagggc agccccgaga accacaggtg tacaccctgc ccccatgccg ggatgagctg | 1800 |
| accaagaacc aggtcagcct gtggtgcctg gtcaaaggct tctatcccag cgacatcgcc | 1860 |
| gtggagtggg agagcaatgg gcagccggag aacaactaca agaccacgcc tcccgtgctg | 1920 |
| gactccgacg gctccttctt cctctacagc aagctcaccg tggacaagag caggtggcag | 1980 |
| caggggaacg tcttctcatg ctccgtgatg catgaggctc tgcacaacca ctacacgcag | 2040 |
| aagagcctct ccctgtctcc gggtaaa | 2067 |

<210> SEQ ID NO 193
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 193

| | |
|---|---|
| gaggtgcagc tgctggaatc tggcggcgga ctggtgcagc ctggcggatc tctgagactg | 60 |
| agctgtgccg ccagcggctt caccttcagc acctacgcca tgaactgggt gcgccaggcc | 120 |
| cctggcaaag gcctggaatg ggtgtcccgg atcagaagca agtacaacaa ctacgccacc | 180 |
| tactacgccg acagcgtgaa gggccggttc accatcagcc gggacgacag caagaacacc | 240 |
| ctgtacctgc agatgaacag cctgcgggcc gaggacaccg ccgtgtacta ttgtgtgcgg | 300 |
| cacggcaact tcggcaacag ctatgtgtct tggtttgcct actggggcca gggcacccta | 360 |
| gtgaccgtgt catctgctag caccaagggc ccatcggtct tccccctggc accctcctcc | 420 |
| aagagcacct ctgggggcac agcggccctg ggctgcctgg tcaaggacta cttccccgaa | 480 |
| ccggtgacgg tgtcgtggaa ctcaggcgcc ctgaccagcg gcgtgcacac cttcccggct | 540 |
| gtcctacagt cctcaggact ctactccctc agcagcgtgg tgaccgtgcc ctccagcagc | 600 |
| ttgggcaccc agacctacat ctgcaacgtg aatcacaagc ccagcaacac caaggtggac | 660 |
| aagaaagttg agcccaaatc ttgtgacaaa actcacacat gcccaccgtg cccagcacct | 720 |
| gaagctgcag gggaccgtc agtcttcctc ttccccccaa acccaaggac acccctcatg | 780 |
| atctcccgga cccctgaggt cacatgcgtg gtggtggacg tgagccacga agaccctgag | 840 |
| gtcaagttca actggtacgt ggacggcgtg gaggtgcata atgccaagac aaagccgcgg | 900 |
| gaggagcagt acaacagcac gtaccgtgtg gtcagcgtcc tcaccgtcct gcaccaggac | 960 |
| tggctgaatg gcaaggagta caagtgcaag gtctccaaca aagccctcgg cgcccccatc | 1020 |
| gagaaaacca tctccaaagc caagggcag ccccgagaac acaggtgta caccctgccc | 1080 |
| ccatgccggg atgagctgac caagaaccag gtcagcctgt ggtgcctggt caaaggcttc | 1140 |
| tatcccagcg acatcgccgt ggagtgggag agcaatgggc agccggagaa caactacaag | 1200 |
| accacgcctc ccgtgctgga ctccgacggc tccttcttcc tctacagcaa gctcaccgtg | 1260 |
| gacaagagca ggtggcagca ggggaacgtc ttctcatgct ccgtgatgca tgaggctctg | 1320 |
| cacaaccact acacgcagaa gagcctctcc ctgtctccgg gtaaa | 1365 |

```
<210> SEQ ID NO 194
<211> LENGTH: 681
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 194
gacaaaactc acacatgccc accgtgccca gcacctgaac tcctgggggg accgtcagtc    60
ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcccagcc cccatcgaga aaaccatctc caaagccaaa   360
gggcagcccc gagaaccaca ggtgtgcacc ctgcccccat cccgggatga gctgaccaag   420
aaccaggtca gcctctcgtg cgcagtcaaa ggcttctatc ccagcgacat cgccgtggag   480
tgggagagca atgggcagcc ggagaacaac tacaagacca cgcctcccgt gctggactcc   540
gacggctcct tcttcctcgt gagcaagctc accgtggaca agagcaggtg gcagcagggg   600
aacgtcttct catgctccgt gatgcatgag gctctgcaca accgcttcac gcagaagagc   660
ctctccctgt ctccgggtaa a                                             681

<210> SEQ ID NO 195
<211> LENGTH: 2070
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 195
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggccc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcggtgac   300
ttcgcttggc tggactattg gggtcaaggc accctcgtaa cggtttcttc tgctagcaca   360
aagggcccca gcgtgttccc tctggcccct agcagcaaga gcacatctgg cggaacagcc   420
gccctgggct gcctcgtgaa ggactacttt cccgagcctg tgaccgtgtc ctggaactct   480
ggcgccctga caagcggcgt gcacaccttt ccagccgtgc tgcagagcag cggcctgtac   540
tctctgagca gcgtggtcac cgtgcctagc agcagcctgg gcacccagac ctacatctgc   600
aacgtgaacc acaagcccag caacaccaaa gtggacaaga aggtggagcc caagagctgt   660
gatggcggag agggtccgg  aggcggagga tccgaggtgc agctgctgga atctggcggc   720
ggactggtgc agcctggcgg atctctgaga ctgagctgtg ccgccagcgg cttcaccttc   780
agcacctacg ccatgaactg ggtgcgccag gcccctggca aaggcctgga atgggtgtcc   840
cggatcagaa gcaagtacaa caactacgcc acctactacg ccgacagcgt gaagggccgg   900
ttcaccatca gccgggacga cagcaagaac accctgtacc tgcagatgaa cagcctgcgg   960
```

```
gccgaggaca ccgccgtgta ctattgtgtg cggcacggca acttcggcaa cagctatgtg    1020
tcttggtttg cctactgggg ccagggcacc ctcgtgaccg tgtcaagcgc tagtgtggcc    1080
gctccctccg tgtttatctt tccccccatcc gatgaacagc tgaaaagcgg caccgcctcc   1140
gtcgtgtgtc tgctgaacaa tttttaccct agggaagcta aagtgcagtg gaaagtggat    1200
aacgcactgc agtccggcaa ctcccaggaa tctgtgacag aacaggactc caaggacagc    1260
acctactccc tgtcctccac cctgacactg tctaaggctg attatgagaa acacaaagtc    1320
tacgcctgcg aagtcaccca tcagggcctg agctcgcccg tcacaaagag cttcaacagg    1380
ggagagtgtg acaagaccca cacctgtccc ccttgtcctg cccctgaagc tgctggcggc    1440
ccttctgtgt tcctgttccc cccaaagccc aaggacaccc tgatgatcag ccggacccccc  1500 gaagtgacct gcgtggtggt ggatgtgtcc cacgaggacc ctgaagtgaa gttcaattgg    1560
tacgtggacg gcgtggaagt gcacaacgcc aagacaaagc cgcgggagga gcagtacaac    1620
agcacgtacc gtgtggtcag cgtcctcacc gtcctgcacc aggactggct gaatggcaag    1680
gagtacaagt gcaaggtctc caacaaagcc ctcggcgccc ccatcgagaa aaccatctcc    1740
aaagccaaag ggcagccccg agaaccacag gtgtacaccc tgcccccatg ccgggatgag    1800
ctgaccaaga accaggtcag cctgtggtgc ctggtcaaag cttctatcc cagcgacatc     1860 gccgtggagt gggagagcaa tgggcagccg gagaacaact acaagaccac gcctcccgtg    1920
ctggactccg acggctcctt cttcctctac agcaagctca ccgtggacaa gagcaggtgg    1980
cagcagggga acgtcttctc atgctccgtg atgcatgagg ctctgcacaa ccactacacg    2040
cagaagagcc tctccctgtc tccgggtaaa                                     2070
```

<210> SEQ ID NO 196
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 196

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggccc tacctcctac    180
gcgcagaaat tccagggtcg cgtcacgatg accccgtgaca ctagcacctc taccgtttat   240
atggagctgt ccagcctgcg ttctgaagat actgcagtgt actactgtgc acgcggtgac    300
ttcgcttggc tggactattg gggtcaaggc accctcgtaa cggttctctc tgctagcacc    360
aagggcccct ccgtgttccc cctggccccc agcagcaaga gcaccagcgg cggcacagcc    420
gctctgggct gcctggtcaa ggactacttc cccgagcccg tgaccgtgtc ctggaacagc    480
ggagccctga cctccggcgt gcacaccttc cccgccgtgc tgcagagttc tggcctgtat    540
agcctgagca gcgtggtcac cgtgccttct agcagcctgg gcacccagac ctacatctgc    600
aacgtgaacc acaagcccag caacaccaag gtggacaaga aggtggagcc caagagctgc    660
gacaaaactc acacatgccc accgtgccca gcacctgaag ctgcagggg accgtcagtc    720 ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
```

```
cgtgtggtca gcgtcctcac cgtcctgcac caggactggc tgaatggcaa ggagtacaag    960
tgcaaggtct ccaacaaagc cctcggcgcc cccatcgaga aaccatctc caaagccaaa    1020 gggcagcccc gagaaccaca ggtgtgcacc ctgcccccat cccgggatga gctgaccaag    1080
aaccaggtca gcctctcgtg cgcagtcaaa ggcttctatc ccagcgacat cgccgtggag    1140
tgggagagca atgggcagcc ggagaacaac tacaagacca cgcctcccgt gctggactcc    1200
gacggctcct tcttcctcgt gagcaagctc accgtggaca gagcaggtg gcagcagggg    1260 aacgtcttct catgctccgt gatgcatgag gctctgcaca accactacac gcagaagagc    1320
ctctccctgt ctccgggtaa a                                              1341

<210> SEQ ID NO 197
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 197
gatattgtta tgactcaatc tccactgtct ctgccggtga ctccaggcga accggcgagc     60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcaag cattatgaac    300
cggacttttg gtcaaggcac caaggtcgaa attaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657

<210> SEQ ID NO 198
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 198
caggccgtcg tgacccagga acccagcctg acagtgtctc ctggcggcac cgtgaccctg     60
acatgtggca gttctacagg cgccgtgacc accagcaact acgccaactg ggtgcaggaa    120
aagcccggcc aggccttcag aggactgatc ggcggcacca caagagagc ccctggcacc     180 cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtgctgagc agcgcttcca ccaaaggccc ttccgtgttt    360
cctctggctc ctagctccaa gtccacctct ggaggcaccg ctgctctcgg atgcctcgtg    420
aaggattatt ttcctgagcc tgtgacagtg tcctggaata gcggagcact gacctctgga    480
```

| | |
|---|---|
| gtgcatactt tccccgctgt gctgcagtcc tctggactgt acagcctgag cagcgtggtg | 540 |
| acagtgccca gcagcagcct gggcacccag acctacatct gcaacgtgaa ccacaagccc | 600 |
| agcaacacca aggtggacaa gaaggtggaa cccaagtctt gt | 642 |

<210> SEQ ID NO 199
<211> LENGTH: 1377
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 199

| | |
|---|---|
| gaggtgcagc tgctggaatc tggcggcgga ctggtgcagc ctggcggatc tctgagactg | 60 |
| agctgtgccg ccagcggctt caccttcagc acctacgcca tgaactgggt gcgccaggcc | 120 |
| cctggcaaag gcctggaatg ggtgtcccgg atcagaagca gtacaacaa ctacgccacc | 180 |
| tactacgccg acagcgtgaa gggccggttc accatcagcc gggacgacag caagaacacc | 240 |
| ctgtacctgc agatgaacag cctgcgggcc gaggacaccg ccgtgtacta ttgtgtgcgg | 300 |
| cacggcaact tcggcaacag ctatgtgtct tggtttgcct actggggcca gggcaccctc | 360 |
| gtgaccgtgt catctgctag cgtggccgct ccctccgtgt ttatctttcc cccatccgat | 420 |
| gaacagctga aaagcggcac cgcctccgtc gtgtgtctgc tgaacaattt ttaccctagg | 480 |
| gaagctaaag tgcagtggaa agtggataac gcactgcagt ccggcaactc ccaggaatct | 540 |
| gtgacagaac aggactccaa ggacagcacc tactccctgt cctccaccct gacactgtct | 600 |
| aaggctgatt atgagaaaca caaagtctac gcctgcgaag tcacccatca gggcctgagc | 660 |
| tcgcccgtca caaagagctt caacagggga gagtgtgaca agacccacac ctgtccccct | 720 |
| tgtcctgccc ctgaagctgc tggcggccct tctgtgttcc tgttcccccc aaagcccaag | 780 |
| gacaccctga tgatcagccg gacccccgaa gtgacctgcg tggtggtgga tgtgtcccac | 840 |
| gaggaccctg aagtgaagtt caattggtac gtggacggcg tggaagtgca caacgccaag | 900 |
| acaaagccgc gggaggagca gtacaacagc acgtaccgtg tggtcagcgt cctcaccgtc | 960 |
| ctgcaccagg actggctgaa tggcaaggag tacaagtgca aggtctccaa caaagccctc | 1020 |
| ggcgccccca tcgagaaaac catctccaaa gccaaagggc agccccgaga accacaggtg | 1080 |
| tacaccctgc ccccatgccg ggatgagctg accaagaacc aggtcagcct gtggtgcctg | 1140 |
| gtcaaaggct tctatcccag cgacatcgcc gtggagtggg agagcaatgg gcagccggag | 1200 |
| aacaactaca agaccacgcc tcccgtgctg gactccgacg gctccttctt cctctacagc | 1260 |
| aagctcaccg tggacaagag caggtggcag caggggaacg tcttctcatg ctccgtgatg | 1320 |
| catgaggctc tgcacaacca ctacacgcag aagagcctct ccctgtctcc gggtaaa | 1377 |

<210> SEQ ID NO 200
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 200

| | |
|---|---|
| gaggtgcaat tggttgaatc tggtggtggt ctggtaaaac cgggcggttc cctgcgtctg | 60 |
| agctgcgcgg cttccggatt caccttctcc aacgcgtgga tgagctgggt tcgccaggcc | 120 |

```
ccgggcaaag gcctcgagtg ggttggtcgt atcaagtcta aaactgacgg tggcaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacaa agggccctag cgtgttccct ctggccccca gcagcaagag cacaagcggc     420
ggaacagccg ccctgggctg cctcgtgaag gactacttcc ccgagcccgt gacagtgtct     480
tggaacagcg gagccctgac aagcggcgtg cacacttcc ctgccgtgct gcagagcagc     540
ggcctgtact ccctgagcag cgtggtcacc gtgcctagca gcagcctggg cacccagacc     600
tacatctgca acgtgaacca caagcccagc aacaccaaag tggacaagaa ggtggagccc     660
aagagctgtg atggcggagg agggtccgga ggcggaggat ccgaggtgca gctgctggaa     720
tctggcggcg gactggtgca gcctggcgga tctctgagac tgagctgtgc cgccagcggc     780
ttcaccttca gcacctacgc catgaactgg gtgcgccagg cccctggcaa aggcctggaa     840
tgggtgtccc ggatcagaag caagtacaac aactacgcca cctactacgc cgacagcgtg     900
aagggccggt tcaccatcag ccgggacgac agcaagaaca ccctgtacct gcagatgaac     960
agcctgcggg ccgaggacac cgccgtgtac tattgtgtgc ggcacggcaa cttcggcgcc    1020
agctatgtgt cttggtttgc ctactggggc cagggcaccc tcgtgaccgt gtcaagcgct    1080
agtaccaagg gcccagcgt gttcccctg gcacccagca gcaagagcac atctggcgga    1140
acagccgctc tgggctgtct ggtgaaagac tacttccccg agcccgtgac cgtgtcttgg    1200
aactctggcg ccctgaccag cggcgtgcac acctttccag ccgtgctgca gagcagcggc    1260
ctgtactccc tgtcctccgt ggtcaccgtg ccctctagct ccctgggaac acagacatat    1320
atctgtaatg tcaatcacaa gccttccaac accaaagtcg ataagaaagt cgagcccaag    1380
agctgcgaca aaactcacac atgcccaccg tgcccagcac ctgaagctgc aggggaccg    1440
tcagtcttcc tcttcccccc aaaacccaag gacaccctca tgatctcccg gacccctgag    1500
gtcacatgcg tggtggtgga cgtgagccac gaagaccctg aggtcaagtt caactggtac    1560
gtggacggcg tggaggtgca taatgccaag acaaagccgc gggaggagca gtacaacagc    1620
acgtaccgtg tggtcagcgt cctcaccgtc ctgcaccagg actggctgaa tggcaaggag    1680
tacaagtgca aggtctccaa caaagccctc ggcgccccca tcgagaaaac catctccaaa    1740
gccaaagggc agccccgaga accacaggtg tacaccctgc ccccatgccg ggatgagctg    1800
accaagaacc aggtcagcct gtggtgcctg gtcaaaggct tctatcccag cgacatcgcc    1860
gtggagtggg agagcaatgg gcagccggag aacaactaca agaccacgcc tcccgtgctg    1920
gactccgacg gctccttctt cctctacagc aagctcaccg tggacaagag caggtggcag    1980
caggggaacg tcttctcatg ctccgtgatg catgaggctc tgcacaacca ctacacgcag    2040
aagagcctct ccctgtctcc gggtaaa                                        2067
```

<210> SEQ ID NO 201
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 201

```
gaggtgcaat tggttgaatc tggtggtggt ctggtaaaac cgggcggttc cctgcgtctg    60
agctgcgcgg cttccggatt caccttctcc aacgcgtgga tgagctgggt tcgccaggcc   120
ccgggcaaag gcctcgagtg ggttggtcgt atcaagtcta aaactgacgg tggcaccacg   180
gattacgcgg ctccagttaa aggtcgtttt accatttccc gcgacgatag caaaaacact   240
ctgtatctgc agatgaactc tctgaaaact gaagacaccg cagtctacta ctgtactacc   300
ccgtgggaat ggtcttggta cgattattgg ggccagggca cgctggttac ggtgtcttcc   360
gctagcacaa agggccctag cgtgttccct ctggccccca gcagcaagag cacaagcggc   420
ggaacagccg ccctgggctg cctcgtgaag gactacttcc ccgagcccgt gacagtgtct   480
tggaacagcg gagccctgac aagcggcgtg cacacttttc ctgccgtgct gcagagcagc   540
ggcctgtact ccctgagcag cgtggtcacc gtgcctagca gcagcctggg cacccagacc   600
tacatctgca acgtgaacca caagcccagc aacaccaaag tggacaagaa ggtggagccc   660
aagagctgtg atggcggagg agggtccgga ggcggaggat ccgaggtgca gctgctggaa   720
tctggcggcg gactggtgca gcctggcgga tctctgagac tgagctgtgc cgccagcggc   780
ttcaccttca gcacctacgc catgaactgg gtgcgccagg cccctggcaa aggcctggaa   840
tgggtgtccc ggatcagaag caagtacaac aactacgcca cctactacgc cgacagcgtg   900
aagggccggt tcaccatcag ccgggacgac agcaagaaca ccctgtacct gcagatgaac   960
agcctgcggg ccgaggacac cgccgtgtac tattgtgtgc ggcacggcaa cttcggcaac  1020
gcctatgtgt cttggtttgc ctactggggc cagggcaccc tcgtgaccgt gtcaagcgct  1080
agtaccaagg gcccaagcgt gttccccctg cacccagca gcaagagcac atctggcgga  1140
acagccgctc tgggctgtct ggtgaaagac tacttccccg agcccgtgac cgtgtcttgg  1200
aactctggcg ccctgaccag cggcgtgcac acctttccag ccgtgctgca gagcagcggc  1260
ctgtactccc tgtcctccgt ggtcaccgtg ccctctagct ccctgggaac acagacatat  1320
atctgtaatg tcaatcacaa gccttccaac accaaagtcg ataagaaagt cgagcccaag  1380
agctgcgaca aaactcacac atgcccaccg tgcccagcac ctgaagctgc aggggaccg   1440 tcagtcttcc tcttcccccc aaaacccaag gacaccctca tgatctcccg gacccctgag  1500
gtcacatgcg tggtggtgga cgtgagccac gaagaccctg aggtcaagtt caactggtac  1560
gtggacggcg tggaggtgca taatgccaag acaaagccgc gggaggagca gtacaacagc  1620
acgtaccgtg tggtcagcgt cctcaccgtc ctgcaccagg actggctgaa tggcaaggag  1680
tacaagtgca aggtctccaa caaagccctc ggcgccccca tcgagaaaac catctccaaa  1740
gccaaagggc agccccgaga accacaggtg tacaccctgc cccatgccg ggatgagctg   1800 accaagaacc aggtcagcct gtggtgcctg gtcaaaggct tctatcccag cgacatcgcc  1860
gtggagtggg agagcaatgg gcagccggag aacaactaca agaccacgcc tcccgtgctg  1920
gactccgacg gctccttctt cctctacagc aagctcaccg tggacaagag caggtggcag  1980
caggggaacg tcttctcatg ctccgtgatg catgaggctc tgcacaacca ctacacgcag  2040
aagagcctct ccctgtctcc gggtaaa                                      2067

<210> SEQ ID NO 202
<211> LENGTH: 1323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 202

| | | | | | |
|---|---|---|---|---|---|
| caggccgtcg | tgacccagga | acccagcctg | acagtgtctc | ctggcggcac | cgtgaccctg | 60 |
| acatgtggca | gttctacagg | cgccgtgacc | accagcaact | acgccaactg | ggtgcaggaa | 120 |
| aagcccggcc | aggccttcag | aggactgatc | ggcggcacca | caagagagc | ccctggcacc | 180 |
| cctgccagat | tcagcggatc | tctgctggga | ggaaaggccg | ccctgacact | gtctggcgcc | 240 |
| cagccagaag | atgaggccga | gtactactgc | gccctgtggt | acagcaacct | gtgggtgttc | 300 |
| ggcggaggca | ccaagctgac | agtgctgagc | agcgctagca | ccaagggccc | atcggtcttc | 360 |
| cccctggcac | cctcctccaa | gagcacctct | gggggcacag | cggccctggg | ctgcctggtc | 420 |
| aaggactact | tccccgaacc | ggtgacggtg | tcgtggaact | caggcgccct | gaccagcggc | 480 |
| gtgcacacct | tcccggctgt | cctacagtcc | tcaggactct | actccctcag | cagcgtggtg | 540 |
| accgtgccct | ccagcagctt | gggcacccag | acctacatct | gcaacgtgaa | tcacaagccc | 600 |
| agcaacacca | aggtggacaa | gaaagttgag | cccaaatctt | gtgacaaaac | tcacacatgc | 660 |
| ccaccgtgcc | cagcacctga | agctgcaggg | ggaccgtcag | tcttcctctt | ccccccaaaa | 720 |
| cccaaggaca | ccctcatgat | ctcccggacc | cctgaggtca | catgcgtggt | ggtggacgtg | 780 |
| agccacgaag | accctgaggt | caagttcaac | tggtacgtgg | acggcgtgga | ggtgcataat | 840 |
| gccaagacaa | agccgcggga | ggagcagtac | aacagcacgt | accgtgtggt | cagcgtcctc | 900 |
| accgtcctgc | accaggactg | gctgaatggc | aaggagtaca | agtgcaaggt | ctccaacaaa | 960 |
| gccctcggcg | cccccatcga | gaaaaccatc | tccaaagcca | aagggcagcc | ccgagaacca | 1020 |
| caggtgtaca | ccctgccccc | atcccgggat | gagctgacca | agaaccaggt | cagcctgacc | 1080 |
| tgcctggtca | aaggcttcta | tcccagcgac | atcgccgtgg | agtgggagag | caatgggcag | 1140 |
| ccggagaaca | actacaagac | cacgcctccc | gtgctggact | ccgacggctc | cttcttcctc | 1200 |
| tacagcaagc | tcaccgtgga | caagagcagg | tggcagcagg | ggaacgtctt | ctcatgctcc | 1260 |
| gtgatgcatg | aggctctgca | caaccactac | acgcagaaga | gcctctccct | gtctccgggt | 1320 |
| aaa | | | | | | 1323 |

<210> SEQ ID NO 203
<211> LENGTH: 681
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 203

| | | | | | |
|---|---|---|---|---|---|
| gaggtgcaat | tggttgaatc | tggtggtggt | ctggtaaaac | cgggcggttc | cctgcgtctg | 60 |
| agctgcgcgg | cttccggatt | caccttctcc | aacgcgtgga | tgagctgggt | tcgccaggcc | 120 |
| ccgggcaaag | gcctcgagtg | ggttggtcgt | atcaagtcta | aaactgacgg | tggcaccacg | 180 |
| gattacgcgg | ctccagttaa | aggtcgtttt | accatttccc | gcgacgatag | caaaaacact | 240 |
| ctgtatctgc | agatgaactc | tctgaaaact | gaagacaccg | cagtctacta | ctgtactacc | 300 |
| ccgtgggaat | ggtcttggta | cgattattgg | ggccagggca | cgctggttac | ggtgtcttcc | 360 |
| gctagcgtgg | ccgctccctc | cgtgttcatc | ttcccacctt | ccgacgagca | gctgaagtcc | 420 |
| ggcaccgctt | ctgtcgtgtg | cctgctgaac | aacttctacc | ccgcgaggc | caaggtgcag | 480 |
| tggaaggtgg | acaacgccct | gcagtccggc | aacagccagg | aatccgtgac | cgagcaggac | 540 |

```
tccaaggaca gcacctactc cctgtcctcc accctgaccc tgtccaaggc cgactacgag      600
aagcacaagg tgtacgcctg cgaagtgacc caccagggcc tgtctagccc cgtgaccaag      660
tctttcaacc ggggcgagtg c                                                681
```

<210> SEQ ID NO 204
<211> LENGTH: 693
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 204

```
gaagtgcagc tgctggaatc cggcggagga ctggtgcagc ctggcggatc tctgagactg       60
tcttgtgccg cctccggctt caccttctcc acctacgcca tgaactgggt gcgacaggct      120
cctggcaagg gcctggaatg ggtgtcccgg atcagatcca agtacaacaa ctacgccacc      180
tactacgccg actccgtgaa gggccggttc accatctctc gggacgactc caagaacacc      240
ctgtacctgc agatgaactc cctgcgggcc gaggacaccg ccgtgtacta ttgtgtgcgg      300
cacggcaact tcggcaactc ctatgtgtct tggtttgcct actggggcca gggcaccctc      360
gtgaccgtgt catctgctag ccccaaggct gcccccagcg tgaccctgtt cccccccagc      420
agcgaggaac tgcaggccaa caaggccacc ctggtctgcc tgatcagcga cttctaccca      480
ggcgccgtga ccgtggcctg gaaggccgac agcagccccg tgaaggccgg cgtggagacc      540 accacccccca gcaagcagag caacaacaag tacgccgcca gcagctacct gagcctgacc      600
cccgagcagt ggaagagcca caggtcctac agctgccagg tgacccacga gggcagcacc      660
gtggagaaaa ccgtggcccc caccgagtgc agc                                   693
```

<210> SEQ ID NO 205
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 205

```
cagaccgtcg tgacccagga acccagcctg acagtgtctc ctggcggcac cgtgaccctg       60
acatgtggca gttctacagg cgccgtgacc accagcaact acgccaactg ggtgcagcag      120
aagccaggcc aggctcccag aggactgatc ggcggcacca cgccagagc ccctggcacc       180 cctgccagat tcagcggatc tctgctggga ggaaaggccg ccctgacact gtctggcgtg      240
cagcctgaag atgaggccga gtactactgc gccctgtggt acagcaacct gtgggtgttc      300
ggcggaggca ccaagctgac agtccta                                          327
```

<210> SEQ ID NO 206
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 206

```
cagaccgtcg tgacccagga acccagcctg acagtgtctc ctggcggcac cgtgaccctg       60
```
acatgtggca gttctacagg cgccgtgacc accagcaact acgccaactg ggtgcagcag    120
aagccaggcc aggctcccag aggactgatc ggcggcacca acaagagagc ccctggcacc    180
cctgccagat tcagcggatc tctgctggga ggaaaggccg ccctgacact gtctggcgtg    240
cagcctgaag atgaggccga gtactactgc gccctgtggt acgccaacct gtgggtgttc    300
ggcggaggca ccaagctgac agtccta                                        327

<210> SEQ ID NO 207
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 207
gaggtgcaat tggtggaaag cggaggcggc ctcgtgaagc ctggcggatc tctgagactg     60
agctgtgccg ccagcggctt caccttcagc aacgcctgga tgcactgggt gcgccaggcc    120
cctggaaaag gactcgagtg ggtgggacgg atcaagagca agaccgatgg cggcaccacc    180
gactatgccg cccctgtgaa gggccggttc accatcagca gggacgacag caagaacacc    240
ctgtacctgc agatgaacag cctgaaaacc gaggacaccg ccgtgtacta ctgcaccacc    300
ccctgggagt ggtcttggta cgactattgg ggccagggca ccctcgtgac cgtgtcctct    360
gctagc                                                               366

<210> SEQ ID NO 208
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 208
gaggtgcaat tggtggaaag cggaggcggc ctcgtgaagc ctggcggatc tctgagactg     60
agctgtgccg ccagcggctt caccttcagc aacgcctgga tgagctgggt gcgccaggcc    120
cctggaaaag gactcgagtg ggtgtcccgg atcaagagca agaccgatgg cggcaccacc    180
gactatgccg cccctgtgaa gggccggttc accatcagca gggacgacag caagaacacc    240
ctgtacctgc agatgaacag cctgaaaacc gaggacaccg ccgtgtacta ctgcaccacc    300
ccctgggagt ggtcttggta cgactattgg ggccagggca ccctcgtgac cgtgtcctct    360
gctagc                                                               366

<210> SEQ ID NO 209
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 209
gaggtgcaat tggtggaaag cggaggcggc ctcgtgaagc ctggcggatc tctgagactg     60
agctgtgccg ccagcggctt caccttcagc aacgcctgga tgagctgggt gcgccaggcc    120

```
cctggaaaag gactcgagtg ggtgggatct atcaagagca agaccgacgg cggcaccacc      180
gactatgccg cccctgtgaa gggccggttc accatcagca gggacgacag caagaacacc      240
ctgtacctgc agatgaacag cctgaaaacc gaggacaccg ccgtgtacta ctgcaccacc      300
ccctgggagt ggtcttggta cgactattgg ggccagggca ccctcgtgac cgtgtcctct      360
gctagc                                                                 366
```

<210> SEQ ID NO 210
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 210

```
gaggtgcaat tggtggaaag cggaggcggc ctcgtgaagc ctggcggatc tctgagactg       60
agctgtgccg ccagcggctt caccttcagc aacgcctgga tgagctgggt cgcccaggcc      120
cctggaaaag gactcgagtg ggtgggacgg atcaagagca agaccgatgg cggcaccacc      180
gactatgccg cccctgtgaa gggccggttc accatcagca gggacgacag caagaacacc      240
ctgtacctgc agatgaacag cctgaaaacc gaggacaccg ccgtgtacta ctgcaccacc      300
ccctacgagt ggtcttggta cgactactgg ggccagggca ccctcgtgac cgtgtcatct      360
gctagc                                                                 366
```

<210> SEQ ID NO 211
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 211

```
gaggtgcaat tggtggaaag cggaggcggc ctcgtgaagc ctggcggatc tctgagactg       60
agctgtgccg ccagcggctt caccttcagc aacgcctgga tgagctgggt cgcccaggcc      120
cctggaaaag gactcgagtg ggtgggacgg atcaagagca agaccgatgg cggcaccacc      180
gactatgccg cccctgtgaa gggccggttc accatcagca gggacgacag caagaacacc      240
ctgtacctgc agatgaacag cctgaaaacc gaggacaccg ccgtgtacta ctgcaccacc      300
ccctgggagt actcttggta cgactactgg ggccagggca ccctcgtgac cgtgtcatct      360
gctagc                                                                 366
```

<210> SEQ ID NO 212
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 212

```
caggtgcaat tggttcaatc tggtgctgaa gtaaaaaaac cgggcgcttc cgttaaagtg       60
agctgcaaag catccggata caccttcact tcctattaca tgcactgggt tcgtcaagcc      120
ccgggccagg gtctggaatg gatgggcatc attaacccaa gcggtggctc tacctcctac      180
```

```
gcgcagaaat tccagggtcg cgtcacgatg acccgtgaca ctagcacctc taccgtttat    240
atggagctgt ccagcctgcg ttctgaagat actgcagtgt actactgtgc acgcaactac    300
actatcgttg tttctccgtt cgactattgg ggtcaaggca ccctcgtaac ggtttcttct    360
gctagc                                                                366
```

<210> SEQ ID NO 213
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 213

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcaactac    300
ttcatcggtt ctgttgctat ggactattgg ggtcaaggca ccctcgtaac ggtttcttct    360
gctagc                                                                366
```

<210> SEQ ID NO 214
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 214

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcggtctg    300
acttactcta tggactattg gggtcaaggc accctcgtaa cggtttcttc tgctagc       357
```

<210> SEQ ID NO 215
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 215

```
gatattgtta tgactcaatc tccactgtct ctgccggtga ctccaggcga accggcgagc     60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
```

```
agccgtgttg aagcagaaga cgtgggcgtt tattactgta tgcaggcact gcagattcca    300 aacactttg gtcaaggcac caaggtcgaa attaaacgta cg                        342
```

<210> SEQ ID NO 216
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 216

```
gaggtgcaat tgttggagtc tgggggaggc ttggtacagc ctgggggtc cctgagactc     60 tcctgtgcag cctccggatt cacctttagc agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaatacgct   300
tacgctctgg actactgggg ccaaggaacc ctggtcaccg tctcgagtgc tagc          354
```

<210> SEQ ID NO 217
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 217

```
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagcatggca gcagcagcac gttcggccag   300
gggaccaaag tggaaatcaa acgtacg                                        327
```

<210> SEQ ID NO 218
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 218

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg accgtgaca ctagcacctc taccgtttat    240
atggagctgt ccagcctgcg ttctgaagat actgcagtgt actactgtgc acgcggtgac   300
ttctctgctg gtcgtctgat ggactattgg ggtcaaggca ccctcgtaac ggtttcttct   360
gctagc                                                               366
```

<210> SEQ ID NO 219
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 219
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcact gcagacccca   300
ccaattacct ttggtcaagg caccaaggtc gaaattaaac gtacg                   345

<210> SEQ ID NO 220
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 220
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg accgtgaca ctagcacctc taccgtttat   240
atggagctgt ccagcctgcg ttctgaagat actgcagtgt actactgtgc acgcggtgac   300
tacaacgctt tcgactattg gggtcacggc accctcgtaa cggtttcttc tgctagc     357

<210> SEQ ID NO 221
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 221
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcatg gcatagccca   300
acttttggtc aaggcaccaa ggtcgaaatt aaacgtacg                          339

<210> SEQ ID NO 222
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 222

| | | | | | |
|---|---|---|---|---|---|
| caggtgcaat | tggttcaatc | tggtgctgaa | gtaaaaaaac | cgggcgcttc | cgttaaagtg | 60 |
| agctgcaaag | catccggata | caccttcact | tcctattaca | tgcactgggt | tcgtcaagcc | 120 |
| ccgggccagg | gtctggaatg | gatgggcatc | attaacccaa | gcggtggctc | tacctcctac | 180 |
| gcgcagaaat | tccagggtcg | cgtcacgatg | acccgtgaca | ctagcacctc | taccgtttat | 240 |
| atggagctgt | ccagcctgcg | ttctgaagat | actgcagtgt | actactgtgc | acgcggtgct | 300 |
| acttacacta | tggactattg | gggtcaaggc | accctcgtaa | cggtttcttc | tgctagc | 357 |

<210> SEQ ID NO 223
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 223

| | | | | | |
|---|---|---|---|---|---|
| gatattgtta | tgactcaatc | tccactgtct | ctgccggtga | ctccaggcga | accggcgagc | 60 |
| atttcttgcc | gttccagcca | gtctctgctg | cactccaacg | gctacaacta | tctcgattgg | 120 |
| tacctgcaaa | aaccgggtca | gagccctcag | ctgctgatct | acctgggctc | taaccgcgct | 180 |
| tccggtgtac | cggaccgttt | cagcggctct | ggatccggca | ccgatttcac | gttgaaaatc | 240 |
| agccgtgttg | aagcagaaga | cgtgggcgtt | tattactgta | tgcaggcact | gcagacccca | 300 |
| attacttttg | gtcaaggcac | caaggtcgaa | attaaacgta | cg | | 342 |

<210> SEQ ID NO 224
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224

| | | | | | |
|---|---|---|---|---|---|
| caggtgcagc | tgcagcagtc | tggcgccgag | ctcgtgaaac | ctggcgcctc | cgtgaagatc | 60 |
| agctgcaagg | ccagcggcta | cagcttcacc | ggctacttca | tgaactgggt | caagcagagc | 120 |
| cacggcaaga | gcctggaatg | gatcggcaga | atccaccccc | tacgacggcga | caccttctac | 180 |
| aaccagaact | tcaaggacaa | ggccaccctg | accgtggaca | agagcagcaa | caccgcccac | 240 |
| atggaactgc | tgagcctgac | cagcgaggac | ttcgccgtgt | actactgcac | cagatacgac | 300 |
| ggcagccggg | ccatggatta | ttggggccag | ggcaccaccg | tgacagtgtc | cagcgctagc | 360 |
| accaagggcc | cctccgtgtt | ccccctggcc | ccagcagca | agagcaccag | cggcggcaca | 420 |
| gccgctctgg | gctgcctggt | caaggactac | ttccccgagc | ccgtgaccgt | gtcctggaac | 480 |
| agcggagccc | tgacctccgg | cgtgcacacc | ttcccgccg | tgctgcagag | ttctggcctg | 540 |
| tatagcctga | gcagcgtggt | caccgtgcct | tctagcagcc | tgggcaccca | gacctacatc | 600 |
| tgcaacgtga | accacaagcc | cagcaacacc | aaggtggaca | agaaggtgga | gcccaagagc | 660 |
| tgcgacaaaa | ctcacacatg | cccaccgtgc | ccagcacctg | aagctgcagg | ggaccgtca | 720 |
| gtcttcctct | tccccccaaa | acccaaggac | accctcatga | tctcccggac | ccctgaggtc | 780 |
| acatgcgtgg | tggtggacgt | gagccacgaa | gaccctgagg | tcaagttcaa | ctggtacgtg | 840 |

```
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctcggc gcccccatcg agaaaaccat ctccaaagcc   1020
aaagggcagc cccgagaacc acaggtgtgc accctgcccc catcccggga tgagctgacc   1080
aagaaccagg tcagcctctc gtgcgcagtc aaaggcttct atcccagcga catcgccgtg   1140
gagtgggaga gcaatgggca gccggagaac aactacaaga ccacgcctcc cgtgctggac   1200
tccgacggct ccttcttcct cgtgagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 225
<211> LENGTH: 2073
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 225

```
caggtgcagc tgcagcagtc tggcgccgag ctcgtgaaac ctggcgcctc cgtgaagatc     60
agctgcaagg ccagcggcta cagcttcacc ggctacttca tgaactgggt caagcagagc    120
cacggcaaga gcctggaatg gatcggcaga atccaccccct acgacggcga cccttctac    180 aaccagaact tcaaggacaa ggccaccctg accgtggaca gagcagcaa caccgcccac    240 atggaactgc tgagcctgac cagcgaggac ttcgccgtgt actactgcac cagatacgac    300
ggcagccggg ccatggatta ttggggccag ggcaccaccg tgacagtgtc cagcgctagc    360
acaaagggcc ccagcgtgtt ccctctggcc cctagcagca gagcacatc tggcggaaca    420 gccgccctgg gctgcctcgt gaaggactac tttcccgagc ctgtgaccgt gtcctggaac    480
tctggcgccc tgacaagcgg cgtgcacacc tttccagccg tgctgcagag cagcggcctg    540
tactctctga gcagcgtggt caccgtgcct agcagcagcc tgggcaccca gacctacatc    600
tgcaacgtga accacaagcc cagcaacacc aaagtggaca gaaggtgga gcccaagagc    660 tgtgatggcg aggagggtc cggaggcgga ggatccgaag tgcagctggt ggaaagcggc    720
ggaggcctgg tgcagcctaa gggctctctg aagctgagct gtgccgccag cggcttcacc    780
ttcaacacct acgccatgaa ctgggtgcgc caggcccctg gcaaaggcct ggaatgggtg    840
gcccggatca gaagcaagta caacaattac gccacctact acgccgacag cgtgaaggac    900
cggttcacca tcagccggga cgacagccag agcatcctgt acctgcagat gaacaacctg    960
aaaaccgagg acaccgccat gtactactgc gtgcggcacg gcaacttcgg caacagctat   1020
gtgtcttggt ttgcctactg gggccagggc accctcgtga cagtgtctgc tgctagcgtg   1080
gccgctccct ccgtgtttat ctttcccccca tccgatgaac agctgaaaag cggcaccgcc   1140
tccgtcgtgt gtctgctgaa caattttac cctagggaag ctaaagtgca gtggaaagtg   1200
gataacgcac tgcagtccgg caactcccag gaatctgtga cagaacagga ctccaaggac   1260
agcacctact cctgtcctc caccctgaca ctgtctaagg ctgattatga gaaacacaaa   1320
gtctacgcct gcgaagtcac ccatcagggc ctgagctcgc cgtcacaaa gagcttcaac   1380 aggggagagt gtgacaagac ccacacctgt cccccttgtc ctgcccctga agctgctggc   1440
```

```
ggcccttctg tgttcctgtt ccccccaaag cccaaggaca ccctgatgat cagccggacc   1500
cccgaagtga cctgcgtggt ggtggatgtg tcccacgagg accctgaagt gaagttcaat   1560
tggtacgtgg acggcgtgga agtgcacaac gccaagacaa agccgcggga ggagcagtac   1620
aacagcacgt accgtgtggt cagcgtcctc accgtcctgc accaggactg gctgaatggc   1680
aaggagtaca agtgcaaggt ctccaacaaa gccctcggcg cccccatcga gaaaaccatc   1740
tccaaagcca agggcagccc cgagaaccac aggtgtaca ccctgccccc atgccgggat    1800
gagctgacca agaaccaggt cagcctgtgg tgcctggtca aaggcttcta tcccagcgac   1860
atcgccgtgg agtgggagag caatgggcag ccggagaaca actacaagac cacgcctccc   1920
gtgctggact ccgacggctc cttcttcctc tacagcaagc tcaccgtgga caagagcagg   1980
tggcagcagg ggaacgtctt ctcatgctcc gtgatgcatg aggctctgca caaccactac   2040
acgcagaaga gcctctccct gtctccgggt aaa                                2073

<210> SEQ ID NO 226
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 226
gacatcgagc tgacccagag ccctgcctct ctggccgtgt ctctgggaca gagagccatc     60
atcagctgca aggccagcca gagcgtgtcc tttgccggca cctctctgat gcactggtat    120
caccagaagc ccggccagca gcccaagctg ctgatctaca gagccagcaa cctggaagcc    180
ggcgtgccca agatttttc ggcagcggc agcaagaccg acttcaccct gaacatccac      240
cccgtggaag aagaggacgc cgccacctac tactgccagc agagcagaga gtacccctac    300
accttcggcg gaggcaccaa gctggaaatc aagcgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc ctccaatcg     480 ggtaactccc aggagagtgt cacagagcag gacagcaagg acagcaccta cagcctcagc   540
agcaccctga cgctgagcaa agcagactac gagaaacaca agtctacgc ctgcgaagtc    600 acccatcagg gcctgagctc gcccgtcaca aagagcttca caggggaga gtgt           654

<210> SEQ ID NO 227
<211> LENGTH: 209
<212> TYPE: PRT
<213> ORGANISM: Homo sapiens

<400> SEQUENCE: 227

Arg Ile Ala Trp Ala Arg Thr Glu Leu Leu Asn Val Cys Met Asn Ala
1               5                   10                  15

Lys His His Lys Glu Lys Pro Gly Pro Glu Asp Lys Leu His Glu Gln
            20                  25                  30

Cys Arg Pro Trp Arg Lys Asn Ala Cys Cys Ser Thr Asn Thr Ser Gln
        35                  40                  45

Glu Ala His Lys Asp Val Ser Tyr Leu Tyr Arg Phe Asn Trp Asn His
    50                  55                  60

Cys Gly Glu Met Ala Pro Ala Cys Lys Arg His Phe Ile Gln Asp Thr
65                  70                  75                  80
```

```
Cys Leu Tyr Glu Cys Ser Pro Asn Leu Gly Pro Trp Ile Gln Gln Val
                85                  90                  95

Asp Gln Ser Trp Arg Lys Glu Arg Val Leu Asn Val Pro Leu Cys Lys
            100                 105                 110

Glu Asp Cys Glu Gln Trp Trp Glu Asp Cys Arg Thr Ser Tyr Thr Cys
            115                 120                 125

Lys Ser Asn Trp His Lys Gly Trp Asn Trp Thr Ser Gly Phe Asn Lys
            130                 135                 140

Cys Ala Val Gly Ala Ala Cys Gln Pro Phe His Phe Tyr Phe Pro Thr
145                 150                 155                 160

Pro Thr Val Leu Cys Asn Glu Ile Trp Thr His Ser Tyr Lys Val Ser
                165                 170                 175

Asn Tyr Ser Arg Gly Ser Gly Arg Cys Ile Gln Met Trp Phe Asp Pro
            180                 185                 190

Ala Gln Gly Asn Pro Asn Glu Glu Val Ala Arg Phe Tyr Ala Ala Ala
            195                 200                 205

Met

<210> SEQ ID NO 228
<211> LENGTH: 214
<212> TYPE: PRT
<213> ORGANISM: Homo sapiens

<400> SEQUENCE: 228

Thr Met Cys Ser Ala Gln Asp Arg Thr Asp Leu Leu Asn Val Cys Met
1               5                   10                  15

Asp Ala Lys His His Lys Thr Lys Pro Gly Pro Glu Asp Lys Leu His
            20                  25                  30

Asp Gln Cys Ser Pro Trp Lys Lys Asn Ala Cys Cys Thr Ala Ser Thr
            35                  40                  45

Ser Gln Glu Leu His Lys Asp Thr Ser Arg Leu Tyr Asn Phe Asn Trp
    50                  55                  60

Asp His Cys Gly Lys Met Glu Pro Ala Cys Lys Arg His Phe Ile Gln
65                  70                  75                  80

Asp Thr Cys Leu Tyr Glu Cys Ser Pro Asn Leu Gly Pro Trp Ile Gln
                85                  90                  95

Gln Val Asn Gln Ser Trp Arg Lys Glu Arg Phe Leu Asp Val Pro Leu
            100                 105                 110

Cys Lys Glu Asp Cys Gln Arg Trp Trp Glu Asp Cys His Thr Ser His
            115                 120                 125

Thr Cys Lys Ser Asn Trp His Arg Gly Trp Asp Trp Thr Ser Gly Val
130                 135                 140

Asn Lys Cys Pro Ala Gly Ala Leu Cys Arg Thr Phe Glu Ser Tyr Phe
145                 150                 155                 160

Pro Thr Pro Ala Ala Leu Cys Glu Gly Leu Trp Ser His Ser Tyr Lys
                165                 170                 175

Val Ser Asn Tyr Ser Arg Gly Ser Gly Arg Cys Ile Gln Met Trp Phe
            180                 185                 190

Asp Ser Ala Gln Gly Asn Pro Asn Glu Glu Val Ala Arg Phe Tyr Ala
            195                 200                 205

Ala Ala Met His Val Asn
210

<210> SEQ ID NO 229
<211> LENGTH: 220
```

```
<212> TYPE: PRT
<213> ORGANISM: Homo sapiens

<400> SEQUENCE: 229

Ser Ala Arg Ala Arg Thr Asp Leu Leu Asn Val Cys Met Asn Ala Lys
1               5                   10                  15

His His Lys Thr Gln Pro Ser Pro Glu Asp Leu Tyr Gly Gln Cys
            20                  25                  30

Ser Pro Trp Lys Lys Asn Ala Cys Cys Thr Ala Ser Thr Ser Gln Glu
            35                  40                  45

Leu His Lys Asp Thr Ser Arg Leu Tyr Asn Phe Asn Trp Asp His Cys
    50                  55                  60

Gly Lys Met Glu Pro Thr Cys Lys Arg His Phe Ile Gln Asp Ser Cys
65                  70                  75                  80

Leu Tyr Glu Cys Ser Pro Asn Leu Gly Pro Trp Ile Arg Gln Val Asn
                85                  90                  95

Gln Ser Trp Arg Lys Glu Arg Ile Leu Asn Val Pro Leu Cys Lys Glu
            100                 105                 110

Asp Cys Glu Arg Trp Trp Glu Asp Cys Arg Thr Ser Tyr Thr Cys Lys
        115                 120                 125

Ser Asn Trp His Lys Gly Trp Asn Trp Thr Ser Gly Ile Asn Glu Cys
    130                 135                 140

Pro Ala Gly Ala Leu Cys Ser Thr Phe Glu Ser Tyr Phe Pro Thr Pro
145                 150                 155                 160

Ala Ala Leu Cys Glu Gly Leu Trp Ser His Ser Phe Lys Val Ser Asn
                165                 170                 175

Tyr Ser Arg Gly Ser Gly Arg Cys Ile Gln Met Trp Phe Asp Ser Ala
            180                 185                 190

Gln Gly Asn Pro Asn Glu Glu Val Ala Lys Phe Tyr Ala Ala Ala Met
        195                 200                 205

Asn Ala Gly Ala Pro Ser Arg Gly Ile Ile Asp Ser
    210                 215                 220

<210> SEQ ID NO 230
<211> LENGTH: 208
<212> TYPE: PRT
<213> ORGANISM: Mus musculus

<400> SEQUENCE: 230

Thr Arg Ala Arg Thr Glu Leu Leu Asn Val Cys Met Asp Ala Lys His
1               5                   10                  15

His Lys Glu Lys Pro Gly Pro Glu Asp Asn Leu His Asp Gln Cys Ser
            20                  25                  30

Pro Trp Lys Thr Asn Ser Cys Cys Ser Thr Asn Thr Ser Gln Glu Ala
            35                  40                  45

His Lys Asp Ile Ser Tyr Leu Tyr Arg Phe Asn Trp Asn His Cys Gly
    50                  55                  60

Thr Met Thr Ser Glu Cys Lys Arg His Phe Ile Gln Asp Thr Cys Leu
65                  70                  75                  80

Tyr Glu Cys Ser Pro Asn Leu Gly Pro Trp Ile Gln Gln Val Asp Gln
                85                  90                  95

Ser Trp Arg Lys Glu Arg Ile Leu Asp Val Pro Leu Cys Lys Glu Asp
            100                 105                 110

Cys Gln Gln Trp Trp Glu Asp Cys Gln Ser Ser Phe Thr Cys Lys Ser
        115                 120                 125
```

```
Asn Trp His Lys Gly Trp Asn Trp Ser Ser Gly His Asn Glu Cys Pro
    130                 135                 140

Val Gly Ala Ser Cys His Pro Phe Thr Phe Tyr Phe Pro Thr Ser Ala
145                 150                 155                 160

Ala Leu Cys Glu Glu Ile Trp Ser His Ser Tyr Lys Leu Ser Asn Tyr
                165                 170                 175

Ser Arg Gly Ser Gly Arg Cys Ile Gln Met Trp Phe Asp Pro Ala Gln
            180                 185                 190

Gly Asn Pro Asn Glu Glu Val Ala Arg Phe Tyr Ala Glu Ala Met Ser
        195                 200                 205
```

<210> SEQ ID NO 231
<211> LENGTH: 213
<212> TYPE: PRT
<213> ORGANISM: Macaca fascicularis

<400> SEQUENCE: 231

```
Glu Ala Gln Thr Arg Thr Ala Arg Ala Arg Thr Glu Leu Leu Asn Val
1               5                   10                  15

Cys Met Asn Ala Lys His His Lys Glu Lys Pro Gly Pro Glu Asp Lys
            20                  25                  30

Leu His Glu Gln Cys Arg Pro Trp Lys Lys Asn Ala Cys Cys Ser Thr
        35                  40                  45

Asn Thr Ser Gln Glu Ala His Lys Asp Val Ser Tyr Leu Tyr Arg Phe
50                  55                  60

Asn Trp Asn His Cys Gly Glu Met Ala Pro Ala Cys Lys Arg His Phe
65                  70                  75                  80

Ile Gln Asp Thr Cys Leu Tyr Glu Cys Ser Pro Asn Leu Gly Pro Trp
                85                  90                  95

Ile Gln Gln Val Asp Gln Ser Trp Arg Lys Glu Arg Val Leu Asn Val
            100                 105                 110

Pro Leu Cys Lys Glu Asp Cys Glu Arg Trp Trp Glu Asp Cys Arg Thr
        115                 120                 125

Ser Tyr Cys Lys Ser Asn Trp His Lys Gly Trp Asn Trp Thr Ser Gly
    130                 135                 140

Phe Asn Lys Cys Pro Val Gly Ala Ala Cys Gln Pro Phe His Phe Tyr
145                 150                 155                 160

Phe Pro Thr Pro Thr Val Leu Cys Asn Glu Ile Trp Thr Tyr Ser Tyr
                165                 170                 175

Lys Val Ser Asn Tyr Ser Arg Gly Ser Gly Arg Cys Ile Gln Met Trp
            180                 185                 190

Phe Asp Pro Ala Gln Gly Asn Pro Asn Glu Glu Val Ala Arg Phe Tyr
        195                 200                 205

Ala Ala Ala Met Ser
    210
```

<210> SEQ ID NO 232
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 232

```
Pro Trp Glu Tyr Ser Trp Tyr Asp Tyr
1               5
```

```
<210> SEQ ID NO 233
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Asn Tyr Thr Ile Val Val Ser Pro Phe Asp Tyr
1               5                   10

<210> SEQ ID NO 234
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Asn Tyr Phe Ile Gly Ser Val Ala Met Asp Tyr
1               5                   10

<210> SEQ ID NO 235
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Gly Leu Thr Tyr Ser Met Asp Tyr
1               5

<210> SEQ ID NO 236
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Met Gln Ala Leu Gln Ile Pro Asn Thr
1               5

<210> SEQ ID NO 237
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Tyr Ala Tyr Ala Leu Asp Tyr
1               5

<210> SEQ ID NO 238
<211> LENGTH: 8
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Gln Gln His Gly Ser Ser Ser Thr
1               5

<210> SEQ ID NO 239
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Gly Asp Phe Ser Ala Gly Arg Leu Met Asp Tyr
1               5                   10

<210> SEQ ID NO 240
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Met Gln Ala Leu Gln Thr Pro Pro Ile Thr
1               5                   10

<210> SEQ ID NO 241
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Gly Asp Tyr Asn Ala Phe Asp Tyr
1               5

<210> SEQ ID NO 242
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Met Gln Ala Trp His Ser Pro Thr
1               5

<210> SEQ ID NO 243
<211> LENGTH: 8
<212> TYPE: PRT
<213> ORGANISM: Artificial Sequence
<220> FEATURE:
<221> NAME/KEY: source
```

<223> OTHER INFORMATION: /note="Description of Artificial Sequence:
     Synthetic peptide"

<400> SEQUENCE: 243

Gly Ala Thr Tyr Thr Met Asp Tyr
1               5

<210> SEQ ID NO 244
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 244

Met Gln Ala Leu Gln Thr Pro Ile Thr
1               5

<210> SEQ ID NO 245
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 245

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 246
<211> LENGTH: 2076
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 246

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccatgaca ctagcacctc taccgtttat     240
atggagctgt ccagcctgcg ttctgaagat actgcagtgt actactgtgc acgctctttc     300
ttcactggtt tccatctgga ctattggggt caaggcaccc tcgtaacggt ttcttctgct     360
agcacaaagg gccccagcgt gttccctctg gcccctagca gcaagagcac atctggcgga     420
acagccgccc tgggctgcct cgtgaaggac tactttcccg agcctgtgac cgtgtcctgg     480
aactctggcg ccctgacaag cggcgtgcac acctttccag ccgtgctgca gagcagcggc     540
ctgtactctc tgagcagcgt ggtcaccgtg cctagcagca gcctgggcac ccagacctac     600
atctgcaacg tgaaccacaa gcccagcaac accaaagtgg acaagaaggt ggagcccaag     660
agctgtgatg gcggaggagg gtccggaggc ggaggatccg aggtgcagct gctggaatct     720
ggcggcggac tggtgcagcc tggcggatct ctgagactga gctgtgccgc cagcggcttc     780
accttcagca cctacgccat gaactgggtg cgccaggccc ctggcaaagg cctggaatgg     840
gtgtcccgga tcagaagcaa gtacaacaac tacgccacct actacgccga cagcgtgaag     900
ggccggttca ccatcagccg ggacgacagc aagaacaccc tgtacctgca gatgaacagc     960
ctgcgggccg aggacaccgc cgtgtactat tgtgtgcggc acggcaactt cggcaacagc    1020
tatgtgtctt ggtttgccta ctggggccag ggcaccctcg tgaccgtgtc aagcgctagt    1080
gtggccgctc cctccgtgtt tatctttccc ccatccgatg aacagctgaa aagcggcacc    1140
gcctccgtcg tgtgtctgct gaacaatttt tacccctagg aagctaaagt gcagtggaaa    1200
gtggataacg cactgcagtc cggcaactcc caggaatctg tgacagaaca ggactccaag    1260
gacagcacct actccctgtc ctccaccctg acactgtcta aggctgatta tgagaaacac    1320
aaagtctacg cctgcgaagt cacccatcag ggcctgagct cgcccgtcac aaagagcttc    1380
aacaggggag agtgtgacaa gacccacacc tgtccccctt gtcctgcccc tgaagctgct    1440
ggcggcccctt ctgtgttcct gttccccccca agcccaagg acaccctgat gatcagccgg    1500
accccccgaag tgacctgcgt ggtggtggat gtgtcccacg aggaccctga agtgaagttc    1560
aattggtacg tggacggcgt ggaagtgcac aacgccaaga caaagccgcg ggaggagcag    1620
tacaacagca cgtaccgtgt ggtcagcgtc ctcaccgtcc tgcaccagga ctggctgaat    1680
ggcaaggagt acaagtgcaa ggtctccaac aaagccctcg cgcccccat cgagaaaacc    1740
atctccaaag ccaagggca gccccagaa ccacaggtgt acaccctgcc ccatgccgg     1800
gatgagctga ccaagaacca ggtcagcctg tggtgcctgg tcaaaggctt ctatcccagc    1860
gacatcgccg tggagtggga gagcaatggg cagccggaga caactacaa gaccacgcct    1920
cccgtgctgg actccgacgg ctccttcttc ctctacagca agctcaccgt ggacaagagc    1980
```
aggtggcagc agggaacgt cttctcatgc tccgtgatgc atgaggctct gcacaaccac    2040
tacacgcaga gagcctctc cctgtctccg ggtaaa    2076

<210> SEQ ID NO 247
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 247
caggtgcaat tggttcaatc tggtgctgaa gtaaaaaaac cgggcgcttc cgttaaagtg     60
agctgcaaag catccggata caccttcact tcctattaca tgcactgggt cgtcaagcc    120 ccgggccagg gtctggaatg gatgggcatc attaacccaa gcgtggctc tacctcctac    180 gcgcagaaat tccagggtcg cgtcacgatg acccatgaca ctagcacctc taccgtttat    240
atggagctgt ccagcctgcg ttctgaagat actgcagtgt actactgtgc acgctcttc    300 ttcactggtt tccatctgga ctattgggt caaggcaccc tcgtaacggt ttcttctgct    360
agcaccaagg gccctccgt gttcccctg gcccccagca gcagagcac cagcggcggc      420 acagccgctc tgggctgcct ggtcaaggac tacttccccg agcccgtgac cgtgtcctgg    480
aacagcggag ccctgacctc cggcgtgcac accttcccg ccgtgctgca gagttctggc    540
ctgtatagcc tgagcagcgt ggtcaccgtg ccttctagca gcctgggcac ccagacctac    600
atctgcaacg tgaaccacaa gcccagcaac accaaggtgg acaagaaggt ggagcccaag    660
agctgcgaca aaactcacac atgcccaccg tgcccagcac ctgaagctgc aggggaccg    720 tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagcccctc ggcgccccca tcgagaaaac catctccaaa   1020
gccaaagggc agccccgaga accacaggtg tgcaccctgc ccccatcccg ggatgagctg    1080
accaagaacc aggtcagcct ctcgtgcgca gtcaaaggct tctatcccag cgacatcgcc    1140
gtggagtggg agagcaatgg gcagccggag aacaactaca agaccacgcc tcccgtgctg    1200
gactccgacg gctccttctt cctcgtgagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa    1347

<210> SEQ ID NO 248
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 248

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

```
Trp Met Ser Trp Val Arg Gln Ala Pro Gly Lys Gly Leu Glu Trp Val
        35                  40                  45

Gly Arg Ile Lys Ser Lys Thr Glu Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser
            115                 120
```

<210> SEQ ID NO 249
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 249

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Gln Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser
            115                 120
```

<210> SEQ ID NO 250
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 250

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60
```

```
Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Ala Ser Tyr Val Ser Trp Phe
                100                 105                 110

Ala Tyr Trp Gly Gln Gly Thr Leu Val Thr Val Ser Ser
            115                 120                 125

<210> SEQ ID NO 251
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 251

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
                 20                  25                  30

Ala Met Asn Trp Val Arg Gln Ala Pro Gly Lys Gly Leu Glu Trp Val
             35                  40                  45

Ser Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ala Tyr Val Ser Trp Phe
                100                 105                 110

Ala Tyr Trp Gly Gln Gly Thr Leu Val Thr Val Ser Ser
            115                 120                 125

<210> SEQ ID NO 252
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 252

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
                 20                  25                  30

Trp Met Ser Trp Val Arg Gln Ala Pro Gly Lys Gly Leu Glu Trp Val
             35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Pro Trp Glu Trp Ser Trp Tyr Asp Tyr Trp Gly Gln
```

-continued

```
               100                 105                 110
Gly Thr Leu Val Thr Val Ser Ser Ala Ser Thr Lys Gly Pro Ser Val
           115                 120                 125

Phe Pro Leu Ala Pro Ser Ser Lys Ser Thr Ser Gly Gly Thr Ala Ala
           130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
               165                 170                 175

Leu Gln Ser Ser Gly Leu Tyr Ser Leu Ser Ser Val Val Thr Val Pro
           180                 185                 190

Ser Ser Ser Leu Gly Thr Gln Thr Tyr Ile Cys Asn Val Asn His Lys
           195                 200                 205

Pro Ser Asn Thr Lys Val Asp Lys Lys Val Glu Pro Lys Ser Cys Asp
           210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
               245                 250                 255

Ala Ala Ser Gly Phe Thr Phe Ser Thr Tyr Ala Met Asn Trp Val Arg
               260                 265                 270

Gln Ala Pro Gly Lys Gly Leu Glu Trp Val Ser Arg Ile Arg Ser Lys
           275                 280                 285

Tyr Asn Asn Tyr Ala Thr Tyr Tyr Ala Asp Ser Val Lys Gly Arg Phe
           290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
               325                 330                 335

Asn Phe Gly Ala Ser Tyr Val Ser Trp Phe Ala Tyr Trp Gly Gln Gly
               340                 345                 350

Thr Leu Val Thr Val Ser Ser Ala Ser Thr Lys Gly Pro Ser Val Phe
           355                 360                 365

Pro Leu Ala Pro Ser Ser Lys Ser Thr Ser Gly Gly Thr Ala Ala Leu
           370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
               405                 410                 415

Gln Ser Ser Gly Leu Tyr Ser Leu Ser Ser Val Val Thr Val Pro Ser
           420                 425                 430

Ser Ser Leu Gly Thr Gln Thr Tyr Ile Cys Asn Val Asn His Lys Pro
           435                 440                 445

Ser Asn Thr Lys Val Asp Lys Lys Val Glu Pro Lys Ser Cys Asp Lys
           450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
               485                 490                 495

Arg Thr Pro Glu Val Thr Cys Val Val Val Asp Val Ser His Glu Asp
           500                 505                 510

Pro Glu Val Lys Phe Asn Trp Tyr Val Asp Gly Val Glu Val His Asn
           515                 520                 525
```

Ala Lys Thr Lys Pro Arg Glu Glu Gln Tyr Asn Ser Thr Tyr Arg Val
            530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
        595                 600                 605

Cys Leu Val Lys Gly Phe Tyr Pro Ser Asp Ile Ala Val Glu Trp Glu
        610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys

<210> SEQ ID NO 253
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro

```
                180             185             190
Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
        340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn Arg Phe Thr Gln Lys Ser Leu Ser Leu Ser Pro
        435                 440                 445

Gly Lys
    450

<210> SEQ ID NO 254
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 254

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80
```

```
Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 255
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 255

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220
Gly Gly Gly Gly Ser Gly Gly Gly Ser Glu Val Gln Leu Leu Glu
225                 230                 235                 240
Ser Gly Gly Gly Leu Val Gln Pro Gly Gly Ser Leu Arg Leu Ser Cys
                245                 250                 255
Ala Ala Ser Gly Phe Thr Phe Ser Thr Tyr Ala Met Asn Trp Val Arg
                260                 265                 270
Gln Ala Pro Gly Lys Gly Leu Glu Trp Val Ser Arg Ile Arg Ser Lys
            275                 280                 285
Tyr Asn Asn Tyr Ala Thr Tyr Tyr Ala Asp Ser Val Lys Gly Arg Phe
    290                 295                 300
Thr Ile Ser Arg Asp Asp Ser Lys Asn Thr Leu Tyr Leu Gln Met Asn
305                 310                 315                 320
Ser Leu Arg Ala Glu Asp Thr Ala Val Tyr Tyr Cys Val Arg His Gly
                325                 330                 335
Asn Phe Gly Asn Ala Tyr Val Ser Trp Phe Ala Tyr Trp Gly Gln Gly
                340                 345                 350
Thr Leu Val Thr Val Ser Ser Ala Ser Thr Lys Gly Pro Ser Val Phe
                355                 360                 365
Pro Leu Ala Pro Ser Ser Lys Ser Thr Ser Gly Gly Thr Ala Ala Leu
    370                 375                 380
Gly Cys Leu Val Lys Asp Tyr Phe Pro Glu Pro Val Thr Val Ser Trp
385                 390                 395                 400
Asn Ser Gly Ala Leu Thr Ser Gly Val His Thr Phe Pro Ala Val Leu
                405                 410                 415
Gln Ser Ser Gly Leu Tyr Ser Leu Ser Ser Val Val Thr Val Pro Ser
                420                 425                 430
Ser Ser Leu Gly Thr Gln Thr Tyr Ile Cys Asn Val Asn His Lys Pro
            435                 440                 445
Ser Asn Thr Lys Val Asp Lys Lys Val Glu Pro Lys Ser Cys Asp Lys
    450                 455                 460
Thr His Thr Cys Pro Pro Cys Pro Ala Pro Glu Ala Ala Gly Gly Pro
465                 470                 475                 480
Ser Val Phe Leu Phe Pro Pro Lys Pro Lys Asp Thr Leu Met Ile Ser
                485                 490                 495
Arg Thr Pro Glu Val Thr Cys Val Val Val Asp Val Ser His Glu Asp
                500                 505                 510
Pro Glu Val Lys Phe Asn Trp Tyr Val Asp Gly Val Glu Val His Asn
            515                 520                 525
Ala Lys Thr Lys Pro Arg Glu Glu Gln Tyr Asn Ser Thr Tyr Arg Val
    530                 535                 540
Val Ser Val Leu Thr Val Leu His Gln Asp Trp Leu Asn Gly Lys Glu
545                 550                 555                 560
Tyr Lys Cys Lys Val Ser Asn Lys Ala Leu Gly Ala Pro Ile Glu Lys
                565                 570                 575
Thr Ile Ser Lys Ala Lys Gly Gln Pro Arg Glu Pro Gln Val Tyr Thr
                580                 585                 590
Leu Pro Pro Cys Arg Asp Glu Leu Thr Lys Asn Gln Val Ser Leu Trp
            595                 600                 605
Cys Leu Val Lys Gly Phe Tyr Pro Ser Asp Ile Ala Val Glu Trp Glu
    610                 615                 620
Ser Asn Gly Gln Pro Glu Asn Asn Tyr Lys Thr Thr Pro Pro Val Leu
```

```
625                 630                 635                 640
Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys

<210> SEQ ID NO 256
<211> LENGTH: 690
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Pro Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Gly Gly Gly
    210                 215                 220

Gly Ser Gly Gly Gly Gly Ser Glu Val Gln Leu Leu Glu Ser Gly Gly
225                 230                 235                 240

Gly Leu Val Gln Pro Gly Gly Ser Leu Arg Leu Ser Cys Ala Ala Ser
                245                 250                 255

Gly Phe Thr Phe Ser Thr Tyr Ala Met Asn Trp Val Arg Gln Ala Pro
            260                 265                 270

Gly Lys Gly Leu Glu Trp Val Ser Arg Ile Arg Ser Lys Tyr Asn Asn
        275                 280                 285
```

```
Tyr Ala Thr Tyr Tyr Ala Asp Ser Val Lys Gly Arg Phe Thr Ile Ser
    290             295                 300
Arg Asp Asp Ser Lys Asn Thr Leu Tyr Leu Gln Met Asn Ser Leu Arg
305                 310                 315                 320
Ala Glu Asp Thr Ala Val Tyr Tyr Cys Val Arg His Gly Asn Phe Gly
                325                 330                 335
Ala Ser Tyr Val Ser Trp Phe Ala Tyr Trp Gly Gln Gly Thr Leu Val
            340                 345                 350
Thr Val Ser Ser Ala Ser Val Ala Ala Pro Ser Val Phe Ile Phe Pro
        355                 360                 365
Pro Ser Asp Glu Gln Leu Lys Ser Gly Thr Ala Ser Val Val Cys Leu
370                 375                 380
Leu Asn Asn Phe Tyr Pro Arg Glu Ala Lys Val Gln Trp Lys Val Asp
385                 390                 395                 400
Asn Ala Leu Gln Ser Gly Asn Ser Gln Glu Ser Val Thr Glu Gln Asp
                405                 410                 415
Ser Lys Asp Ser Thr Tyr Ser Leu Ser Ser Thr Leu Thr Leu Ser Lys
            420                 425                 430
Ala Asp Tyr Glu Lys His Lys Val Tyr Ala Cys Glu Val Thr His Gln
        435                 440                 445
Gly Leu Ser Ser Pro Val Thr Lys Ser Phe Asn Arg Gly Glu Cys Asp
450                 455                 460
Lys Thr His Thr Cys Pro Pro Cys Pro Ala Pro Glu Ala Ala Gly Gly
465                 470                 475                 480
Pro Ser Val Phe Leu Phe Pro Pro Lys Pro Lys Asp Thr Leu Met Ile
                485                 490                 495
Ser Arg Thr Pro Glu Val Thr Cys Val Val Val Asp Val Ser His Glu
            500                 505                 510
Asp Pro Glu Val Lys Phe Asn Trp Tyr Val Asp Gly Val Glu Val His
        515                 520                 525
Asn Ala Lys Thr Lys Pro Arg Glu Glu Gln Tyr Asn Ser Thr Tyr Arg
530                 535                 540
Val Val Ser Val Leu Thr Val Leu His Gln Asp Trp Leu Asn Gly Lys
545                 550                 555                 560
Glu Tyr Lys Cys Lys Val Ser Asn Lys Ala Leu Gly Ala Pro Ile Glu
                565                 570                 575
Lys Thr Ile Ser Lys Ala Lys Gly Gln Pro Arg Glu Pro Gln Val Tyr
            580                 585                 590
Thr Leu Pro Pro Cys Arg Asp Glu Leu Thr Lys Asn Gln Val Ser Leu
        595                 600                 605
Trp Cys Leu Val Lys Gly Phe Tyr Pro Ser Asp Ile Ala Val Glu Trp
610                 615                 620
Glu Ser Asn Gly Gln Pro Glu Asn Asn Tyr Lys Thr Thr Pro Pro Val
625                 630                 635                 640
Leu Asp Ser Asp Gly Ser Phe Phe Leu Tyr Ser Lys Leu Thr Val Asp
                645                 650                 655
Lys Ser Arg Trp Gln Gln Gly Asn Val Phe Ser Cys Ser Val Met His
            660                 665                 670
Glu Ala Leu His Asn His Tyr Thr Gln Lys Ser Leu Ser Leu Ser Pro
        675                 680                 685
Gly Lys
690
```

```
<210> SEQ ID NO 257
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Pro Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365
```

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 258
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 258

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Ile Met Gln Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 259
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 259

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210
```

<210> SEQ ID NO 260
<211> LENGTH: 690
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 260

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Pro Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Trp Leu Asp Tyr Trp Gly Gln Gly Thr Leu
            100                 105                 110

Val Thr Val Ser Ser Ala Ser Thr Lys Gly Pro Ser Val Phe Pro Leu
```

-continued

```
            115                 120                 125
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Gly Gly Gly
210                 215                 220

Gly Ser Gly Gly Gly Ser Glu Val Gln Leu Leu Glu Ser Gly Gly
225                 230                 235                 240

Gly Leu Val Gln Pro Gly Gly Ser Leu Arg Leu Ser Cys Ala Ala Ser
                245                 250                 255

Gly Phe Thr Phe Ser Thr Tyr Ala Met Asn Trp Val Arg Gln Ala Pro
            260                 265                 270

Gly Lys Gly Leu Glu Trp Val Ser Arg Ile Arg Ser Lys Tyr Asn Asn
        275                 280                 285

Tyr Ala Thr Tyr Tyr Ala Asp Ser Val Lys Gly Arg Phe Thr Ile Ser
290                 295                 300

Arg Asp Asp Ser Lys Asn Thr Leu Tyr Leu Gln Met Asn Ser Leu Arg
305                 310                 315                 320

Ala Glu Asp Thr Ala Val Tyr Tyr Cys Val Arg His Gly Asn Phe Gly
                325                 330                 335

Asn Ala Tyr Val Ser Trp Phe Ala Tyr Trp Gly Gln Gly Thr Leu Val
            340                 345                 350

Thr Val Ser Ser Ala Ser Val Ala Ala Pro Ser Val Phe Ile Phe Pro
        355                 360                 365

Pro Ser Asp Glu Gln Leu Lys Ser Gly Thr Ala Ser Val Val Cys Leu
370                 375                 380

Leu Asn Asn Phe Tyr Pro Arg Glu Ala Lys Val Gln Trp Lys Val Asp
385                 390                 395                 400

Asn Ala Leu Gln Ser Gly Asn Ser Gln Glu Ser Val Thr Glu Gln Asp
                405                 410                 415

Ser Lys Asp Ser Thr Tyr Ser Leu Ser Ser Thr Leu Thr Leu Ser Lys
            420                 425                 430

Ala Asp Tyr Glu Lys His Lys Val Tyr Ala Cys Glu Val Thr His Gln
        435                 440                 445

Gly Leu Ser Ser Pro Val Thr Lys Ser Phe Asn Arg Gly Glu Cys Asp
450                 455                 460

Lys Thr His Thr Cys Pro Pro Cys Pro Ala Pro Glu Ala Ala Gly Gly
465                 470                 475                 480

Pro Ser Val Phe Leu Phe Pro Pro Lys Pro Lys Asp Thr Leu Met Ile
                485                 490                 495

Ser Arg Thr Pro Glu Val Thr Cys Val Val Val Asp Val Ser His Glu
            500                 505                 510

Asp Pro Glu Val Lys Phe Asn Trp Tyr Val Asp Gly Val Glu Val His
        515                 520                 525

Asn Ala Lys Thr Lys Pro Arg Glu Glu Gln Tyr Asn Ser Thr Tyr Arg
530                 535                 540
```

Val Val Ser Val Leu Thr Val Leu His Gln Asp Trp Leu Asn Gly Lys
545                 550                 555                 560

Glu Tyr Lys Cys Lys Val Ser Asn Lys Ala Leu Gly Ala Pro Ile Glu
            565                 570                 575

Lys Thr Ile Ser Lys Ala Lys Gly Gln Pro Arg Glu Pro Gln Val Tyr
            580                 585                 590

Thr Leu Pro Pro Cys Arg Asp Glu Leu Thr Lys Asn Gln Val Ser Leu
            595                 600                 605

Trp Cys Leu Val Lys Gly Phe Tyr Pro Ser Asp Ile Ala Val Glu Trp
610                 615                 620

Glu Ser Asn Gly Gln Pro Glu Asn Asn Tyr Lys Thr Thr Pro Pro Val
625                 630                 635                 640

Leu Asp Ser Asp Gly Ser Phe Phe Leu Tyr Ser Lys Leu Thr Val Asp
                645                 650                 655

Lys Ser Arg Trp Gln Gln Gly Asn Val Phe Ser Cys Ser Val Met His
                660                 665                 670

Glu Ala Leu His Asn His Tyr Thr Gln Lys Ser Leu Ser Leu Ser Pro
                675                 680                 685

Gly Lys
    690

<210> SEQ ID NO 261
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 261
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgaggg tggcaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360

<210> SEQ ID NO 262
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 262
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgaggg tggcaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360

<210> SEQ ID NO 263
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 263

```
gaggtgcagc tgctggaatc tggcggcgga ctggtgcagc ctggcggatc tctgagactg      60
agctgtgccg ccagcggctt caccttcagc acctacgcca tgaactgggt gcgccaggcc     120
cctggcaaag gcctggaatg ggtgtcccgg atcagaagca agtacaacaa ctacgccacc     180
tactacgccg acagcgtgaa gggccggttc accatcagcc gggacgacag caagaacacc     240
ctgtacctgc agatgaacag cctgcgggcc gaggacaccg ccgtgtacta ttgtgtgcgg     300
cacggcaact tcggcgccag ctatgtgtct tggtttgcct actggggcca gggcaccctc     360
gtgaccgtgt caagc                                                      375
```

<210> SEQ ID NO 264
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 264

```
gaggtgcagc tgctggaatc tggcggcgga ctggtgcagc ctggcggatc tctgagactg      60
agctgtgccg ccagcggctt caccttcagc acctacgcca tgaactgggt gcgccaggcc     120
cctggcaaag gcctggaatg ggtgtcccgg atcagaagca agtacaacaa ctacgccacc     180
tactacgccg acagcgtgaa gggccggttc accatcagcc gggacgacag caagaacacc     240
ctgtacctgc agatgaacag cctgcgggcc gaggacaccg ccgtgtacta ttgtgtgcgg     300
cacggcaact tcggcaacgc ctatgtgtct tggtttgcct actggggcca gggcaccctc     360
gtgaccgtgt caagc                                                      375
```

<210> SEQ ID NO 265
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 265

```
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgacgg tggcaccacg     180
gattacgcgc ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacaa agggccctag cgtgttccct ctggccccca gcagcaagag cacaagcggc     420
ggaacagccg ccctgggctg cctcgtgaag gactacttcc ccgagcccgt gacagtgtct     480
```

```
tggaacagcg gagccctgac aagcggcgtg cacactttcc ctgccgtgct gcagagcagc      540
ggcctgtact ccctgagcag cgtggtcacc gtgcctagca gcagcctggg cacccagacc      600
tacatctgca acgtgaacca caagcccagc aacaccaaag tggacaagaa ggtggagccc      660
aagagctgtg atggcggagg agggtccgga ggcggaggat ccgaggtgca gctgctggaa      720
tctggcggcg gactggtgca gcctggcgga tctctgagac tgagctgtgc cgccagcggc      780
ttcacctcca gcacctacgc catgaactgg gtgcgccagg cccctggcaa aggcctggaa      840
tgggtgtccc ggatcagaag caagtacaac aactacgcca cctactacgc cgacagcgtg      900
aagggccggt tcaccatcag ccgggacgac agcaagaaca ccctgtacct gcagatgaac      960
agcctgcggg ccgaggacac cgccgtgtac tattgtgtgc ggcacggcaa cttcggcgcc     1020
agctatgtgt cttggtttgc ctactggggc cagggcaccc tcgtgaccgt gtcaagcgct     1080
agtaccaagg gcccagcgt gttccccctg cacccagca gcaagagcac atctggcgga      1140
acagccgctc tgggctgtct ggtgaaagac tacttccccg agcccgtgac cgtgtcttgg     1200
aactctggcg ccctgaccag cggcgtgcac accttccag ccgtgctgca gagcagcggc     1260
ctgtactccc tgtcctccgt ggtcaccgtg ccctctagct ccctgggaac acagacatat     1320
atctgtaatg tcaatcacaa gccttccaac accaaagtcg ataagaaagt cgagcccaag     1380
agctgcgaca aaactcacac atgcccaccg tgcccagcac ctgaagctgc aggggaccg      1440 tcagtcttcc tcttccccc aaaacccaag gacaccctca tgatctcccg gacccctgag      1500
gtcacatgcg tggtggtgga cgtgagccac gaagaccctg aggtcaagtt caactggtac     1560
gtggacggcg tggaggtgca taatgccaag acaaagccgc gggaggagca gtacaacagc     1620
acgtaccgtg tggtcagcgt cctcaccgtc ctgcaccagg actggctgaa tggcaaggag     1680
tacaagtgca aggtctccaa caaagccctc ggcgccccca tcgagaaaac catctccaaa     1740
gccaaagggc agccccgaga accacaggtg tacaccctgc ccccatgccg ggatgagctg     1800
accaagaacc aggtcagcct gtggtgcctg gtcaaaggct tctatcccag cgacatcgcc     1860
gtggagtggg agagcaatgg gcagccggag aacaactaca agaccacgcc tcccgtgctg     1920
gactccgacg gctccttctt cctctacagc aagctcaccg tggacaagag caggtggcag     1980
caggggaacg tcttctcatg ctccgtgatg catgaggctc tgcacaacca ctacacgcag     2040
aagagcctct ccctgtctcc gggtaaa                                          2067
```

<210> SEQ ID NO 266
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 266

```
gaggtgcaat tggttgaatc tggtggtggt ctggtaaaac cgggcggttc cctgcgtctg       60
agctgcgcgg cttccggatt caccttctcc aacgcgtgga tgagctgggt tcgccaggcc      120
ccgggcaaag gctcgagtg ggttggtcgt atcaagtcta aaactgacgg tggcaccacg      180
gattacgcgg ctccagttaa aggtcgtttt accatttccc gcgacgatag caaaaacact      240
ctgtatctgc agatgaactc tctgaaaact gaagacaccg cagtctacta ctgtactacc      300
ccgtgggaat ggtcttggta cgattattgg ggccagggca ccctggttac ggtgtcttcc      360
```

```
gctagcacca agggcccctc cgtgttcccc ctggccccca gcagcaagag caccagcggc    420
ggcacagccg ctctgggctg cctggtcaag gactacttcc ccgagcccgt gaccgtgtcc    480
tggaacagcg agccctgac ctccggcgtg cacaccttcc ccgccgtgct gcagagttct    540
ggcctgtata gcctgagcag cgtggtcacc gtgccttcta gcagcctggg cacccagacc    600
tacatctgca acgtgaacca caagcccagc aacaccaagg tggacaagaa ggtggagccc    660
aagagctgcg acaaaactca cacatgccca ccgtgcccag cacctgaagc tgcaggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcgcgcccc catcgagaaa aaccatctcc    1020
aaagccaaag gcagccccg agaaccacag gtgtgcaccc tgcccccatc ccgggatgag    1080
ctgaccaaga accaggtcag cctctcgtgc gcagtcaaag gcttctatcc cagcgacatc    1140
gccgtggagt gggagagcaa tgggcagccg gagaacaact acaagaccac gcctcccgtg    1200
ctggactccg acggctcctt cttcctcgtg agcaagctca ccgtggacaa gagcaggtgg    1260 cagcaggga acgtcttctc atgctccgtg atgcatgagg ctctgcacaa ccgcttcacg    1320
cagaagagcc tctccctgtc tccgggtaaa                                    1350
```

<210> SEQ ID NO 267
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 267

```
caggccgtcg tgacccagga acccagcctg acagtgtctc ctggcggcac cgtgaccctg     60
acatgtggca gttctacagg cgccgtgacc accagcaact acgccaactg ggtgcaggaa    120
aagcccggcc aggccttcag aggactgatc ggcggcacca acaagagagc ccctggcacc    180
cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtcctaggt caacccaagg ctgccccag cgtgaccctg    360 ttccccccca gcagcgagga actgcaggcc aacaaggcca cctggtctg cctgatcagc    420 gacttctacc caggcgccgt gaccgtggcc tggaaggccg acagcagccc cgtgaaggcc    480
ggcgtggaga ccaccacccc cagcaagcag agcaacaaca gtacgccgc cagcagctac    540 ctgagcctga cccccgagca gtggaagagc acaggtcct acagctgcca ggtgacccac    600
gagggcagca ccgtggagaa aaccgtggcc cccaccgagt gcagc                    645
```

<210> SEQ ID NO 268
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 268

```
gaggtgcaat tggttgaatc tggtggtggt ctggtaaaac cgggcggttc cctgcgtctg    60
agctgcgcgg cttccggatt caccttctcc aacgcgtgga tgagctgggt tcgccaggcc   120
ccgggcaaag gcctcgagtg ggttggtcgt atcaagtcta aaactgacgg tggcaccacg   180
gattacgcgg ctccagttaa aggtcgtttt accatttccc gcgacgatag caaaaacact   240
ctgtatctgc agatgaactc tctgaaaact gaagacaccg cagtctacta ctgtactacc   300
ccgtgggaat ggtcttggta cgattattgg ggccagggca cgctggttac ggtgtcttcc   360
gctagcacaa agggccctag cgtgttccct ctggccccca gcagcaagag cacaagcggc   420
ggaacagccg ccctgggctg cctcgtgaag gactacttcc ccgagcccgt gacagtgtct   480
tggaacagcg gagccctgac aagcggcgtg cacacttttcc ctgccgtgct gcagagcagc   540
ggcctgtact ccctgagcag cgtggtcacc gtgcctagca gcagcctggg cacccagacc   600
tacatctgca acgtgaacca caagcccagc aacaccaaag tggacaagaa ggtggagccc   660
aagagctgtg atggcggagg agggtccgga ggcggaggat ccgaggtgca gctgctggaa   720
tctggcggcg gactggtgca gcctggcgga tctctgagac tgagctgtgc cgccagcggc   780
ttcaccttca gcacctacgc catgaactgg gtgcgccagg cccctggcaa aggcctggaa   840
tgggtgtccc ggatcagaag caagtacaac aactacgcca cctactacgc cgacagcgtg   900
aagggccggt tcaccatcag ccgggacgac agcaagaaca ccctgtacct gcagatgaac   960
agcctgcggg ccgaggacac cgccgtgtac tattgtgtgc ggcacggcaa cttcggcaac  1020
gcctatgtgt cttggtttgc ctactggggc cagggcaccc tcgtgaccgt gtcaagcgct  1080
agtaccaagg gcccccagcgt gttccccctg gcacccagca gcaagagcac atctggcgga  1140
acagccgctc tgggctgtct ggtgaaagac tacttccccg agcccgtgac cgtgtcttgg  1200
aactctggcg ccctgaccag cggcgtgcac accttttccag ccgtgctgca gagcagcggc  1260
ctgtactccc tgtcctccgt ggtcaccgtg ccctctagct ccctgggaac acagacatat  1320
atctgtaatg tcaatcacaa gccttccaac accaaagtcg ataagaaagt cgagcccaag  1380
agctgcgaca aaactcacac atgcccaccg tgcccagcac ctgaagctgc aggggggaccg  1440 tcagtcttcc tcttccccccc aaaacccaag gacaccctca tgatctcccg gacccctgag  1500
gtcacatgcg tggtggtgga cgtgagccac gaagaccctg aggtcaagtt caactggtac  1560
gtggacggcg tggaggtgca taatgccaag acaaagccgc gggaggagca gtacaacagc  1620
acgtaccgtg tggtcagcgt cctcaccgtc ctgcaccagg actggctgaa tggcaaggag  1680
tacaagtgca aggtctccaa caaagccctc ggcgccccca tcgagaaaac catctccaaa  1740
gccaaagggc agccccgaga accacaggtg tacaccctgc ccccatgccg ggatgagctg  1800
accaagaacc aggtcagcct gtggtgcctg gtcaaaggct tctatcccag cgacatcgcc  1860
gtggagtggg agagcaatgg gcagccggag aacaactaca gaccacgcc tcccgtgctg  1920 gactccgacg gctccttctt cctctacagc aagctcaccg tggacaagag caggtggcag  1980
caggggaacg tcttctcatg ctccgtgatg catgaggctc tgcacaacca ctacacgcag  2040
aagagcctct ccctgtctcc gggtaaa                                     2067
```

<210> SEQ ID NO 269
<211> LENGTH: 2070
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 269

```
caggtgcaat tggttcaatc tggtgctgaa gtaaaaaaac cgggcgcttc cgttaaagtg        60
agctgcaaag catccggata caccttcact tcctattaca tgcactgggt tcgtcaagcc       120
ccgggccagg gtctggaatg gatgggcatc attaacccaa gcggtggccc tacctcctac       180
gcgcagaaat tccagggtcg cgtcacgatg acccgtgaca ctagcacctc taccgttat        240
atggagctgt ccagcctgcg ttctgaagat actgcagtgt actactgtgc acgcggtgac       300
ttcgcttggc tggactattg gggtcaaggc accctcgtaa cggtttcttc tgctagcaca       360
aagggcccca gcgtgttccc tctggcccct agcagcaaga gcacatctgg cggaacagcc       420
gccctgggct gcctcgtgaa ggactacttt cccgagcctg tgaccgtgtc ctggaactct       480
ggcgccctga acgcggcgt gcacaccttt ccagccgtgc tgcagagcag cggcctgtac       540
tctctgagca gcgtggtcac cgtgcctagc agcagcctgg gcacccagac ctacatctgc       600
aacgtgaacc acaagcccag caacaccaaa gtggacaaga aggtggagcc caagagctgt       660
gatggcggag gagggtccgg aggcggagga tccgaggtgc agctgctgga atctggcggc       720
ggactggtgc agcctggcgg atctctgaga ctgagctgtg ccgccagcgg cttcaccttc       780
agcacctacg ccatgaactg ggtgcgccag gcccctggca aaggcctgga atgggtgtcc       840
cggatcagaa gcaagtacaa caactacgcc acctactacg ccgacagcgt gaagggccgg       900
ttcaccatca gccgggacga cagcaagaac accctgtacc tgcagatgaa cagcctgcgg       960
gccgaggaca ccgccgtgta ctattgtgtg cggcacggca acttcggcgc cagctatgtg      1020
tcttggtttg cctactgggg ccagggcacc ctcgtgaccg tgtcaagcgc tagtgtggcc      1080
gctcccctccg tgtttatctt tccccatcc gatgaacagc tgaaaagcgg caccgcctcc      1140
gtcgtgtgtc tgctgaacaa ttttttaccct agggaagcta aagtgcagtg gaaagtggat      1200
aacgcactgc agtccggcaa ctcccaggaa tctgtgacag acaggactc caaggacagc      1260
acctactccc tgtcctccac cctgacactg tctaaggctg attatgagaa acacaaagtc      1320
tacgcctgcg aagtcaccca tcagggcctg agctcgcccg tcacaaagag cttcaacagg      1380
ggagagtgtg acaagaccca cacctgtccc ccttgtcctg cccctgaagc tgctggcggc      1440
ccttctgtgt tcctgttccc cccaaagccc aaggacaccc tgatgatcag ccggacccc       1500
gaagtgacct gcgtggtggt ggatgtgtcc cacgaggacc ctgaagtgaa gttcaattgg      1560
tacgtggacg gcgtggaagt gcacaacgcc aagacaaagc cgcgggagga gcagtacaac      1620
agcacgtacc gtgtggtcag cgtcctcacc gtcctgcacc aggactggct gaatggcaag      1680
gagtacaagt gcaaggtctc caacaaagcc ctcggcgccc catcgagaa aaccatctcc       1740
aaagccaaag gcagccccg agaaccacag gtgtacaccc tgcccccatg ccgggatgag      1800
ctgaccaaga accaggtcag cctgtggtgc ctggtcaaag gcttctatcc cagcgacatc      1860
gccgtggagt gggagagcaa tgggcagccg gagaacaact acaagaccac gcctcccgtg      1920
ctggactccg acggctcctt cttcctctac agcaagctca ccgtggacaa gagcaggtgg      1980
cagcagggga acgtcttctc atgctccgtg atgcatgagg ctctgcacaa ccactacacg      2040
cagaagagcc tctccctgtc tccgggtaaa                                       2070
```

<210> SEQ ID NO 270
<211> LENGTH: 1341
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 270
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcgtggccc tacctcctac    180 gcgcagaaat tccagggtcg cgtcacgatg accgtgaca ctagcacctc taccgtttat    240
atggagctgt ccagcctgcg ttctgaagat actgcagtgt actactgtgc acgcggtgac   300
ttcgcttggc tggactattg gggtcaaggc accctcgtaa cggtttcttc tgctagcacc   360
aagggcccct ccgtgttccc cctggcccc agcagcaaga gcaccagcgg cggcacagcc    420
gctctgggct gcctggtcaa ggactacttc cccgagcccg tgaccgtgtc ctggaacagc   480
ggagccctga cctccggcgt gcacaccttc ccgccgtgc tgcagagttc tggcctgtat    540
agcctgagca gcgtggtcac cgtgccttct agcagcctgg gcacccagac ctacatctgc   600
aacgtgaacc acaagcccag caacaccaag gtggacaaga aggtggagcc caagagctgc   660
gacaaaactc acacatgccc accgtgccca gcacctgaag ctgcagggg accgtcagtc    720 ttcctcttcc ccccaaaacc caaggacacc ctcatgatct cccggacccc tgaggtcaca   780
tgcgtggtgg tggacgtgag ccacgaagac cctgaggtca agttcaactg gtacgtggac   840
ggcgtggagg tgcataatgc caagacaaag ccgcggagg agcagtacaa cagcacgtac    900
cgtgtggtca gcgtcctcac cgtcctgcac caggactggc tgaatggcaa ggagtacaag   960
tgcaaggtct ccaacaaagc cctcggcgcc cccatcgaga aaccatctc caaagccaaa    1020 gggcagcccc gagaaccaca ggtgtgcacc ctgccccat cccgggatga gctgaccaag    1080
aaccaggtca gcctctcgtg cgcagtcaaa ggcttctatc ccagcgacat cgccgtggag   1140
tgggagagca atgggcagcc ggagaacaac tacaagacca cgcctcccgt gctggactcc   1200
gacggctcct tcttcctcgt gagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                             1341

<210> SEQ ID NO 271
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 271
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcaag cattatgcag   300 cggactttg gtcaaggcac caaggtcgaa attaaacgta cggtggctgc accatctgtc   360
ttcatcttcc cgccatctga tgagcagttg aaatctggaa ctgcctctgt tgtgtgcctg   420
```

```
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacaggggg agagtgt      657

<210> SEQ ID NO 272
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 272
caggccgtcg tgacccagga acccagcctg acagtgtctc ctggcggcac cgtgaccctg     60
acatgtggca gttctacagg cgccgtgacc accagcaact acgccaactg ggtgcaggaa    120
aagcccggcc aggccttcag aggactgatc ggcggcacca caagagagc ccctggcacc     180 cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtgctgagc agcgcttcca ccaaaggccc ttccgtgttt    360
cctctggctc ctagctccaa gtccacctct ggaggcaccg ctgctctcgg atgcctcgtg    420
aaggattatt ttcctgagcc tgtgacagtg tcctggaata gcggagcact gacctctgga    480
gtgcatactt tccccgctgt gctgcagtcc tctggactgt acagcctgag cagcgtggtg    540
acagtgccca gcagcagcct gggcacccag acctacatct gcaacgtgaa ccacaagccc    600
agcaacacca aggtggacaa gaaggtggaa cccaagtctt gt                       642

<210> SEQ ID NO 273
<211> LENGTH: 2070
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 273
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggccc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcggtgac    300
ttcgcttggc tggactattg gggtcaaggc accctcgtaa cggtttcttc tgctagcaca    360 aagggccccca gcgtgttccc tctggcccct agcagcaaga gcacatctgg cggaacagcc    420
gccctgggct gcctcgtgaa ggactacttt cccgagcctg tgaccgtgtc ctggaactct    480
ggcgccctga caagcggcgt gcacaccttt ccagccgtgc tgcagagcag cggcctgtac    540
tctctgagca gcgtggtcac cgtgcctagc agcagcctgg gcacccagac ctacatctgc    600
aacgtgaacc acaagcccag caacaccaaa gtggacaaga aggtggagcc caagagctgt    660
gatgcgggag gagggtccgg aggcggagga tccgaggtgc agctgctgga atctggcggc    720
ggactggtgc agcctggcgg atctctgaga ctgagctgtg ccgccagcgg cttcaccttc    780
```

```
agcacctacg ccatgaactg ggtgcgccag gcccctggca aaggcctgga atgggtgtcc    840
cggatcagaa gcaagtacaa caactacgcc acctactacg ccgacagcgt gaagggccgg    900
ttcaccatca gccgggacga cagcaagaac accctgtacc tgcagatgaa cagcctgcgg    960
gccgaggaca ccgccgtgta ctattgtgtg cggcacggca cttcggcaa cgcctatgtg   1020
tcttggtttg cctactgggg ccagggcacc ctcgtgaccg tgtcaagcgc tagtgtggcc   1080
gctccctccg tgtttatctt tccccccatcc gatgaacagc tgaaaagcgg caccgcctcc   1140
gtcgtgtgtc tgctgaacaa ttttttaccct agggaagcta aagtgcagtg aaagtggat    1200
aacgcactgc agtccggcaa ctcccaggaa tctgtgacag acaggactc caaggacagc    1260
acctactccc tgtcctccac cctgacactg tctaaggctg attatgagaa cacaaagtc    1320
tacgcctgcg aagtcaccca tcagggcctg agctcgcccg tcacaaagag cttcaacagg    1380
ggagagtgtg acaagaccca cacctgtccc ccttgtcctg cccctgaagc tgctggcggc    1440
ccttctgtgt tcctgttccc cccaaagccc aaggacaccc tgatgatcag ccggaccccc    1500
gaagtgacct gcgtggtggt ggatgtgtcc cacgaggacc ctgaagtgaa gttcaattgg    1560
tacgtggacg gcgtggaagt gcacaacgcc aagacaaagc cgcgggagga gcagtacaac    1620
agcacgtacc gtgtggtcag cgtcctcacc gtcctgcacc aggactggct gaatggcaag    1680
gagtacaagt gcaaggtctc caacaaagcc ctcggcgccc ccatcgagaa aaccatctcc    1740
aaagccaaag ggcagccccg agaaccacag gtgtacaccc tgcccccatg ccgggatgag    1800
ctgaccaaga accaggtcag cctgtggtgc ctggtcaaag gcttctatcc cagcgacatc    1860
gccgtggagt gggagagcaa tgggcagccg gagaacaact acaagaccac gcctcccgtg    1920
ctggactccg acggctcctt cttcctctac agcaagctca ccgtggacaa gagcaggtgg    1980
cagcagggga acgtcttctc atgctccgtg atgcatgagg ctctgcacaa ccactacacg    2040
cagaagagcc tctccctgtc tccgggtaaa                                     2070
```

<210> SEQ ID NO 274
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 274

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Glu Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Tyr Glu Trp Ser Trp Tyr Asp Tyr Trp Gly Gln
            100                 105                 110

Gly Thr Leu Val Thr Val Ser Ser
        115                 120

```
<210> SEQ ID NO 275
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Arg Ile Lys Ser Lys Thr Glu Gly Gly Thr Thr Asp Tyr Ala Ala Pro
1               5                   10                  15

Val Lys Gly

<210> SEQ ID NO 276
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 276

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Glu Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Tyr Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                245                 250                 255
```

```
Ala Ala Ser Gly Phe Thr Phe Ser Thr Tyr Ala Met Asn Trp Val Arg
            260                 265                 270

Gln Ala Pro Gly Lys Gly Leu Glu Trp Val Ser Arg Ile Arg Ser Lys
            275                 280                 285

Tyr Asn Asn Tyr Ala Thr Tyr Tyr Ala Asp Ser Val Lys Gly Arg Phe
            290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
            325                 330                 335

Asn Phe Gly Asn Ser Tyr Val Ser Trp Phe Ala Tyr Trp Gly Gln Gly
            340                 345                 350

Thr Leu Val Thr Val Ser Ser Ala Ser Thr Lys Gly Pro Ser Val Phe
            355                 360                 365

Pro Leu Ala Pro Ser Ser Lys Ser Thr Ser Gly Gly Thr Ala Ala Leu
            370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
            405                 410                 415

Gln Ser Ser Gly Leu Tyr Ser Leu Ser Ser Val Val Thr Val Pro Ser
            420                 425                 430

Ser Ser Leu Gly Thr Gln Thr Tyr Ile Cys Asn Val Asn His Lys Pro
            435                 440                 445

Ser Asn Thr Lys Val Asp Lys Lys Val Glu Pro Lys Ser Cys Asp Lys
450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
            485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
            515                 520                 525

Ala Lys Thr Lys Pro Arg Glu Glu Gln Tyr Asn Ser Thr Tyr Arg Val
            530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
            565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
            595                 600                 605

Cys Leu Val Lys Gly Phe Tyr Pro Ser Asp Ile Ala Val Glu Trp Glu
610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
            645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
```

675             680             685
Lys

<210> SEQ ID NO 277
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 277

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Glu Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Tyr Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

```
Lys Thr Ile Ser Lys Ala Lys Gly Gln Pro Arg Glu Pro Gln Val Cys
                340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 278
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 278

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Arg Tyr Arg Tyr Phe Asp Tyr Trp Gly Gln Gly
            100                 105                 110

Thr Leu Val Thr Val Ser Ser
        115

<210> SEQ ID NO 279
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 279

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
```

```
                35                  40                  45
Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Glu Ser Pro Pro Thr Gly
                85                  90                  95

Leu Val Val Phe Gly Gly Gly Thr Lys Leu Thr Val Leu
            100                 105

<210> SEQ ID NO 280
<211> LENGTH: 674
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 280

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Arg Tyr Arg Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Gly
210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
            260                 265                 270

Glu Lys Pro Gly Gln Ala Phe Arg Gly Leu Ile Gly Gly Thr Asn Lys
        275                 280                 285
```

```
Arg Ala Pro Gly Thr Pro Ala Arg Phe Ser Gly Ser Leu Leu Gly Gly
    290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
        355                 360                 365

Leu Gly Cys Leu Val Lys Asp Tyr Phe Pro Glu Pro Val Thr Val Ser
370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
        435                 440                 445

Lys Thr His Thr Cys Pro Pro Cys Pro Ala Pro Glu Ala Ala Gly Gly
450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys

<210> SEQ ID NO 281
<211> LENGTH: 449
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 281

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Arg Tyr Arg Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380
```

```
Ser Asn Gly Gln Pro Glu Asn Tyr Lys Thr Thr Pro Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 282
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 282

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Glu Ser Pro Pro Thr Gly
                85                  90                  95

Leu Val Val Phe Gly Gly Gly Thr Lys Leu Thr Val Leu Gly Gln Pro
            100                 105                 110

Lys Ala Ala Pro Ser Val Thr Leu Phe Pro Pro Ser Ser Lys Lys Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 283
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 283

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Trp Ser Tyr Tyr Met Asp Tyr Trp Gly Gln Gly Thr
            100                 105                 110

Leu Val Thr Val Ser Ser
        115

<210> SEQ ID NO 284
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 284

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Thr Phe Gly Gln Gly Thr Lys Val Glu Ile Lys
            100                 105                 110

<210> SEQ ID NO 285
<211> LENGTH: 673
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 285

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

```
Gly Ile Ile Asn Pro Ser Gly Ser Thr Ser Tyr Ala Gln Lys Phe
             50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Asp Trp Ser Tyr Tyr Met Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Gly Gly
    210                 215                 220

Gly Gly Ser Gly Gly Gly Ser Gln Ala Val Val Thr Gln Glu Pro
225                 230                 235                 240

Ser Leu Thr Val Ser Pro Gly Gly Thr Val Thr Leu Thr Cys Gly Ser
                245                 250                 255

Ser Thr Gly Ala Val Thr Thr Ser Asn Tyr Ala Asn Trp Val Gln Glu
            260                 265                 270

Lys Pro Gly Gln Ala Phe Arg Gly Leu Ile Gly Gly Thr Asn Lys Arg
        275                 280                 285

Ala Pro Gly Thr Pro Ala Arg Phe Ser Gly Ser Leu Leu Gly Gly Lys
    290                 295                 300

Ala Ala Leu Thr Leu Ser Gly Ala Gln Pro Glu Asp Glu Ala Glu Tyr
305                 310                 315                 320

Tyr Cys Ala Leu Trp Tyr Ser Asn Leu Trp Val Phe Gly Gly Gly Thr
                325                 330                 335

Lys Leu Thr Val Leu Ser Ser Ala Ser Thr Lys Gly Pro Ser Val Phe
            340                 345                 350

Pro Leu Ala Pro Ser Ser Lys Ser Thr Ser Gly Gly Thr Ala Ala Leu
        355                 360                 365

Gly Cys Leu Val Lys Asp Tyr Phe Pro Glu Pro Val Thr Val Ser Trp
    370                 375                 380

Asn Ser Gly Ala Leu Thr Ser Gly Val His Thr Phe Pro Ala Val Leu
385                 390                 395                 400

Gln Ser Ser Gly Leu Tyr Ser Leu Ser Ser Val Val Thr Val Pro Ser
                405                 410                 415

Ser Ser Leu Gly Thr Gln Thr Tyr Ile Cys Asn Val Asn His Lys Pro
            420                 425                 430

Ser Asn Thr Lys Val Asp Lys Lys Val Glu Pro Lys Ser Cys Asp Lys
        435                 440                 445

Thr His Thr Cys Pro Pro Cys Pro Ala Pro Glu Ala Ala Gly Gly Pro
    450                 455                 460
```

```
Ser Val Phe Leu Phe Pro Pro Lys Pro Lys Asp Thr Leu Met Ile Ser
465                 470                 475                 480

Arg Thr Pro Glu Val Thr Cys Val Val Val Asp Val Ser His Glu Asp
                485                 490                 495

Pro Glu Val Lys Phe Asn Trp Tyr Val Asp Gly Val Glu Val His Asn
            500                 505                 510

Ala Lys Thr Lys Pro Arg Glu Glu Gln Tyr Asn Ser Thr Tyr Arg Val
        515                 520                 525

Val Ser Val Leu Thr Val Leu His Gln Asp Trp Leu Asn Gly Lys Glu
    530                 535                 540

Tyr Lys Cys Lys Val Ser Asn Lys Ala Leu Gly Ala Pro Ile Glu Lys
545                 550                 555                 560

Thr Ile Ser Lys Ala Lys Gly Gln Pro Arg Glu Pro Gln Val Tyr Thr
                565                 570                 575

Leu Pro Pro Cys Arg Asp Glu Leu Thr Lys Asn Gln Val Ser Leu Trp
            580                 585                 590

Cys Leu Val Lys Gly Phe Tyr Pro Ser Asp Ile Ala Val Glu Trp Glu
        595                 600                 605

Ser Asn Gly Gln Pro Glu Asn Asn Tyr Lys Thr Thr Pro Pro Val Leu
    610                 615                 620

Asp Ser Asp Gly Ser Phe Phe Leu Tyr Ser Lys Leu Thr Val Asp Lys
625                 630                 635                 640

Ser Arg Trp Gln Gln Gly Asn Val Phe Ser Cys Ser Val Met His Glu
                645                 650                 655

Ala Leu His Asn His Tyr Thr Gln Lys Ser Leu Ser Leu Ser Pro Gly
            660                 665                 670

Lys

<210> SEQ ID NO 286
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 286

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Trp Ser Tyr Tyr Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Glu Lys Val Glu Pro Lys Ser Cys Asp Lys Thr
            210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
            325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

<210> SEQ ID NO 287
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 287

```
gaggtgcaat tggtggaaag cggaggcggc ctcgtgaagc ctggcggatc tctgagactg      60
agctgtgccg ccagcggctt caccttcagc aacgcctgga tgagctgggt gcgccaggcc     120
cctggaaaag gactcgagtg ggtgggacgg atcaagagca agaccgaggg cggcaccacc     180
gactatgccg cccctgtgaa gggccggttc accatcagca gggacgacag caagaacacc     240
ctgtacctgc agatgaacag cctgaaaacc gaggacaccg ccgtgtacta ctgcaccacc     300
```

```
ccctacgagt ggtcttggta cgactactgg ggccagggca ccctcgtgac cgtgtcatct    360
```

<210> SEQ ID NO 288
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 288

```
gaggtgcaat tggtggaaag cggaggcggc ctcgtgaagc ctggcggatc tctgagactg      60
agctgtgccg ccagcggctt caccttcagc aacgcctgga tgagctgggt gcgccaggcc     120
cctggaaaag gactcgagtg ggtgggacgg atcaagagca agaccgaggg cggcaccacc     180
gactatgccg cccctgtgaa gggccggttc accatcagca gggacgacag caagaacacc     240
ctgtacctgc agatgaacag cctgaaaacc gaggacaccg ccgtgtacta ctgcaccacc     300
ccctacgagt ggtcttggta cgactactgg ggccagggca ccctcgtgac cgtgtcatct     360
gctagcacaa agggccctag cgtgttccct ctggccccca gcagcaagag cacaagcggc     420
ggaacagccg ccctgggctg cctcgtgaag gactacttcc ccgagcccgt gacagtgtct     480
tggaacagcg gagccctgac aagcggcgtg cacaccttcc ctgccgtgct gcagagcagc     540
ggcctgtact ccctgagcag cgtggtcacc gtgcctagca gcagcctggg cacccagacc     600
tacatctgca acgtgaacca caagcccagc aacaccaaag tggacaagaa ggtggagccc     660
aagagctgtg atggcggagg agggtccgga ggcggaggat ccgaggtgca gctgctggaa     720
tctggcggcg gactggtgca gcctggcgga tctctgagac tgagctgtgc cgccagcggc     780
ttcaccttca gcacctacgc catgaactgg gtgcgccagg ccctggcaa aggcctggaa     840
tgggtgtccc ggatcagaag caagtacaac aactacgcca cctactacgc cgacagcgtg     900
aagggccggt tcaccatcag ccgggacgac agcaagaaca ccctgtacct gcagatgaac     960
agcctgcggg ccgaggacac cgccgtgtac tattgtgtgc ggcacggcaa cttcggcaac    1020
agctatgtgt cttggtttgc ctactggggc cagggcaccc tcgtgaccgt gtcaagcgct    1080
agtaccaagg gcccccagcgt gttccccctg cacccagca gcaagagcac atctggcgga    1140
acagccgctc tgggctgtct ggtgaaagac tacttccccg agcccgtgac cgtgtcttgg    1200
aactctggcg ccctgaccag cggcgtgcac accttccagc cgtgctgca gagcagcggc    1260
ctgtactccc tgtcctccgt ggtcaccgtg ccctctagct ccctgggaac acagacatat    1320
atctgtaatg tcaatcacaa gccttccaac accaaagtcg ataagaaagt cgagcccaag    1380
agctgcgaca aaactcacac atgcccaccg tgcccagcac ctgaagctgc aggggaccg    1440
tcagtcttcc tcttcccccc aaaacccaag gacaccctca tgatctcccg gacccctgag    1500
gtcacatgcg tggtggtgga cgtgagccac gaagaccctg aggtcaagtt caactggtac    1560
gtggacggcg tggaggtgca taatgccaag acaaagccgc gggaggagca gtacaacagc    1620
acgtaccgtg tggtcagcgt cctcaccgtc ctgcaccagg actggctgaa tggcaaggag    1680
tacaagtgca aggtctccaa caaagccctc ggcgccccca tcgagaaaac catctccaaa    1740
gccaaagggc agccccgaga accacaggtg tacaccctgc ccccatgccg ggatgagctg    1800
accaagaacc aggtcagcct gtggtgcctg gtcaaaggct tctatcccag cgacatcgcc    1860
gtggagtggg agagcaatgg gcagccggag aacaactaca agaccacgcc tcccgtgctg    1920
```

```
gactccgacg gctccttctt cctctacagc aagctcaccg tggacaagag caggtggcag    1980
caggggaacg tcttctcatg ctccgtgatg catgaggctc tgcacaacca ctacacgcag    2040
aagagcctct ccctgtctcc gggtaaa                                         2067
```

<210> SEQ ID NO 289
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 289

```
gaggtgcaat tggtggaaag cggaggcggc ctcgtgaagc ctggcggatc tctgagactg     60
agctgtgccg ccagcggctt caccttcagc aacgcctgga tgagctgggt gcgccaggcc    120
cctggaaaag gactcgagtg ggtgggacgg atcaagagca agaccgaggg cggcaccacc    180
gactatgccg cccctgtgaa gggccggttc accatcagca gggacgacag caagaacacc    240
ctgtacctgc agatgaacag cctgaaaacc gaggacaccg ccgtgtacta ctgcaccacc    300
ccctacagtg gtcttggta cgactactgg ggccagggca cctcgtgac cgtgtcatct     360 gctagcacca agggcccctc cgtgttcccc ctggccccca gcagcaagag caccagcggc    420
ggcacagccg ctctgggctg cctggtcaag gactacttcc ccgagcccgt gaccgtgtcc    480
tggaacagcg gagccctgac ctccggcgtg cacaccttcc ccgccgtgct gcagagttct    540
ggcctgtata gcctgagcag cgtggtcacc gtgccttcta gcagcctggg cacccagacc    600
tacatctgca acgtgaacca caagcccagc aacaccaagg tggacaagaa ggtggagccc    660
aagagctgcg acaaaactca cacatgccca ccgtgcccag cacctgaagc tgcagggga    720 ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcggcgccc ccatcgagaa aaccatctcc   1020
aaagccaaag gcagccccg agaaccacag gtgtgcaccc tgcccccatc ccgggatgag   1080
ctgaccaaga accaggtcag cctctcgtgc gcagtcaaag gcttctatcc cagcgacatc   1140
gccgtggagt gggagagcaa tgggcagccg gagaacaact acaagaccac gcctcccgtg   1200
ctggactccg acggctcctt cttcctcgtg agcaagctca ccgtggacaa gagcaggtgg   1260
cagcagggga acgtcttctc atgctccgtg atgcatgagg ctctgcacaa ccgcttcacg   1320
cagaagagcc tctccctgtc tccgggtaaa                                    1350
```

<210> SEQ ID NO 290
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 290

```
gaggtgcaat tgttggagtc tgggggaggc ttggtacagc ctgggggtc cctgagactc     60 tcctgtgcag cctccggatt cacctttagc agttatgcca tgagctgggt ccgccaggct    120
```

```
ccagggaagg ggctggagtg ggtctcagct attagtggta gtggtggtag cacatactac      180
gcagactccg tgaagggccg gttcaccatc tccagagaca attccaagaa cacgctgtat      240
ctgcagatga acagcctgag agccgaggac acggccgtat attactgtgc gcgtggtgac      300
taccgttacc gttacttcga ctactggggc caaggaaccc tggtcaccgt ctcgagt        357

<210> SEQ ID NO 291
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 291
tcttctgaac tgactcaaga tccagctgtt agcgtggctc tgggtcagac tgtacgtatc       60
acctgccaag gcgattctct gcgctcctac tacgcaagct ggtaccagca gaaaccgggt      120
caggccccag ttctggtgat ttacggcaaa acaaccgtc cgtctgggat cccggaccgt       180
ttctccggca gctcttccgg taacacggcg agcctcacca tcactggcgc tcaagcagaa      240
gacgaggccg actattactg taactctcgg gaaagcccac caaccggcct ggttgtcttc      300
ggtggcggta ccaagctgac cgtccta                                          327

<210> SEQ ID NO 292
<211> LENGTH: 2022
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 292
gaggtgcaat tgttggagtc tgggggaggc ttggtacagc ctggggggtc cctgagactc        60
tcctgtgcag cctccggatt cacctttagc agttatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcagatga acagcctgag agccgaggac acggccgtat attactgtgc gcgtggtgac      300
taccgttacc gttacttcga ctactggggc caaggaaccc tggtcaccgt ctcgagtgct      360
agcaccaagg gcccctccgt gtttcctctg gcccccttcca gcaagtccac ctctggcgga      420
actgccgctc tgggctgcct ggtggaagat tacttccccg agcccgtgac cgtgtcctgg      480
aattctggcg ctctgacctc cggcgtgcac acctttccag ctgtgctgca gtcctccggc      540
ctgtactccc tgtcctccgt cgtgacagtg ccctccagct ctctgggcac ccagacctac      600
atctgcaacg tgaaccacaa gcccatccaac accaaggtgg acgagaaggt ggaacccaag      660
tcctgcgacg gtggcggagg ttccggaggc ggaggatccc aggctgtcgt gacccaggaa      720
ccctccctga cagtgtctcc tggcggcacc gtgaccctga cctgtggatc ttctaccggc      780
gctgtgacca cctccaacta cgccaattgg gtgcaggaaa agcccggcca ggccttcaga      840
ggactgatcg gcggcaccaa caagagagcc cctggcaccc ctgccagatt ctccggttct      900
ctgctgggcg gcaaggctgc cctgactctg tctggtgctc agcctgagga cgaggccgag      960
tactactgcg ccctgtggta ctccaacctg tgggtgttcg gcggaggcac caagctgacc     1020
```

| | |
|---|---|
| gtgctgtcca gcgcttccac caagggaccc agtgtgttcc ccctggcccc cagctccaag | 1080 |
| tctacatccg gtggcacagc tgccctggga tgtctcgtga aggactactt tcctgagcct | 1140 |
| gtgacagtgt cttggaacag cggagccctg accagcggag tgcacacatt ccctgcagtg | 1200 |
| ctgcagagca gcggcctgta tagcctgagc agcgtcgtga ccgtgccttc ctctagcctg | 1260 |
| ggaacacaga catatatctg taatgtgaat cataagccca gtaataccaa agtggataag | 1320 |
| aaagtggaac ctaagagctg cgataagacc cacacctgtc cccctgccc tgctcctgaa | 1380 |
| gctgctggtg gccctagcgt gttcctgttc cccccaaagc caaggacac cctgatgatc | 1440 |
| tcccggaccc ccgaagtgac ctgcgtggtg gtggatgtgt cccacgagga ccctgaagtg | 1500 |
| aagttcaatt ggtacgtgga cggcgtggaa gtgcacaacg ccaagaccaa gcctagagag | 1560 |
| gaacagtaca actccaccta ccgggtggtg tccgtgctga cagtgctgca ccaggactgg | 1620 |
| ctgaacggca aagagtacaa gtgcaaggtg tccaacaagg ccctgggcgc tcccatcgaa | 1680 |
| aagaccatct ccaaggccaa gggccagccc cgggaacccc aggtgtacac cctgcccca | 1740 |
| tgccgggatg agctgaccaa gaaccaggtc agcctgtggt gcctggtcaa aggcttctat | 1800 |
| cccagcgaca tcgccgtgga gtgggagagc aatgggcagc cggagaacaa ctacaagacc | 1860 |
| acgcctcccg tgctggactc cgacggctcc ttcttcctct acagcaagct caccgtggac | 1920 |
| aagagcaggt ggcagcaggg gaacgtcttc tcatgctccg tgatgcatga ggctctgcac | 1980 |
| aaccactaca cgcagaagag cctctccctg tctccgggta aa | 2022 |

<210> SEQ ID NO 293
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 293

| | |
|---|---|
| gaggtgcaat tgttggagtc tgggggaggc ttggtacagc ctgggggtc cctgagactc | 60 |
| tcctgtgcag cctccggatt cacctttagc agttatgcca tgagctgggt ccgccaggct | 120 |
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcagatga acagcctgag agccgaggac acggccgtat attactgtgc gcgtggtgac | 300 |
| taccgttacc gttacttcga ctactgggc caaggaaccc tggtcaccgt ctcgagtgct | 360 |
| agcaccaagg gcccctccgt gttccccctg gccccagca gcaagagcac cagcggcggc | 420 |
| acagccgctc tgggctgcct ggtcgaggac tacttccccg agcccgtgac cgtgtcctgg | 480 |
| aacagcggag ccctgaccct cggcgtgcac accttccccg ccgtgctgca gagttctggc | 540 |
| ctgtatagcc tgagcagcgt ggtcaccgtg ccttctagca gcctgggcac ccagacctac | 600 |
| atctgcaacg tgaaccacaa gcccagcaac accaaggtgg acgagaaggt ggagcccaag | 660 |
| agctgcgaca aaactcacac atgcccaccg tgcccagcac ctgaagctgc aggggaccg | 720 |
| tcagtcttcc tcttcccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccgtg tggtcagcgt cctcaccgtc ctgccagg actggctgaa tggcaaggag | 960 |
| tacaagtgca aggtctccaa caaagccctc ggcgccccca tcgagaaaac catctccaaa | 1020 |

```
gccaaagggc agccccgaga accacaggtg tgcaccctgc ccccatcccg ggatgagctg      1080
accaagaacc aggtcagcct ctcgtgcgca gtcaaaggct tctatcccag cgacatcgcc      1140
gtggagtggg agagcaatgg gcagccggag aacaactaca agaccacgcc tcccgtgctg      1200
gactccgacg gctccttctt cctcgtgagc aagctcaccg tggacaagag caggtggcag      1260
caggggaacg tcttctcatg ctccgtgatg catgaggctc tgcacaacca ctacacgcag      1320
aagagcctct ccctgtctcc gggtaaa                                          1347
```

<210> SEQ ID NO 294
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 294

```
tcttctgaac tgactcaaga tccagctgtt agcgtggctc tgggtcagac tgtacgtatc       60
acctgccaag gcgattctct gcgctcctac tacgcaagct ggtaccagca gaaaccgggt      120
caggccccag ttctggtgat ttacggcaaa aacaaccgtc cgtctgggat cccggaccgt      180
ttctccggca gctcttccgg taacacggcg agcctcacca tcactggcgc tcaagcagaa      240
gacgaggccg actattactg taactctcgg gaaagcccac caaccggcct ggttgtcttc      300
ggtggcggta ccaagctgac cgtcctaggt caacccaagg ctgccccag cgtgaccctg      360 ttccccccca gcagcaagaa actgcaggcc aacaaggcca cctggtctg cctgatcagc      420 gacttctacc caggcgccgt gaccgtggcc tggaaggccg acagcagccc cgtgaaggcc      480
ggcgtggaga ccaccacccc cagcaagcag agcaacaaca gtacgccgc cagcagctac      540 ctgagcctga cccccgagca gtggaagagc cacaggtcct acagctgcca ggtgacccac      600
gagggcagca ccgtggagaa aaccgtggcc cccaccgagt gcagc                      645
```

<210> SEQ ID NO 295
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 295

```
caggtgcaat tggttcaatc tggtgctgaa gtaaaaaaac cgggcgcttc cgttaaagtg       60
agctgcaaag catccggata caccttcact tcctattaca tgcactgggt tcgtcaagcc      120
ccgggccagg gtctggaatg gatgggcatc attaacccaa gcggtggctc tacctcctac      180
gcgcagaaat tccagggtcg cgtcacgatg accgtgaca ctagcacctc taccgtttat      240
atggagctgt ccagcctgcg ttctgaagat actgcagtgt actactgtgc acgcggtgac      300
tggtcttact acatggacta ttggggtcaa ggcaccctcg taacggtttc ttct            354
```

<210> SEQ ID NO 296
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 296

| gatattgtta tgactcaatc tccactgtct ctgccggtga ctccaggcga accggcgagc | 60 |
|---|---|
| atttcttgcc gttccagcca gtctctgctg cactccaacg gctacaacta tctcgattgg | 120 |
| tacctgcaaa aaccgggtca gagccctcag ctgctgatct acctgggctc taaccgcgct | 180 |
| tccggtgtac cggaccgttt cagcggctct ggatccggca ccgatttcac gttgaaaatc | 240 |
| agccgtgttg aagcagaaga cgtgggcgtt tattactgta tgcaggcacg gcagacccca | 300 |
| actttttggtc aaggcaccaa ggtcgaaatt aaa | 333 |

<210> SEQ ID NO 297
<211> LENGTH: 2019
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 297

| caggtgcaat tggttcaatc tggtgctgaa gtaaaaaaac cgggcgcttc cgttaaagtg | 60 |
|---|---|
| agctgcaaag catccggata caccttcact tcctattaca tgcactgggt tcgtcaagcc | 120 |
| ccgggccagg gtctggaatg gatgggcatc attaacccaa gcggtggctc tacctcctac | 180 |
| gcgcagaaat tccagggtcg cgtcacgatg acccgtgaca ctagcacctc taccgtttat | 240 |
| atggagctgt ccagcctgcg ttctgaagat actgcagtgt actactgtgc acgcggtgac | 300 |
| tggtcttact acatggacta ttggggtcaa ggcaccctcg taacggtttc ttctgctagc | 360 |
| accaagggcc cctccgtgtt tcctctggcc ccttccagca gtccacctc tggcggaact | 420 |
| gccgctctgg gctgcctggt ggaagattac ttccccgagc ccgtgaccgt gtcctggaat | 480 |
| tctggcgctc tgacctccgg cgtgcacacc tttccagctg tgctgcagtc ctccggcctg | 540 |
| tactccctgt cctccgtcgt gacagtgccc tccagctctc tgggcaccca gacctacatc | 600 |
| tgcaacgtga accacaagcc ctccaacacc aaggtggacg agaaggtgga acccaagtcc | 660 |
| tgcgacggtg gcggaggttc cggaggcgga ggatcccagg ctgtcgtgac ccaggaaccc | 720 |
| tccctgacag tgtctcctgg cggcaccgtg accctgacct gtggatcttc taccggcgct | 780 |
| gtgaccacct ccaactacgc caattgggtg caggaaaagc ccggccaggc cttcagagga | 840 |
| ctgatcggcg gcaccaacaa gagagcccct ggcaccctg ccagattctc cggttctctg | 900 |
| ctgggcggca aggctgccct gactctgtct ggtgctcagc ctgaggacga ggccgagtac | 960 |
| tactgcgccc tgtggtactc caacctgtgg gtgttcggcg gaggcaccaa gctgaccgtg | 1020 |
| ctgtccagcg cttccaccaa gggacccagt gtgttccccc tggcccccag ctccaagtct | 1080 |
| acatccggtg gcacagctgc cctgggatgt ctcgtgaagg actactttcc tgagcctgtg | 1140 |
| acagtgtctt ggaacagcgg agccctgacc agcggagtgc acacattccc tgcagtgctg | 1200 |
| cagagcagcg gcctgtatag cctgagcagc gtcgtgaccg tgccttcctc tagcctggga | 1260 |
| acacagacat atatctgtaa tgtgaatcat aagcccagta ataccaaagt ggataagaaa | 1320 |
| gtggaaccta agagctgcga taagacccac acctgtcccc cctgccctgc tcctgaagct | 1380 |
| gctggtggcc ctagcgtgtt cctgttcccc ccaaagccca aggacaccct gatgatctcc | 1440 |
| cggacccccg aagtgacctg cgtggtggtg gatgtgtccc acgaggaccc tgaagtgaag | 1500 |
| ttcaattggt acgtggacgg cgtggaagtg cacaacgcca agaccaagcc tagagaggaa | 1560 |

```
cagtacaact ccacctaccg ggtggtgtcc gtgctgacag tgctgcacca ggactggctg      1620
aacggcaaag agtacaagtg caaggtgtcc aacaaggccc tgggcgctcc catcgaaaag      1680
accatctcca aggccaaggg ccagccccgg gaaccccagg tgtacaccct gcccccatgc      1740
cgggatgagc tgaccaagaa ccaggtcagc ctgtggtgcc tggtcaaagg cttctatccc      1800
agcgacatcg ccgtggagtg ggagagcaat gggcagccgg agaacaacta caagaccacg      1860
cctcccgtgc tggactccga cggctccttc ttcctctaca gcaagctcac cgtggacaag      1920
agcaggtggc agcaggggaa cgtcttctca tgctccgtga tgcatgaggc tctgcacaac      1980
cactacacgc agaagagcct ctccctgtct ccgggtaaa                              2019

<210> SEQ ID NO 298
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 298
caggtgcaat tggttcaatc tggtgctgaa gtaaaaaaac cgggcgcttc cgttaaagtg        60
agctgcaaag catccggata caccttcact tcctattaca tgcactgggt tcgtcaagcc       120
ccgggccagg gtctggaatg gatgggcatc attaacccaa gcggtggctc tacctcctac       180
gcgcagaaat tccagggtcg cgtcacgatg acccgtgaca ctagcacctc taccgtttat       240
atggagctgt ccagcctgcg ttctgaagat actgcagtgt actactgtgc acgcggtgac       300
tggtcttact acatggacta ttggggtcaa ggcaccctcg taacggtttc ttctgctagc       360
accaagggcc cctccgtgtt ccccctggcc ccagcagca agagcaccag cggcggcaca       420
gccgctctgg gctgcctggt cgaggactac ttccccgagc ccgtgaccgt gtcctggaac       480
agcggagccc tgacctccgg cgtgcacacc ttccccgccg tgctgcagag ttctggcctg       540
tatagcctga gcagcgtggt caccgtgcct tctagcagcc tgggcaccca gacctacatc       600
tgcaacgtga accacaagcc cagcaacacc aaggtggacg agaaggtgga gcccaagagc       660
tgcgacaaaa ctcacacatg cccaccgtgc ccagcacctg aagctgcagg ggaccgtca       720 gtcttcctct tccccccaaa acccaaggac accctcatga tctcccggac ccctgaggtc       780
acatgcgtgg tggtggacgt gagccacgaa gaccctgagg tcaagttcaa ctggtacgtg       840
gacggcgtgg aggtgcataa tgccaagaca agccgcggg aggagcagta caacagcacg        900
taccgtgtgg tcagcgtcct caccgtcctg caccaggact ggctgaatgg caaggagtac       960
aagtgcaagg tctccaacaa agccctcggc gcccccatcg agaaaaccat ctccaaagcc      1020
aaagggcagc cccgagaacc acaggtgtgc accctgcccc catcccggga tgagctgacc      1080
aagaaccagg tcagcctctc gtgcgcagtc aaaggcttct atcccagcga catcgccgtg      1140
gagtgggaga gcaatgggca gccggagaac aactacaaga ccacgcctcc cgtgctggac      1200
tccgacggct ccttcttcct cgtgagcaag ctcaccgtgg acaagagcag gtggcagcag      1260
gggaacgtct tctcatgctc cgtgatgcat gaggctctgc acaaccacta cacgcagaag      1320
agcctctccc tgtctccggg taaa                                              1344

<210> SEQ ID NO 299
<211> LENGTH: 654
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 299
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatcg acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcacg gcagacccca   300
acttttggtc aaggcaccaa ggtcgaaatt aaacgtacgg tggctgcacc atctgtcttc   360
atcttcccgc catctgatcg aagttgaaa tctggaactg cctctgttgt gtgcctgctg    420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600 acccatcagg gcctgagctc gcccgtcaca aagagcttca caggggaga gtgt          654

<210> SEQ ID NO 300
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(50)
<223> OTHER INFORMATION: /note="This sequence may encompass 1-10 'Gly
      Gly Gly Gly Ser' repeating units, wherein some positions may be
      absent"
<220> FEATURE:
<221> NAME/KEY: source
<223> OTHER INFORMATION: /note="See specification as filed for detailed
      description of substitutions and preferred embodiments"

<400> SEQUENCE: 300

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 301
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(50)
<223> OTHER INFORMATION: /note="This sequence may encompass 1-10 'Ser
      Gly Gly Gly Gly' repeating units, wherein some positions may be
      absent"
```

<220> FEATURE:
<221> NAME/KEY: source
<223> OTHER INFORMATION: /note="See specification as filed for detailed
      description of substitutions and preferred embodiments"

<400> SEQUENCE: 301

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
                20                  25                  30

Gly Gly Gly Ser Gly Gly Gly Gly Ser Gly Gly Gly Gly Ser Gly Gly
            35                  40                  45

Gly Gly
    50

<210> SEQ ID NO 302
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (5)..(54)
<223> OTHER INFORMATION: /note="This region may encompass 1-10 'Ser Gly
      Gly Gly Gly' repeating units, wherein some positions may be
      absent"
<220> FEATURE:
<221> NAME/KEY: source
<223> OTHER INFORMATION: /note="See specification as filed for detailed
      description of substitutions and preferred embodiments"

<400> SEQUENCE: 302

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly
    50

<210> SEQ ID NO 303
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Gly Gly Gly Gly Ser Gly Gly Gly Gly Ser
1               5                   10

<210> SEQ ID NO 304
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

```
Glu Pro Lys Ser Cys Gly Gly Gly Ser Gly Gly Gly Gly Ser
1               5                   10                  15

<210> SEQ ID NO 305
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Glu Pro Lys Ser Cys Asp Gly Gly Gly Ser Gly Gly Gly Gly Ser
1               5                   10                  15

<210> SEQ ID NO 306
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Penta-His tag"

<400> SEQUENCE: 306

His His His His His
1               5

<210> SEQ ID NO 307
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 307

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100

<210> SEQ ID NO 308
<211> LENGTH: 692
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 308
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr His Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Gly Phe His Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Gly
    210                 215                 220

Gly Gly Gly Ser Gly Gly Gly Gly Ser Glu Val Gln Leu Leu Glu Ser
225                 230                 235                 240

Gly Gly Gly Leu Val Gln Pro Gly Gly Ser Leu Arg Leu Ser Cys Ala
                245                 250                 255

Ala Ser Gly Phe Thr Phe Ser Thr Tyr Ala Met Asn Trp Val Arg Gln
            260                 265                 270

Ala Pro Gly Lys Gly Leu Glu Trp Val Ser Arg Ile Arg Ser Lys Tyr
        275                 280                 285

Asn Asn Tyr Ala Thr Tyr Tyr Ala Asp Ser Val Lys Gly Arg Phe Thr
    290                 295                 300

Ile Ser Arg Asp Asp Ser Lys Asn Thr Leu Tyr Leu Gln Met Asn Ser
305                 310                 315                 320

Leu Arg Ala Glu Asp Thr Ala Val Tyr Tyr Cys Val Arg His Gly Asn
                325                 330                 335

Phe Gly Asn Ser Tyr Val Ser Trp Phe Ala Tyr Trp Gly Gln Gly Thr
            340                 345                 350

Leu Val Thr Val Ser Ser Ala Ser Val Ala Ala Pro Ser Val Phe Ile
        355                 360                 365

Phe Pro Pro Ser Asp Glu Gln Leu Lys Ser Gly Thr Ala Ser Val Val
    370                 375                 380

Cys Leu Leu Asn Asn Phe Tyr Pro Arg Glu Ala Lys Val Gln Trp Lys
385                 390                 395                 400

Val Asp Asn Ala Leu Gln Ser Gly Asn Ser Gln Glu Ser Val Thr Glu
                405                 410                 415

Gln Asp Ser Lys Asp Ser Thr Tyr Ser Leu Ser Ser Thr Leu Thr Leu
```

```
                420             425              430

Ser Lys Ala Asp Tyr Glu Lys His Lys Val Tyr Ala Cys Glu Val Thr
            435                 440                 445

His Gln Gly Leu Ser Ser Pro Val Thr Lys Ser Phe Asn Arg Gly Glu
        450                 455                 460

Cys Asp Lys Thr His Thr Cys Pro Pro Cys Pro Ala Pro Glu Ala Ala
465                 470                 475                 480

Gly Gly Pro Ser Val Phe Leu Phe Pro Pro Lys Pro Lys Asp Thr Leu
                485                 490                 495

Met Ile Ser Arg Thr Pro Glu Val Thr Cys Val Val Val Asp Val Ser
            500                 505                 510

His Glu Asp Pro Glu Val Lys Phe Asn Trp Tyr Val Asp Gly Val Glu
        515                 520                 525

Val His Asn Ala Lys Thr Lys Pro Arg Glu Glu Gln Tyr Asn Ser Thr
    530                 535                 540

Tyr Arg Val Val Ser Val Leu Thr Val Leu His Gln Asp Trp Leu Asn
545                 550                 555                 560

Gly Lys Glu Tyr Lys Cys Lys Val Ser Asn Lys Ala Leu Gly Ala Pro
                565                 570                 575

Ile Glu Lys Thr Ile Ser Lys Ala Lys Gly Gln Pro Arg Glu Pro Gln
            580                 585                 590

Val Tyr Thr Leu Pro Pro Cys Arg Asp Glu Leu Thr Lys Asn Gln Val
        595                 600                 605

Ser Leu Trp Cys Leu Val Lys Gly Phe Tyr Pro Ser Asp Ile Ala Val
    610                 615                 620

Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Tyr Ser Lys Leu Thr
                645                 650                 655

Val Asp Lys Ser Arg Trp Gln Gln Gly Asn Val Phe Ser Cys Ser Val
            660                 665                 670

Met His Glu Ala Leu His Asn His Tyr Thr Gln Lys Ser Leu Ser Leu
        675                 680                 685

Ser Pro Gly Lys
    690

<210> SEQ ID NO 309
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 309

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr His Asp Thr Ser Thr Ser Thr Val Tyr
65                  70                  75                  80
```

Met Glu Leu Ser Ser Leu Arg Ser Glu Asp Thr Ala Val Tyr Tyr Cys
                85                  90                  95

Ala Arg Ser Phe Phe Thr Gly Phe His Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 310
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (201)..(201)
<223> OTHER INFORMATION: Any amino acid

<400> SEQUENCE: 310

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Thr Asn Glu His
                85                  90                  95

Tyr Tyr Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Xaa Gly Leu Ser Ser Pro Val Thr
        195                 200                 205

Lys Ser Phe Asn Arg Gly Glu Cys
    210                 215

<210> SEQ ID NO 311
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Gly Thr Asn Ala Arg Ala Pro
1               5

<210> SEQ ID NO 312
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Ala Leu Trp Tyr Ala Asn Leu Trp Val

-continued

```
<210> SEQ ID NO 313
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Asn Ala Trp Met His
1               5

<210> SEQ ID NO 314
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Ser Ile Lys Ser Lys Thr Asp Gly Gly Thr Thr Asp Tyr Ala Ala Pro
1               5                   10                  15

Val Lys Gly

<210> SEQ ID NO 315
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Pro Tyr Glu Trp Ser Trp Tyr Asp Tyr
1               5

<210> SEQ ID NO 316
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 316

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

-continued

```
Arg Gln Thr Pro Thr Phe Gly Gln Gly Thr Lys Val Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```